US009688697B2

(12) United States Patent
Achiron et al.

(10) Patent No.: US 9,688,697 B2
(45) Date of Patent: Jun. 27, 2017

(54) RNA POLYMERASE I INHIBITORS AND USES THEREOF

(71) Applicant: Tel HaShomer Medical Research Infrastructure and Services Ltd., Ramat-Gan (IL)

(72) Inventors: Anat Achiron, Tel-Aviv (IL); Roi Mashiach, Kiryat-Ono (IL); Michael Gurevich, Rechovot (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 14/742,907

(22) Filed: Jun. 18, 2015

(65) Prior Publication Data

US 2015/0284410 A1 Oct. 8, 2015

Related U.S. Application Data

(63) Continuation-in-part of application No. PCT/IB2014/066402, filed on Nov. 27, 2014.

(60) Provisional application No. 61/910,060, filed on Nov. 28, 2013.

(51) Int. Cl.
| | | |
|---|---|---|
| *A61K 31/55* | (2006.01) | |
| *C07D 471/12* | (2006.01) | |
| *C07D 513/14* | (2006.01) | |
| *A61K 31/551* | (2006.01) | |
| *C12Q 1/68* | (2006.01) | |

(52) U.S. Cl.
CPC .......... *C07D 513/14* (2013.01); *A61K 31/551* (2013.01); *C12Q 1/6876* (2013.01); *C12Q 2600/136* (2013.01); *C12Q 2600/158* (2013.01)

(58) Field of Classification Search
CPC .......................... A61K 31/551; C07D 471/12
USPC ........................................... 514/218; 540/575
See application file for complete search history.

(56) References Cited

U.S. PATENT DOCUMENTS

| | | |
|---|---|---|
| 2007/0117770 A1 | 5/2007 | Drygin et al. |
| 2008/0248001 A1 | 10/2008 | Bourke |
| 2009/0093455 A1 | 4/2009 | Nagasawa et al. |
| 2009/0093465 A1 | 4/2009 | Pierre et al. |
| 2014/0086839 A1 | 3/2014 | Achiron et al. |

FOREIGN PATENT DOCUMENTS

| | | |
|---|---|---|
| EP | 0983256 | 3/1997 |
| WO | WO 98/52933 | 11/1998 |
| WO | WO 03/081201 | 10/2003 |
| WO | WO 2007/022474 | 2/2007 |
| WO | WO 2008/081435 | 7/2008 |
| WO | WO 2008/131134 | 10/2008 |
| WO | WO 2009/046383 | 4/2009 |
| WO | WO 2010/113096 | 10/2010 |
| WO | WO 2012/123938 | 9/2012 |
| WO | WO 2015/079411 | 6/2015 |

OTHER PUBLICATIONS

Official Action Dated Apr. 14, 2016 From the US Patent and Trademark Office Re. U.S. Appl. No. 14/005,583.
Office Action Dated Jun. 24, 2015 From the State Intellectual Property Office of the People's Republic of China Re. Application No. 201280023297.2 and Its Translation Into English.
Official Action Dated Dec. 31, 2015 From the US Patent and Trademark Office Re. U.S. Appl. No. 14/005,583.
Bratrude "The Anti-Inflammatory Diet and Multiple Sclerosis", Swedish Medical Center, 4 Pages, Aug. 12, 2013.
Office Action Dated Jan. 17, 2016 From the Israel Patent Office Re. Application No. 228464 and Its Translation Into English.
International Preliminary Report on Patentability Dated Jun. 9, 2016 From the International Bureau of WIPO Re. Application No. PCT/IB2014/066402.
Advisory Action Before the Filing of an Appeal Brief Dated Mar. 28, 2016 From the US Patent and Trademark Office Re. U.S. Appl. No. 14/005,583.
Communication Pursuant to Article 94(3) EPC Dated Apr. 5, 2016 From the European Patent Office Re. Application No. 12710797.7.
Communication Pursuant to Rules 161(1) and 162 EPC Dated Oct. 24, 2013 From the European Patent Office Re. Application No. 12710797.7.
International Preliminary Report on Patentability Dated Sep. 26, 2013 From the International Bureau of WIPO Re. Application No. PCT/IL2012/050061.
International Search Report and the Written Opinion Dated Jul. 9, 2012 From the International Searching Authority Re. Application No. PCT/IL2012/050061.
International Search Report and the Written Opinion Dated Feb. 15, 2015 From the International Searching Authority Re. Application No. PCT/IB2014/066402.
Notification of Office Action Dated Sep. 30, 2014 From the State Intellectual Property Office of the People's Republic of China Re. Application No. 201280023297.2 and Its Translation Into English.
Official Action Dated Apr. 3, 2015 From the US Patent and Trademark Office Re. U.S. Appl. No. 14/005,583.
Restriction Official Action Dated Nov. 28, 2014 From the US Patent and Trademark Office Re. U.S. Appl. No. 14/005,583.
Search Report Dated Sep. 30, 2014 From the State Intellectual Property Office of the People's Republic of China Re. Application No. 201280023297.2 and Its Translation Into English.
Achiron et al. "Zinc-Ion Binding and Cytokine Activity Regulation Pathways Predicts Outcome in Relapsing-Remitting Multiple Sclerosis", Clinical and Experimental Immunology, 149: 235-242, 2007.
Banti et al. Synthesis and In-Vitro Antitumour Activity of New Naphthyridine Derivatives on Human Pancreatic Cancer Cells, Journal of Pharmacy and Pharmacology, JPP, 61: 1057-1066, First Published Jan. 8, 2010. Abstract.

(Continued)

*Primary Examiner* — Brenda Coleman

(57) ABSTRACT

Provided are novel compounds which are capable of inhibiting an activity of RNA polymerase I, and uses thereof in treating diseases or disorders modulated by RNA polymerase I, preferably autoimmune diseases such as multiple sclerosis and proliferative diseases.

9 Claims, 16 Drawing Sheets

(56) References Cited

OTHER PUBLICATIONS

Cavanaugh et al. "Mammalian Rrn3 Is Required for the Formation of a Transcription Competent Preinitiation Complex Containing RNA Polymerase I", Gene Expression, 14(3): 131-147, 2008.
Cavanaugh et al. "Rrn3 Phosphorylation Is a Regualtory Checkpoint for Ribosome Biogenesis", The Journal of Biological Chemistry, 277(30): 27423-27432, Jul. 26, 2002.
Costelloe et al. "Long-Term Clinical Relevance of Criteria for Designating Multiple Sclerosis as Benign After 10 Years of Disease", Journal of Neurology, Neurosurgery, and Psychiatry, 79(11): 1245-1248, Nov. 2008.
Drygin et al. "Targeting RNA Polymerase I With an Oral Small Molecule CX-5461 Inhibitis Ribosomal RNA Synthesis and Solid Tumor Growth", Cancer Research, XP002678820, 71(4): 1418-1430, Feb. 15, 2011.
Drygin et al. "The RNA Polymerase I Transcription Machinery: An Emerging Target for the Treatment of Cancer", Annual Review of Pharmacology and Toxicology, 50: 131-156, 2010.
Kalita et al. "Inhibition of Nucleolar Transcription as a Trigger for Neuronal Apoptosis", Journal of Neurochemistry, 105(6): 2286-2299, Jun. 1, 2008.
Leuenroth et al. "Triptolide-Induced Transcriptional Arrest Is Associated With Changes in Nuclear Substructure", Cancer Research, 68: 5257-5266, Jul. 1, 2008.
Liu et al. "Triptolide, a Component of Chinese Herbal Medicine, Modulates the Functional Phenotype of Dendritic Cells", Transplantation, 84(11): 1517-1526, Dec. 15, 2007.
Pittock et al. "Benign Multiple Sclerosis: A Distinct Clinical Entity With Therapeutic Implications", Current Topics in Microbiology and Immunology, 318: 1-17, 2008.
Reagan-Shaw et al. "Dose Translation From Animal to Human Studies Revisited", The FASEB Journal, 22: 659-661, 2007.
Russell et al. "RNA-Polymcrase-I-Directed rDNA Transcription, Life and Works", Trends in Biochemical Sciences, 30(2): 87-96, Feb. 2005.
Wang et al. "Triptolide Modulates T-Cell Inflammatory Responses and Ameliorates Experimental Autoimmune Encephalomyelitis", Journal of Neuroscience Research, 86: 2441-2449, 2008.
Office Action Dated Jul. 17, 2016 From the Israel Patent Office Re. Application No. 228464 and Its Translation Into English.
Supplementary European Search Report and the European Search Opinion Dated Mar. 17, 2017 From the European Patent Office Re. Application No. 14865441.1. (11 Pages).
Haddach et al. "Discovery of CX-5461, the First Direct and Selective Inhibitor of RNA Polymerase I, for Cancer Therapeutics", ACS Medical Chemistry Letters, XP055350883, 3(7): 602-606, May 8, 2012. p. 602, Compound 7c.

RNA POLYMERASE I INHIBITORS AND USES THEREOF

RELATED APPLICATIONS

This application is a Continuation in Part of PCT Patent Application No. PCT/IB2014/066402 having International filing date of Nov. 27, 2014, which claims the benefit of priority under 35 USC §119(e) of U.S. Provisional Patent Application No. 61/910,060 filed on Nov. 28, 2013. The contents of the above applications are all incorporated by reference as if fully set forth herein in their entirety.

SEQUENCE LISTING STATEMENT

The ASCII file, entitled 62593SequenceListing.txt, created on Jun. 18, 2015, comprising 574,287 bytes, submitted concurrently with the filing of this application is incorporated herein by reference.

FIELD AND BACKGROUND OF THE INVENTION

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Autoimmune diseases are caused by an autoimmune response, i.e., an immune response directed to a substance in the body of the subject. The characteristics of the autoimmune diseases vary and depend on the site affected by the autoimmune response.

Multiple sclerosis (MS) is the most common demyelinating disease of the central nervous system (CNS) affecting young adults (disease onset between 20 to 40 years of age) and is the third leading cause for disability after trauma and rheumatic diseases, with an estimated annual cost of 34,000 USD per patient (total life time cost of 2.2 million USD per patient).

The disease is characterized by destruction of myelin, associated with death of oligodendrocytes and axonal loss. The main pathologic finding in MS is the presence of infiltrating mononuclear cells, predominantly T lymphocytes and macrophages, which surpass the blood brain barrier and induce an active inflammation within the brain and spinal cord. The neurological symptoms that characterize MS include complete or partial vision loss, diplopia, sensory symptoms, motor weakness that can worsen to complete paralysis, bladder dysfunction and cognitive deficits, which eventually may lead to a significant disability. The associated multiple inflammatory foci lead to myelin destruction, plaques of demyelination, gliosis and axonal loss within the brain and spinal cord and are the reasons which contribute to the clinical manifestations of neurological disability.

The etiology of MS is not fully understood. The disease develops in genetically predisposed subjects exposed to yet undefined environmental factors and the pathogenesis involves autoimmune mechanisms associated with autoreactive T cells against myelin antigens. It is well established that not one dominant gene determines genetic susceptibility to develop MS, but rather many genes, each with different influence, are involved.

Clinically, in 85% of MS patients the illness is initiated with a relapsing-remitting course (RRMS), and in about 10-15% of MS patients have an a-priori primary progressive course (PPMS) without relapses. RRMS is characterized by inflammatory attacks associated with neurological deficits with periods of remissions between the relapses that vary in time. After a period of 10 years, about 50% of RRMS patients will progress to a secondary progressive MS (SPMS) course, characterized by permanent neurological dysfunction, with or without relapses and progressive disability.

Benign MS (BMS) is a clinical variant of RRMS in which the patients develop low neurological disability if at all after a disease duration of at least 10 years. Accordingly, this group of MS patients do not experience devastating accumulating disability over-time and when these patients are examined neurologically and scored by the Expanded Disability Status Scale (EDSS) they receive a score that is equal to or lower than 3.0. This low EDSS score signifies mild disability and when this low disability occurs more than 10 years after disease onset, the course of MS is defined as benign. Prediction of patients that will have BMS is currently impossible and the definition of these patients is retrospective. The molecular events accountable for the BMS variant of disease are not understood.

WO 2008/081435 discloses methods and kits for predicting the prognosis of a subject diagnosed with multiple sclerosis and methods of selecting a treatment regimen of a subject diagnosed with multiple sclerosis.

Achiron A, et al., 2007 [Clinical and Experimental Immunology, 149: 235-242] describe genes of the zinc-ion binding and cytokine activity regulation pathways which predict outcome in relapsing-remitting multiple sclerosis.

WO 2010/113096 discloses methods of predicting clinical course and treating multiple sclerosis.

Current approved drugs for the treatment of MS are either general anti-inflammatory agents or immunomodulators and consequently result only in moderate beneficial effects suppressing disease activity.

CX-5461 (see, Table 1 hereinunder) is a small molecule that was designed to selectively inhibit rRNA synthesis by inhibiting RNA Polymerase I (POL I or POL1), without affecting mRNA synthesis by RNA Polymerase II (POL II), and without inhibiting DNA replication or protein synthesis (Russell J, Zomerdijk J C. Trends Biochem Sci 30:87-96, 2005; Drygin D, et al. Annu Rev Pharmacol Toxicol 50:131-156, 2010).

The inhibition of POL1 results in nucleolar stress which causes the release of ribosomal proteins (RP) from the nucleolus and subsequent activation of p53, resulting in cell apoptosis [Kalita K, et al. J Neurochem 105:2286-2299, 2008]. In a previous study [Drygin D, et al. Cancer Res 71:1418-1430, 2011], the antiproliferative activity of CX-5461 was studied in cell lines and it was shown that CX-5461 inhibited POL-I activity in human cancer cell lines.

Recent studies indicate that disruption of the SL1/rDNA complex by CX-5461 results from the interference between SL1 and rDNA. SL1, a protein complex containing TATA binding protein-associated factors, is responsible for POL1 promoter specificity. SL1 performs important tasks in the transcription complex assembly, mediating specific interactions between the rDNA promoter region and the POL1 enzyme complex, thereby recruiting POL1, together with a collection of POL1-associated factors like RRN3 to rDNA (Cavanaugh A, et al. *Gene Expr* 14:131-147, 2008).

U.S. Patent Application Publication No. 2009/0093465 discloses a family of compounds, including CX-5461, as kinase modulators useful in the treatment of proliferative diseases such as cancer.

Recently, a role for inhibition of RNA polymerase I (POL1) pathway in the regulation of MS disease activity by suppression of inflammation and enhancement of apoptosis of autoreactive lymphocytes has been uncovered. The suggested mechanism by which POL1 pathway inhibition affects the disease process is demonstrated in Background Art FIGS. 1 and 2A-B.

The above findings have supported a basis for direct targeting of RNA Polymerase-I transcription pathway as a strategy for selective induction of apoptosis in MS in order to transform the active disease of RRMS to the preferable BMS subtype. Administration of a specific POL1 inhibitor (POL1-I) was demonstrated to prevent animal Experimental Autoimmune Encephalomyelitis (EAE) when administered at disease induction and to reduce the disease severity when administered at clinical disease onset [Achiron et al. 2013, J Neuroimmunol 263:91-97], thus confirming that a POL1 inhibitor acts specifically by inhibiting the polymerase I associated molecules.

WO 2012/123938 discloses uses of family of compounds, including CX-5461 and derivatives thereof, in the treatment of autoimmune diseases such as MS.

Additional background art includes Leuenroth S J and Crews C M (Triptolide-induced transcriptional arrest is associated with changes in nuclear substructure. Cancer Res. 2008; 68:5257-5266); Liu Y, et al. (Triptolide, a component of Chinese herbal medicine, modulates the functional phenotype of dendritic cells. Transplantation. 2007; 84:1517-1526); Wang Y, et al. (Triptolide modulates T-cell inflammatory responses and ameliorates experimental autoimmune encephalomyelitis. J Neurosci Res. 2008; 86:2441-2449; EP 0983256; PCT/US1998/008562; WO9852933A1; Alice H. Cavanaugh, et al., 2002 (Rrn3 Phosphorylation is a regulatory checkpoint for ribosome biogenesis J. Biol. Chem., 2002; 277: 27423-27432); PCT Pub. No. WO 03/081201.

SUMMARY OF THE INVENTION

Based on the findings that inhibition of RNA Polymerase-I plays a role in regulation of MS and other autoimmune diseases, as well as cell proliferation, the present inventors have searched for POL-1 inhibitors (denoted herein as POL1-I) that would exhibit an improved effect as compared to the presently known POL1 inhibitors (e.g., POL1-I and structural analogs thereof).

The present inventors have uncovered that by modifying a structural feature of CX-5461 or analogs thereof, so as to reduce or even reverse its capability of participating in hydrogen bond formation, inhibitors which exhibit improved performance are obtained.

According to an aspect of some embodiments of the present invention there is provided a compound represented by general Formula I:

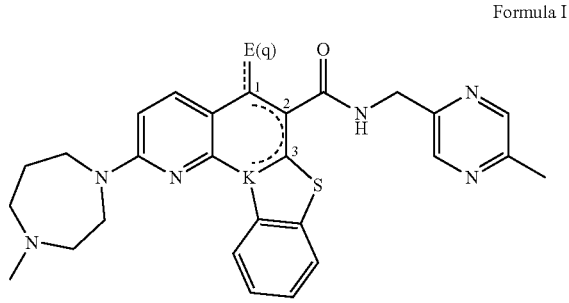

Formula I wherein ===== or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or $N^{(+)}$, depending on the nature and valency of E.

According to some embodiments of the present invention, E forms a chemical moiety selected from the group consisting of thiocarbonyl and a substituted or unsubstituted imine.

According to some embodiments of the present invention, q is 1, K is N, E is linked to carbon 1 of the ring via an unsaturated double bond, and another unsaturated double bond is present between carbons 2 and 3 of the ring, the compound being represented by Formula Ia:

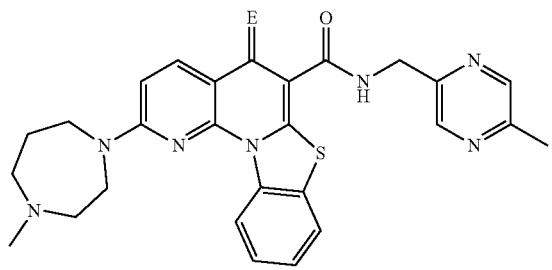

Formula Ia

According to some embodiments of the present invention, E forms a substituted or unsubstituted imine, the compound being represented by Formula Ib:

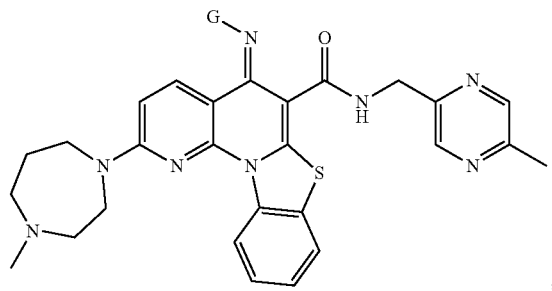

Formula Ib wherein G is selected from the group consisting of hydrogen, alkyl, cycloalkyl, aryl, heteroaryl, heteroalicyclic, alkoxy, thioalkoxy, thiol, hydroxyl, aryloxy, and thioaryloxy.

According to some embodiments of the present invention, G is aryl.

According to an aspect of some embodiments of the present invention there is provided a compound as described herein, for use in the treatment of an autoimmune disease.

According to an aspect of some embodiments of the present invention there is provided a compound as described herein, for use in the manufacture of a medicament for treating an autoimmune disease.

According to an aspect of some embodiments of the present invention there is provided a method of treating an autoimmune disease in a subject, the method comprising administering to the subject a therapeutically effective amount of the compound of Formula I as described in any one of the respective embodiments herein.

According to some embodiments of the present invention, the autoimmune disease is multiple sclerosis.

According to some embodiments of the present invention, the multiple sclerosis is a relapsing-remitting multiple sclerosis (RRMS) or benign multiple sclerosis (BMS).

According to some embodiments of the present invention, treating the multiple sclerosis comprises changing the course of the disease from the RRMS to BMS.

According to some embodiments of the present invention, the autoimmune disease is treatable by inhibiting an activity of RNA Polymerase I.

According to an aspect of some embodiments of the present invention there is provided a compound as described herein, for use in the treatment of a proliferative disease or disorder.

According to an aspect of some embodiments of the present invention there is provided a use of the compound as described herein, in the manufacture of a medicament for the treatment of a proliferative disease or disorder.

According to an aspect of some embodiments of the present invention there is provided a method of treating a proliferative disease or disorder, the method comprising administering to a subject in need thereof a therapeutically effective amount of the compound as described herein.

According to some embodiments of the present invention, the proliferative disease or disorder is treatable by inhibiting an activity of a protein kinase.

According to an aspect of some embodiments of the present invention there is provided a compound as described herein, for use in inhibiting an activity of RNA Polymerase I and/or for treating a disease or disorder treatable by inhibiting an activity of RNA Polymerase I.

According to an aspect of some embodiments of the present invention there is provided a use of a compound as described herein, in the manufacture of a medicament for inhibiting an activity of RNA Polymerase I and/or for treating a disease or disorder treatable by inhibiting an activity of RNA Polymerase I.

According to an aspect of some embodiments of the present invention there is provided a method of inhibiting an activity of RNA Polymerase I, the method comprising contacting the RNA Polymerase I with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of RNA Polymerase I.

According to an aspect of some embodiments of the present invention there is provided a compound as described herein, for use in inhibiting an activity of a protein kinase and/or for treating a disease or disorder treatable by inhibiting an activity of a protein kinase.

According to an aspect of some embodiments of the present invention there is provided a use of a compound as described herein, in the manufacture of a medicament for inhibiting an activity of a kinase and/or for treating a disease or disorder treatable by inhibiting an activity of a protein kinase.

According to an aspect of some embodiments of the present invention there is provided a method of inhibiting an activity of a protein kinase, the method comprising contacting the protein kinase with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of a protein kinase.

According to some embodiments of the present invention, there is provided a method of monitoring an efficiency of the compound of claim 1 in treating a disease associated with a subject, the method comprising:

(a) administering to the subject a therapeutically effective amount of the compound, and (b) comparing a level of expression of at least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring the efficiency of the compound in treating the disease in the subject.

According to some embodiments of the present invention, the disease is selected from the group consisting of an autoimmune disease and a proliferative disease or disorder.

According to some embodiments of the present invention, the compound is:

Compound 10

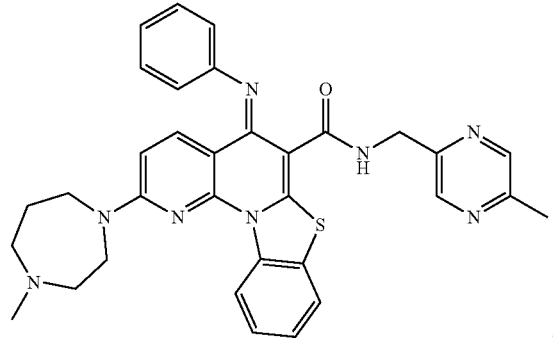

According to some embodiments of the present invention, the at least one gene involved in the RNA polymerase 1 pathway is selected from the group consisting of POLR1D, LRPPRC, RRN3, pre-rRNA and NCL.

According to some embodiments of the present invention, the at least one gene involved in the RNA polymerase 1 pathway is selected from the group consisting of POLR1D, LRPPRC, RRN3 and pre-rRNA.

According to some embodiments of the present invention, the cell is comprised in a biological sample.

According to some embodiments of the present invention, the biological sample is a blood sample.

According to some embodiments of the present invention, the level of expression of the at least one gene is determined using an RNA and/or a protein detection method.

According to some embodiments of the present invention, the detection method is selected from the group consisting of RT-PCR, oligonucleotide microarray, immunoprecipitation, Western blot analysis and FACS.

According to some embodiments of the present invention, the level of expression of the at least one gene is determined by hybridizing the cell or fractions or extracts thereof of the subject with an oligonucleotide which specifically hybridizes with a polynucleotide expressed from the at least one gene and/or by contacting the cell or fractions or extracts thereof of the subject with an antibody which specifically binds a polypeptide expressed from the at least one gene.

A "compound" as described herein refers to a compound having Formula I as described in any one of its respective embodiments, and further to any other compound described in the following description as being contemplated by embodiments of the present invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 6A shows the results of a representative experiment and FIGS. 6B-D show the mean results of 3 independent experiments. Error bars represent mean±SEM.

DESCRIPTION OF SPECIFIC EMBODIMENTS OF THE INVENTION

Figure 1:
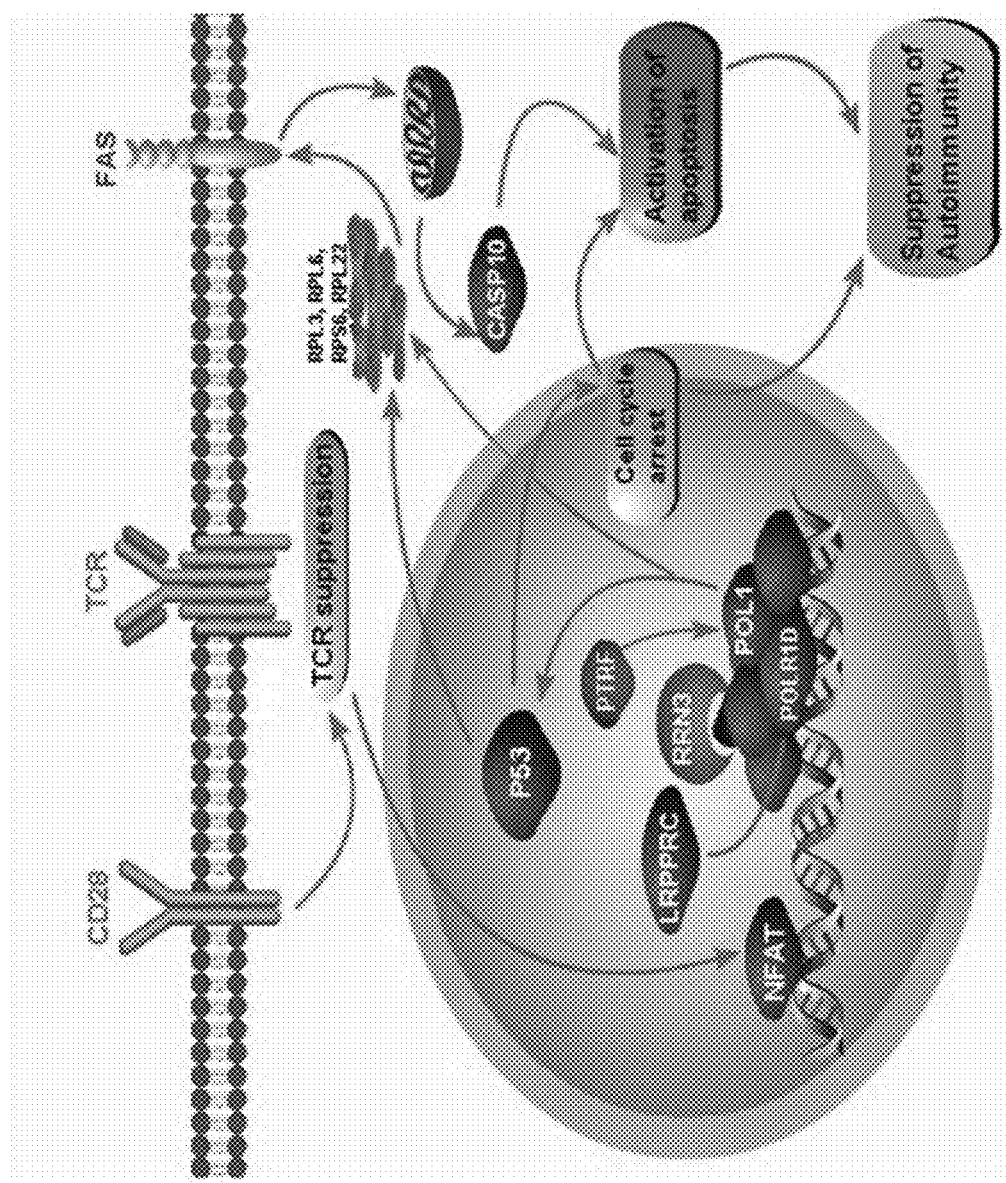
FIG. 1 (Background Art) presents a schematic illustration of POL1 molecular mechanism, showing the effect of POL1 on apoptosis and proliferation.
Figure 2B:
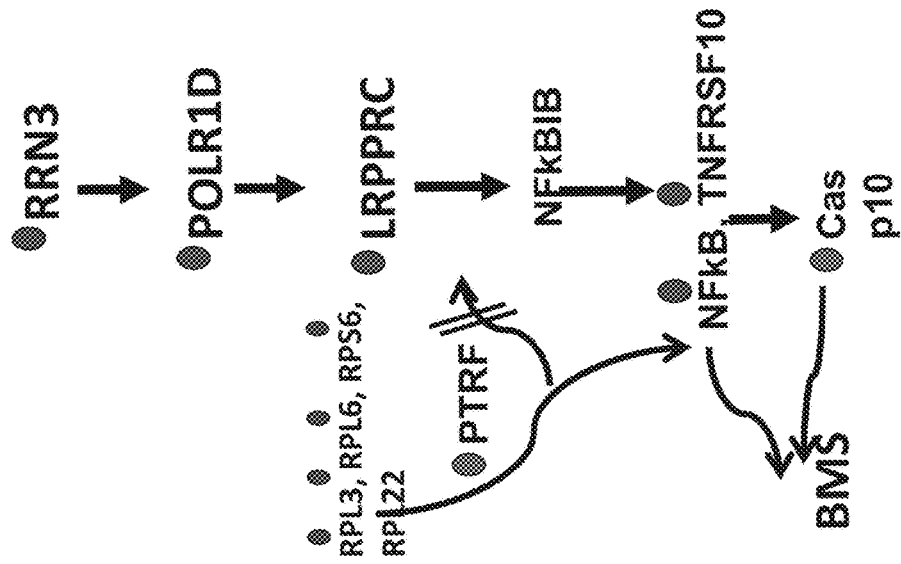
FIGS. 2A-B (Background Art) present schematic illustrations of the effect of POL1 inhibition on multiple sclerosis.
Figure 2A:
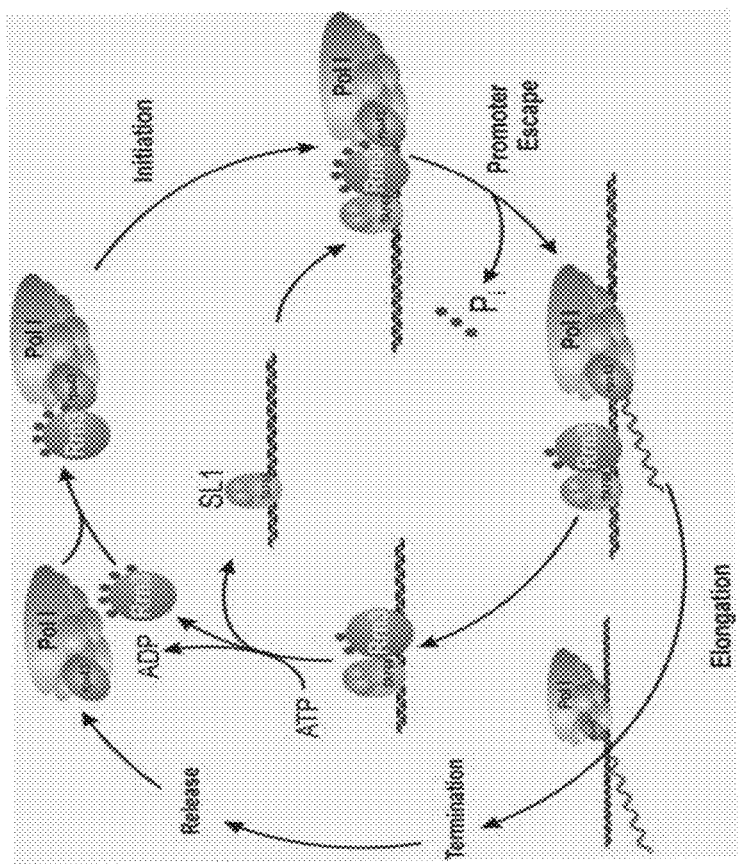

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Embodiments of the present invention stem, at least on part, from previous findings that demonstrated a characterizing gene expression signature in blood sample of RRMS and BMS subjects, whereby the major operating pathway was RNA Polymerase I (POL1). These findings have previously led the present inventors to explore a role for POL1 inhibitors in the treatment, and optionally personalized treatment, of MS.

Led by the fact that the current commercial products for the treatment of autoimmune diseases, and particularly MS, are used intramuscularly, intradermally or as intravenous injections for drug delivery, and lead to uncontrolled plasma peaks, undesired side effects such as flu like reactions and painful local reactions, and thus are accompanied by a high rate of non-compliance to these treatments, the present inventors have explored utilizing inhibitors of POL1-I, which are characterized by oral bioavailability, and improve patients' compliance and benefit patients in the aspect of side effects and pain relief.

As described hereinabove, a POL1 inhibitor, termed CX-5461, and structural analogs thereof, and their use in inhibiting a protein kinase activity and an abbrant cell proliferation, has been previously disclosed. See, for example, U.S. Patent Application Publication No. 2009/0093465.

A family of such POL1 inhibitors, including CX-5461, for use in the treatment of autoimmune diseases has been disclosed in WO 2012/123938.

In a search for POL1 inhibitors that exhibit an improved therapeutic effect, such as, for example, an improved (wider) therapeutic window, the present inventors have devised and successfully prepared and practiced a novel family of POL1 inhibitors, which can be used to treat autoimmune diseases such as multiple sclerosis, proliferative diseases such as cancer, and other medical conditions which are associated with inhibition of POL1 and/or a protein kinase.

According to an aspect of some embodiments of the present invention there are provided compounds which can be collectively represented by Formula I:

Formula I

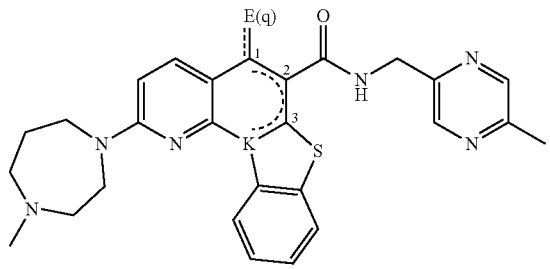

wherein ══ or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or N$^{(+)}$, depending on the nature and valency of E.

Compounds represented by Formula I feature structural similarity of CX5461 (POL1-I, RAM-0, Compound 1; See, for example, FIG. 3A and Table 1 hereinbelow), yet the structure of CX5461 is modified so as to longer include a carbonyl (oxo substituent) at a position equivalent to variable E in Formula I.

The variable E therefore represents a chemical group that, when attached to the carbon marked as carbon "1" in Formula I of the quinazoline ring, forms a chemical moiety other than carbonyl (C═O). E is therefore a chemical group other than oxo (═O).

The chemical group of variable E in Formula I herein can be attached to carbon "1" via a double (unsaturated bond), in which case, q is 1. In such cases, the valency of E is such that is suitable to be attached via an unsaturated bond to carbon "1" (as in the case of, for example, an oxo group ═O that forms a carbonyl C═O group.

In such cases, the electronic structure of the quinazoline ring of CX-5461 is maintained, such that an unsaturated (double) bond also exists between carbons "2" and "3" of the ring, and K is nitrogen in a neutral form (N).

Compound exhibiting such structures are represented by Formula Ia:

Formula Ia

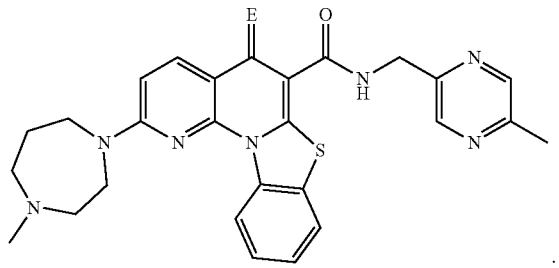

Exemplary chemical groups formed by "E" in such cases include, but are not limited to, thiocarbonyl (C═S), formed of thioxo (═S) group; and imine (e.g., C═N-G, with being as defined hereinafter), formed of e.g., a corresponding ═N-G group.

Alternatively, the group represented by variable E is attached to carbon "1" via a single bond, and q is 2. Thus each E group is attached to the ring via a single bond (saturated bond). In such cases, the electronic structure of the quinazoline ring is maintained, such that an unsaturated (double) bond also exists between carbons "2" and "3" of the ring, and K is nitrogen in a neutral form (N).

Compound exhibiting such structures are represented by Formula Ic:

Formula Ic

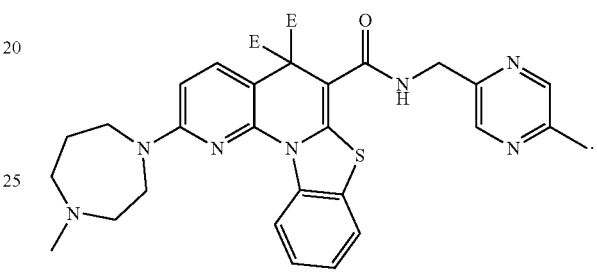

Exemplary chemical groups formed by "E" in such cases include, for example, two halides, preferably two fluorides, as explained hereinafter.

Further alternatively, the group represented by variable E is attached to carbon "1" via a single (saturated) bond, and q is 1. In such cases, the electronic structure of the quinazoline ring undergoes a rearrangement (a tautomerization rearrangement), such that an unsaturated bond exists between carbons "1" and "2" of the ring, and between carbon "3" and K, and K is a positively charged nitrogen N$^+$.

Compound exhibiting such structures are represented by Formula Id:

Formula Id

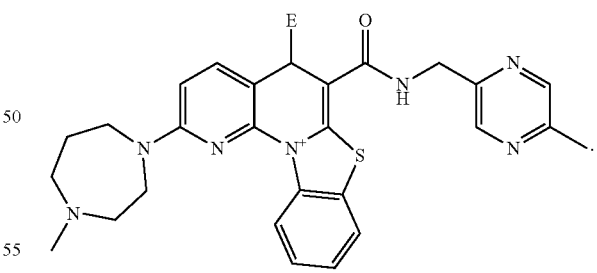

Exemplary chemical groups formed by "E" in such cases include, for example, halides, preferably a chloride.

While the above formulae provide an exemplary illustration for some preferred embodiments of the invention, generally, the chemical moiety formed by variable E is selected so as to modulate the hydrogen bonding capacity of the compound.

As used herein and known in the art, a "hydrogen bond" is a relatively weak bond that forms a type of dipole-dipole attraction which occurs when a hydrogen atom bonded to a strongly electronegative atom exists in the vicinity of another electronegative atom with a lone pair of electrons.

The hydrogen atom in a hydrogen bond is partly shared between two relatively electronegative atoms.

Hydrogen bonds typically have energies of 1-3 kcal mol$^{-1}$ (4-13 kJ mol$^{-1}$), and their bond distances (measured from the hydrogen atom) typically range from 1.5 to 2.6 Å.

A hydrogen-bond donor is the group that includes both the atom to which the hydrogen is more tightly linked and the hydrogen atom itself, whereas a hydrogen-bond acceptor is the atom less tightly linked to the hydrogen atom. The relatively electronegative atom to which the hydrogen atom is covalently bonded pulls electron density away from the hydrogen atom so that it develops a partial positive charge ($\delta^+$). Thus, it can interact with an atom having a partial negative charge ($\delta^-$) through an electrostatic interaction.

Atoms that typically participate in hydrogen bond interactions, both as donors and acceptors, include oxygen, nitrogen and fluorine. These atoms typically form a part of chemical group or moiety such as, for example, carbonyl, carboxylate, amide, hydroxyl, amine, imine, alkylfluoride, F$_2$, and more. However, other electronegative atoms and chemical groups or moieties containing same may participate in hydrogen bonding.

By "modulating the hydrogen bonding capacity" it is meant altering the number and/or strength of hydrogen bonds that the compound may form intramolecularly or intermolecularly, as compared to a carbonyl moiety at the same position.

For example, the group formed by variable E can be, for example, a stronger donor for a hydrogen bond compared to carbonyl, a weaker donor for a hydrogen bond, compared to carbonyl, or be a stronger or a weaker acceptor of a hydrogen bond, compared to carbonyl.

Without being bound by any particular theory, it is assumed that hydrogen bonds may form upon a keto-enol-type tautomerization of the amide group attached to carbon "2" in Formula I, which results in a hydroxyl group (—OH), the latter participates in hydrogen bonding.

The hydroxyl group thus formed is a strong donor of a hydrogen bond and may form a hydrogen bond intermolecularly, with, for example, a hydrogen bond acceptor group of a targeted molecule (e.g., a targeted enzyme such as POL1).

The hydroxyl group may also form hydrogen bond with a carbonyl, when it is the substituent of carbon "1", so as to form a six-membered ring structure, by intramolecular hydrogen bonding.

Alternatively, both a carbonyl at carbon "1" and the hydroxyl group may participate in hydrogen bonds with compatible groups of a targeted biomolecule (e.g., a targeted enzyme).

The modification of substituent E so as to no longer include a carbonyl group may therefore alter the compound's hydrogen bonding capacity by, for example, reducing or increasing the probability of hydrogen bond formation intramolecularly, reducing or increasing the probability of hydrogen bond formation intermolecularly, and/or reducing the strength of an intermolecular or intramolecular hydrogen bond.

In some embodiments, group E is selected such that the chemical moiety formed therewith increases the probability of forming a hydrogen bond intermolecularly and reduces the probability of forming a hydrogen bond intramolecularly (e.g., due to the formation of a group that forms a less stable hydrogen bond with the hydroxyl).

In some embodiments, E is such that the energy of a hydrogen bond formed between a highly electronegative atom therein and hydrogen of the neighboring hydroxyl is lower than the energy of a hydrogen bond formed with the same hydroxyl by carbonyl's oxygen.

In some embodiments, the energy is lower by at least 0.1 kcal/mol, and can be lower by, for example, 0.1, 0.2, 0.3, 0.5, 0.7, 0.8, 1, 1.5, or 2 kcal/mol, including any subranges and intermediates between these values. A person skilled in the art would recognize which groups are encompassed by this definition based on art-recognized tables that define the energies of hydrogen bonds formed with a hydroxyl group.

In some embodiments, the electron density on such an electronegative atom is lower than an electron density of carbonyl's oxygen, that is, the atom is less electronegative than the oxygen in carbonyl.

Without being bound by any particular theory, it is assumed that by interfering with the hydrogen bond capacity of the compound, by e.g., reducing the number (e.g., from 1 to 0) and/or strength of intramolecular bonds, and at the same time increasing the number and/or strength of intermolecular bonds, the compound may better interact with the targeted biomolecule (e.g., POL1), even more electively, and also may have a weaker or no interaction with an unknown off-target protein. It may also further exhibit improved water dissolution kinetics, which facilitates its administration.

In some embodiments, E is an imine group, which can be substituted or non-substituted, as depicted for compounds represented by Formula Ib:

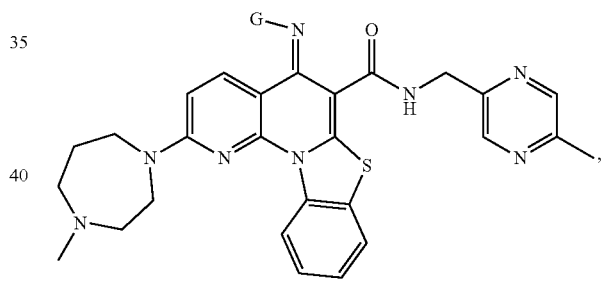

Formula Ib wherein G can be, for example, hydrogen, alkyl, cycloalkyl, aryl, heteroaryl, heteroalicyclic, alkoxy, thioalkoxy, thiol, hydroxyl, aryloxy, or thioaryloxy.

Exemplary such compounds are presented in Table 1 hereinafter as Compounds 3, 4, 5, 6, 7, 8 and 10.

In some embodiments, G is an electron withdrawing group.

Without being bound by any particular theory, it is assumed that electron withdrawing groups reduce the electronegativity of the imine's nitrogen and hence result in a weaker hydrogen bond intramolecular interaction with the presumably formed neighboring hydroxyl described hereinabove, and increase the hydrogen bond intermolecular interactions of the hydroxyl group.

In some embodiments, G is a bulky group as defined herein.

As used herein, the phrase "bulky" describes a group that occupies a large volume. A bulkiness of a group is determined by the number and size of the atoms composing the group, by their arrangement, and by the interactions between the atoms (e.g., bond lengths, repulsive interactions). Typically, lower, linear alkyls are less bulky than branched alkyls; cyclic moieties are more bulky than liner moieties; bicyclic molecules are more bulky than cycloalkyls, etc.

Exemplary suitable electron-withdrawing substituents of an imine include, but are not limited to, substituted or unsubstituted aryls, which, when substituted, preferably are substituted by chemical moieties and at position which strengthen the electron-withdrawing nature of the aryl; heteroaryls in which the heteroatom is positioned such that it exhibits electron-withdrawal with respect to the imine nitrogen; and bulky cycloalkyls substituted by one or more electron withdrawing substituents.

The phrases "electron-withdrawing substituent" or "electron-withdrawing group" are well known to those of skill in the art and are used herein interchangeably as their standard meaning which is a functional group that draws electrons to itself more than a hydrogen atom would if it occupied the same position in the molecule, as described in J. March, Advanced Organic Chemistry, third edition, Pub: John Wiley & Sons, Inc. (1985).

Exemplary electron-withdrawing substituents include, but are not limited to, halogen, pseudohalogen, haloalkyl, haloalicyclic, haloaryl, haloheteroaryl, carbonyl, ester, —C(=O)H and any combination thereof.

Figure 3A:
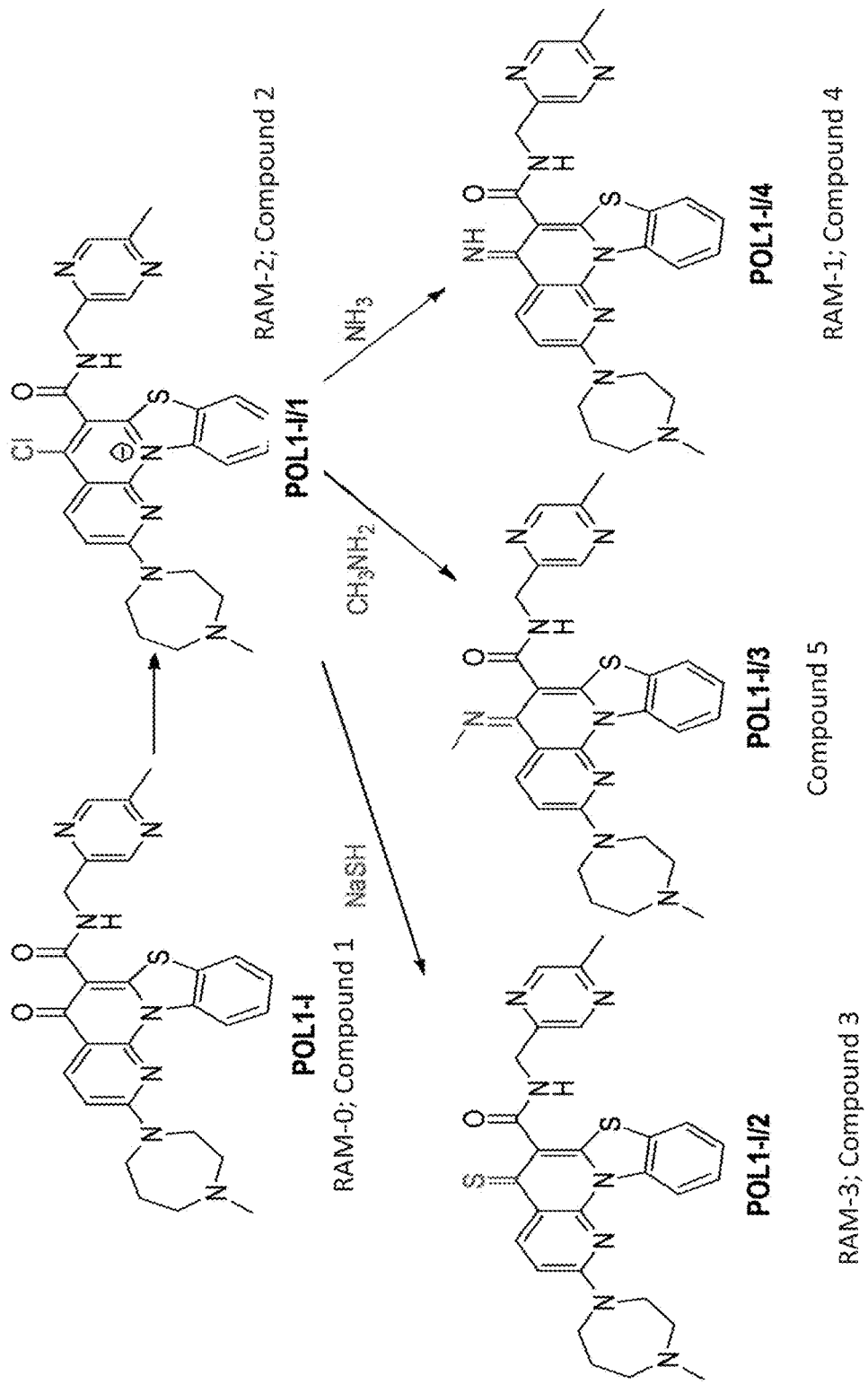
FIGS. 3A-B present chemical structures and synthetic pathways of exemplary compounds according to some embodiments of the present invention.
Figure 3B:
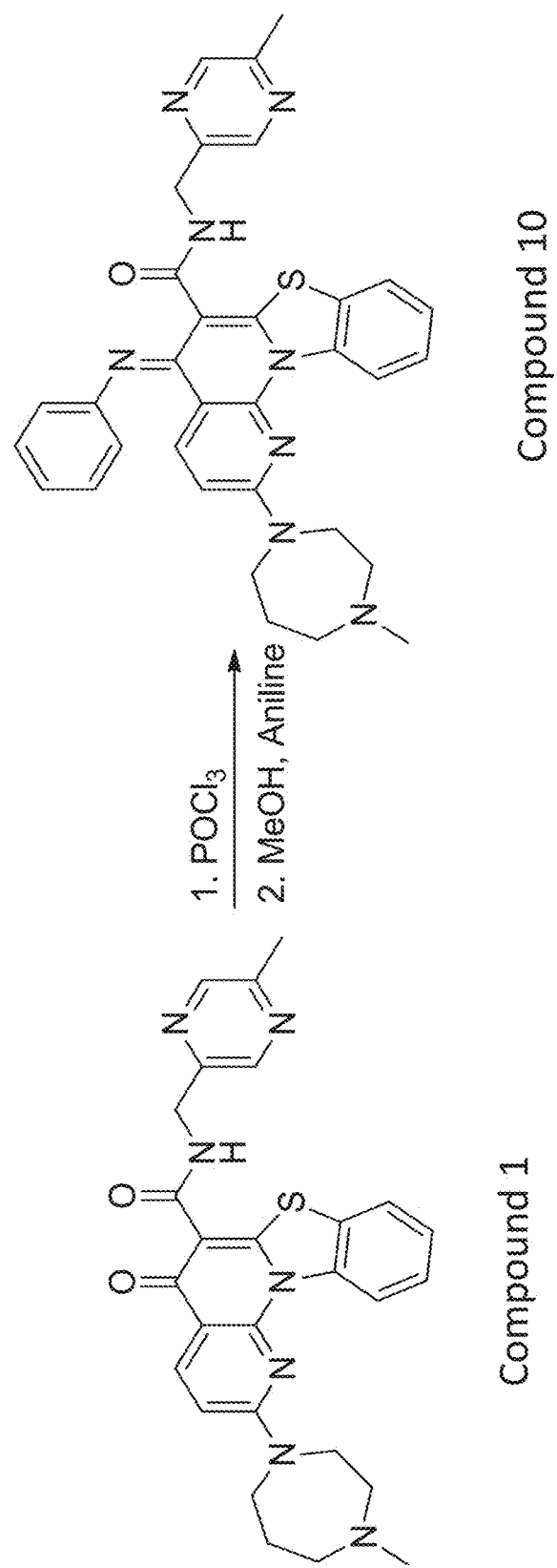

In some embodiments, G is aryl and the compound is Compound 10 (see, Table 1 and FIG. 3B).

It is to be noted that an inclusion of moieties that enhance the hydrophobicity of the compound, such as, for example, aryl, are assumed, without being by bond by any particular theory, to enhance the bioavailability of the compound, compared to compounds featuring a carbonyl moiety at the same position.

Thus, in some embodiments, there are provided compounds having Formula I as described herein, or Formula Ia or Ib, as described herein, which are characterized by higher hydrophobicity compared to corresponding compound in which E is oxo.

The term "hydrophobic" thus often translates into values such as Log P, which describes the partition coefficient of a substance between an aqueous phase (water) and an oily phase (1-octanol).

In some of these embodiments, the group denoted as E in these formulae increases the Log P of the compound, compared to CX-5461, by at least 0.5, or by at least 0.6, 0.7, 0.8, 0.9, 1, 1.2, 1.5, 2, 3, or 4 and any intermediate value therebetween.

According to some embodiments of the present invention, additional compounds, featuring or encompassing the main structural features described herein for compounds represented by Formula I are encompassed by the present embodiments.

According to some of these embodiments, there are provided compounds represented by Formula II:

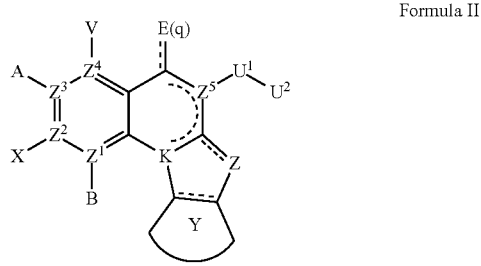

Formula II wherein E, q and K are as defined for any one of the embodiments of Formula I hereinabove;

===== indicates an optionally unsaturated bond;

each of B, X, A or V is absent if $Z^1$, $Z^2$, $Z^3$ and $Z^4$, respectively, is N; and each of B, X, A and V is independently H, halo, azido, —CN, —CF$_3$, —CONR$^1$R$^2$, —NR$^1$R$^2$, —SR$^2$, —OR$^2$, —R$^3$, —W, -L-W, —W$^0$, -L-N(R)—W$^0$, A$^2$ or A$^3$, when each of $Z^1$, $Z^2$, $Z^3$ and $Z^4$, respectively, is C;

Z is O, S, CR$^4_2$, NR$^4$CR$^4$, CR$^4$NR$^4$, CR$^4$, NR$^4$ or N;

each of $Z^1$, $Z^2$, $Z^3$ and $Z^4$ is independently C or N, provided any three N are non-adjacent;

$Z^5$ is C; or $Z^5$ may be N when Z is N;

Y is an optionally substituted 5-6 membered carbocyclic or heterocyclic ring;

$U^1$ is —C(=T)N(R)—, —C(=T)N(R)O—, —C(=T)-, —SO$_2$N(R$^0$)—, —SO$_2$N(R)N(R$^0$)—, —SO$_2$—, or —SO$_3$—, where T is O, S, or NH; or $U^1$ may be a bond when $Z^5$ is N or $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—W$^0$, A$^2$ or A$^3$;

in each —NR$^1$R$^2$, R$^1$ and R$^2$ together with N may form an optionally substituted azacyclic ring, optionally containing an additional heteroatom selected from N, O and S as a ring member;

R$^1$ is H or C1-C6 alkyl, optionally substituted with one or more halogens, or =O;

R$^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R$^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R$^4$ is independently H, or C1-C6 alkyl; or R$^4$ may be —W, -L-W or -L-N(R)—W$^0$;

each R and R$^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl; W is an optionally substituted 4-7 membered azacyclic ring, optionally containing an additional heteroatom selected from N, O and S as a ring member;

W$^0$ is an optionally substituted 3-4 membered carbocyclic ring, or a C1-C6 alkyl group substituted with from 1 to 4 fluorine atoms;

provided one of $U^2$, V, A, X and B is a secondary amine A$^2$ or a tertiary amine A$^3$, wherein the secondary amine A$^2$ is —NH—W$^0$, and the tertiary amine A$^3$ is a fully saturated and optionally substituted six-membered or seven-membered azacyclic ring optionally containing an additional heteroatom selected from N, O or S as a ring member, or the tertiary amine A$^3$ is a partially unsaturated or aromatic optionally substituted five-membered azacyclic ring, optionally containing an additional heteroatom selected from N, O or S as a ring member.

According to some embodiments of the invention, $Z^1$ is N, and each of $Z^2$, $Z^3$ and $Z^4$ is C.

According to some embodiments of the invention, U is —W or -L-W, where W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

According to some embodiments of the invention, $U^2$ is $-L-N(R)-W^0$.

According to some embodiments of the invention, Y is an optionally substituted phenyl ring.

According to some embodiments of the invention, the compound with the proviso that when $Z^1$ is N, $Z^2$ and $Z^4$ are C, $Z^5$ is C, $U^1$ is $-C(O)NH-$, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to any one of the embodiments of the invention, compounds having a general structure represented by Formula III, are also contemplated:

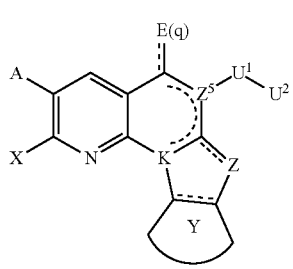

Formula III wherein E, q and K are as defined for any one of the embodiments of Formula I hereinabove;

and wherein:

----- indicates an optionally unsaturated bond;

each of A and X is independently H, halo, azido, $-CN$, $-CF_3$, $-CONR^1R^2$, $-NR^1R^2$, $-SR^2$, $-OR^2$, $-R^3$, $-W$, -L-W, $-W^0$, -L-N(R)$-W^0$, $A^2$ or $A^3$;

Z is O, S, $CR^4_2$, $NR^4CR^4$, $CR^4NR^4$ or $NR^4$;

Y is an optionally substituted 5-6 membered carbocyclic or heterocyclic ring;

$U^1$ is $-C(=T)N(R)-$, $-C(=T)N(R)O-$, $-C(=T)-$, $-SO_2N(R^0)-$, $-SO_2N(R)N(R^0)-$, $-SO_2-$, or $-SO_3-$, where T is O, S, or NH; or $U^1$ may be a bond when U2 is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, $=O$, or an optionally substituted 3-7 membered carbocyclic or heterocyclic ring; or $U^2$ is $-W$, -L-W, -L-N(R)$-W^0$, $A^2$ or $A^3$;

in each $-NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or $=O$;

R2 is H, or C1-C10 alkyl, C1-C10 heteroalkyl, C2-C10 alkenyl, or C2-C10 heteroalkenyl, each of which may be optionally substituted with one or more halogens, $=O$, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, $=O$, or an optionally substituted 3-6 membered carbocyclic or heterocyclic ring;

each $R^4$ is independently H, or C1-C6 alkyl; or $R^4$ may be $-W$, -L-W or -L-N(R)$-W0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo ($=O$), or C1-C6 alkyl; W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided that one of $U^2$, A, and X is a secondary amine $A^2$ or a tertiary amine $A^3$, wherein the secondary amine $A^2$ is $-NH-W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According to some embodiments of the invention, with the proviso that when $U^1$ is $-C(O)NH-$, $U^2$ is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to some embodiments of the invention, at least one of A and X is a tertiary amine $A^3$.

According to some embodiments of the invention, $A^3$ is selected from the group consisting of imidazole, imidazoline, pyrroline, piperidine, piperazine, morpholine, thiomorpholine and homopiperazine.

According to some embodiments of the invention, $U^1$ is a $-C(=T)N(R)-$, T is O, and $U^2$ is -L-W or -L-N(R)$-W^0$.

According any one of the embodiments of the invention, compounds having a general structure represented by Formula IV, are also contemplated:

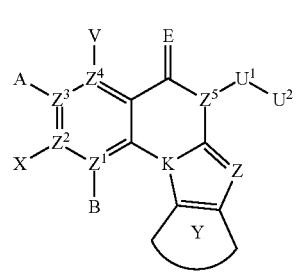

Formula IV wherein E is as defined for any one of the respective embodiments of Formula I, and K is N; and wherein ===== indicates an optionally unsaturated bond; and each of B, X, A or V is absent if $Z^1$, $Z^2$, $Z^3$ and $Z^4$, respectively, is N; and each of B, X, A and V is independently H, halo, azido, $-CN$, $-CF_3$, $-CONR^1R^2$, $-NR^1R^2$, $-SR^2$, $-OR^2$, —R³, —W, -L-W, —W⁰, -L-N(R)—W⁰, A² or A³, when each of Z¹, Z², Z³ and Z⁴, respectively, is C;

each of Z¹, Z², Z³ and Z⁴ is independently C or N, provided any three N are non-adjacent;

Y is an optionally substituted 5-6 membered carbocyclic or heterocyclic ring; U¹ is —C(=T)N(R)—, —C(=T)N(R)O—, —C(=T)-, —SO₂N(R⁰)—, —SO₂N(R)N(R⁰)—, —SO₂—, or —SO₃—, where T is O, S, or NH; or U¹ may be a bond when Z⁵ is N or U² is H;

U² is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or U² is —W, -L-W, -L-N(R)—W⁰, A² or A³;

in each —NR¹R², R¹ and R² together with N may form an optionally substituted azacyclic ring, optionally containing an additional heteroatom selected from N, O and S as a ring member;

R¹ is H or C1-C6 alkyl, optionally substituted with one or more halogens, or =O;

R² is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R⁴ may be —W, -L-W or -L-N(R)—W⁰;

each R and R⁰ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

W⁰ is an optionally substituted 3-4 membered carbocyclic ring, or a C1-C6 alkyl group substituted with from 1 to 4 fluorine atoms;

provided that one of U², V, A, X and B is a secondary amine A² or a tertiary amine A3, wherein the secondary amine A² is —NH—W⁰, and the tertiary amine A³ is a fully saturated and optionally substituted six-membered or seven-membered azacyclic ring optionally containing an additional heteroatom selected from N, O or S as a ring member, or the tertiary amine A³ is a partially unsaturated or aromatic optionally substituted five-membered azacyclic ring, optionally containing an additional heteroatom selected from N, O or S as a ring member.

According to any one of the embodiments of the invention, compounds having a general structure represented by Formula V, are also contemplated:

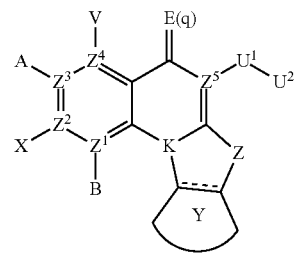

Formula V wherein E, q and K are as defined for any one of the embodiments of Formula I hereinabove;

and wherein:

═ indicates an optionally unsaturated bond;

A and V independently are H, halo, azido, —CN, —CF₃, —CONR¹R², —NR¹R², —SR², —OR², —R³, —W, -L-W, —W⁰, -L-N(R)—W⁰, A² or A³;

Z is O, S, CR⁴₂, NR⁴CR⁴, CR⁴NR⁴ or NR⁴;

Y is an optionally substituted 5-6 membered carbocyclic or heterocyclic ring;

U¹ is —C(=T)N(R)—, —C(=T)N(R)O—, —C(=T)-, —SO₂N(R⁰)—, —SO₂N(R)N(R⁰)—, —SO₂—, or —SO₃—, where T is O, S, or NH; or U¹ may be a bond when U2 is H;

U² is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or U² is —W, -L-W or -L-N(R)—W⁰, A² or A³;

in each —NR¹R², R¹ and R² together with N may form an optionally substituted azacyclic ring, optionally containing an additional heteroatom selected from N, O and S as a ring member;

R¹ is H or C1-C6 alkyl, optionally substituted with one or more halogens, or =O;

R² is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

R³ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each R⁴ is independently H, or C1-C6 alkyl; or R4 may be —W, -L-W or -L-N(R)—W⁰;

each R and R⁰ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

W⁰ is an optionally substituted 3-4 membered carbocyclic ring, or a C1-C6 alkyl group substituted with from 1 to 4 fluorine atoms;

provided one of $U^2$, A, and V is a secondary amine $A^2$ or a tertiary amine $A^3$, wherein the secondary amine $A^2$ is —NH—WO, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According any one of the embodiments of the invention, compounds having a general structure represented by Formula VI, are also contemplated:

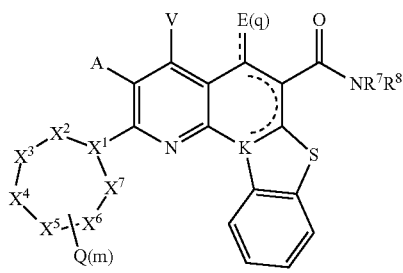

Formula VI wherein E, q and K are as defined for any one of the embodiments of Formula I hereinabove;

and wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$ and $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

R is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, $X^1$ is CH and two of $X^2$, $X^3$, $X^4$, $X^5$, $X^6$ and $X^7$ are $NR^4$.

According to some embodiments of the invention, wherein $X^1$ is CH and one of $X^2$, $X^3$, $X^4$, $X^5$, $X^6$ and $X^7$ are $NR^4$.

According to some embodiments of the invention, $X^1$ is CH and none of $X^2$, $X^3$, $X^4$, $X^5$, $X^6$ and $X^7$ are $NR^4$.

According to some embodiments of the invention, wherein $X^1$ is N and none of $X^2$, $X^3$, $X^4$, $X^5$, $X^6$ and $X^7$ are $NR^4$.

According to some embodiments of the invention, $X^1$ is N and one of $X^4$ or $X^5$ is $NR^4$.

According any one of the embodiments of the invention, compounds having a general structure represented by Formula VIII, are also contemplated:

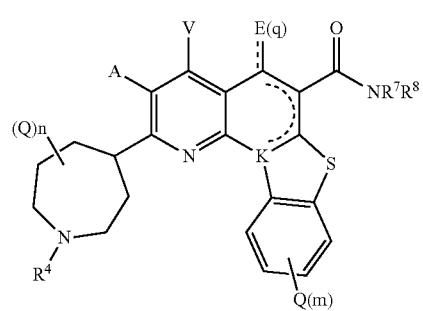

Formula (VIII)

wherein E, q and K are as defined for any one of the embodiments of Formula I hereinabove;

and wherein:

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

$R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;
n is 0, 1, 2, 3, 4 or 5;
p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, $R^7$ is H and $R^8$ is a $C_{1-4}$ alkyl substituted with an optionally substituted aromatic heterocyclic ring.

According to some embodiments of the invention, the optionally substituted aromatic heterocyclic ring is selected from pyridine, pyrimidine, pyrazine, imidazole, pyrrolidine, and thiazole.

According to some embodiments of the invention, $R^7$ and $R^8$ together with N in —$NR^7R^8$ form an optionally substituted azacyclic ring selected from the group consisting of morpholine, thiomorpholine, piperidine or piperazine ring.

According to any one of the embodiments of the invention, compounds having a general structure represented by Formula VII are also contemplated:

Formula VII

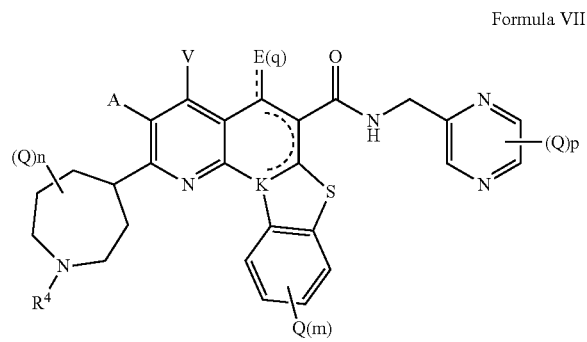

wherein E, q and K are as defined for any one of the embodiments of Formula I hereinabove;

and wherein:

A and V independently are H, halo, azido, —CN, —$CF_3$, —CONR1R2, —NR1R2, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O;

R2 is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R is independently H or C1-C6 alkyl;
m is 0, 1, 2, 3 or 4;
n is 0, 1, 2, 3, 4 or 5;
p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, A and V are independently H or halo.

According to some embodiments of the invention, $R^4$ is H or C1-4 alkyl.

According to some embodiments of the invention, m and n are each 0.

According to some embodiments of the invention, p is 0 or 1.

Methods of synthesizing the compounds of some embodiments of the invention are described in Example 1 in the Examples section the follows.

According to some embodiments, compounds represented by Formula I as described herein, or by any one of Formulae II-VIII are prepared by converting a compound encompassed by these formulae into a corresponding chloride such as depicted for Compound 2 herein (see, Table 1) and the chloride is thereafter reacted with a suitable precursor (e.g., an amine) to form the desired compound (e.g., a corresponding imine).

For use as pharmaceutical agents, the compound of some embodiments of the invention is sterile.

According to some embodiments of the invention, the compound is purified using known methods.

According to some embodiments of the invention, the compound has 95-99.9% purity.

For any of the embodiments described herein, the compound may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound. A prodrug is typically designed to facilitate administration, e.g., by enhancing absorption. A prodrug may comprise, for example, the active compound modified with ester groups, for example, wherein one or more hydroxy groups of the active compound is modified by an acyl (e.g., acetyl) group to form an ester group, and/or wherein one or more carboxylic acid of the active compound is modified by an alkyl (e.g., ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, except in embodiments wherein a specific stereoisomer is explicitly required, as well as any isomorph thereof.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

A "hydroxy" group refers to an —OH group.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A disulfide bond describes a —S—S— bond.

A "carbonyl" group refers to a —C(=O)—R' group, where R' is defined as hereinabove, or where R' and C form a part of a cyclic moiety such as cycloalkyl, aryl, heteroaryl and heteroalicyclic, as defined herein.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "thioxo" group refers to a =S group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

A "urea" group refers to an —N(R')—C(=O)—NR"R'" "group, where each of R' and R" is as defined herein, and R'" is defined as R' and R" are defined herein.

A "nitro" group refers to an —NO$_2$ group.

A "cyano" group refers to a —C≡N group.

The term "hydrazine" describes a —N(R')—N(R")R'" group, with each of R', R" and R'" as defined hereinabove.

Treatment of Autoimmune Diseases:

According to an aspect of some embodiments of the present invention any one of the compounds as described herein is for use in the treatment of an autoimmune disease in a subject in need thereof.

According to an aspect of some embodiments of the present invention any one of the compounds as described herein is for use in the manufacture of a medicament for treating an autoimmune disease in a subject in need thereof.

According to an aspect of some embodiments of the present invention there is provided a method of treating an autoimmune disease, which is effected by administering to the subject a therapeutically effective amount of any one of the compounds as described herein.

As used in the context of this aspect of the present embodiments, the phrase "treating" refers to inhibiting or arresting the development of the autoimmune disease (e.g., multiple sclerosis) and/or causing the reduction, remission, or regression of the autoimmune disease and/or optimally curing the autoimmune disease. Those of skill in the art will understand that various methodologies and assays can be used to assess the development of autoimmune disease, and similarly, various methodologies and assays may be used to assess the reduction, remission or regression of the autoimmune disease.

As used herein, the term "subject" includes mammals, preferably human beings at any age which suffer from the pathology (the autoimmune disease) or which have been diagnosed as being afflicted by the pathology.

According to some embodiments of the invention, the term "subject" encompasses individuals who are at risk to develop the pathology or are suspected of having the pathology. As used herein the phrase "autoimmune disease" refers to any disease caused by an autoimmune response, i.e., an immune response directed to a substance in the body of the subject.

It should be noted that since autoimmunity can affect any organ or tissue of the subject, e.g., the brain, skin, kidney, lungs, liver, heart, or thyroid of the subject, the clinical expression of the disease depends upon the site affected.

Following is a non-limiting list of autoimmune diseases or disorders (including autoimmune-related diseases or disorders) which can be treated by the compound of some embodiments of the invention: Acute Disseminated Encephalomyelitis (ADEM); Acute necrotizing hemorrhagic leukoencephalitis; Addison's disease; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune hepatitis; Autoimmune hyperlipidemia; Autoimmune immunodeficiency; Autoimmune inner ear disease (AIED); Autoimmune myocarditis; Autoimmune pancreatitis; Autoimmune retinopathy; Autoimmune thrombocytopenic purpura (ATP); Autoimmune thyroid disease; Autoimmune urticaria; Axonal & neuronal neuropathies; Balo disease; Behcet's disease; Bullous pemphigoid; Cardiomyopathy; Castleman disease; Celiac disease; Chagas disease; Chronic inflammatory demyelinating polyneuropathy (CIDP); Chronic recurrent multifocal ostomyelitis (CRMO); Churg-Strauss syndrome; Cicatricial pemphigoid/benign mucosal pemphigoid; Crohn's disease; Cogans syndrome; Cold agglutinin disease; Congenital heart block; Coxsackie myocarditis; CREST disease; Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic fasciitis; Erythema nodosum; Experimental allergic encephalomyelitis; Evans syndrome; Fibrosing alveolitis; Giant cell arteritis (temporal arteritis); Glomerulonephritis; Goodpasture's syndrome; Granulomatosis with Polyangiitis (GPA) see Wegener's; Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Idiopathic thrombocytopenic purpura (ITP); IgA nephropathy; IgG4-related sclerosing disease; Immunoregulatory lipoproteins; Inclusion body myositis; Insulin-dependent diabetes (type 1); Interstitial cystitis; Juvenile arthritis; Juvenile diabetes; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Ocular cicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Peripheral neuropathy; Perivenous encephalomyelitis; Pernicious anemia; POEMS syndrome; Polyarteritis nodosa; Type I, II, & III autoimmune polyglandular syndromes; Polymyalgia rheumatica; Polymyositis; Postmyocardial infarction syndrome; Postpericardiotomy syndrome; Progesterone dermatitis; Primary biliary cirrhosis; Primary sclerosing cholangitis; Psoriasis; Psoriatic arthritis; Idiopathic pulmonary fibrosis; Pyoderma gangrenosum; Pure red cell aplasia; Raynauds phenomenon; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sjogren's syndrome; Sperm & testicular autoimmunity; Stiff person syndrome; Subacute bacterial endocarditis (SBE); Susac's syndrome; Sympathetic ophthalmia; Takayasu's arteritis; Temporal arteritis/Giant cell arteritis; Thrombocytopenic purpura (TTP); Tolosa-Hunt syndrome; Transverse myelitis; Ulcerative colitis; Undifferentiated connective tissue disease (UCTD); Uveitis; Vasculitis; Vesiculobullous dermatosis; Vitiligo; Wegener's granulomatosis (now termed Granulomatosis with Polyangiitis (GPA).

According to some embodiments of the invention, the autoimmune disease is multiple sclerosis.

According to some embodiments of the invention, the subject is diagnosed with multiple sclerosis.

The diagnosis of "multiple sclerosis" can be made when a subject has experienced at least one neurological attack affecting the central nervous system (CNS) accompanied by demyelinating lesions within the brain or spinal cord, which may have, but not necessarily confirmed by magnetic resonance imaging (MRI). The neurological attack can involve acute or sub-acute neurological symptomotology (attack) manifested by various clinical presentations like unilateral loss of vision, vertigo, ataxia, incoordination, gait difficulties, sensory impairment characterized by paresthesia, dysesthesia, sensory loss, urinary disturbances until incontinence, diplopia, dysarthria, various degrees of motor weakness until paralysis, cognitive decline either as a monosymptomatic or in combination. The symptoms usually remain for several days to few weeks, and then partially or completely resolve.

Further details on the diagnosis of multiple sclerosis according to 2010 McDonald Criteria for Diagnosis of MS are provided in Polman C H., et al., 2011 ("Diagnostic criteria for multiple sclerosis: 2010 revisions to the McDonald criteria" Annals of Neurology, vol. 69 (2): pages 292-302) which is fully incorporated herein by reference in its entirety.

For example, the diagnosis of multiple sclerosis can be made upon (I): Clinical presentation of ≥2 attacks, with objective clinical evidence of ≥2 lesions or objective clinical evidence of 1 lesion with reasonable historical evidence of a prior attack; (II): Clinical presentation of ≥2 attacks, with objective clinical evidence of 1 lesion, additional data have to include dissemination in space, demonstrated by: ≥1 T2 lesion in at least 2 of 4 MS-typical regions of the CNS (periventricular, juxtacortical, infratentorial, or spinal cord); (III): Clinical presentation of 1 attack, with objective clinical evidence of ≥2 lesions, additional data have to include dissemination in time, demonstrated by: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (IV): Clinical presentation of 1 attack, additional data have to include dissemination in space and time, demonstrated by: For DIS: ≥1 T2 lesion in at least 2 of 4 MS-typical regions of the CNS (periventricular, juxtacortical, infratentorial, or spinal cord) and for DIT: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (V): Clinical presentation of Insidious neurological progression suggestive of MS (PPMS), additional data have to include 1 year of disease progression (retrospectively or prospectively determined) plus 2 of 3 of the following criteria: 1. Evidence for DIS in the brain based on 1 T2 lesions in the MS-characteristic (periventricular, juxtacortical, or infratentorial) regions 2. Evidence for DIS in the spinal cord based on T2 lesions in the cord 3. Positive CSF (isoelectric focusing evidence of oligoclonal bands and/or elevated IgG index).

According to some embodiments of the invention, the subject has relapsing-remitting multiple sclerosis (RRMS).

According to some embodiments of the invention, the subject has a primary progressive multiple sclerosis (PPMS).

According to some embodiments of the invention, the subject has a secondary progressive MS (SPMS).

According to some embodiments of the invention, the subject has benign multiple sclerosis (BMS).

According to some embodiments of the invention, the subject has a progressive-relapsing course of MS.

According to some embodiments of the invention, treating the subject refers to changing the disease course of the subject from a typical RRMS course to a BMS course.

According to some embodiments of the invention, treating the subject refers to suppressing the activity of typical RRMS course.

According to some embodiments of the invention, administering the compound is performed after diagnosing the subject as having the autoimmune disease.

According to some embodiments of the invention, the autoimmune disease is multiple sclerosis and the diagnosis comprises appearance of brain lesions characteristics of the multiple sclerosis.

According to some embodiments of the invention, the compound prevents the appearance of additional neurological attack(s) and/or brain lesion(s) as compared to the number of neurological attack(s) and/or brain lesion(s) present at time of diagnosing multiple sclerosis.

According to an aspect of some embodiments of the present invention the compounds as described herein, in any one of the embodiments thereof are useful in inhibiting an activity of RNA Polymerase I, or in modulating a RNA Polymerase I pathway. These compounds are therefore useful in the treatment of any disease or disorder that is associated the RNA Polymerase I or which is treatable by modulating (e.g., inhibiting), a RNA Polymerase I activity or pathway, as is described in further detail hereinafter.

Such diseases and disorders include, in addition to autoimmune diseases as described herein, also proliferative diseases or disorders, as described herein, and any other medical conditions which would be recognized by any person skilled in the art.

Treatment of Proliferative Diseases or Disorders:

According to some embodiments of the invention, any of the compounds described herein are useful in treating a proliferative disease or disorder and/or in modulating (e.g., inhibiting) a protein kinase activity.

As used herein the phrase "proliferative disease" refers to diseases manifested by abnormal cell proliferation, and includes, for example, benign tumors, pre-malignant tumors, and malignant tumors, such as cancer.

As used herein the terms "cancer" and "malignant tumor" are interchangeably used. The term refers to a malignant growth or tumor caused by abnormal and uncontrolled cell proliferation (cell division). Exemplary cancers include, without limitation, cancers of the colorectum, breast, lung, liver, pancreas, lymph node, colon, prostate, brain, head and neck, skin, liver, kidney, blood and heart (e.g., leukemia, lymphoma, carcinoma).

The terms "treat" and "treating" and "treatment" as used herein refer to ameliorating, alleviating, lessening, and removing symptoms of a disease or condition. In some embodiments, "treating" is effected by a compound as described herein, which, when administered to a subject in need thereof, exhibit a biological effect such as apoptosis of certain cells (e.g., cancer cells), reduction of proliferation of certain cells, or lead to ameliorating, alleviating, lessening, or removing symptoms of a disease or condition. "The terms "treat" and "treating" and "treatment" as used herein in some embodiments, also can refer to reducing or stopping a cell proliferation rate (e.g., slowing or halting tumor growth) or reducing the number of proliferating cancer cells (e.g., removing part or all of a tumor). The terms "treat" and "treating" and "treatment" as used herein also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Also provided herein are methods and uses of any one of the compounds described herein, for modulating the activity of a protein kinase, which are effected by contacting a system comprising the protein kinase with a compound as described herein in an amount effective for modulating (e.g., inhibiting) the activity of the kinase. The system in such embodiments can be a cell-free system or a system comprising cells. Also provided are methods and uses utilizing the compounds as described herein for reducing cell proliferation, and optionally inducing apoptosis, which are effected by contacting cells with a compound as described herein in an amount effective to reduce proliferation of the cells. The cells in such embodiments can be in a cell line, in a tissue or in a subject (e.g., a research animal or human). Protein kinases are a family of enzyme which catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods and uses which are effected by contacting a system comprising a protein kinase with a compound as described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). Systems in such embodiments can be a cell-free system or a system comprising cells (e.g., in vitro).

In some embodiments, the protein kinase is a serine-threonine protein kinase or a tyrosine protein kinase. In some embodiments, the protein kinase is a protein kinase fragment having compound-binding activity.

In some embodiments, the protein kinase is, or contains a subunit (e.g., catalytic subunit, SH2 domain, SH3 domain) of, CK2, Pim subfamily protein kinase (e.g., PIM1, PIM2, PIM3) or Flt subfamily protein kinase (e.g, FLT1, FLT3, FLT4).

In some embodiments the protein kinase is a recombinant protein. The protein kinase can be from any source, such as cells from a mammal, ape or human, for example. In some embodiments, the protein kinase is a human protein kinase.

In some embodiments, any of the compounds described herein is also useful in the treatment of a condition related to inflammation or pain. Conditions associated with inflammation and pain include without limitation, acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjogren's syndrome, spastic colon, systemic candidiasis, tendonitis, urinary tract infections, vaginitis, inflammatory cancer (e.g., inflammatory breast cancer) and the like.

In some embodiments, any of the compounds described herein is also useful for modulating angiogenesis in a subject, and for treating a condition associated with aberrant angiogenesis in a subject.

Pharmaceutical Compositions:

In any one of the methods and uses described herein, and any one of the embodiments thereof, a compound as described herein can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound of some embodiments of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to some embodiments of the invention, the compound is administered by oral administration.

Conventional approaches for drug delivery to the central nervous system (CNS) include: neurosurgical strategies (e.g., intracerebral injection or intracerebroventricular infusion); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the compound of some embodiments of the invention) effective to prevent, alleviate or ameliorate symptoms of a disorder (e.g., an autoimmune disease such as multiple sclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue or blood levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The doses shown herein with respect to the mouse animal model can be converted for the treatment other species such as human and other animals diagnosed with the autoimmune disease. Conversion Table approved by the FDA is shown in Reagan-Shaw S., et al., FASEB J. 22:659-661 (2007).

The human equivalent dose is calculated as follows: HED (mg/kg)=Animal dose (mg/kg) multiplied by (Animal $K_m$/human $K_m$).

According to some embodiments of the invention, the compound is provided at an amount equivalent to a range of from about 3-30 mg/kg/day in mice, including any intermediate subranges and values therebetween.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is detailed herein.

Monitoring Treatment Efficacy:

As shown in Examples 2 and 3 in the Examples section which follows, treatment with the compound of some embodiments of the invention (e.g. Compound 10) suppresses transcription of genes of the RNA polymerase pathway e.g. pre-rRNA. Thus, the teachings of the invention can be also used to determine efficiency of the compound of some embodiments of the invention in treating a disease, e.g. autoimmune disease (e.g., multiple sclerosis) and/or a proliferative disease, by determining the effect of the compound on the expression level of at least one gene of the RNA polymerase I pathway. This can be used to develop a tailored treatment of a disease by monitoring drug efficacy. This system is based on measuring the level of genes of the RNA polymerase I pathway during treatment with the compound and the ability to perform an ongoing fine-tuning drug efficacy assessment.

Thus, according to an aspect of some embodiments of the invention, there is provided a method of monitoring treatment efficiency of the compound of some embodiments of the invention, the method comprising:

(a) treating the subject with the compound according to the method of some embodiments of the invention, and (b) comparing a level of expression of least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring treatment efficiency of the subject having disease or disorder as described herein.

As used herein, the phrase "level of expression" refers to the degree of gene expression and/or gene product activity in a specific cell. For example, up-regulation or down-regulation of various genes can affect the level of the gene product (i.e., RNA and/or protein) in a specific cell.

It should be noted that the level of expression can be determined in arbitrary absolute units, or in normalized units (relative to known expression levels of a control reference). For example, when using DNA chips, the expression levels are normalized according to the chips' internal controls or by using quantile normalization such as RMA.

As used herein the phrase "a cell of the subject" refers to at least one cell (e.g., an isolated cell), cell culture, cell content and/or cell secreted content which contains RNA and/or proteins of the subject. Examples include a blood cell, a cell obtained from any tissue biopsy [e.g., cerebrospinal fluid, (CSF), brain biopsy], a bone marrow cell, body fluids such as blood, plasma, serum, saliva, spinal fluid, lymph fluid, the external sections of the skin, respiratory, intestinal, and genitourinary tracts, tears, saliva, sputum and milk. According to an embodiment of the invention, the cell is a blood cell (e.g., white blood cells, macrophages, B- and T-lymphocytes, monocytes, neutrophiles, eosinophiles, and basophiles) which can be obtained using a syringe needle from a vein of the subject. It should be noted that the cell may be isolated from the subject (e.g., for in vitro detection) or may optionally comprise a cell that has not been physically removed from the subject (e.g., in vivo detection). According to specific embodiments the cell is comprised in a biological sample (e.g. a blood sample). Thus, according to a specific embodiment, the method further comprises obtaining the biological sample from the subject. It should be noted that a specific cell type may be further isolated from the biological sample directly obtained from the subject e.g. a white blood can be isolated from a blood sample. Methods of isolating specific cell types are well known in the art including, but not limited to, density gradient centrifugation, flow cytometry and magnetic beads separation.

According to some embodiments of the invention, the white blood cell comprises peripheral blood mononuclear cells (PBMC). The phrase, "peripheral blood mononuclear cells (PBMCs)" as used herein, refers to a mixture of monocytes and lymphocytes. Several methods for isolating white blood cells are known in the art. For example, PBMCs can be isolated from whole blood samples using density gradient centrifugation procedures. Typically, anticoagulated whole blood is layered over the separating medium. At the end of the centrifugation step, the following layers are visually observed from top to bottom: plasma/platelets, PBMCs, separating medium and erythrocytes/granulocytes. The PBMC layer is then removed and washed to remove contaminants (e.g., red blood cells) prior to determining the expression level of the polynucleotide(s) therein.

According to some embodiments of the invention, the level of expression of the gene(s) of the invention is determined using an RNA and/or a protein detection method.

According to some embodiments of the invention, the RNA or protein molecules are extracted from the cell of the subject. Thus, according to specific embodiments, the method further comprises extracting a RNA or a protein from the cell prior to the comparing.

Methods of extracting RNA or protein molecules from cells of a subject are well known in the art. The extracted RNA can be further processed to a cDNA. Methods of and commercially available kits for converting RNA to cDNA are well known in the art and include e.g. the use of the enzyme reverse transcriptase. Once obtained, the RNA, cDNA or protein molecules can be characterized for the expression and/or activity level of various RNA, cDNA and/or protein molecules using methods known in the arts.

According to specific embodiment, the expression of the POL1 pathway gene can be determined at the nucleic acid level using RNA or DNA detection methods.

Thus, according to some embodiments of the invention, detection of the expression level of the RNA of the POL1 pathway is performed by contacting the biological sample, the cell, or fractions or extracts thereof with a probe (e.g. oligonucleotide probe or primer) which specifically hybridizes to a polynucleotide expressed from the gene of the POL1 pathway (e.g., including any alternative spliced form which is known in the art). Such a probe can be at any size, such as a short polynucleotide (e.g., of 15-200 bases), an intermediate polynucleotide of 100-2000 bases and a long polynucleotide of more than 2000 bases.

The probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the RNA transcript of the gene involved in the POL1 pathway. According to specific embodiments, the probe is bound to a detectable moiety.

Oligonucleotides designed according to the teachings of the present invention can be generated according to any oligonucleotide synthesis method known in the art such as enzymatic synthesis or solid phase synthesis.

According to specific embodiments, the contacting is effected under conditions which allow the formation of a complex comprising mRNA or cDNA of a gene involved in the POL1 pathway present in the cell and the probe. The complex can be formed at a variety of temperatures, salt concentration and pH values which may vary depending on the method and the biological sample used and those of skills in the art are capable of adjusting the conditions suitable for the formation of each nucleotide/probe complex.

Thus, according to an aspect of the present invention there is provided a composition of matter comprising a biological sample of a subject, and a probe capable of detecting a polynucleotide expressed from a gene involved in the POL1 pathway.

Non-limiting examples of methods of detecting RNA and/or cDNA molecules in a cell sample include Northern blot analysis, RT-PCR [e.g., a semi-quantitative RT-PCR, quantitative RT-PCR using e.g., the Light Cycler™ (Roche)], RNA in situ hybridization (using e.g., DNA or RNA probes to hybridize RNA molecules present in the cells or tissue sections), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface [e.g., a glass wafer) with addressable location, such as Affymetrix microarray (Affymetrix®, Santa Clara, Calif.)].

For example, the level of RRN3 in a sample can be determined by RT-PCR using primers available from Santa Cruz Biotechnology Inc. (sc-106866-PR), or Taqman Gene Expression Assay HS00607907_m1 (Applied Biosystems, Foster City, Calif., USA), according to manufacturer's recommendation.

For example, the level of human pre-rRNA (Accession No: NR_046235, SEQ ID NO: 68) in a sample can be determined by RT-PCR using the RT2 qPCR Primer Assay for Human RNA45S5 (330001, Cat. N PPH82089A-200, Qiagen).

As mentioned, according to specific embodiments, the expression of the POL1 pathway gene can be determined at the amino acid level using protein detection methods.

Thus, according to some embodiments of the invention, detection of the expression level of the protein of the POL1 pathway is performed by contacting the biological sample, the cell, or fractions or extracts thereof with an antibody which specifically binds to a polypeptide expressed from the gene of the Pol I pathway (e.g., including any variants thereof which is known in the art). According to specific embodiments, the contacting is effected under conditions which allow the formation of a complex comprising polypeptide of a gene involved in the POL1 pathway present in the cell and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Thus, according to an aspect of the present invention there is provided a composition of matter comprising a biological sample of a subject, and an antibody capable of detecting a polypeptide expressed from a gene involved in the POL1 pathway. According to a specific embodiment, the composition further comprises a secondary antibody capable of binding the antibody.

The antibody used by the present invention can be any directly or indirectly labeled antibody. According to specific embodiments, the probe is bound to a detectable moiety.

The detectable moiety used by some embodiments of the invention can be, but is not limited to a fluorescent chemical (fluorophore), a phosphorescent chemical, a chemiluminescent chemical, a radioactive isotope (such as [$^{125}$]iodine), an enzyme, a fluorescent polypeptide, an affinity tag, and molecules (contrast agents) detectable by Positron Emission Tomography (PET) or Magnetic Resonance Imaging (MRI).

Non-limiting examples of methods of detecting the level and/or activity of specific protein molecules in a cell sample include Enzyme linked immunosorbent assay (ELISA), Western blot analysis, immunoprecipitation (IP), radio-immunoassay (RIA), Fluorescence activated cell sorting (FACS), immunohistochemical analysis, in situ activity assay (using e.g., a chromogenic substrate applied on the cells containing an active enzyme), in vitro activity assays (in which the activity of a particular enzyme is measured in a protein mixture extracted from the cells) and molecular weight-based approach. For example, in case the detection of the expression level of a secreted protein is desired, ELISA assay may be performed on a sample of fluid obtained from the subject (e.g., serum), which contains cell-secreted content.

As described above, the level of expression of least one gene involved in the RNA polymerase I pathway in a cell of the subject following treating with the compound is compared to the level of expression of the at least one gene in a cell of the subject prior to treating the subject with the compound.

As used herein the phrase "following treating with the compound" refers to any time period after administering the compound to the subject, e.g., from a few minutes to hours, or from a few days to weeks or months after drug administration.

According to some embodiments of the invention the level of expression is determined following administration of the first dose of the compound.

According to some embodiments of the invention the level of expression is determined following administration of any dose of the compound.

As used herein the phrase "prior to treating with the compound" refers to any time period prior administering the compound to the subject, e.g., from a few minutes to hours, or from a few days to weeks or months prior to drug administration.

According to some embodiments of the invention the level of expression is determined prior any dose of the compound (e.g., when the subject is naïve to treatment).

According to some embodiments of the invention prior to treating refers to when the subject is first diagnosed with autoimmune disease, e.g., multiple sclerosis.

According to some embodiments of the invention prior to treating refers to when the subject is suspected of having the autoimmune disease (e.g., multiple sclerosis), or diagnosed with probable autoimmune disease (e.g., probable multiple sclerosis).

According to some embodiments of the invention prior to treating refers to upon the onset of the autoimmune disease.

According to some embodiments of the invention the effect of the treatment on the subject can be evaluated by monitoring the level of expression of at least one of the polynucleotides described hereinabove and below. For example, downregulation in the level of RRN3 in the subject following treatment can be indicative of the positive effect of the treatment on the subject, e.g., switching from a typical RRMS to a BMS course of multiple sclerosis.

As described above, a decrease above a predetermined threshold in the level of expression of the at least one gene following treating with the compound relative to the level of expression of the at least one gene prior to treating with the compound indicates that the compound is efficient for treating the subject.

As used herein the phrase "a decrease above a predetermined threshold" refers to a decrease in the level of expression in the cell of the subject following treating with the compound which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression prior to treating with the compound.

As described, an increase above a predetermined threshold in the level of expression of the at least one gene following treating with the compound relative to the level of expression of the at least one gene prior to treating with the compound indicates that the compound is not efficient for treating the subject.

As used herein the phrase "an increase above a predetermined threshold" refers to an increase in the level of expression in the cell of the subject following treating with the compound, which is higher than a predetermined threshold such as about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression of the at least one gene prior to treating with the compound.

As described, a level of expression of the at least one gene following treating with the compound which is identical or changed below a predetermined threshold as compared to prior to treating with the compound is indicative that the treatment is not efficient for treating the subject.

As used herein the phrase "changed below a predetermined threshold as compared to prior to treating with the compound" refers to an increase or a decrease in the level of expression in the cell of the subject following treating with the compound, which is lower than a predetermined threshold, such as lower than about 10 times, e.g., lower than about 9 times, e.g., lower than about 8 times, e.g., lower than about 7 times, e.g., lower than about 6 times, e.g., lower than about 5 times, e.g., lower than about 4 times, e.g., lower than about 3 times, e.g., lower than about 2 times, e.g., lower than about 90%, e.g., lower than about 80%, e.g., lower than about 70%, e.g., lower than about 60%, e.g., lower than about 50%, e.g., lower than about 40%, e.g., lower than about 30%, e.g., lower than about 20%, e.g., lower than about 10%, e.g., lower than about 9%, e.g., lower than about 8%, e.g., lower than about 7%, e.g., lower than about 6%, e.g., lower than about 5%, e.g., lower than about 4%, e.g., lower than about 3%, e.g., lower than about 2%, e.g., lower than about 1% relative to the level of expression of the at least one gene prior to treating with the compound.

Non-limiting examples of genes involved in the RNA polymerase I pathway which can be used according to the method of the invention include RRN3, LRPPRC, POLR1A, POLR1B, POLR1C, POLR1D, POLR1E, PTRF, NIP7, ISF1, TAF1A, TAF1B, TAF1C, TAF1D, UBTF, TTF1 NCL and RNA45S5 (45S Pre-rRNA).

Sequence information regarding gene products (i.e., RNA transcripts and polypeptide sequences) of the genes of RNA polymerase I pathway which can be used for detection thereof can be found according to the following access numbers.

According to some embodiments of the invention, the at least one gene involved in the RNA polymerase 1 pathway is selected from the group consisting of POLR1D, LRPPRC, RRN3, pre-rRNA and NCL.

According to some embodiments of the invention, the at least one gene involved in the RNA polymerase 1 pathway is selected from the group consisting of POLR1D, LRPPRC, RRN3, and NCL.

According to some embodiments of the invention, the at least one gene involved in the RNA polymerase 1 pathway is RRN3.

According to some embodiments of the invention, the at least one gene involved in the RNA polymerase 1 pathway is LRPPRC.

According to some embodiments of the invention, the at least one gene involved in the RNA polymerase 1 pathway is POLR1D.

According to some embodiments of the invention, the at least one gene involved in the RNA polymerase 1 pathway is pre-rRNA.

According to some embodiments of the invention, the at least one gene involved in the RNA polymerase 1 pathway comprises RRN3 and POLR1D.

According to some embodiments of the invention, the at least one gene involved in the RNA polymerase 1 pathway comprises RRN3 and LRPPRC.

| Affymetrix ProbSet/ SEQ ID NO: | Representative Public ID/ SEQ ID NO: | Representative polypeptide Public ID/ SEQ ID NO: | Gene Symbol | Gene Title |
|---|---|---|---|---|
| 216902_s_at/1 | AF001549/18 NM_018427/19 | NP_060897/38 | RRN3 | RRN3 RNA polymerase I transcription factor homolog |
| 211971_s_at/2 | AI653608/20 NM_133259/21 | NP_573566/39 | LRPPRC | leucine-rich PPR-motif containing |
| 220113_x_at/3 | NM_019014/22 | NP_001131076/40 NP_061887/41 | POLR1B | polymerase (RNA) I polypeptide B, 128 kDa |
| 207515_s_at/4 | NM_004875/23 | NP_976035/42 | POLR1C | polymerase (RNA) I polypeptide C, 30 kDa |
| 218258_at/5 | NM_015972/24 | NP_057056/43 NP_689918/44 | POLR1D | polymerase (RNA) I polypeptide D, 16 kDa |
| 200610_s_at/6 | NM_005381/25 | NP_005372/45 | NCL | nucleolin |
| 222704_at/7 | W93584/26 | NM_015425/46 | POLR1A | polymerase (RNA) I polypeptide A, 194 kDa |
| 218997_at/8 | NM_022490/27 | NP_071935/47 | POLR1E | polymerase (RNA) I polypeptide E, 53 kDa |
| 218859_s_at/9 | NM_016649/28 | NP_001263309/48 NP_057733/49 | ESF1 | ESF1, nucleolar pre-rRNA processing protein, homolog (S. cerevisiae) |
| 206613_s_at/10 | NM_005681/29 | NP_001188465/50 NP_005672/51 NP_647603/52 | TAF1A | TATA box binding protein (TBP)-associated factor, RNA polymerase I, A, 48 kDa |
| 214690_at/11 | AA004579/30 | NP_005671/53 | TAF1B | TATA box binding protein (TBP)-associated factor, RNA polymerase I, B, 63 kDa |
| 203937_s_at/12 | AW015313/31 | NP_001230085/54 NP_001230086/55 NP_001230087/56 NP_001230088/57 NP_001230089/58 | TAF1C | TATA box binding protein (TBP)-associated factor, RNA polymerase I, C, 110 kDa |
| 218750_at/13 | NM_024116/32 | NP_077021/59 | TAF1D | TATA box binding protein (TBP)-associated factor, RNA polymerase I, D, 41 kDa |
| 214881_s_at/14 | X56687/33 | NP_001070151/60 NP_001070152/61 NP_055048/62 | UBTF | upstream binding transcription factor, RNA polymerase I |
| 204771_s_at/15 | NM_007344/34 | NP_001192225/63 NP_031370/64 | TTF1 | transcription termination factor, RNA polymerase I |
| 208790_s_at/16 | AF312393/35 | NP_036364/65 | PTRF | polymerase I and transcript release factor |
| 219031_s_at/17 | NM_016101/36 | NP_001186363/66 NP_057185/67 | NIP7 | NIP7, nucleolar pre-rRNA processing protein |
| Not Applicable | NR_046235/37 | Not Applicable | RNA45S5 | 45S rRNA precursor for the 18S, 5.8S and 28S rRNA |

According to some embodiments of the invention, the at least one gene involved in the RNA polymerase 1 pathway comprises POLR1D and LRPPRC.

According to some embodiments of the invention, the at least one gene involved in the RNA polymerase 1 pathway comprises RRN3, LRPPRC and POLR1D.

According to some embodiments of the invention, the at least one gene involved in the RNA polymerase 1 pathway is RRN3 and NCL.

According to some embodiments of the invention, the at least one gene involved in the RNA polymerase 1 pathway is LRPPRC and NCL.

According to some embodiments of the invention, the at least one gene involved in the RNA polymerase 1 pathway is POLR1D and NCL.

According to some embodiments of the invention, the at least one gene involved in the RNA polymerase 1 pathway comprises RRN3, POLR1D and NCL.

According to some embodiments of the invention, the at least one gene involved in the RNA polymerase 1 pathway comprises RRN3, LRPPRC and NCL.

According to some embodiments of the invention, the at least one gene involved in the RNA polymerase 1 pathway comprises POLR1D, LRPPRC and NCL.

According to some embodiments of the invention, the at least one gene involved in the RNA polymerase 1 pathway comprises RRN3, LRPPRC, POLR1D and NCL.

According to some embodiments of the invention, the at least one gene involved in the RNA polymerase 1 pathway comprises pre-rRNA and RRN3.

According to some embodiments of the invention, the at least one gene involved in the RNA polymerase 1 pathway comprises pre-rRNA and LRPPRC.

According to some embodiments of the invention, the at least one gene involved in the RNA polymerase 1 pathway comprises pre-rRNA and POLR1D.

According to some embodiments of the invention, the at least one gene involved in the RNA polymerase 1 pathway comprises pre-rRNA and NCL.

According to some embodiments of the invention, the at least one gene involved in the RNA polymerase 1 pathway comprises pre-rRNA, RRN3 and LRPPRC.

According to some embodiments of the invention, the at least one gene involved in the RNA polymerase 1 pathway comprises pre-rRNA, RRN3 and POLR1D.

According to some embodiments of the invention, the at least one gene involved in the RNA polymerase 1 pathway comprises pre-rRNA, LRPPRC and POLR1D.

According to some embodiments of the invention, the at least one gene involved in the RNA polymerase 1 pathway comprises pre-rRNA, RRN3, and NCL.

According to some embodiments of the invention, the at least one gene involved in the RNA polymerase 1 pathway comprises pre-rRNA, LRPPRC and NCL.

According to some embodiments of the invention, the at least one gene involved in the RNA polymerase 1 pathway comprises pre-rRNA, POLR1D and NCL.

According to some embodiments of the invention, the at least one gene involved in the RNA polymerase 1 pathway comprises pre-rRNA, RRN3, LRPPRC and POLR1D.

According to some embodiments of the invention, the at least one gene involved in the RNA polymerase 1 pathway comprises pre-rRNA, RRN3, LRPPRC and NCL.

According to some embodiments of the invention, the at least one gene involved in the RNA polymerase 1 pathway comprises pre-rRNA, RRN3, POLR1D and NCL.

According to some embodiments of the invention, the at least one gene involved in the RNA polymerase 1 pathway comprises pre-rRNA, LRPPRC, POL1RD and NCL.

Qualifying the compound as being suitable for treating the autoimmune disease in the subject can be also performed by an in-vitro method.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Chemical Syntheses and Characterization of POL1 Inhibitors

Materials and Methods:
2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (also referred to herein interchangeably as CX-5461, POL1-I, RAM-0 or Compound 1; see, chemical structure as presented in FIG. 3A and Table 1 below) was synthesized according to known procedures (see, for example, U.S. Patent Application Publication No. 2009/0093465 and WO 2012/123938).

All of the reagents were obtained from Sigma Aldrich.
$^1$H NMR analyses were performed using a Bruker Avance DPX-400 Ultra shield or alternatively Bruker Avance DMX-500. All the chemical shifts are referenced to the residual solvent signal.

All Mass Spectra analyses were performed on a Thermo Scientific LCQ Fleet mass spectrometer with an ESI source. All the spectra were recorded in the positive mode (unless mentioned otherwise) and were analyzed by the Thermo Scientific Xcalibur software.

General Synthetic Procedure:
POL1-I (CX-5461, Compound 1) is refluxed in phosphoryl chloride for several hours to afford the chlorinated analog 5-chloro-2-(4-methyl-1,4-diazepan-1-yl)-6-(((5-methylpyrazin-2-yl)methyl)carbamoyl)benzo[4,5]thiazolo[3,2-a][1,8]naphthyridin-12-ium (also referred to herein interchangeably as POL14/1, RAM-2, RAM Cl or Compound 2; see, FIG. 3A and Table 1 below).

The phosphoryl chloride is thereafter removed by evaporation and the crude product 2 is dissolved or suspended in an alcoholic solvent (e.g., methanol or ethanol). An amine or thiol compound, as desired, is then added and the resulting reaction mixture is stirred, possibly under reflux, until reaction completion. The solvent is then removed by evaporation and the resulting crude is purified, typically by preparative HPLC.

The chemical structure of the obtained product was verified by MS [ESI] and/or $^1$H NMR, as detailed hereinbelow.

An exemplary synthetic pathway of exemplary compounds according to some embodiments of the present invention is presented in FIGS. 3A-B.

5-chloro-2-(4-methyl-1,4-diazepan-1-yl)-6-(((5-methylpyrazin-2-yl)methyl) carbamoyl)benzo[4,5]thiazolo[3,2-a][1,8]naphthyridin-12-ium (POL1-Ill; Compound 2)

MS [ESI]: calcd. 532.1. found [M+H] 532.2.

Preparation of 2-(4-methyl-1,4-diazepan-1-yl)-N-((5-methylpyrazin-2-yl)methyl)-5-thioxo-5H-benzo[4,5]thiazolo[3,2-a][1,8]naphthyridine-6-carboxamide (referred to herein interchangeably as POL1-I/2; RAM-3; or Compound 3)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Sodium hydrosulfide was then added (100 mg) and the resulting solution was stirred for 5 minutes. The obtained compound 3 was purified by preparative HPLC to yield 82.4 mg 80% yield).
$^1$H NMR (500 MHz, CDCl$_3$): δ=13.02 (t, J=5.58 Hz, 1H), 9.50 (d, J=7.01 Hz, 1H), 9.23 (d, J=9.38 Hz, 1H), 8.64 (d, J=1.13 Hz, 1H), 8.43 (s, 1H), 7.75 (m, 1H), 7.45 (m, 2H), 6.82 (d, J=9.42 Hz, 1H), 4.89 (d, J=5.61 Hz, 2H), 4.17-3.64 (m, 4H), 2.88-2.79 (m, 2H), 2.64-2.57 (m, 2H), 2.56-2.53 (s, 3H), 2.39 (s, 3H), 2.11 (m, 2H) ppm.
MS [ESI]: calcd. 530.6. found [M+H] 530.2.

Preparation of 5-imino-2-(4-methyl-1,4-diazepan-1-yl)-N-((5-methylpyrazin-2-yl)methyl)-5H-benzo[4,5]thiazolo[3,2-a][1,8]naphthyridine-6-carboxamide (referred to herein, interchangeably, as POL1-I/4; RAM-1 or Compound 4)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Gaseous ammonia was then bubbled into the methanol for 1 minute and the resulting solution was stirred for 5 minutes. The obtained compound 4 was purified by preparative HPLC to yield 64 mg (64% yield).

$^1$H NMR (400 MHz, CDCl$_3$ ppm): 9.28 (d, J=8.21 Hz, 1H), 8.58 (m, 1H), 8.44 (m, 1H), 8.04 (d, J=8.72 Hz, 1H), 7.64 (dd, J=7.62, 1.35 Hz, 1H), 7.34 (m, 2H), 6.68 (d, J=9.23 Hz, 1H), 4.86 (s, 2H), 3.98-3.74 (m, 4H), 2.84 (m, 2H), 2.66-2.60 (m, 2H), 2.54 (s, 3H), 2.41 (s, 3H), 2.12 (m, 2H), MS [ESI]: calcd. 513.2. found [M+H] 513.3.

Preparation of (E/Z)-2-(4-methyl-1,4-diazepan-1-yl)-5-(methylimino)-N-((5-methylpyrazin-2-yl)methyl)-5H-benzo[4,5]thiazolo[3,2-a][1,8]naphthyridine-6-carboxamide (referred to herein, interchangeably, as POL1-I/3; or Compound 5)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Methylamine was then added (3 mL) and the resulting solution was stirred for 5 minutes. The obtained compound 5 was purified by preparative HPLC to yield 74 mg (73% yield).

MS [ESI]: calcd. 527.6. found [M+H] 527.3.

Preparation of Compounds 6 and 7

(see, Table 1) was performed similarly to Compound 5, using propylamine and isopropylamine, respectively, and yielding 82 mg (76% yield) and 85 mg (79% yield), respectively.

MS [ESI]: calcd. 555.7. found [M+H] 555.4, MS [ESI]: calcd. 555.7. found [M+H] 555.3.

Preparation of Compound 8 (see, Table 1):

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 3 mL of Triethylamine and 100 mg of [Methoxyamine hydrogen chloride] were then added and the resulting solution was stirred for 5 minutes. The obtained compound 5 was purified by preparative HPLC to yield 34 mg (32% yield).

MS [ESI]: calcd. 543.6. found [M+H] 543.2.

Preparation of Compound 9 (see, Table 1):

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 100 mg of urea were added and the resulting solution was left to stir for 4 hours. The title compound was purified by preparative HPLC to yield 78 mg (75% yield)

MS [ESI]: calcd. 537.2. found [M+H] 537.6.

Preparation of (E)-2-(4-methyl-1,4-diazepan-1-yl)-N-((5-methylpyrazin-2-yl)methyl)-5-(phenylimino)-5H-benzo[4,5]thiazolo[3,2-a][1,8]naphthyridine-6-carboxamide (Compound 10; See, Table 1 and FIG. 3B)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (100 mg) was suspended in 3 mL of phosphoryl chloride, and the resulting mixture was refluxed for 3 hours. The phosphoryl chloride was thereafter removed by evaporation and the resulting crude product was dissolved in MeOH. Aniline was then added (2 mL) and the resulting solution was stirred for 5 minutes. The compound was purified by preparative HPLC to yield 56 mg (50% yield).

MS [ESI]: calcd. 589.7. found [M+H] 589.4.

Compound 11

(see, Table 1) was prepared similarly to Compound 10, using 3-fluoroaniline instead of aniline.

MS [ESI]: calcd. 607.2. found [M+H] 607.5.

Solubility:

The solubility of Compounds 1 and 10 was determined by dissolving 50 mg of the tested compound in 0.5 mL of mQ water, at room temperature.

Compound 10 immediately dissolved in the aqueous solution, whereby Compound 1 dissolved only in a pH 4.5 buffered solution after vigorous stirring for 30 minutes.

Example 2

Cell Viability Assay

Cell viability was assessed by the 2,3 bis[2-Methoxy-4-nitro-5-sulfophenyl]-2H-tetrazolium-5-carboxanilide (XTT) assay (Biological Industries, Kibbutz Beit Hemeek, Israel), which measures the reduction of a tetrazolium component (XTT) into soluble formazan product by the mitochondria of viable cells. The intensity of the dye obtained is proportional to the number of metabolic active cells. On the day of measurement, cells were washed and XTT was added according to the manufacturer's instructions. Plates were incubated at 37° C. for 2-5 hours. The absorbance was read at 450 nm.

Mouse splenocytes were removed and splenocytes were plated (250,000 cell/well) in DMEM+10% FCS+P/S+Q and 10 mg/ml Phytohaemaglutinin (PHA), in the presence of elevated concentrations (25-400 nM) of RAM-0 (Compound 1), RAM-1 (Compound 4), RAM-2 (Compound 2) or RAM-3 (Compound 3) for 72 hours. Cells cultured without PHA served as control. Control mice at zero are mice splenocytes with PHA stimulation.

Following incubation, cell viability was determined by XTT assay, as described above.

RNA samples from similar cultures were also prepared and tested by Q-RT-PCR for pre-rRNA expression levels as described in Example herein below.

Figure 4A:
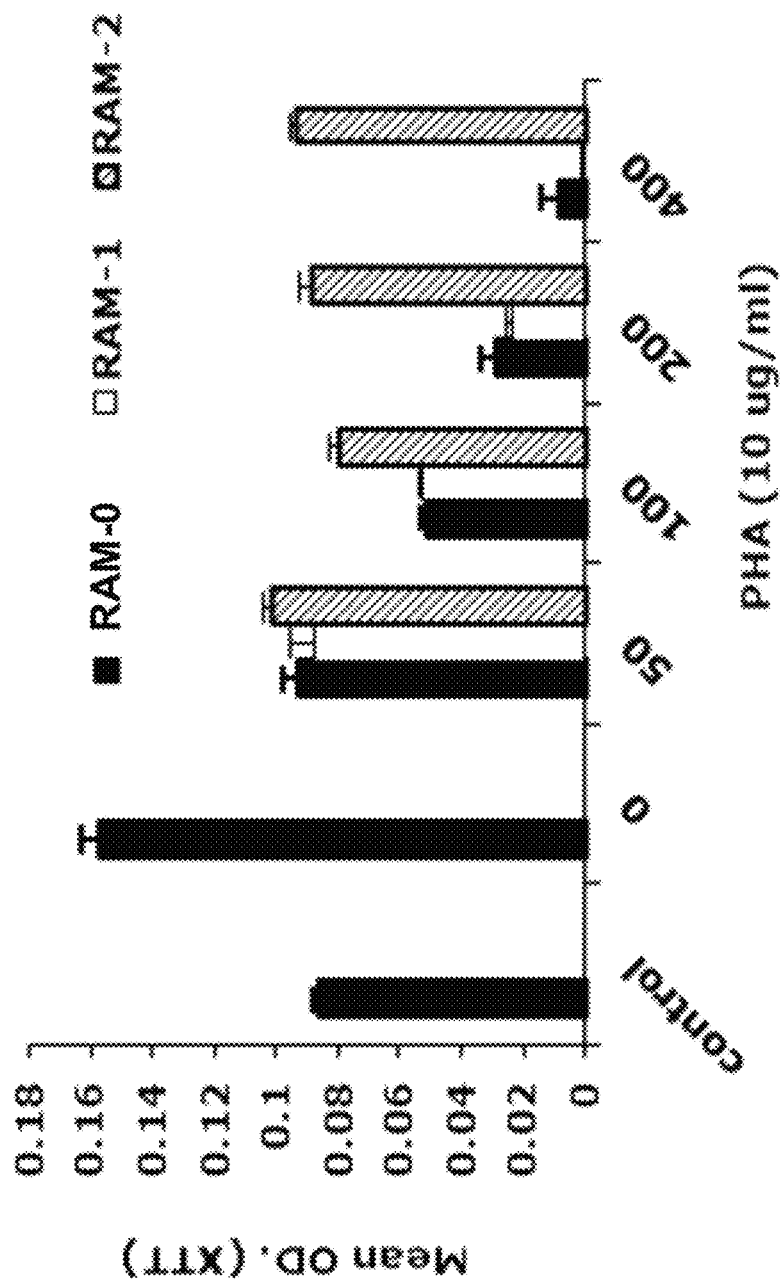
FIGS. 4A-C present bar graphs showing the effect of exemplary compounds according to some embodiments of the present invention in suppressing proliferation of mouse splenocytes, as determined in an XTT assay.

The obtained XTT data is presented in FIG. 4A (for Compound 1 compared with Compounds 2 and 4), in FIG.

Figure 4B:
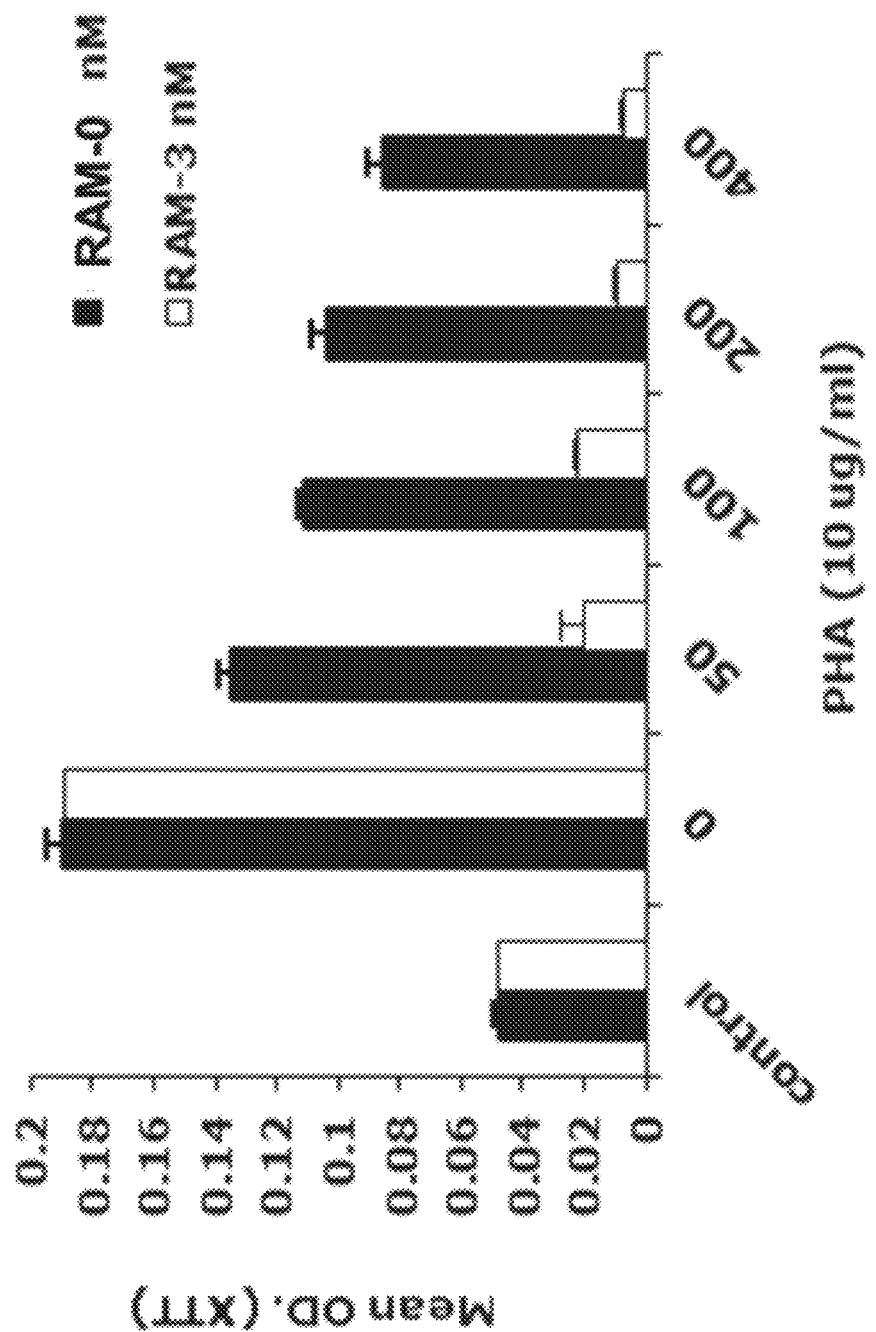
Figure 4C:
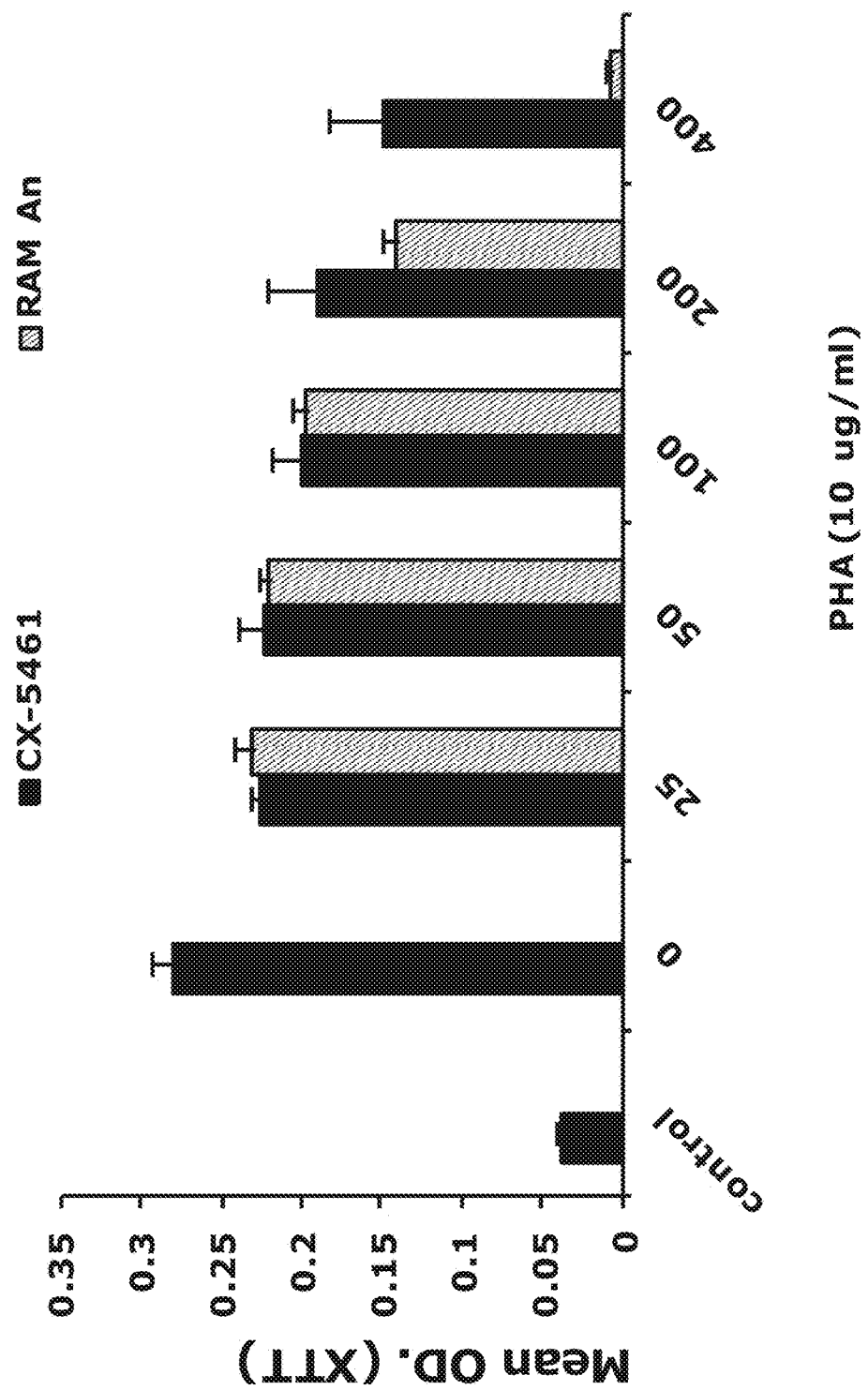

4B (for Compound 1 compared with Compound 3), and FIG. 4C (for Compound 1 compared with Compound 10).

As shown, PHA stimulation resulted in substantial increase in proliferation as compared to control. As shown in FIG. 4A, Compound 4 (RAM-1) exhibited a dose response curve similar to RAM-0 (Compound 1), while RAM-2 (Compound 2) showed no substantial effect. As shown in FIG. 4B, RAM-3 (Compound 3) was 6-folds more effective in suppressing proliferation compared to Compound 1 (RAM-0), suggesting much lower therapeutic doses of this compound. As shown in FIG. 4C, Compound 10 exhibits an improved performance is suppressing proliferation compared to Compound 1. As indicated below, this compound was also found to feature a larger therapeutic window and improved solubility and pharmacokinetic properties, compared to Compound 1.

$IC_{50}$ values as determined in these assays for Compounds 1-4 and 10, and for all other tested compounds, are presented in Table 1 below.

Figure 5:
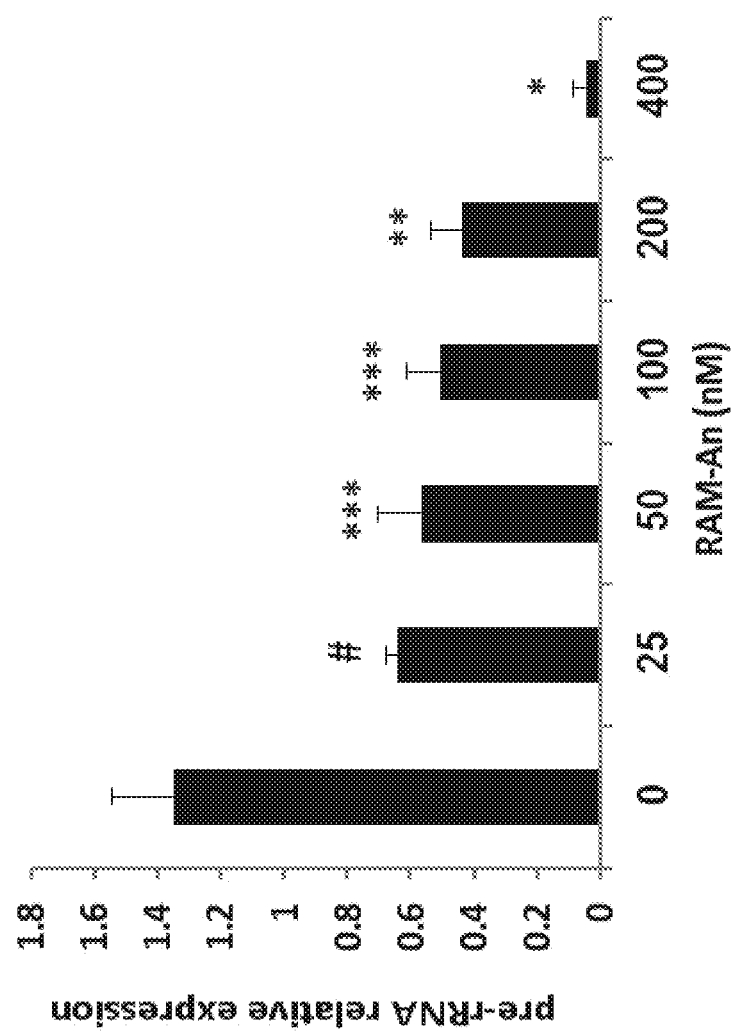
FIG. 5 is a graph showing mRNA levels of pre-rRNA in splenocytes of naïve mice following 72 hours stimulation with PHA in the presence of elevated concentrations of Compound 10. Bars represent mean±SEM; *p=0.0003, **p=8.8*10$^{-5}$, ***p<0.009 and #p=0.03.

The effect of Compound 10 on splenocytes proliferation was accompanied by suppression of pre-rRNA transcription, a key gene representing overall activity of the RNA polymerase I pathway. As shown in FIG. 5, 72 hours incubation with Compound 10 in concentrations of 25 to 400 nM resulted in a significant dose dependent decrease in pre-rRNA mRNA levels expressed by the splenocytes.

TABLE 1

| No. | Structure | Mw | Name | XTT |
|---|---|---|---|---|
| 1 | 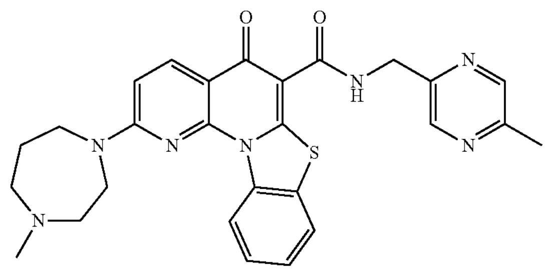 [SMILES: Cc1cnc(CNC(=O)c2c(=O)c3ccc(N4CCCN(C)CC4)nc3n3c2sc2ccccc23)cn1] | 513.2 | CX-5461; RAM-0; POL1-I | $IC_{50}$ = 50 nM |
| 2 | 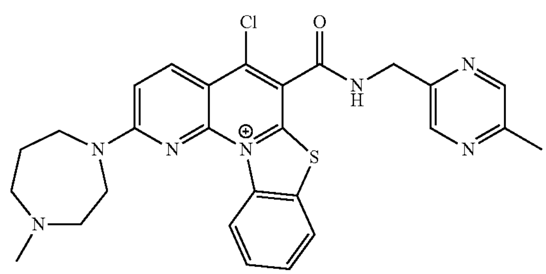 [SMILES: Cc1cnc(CNC(=O)c2c(Cl)c3ccc(N4CCCN(C)CC4)nc3[n+]3c2sc2ccccc23)cn1] | 532.7 | RAM-2 POL1-I/1 | No Effect |
| 3 | 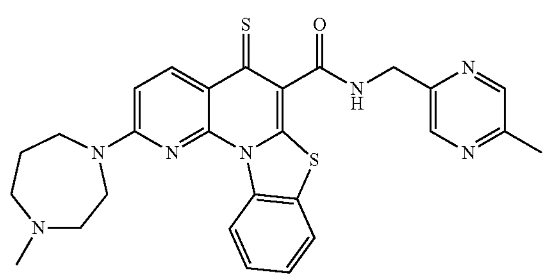 [SMILES: Cc1cnc(CNC(=O)c2c(=S)c3ccc(N4CCCN(C)CC4)nc3n3c2sc2ccccc23)cn1] | 529.6 | RAM-3; POL1-I/2 | $IC_{50}$ = 20 nM* |
| 4 | 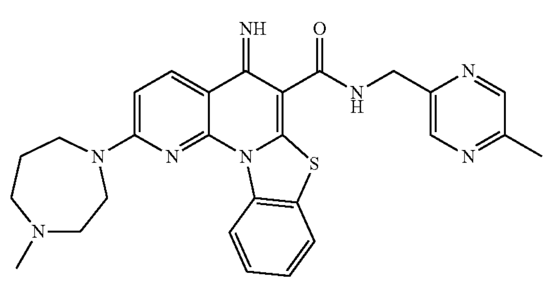 [SMILES: Cc1cnc(CNC(=O)c2c(=N)c3ccc(N4CCCN(C)CC4)nc3n3c2sc2ccccc23)cn1] | 512.6 | RAM-1; POL1-I/4 | $IC_{50}$ = 50 nM |

TABLE 1-continued

| No. | Structure | Mw | Name | XTT |
|---|---|---|---|---|
| 5 | 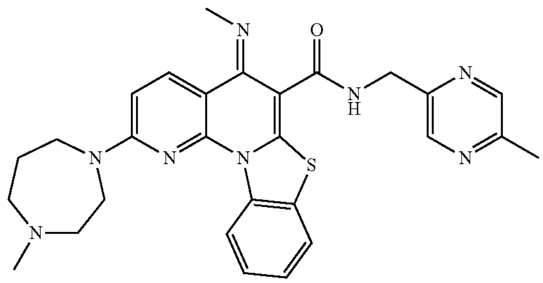 [SMILES: C/N=c1/c(C(=O)NCc2cnc(C)cn2)c2sc3ccccc3n2c2nc(N3CCCN(C)CC3)ccc12] | 526.2 | RAM Me | $IC_{50}$ = 50 nM |
| 6 | 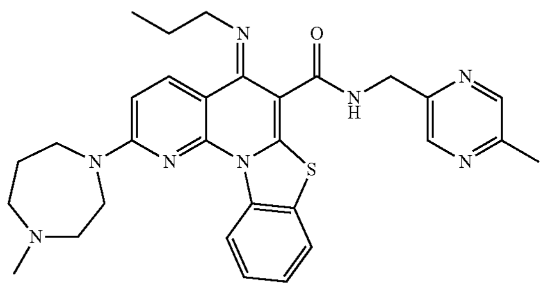 [SMILES: CCC/N=c1/c(C(=O)NCc2cnc(C)cn2)c2sc3ccccc3n2c2nc(N3CCCN(C)CC3)ccc12] | 554.2 | RAM Pr | $IC_{50}$ = 50 nM |
| 7 | 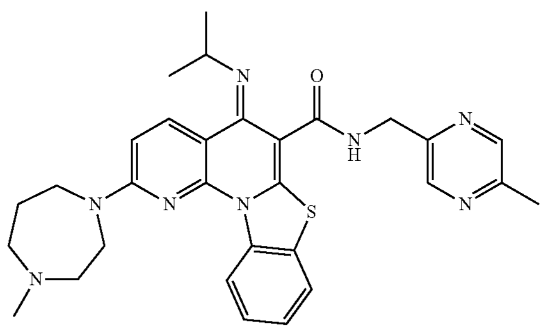 [SMILES: Cc1cnc(CNC(=O)c2/c(=N/C(C)C)c3ccc(N4CCCN(C)CC4)nc3n3c2sc2ccccc23)cn1] | 554.3 | RAM iPr | $IC_{50}$ = 50 nM |
| 8 | 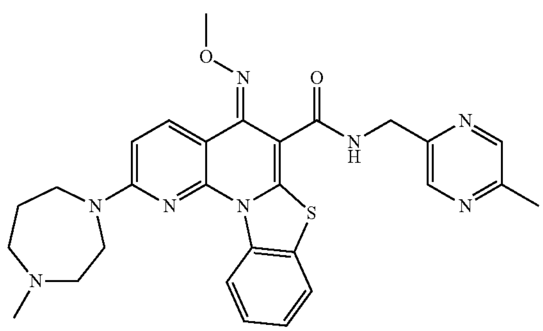 [SMILES: CO/N=c1/c(C(=O)NCc2cnc(C)cn2)c2sc3ccccc3n2c2nc(N3CCCN(C)CC3)ccc12] | 542.2 | RAM MeAM | $IC_{50}$ = 50 nM |
| 9 | 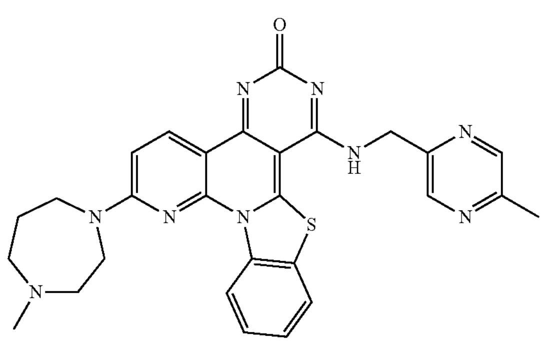 [SMILES: Cc1cnc(CNc2nc(=O)nc3c4ccc(N5CCCN(C)CC5)nc4n4c(sc5ccccc54)c2-3)cn1] | 555.2 | RAM urea | No Effect |

TABLE 1-continued

| No. | Structure | Mw | Name | XTT |
|---|---|---|---|---|
| 10 | 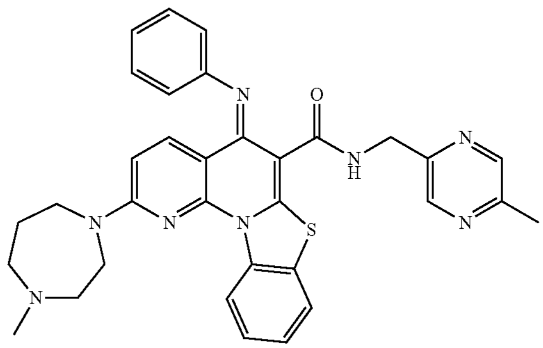 [SMILES: Cc1cnc(CNC(=O)c2/c(=N/c3ccccc3)c3ccc(N4CCCN(C)CC4)nc3n3c2sc2ccccc23)cn1] | 588.2 | RAM An | IC$_{50}$ = 40 nM |
| 11 | 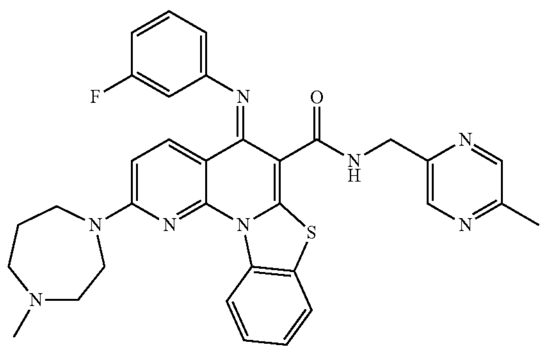 [SMILES: Cc1cnc(CNC(=O)c2/c(=N/c3cccc(F)c3)c3ccc(N4CCCN(C)CC4)nc3n3c2sc2ccccc23)cn1] | 606.2 | RAM 3Fan | ND |

*Compound 2, although effective, was found to decompose in some of the experiments conducted.

Example 3

In Vivo Assays

Experimental Methods:
Mice:

Eight-weeks-old female C57BL/6J mice (15-20 g, Harlan laboratories, Rehovot, Israel) were used in all experiments. Animal maintenance and experimental protocols were performed in accordance with the Israeli Council for Animal Care guidelines and approved by Sheba IRB Animal Care Committee. Mice were kept in an SPF environment, maintained on a 12-h light/dark cycle at a constant environmental temperature with free access to food and water in their home cages.

Induction of MOG35-55 EAE (Prevention Model):

EAE (Experimental Autoimmune Encephalomyelitis) was induced in 8 week old female C57BL/6J mice (15-20 g, Harlan laboratories, Rehovot, Israel) by immunization with an emulsion containing 300 μg of purified myelin oligodendrocyte glycoprotein (MOG) peptide (MEVGWYR-SPFSRVVHLYRNGK, corresponding to residues 35-55; obtained from (Difco, Detroit, Mich.) in saline and an equal volume of complete Freund's adjuvant containing 5 mg H37RA (Difco, Detroit, Mich.). 0.2 ml of the inoculum was injected subcutaneously. In addition, 300 ng of *Bordetella pertusis* toxin (Sigma) in 0.2 ml saline was injected intraperitoneally at the day of induction and two days later.

Oral gavages with the tested compound, at various concentrations ranging from 3 mg/kg-30 mg/kg in PBS or 50 mM NaH$_2$PO$_4$ (PH 4.5), or with vehicle only, were initiated at day of immunization. Mice were monitored daily for clinical signs of EAE, scored as: 1, flaccid tail; 2, forelimb weakness and poor righting ability; 3, hind limb paralysis; 4, quadriplegia; 5, moribund. Animal reaching a score of 4 were scarified using CO$_2$.

Treatment was stopped once 30% of the vehicle-treated animals scored 1 on the EAE score. The experiment was terminated after 28 days.

Toxicity:

The lethal dose for 50% of animals (LD$_{50}$), was determined for the EAE model, and was estimated in a continuous administration model. The animals were evaluated for signs of acute toxicity and survival during the entire administration period in the EAE model. Various concentrations were evaluated for efficacy, and when 50% mortality was observed in a specific concentration, this concentration was determined as the LD$_{50}$.

The therapeutic index (LD$_{50}$/ED$_{50}$), which is also referred to herein as Safety Margin (SM), was then determined based on the EAE model. ED$_{50}$ is the minimum effective dose observed for 50% of the tested animals.

Bioavailability:

Determination of the level of the tested compound in serum was done following oral gavage. Blood samples (0.5 mL) were collected and immediately centrifuged at 5,000 rpm for 10 minutes. The serum was separated and stored at −20° C. until fluorometric analysis by Tecan SpectraFluor, based on the specific excitation/emission values of the tested compound was conducted. The pharmacokinetic parameters including serum maximum concentration (Cmax), the time needed to reach Cmax (Tmax), and half-life (T½), were calculated to evaluate oral bioavailability. The serum concentration after oral gavages was calculated according to a calibration curve for each compound in the serum.

The Pharmacokinetic properties of compound 10 were quantified by the LCMS method described below. The concentration of Compound 10 was calculated with a calibration curve. The serum was prepared for analysis using protein precipitation. 15 μL of water were added to 15 μL of serum and a $H_2O:MeOH:CHCl_3$ (90:120:30) solution was added. The supernatant was subjected to LCMS analysis equipped with a PHENOMENEX® C-18 RP column.

RNA Extraction:

For in vivo experiments spleens from EAE mice were isolated at day 17 post immunization and splenocytes were re-stimulated for 72 h hours in the presence of 5.0 μg/ml MOG35-55. For in-vitro experiments spleens from intact mice were isolated and splenocytes were stimulated with for 72 h in the presence of PHA. RNA was extracted from splenocytes of both the in-vitro and in-vivo experiments by robotic ABI PRISM, Applied biosystem 6100 Nucleic Acid Prep Station. To avoid genomic DNA contamination samples were treated with DNase I (Roche). The quality and integrity of the total RNA preparation was confirmed using a NanoDrop 2000c Spectrophotometer (Thermo Scientific).

Quantitative RT-PCR of Pre-rRNA:

Complementary DNA was obtained from the extracted RNA by the High capacity cDNA reverse transcription kit (Applied Biosystems, CA, USA) following manufacturer's instructions. To confirm the role of POL1 pathway suppression by POL1-Inhibitors, the expression level of pre-rRNA transcript, a key gene of the RNA polymerase I pathway, was evaluated by Q-RT-PCR (n=3 per group). All PCR reactions were performed on a Light Cycler 480 instrument (Roche Diagnostic). The pre-rRNA, specific primers used were Forward: tttcttgtaagcgtcgaggtg (SEQ ID NO: 69) and Reverse: agcaggcacctaggagacaa (SEQ ID NO: 70) with a quantification probe (Roche, Probe ID #1, cat. no. 04684974001). For sample normalization, actin expression level was used as an internal control.

Statistical Analysis:

All statistical analyses to evaluate differences between groups are performed by T-test and p value<0.05 is considered significant.

Figure 6A:
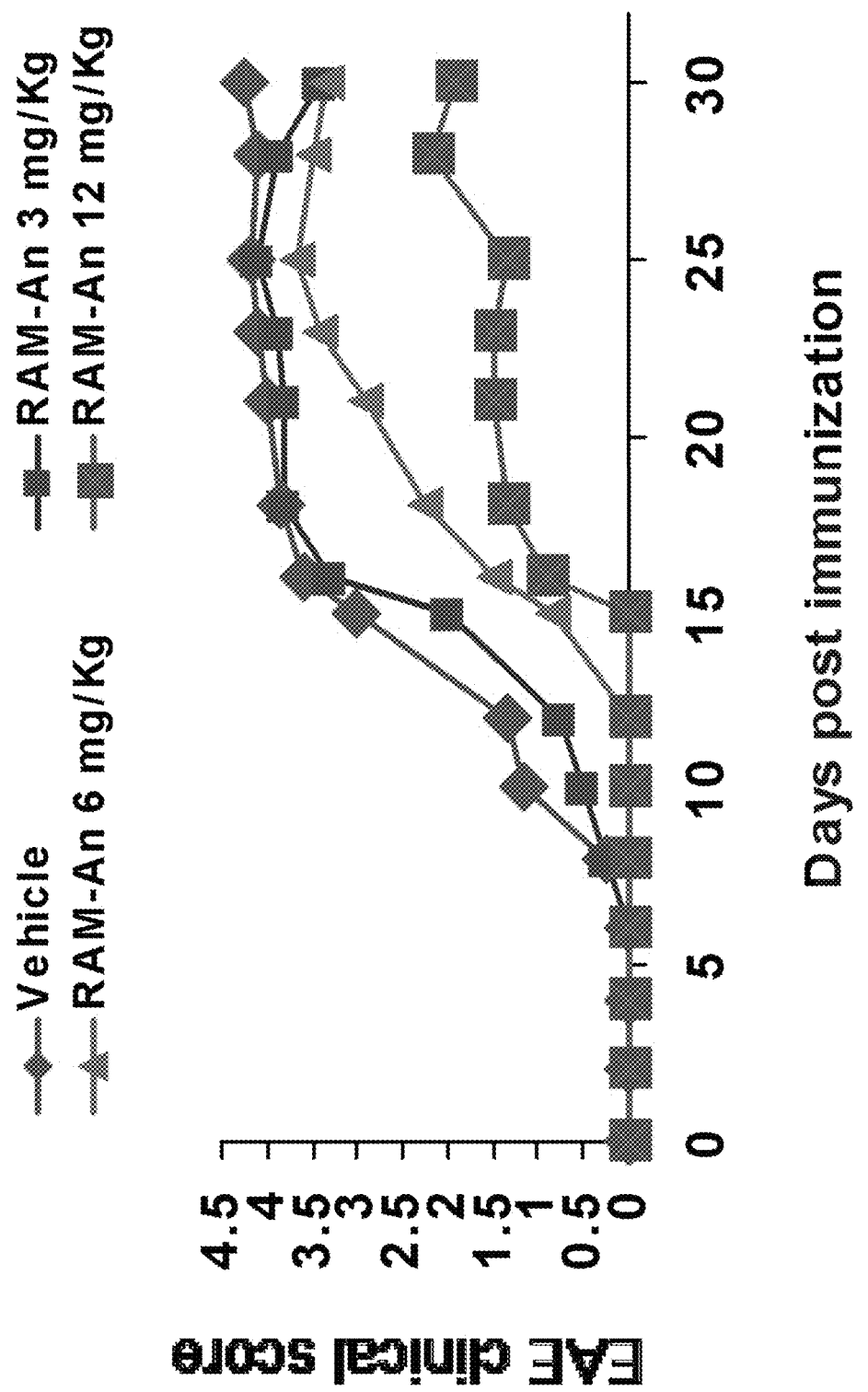
FIGS. 6A-D present plots showing the effect of various concentration of Compound 10 (RAM-An) on the EAE clinical score and disease incidence, as observed in an EAE prevention mice model, following daily (FIG. 6D) or every other day administration (FIGS. 6A-C).
Figure 6B:
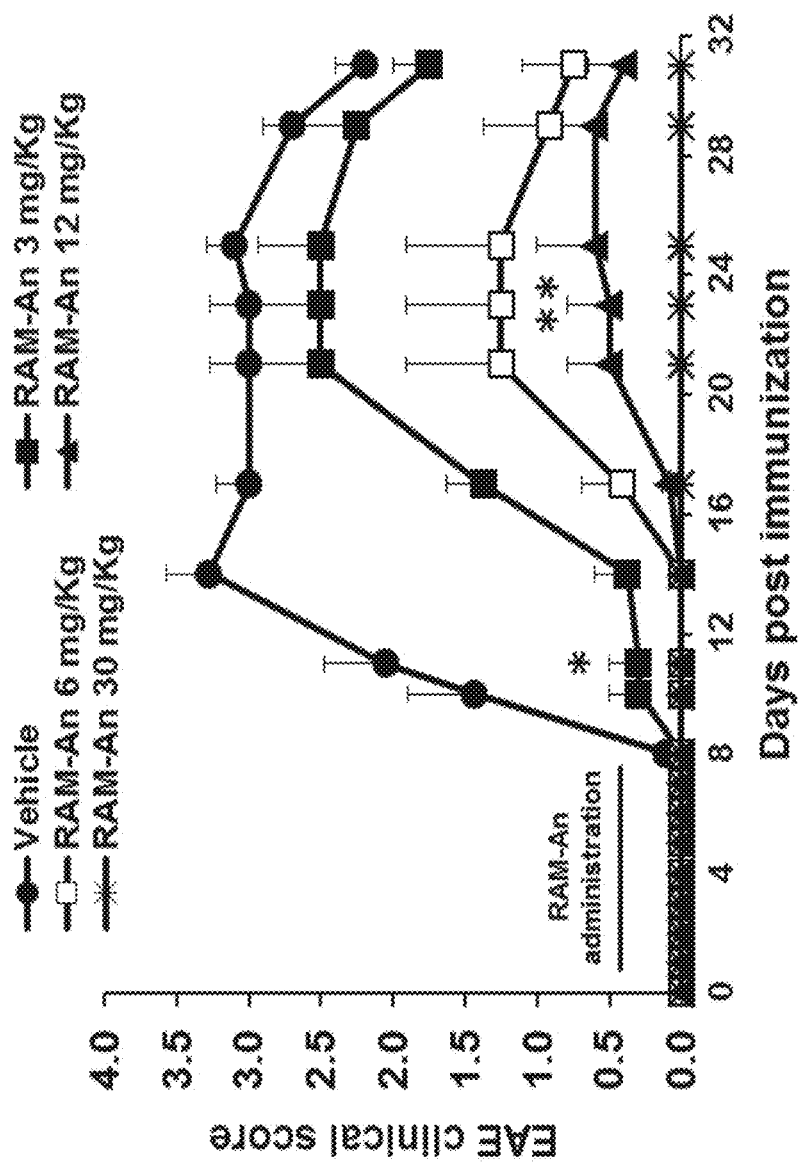
Figure 6C:
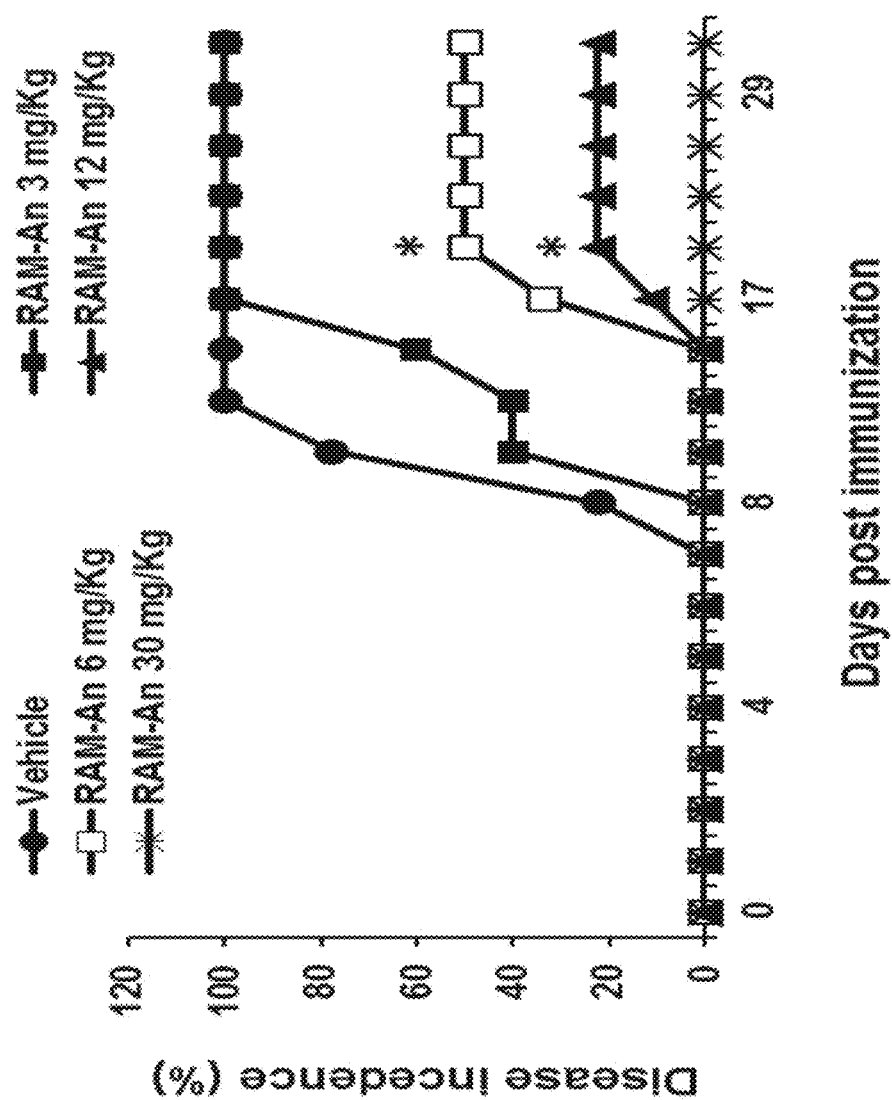

Experimental Results:

FIGS. 6A-C present the minimal clinically effective dose and optimal dosing schedule for Compound 10 by evaluating its efficacy in an EAE immunization model by oral administration at alternate days starting at the day of immunization. As shown in FIG. 6A administration of 12.0 mg/kg of Compound 10 significantly delayed disease development by 10 days; p<0.001, and suppressed EAE severity (as shown by decreased activity at 23 day post immunization, p=4.57E-05).

As also evident in FIG. 6B, the disease incidence gradually decreased with elevation of the dose and ranged between 98% at a dose of 3 mg/kg and 22% at a dose of 12.5 mg/kg (p<0.0001 for 6.125 and 12.5 mg/kg as compared to the vehicle treated group). Moreover, administration of 30 mg/kg completely inhibited disease development. Notably, mice in all treated groups showed 100% survival without apparent signs of toxicity.

As summarized in Table 2 below, analysis of 15 mice per group showed that mice treated with Compound 10 remained free of disease for 10 additional days as compared to mice treated with vehicle. Even following disease onset, the treated mice reached the peak of disease 6 days following the vehicle treated group and the peak itself was significantly lower in the Compound 10 treated animals ($p=4.8*10^{-6}$).

TABLE 2

Effects of Compound 10 in EAE, immunization model

| Treatment | No. of mice | EAE onset (dpi) | Peak of EAE (dpi) | Max clinical score | Cumulative disease score * |
|---|---|---|---|---|---|
| Vehicle | 15 | 9.5 ± 0.4 | 14.4 ± 1.2 | 3.8 ± 0.1 | 30.3 ± 2.4 |
| RAM-An/ 589.555 12.5 mg/Kg | 15 | 19.2 ± 0.6 | 20.4 ± 0.7 | 1.2 ± 0.4 | 7.2 ± 1.9 |
| p-value | | $1.3*10^{-12}$ | $2*10^{-4}$ | $4.8*10^{-6}$ | $3.3*10^{-7}$ |

* The cumulative scores represent the summation of each single score recorded for each mouse from the day of immunization (day 0) to the day of sacrifice (day 31).
dpi—days post immunization As shown in FIG. 6A, the minimal effective dose was 6 mg/kg.

Figure 6D:
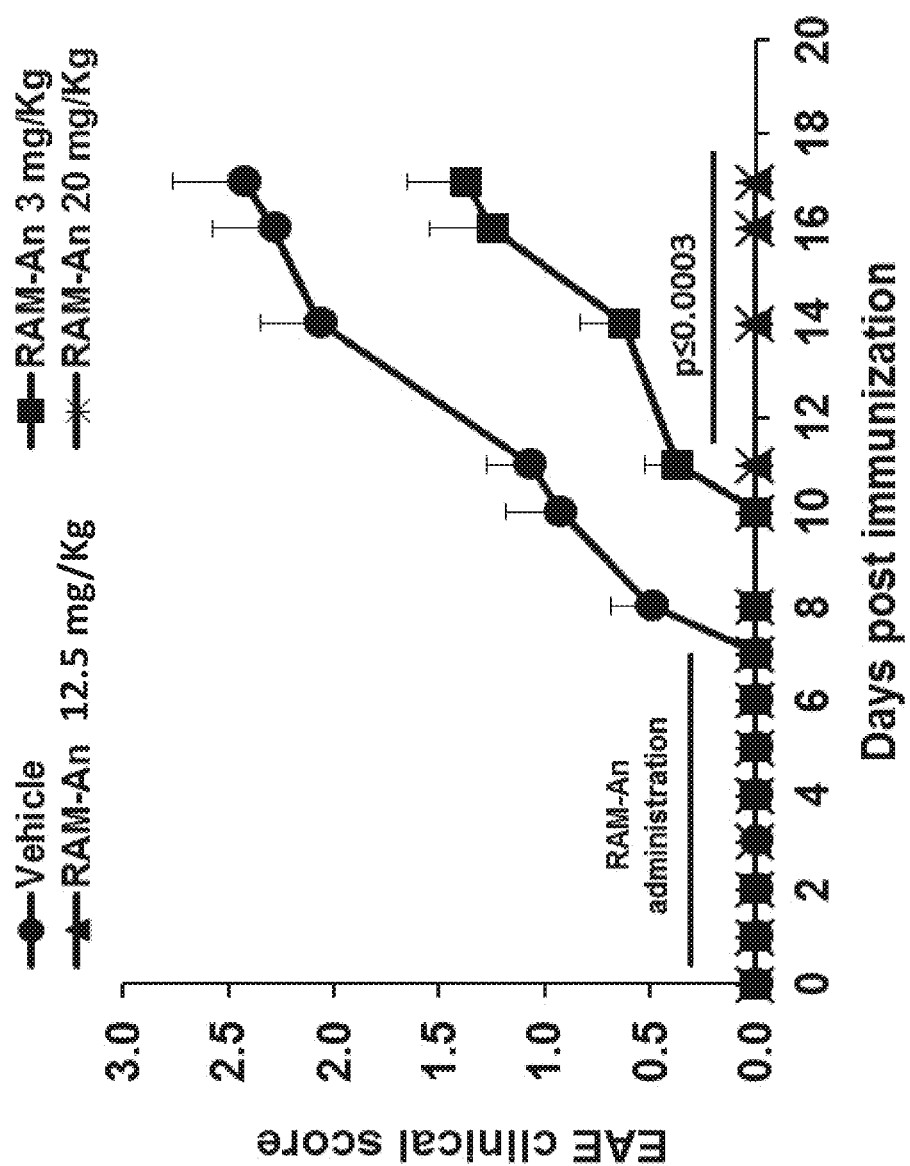

FIG. 6D demonstrated that the minimal effective dose was even lower in daily administration regimen in which efficacy of Compound 10 was evaluated using daily doses of 3.0, 6.0, 12.5 and 20 mg/kg starting at the day of immunization until disease onset at the vehicle treated group. Thus, daily administration of Compound 10 at a dose of 12.5 mg/kg resulted in complete inhibition of EAE (p≤0.0003 as compared with vehicle treated at 11-17 days post immunization and the minimal effective dose was 3.0 mg/kg.

Table 3 below presents comparative data for the effective and toxic doses as determined in the EAE prevention model assay described hereinabove, as determined for Compounds 1 and 10.

TABLE 3

Compounds effective and toxic doses as determined in the EAE prevention model

| No. | Structure | EAE ED$_{50}$ | LD$_{50}$ | SM |
|---|---|---|---|---|
| 1 CX-5461; RAM-0; POL1-I | 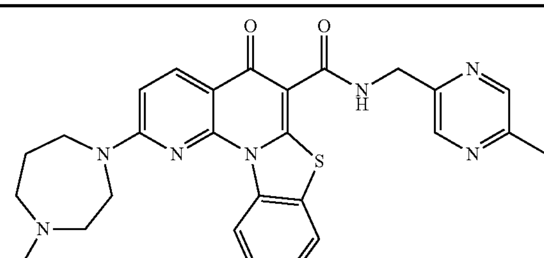 | 12.5 mg/kg | 25 mg/kg | 2 |

TABLE 3-continued

Compounds effective and toxic doses as determined in the EAE prevention model

| No. | Structure | EAE | | |
|---|---|---|---|---|
| | | $ED_{50}$ | $LD_{50}$ | SM |
| 10 RAM An | | 3 mg/kg | 30 mg/kg | 10 |

Compounds 2 and 9 were not tested; Compounds 3-7 were found relatively toxic during these preliminary studies.

It is shown in Table 3 that Compound 10 exhibits a substantially superior therapeutic index compared to CX-5641 (Compound 1).

Figure 7:
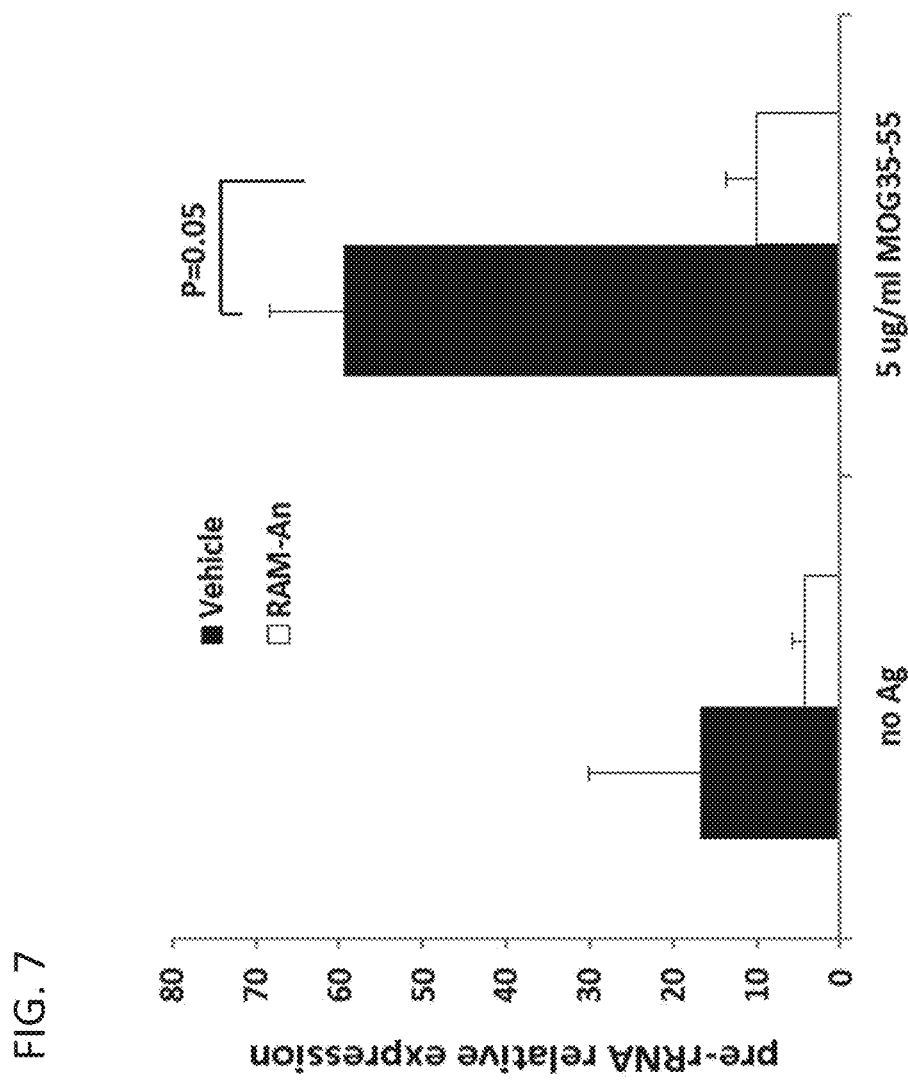
FIG. 7 is a graph showing mRNA levels of pre-rRNA in splenocytes isolated from spleens of EAE mice treated with 12.5 mg/Kg Compound 10 (RAM-An) for 17 days following immunization with MOG 35-55, as compared to vehicle-treated control mice. Bars represent mean±SEM.

The effects of Compound 10 in the EAE mouse model were accompanied by suppression of pre-rRNA transcription. As shown in FIG. 7, treatment with Compound 10 resulted in a significant decrease (5.9 folds) in pre-rRNA mRNA levels expressed by splenocytes 17 days following immunization, as compared to treatment with vehicle-control (p=0.05).

Figure 8A:
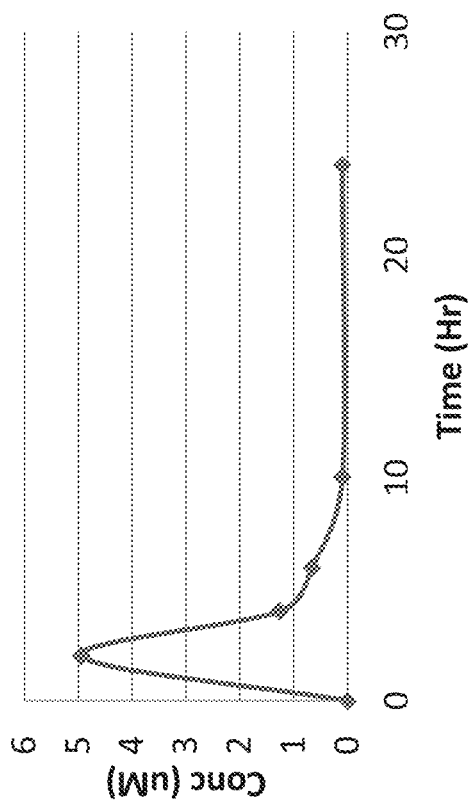
FIGS. 8A-B present graphs showing the time-dependent profile of Compound 10 (FIG. 8A) and Compound 1 (FIG. 8B) in mice serum following administration by oral gavage.
Figure 8B:
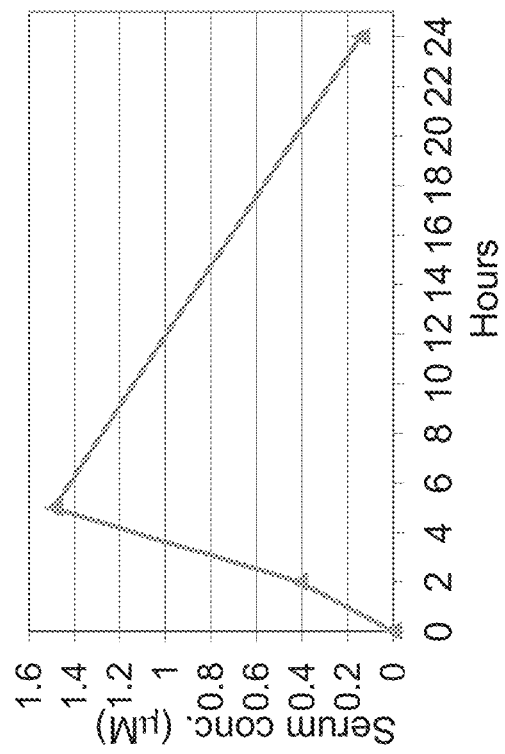

FIGS. 8A-B present the data obtained in the bioavailability assay for Compounds 1 and 10. As shown therein, Compound 10 exhibits a more favorable pharmacokinetic compound to Compound 1, as reflected by the higher Cmax, the lower Tmax, and the faster clearance.

Figure 9A:
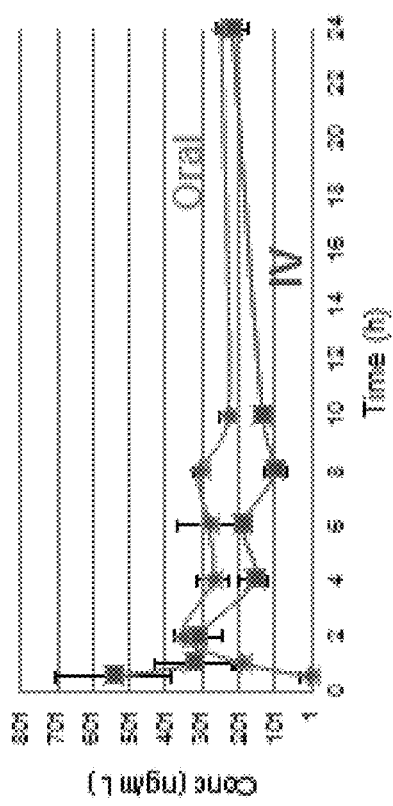
FIGS. 9A-B present graphs showing the bioavailability profile of Compound 10 for 24 (FIG. 9A) and 168 hours (FIG. 9B) in the serum of naive C57Bl female mice following single administration of 12.5 mg/kg by IV and of 12.5 mg/kg by oral gavage.

FIG. 9A presents the data obtained in the bioavailability assay for Compound 10 after oral and IV administration up to 24 h. As shown therein, Compound 10 is rapidly absorbed following both oral and IV administration; Compound 10 reaches maximal concentration after 0.5 h following IV administration and maximal concentration after 2 h following oral administration in healthy C57B6J, female mice.

Figure 9B:
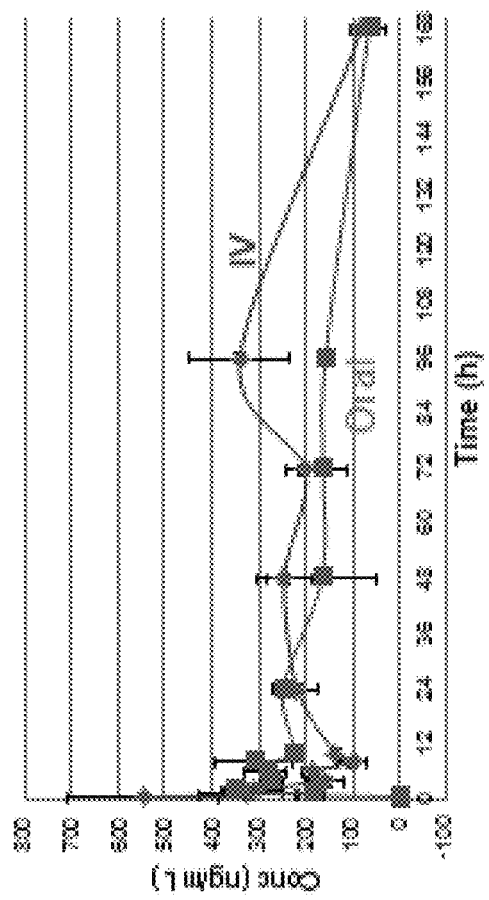

FIG. 9B presents the data obtained in the bioavailability assay for Compound 10 after oral and IV administration up to 168 h. As shown therein, the calculated bioavailability of Compound 10 is AUC(oral)/AUC(IV)=72%.

Compound 10: Single Dose Toxicity

The toxicity of oral administration of a single dose of Compound 10 was tested in naïve mice using range from 3 mg/kg to 500.0 mg/kg. No effect on survival was observed at 24 h. No behavioral changes were observed at 24 h.

Compound 10 Chronic Toxicity

Compound 10 was well tolerated when administered to EAE mice every alternate day until disease onset at a dose of 30 mg/kg. No effect on survival was observed. No behavioral changes were observed.

Example 4

Experimental Methods

Cell-Free Polymerase I Transcription Assay:

Cell-free Pol I transcription assay was performed according to Drygin et al. (2010). Briefly, a reaction mixture consisting of 8 units of HeLa scribe nuclear extract (Promega) in transcription buffer and $MgCl_2$ (4 mM) was combined with POL1-Inhibitor (200 nM) and 10 mg/ml α-amanitin (Sigma) for 20 minutes at ambient temperature. Following, 10 ng DNA template (GENEWIZ, Inc.; http://www(dot)genewiz(dot)com(dot)cn) corresponding to the (−160/+350) region on human rDNA was added and the reaction was incubated for 5 minutes at ambient temperature. Transcription was initiated by adding rNTPs mix to a final concentration of 1 mM and the reaction was incubated for 1 hour at 30° C. Afterward, DNase I (Ambion kit) was added and the reaction was further incubated for 25 minutes at 37° C. DNase activity was terminated with adding an inactivation solution according to the manufacturer's protocol. The samples were then subjected for RNA isolation (following the same procedure described in Example 3 hereinabove). Pellets of RNA were re-suspended in DEPC-treated double distilled water and subjected for reverse transcription by a High capacity kit (Applied Biosystems). The resultant transcripts were analyzed by qRT-PCR in a Light cycler 480 system using primer pairs (Sigma) and probe for real-time PCR. Primers were designed from the Assay Design Centre of the Universal ProbeLibrary (Roche Applied Science, USA) as follows: Pol I forward primer: tcaggcgttctcgtctcc (SEQ ID NO: 71), Pol I reverse primer: caccacatcgatcacgaaga (SEQ ID NO: 72).

Transcription by polymerase II from CMV promoter was tested similarly using the template provided HeLa scribe kit of Promega, further processing as described above and analysis of transcript with template specific primers: POL II forward primer: ctatgcgcacccgttctc (SEQ ID NO: 73), Pol II reverse primer: gtagcgaagcgagcagga (SEQ ID NO: 74). Probe ID: #70, cat. no. 04688937001 (Roche), was used for both reactions.

Figure 10:
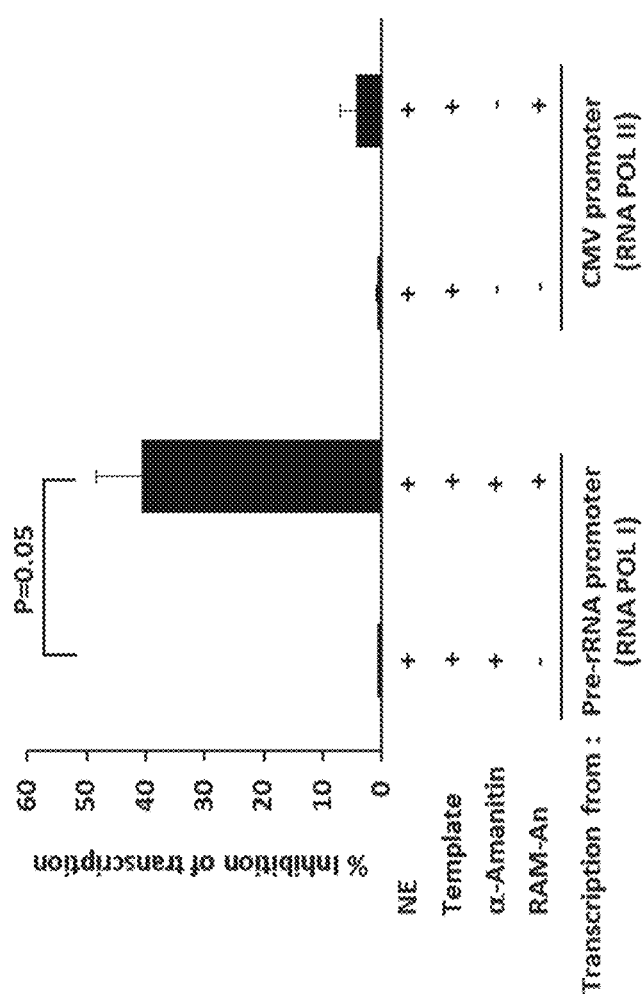
FIG. 10 is a graph shown effect of Compound 10 (RAM-An) on POL1 activity in cell-free transcription assay.

Experimental Results:

The analysis of the POL1 cell free assay showed that addition of 200 nM Compound 10 resulted in about 40% inhibition of Pol I transcription from the pre-rRNA promoter (p=0.05, FIG. 10), whereas Compound 10 only minimally affected Pol II transcription by 5% from the CMV promoter. These data indicate that Compound 10 directly targets the Pol I machinery.

In addition, viability, proliferation and apoptosis of splenocytes isolated from mice 14 days post immunization and incubated for 72 h with MOG 35-55 were assessed by XTT, BrdU and flow cytometry (Annexin V and propidium iodide double staining) assays, respectively. The results indicated that treatment with Compound 10 (Ram-An lot no. 589.555) reduced viability, suppressed cell proliferation specifically more affecting cells with high proliferation index, and induced apoptosis in CD4+ lymphocytes, as compared to treatment with the vehicle (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound represented by Formula Ia or Ic:

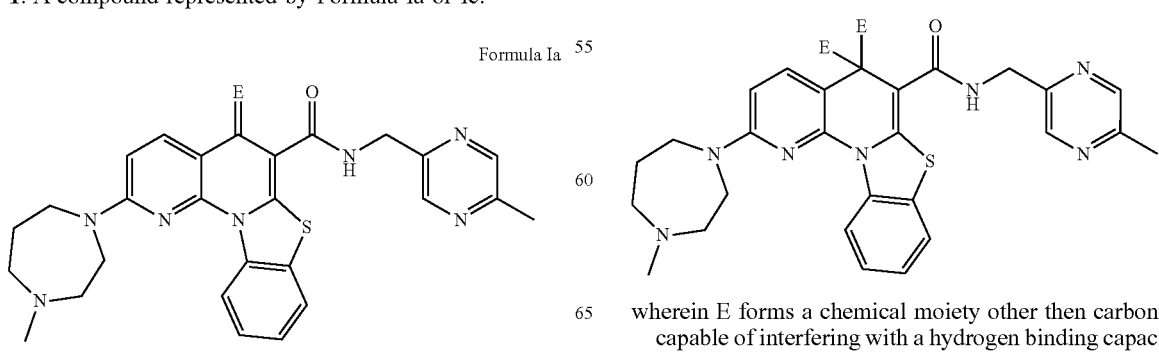

wherein E forms a chemical moiety other then carbonyl, capable of interfering with a hydrogen binding capacity of the compound.

2. The compound of claim 1, represented by Formula Ia, wherein E forms a chemical moiety selected from the group consisting of thiocarbonyl and a substituted or unsubstituted imine.

3. The compound of claim 1, represented by Formula I, wherein E forms a substituted or unsubstituted imine, the compound being represented by Formula Ib:

Formula Ib

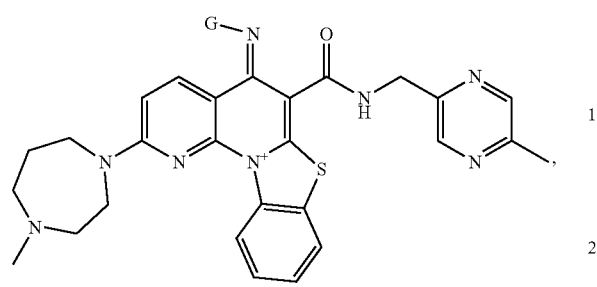

wherein G is selected from the group consisting of hydrogen, alkyl, cycloalkyl, aryl, heteroaryl, heteroalicyclic, alkoxy, thioalkoxy, thiol, hydroxyl, aryloxy, and thioaryloxy.

4. The compound of claim 3, wherein G is aryl.

5. The compound of claim 1, being selected from:

Compound 3

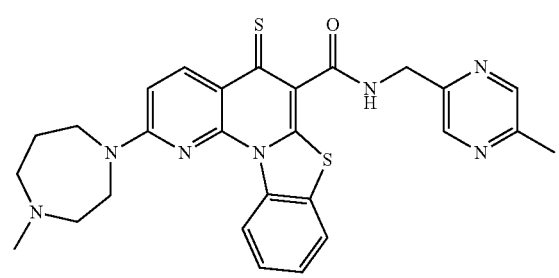

Compound 4

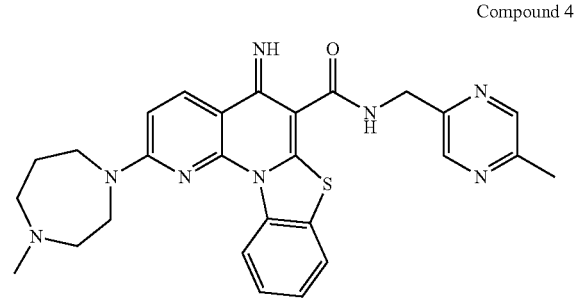

Compound 5

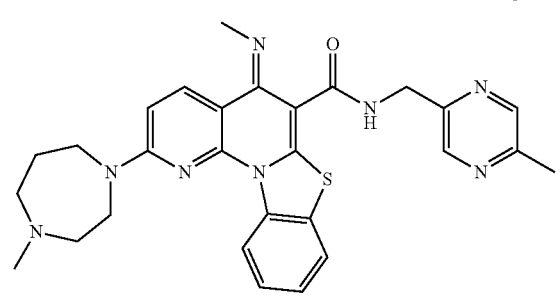

Compound 6

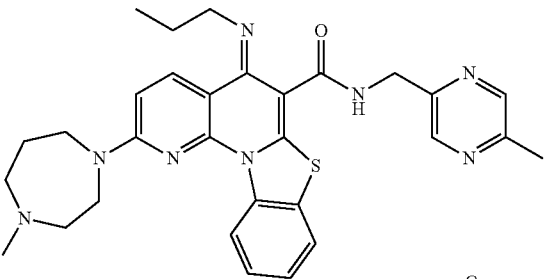

Compound 7

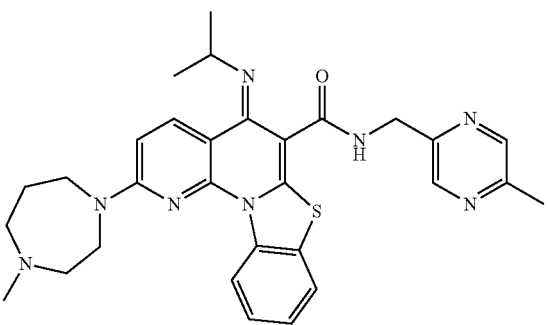

Compound 8

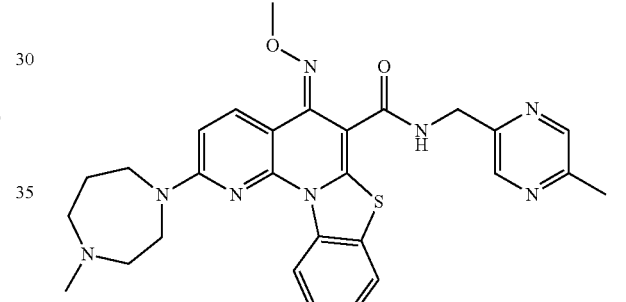

Compound 10

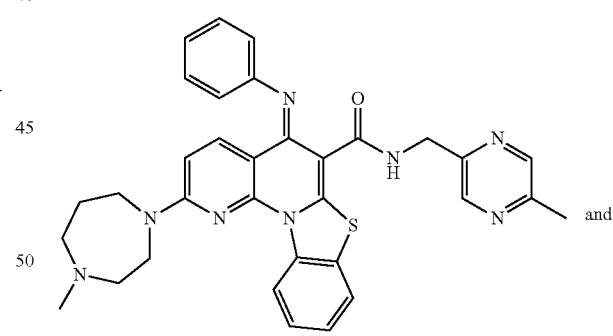

Compound 11

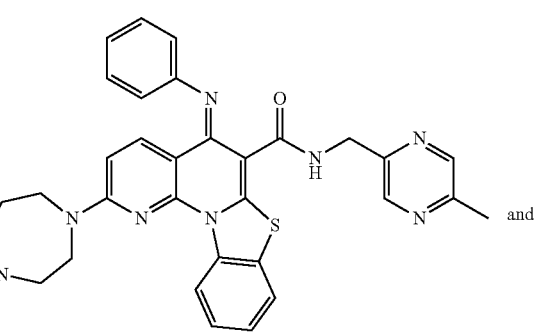

and

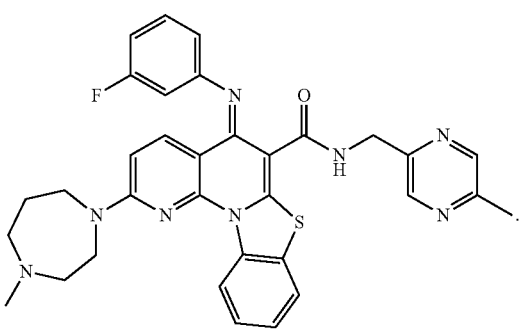

6. The compound of claim 1, being:

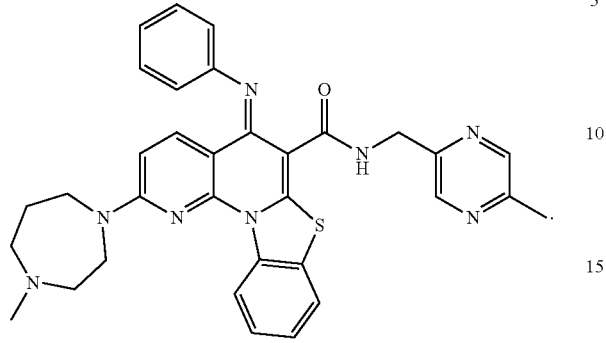

Compound 10

7. A method of treating multiple sclerosis in a subject, the method comprising administering to the subject a therapeutically effective amount of the compound of claim 1.

8. The method of claim 7, wherein said multiple sclerosis is a relapsing-remitting multiple sclerosis (RRMS) or benign multiple sclerosis (BMS).

9. The method of claim 8, wherein treating said multiple sclerosis comprises changing the course of the disease from said RRMS to BMS.

* * * * *

SEQUENCE LISTING

```
<160> NUMBER OF SEQ ID NOS: 74

<210> SEQ ID NO 1
<211> LENGTH: 296
<212> TYPE: DNA
<213> ORGANISM: Artificial sequence
<220> FEATURE:
<223> OTHER INFORMATION: Affymetrix ProbSet target nucleotide sequence

<400> SEQUENCE: 1
gatgaccaga tcatcaactg gctgctagaa ttccgttctt ctgtcatgta cttgacaaaa      60
gactttgagc aacttatcag tattatattg agattgcctt ggttgaatag aagtcaaaca     120
gtagtggaag agtatttggc ttttcttggt aatcttgtat cagcatagac tgttttcctc     180
agaccgtgtc tcagcatgat tgcttcccat tttgtgcctc cccgagtgat cattaaggaa     240
ggcgatgtag atgtttcaga ttctgatgat gaagatgata atcttcctgc aaattt         296

<210> SEQ ID NO 2
<211> LENGTH: 476
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 2
tttccttcaa cttgtggatg caggcaaggt ggatgatgcc agagctctcc tacagagnat      60
gtggtgcnaa ttgctgaaca aacccgatt tgttgttgt tcctccttag gaattctagg       120
aaacaaggaa aggcatcaac tgtgaaatct gtgttagaat tgattcctga attaaatgaa     180
aaggaagaag catacaattc cctcatgaaa agctatgtct cagagaaaga tgtcacatct     240
gctaaagcac tgtatgaaca tttgactgca aagaatacaa aattggatga tctgtttcta     300
aagcgttacg catctttgct gaagtatgct ggagagcctg tcccttcat tgaaccccct      360 gaaagctttg aattttatgc acagcagcta agaaaattga gggaaaactc ttcttgaaat     420
aaccaggcga tactttgttt tgtatatatt tgtgattctg tgtctacatg ttattt         476

<210> SEQ ID NO 3
<211> LENGTH: 533
<212> TYPE: DNA
<213> ORGANISM: Artificial sequence
<220> FEATURE:
<223> OTHER INFORMATION: Affymetrix ProbSet target nucleotide sequence
```

```
<400> SEQUENCE: 3
aggcttagca ggatgggcgc agtggctcac gccactaatc ccaacatttt aggaggccta      60
ggcaggagca atcacttgtg cctgggagtt ctagactagc ctgggcgaga cttcatctct     120
acaaaaaaag caacaacgac aaaaaaaatt agccaagcat agtggcacac ccctgtagtc     180
ccagctactt gggaggctga ggtgggagga ttgcttgaac ccaagaggtc gaggctgcag     240
tgagccaaga ttgtgccact gcactccagc ctgggtgaca gagcaggacc ctgtctctat     300
tttataaatt aaaaaaggct gggtgtggtg gctcacaccc ataatcccaa cactttggct     360
cagcagattg cttgaaccca ggaattcaag tccaatctgg caacatggg gaaaccccag      420 ctctacaaaa aaaattagcc tggtgtggtg gcacatgcct gtagttccag ctactcagga     480
ggctgaggtg ggagaatctc ctgagcctgg aaggtccagg cagtgagcca aga            533

<210> SEQ ID NO 4
<211> LENGTH: 411
<212> TYPE: DNA
<213> ORGANISM: Artificial sequence
<220> FEATURE:
<223> OTHER INFORMATION: Affymetrix ProbSet target nucleotide sequence

<400> SEQUENCE: 4
ccaggcatat gacatggatc cccctgggga accaggctga tctctttcca gagggcacta      60
tccgaccagt gcatgatgat atcctcatcg ctcagctgcg gcctggccaa gaaattgacc     120
tgctcatgca ctgtgtcaag ggcattggca agatcatgc caagttttca ccagtggcaa      180
cagccagtta caggctcctg ccagacatca ccctgcttga gcccgtggaa ggggaggcag     240
ctgaggagtt gagcaggtgc ttctcacctg gtgttattga ggtgcaggaa gtccaaggta     300
aaaaggtggc cagagttgcc aaccccggc tggataccttt cagcagagaa atcttccgga     360
atgagaagct aaagaaggtt gtgaggcttg cccggggttcg agatcattat a              411

<210> SEQ ID NO 5
<211> LENGTH: 441
<212> TYPE: DNA
<213> ORGANISM: Artificial sequence
<220> FEATURE:
<223> OTHER INFORMATION: Affymetrix ProbSet target nucleotide sequence

<400> SEQUENCE: 5
gcacgaggaa gaccataccc taggaaattc tctacgttac atgatcatga agaacccgga      60
agtggaattt tgtggttaca ctacgaccca tccttcagag agcaaaatta atttacgcat     120
tcagactcga ggtacccttc agctgttgga gccatttcag agaggcctga atgagctcat     180
gaatgtctgc aacatgtgc ttgacaagtt tgaggccagc ataaaggact ataaggatca      240
aaaagcaagc agaaatgaat ccacattcta gtcctttatg cagtatacaa ggagaactgt     300
cctgtaggat attctcttcc tgatggtgca gaacccagaa ttagaagttt gtggttacag     360
catactctgt ccttcagaaa ggcgtgattc tagctgttga ccccttgcag ctgttggaat     420
ctctgcaaga acctctgtat t                                               441

<210> SEQ ID NO 6
<211> LENGTH: 528
<212> TYPE: DNA
<213> ORGANISM: Artificial sequence
<220> FEATURE:
<223> OTHER INFORMATION: Affymetrix ProbSet target nucleotide sequence
```

<400> SEQUENCE: 6

```
ggtttggttt tgtagacttc aacagtgagg aggatgccaa ggaggccatg gaagacggtg        60
aaattgatgg aaataaagtt accttggact gggccaaacc taagggtgaa ggtggcttcg       120
ggggtcgtgg tggaggcaga ggcggctttg gaggacgagg tggtggtaga ggaggccgag       180
gaggatttgg tggcagaggc cggggaggct ttggagggcg aggaggcttc cgaggaggca       240
gaggaggagg aggtgaccac aagccacaag gaaagaagac gaagtttgaa tagcttctgt       300
ccctctgctt tccctttttcc atttgaaaga aaggactctg gggttttttac tgttacctga      360
tcaatgacag agccttctga ggacattcca agacagtata cagtcctgtg gtctccttgg       420
aaatccgtct agttaacatt tcaagggcaa taccgtgttg gttttgactg gatattcata       480
taaacttttt aaagagttga gtgatagagc taacccttat ctgtaagt                    528
```

<210> SEQ ID NO 7
<211> LENGTH: 488
<212> TYPE: DNA
<213> ORGANISM: Artificial sequence
<220> FEATURE:
<223> OTHER INFORMATION: Affymetrix ProbSet target nucleotide sequence

<400> SEQUENCE: 7

```
aagagtcccc atcaagactt cttccctgag tcaagtacag cgtagcatag tcctccaccc        60
acccaacctc tctgcctggc cagggtcctg gccctgccac tgtgtggcga ggtgtccttc       120
tagaccacat cagccccaag gctgggagca gtcgctccag ggccgcagca gttcactccc       180
acacatagaa cccaggtcac tgctggggcg attgaacagg ttgcctggct tttctctgct       240
gtcagtttgg tgtggaggcc tatgttctgc cccatacacc ccacaggccc tgcttatggg       300
aaggaacaca ggcctccagc ccagaggact gtgccgccct gttcttggcc gtccacgttt       360
cctctcccctc tagcaccagc aatacatttc cctggcatgg acagaaaaga cagagaggac      420
ttgtacaaag gctttgtaaa accagaggct agcttctatc tttgtctact gttatttcag       480
ctcagggc                                                                488
```

<210> SEQ ID NO 8
<211> LENGTH: 566
<212> TYPE: DNA
<213> ORGANISM: Artificial sequence
<220> FEATURE:
<223> OTHER INFORMATION: Affymetrix ProbSet target nucleotide sequence

<400> SEQUENCE: 8

```
gtggccgccg gcagtgaaga agatcacaaa ctgggcaccc tgtccctccc gctgcctcca        60
gcccagacct cagaccgcct ggcaaagcgg aggaagatta cctagacgca tgctttccag       120
acagggcgtt ttggctgcat cacagccact ggctggtcct attcatttcc attttatgt       180
atgttttgaa aagaaaaggt ccggggatgg tggctcacac ctgaaatccc agcactttgg       240
gaggccgagg caggaagatc attgagctca ggagtttgaa accagtctgg acaacatggg       300
gagaccccat ctctaccgga ggaaaaaaaa aagagtcagg cctggtggtg tgcgcctgta       360
atcccagcta ctcgggaggc tgaggcagga cgattacttg agcttgggaa atcaaggttg       420
cagtgagcta tgattgtgtg ccacactcc atcctgggtc acagagtgag accttgtctc       480
aaaaaagtaa cataaggaaa aaagaagcct tgctttagca caggtatgaa gccagaagcc       540
agcatctcaa ctgtgcttgt cttatg                                            566
```

<210> SEQ ID NO 9
<211> LENGTH: 459
<212> TYPE: DNA
<213> ORGANISM: Artificial sequence
<220> FEATURE:
<223> OTHER INFORMATION: Affymetrix ProbSet target nucleotide sequence

<400> SEQUENCE: 9

```
gggaacatca acggtggaaa tcacttggga tgagactgat catgaaagaa ttacaatgct      60
caacaggaag tttaaaaagg aagagctttt ggacatggat tttcaagcct acttagcttc     120
ctctagtgaa gacgaagagg agatagaaga ggagctacaa ggtgatgatg gagtcaatgt     180
agaagaagat gggaaaacaa agaaaagtca gaaggatgat gaagagcaaa ttgctaaata     240
caggcagctc ttgcaggtta ttcaagaaaa agaaagaaa ggcaaagaaa atgatatgga      300
aatggaaatt aaatgggttc caggtcttaa agaaagtgca gaagagatgg tcaaaaacaa     360
attggaagga aaggataaac tgaccccttg ggaacaattt ttagaaaaga gaaagagaa      420
aaaaagactg aaaaggaaac agaaggctct tgctgaaga                            459
```

<210> SEQ ID NO 10
<211> LENGTH: 387
<212> TYPE: DNA
<213> ORGANISM: Artificial sequence
<220> FEATURE:
<223> OTHER INFORMATION: Affymetrix ProbSet target nucleotide sequence

<400> SEQUENCE: 10

```
gagtcttaga ttttgccgga tgcactaaga atataactgc ttggaaatac ttggcaaaat      60
atctgaaaaa tatcttaatg ggaaaccacc ttgcgtgggt tcaagaagag tggaactcca     120
ggaaaaactg gtggccaggg tttcatttca gctactttttg ggcaaaaagt gattggaagg    180
aagatacagc tttggcctgt gagaaagctt ttgtggctgg tttactgtta ggaaaaggtt     240
gtagatattt ccggtatatt ttaaagcaag atcaccaaat cttagggaag aaaattaagc     300
ggatgaagag atctgtgaaa aaatacagta ttgtaaatcc aagactctga tactgaattt     360
tagttatttc acagttgtag ctacaca                                         387
```

<210> SEQ ID NO 11
<211> LENGTH: 530
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (452)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t

<400> SEQUENCE: 11

```
gaaagtgaga cgacattgag aaaatgaaat agaaactttc tggaNaaata ttttaatagt      60
gataataaca tcagatttta atataacatt ccagagaatt gtggaaaata ctgcatatat     120
atgtatagac tctgacacat atttacatat atatcaagtg tgcttagaaa aatgtatatt     180
gtaaagcagg tgagcttcat ttgattttat ttttcagagt atgaacattc taagagaaag     240
ttaaaacaat agcaaattgt ataattgtat ccagaaatgt atactcatcn tattttaaag     300
ctaaatttat tttttaaact agatcccttc attattcttt atgccccaga gtaaatccca     360
gatggatcaa agatctaaac ataatctttc atatgtaaaa atataaaagt attagtagaa     420
aacanatatg aatgctttga tgatcttgga annnnaangt caattttttgc agcatatggt     480 ggacaaagga gataaatttct ttaatgtatc aatagctctt gcaaagcaaa              530
```

<210> SEQ ID NO 12
<211> LENGTH: 407
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t
<400> SEQUENCE: 12

```
ccctcccagg agttgactcc ggatgcatgc gcccagggcg tcccatcaga gnnncgnnng      60
atgctccgtg actacatggc caagctacca ccccagaggg acaccccagg ctgtgccacc     120
acacctcccc actcccaggc ctccagcgtc cgggccactc gctcccagca gcacacaccc     180
gtcctctcta gctctcagcc cctccggaag aagcctcgaa tgggcttctg aggacacaag     240
gtgggctgcc ctcaagcccc agagagcccc tcatccttcc tctgggacca gatgtgcctt     300
ccacagttga aacttgagaa gcagagctcg ccaccttctg gaggccactg tgatgatgag     360
ccaagcaatt tggagccaag ttgaagggac agggcaacaa aatacag                  407
```

<210> SEQ ID NO 13
<211> LENGTH: 427
<212> TYPE: DNA
<213> ORGANISM: Artificial sequence
<220> FEATURE:
<223> OTHER INFORMATION: Affymetrix ProbSet target nucleotide sequence
<400> SEQUENCE: 13

```
gtatgggtca tttcaaagag ggcttatgag gctgtgaaac ccagagctct taacgctgtg      60
accaaagatg gaagttctct ataggaagcc atagcactcc taatgtttgg tgctatgttt     120
tcctgaggag atataaaacg taataatcca tgattgttgc catgtgagag ttttaaaggt     180
taatcaaaat ttctcttctt cagggcaaac ttgaagataa atcttttgac tccagctctt     240
tagaggatct aaagtgacct tgatggacag tggaagaaat cacaacatgg aattcctcga     300
ataacaattt attgacttta aataattttg tctaatgcta catatacaca attaaaaaac     360
ctttacacta tttctagaaa gtcagcatgt attttttggct cgaagtttct ctagtgtttt     420
ctgtgga                                                              427
```

<210> SEQ ID NO 14
<211> LENGTH: 413

<212> TYPE: DNA
<213> ORGANISM: Artificial sequence
<220> FEATURE:
<223> OTHER INFORMATION: Affymetrix ProbSet target nucleotide sequence

<400> SEQUENCE: 14

```
ggagcactac aaaaagctgg ccgaggagca gcaaaagcag tacaaggtgc acctggacct      60
ctgggttaag agcctgtctc cccaggaccg tgcagcatat aaagagtaca tctccaataa     120
acgtaagagc atgaccaagc tgcgaggccc aaaccccaaa tccagccgga ctactctgca     180
gtccaagtcg gagtccgagg aggatgatga agaggatgag gatgacgagg acgaggatga     240
agaagaggaa gatgatgaga atggggactc ctctgaagat ggcggcgact cctctgagtc     300
cagcagcgag gacgagagcg aggatgggga tgagaatgaa gaggatgacg aggacgaaga     360
cgacgacgag gatgacgatg aggatgaaga taatgagtcc gagggcagca gct            413
```

<210> SEQ ID NO 15
<211> LENGTH: 514
<212> TYPE: DNA
<213> ORGANISM: Artificial sequence
<220> FEATURE:
<223> OTHER INFORMATION: Affymetrix ProbSet target nucleotide sequence

<400> SEQUENCE: 15

```
gcaggtgtta cagttgtcct tgtggataaa gaaaatatta caacacacc aaagcatttt       60
agaaaggatg ttgatgttgt ttgtgttgat atgagcatag aacagaagtt accaagaaag     120
cctaaaacag acaaatttca ggtacttgct aagtcacatg cacataaatc agaagccctg     180
cacagtaaag ttagggagaa aaagaataaa aagcatcaga ggaaagctgc atcctgggag     240
agccagcggg caaggacac cctgcctcag tcagaatccc accaggagga gtcctggctt      300
tctgtgggtc caggggtga aattacagaa ctaccagcat ctgctcataa aaacaagtct      360
aagaaaaaaa agaaaaagtc cagtaaccgg gaatatgaga cactggccat gcctgaagga     420
tcgcaagcag gcagagaggc cgggactgat atgcaggaat cccagcctac tgtgggcttg     480
gatgatgaaa ctccacaact actaggacct actc                                 514
```

<210> SEQ ID NO 16
<211> LENGTH: 529
<212> TYPE: DNA
<213> ORGANISM: Artificial sequence
<220> FEATURE:
<223> OTHER INFORMATION: Affymetrix ProbSet target nucleotide sequence

<400> SEQUENCE: 16

```
ccccgcttgg acacagtccg agtggaatgg gaagggaatg gtcaatccct gtcctggttg      60
tccaagtcgg gatctcagag gaaattgcag tgattccacg gttaggcccc ctggggggg     120
ctgccttccc ctcagcctct ccccacacca cccacccagc tgctgtcatt ccgctcactg     180
agctcttctt cattctcacc ctgatccctg ggggactcaa agccaaaact gcccaaagag     240
gaaagattga atcctaaagg ggatccttgc ccccatggga ggcccctac tagaaggacg      300
tgaaagcagc ttttggggga aactgaggca gtggggaaga cagagcagaa tgagccctca     360
ccctggctgg gggtccagca caggctgtat ctgcagaggg tcccagagga acgctggagc     420
caagagaagc cctgggaagg aggggtgggg aacgacatgc atgtgaggga tggcacactg     480
atgtgtttat gcacctgtac acaggagcgc atggccatgg ctttggaaa                 529
```

<210> SEQ ID NO 17

<211> LENGTH: 481
<212> TYPE: DNA
<213> ORGANISM: Artificial sequence
<220> FEATURE:
<223> OTHER INFORMATION: Affymetrix ProbSet target nucleotide sequence

<400> SEQUENCE: 17

| | | | | | |
|---|---|---|---|---|---|
| atggggtttc | agatctttgt | gacgaaatag | aatactgttt | catatttgaa | tcagagggct | 60 |
| tcttgttctg | agaaataggt | tcaaaatcat | tggaaccagg | aacaagaata | gcttattgtt | 120 |
| atctgtgata | acactgtttt | ctaaacacaa | ggattttctt | ttttattaat | atgcaacata | 180 |
| gacattgcca | taacagaata | ataaaccaca | tgtggggttt | taaaaatgaa | atttggctaa | 240 |
| taggagcaat | tcagctattt | ttctatacag | taattggtgt | gtggtataga | agaaaaacgg | 300 |
| gttcaaaccc | cacttctgcc | acctaccagc | tatatggcct | tgaatgagtc | attcagcttt | 360 |
| aataaggttc | attttcttct | gtttaaaaag | acacaaaact | tgaaaatcag | ctttggccat | 420 |
| ctacctgaga | attagaaagt | ctgatttttg | gaattagaaa | tcatgattgt | aggctgggca | 480 |
| c | | | | | | 481 |

<210> SEQ ID NO 18
<211> LENGTH: 202004
<212> TYPE: DNA
<213> ORGANISM: Homo sapiens

<400> SEQUENCE: 18

| | | | | | |
|---|---|---|---|---|---|
| aagcttgcag | taagccgaga | tcgcgccact | gcactccagc | ctgggtgaca | gagggagact | 60 |
| ccatctcaaa | aaaaaagag | agaaagtaaa | ggaataaaag | aatggctacc | ccatagacgg | 120 |
| agcagccgtg | agggctgctg | gttgcccatt | tttatggtta | tttgttgatg | atatgctaaa | 180 |
| caaggagtgg | attttttcatg | cctcctcttt | ttagaccata | tagggtaact | tcttgatgtt | 240 |
| gccgtggcat | ttgtaaactg | tcatggtgct | ggtaggagtg | tagcagggag | gatgatggga | 300 |
| ggtcagtctt | gtctctattt | tggttttggt | gggttttggc | cagctccttc | actgcaacct | 360 |
| gttttatcag | caaggtcttt | atgactggta | ttttgtgctg | accttctatg | tcatcctgtg | 420 |
| acttagaatg | ccttaaccat | cagggaatgc | agcccagtag | tttcagcctc | attttttcccg | 480 |
| gctcctatttt | aagatggagt | tgctctggtt | cacacacctc | tgacatgatc | attgcccact | 540 |
| gcggcttcca | cctcccgggt | tcaagagatc | ctcctgcctc | accctcccaa | ggtgctggga | 600 |
| ctacaggtgt | gtgccaccag | ctcagctaat | ttttgtattt | tttgtagaga | tggtgttttt | 660 |
| ccatgttgcc | caggctggtc | tcaaactcct | gggctcaagc | aatccttctg | tctcagcctc | 720 |
| ccaaagtact | gggattacag | gcatgtccca | ccatgcccag | actaatattt | acttttaatc | 780 |
| agactaagat | agggttacta | cttgagttgc | tatggctcca | gctgaaagaa | agcccgtgca | 840 |
| gtcatatcac | gcgtaaacat | ttgctttatg | ctaaaaatat | ggtggacctg | gcattacagc | 900 |
| tattacaaat | ctcctaagat | gtctcgggta | gtgtattagt | tacttttcat | actgctatga | 960 |
| agaaatactg | gaaactgggt | aatttataaa | gaaaagagg | tttaatgtac | tcacagttcc | 1020 |
| acaaggctgg | agaggcctca | gaatcatggt | ggaaggcaaa | gaaggagcaa | aaaggtatgt | 1080 |
| cttccatggc | agcaggcaag | agagcacgtg | cagggaaact | gcccctttata | aaaccatcag | 1140 |
| atttagtgag | atgtattcac | tatcacgaga | acagtatggg | aaaaacctgc | ccccatgatt | 1200 |
| cgattacctc | ctaccgggtc | cctcccacga | cacatgggga | ttatgggaac | tacaattcaa | 1260 |
| gatgaaattt | gggtggggac | gcagccaaac | catatcgggt | agcaacaacc | tagggtcagt | 1320 |
| tttgcaggtg | gtaaagccat | ttaccaagat | agttgtgggt | aaagaagggc | agatttatta | 1380 |

```
gagaaattgt gaaaatatgt tgcagtgggc agctcagcag agaaggggct acctgcaaag    1440
aggcaagggc tggaggaaag ttttataggg tcctgctgaa gggtgctacg tgtggaatga    1500
ggtcattgtg cccgcaggtt gtttgtgatt agctgtctct aacaattgtt catacaataa    1560
ttgttcatta ttgttctcaa cttggggctc tccccaacct ggggacccct ccttattgtt    1620
gcttacttat caggtctcca cataaaggtg tggaaacttc attcattcat atcttcaaca    1680
caaattgtag gtagcctgtt ttttaaaaca tttattcaac aaatatttag tccaagccac    1740
tattacttac taccttctct actattgtat ggactttaa ctatctctga cactattcac     1800
tattcttcca cattctctat tatttatacc tatggtaaaa tttgccagtt tgaccataca    1860
actaatactc acagggaata tatagagtct agaagaaaat atacaggtcc ttaaaggctg    1920
ccctgccaac aaaaccataa cgcaggaaca aacatcacaa ctatgccaaa taatcaatcc    1980
tacaatgtcc aaaattttac tttaaaactg gaattaccag acttcctttc tgcattaacc    2040
agtttaacta gacagtaacg aaatattcct actttatgct gtgatagttt gtttgtttgt    2100
ttgtttgttt atttatttat ttatttattt aagacagagt ttcgctcttg ttgcccaggc    2160
tggagtgcag tggcacgatc tcagctcacc acaacctccg cctcccaggt tcaagcgatt    2220
ctcctgcctc agcctcccga gtagctggga ttacaggcat gtaccaccac gcccgggtaa    2280
ttttgtattt ttagtagaga cggggggttt ctccatgttg gtcaggctgg tctagaactc    2340
cagacctcag gtgataccc tgcctcagcc tcccaatgtg ctgggattac agctgtgaag     2400
ccaccgcgcc cggctgctgt gatagttgag atgtaaacca aaataaaat tctaagccac     2460 ccaatccgac tgaatggacc cttcctgttg agcaaggaca ttccaaagta aactgaaaag    2520
accagcttag gccatgatgg gaaggggagg tgtcaacatg cctcattcta ccttcctccc    2580
tctggaatcc agacacaact gaccagcatt aacattaaaa cagagatctt aagctgggca    2640
cagtggctca tgcctgtaat cccagcactt gggaggcca aggtgggatc acctgaggtc      2700
agaagttcaa gaccagcctg ccagtatgg tgaagccatg tctctactaa aaatacaaaa     2760
ttagccggac attgtggtgc acgtctgtca tcccagcaag gcaggcgaat cacttgaacc    2820
caggaagcag aggttgcagt gagccaggat catgccattg cactccagcc tggtcaacag    2880
agcgagactc cgcctcatta aaaaaaaaa aaaaaaaaa ttagccgggc gtggtggcgg      2940
gcacatgtag tcccagctac tagggaggct gaggcaggag aatggtgtga accagggagg    3000
cggagcttgc agtgagccga gattgtgcca ctgcactcca gcctggacag aagtgcattt    3060
cataatgcat tttaattgca ttagcagtga tttaatttt ttagatgcta aaacttatgg     3120
gtgaaagtgg attaaatgta gccaaatgca acatcaaaat cttcaggcac aaaaacccat    3180 taacttttc atactctcag aaggtgaacc taatttcaaa tgaaagctgc ctccagaata     3240
tattgttaag cgtattctag atataattca ttttggcaaa catactgtag aaattcacat    3300
aacattttac tgtactaaaa gtaaattgcc catgtaacaa aaaatatctt ttcagagctt    3360
gaaatgaatt ttaaaggatg actgatggtc cctggaagag aaacagtaaa caaataaggt    3420
ttgtagcaat gatgtatgag ttagaaattg cagttccaga tgatctcttt attaaagaga    3480
cgatctacac ttaatttgat caagtgttat gaacatagtt catgttaagt ctccattaa     3540 atacaacctg aaataccaaa gttaattttc ttttctttct ttcttttttt ttttttttag    3600
aaggagtctt gctctgttgc ccttcctgga gtgcagtgac gtgatcttgg ctcactgcaa    3660
cctccacctc ctgggcttga gcgatcctac tgcctcagcc ccccaagtag ctgggaggac    3720
```

```
aggcgcaagc cacggcactc agctaatttt tgtattttc gtagagatag ggtttcacca    3780
tgttgcccaa tttggtctcg aactcctgag ctcaagtgat ccgcccgcct tggcctccca    3840
aagtgctggg attacaggca tgagccaccg tgcctggcca gaaaattgta aacacacaca    3900
aactctcaag tggcctaatt ccctctcacc aaaccaatca aatacagat aaaagagaat     3960
aacttgtgtt cattttgta caaacaaaaa agatataaat tgtgaatgat gcatgatttt    4020
taattacaag taaactgggc aaatgcttct gcattattta aagctaaaag gtgatcagtg    4080
gaaactttcc tctgttagta ctctaatact ttttatattt atcggctcac tacaacctgt    4140
gcctaccagg ttcaagcgat tctcctgtct cagccacctg agtagccgag accacaggca    4200
cgcactacca tgtccggcta attttgtatt tttaatagag acagggtttc accgtgttgg    4260
ccatgctggt cttgaactcc tgacctcaac cgatccgcct gccttggcct cccaaagttc    4320
tgggattaca agcgtgagcc acagcgccca gccttattat aattgttact atttaaatct    4380
cttttgctct ctccttcaag agagacctca tcccattcag ttgcttccat ttatttattc    4440
atcttctgcc tcctgggctc gagagatcct ccagcgtgag tctcccaagt agctgggact    4500
acaggctcac accaccaagc ttggctaaat tttgtaggtt ttggagagac aggctcttgc    4560
cacgttgcct aggctggtct caaactcctg ggctcagatg atccacctgc cttcgcctcc    4620
caaagcactg ggacatgagc caccacgccc agccgcaagt acttttacac aaaatgcaaa    4680
caccattctt ccatcataaa agtgatacca cagcttccgt gaagttttgc caggtagtac    4740
tcataattac cttgggtaaa cttttttgatg ttaaactgta tcttcttatt acgagttttt    4800
ccattgtatt aactgctttt acaacaacac aaataacaag ttattttaca aaccatttag    4860
aaatttctgt actatggtcc cagtaatgta aaatatatta atgcctatta cattcagata    4920
aattatacac ttgaaaacca catacttatg acttacagaa acttacataa acaaattata    4980
gaaattacat gctcaatttt taggtatata gtcttaaatt aagcttaaat atacattctc    5040
aagataaatt aacagttcag ggcttcacaa cttgaaatct gtggaagatg acattggaga    5100
caacagaact ctggtggaat cttagatgg aatttgccga aacttttttt ttttttttt     5160
tttgagatgg agtgtcgctc tgtcgcccag gctggagtgc agtggcgcaa tctcagctca    5220
ctgcaagctc tgcctcccgg gttcacgcca ttcttctgcc tcagcctccc gagtagctgg    5280
gactacaggc gcccaccgcc acgcccggct aattttttat attttagta gagatggggt    5340
tttactatgt tagccaggat ggtctcgatc tcttgacctt gtgatctacc cgccttggcc    5400
tcccaaagtg aaacttttct ttaaaataga gatgggatct tgctgtattg cccaggctgg    5460
tctcagactc cttgccttaa gcagtcctcc cacctcagcc tcctaaagtg ctgggattac    5520
aagcgtgaag cattcatcc aagtgaaact tcttgagatg gttacataat gtctaaatct    5580
gctggtgtag aagttaataa agtgtagaac tgaataacta ttaaatatta gatcaagttt    5640
ctcatgttta tcttaacgta taacgattta tcttaaagca ctgatttca caaaataaca    5700
tcagtgtgaa attggaaaag aagccaaata tttatttca cgtatctggg aaatgaggtg    5760
ctttagtcaa ctgaatctgc ccaaaactaa aaagcattaa ttaaaaagta cttaactcag    5820
aaattataaa aataggagac atcaataaaa tacattctac acagaatacg ccaaccatac    5880
actactcttt tttgataata aaaaatgtat ttactgagcc agttgtggtg gctcacgcct    5940
ataatcccag caccttggaa ggccaatgag agtggatcag ttgaggccag gagtttgaga    6000
ccagcctggc caacatggtg aaatgccgtc tctactaaga atacaaaaat gagccgggca    6060
cggtggcacg cacctgtaat cccaggtact ccgaaggatg aggcaggata attgtttgaa    6120
```

```
ctcaggaggt ggaggttgca gtgagccaaa atcatgccac tgcactccag cctgggtgac   6180
agagtgagtc tctgtctcaa aaaaaaaaaa aaaaaaaaag aaaaaaagtc agttgcagtg   6240
gctcacgcct gtaatcccag cactttggga ggctgaggca ggcggattac aaggtcagga   6300
gatcgagacc accctggcca acatggtgaa acctcctctc tactaaaaat gcaaaaatta   6360
ggctgggcac ggtggctcac acctgtaatc ccagcacttt gggaggccga ggcgcggaga   6420
tcacgaggtc aggagattga gaccatcctg gctaacacag tgaaaccctg tctctactaa   6480
aaatacaaaa aattagctgg atgtggtggc agcacttgta gtcccagcta cttgggtggc   6540
tgaggcagga gaatggcgtg aacccgggag gcagagtttg cagtgagccg agatcccacc   6600
actgcactcc agcttaggcg acagagccag actgtgtctc aaaaacagga agaaaacaa    6660 aagaaaattt ggactattgc caattacaaa tatttttaga gaagaattca aaacagtaac   6720
tgtggatgat ggaaacaata gttatgataa aagtctgatg aaacttccca gttcacaagg   6780
aaatttaatt acttatgtgc agcattttaa gacagtaatc agaatcatga ctgacagcat   6840
catatcaggg ccagcagact tttataaatt tcatacaatc ttcagaaata taacttttt    6900 tttttttttt tggatagatt ctacctttgt cacccaggcg ggagtgcagt ggcatgatct   6960
cggctcacta acctccgc atcctgggtt caagcagttc tcctgtctca gcctcccgag     7020
tagctgagat tacaggcatg tgccaccagg catggctaat ttttgtattt ttagtggaga   7080
cagggtttca ctctattagg ctggtctgga actcccgacc tcaggtgatc cacgtgcctt   7140
tgtctcccaa agtgctggga ttacaggcat gagtgacagt gcccagccat tcgtgacatg   7200
tttatacaaa tataacttta gcaaatattt agcataacta tcaaaattac aaatcatatt   7260
aaatttgtat aaatgtatgc aattttcgga acacgcatat caacaacata cccataaata   7320
taactgagat gagatctaat gtcacctcac ttgacagtgc cctcccatgc agtatcgcca   7380
catttgacaa tgcctgccca tttaatctac caaataaatc gaatcactta atacctctac   7440
aagatgagag atacattctt tagactcccc aagggatgca gctgaaaaaa atcccaaagt   7500
tagttttaag ccaaaaagac ttgatttagg attttgacac tggagaaacc catcaaagat   7560
gtcaagtttg aaaacacttg atcaaaacag aatcacaggt cactattaaa agagtattaa   7620
tttaaccaga gacttccaaa gcaatacaga aacttacatg gatataaaaa ccctaaccct   7680
tttaaaggtc agatttgcta agtgatcaaa agggtactt gaattgaatc gacacaggaa    7740
gagtgtgtac agggttatga gtgtaggcag gtggttactt tggtcatatc tccatttgcc   7800
acctgattac acatgagaat ggcatcttta ctcaccagaa agccagtatt ataggaggtg   7860
taggaggcat tcttggactt gagacaagaa cattgttgtg tagaaatttc attgactgtg   7920
ttaaaattat tctccatggg ctggagaaca cataacatgg cctttagaat gagacgggca   7980
ttgattggat gcaaggtctc cacacttact agctgtgtga cattggacag agtgcttcat   8040
cattccgaga ctcagttttt aaaggaaaaa caactaacta ccttgcaagc ttgctagcag   8100
gtttaagtgt aataatgtgt gggaatgact gcaccgtgac taacatgcag tgacagctta   8160
attaatgtta acccttatca ttatcatata agaatgtgag ttacataaga gaggagtcct   8220
gtcagttcgt tctctgctgt gtccccaaga ccatgaatca tggctggcat gtagtaggca   8280
tttaataata tatgttcaac aagtatttgg cagtcttgga gggcagaaaa ggaggtgggg   8340
aagattttta aataacattc tttaaaaagt cacattgtcc tacaataccg atttttcttg   8400
catatttagg aaattgaggg ttttttttcta aaacatgcgg acatatggga aataggatgc   8460
```

```
aacatttgca ctaatgtttc agacacagtt agaggtttcc aagagatttt gcgctgggga    8520
ggctgcttgc tacaagctcc caaagctctg ggaggacata gtattcattc ctccctcagc    8580
agaagcggtg aggcaagaag ctctggggag cacccagcgt tggactttta gcatagtgtg    8640
tcaggtcttc atagtttggg cccagggcac agagaagtca cagctctccg gcatcctgtg    8700
acctttaccc tctttgccaa gggaaaatgt ggcccaccaa agcaagaaac ttgagggcat    8760
gggtcacccc agccctggca tctgcccaga gcccgagaag gaaggaacaa tgatcctcca    8820
gctacctcac ggggctggca caggtgacca ctgccctggc atcacccagc tgtgtccggc    8880
agcctgaacc ccatctgtgg ggatgcgagg aggaaaatac aaaagtcctt aggtgaacac    8940
tgagaaggca gatgcagcag aaacctccag gccagaacta cccagtcttg gacctatggt    9000
ggagatagag catagctggc gatcatgtgt acttacactc taaggtcacc tggttgcact    9060
atggcctcat ctgtggctct gaaaatgaag atttggaagg agatcatcac agctaatgtt    9120
taacaagccc ctcctgtgtg ccaaatcatt caccccctcac cacaaccgaa tgagctaagg    9180
attctcatta tatatagttt atggagaggg aagtgcagac ataaagaggt gaattatctt    9240
acccagatca cacagctgat aagtggtgga ggcagaatag aatctaaaca gtgtggctcc    9300
ggagcccaca tgcattgatt cgacaagtgt ttattgagca cctgccgcgg acaaggcctt    9360
gtgtgattaa atagggttat aattagtaat ataaaaatga gaaatcacta atgctttta    9420 gacttaacat tttgttttt tgtaggtttc aggcacagaa ctgtatatcc aataatagtg    9480
aaatggatcc cactaattat gacagaaatg atgatacatt taaatgactt ggatgtttta    9540
taggtatgat ctcgtgaaat cttgagagaa actgaatgac gaatgaaact attgttcctg    9600
tttcacacag aagaaaactg aggttaaaag gggtaaagta attttgcatg gcatgaagta    9660
gaaattcaaa gtacaggaat ttgaacttgg ttctgtcctt ttctgaagcc cttgaccact    9720
atagactcaa acatcacctt gttttttccac tcattcaaca cttttttttt taaattatct    9780
aataggttgg cactcatcat gagccccgt tctcattctg caaatggtga agctctctat    9840
tgtcctgacc ccacagttcc tgtcccatga ccagggccag ctcaccaagg agctgcagca    9900
gcatgtaaag tcagtgacat gcccatgcga gtacctgagg aaggtgagtg agtgcagaca    9960
gatggggcct ggtgcccttg agcagttccc gggtctcagc tgccacacat ctcatagccg    10020
gtgatgctgg gggaagctta cgcagtcaca gtactggctt cttcctctctt ttcttccat    10080 acaagtggct tagggatggg gtagagtagt tgacttattt ggatgaaaac cactatcttc    10140
tgtcagaaac tcaaaggaa tcattgctgg catggtaacc taaagaaaaa caaccagaca    10200
agtgcccaac gacacttaaa aaggtgattt attatcttgc caagtttagg ctgggcatgg    10260
tgactcatgc ctctaatccc agcattttgg gaggctgagg ctggtggatc accgaggcc    10320 aggactttga gaccagcctg accaatatgg caaaacctcg tccctactaa aaatacaaaa    10380
attagccggg catggtggtg tgagcctgta gtcccagcta ctcaggaggc tgagacagga    10440
gaattgctta gattcaggag gtgggggttt tagtgggccg agatcacgcc attgcactcc    10500
agactgtgcg acagagcgag actctgtcaa aaaaaaaaa aaaaattat cctgcaaaat    10560 ttgaaaagga aattcaaatc aacagcttct aaactacttt ttaacatgac tcataataat    10620
acattctata gtacatatgt atgttctata actttgaata aaagagttaa ccacatcaca    10680
tttattttat aacatgtaat acatatttt tattctcctt catttgtttt gaatgctctg    10740
tgcagtctac aaaaagtcca atagtaataa ttaaattagt cattaagttg aacattatct    10800
tgtcttttaa aatgataatc tcaaaaatga tcttttattt ttgagattta tatagataca    10860
```

```
cacacacaca cacacacaca cacacacaca cacacacaca cacacacaca catatttttt    10920
gagacagagt tcactctgt cccccaggct ggagtgcaat ggcacaatct tggctcactg    10980
caacctctgt ctcccgggtt caagcaattc tctgcctca gcctctgagt agctgggact    11040
acaggtgtgt gccaccatgc ccagctaatt tttgtattct tagtagagat ggggtttcac    11100
catattggcc aggctcgtgt caactcctga cctcgtgatc tgcccaccgc ggcctcccaa    11160
agtgctggga ctataggtgt gagccgctgc acccggtcca agtaaaatta ttttaacaat    11220
atactatgaa gagaaaaaca ctggctatga agaatatgc atagttttac cctgtttaaa     11280
aataaagatt gaaagaatac atatgcaaat aagtttactt ttattttggg taacacttta    11340
ctgcattgtc tgaatattga caatcagtat gcattatgaa gctacctggc taacattgtg    11400
tactcactgt gtgtgccagg ccctgggttc aatgctctac atgcacttat atttcattta    11460
attctctctg caacctgaga tggtatagcc acctcatttt acagagttga aactgaggct    11520
cagagactga aagttaagcc tgaggttgca gtcaataaga ggcagagctg gaactgaaac    11580
ctacctgtgt ctgaccacca gttcgtgttc tgacggcagg ctagtctgca tcacagagtg    11640
tggagtagat ggtgcatgcc tgctaggatg ggctaggtat cactgtaggt aagaaacagc    11700
cccaaactat ggaaatgtac accactgaag ctcttttcc tgcccatgct gcacatcctc     11760
catggctctc ctgtgccctg tgccccacat gccctcatcc tgccacgaga ataaaggagc    11820
agcctccata tgggagctgt cagctgctct aagagatgaa ggagagagtg gcccgtctca    11880
atggctccca actcttttgc ctcgaggtga cacgcttcac ttccacgcac atctcctggg    11940
tcaaagcaaa tcccatgggt acatccactt tcaagtggcc caggagagaa cctgaaatac    12000
tcggtggact ccattaaggc cgtcatatgg tgtcagcctg catgggagac tgtggagggg    12060
cagaggagga gagtggggaa ctgatgggaa atgacaggag gactaagtca ccgcagattt    12120
gctttatctt cagccaggtg gagtttgtcc cagagccgca caaaatcatc accagcatga    12180
ttaaacggag tagacttcag aaaaagcagt ttggtcggat gtaatcagca gtgaactcag    12240
aatcaattga gtgacattga gtcagtaaat ctctgactgc ctcagttacc ccatatgata    12300
gttttgagga tgggaacatt gagagagttg atttggaagg atatcaagag taaaaattcc    12360 aacatttta gttcctttaa gttaaatcca ggcactgtct ttcctgcaag tctcctgttc     12420
ctttcagatt gcacaggtga gagtgctcag attagggctg gaggttgtaa accattgctc    12480
ccacactgac agtgccccg tgtcgtgcgt gtattctgcg catttcctg tgctaaacac      12540 tctcccaaaa catcgtgggg cctgattctt cctctttgtt ccaatggccc tgggtgactc    12600
aagtgcccat tcaatgacca ggacacagag gtcttagaga gatgctcctt gaggccccag    12660
gtgcgagcct gtaccctgcc ggagcatgag gcaaggaca gggcatcgtc tgtgggata     12720 gtgggggtag tgggggtagt ggtcagccag atttggtgac tctacttgct caccagacga    12780
tcctacacct gccacctccg atggatccac tgcctctgtg cctgcctgta ctgctgatgc    12840
tccagtggat aactcagcat cccagcctag gcccaatgcc actgaagatg gacctgcccc    12900
ctggggaccc aggagtccta ccactcagct gtccccagga gtgcccagac cctcattctt    12960
atccaggacc taggagccct accctgcc ttccctcatc agccgtaaat gatgatttac       13020
tgctgttacc atcatcactg ccttcagtga ccaagggcct tccaaggtgc cagctctgga    13080
acgaaggatg cccttgggag gtgatgacac tcaggtacac gggtgctcaa cagattgctt    13140
cctcctatcc tcagacggtc tttgcatgca tgcagccatt ggcactccca ttgtgtggaa    13200
```

```
ggaaaccagc ccagggtcac acagctggtc agcagcaaca tagctggtct caaatctaag    13260
gtgcctgacc atgcctccat gagggaccgc ctccaaggga ggttgatcct ggctttgggg    13320
agcctttcct gggctgcacg aataacctcc attgttcgag accccaaact ctgctcacat    13380
cttcctttcc ctatctctgc ttgggctatg atcacggtga ctctagcagc ccttcatgga    13440
cattatagta ctctctgcca ttcactttig ctctaatctg acttcaaccc ccacttactt    13500
ggtctctcct tttacaacca ccacaaccga aatctagggc tgcttttttt tttttttttt    13560
tttgagacag agtctcattc cattctgtca cccaggctgg agtgcaatgg tacgatctcg    13620
gctcactgca acctccgcct cccgggtcca agggattgtc ctgcctcagc ctcctgagta    13680
gctgggatta caggcgtgtg ccaccatgcc tggctaattt ttgtattttt agtagagacg    13740
gggtttcacc atgttggtca ggctggtctc gaactcctaa cctcgtgatc cgcctgcctc    13800
agcctcccaa agtgctggga ttacaggcgt gagccaccat gcccagccaa atctaggca    13860 ggaacatggc tgcagcatat aaaaagaatt gaattccata cttttgttaa ccctgttttt    13920
tgtttgtttg tagttgttgc tgttttt gag acagagtctc gctctgtcgc ctaggctgga    13980
gtgcagtggt gcaatctcgg ctcactgcag actctgcctc ccgggttcaa actattctcc    14040
tgcctcagcc tcccaagtag gtgggactac aggcgcccac caccacccc ggctaatttt    14100 tgtattttat tagagacagg gtttcaccat attggccagg ctggtctgga actcctgacc    14160
ttgtgatccg cccacctcgg cctcccaaag tgctgggatt acaggcgtga gccaccacac    14220
ccagcccctg ttttgttttt gttttgcttg cttcttaggg ttgttttct atttatggta    14280 aaggcattgg ctttccattt gtagcatcaa tagaatattt cctgtttaca ataaccttat    14340
gtcatagtaa atggtaaagg gatttaaagc agtggttttc agctgccaga ggcctgagag    14400
agtttgggca tactctgtgt gatcgggcag aaggcctgtg ggaagtttag cagaggacag    14460
ggccaggaaa ggtgatggac agtggggtc tgtcctggtc accaggcccc tgggtcctgc    14520
ccacctgctt ggagctcccc acccatcaca catgatgctg ccaagccctc tgggtattgt    14580
gggcaaatac cttaggagag aagctgatga actttgtttc ttgaaatgca cagattcctt    14640
ggacgtccct gagagctcag tcatgaaagt caacttggtt ttctccccct catttgggtt    14700
cagaatttaa agtccacaca cacaggcagt aagatgatat agataaggac gtcatcactc    14760
ggtttcggat gttaaaatgt ctaggtgggt tagcggtgat ttgagatcac acaaccttgt    14820
gccacaaaga ggaattccca ggccagaggg agacatttta ttgccatgtt atgatctcat    14880
cattgagttg aaaggcaatc ttgtttcatt ttggattctt tcttatgttt atgtcttata    14940
agggcacttt gaatttccaa gcaaataata attttgaatt agcttttaat cattgacttc    15000
tagcacagtt atatgatcag aaacatgctg tgtgatttga ttgctctcaa atatattgag    15060
atttgctgga acaaaataag tcaggttaat ttttgtaaat gtaccaggca tgcttaaaat    15120
gaatgtatct acatttgttc ccagatacag gttgatgga cggatggcta catgatgtg     15180 atggagatgg tttactatcg ggaccttccg caccctgctg atgttttgtt gcttaggata    15240
tgaatggctg agcggaggct gtaaaacctg gcactctgct tgggtatgag gttcttcctg    15300
ccatcctgcc atcatttgtt ttttatgttt tgtcgccata agtgaccttg aggaaccctg    15360
ggagctcagg aaggaaggag cgcccagaag cagggacagg gagctggttg ggaggaccca    15420
gaaatcaggt ttgtgaaggt tccagagagg acctgtcttt ggaggagtg tgggagactg     15480 agatggggga ggggtcattg gaatgatgcg ggcgctactt ggcattgtcc attgtgaggc    15540
actgtccatt gtgaggcacc accggggtca tcagggattg gtggagaggg agtataaagc    15600
```

```
cccagggttg gtaagggagg gcccagaccg aagaaggttt ggtggatagc agaaccttt     15660 tgtctccctc tgattgctcc taagcctcac gctcccttgc cccgcgtgtc ctgttgcttc    15720
cctgatcttc tccgtgacct gtagctaaac cttccaccag cgcttgagaa cttaatttga    15780
accggatcct ttcccagacc cctttcttct tctcctcctc ctcctccacc tcctccaggt    15840
gcccaacagc cccttctcc tccttccct tcccttactt ccccccttcc cctcccttc      15900 ccctcccct ccctccccc tccctccc ctcccctccc caactcagat ccggcccgg        15960 tccccgtccc cttccctccc cctgccta agccacctcc acctctgtcc tggccgcctc     16020
agggcgccct gaaaggacca ggacatgcgg gtgcggtgga tgctcttttg gctcctcttt    16080
gggctcctac tggaatttat cagccatcag tgcatctctg tgagtagacg ctggacccgt    16140
ggggtttctt ccttttact gggctgtatc acgtggcatg aaattacaca gctcaggcct    16200
gtaatcccag cactttaggg ggccgaggtg ggcagatcac ttgagtccag gagttgaaga    16260
ctagccaggg catcatagcg aaaccccatc tctacaaaaa attccaataa agattagtcg    16320
ggcctggtgg tgcgtacctg ttatcccagt tactggagag gctgaggtgg gaggatcgct    16380
tgggcccagg agctggacgt tgcagtgagc cgagatggcc ccgctgcact cttgtttta    16440 acaaagaaaa tggaccaaaa caaagtgaaa tgtcatttga tttgtgtcat ctggtttgat    16500 gactttttt tttttttt ttttttaga cagagtctca ctctgtcgcc caggctggag       16560
tgcagtggca agatctcggc tcactgcaac ctccgcttct ggggttcaag caattgtcct    16620
gcctcagcct cctgagtagc tcagattaca acgcctggct aattttgta tttttagtag    16680 accaccacgc ctggctaatt tttgtgtttt tagtagagat ggggtttcac catgttcgcc    16740
aggatagtct ccatctcttg acctcgtgat ctgcctgcct cagcctccca gtgctgggat    16800
tacaggcgtg agccaccgcg cctggccaaa atatataacc ttaagtgtaa gtttactaac    16860
tttggaaagt acatacacca gcataaacca acccccttc aagatctaca ttattttatt    16920
tatttattta tttatttga gacagtttct cccttgttgc ccaggctgga gtgcaatggg    16980
gcaatatcag ctcaccgcaa cctctgcttc ccaggttcga gcgattctcc tgcctcagcc    17040
tcccgagtgg ctgggattac agacatgtgg caccactccc agctaatttt gtattttag    17100 tagagatagg gtttctccat gttggtcagg ctggttttga actcccgacc tcaggtgatc    17160
cgcccgcctc ggcctcccaa agcgttggga ttacaggcgt gaaccaccat gcccagccaa    17220
gatctacact attatgtcac cccagaaagt gaactctcag tcttcccagc cagtctcttt    17280
cttatcatag gttagcttgc ttattctgga atttcgcgta tacagatgca tgccatgcca    17340
taggtactct tttgtgtctg ctttgttctg ctcaacacca tgtttctgaa atcattacca    17400
ttgttgtatg gttctctaac ttcatcattt ccatttcaga ctcagcatat gctgagttca    17460
acctgttgaa gggctatctc tgtttaattc accatcttga aagaaacatt taaaattgag    17520
atgttttcaa gaatatatag ttaaatcctg aggaatcgac gtagaaatgt tatcacaagc    17580
tgtctgaact tactcagggg aagtcttcgt cttcactcac ataagagtct aatggaatta    17640
atatcaacaa tcttagagaa atcccacact attcatgcca ttttcatgat ctccaccttg    17700
ataatttttt tttttttt tttttttt ttttttttt tttgagacag agtctcgctc       17760
tgtcacccag gctgaagtgc agtggtgcga tctcggctca ctgcaacctc tgcctcccgg    17820
gttcaagtga ttcttctgcc tcagcctccc aagtagctgg aactataggc atgtgccacc    17880
atgccctgct aatttttgt attttagta gagacgggtt tcaccgtgtt agctaggatg     17940
```

```
gtctcaatct cctgatctcg tggtccaccc acctcggctt cccaaagtgc tgggattgca   18000
ggcgtgagcc accacgccca gcccaccttg ttaatttta agcactaaaa tttgatactt    18060
atttgtgaat gaagtaatct cttcattgta tttttttt ttttactta tgctgagatt      18120 taaatgacaa agattcatat aatccaagag agaagtatta tttagaggga ttcttttacc   18180
atgtgatata taataaatgc atccaatgtt atacatcaat ttaaaaaaca agtaaataac   18240
tttaaagaaa agataactac tggccaggtg cagtggctca cacctgtatt cccagcactt   18300
tgggaggcca aggcaggtgg atcatgaggt caggagttgg agaccagcct ggccaagatg   18360
gtgaaaccct gtttctacta aaaatacaaa aattagccga gcgtggtggc aggcgcctgt   18420
aatcccagtt actcagtagc tgaggcagga gaatcgcttg aacccgggag gcggaggttg   18480
cagtgagttg agatcatgcc actgcaatct agcctgggtg acagagcaaa actttgtctc   18540
aaaacaaaaa gaaaagaaaa gataagataa ttactttata cttagcttgt cttacccatg   18600
agtgacgggc tgcatgtggc ccaggacagt tttgaatgca gttcaacaca aatttgtaaa   18660 cttctaaa acattaggag attttggcca ggtacagtgg ctcatgcgtg taatcccagc     18720
actttgggag gctgaggcgg gcagattacc tgaggtcagg agttcgagac caccctgacc   18780
aacatggcaa aaccccatct ccacaaaaaa tacaaaaatt tgctgagtgc actgtcaggc   18840
acctgtactc ccagctactc aggaggctga ggcaggagaa tcacttgaac ctgagaggca   18900
gaggttgcag tgagccggga gcacaccact gcactccagc ctgggtgaca gagtgagacc   18960
ccatctcaaa acaacaaac aaaaacaaaa acaaaaaaat ggctgggcac ggtggctcac    19020
acctgtaatc ccagcacttt gggaggccga ggcaggcaga tcgcctgtca ggagttcaag   19080
gccagactgg ccaacatggt gaaacctcat ctctactaaa aatacaaaaa tgagtcgggc   19140
atggtggcag agacctgtaa tctcagctac tcgggaggct gaggcaggag aatggcttga   19200
gcccaggagc tggaggttgc agtgagccga gattgcacca ctgcactcca gcctgggcga   19260
ctgagtggag cggaactctg tctcaaaaaa aaaaaagagg ttttttttag atcatcagct   19320
attgttagtg ttagtgtatg ttatgtgtgg ctcaagacaa cttttgcttct tttaatatag   19380 gcagggaagt caaagattg gatatccctg ctttatacca agaaagacaa cacccacat    19440 ttgcaatgcc tgaaaacact accagccatc tgaaaaacat gtgacttcta acttctgttc   19500
ttttttgtag cagtggaatc ccacggtgat atctgaggga tgtggttacc ttttggagga   19560
ggttgacggt ttctaaggat gattctttct gagtgaaata ttgtcagtgt cattgacctt   19620
ttcattattt caactattat tattccaggt tatcaatact ctggctgacc atcatcatcg   19680
tgggactgac tttggtggaa gtccttggtt acatgtcatt attgcatttc cgacaagtta   19740
taaagttgtc attaccctct ggatagttta cctttgggtg agtatactaa ctttctgtag   19800
aggtatactt gtaatcacaa ataagaataa attatataaa acaattcaca tttctggact   19860
tcattatgaa tatgtggttt tacccaaaaa atcaggaaaa tgatttatta gtataagaat   19920
tatgaaaaca tctgccatt gcattatgaa aattaaatag gtcggtgttt gtttaataga    19980
atgtcaacag agcttttggt caaaaataag ttttttaac ctttgtgcta tttatcacaa    20040
atggagtatg aggtttcgtc acttaaatag gaaattcttt ctaaactctt ctgctttata   20100
gttctatcgt atgggtggaa ggaaagcttc caatctcctc tctgaagatt cactgcagaa   20160
atgagctgac aacagacagc ttaacaggaa aagaaaaaca tagaacaggc ataaacatgg   20220
gaaccagctg aaaatgaga ctgctagaag ggccggatgg ctgatgctta aagagcaccc    20280
tcttctgagg ggagagggag atagatggag atgtaggcca tttagagggg cagcaaatga   20340
```

```
tttttagggg aaatgaaaga ggccaaggaa caaacaattg gcctgagaca aagttcctgt   20400
gaggtcatag ggacgaggtg acaaactgcc ggaaggtgaa gggcagaact gcactgcgtc   20460
tcatgatgca gagaaagccc cagagactct tagaactgcc ctccaagaga atcaatgaaa   20520
agtgtgtctg ggcagggtaa ttttgaatga catcattcaa agtgcatgtt ccgacttgga   20580
actggagaga gatcagtatg tcaaaagtct gtacttggta agaatttggc tgctaagttg   20640
tgccataatt tgtcttttga gccttttttc ctttgggtaa gttgagctct acattttgtc   20700
ttgccattca tgacagtaaa aatgtggttg tctgggggct gaacctcctt ctgaacaatg   20760
atccaagata aaagtactaa taccacaatg cttttttata ttcaagggaa gaggaagtat   20820
gtttcagttt taccacctag ataattacac gtcatttggc actgcctttc aagatatgta   20880
gaaaacagaa aatatatgag ttatgaagat atctaggcac atttaacatt ctctatgcca   20940
cttagtcctg aacagagaat tttcggtata aattggagga agcttttttc ttttttttt    21000 ttcttttctc accccgaaga cgagtctcct tctgttgccc aggctggagt ataatggtgt   21060
gacctcggct cactgcaacc tccacctcct ggcttcaagt gattcccctg cctcagcctc   21120
tcaagtagct gggattgcag gtgcccacca ccatgcccag ctaattttg tatttttagt    21180 agagtcgggg ttttaccatg ttggccaggc tagtctcaaa cccgacctc aaatgatcca    21240 ccaacctcag cctcccaaag tgctgggatt acaagcgtga gccaccacgt gagccagggg   21300
aagtttttaa atttaccact ttttaacaat tccacttagg aaagttcagt tgagctgttg   21360
gacttggaca acttcgcacc tctcatcttt gtccttgtca tctagtcatc tataccatta   21420
cctccttagc agggacatca tgggtgccat gaagcattca tgcgtgatgg catttcttgg   21480
cttctcattt cttcatgtgt ttgacatttc ccctagctcc aaactgggcc agctaccttt   21540
cctatgaaat ctagcagtag ctgtgggatt gacgtggttg ctcttttcat cttttagat    21600 tacccattgc ttctctcgaa atcctagtac atgatttttt ttttatccta tgtgcagaaa   21660
tcaggaaaaa acaaattcta caaagaattt gaaagatatt atttcaggcc aggtgtggtg   21720
gctcatgcct gtaatcccag cactttggga ggctgaagca gatggatcat ttgaggtcag   21780
gagttcaaga ccagatgggc caacatggtg acacccatc tctactaaaa agacaaaaat   21840
tagccaggca tggtagcagg cacctgtaat cccagctact tgggaggctg aggcacaaga   21900
atcgcttgaa tctgggaggt ggaggttgcc gtgagccaag gtagcgccac tgcacttcag   21960
cacggttgag agtgacactc tgtctcaaga aaaagtcat ttcaatgacc acctcaggag    22020
attcataggt atctgaccca catctgagat gggatttgca ttgcatttta gctatgatga   22080
gaagaaatat ttaatatctt agaagattaa aagcatactg tgataatatg gaaatcttgg   22140
tgggaattca gtcattagtg agaatgtttt gcgttaagtt caaaccagcc tcaatgaagc   22200
tgatgtgagg gaagggaaag tgaactctga gtagagcagg gacagaagga agatgctcca   22260
gtgcagatca ggaaggagca ggggatgaaa tgttacaaat tctagaactc agagagctga   22320
aggtaattac ttccttttca agttgtgaaa catgttaacc tgtggtaaaa tacttataag   22380
atgataatta ccatctaacc gtgttgaagt gtacagttca gttgtgtgaa gtatattcat   22440
gtcatttttt tttttttttt tttttttgag acgaagtctc actctgtcac caggctggag   22500
tgcagtggtg ggatcttggc tcactgcaac ctctgcctcc tgggttcaag cagttctcct   22560
gcctcagcct cccgagtagc tgggactaca ggcgtgcatc accatgctca gctaatttt   22620 gtatttttag tagagacggg gtttcaccat gttgcccagg atggtctcca tctccttgacc 22680
```

```
ttgtgattca cccgcctcgg cctcccaaag tgctgggatt acaggcgtga gctaccgcat    22740
ctggcctatt tttttttttt tttttttttt ttttttttgag acagagtttc aattttgttg    22800
cccaggttgg agtgcaatgg cacaatctca gctcaccaca agcttttcct gctgggttca    22860
agtgattctc ctgcctcagc ctcccgacta gctgggatta caggcatgca ccaccatgcc    22920
tggctaattt tgtattttta gcagagacag cgtttctcca tgttggtgag gctggtctca    22980
aactcccgac ctcaggtgat ccgcctgcct cggcctccca aagtgctggg attacaggag    23040
tgagccaccg tgccagcctc atgtcattct tgtgtgtgtg tgtgtgtatg tgacagagtc    23100
tcattctgtc gctcaggctg gagtgcagtg gtgtgatctc ggctcactgc aacctccgcc    23160
tcccagcttc aaacggttct ctgcctcagc ctcccgagta gcttggatta caggcgcccg    23220
ctgccatgcc cggctaattt ttgtatttttt agtagagacg gggtttcacc atcttggcca    23280
ggctggtctt gaactcctga ccccgtgatc cacctgcctc ggcctcccga agtactggga    23340
ttatacgcat gagccaccgt gcccagccgt cattcttata ttattatttc ctaggtgtct    23400
ctcctgaaga ctatcttctg gtctcgaaat ggacatgatg gatccacgga tgtacagcag    23460
agagcctgga ggtccaaccg ccgtagacag gaaggtatgg ctctgttgga atccgcatag    23520
tgtggaaatg agtttgccct ggaaagggaa agaacagctt cttgccctca ggtttctcac    23580
cttctcctct cctcactctc accaagggct gaggtccatt tgtatgcaca caaagaaaag    23640
agtttcttcc tttcgaggaa ataaaattgt cctgaaagac gtcattactc tacgagaca    23700 tgtggaaaca aaagttagag ctaaaatccg taagaggaag gtgacaacga aaatcaacca    23760
tcatgacaaa atcaatggaa agaggaagac cgccagaaaa cagtaagatg tgccttgaca    23820
caaatactgt tgtatgaacc atgtgccaat caaagtagac aactgtaaag tccttgagaa    23880
tattttctac aatatttgtg gcaaattcag tgggttcaaa attgagtttg tcctttctgc    23940
ttcattagtt taagctgtat aattcctttc ccttcctaca ttcttgtttt catttttcg    24000 gaggaagagg agttgctagt actggcattg gttttccttt ctctttttt tttttttttt    24060 ttcctgagat ggagctttgc tgttgttgcc caggctgtag tgcaatggca caatctcagc    24120
tcactgcctt tgggttcaa gcaattctcc tgcctcagcc tcccaagtag ctgggattac    24180
aggtgcccac caccacgccc agctaatttt tgtattttta ctagagatgg ggtttcacca    24240
tgttgtccag gctggtctcg aacttctgac ctcaggtaat ccacctgcct cagcctccca    24300
aagtgctggg attagaggcg tgagccacca cagccagcct tttttttttt tttttttttt    24360
tttaattttg cgatagagtc tcgctctgtc gcccaggctg gagtgctatg gtgcaatctt    24420
ggctcactgc aacctctgcc tcccagtttg aagcaattct gcctcagctt cccgagtagc    24480
ttggattaca ggtgtgtgcc accacatttg accaattttt tttttttttt tttttttga    24540 gacagagtct cactctgtca cccaggctag agtgcagtgg catgatcttg gctcactgca    24600
acctccacct cccaggttca agcgattctt atccctcagc ctcttgagta gctgggacta    24660
caggcatatg ccaccatgcc cggataattt ttgtatttttt agtagaggcg gggtttcacc    24720
atattggcca agctggtcta gaactcctga catgatccgc acacctcggc ctcccaatgt    24780
gctgggatta caggcgtgag ccaccgtgcc cggcccaatt tttgtatttt tagtagagac    24840 agggggttcac catgttggcc aggctagtct tgaactcctg acctcaggtg atctgcctac    24900
ctcagcctcc cagtgtgagc caccgcaccc agcctggatt gttgaattca atgcttgggt    24960
cacctccaga ttcattttca cagtctttca tgttttggtc atatgacatt gtatttgct    25020 gccatatgac tgatctttttt ttgttaaatg tgagatactt gttaaaaaat gtttagcaat    25080
```

```
gaattgaggc ctagtagcat gttatcttgc tgcagaagag atgggagtct acttctgggg   25140
gatggtcagg ggtcctccat acaagctgca attgaagtcg tcggtgcagg ctcagtccct   25200
acaaaggcca gggtatttcc tgtccacctt tattctgatg catgactctt ctgggtctca   25260
accagagcca gcggacttca gtatgggtcg ctttcattgg cagaccctca atccactgt    25320 tttccatcta atcccacgca tgtgtgcaaa agctgctgtg cttctttgca tctcagtagt   25380
tccttctgga attcagcaat gaaactcagg gaaatgggtt ccaaatgcga ggctgacttt   25440
cgtcctgggt ttccttcttc tccatcttca cctcatgtct gtttactgcc atgttagcaa   25500
tttgatgtat tcaatcatgg ttttatatt ctgtttggtg tcccccattg ttctcattgg    25560
agatcagaag cttcagatgc acttatgtca actcaagagt agaatgcttc cttagcttcc   25620
ctccagagtc aggttttgtg tttctagttc ccaagtgcac agcaggagta gtgatgtcct   25680
cactggcttc tcatttgcat taagctgtga gcttctttag cgtggggaca ggaccctgct   25740
cccattgcat tctcagcacc acaccacaca ctccttgttt gaggccactc cagacagcat   25800
gtgctgaagg atgccttgtg gtcagaaaca agttcattaa ctttctcttt gaagtgtttt   25860
cgcccctgtt tcctagcgtt ctgggaattt tacacatcct tcctataaag ccaagtatca   25920
ggtgagatcc ttaggatcag gaccatgaat caagtggtgt gagggcaaca cagcaaactt   25980
acccttttta ggccgtttcc ttttctgcc ctcaatctct gtgaactgaa ccttgttaaa     26040
gtcagtcaac accagggtgg atggtttgcc gttgtcacct attttcagga cataacaccc   26100
tgacttagga gccattccga tcatttctaa ttcaatagat gcgcccagca ttcagattgc   26160
cttttctctc aaccaggatc tttaaagttg atgacaagag ttccagtcct gaatcatggc   26220
aaagtgcagt agtgaactgc ggggttattc tggaaggatc tctctatggc tgatggtctc   26280
agttccggca tcagcctctg actgagaatc aggtctcaca caggaggagt cagatgagga   26340
gcaatcctct gcttccgatg gagttagttg tgatgaattg gtgaggtctg gttttttcaca  26400 ctgaactaaa atgagctttc gctgtgtcaa gcacaagact gaccccagag acacacatag   26460
tgcacctcat agaagctttt aatagtcttt atatttacta aagaatagga ctaactatgg   26520
aactatgaag atgagctgga aatgacaggt gacttgccag caggccagag tgtgactttt   26580
ttttgtccct caatgggagg tgtcaattct cccttcggtt gtgagaatca gttggttcat   26640
ttgtgggaag gttgcagggg ggaatctttg aatcacagcc ttcagatgcc agaagggcag   26700
agggaatccc acacgggctg gtggatcatg tgtgtgcatt tctctcccctt ctaatctgag  26760 gaaactaagc gtgaaagaat gtgagcatgc agaaaaggag aggcaggtat cagaggcaga   26820
ggaaaatggg aaattggata tgaaagaaat acacacctac aagtgagttc agaaactgta   26880 ccccacccctc ttgggaaacg cccattggag tgttgttttt aacctttgta cagtatttag   26940
acccagtaaa tgcagaaata gaaacaaacg gtcagaagac atatcgtgag agagagcgag   27000
agagagttca caaacagaa aacaaagtac cttaatattt accagtgacc aaaagatgtg     27060
aagtagcaaa acgtctcctg accccattgc cagctagact gtgtggaaac tcggttcata   27120
ccagccattc tagggtggg gtgagttgtt gtcatcctta ggaaagtgtg ttgttgtagg    27180
atcaaccaca tccttcaaaa ggactatgcc tgtttataag cccagctgtt tctgccctgt   27240
gaaacacggt aaggatatta atacaaagag aatacagctt tatgataaaa gatgctcaat   27300
gaaggatgaa ttagggatgt actgagaatg gggaaggaaa ctatcatctc agaagtcagc   27360
aggcagtaag caagaggagg aatcaataca gcaacagttt ggatcagact gtacagtttt   27420
```

```
tttgttttg ttttgtttt tctgagatgg agtctcgctg tgtcacccag gctggagtgc    27480
aatgacgtga tcttggctca ctgcaacctc cgcctcccag gttcaagtga ttccctgcc    27540 tcagcctccc gagtagctgg gattacaggt gcctgccacc acgcctggct aattttttgt    27600 attttttagta gagaaggggt ttcaccatat tagccacaat ggtctcaatc tcctgacctc    27660
gtgatccatc cgccccgccc tcccagagtg ctgggattac aggcgtcagc caccgtgacc    27720
ggctcagact gtactcttct agccatctga aatacgtttt ctaggtagag atagattgtg    27780
taagggtaca gttgtgagga taacagaaac atggcagatt atttaaaatc atcctgaaag    27840
tggtgcttta tctgatgaaa gtgattgtaa tccataggaa aatgtttcaa cgtgcgcaag    27900
agttgcggcg gcgagcagag gactaccaca aatgcaaagt aaggagcttc ctccctgcag    27960
ttgcaggata gttcagtgct gatgcagatg atgccacggc ccttagactc tctcaacatt    28020
caatttctca tgtgttggct ttttcagatc ccccttctg caagaaaggc tctttgcaac    28080
tgggtaagtt tgcttgtttt ccttgctttt ggacatagtc tgccaggtca ggacatggat    28140 acattttct ccctacagct ctgtgctcaa gccctgcaga gggagatggc agagagaaag    28200
gctgcctaca agcatcacag tcccatccct gttggtaacc gtgttgcgca aaaacacctt    28260
catccccacc cagtggggcc cctgatctaa tattctaagt gtcagaggtt ccgtatttgt    28320
aatagcagat gggccctgac tgtaaactag tgaagagtga atgtaactta ttacccacag    28380
ggacaattcc aaatgaaggc cttaaatgat gctcagctaa gctggttctt gtgtggcctc    28440
tgtaccttca aaagctgccg agtcctatga ttacacgtga tgggacttgt acacttgaag    28500
tgaaacacag ttttaaaact tgctttgttt agaattccca cctcattttt ccatggacaa    28560
aagtattctt tatgtcctag tgcacttaca atttggtatt acctgggagt gaaaagaaat    28620
attacagcca tgcctaagtg acttcttgag gtgagattgt tctgtcagaa accctctcc    28680 cagttcccct gcagctcttc aggaatccac atctctccag agctctttgt tctcatgggt    28740
ggcacctcca gagtgaagaa gatcctttgt caagaaggga aacagagggg aaatgagagg    28800
gtcctgcagg cagagctgga atcaacttcc actctgcctc ttgcaagctg tgtgacccctg    28860 ggcacaattt ctccttcctc tggaaaacctc tgttttctta gatttggagc agggtggtca    28920
cactgacctt gcagagttct gagaatcaga gacagaacat aaaaggcctg gaaaacattc    28980
tccaaaaaga agctgcaaca tgtgtggaca gtgggctttt catgcctctc ttactgtctc    29040
ttactgtctg ttgacctggt gcaagaaaca tgctctggtg atggctgtga gggaggaatg    29100
aggatagaca tagacactcc tgtgtctcaa acatgcttct ttattactct gttatgactc    29160
tgtcttccct ggggcaggac cccagcctgc ctacatttgc agacagacac agtggcatgt    29220
ggagacaaca gtgtgtccca atgactttcc tttacccctcc agctgtcggc agtactcagt    29280
ggaagggtga tattatgaca ctgatacttc tattttgaaa cctggaggat ggaaaggtgc    29340
aaaaatctat caccagcaac agaaggtgca gactgtgttg gtggcggtaa ttttgtccat    29400
caaatgaata tgtgtgaaaa cattccctcc tttggcccta caggtcagaa tggcggcagc    29460
ggagcatcgt cattcttcag gattgcccta ctggccctac ctcacagctg aaactttaaa    29520
aaacaggatg ggccaccagc cacctcctcc aactcaacaa cattctataa ctgataactc    29580
cctgagcctc aagacacctc ccgagtgtct gctcactccc cttccaccct cagcggatga    29640
taatctcaag acacctcccg agtgtgtgct cactccccttc ccaccctcag cggatgataa    29700
tctcaagaca cctcccgagt gtgtgctcac tccccttcca ccctcagcgg atgataatct    29760
caagacacct cctgagtgtc tcctcactcc ccttccaccc tcagcggatg ataaactcaa    29820
```

```
gacacctccc gagtgtctgc tcactcccct tccaccctca gctctaccct cagctccacc    29880
ctcagcggat gataatctca agacacgtgc cgagtgtctg ctccatcccc ttccaccctc    29940
agcggatgat aatctcaaga caccttccga gcgtcagctc actccccttc caccctcagc   30000
tccaccctca gcagatgata atatcaagac acctgccgag cgtctgcggg ggccgcttcc   30060
accctcagcg gatgataatc tcaagacacc ttccgagcgt cagctcactc ccttccacc    30120 ctcagctcca ccctcagcag atgataatat caagacacct gccgagcgtc tgcggggcc    30180 gcttccaccc tcagcggatg ataatctcaa gacaccttcc gagcgtcagc tcactcccct   30240
tccaccctca gctccaccct cagcagatga taacatcaag acacctgcct ccaccctca    30300 gcggatgata atctcaagac accttccgag cgtcagctca ctcccctccc accctcagct   30360
ccaccctcag cagatgataa tatcaagata cctgctgagc gtctgcggat ccgcttcca    30420 ccatcagccg atgataatct caagacacct tccgagcgtc agctcactcc cttccaccc    30480 tcagctccac cctcagcaga tgataatatc aagacacctg ccgagcgtct gcggggccg    30540 cttccacccct cagcggatga taatctcaag acaccttccg agcgtcagct cactcccctt   30600
ccaccctcag ctccaccctc agcagatgat aatatcaaga cacctgccga gcgtctgcgg   30660
gggccgcttc caccctcagc ggatgataat ctcaagacac cttccgagcg tcagctcact   30720
ccccttccac cctcagctcc accctcagca gatgataata tcaagacacc tgccgagcgt   30780
ctgcgggggc cgcttccacc ctcagcggat gataatctca agacaccttc cgagcgtcag   30840
ctcactgccc ttccaccctc agctccaccc tcagcagatg ataatatcaa gacacctgcc   30900
gagcgtctgc gggggccgct tccaccctca gccgatgata atctcaagac acctcccta    30960 gctactcagg aggctgaggc agaaaaacca cgcaaaccca agaggcagag ggcggctgag   31020
atggaaccac ctcccgaacc caagaggcgg agggtcggtg acgtggaacc gtcacgcaaa   31080
cccaagaggc ggagggccgc tgacgtggaa ccatcatcac ccgaacccaa gaggcggagg   31140
gtcggtgatg tggaaccgtc acgcaaaccc aagaggcgga gggccgctga cgtggaacca   31200
tcatcacccg aacccaagag gcggagggtc ggtgacgtgg aaccgtcacg caaacccaag   31260
aggcggaggg ccgctgacgt ggaaccatca ttacccgaac ccaagaggcg gaggttgagc   31320
tgagaagagg ccagtgcact caagcctgag caataagaat aaaaccgagt agaacaaaat   31380
aaaaaattca aaaacaaaa caaaacccac actccaaaaa ctaacaaaga ataaataaat    31440
aatataaaaa taaataaat actgcagtcc ttatgttatt gctttgtttc gatatctggt    31500
atgattgcct gagggacctg aggttttttaa tcataggggt ttttttttaa tctttagaag   31560
tggttggtta tgtaaaatat tattattttt tttttgaga ctggattttg ctgtgtcacc    31620
caggctggag tgcagtggct cgatcacagc tcactgcagc ctcaacctcc tgggcttcaa   31680
gcaatcctcc tgcctcagcc tcccaagtag ctgggatcac agatatgtgc caccacgcct   31740
ggccaatgtt aaaaaatcct ttaacttttt tgtagagatg cactcctgga ctcaagcgat   31800
cctcctactt gtcccgacca ccagccccctt tctgataaac aaacatttac actgtttatt   31860
atctgatgcc atttctatct tcttccttgt cgtccagaca tcgaataatt aggtttcttc    31920
agggttttct ttttcaagtg ctcagtgtta aagatcactc acattagggc cagacaccat   31980
ggctcatgcc tgtaatccca gcactttggg aggccgaggc gggcagagca cttgaggtgg   32040
ggagtttgag accagcccgg ccaacttggg gaaaccccac ctctactgaa aaaaatacaa   32100
aaattagctg ggcgtgatgg tgcatgtctg tagtcctagc cacttgggag gctgaggcat   32160
```

| | |
|---|---|
| gagaatcgct tgaacccagg aggcagaggt tgtagtgagc caagatcacg tcagcacact | 32220 |
| ctagcctggg tgacagagtg agactctgac tcaaaaaata aataaaataa atatcactta | 32280 |
| catgagatat acccaagggg tggtctacag agacttggaa gcagtggtta ttgcaacagg | 32340 |
| ggcacggaag tcatctggct atgccagggt gcccagggga tactcggggt gggtggcatg | 32400 |
| gtgctgctgg ggactcatcg cacaggacgc tctgattgac gcactgccag gagtagcgct | 32460 |
| ctgtcttggg gctgcagccg gcctcctcag ctcgagtgta acatcagtcg tggccatggc | 32520 |
| agcacctgcg gatgtcacat gggcaggaca gcaggtgggt gaagctctct cctggccctc | 32580 |
| ctctcttgcc aggaccatgg gtgactgaag accccagg aggcacagca tcctcttatc | 32640 |
| taagattttt ttttttttaa gagacagggt ctttaaaaaa gtcctgcagt ctgcagtcgc | 32700 |
| ccaggctgga ctgcagaggc acaatcatag ctcacggcag ccttgaactc ctgggctcaa | 32760 |
| gcgatcctcc cacttcagtg tcccaagtag ctgagactac aggcacacgc cagcatgtcc | 32820 |
| ggctggtttt ttagtttgta tttcctttga gacagcatat ctctctgtcg ctcaggctgg | 32880 |
| ggtgcaatgg ctcaatcagc tcactttagc cttgaactcc cgggctcaag tgatactgcc | 32940 |
| acctcaactt cccaagtatg ctactacagg aacacaaact ccttttttaa attttttgtg | 33000 |
| gatatggggt ctcactatgt tgcctaggct ggtcttgaac tcccaggctc aagcagtcct | 33060 |
| acctcagcct ccccaaatgc tgggattaca ggtgggagct actgtacgcc tggccttatc | 33120 |
| taagctgttt ccctgaaaat gcccgtcttg ggtaatgatt ccattggccc caccatgccc | 33180 |
| tgtcctgcct tcctggctgt gcccaagctt ggtcctgcc tgcctgcctc actctctggg | 33240 |
| tctcgagctc ctgtgacaca tgactcctct ctcttcctgg agtgatccaa gccctgccac | 33300 |
| ttcctgactt tgcccacact gtaccctctg cctgggcaa cttcatgtct gcccattgtc | 33360 |
| ccttaggcct cagcccaggc acaagcccct gcctccggag gtcatccagg cctcaccagg | 33420 |
| ctacaccctc tcgtaaaatt ggattccctc ccttcagggc aggtttataa tgaaatcctc | 33480 |
| ctcagaggcc aggtgcggtg acacccatct gtaatcccag cactttggga ggctgaggtg | 33540 |
| ggaggatcac ttgaggccag ggggtcgaga ccagcctggg caacataaga gagactcttg | 33600 |
| tctctcttgt ctctataaca aatttaaaaa ttagctcacc aggccaggct cagtggctca | 33660 |
| tgcctgtaat cccaacactt tgagaggccg aggcaggtgg atcacgaggt caggagttcg | 33720 |
| agagcagcct gaccaacacg gcgaaaccct gtctctacta acatacaaa attagccagg | 33780 |
| catggtggca cgcacctgta atcccagcta ctcgggaggc tgaggtagga gaattgcttg | 33840 |
| aaccccggag gtgaggttg cggtgagcca agatcacgcc attgcagtcc agcctgagca | 33900 |
| acagagcaag actctgtctc gagagaataa aaacacacaa aaaattaact cgccaggatg | 33960 |
| gcacatgcct atagtcctaa ctacttggga ggctgaggtg ggaggattcc cttcagccca | 34020 |
| ggagtttgag gctgcagtga gccactgtga ttgtgccact gcactctaac ctgggcaaaa | 34080 |
| gcgagacccc aggctagagt gcatgatttt gggtcactgc aacctccacc tcccaggttc | 34140 |
| aagtgattct cctgcctcag cctcttgagt agctgggact acaggcatgt gccaccacgt | 34200 |
| ctgggtaatt tttgtatttt tagtagagac agggtttagt agagaccatg gtgaaacccc | 34260 |
| atctctatta aacaaatctc tactaacccc atctctacaa aaaacagctg ggcgtggtag | 34320 |
| tgcacacctg taattccagc tacttgggag gctgaggcac gagaatcatt tgcatcttgg | 34380 |
| aggcagagtt tgcagtgagc tgagatcgcc ccactgcact ccagccggga tgacagagca | 34440 |
| agaccctgtc tcaaaaaaaa aaaaagggcc gggcgcggtg gctcacgcct gtaatcccag | 34500 |
| cactttggga ggccgaggcg ggcggatcac gaggtcagga gatcgagacc atcctggcta | 34560 |

```
acacggtgaa accccgtctc tactaaaaat acaaaaaatt agccgggcgt ggtggcgggc   34620
gcctgtagtc ccagctactc gggaggctga ggcaggagaa tggcgtgaac ctgggaggcg   34680
gagcttgcag tgagccgaga tcgcgccact gcactccagc ctgggcgaca gagcgagact   34740
ccgtctcaaa aaaaaaaaaa aaaaaaaaaa aagaaaaaag aacaaacaac agcaacaaca   34800
acaaaaaaac ctctgtgtca atcacagcct tcgagctagg ggagaggcgg ccgaattctg   34860
ccctccgcta acgagctata gctttgtgga aatgggcgag tggcgtgccc ttgtgagcct   34920
cagggccgca tctgtaaaat gggcataact gtcatgcctg tctttaagaa cagccttggg   34980
ggtaaatgag tggaactaat ggaaagatct cagcccacaa ccttccacag aacaggcgct   35040
tctcacacag taagtagcag gagtgcagag gctgcaggca tgaatccagt cagactgcag   35100
actgcctggg ttcaagtccc agctcccacg tcttggtaac taagtggcct cagacaagtt   35160
acttagtatt tcttcttctt cttttttttt ttttttcaga cggagttttg ctctgtcacc   35220
caggctggag tgcagtggtg tgatctcggc tcactgcaac ctccgcctcc cgggttcaag   35280
caattctcct gcctcagctt cctgagtagc tggaattaca ggcacctgcc accacatcca   35340
gctaattttt gtattttttag tagagacagg gtttcaccat attggccagg atggtctcga   35400
actcctgacc tcgtgatctg cctgcctcag cctcccaaag tactgggatt ataggcgtga   35460
gccaccgcac ctggacacat tacttaatat ttctgtgcct tggtttcttc atctgtgaaa   35520
tgggattgtt gtgagaatgc aaagggattc ccagggcagt tcctagtgca tagtctggct   35580
gcctttgtgt gtgtgtgtgt gtgtgtgcat gtgtgtgtgt gtttaatata gagacagggt   35640
ctcactatgt tgcctaggct ggtttcaaac tcctgggctc cagtgatcct cctgcttcca   35700
cccaaagtgg tgggataaca ggtgtgagtc accacacctg gtcactttat attattttt    35760
tcttttgaga cagggtctcg cactgttgcc gaggttggaa tgcagtggtg caatctcaac   35820
tcactgcaaa ctccgcctcc cgggttcaag tgtttctcct gcatcagcct cttgagtagc   35880
tggtactata gtcaccgggc tccttgcctg gctaagtttt gtattttag tagagatgcg    35940
gtttagtgat tctcctgcat cagcctcttg agtagctggt actataatca cttagctcct   36000
tgcccagcta attttgtat tgttagtaga tgcgggttt ccttttttt tttttttt        36060
gagatggagt ttcgctcttg ttgcctaggc tggagtgcag tggtgctatc tcggttcacc   36120
acagcctccg cctcctgggt tcaagcgatt ctcctcctca gcctcccgag tagctgggat   36180
tacaggcatg tgccaccgca cctggctaat tttgtatttt tagtagagac ggggtttccc   36240
catgttggtc aggctagtct cgaactcctg atgtcaggtg atctgccttc cttggcctcc   36300
caaagtgctg ggattacagg catgagccag catgccaggc tggccctttt tttttttt     36360
ttaatcactt aacatatatc ttggagaact ttccattttg ggagttaaag agatttgttt   36420
gtttgtttgt tttgagacag ggtctccctc tgtgcccag gctggagctg gaccttggct    36480
cagtccaact tccacccccc gggctcaagc aatcctccca cttcagcctt ccaagtagct   36540
gggtctatgg gcacatgcca ccacatcccg ctacttttta tagtttttgt agagatagga   36600
ttttaccatg ttgcccaggc tggtcttgaa ctcctgagct caagtgatcc acctgcttca   36660
gcctcccaaa ttactgggat tacaggcatg agccatcttg cccagcctgt tttttattta   36720
atatctacta agtgccaact accatagagg acataaagat gattcagtct ctgcagaagt   36780
cattttcttt ctctttcctg ttgtacagca caaaattaat ggactaaata gtctgtcact   36840
agataaagaa gccctaagta atcaggcact tgctgcagtt tttacaaagt ttaaaaagcc   36900
```

```
atatgaaaca cagtatactc caagtaataa gaggcaaaat atgtgaagtg ttactgctgg    36960
ggaatttacg gactattctt ttctacaata tatctgctgt ggtctgaatg tgttccccaa    37020
gattcatatg ttaaaactta accaccagtc tggtagtatt aagaggtggg gcatcattaa    37080
gtcatgaggg catgggatta gtaacctcat aaaaaggttg gcgggaacga gctaggccct    37140
ttcattgccc ttacatccct ctgtcacttg aagacacagc actggtcccc ccgggaggac    37200
atagcagcaa ggtgccgtat tggaaatggc caccatgccc tcaccagata ccaacctgct    37260
ggtaacttaa tcttggcctt cctagcctcc agaactgtga gaaagaaatt tctgggtttt    37320
gtttgtttgt atgagacagg gtctctgtca cctaggctgg agtgcagtgg cacgatctcg    37380
gctcactgca acctctgcct cctgggttca agtgattctc ccacctcagc ctcccgagta    37440
gctgggatta caggtatgca ccaccacacc cagcttttt tttttttcat agcgttgtac    37500
agatagggtt tcgtcatgtt gcccaggctg atctcgaact cctaaggtca cacgatccac    37560
ctgccctggc ctcccagcat gctgggatta aaggcgtgag ccactgtgcc tggccaaaat    37620
ttccgttttt tataaataac ccagtctctg gtactttctt atagccgcac gaacagataa    37680
agactgtacc tatctgttga ctgggcgcag tggctcacgt ctgtaatccc agcacttcgg    37740
gaggcttaga caggtggatc acgaggtgag gagatcgaga ccatcctggc taatatggtg    37800 aaacccccgtc tctactaaaa atacaaaaaa tttagctggg ctcggtggcg ggcgcctgta    37860
gtcccagcta ctcaggaggc tgaggcacga gaatggcatg aacccgggag gcggagcttg    37920
cagtgagccg agatcatgcc actgcagtcc gtcctgggcg aaagagcgag actccgtctc    37980
aaaaaacaaa caaacaaaca aacaaacaaa aaagaccgtg cctttctgtc tgtctccctc    38040
ataggtcagt ttccacctga ttgtaaccac atcaagtatc ctagtatatt tcatatttac    38100
agaaaaataa atgggcaaat actgtcattt acagagaacc tgccctgtcc tgtacactgt    38160
gacatatttt gtggtttgtg attatgtgct ctgatcctta cgatagctct aaaatagctc    38220
aaaaagttat tcccattttg tacataagaa aattgaagtt ctggaaacat aaggcaattg    38280
cccaaagtaa tagagtaaat gacaaagcta ggatttcttt cttctcttcca ttaattaatt    38340 aattatttga gatagggtcc ctgttgtggg atgcagtggg gagatcatag ctcactgcag    38400
tctcgacctc ctgggctcaa ctgatcctca cgtctcagcc tcctgagtag ccgggactac    38460
aggtgcacac caaacactatg gctaattctt gtattttct gtagaggtct gcctaggcta    38520
ggcagagatt ctggctaggc tggtctcaaa ctcctgggct caagcaattc tcctgcctca    38580
ccctcccata tagctgggac cgcaggtgtg tgccaccact cccagctgac ttgtttatac    38640
cagtggttct taattggaag agttttgtac cccggggaca tttggcaaca tctggagatg    38700
tttttgaatg ttacagtggg gaggagggga atgctactgt cacctactgc gtagaggcaa    38760
gggatgctgc tgaacatccc acaatgcaca gaacagcctc ctccccaccc aacagagaag    38820
tatctggttg gcccaaaatc tcaatgatgc caagtctaag aaactgcttt gtatttctct    38880
gagatactgg gatgaggaac gctctaaatt agttgtcttt gaggataatg tatgcataca    38940
tacacatata tgtgtataca tgtatataac taaagatata tagttgagat cttgcatttg    39000
tgttaatgaa tgtagttttt ataaagataa ttgactcata cattaattgt tgactctttg    39060
gaaaggaaaa aggacaaatg agatacatgc tattggtttt gttatttaga aattgttcgt    39120
gtggatcctc cctaccattc agccatttgc aaaccattag ttgagcataa cttaatccct    39180
tctagttcac agcaaagatt catcaaaagc catttggtat actgtcacct catctctcta    39240
ccagtgttga ttagattaca ggagggttac aggagggcac cttatccaaa ttggccaatg    39300
```

```
ataaattctt ttttggtacc ttactatata tttgtatcct cagaacaaat tctcctttct   39360
gcttaagctg gcttgacttc atttctttca ctagcaagct aagaggcttt ggccaacaga   39420
actactctag gggtagctgt aaaatttatc tctaaggaaa ggctgctctt ttgaaaacac   39480
agtttaatgg gtcttctggg tatatgacga tagtaaagca aaattttgtt ctggaatgaa   39540
gaagctgatt acattgttgt attacaaaca atatattact cagtgaagtg aaaggccaca   39600
ctgtgggcag ggtggtgact ttgcagatag catgttaatc cttgcatgct ttttgttgtt   39660
tctcttttg gaggggagg gtcttaattt tctttggccc tcccccaccc cctttatttt   39720
ctctggggaa ggcaagactg gataaggagg cttttatcct gccaagatga gttggcccac   39780
aggacaattt gactgaatag aggctccaca aagaacggac atggccaaag aattacaaca   39840
ggaaattatg catttagttt taaggcttcc ttttctcct tttttttttt tttttttga   39900
gaccgagtct tgctctgttg cccaggctgg agtgcagtgt gcgatctca gctcactgca   39960
acctctgcct cccgggtcca agcgattctc cagcctcagc ctcccgagta gctgggatta   40020
caggtacctg ccaccacacc tggctaattc gtattttgg tagagatggg gtttcaccat   40080
gttggcccgg ctggtcttga actcctggtc tcaagtgatc cacccgcctc agcctcccaa   40140
agtacaggga ttacaggcat gagccacagg gcctggccag tattttctt gtataatgct   40200
cagagtttcc tttaaatctt tttaaaaact tggcagcctt agtcttagct gtgctttggg   40260
aaaataagga gctgcactca agcttaagaa gatattgctg gaagtgtaca ttggcacagc   40320
cttcgaagct tcttggtgcc ctcctgtaac ccaatcgaca ctggctagag agatgaggtc   40380
atattgcatc aaatggcttc cagtgattct ttgctgtgga caagaaagtt gctcttttc   40440
tttgagaaag ttgctctttt tctttgagag ggagttttga tgcctaggct ggagtgcaat   40500
ggcagtgatg tcggctcact gcaacctctg cctcccaggt tcaagtgatt ctcctgcctc   40560
agcctcccga gtagctggga ttacaggaat gtgccaccat gccaggctaa ttttgtattt   40620
ttagtagaga cagggttttt ccatgttggt caggctggtc tcgaactccc gacctcaggt   40680
gatccaccca tgttggcctc caaaagtgct gggattacag gcgtgagcca ccacgcccag   40740
ccaagaaggt cactctttat gctcaacaaa tgtattgcaa atggctgaaa ggtagggagg   40800
atccagatga acaatttcta aataggaaaa ctaatagcca gacacgatgg ctcacacctg   40860
taatcccagc attttaggag gtcgaggcag gcagatcacc tgatgtcagg catttgagac   40920
cagcctgggc aacacggaga acccccatgt ctactaaaaa tacaaaaatt agccaggtgt   40980
ggtggcgggc atgtgtagtc ccagctactc aggaggctga ggcaggagaa tcacttaaac   41040
ccgggaggca gaggttgcag tgagctgagc ttgtgccact gtactccagc ctgggcaaca   41100
gagagagact ctgtctcaaa aaaaaaaaa aaaaatcgta gatatccaat tgttcctttt   41160
ctcctttcct aaaagctttt tgtgccccct ccaacccaac agttccaccc tagaaaaaca   41220
cttgtacaca tacatcagga aacgatacaa gaatattcag gctggtcgcg gtggcttgcc   41280
tataatctca gcattttggg aggccgaggt gggaggacgg cgagagatca tgccactgcg   41340
ctccagcctg ggcaacagag ggagactccg tctcaaaaaa aaaaaaaaaa aaaagcataa   41400
tgttgaaaac aaacagcagt ataatacagc atggagataa ctttataaaa tgcaaagaca   41460
aataaaagta aatatagtgc attgtttagg agtataaata tggtaattat gcaaagaaaa   41520
ctaaaatgac ttttaaaaat catgatggtg actattttg ggaggaaagc aggtagaagg   41580
tgggatctga gagcagcaca cagtaagtgt caattgtcct agttaatgtt cggcttctta   41640
```

```
aattgggtga tatgttcaca ggtgttcatt atgttctttt tttttttttt tttttttgaga   41700
cggagtctga ctctgttgcc caggctgggg tgcagtggtg cgatctcggc tcactgcaag   41760
ctccacctct tgggttcatg ccattctcct gcctcagctt cccaagtagc tgggactaca   41820
ggtgcccgcc accacacccg ctaattttt tttttttttg tattttagt agagacgggg    41880
tttcaccgtg ttagccagga tggtctcgat ctcctgacct cgtgatccac ctgcctcggc   41940
ctcccaaagt gctgggatta caggcgggag ccgctgcgcc cagcccatta tgttcttata   42000
acttacatta acatattatt ttatatatgt caagcttttt ttcccttttt ttttttaag    42060
agatgagatt ttgctttgtc acccaggcca gagagtgtcg tggtgcagtc atagctcaca   42120
gcagcctcca actcctgggt tcaagtgatt ctcccacctc tgtctgccaa ataattggaa   42180
ctacaggcat gtgccaccat gcctgggtaa gtttttttt ttaatttttt atttattatt    42240
atactttaag atttagggta catgtgcaca atgtgcaggt tagttacata tgtatacatg   42300
tgccatgctg gtgcgctgca cccactaact cgtcatctag cattaggtat atctccgaat   42360
gctatccctc cccctcccc caccccaca acagtcccca gagtgtgatg ttccccttcc    42420
tgtgtccatg tgttctcatt gttcaattcc cacctatgag tgagaatatg cagtgttttgg  42480
tttttttgttc ttgcgatagt ttactgagaa tgatgatttc caatttcatc catgtcccta  42540
caaaggatgt gaactcatca tttttatgg ctgcatagta ttccatggca tatatgtgcc   42600
acattttctt aatccagtct atcattgttg gacatttggg ttggttccaa gtctttgcta   42660
ttgtgaataa tgccgcaata aacatatgtg tgcatgtgtc tttaaaacag catgatttat  42720
agtcctttgg gtatcctggg taagttttt aaaagtgtta tttgtagaga cggagtctgg   42780
ctgtgttgcc tgggctggtc tcaaactcct ggcttcaagg tatcctcctg cctcagcctc   42840
ccaaagctct ggcattacag gtgtgagcca ctgcacccag actcagactt tttttaaggg  42900
aaagaatggg agtgtaggtg gggagacaca ctttgggagg ccaaggtggg aggatcactt  42960
gggccggggg ttcaagacca gtctgggcaa caaagtgaga cctcgtattt accaaaaata  43020
caaaaatta gctgggcttg gtggtgtggg tttgggaggc tgaggtgaga ggattgcata   43080
agctgtagga gcccgaggct gcaacgagct gtgatcgcgc cattgcgctc taacttgggc  43140
tagacaatga gatcctgtct caaaccaaaa caaaacaaaa cagataattg tcaaattgct  43200
gttttgctat tgttgctttt tgtttttgct tcgctttgcc ttggaagtga agaagagatt  43260
ctcatttaaa cagttatctt gaagtatctt tgtgaactag ggtgcaatta tttcctctgt  43320
ccttgagaca cagatgattc ctgtccaaca ttcccaagga actcagtaag gaccaaatag  43380
agactcagga aagacagtta ctgattttac actgttgcaa aacagagcta tggtttatgt  43440
ttaacaaact gctggtgggg cgtggtggct catgtctgta atcccagcac tttgggatgc  43500
caaggtgggt ggatcacttg aggtcaagag ttcgagacca gcctggccaa catggtgaaa  43560
ccctgtctct actaaaaata caaaaattag cagggcatgg tggtgcatgc ctgtaatcct  43620
agctactggg gagggtgagg cacaagaatc gcttgaacct gggaatcgga ggatgcagtg  43680
agccgagatc acgacactgt actccatcct gggtgacgga gcgagactgt ctcaaaaaaa  43740
acacaaaaaa caaaaaaacc aaattgctgt attttatttt gtgaaatagg gtctagctct  43800
gttgtccagg ctggagtgca ggggtgcaat cacagctcac tgcagccttg acctccaggg  43860
ctcaatcgat cctccctcct cagttttcaa gtagctgaga ctacaggtat gcaccaccat  43920
atgctgccca ggctggtctt gaactcctgg agagagatac atacacacac acacacacac  43980
acacacacac acacacacac acttttttt ttttttgag acacagtttc gctcgtcacc    44040
```

```
caggctggag tgcaatggca caatcttggc tcattgcaac ctctgcctcc tgggttcaag    44100
ctattatcct gcctcggcct cccaagtagc tgggattagt aaggcactgc caccatgcct    44160
ggctaatttt gtattttag tagagacagg ttttgtcat gttggccagg ctggtctcaa    44220
acttctggcc tcaggtgatc cacttgcctc ggcctcccaa agtgttggga taacaggcat    44280
gagccactgc gccgggccca tacatatgca ttttaaaaaa tttatttatt tatttcgaga    44340
cagggtctca ctctgttgcc caagcaggag tgcagtggtg ctatctccca ggctcaagca    44400
atcctcagcc tcccgagtag ctgggactac aggtgtgtgc catcacaccc agataatttt    44460 tattatttt atttttaaa tttttgtag agatggagtt tcaccgtgtc acccaggctg    44520 gatattttg tattttgat aggcctgtac agtttccaaa gttgcaacct ttcccctcc    44580 ctgagagtag gggcagcccc ggctctccct ctacatcctc cacagtcccg aggttttggc    44640
ctctgtttcc tctgtttcct atgcttggaa caccagtcgc tcttttgttg gtctggctga    44700
cttctgttcc tcttttaaaa atttaagttt ggccgggtgc ggtggctcac gcttgtaatc    44760
ccagcacttt gggagtccga ggcgggtgga tgacctgagg tcatgagttc aagaccagcc    44820
tggccaacac agtgcaaccc cgtctccact aaaaatacga aaattagccg ggtgtggtgg    44880
catgcgcctg taatcccagc tacttgggag gctgaggcaa gagaattgct tgaactgggg    44940
aggcggaggt tgcagtgagc tgagatcacg ccactgcact ccacctgggc aacagggcaa    45000
gactcggtct caaaagaaaa taaataaata aataaataaa taaataaata aataaataaa    45060 gtcaagggg taaacctct tggtaactct cctgttgttt ctcatgccag catcatcaca    45120
gccttgaggc tctggggtag gtcacttcgt cgagctcgtt tccatgagga taacgttatc    45180
ttgggtgtct gtgagaatgc tgcactgagt atagagccca ggctcctggg tcagccgggt    45240
tcgaatcccc tttcctccgt gaagatctgg gtcagtcaca agtgcttcag tttcttcgat    45300
ctgactgagg gaggctttga ctccaaaaaa ttaacacttg agtgtacctg gccacagctt    45360
agcacatcca gggtgtttcc acccttctt tgggatcctc agggctggat ggagccgatc    45420
cttcccgtct ctccttacac tcgcgcactc acgctggctg gaacaagtcc tccaagtaga    45480
acgaagagcg cgttttagcg gcgctctagc ccgccgagag catacgccct ccccacacgg    45540
ggcccctgat tgtctgaagg ttgcgctggc acgcgcaact tccgggacag aggctgtggc    45600
tggaaggagc tgggcatccg gcctgaggcg cagcggtcgc gttagttcgg cccaatggcg    45660
gcaccgctgc ttcacacgtt gtttgtcggg agatgcggcc gcttcgtcct ctgcagtcaa    45720
gacgctgggc gcgtcgagga ctgggtaaga ttcaggccgc ttccttctgc gcgtctggga    45780
ccaaagctca ggaccgcgct tagaggagcg gattgaaagg atgtgggaca aagctaatgg    45840
cgtgtgatag gagcacgggg tcgagggtca tctcacgttc acagaaatga gctcattcct    45900
cctaactggg taatagacat gggtggggcc tggaaaagtg agtatgttct ctgttctgga    45960
ggcccacttt cccgactgtg tctcttcgtg atttcccagg cctgggtact gccttctgcg    46020
ccttgacccc tcttccttcc ctcttcttcg tccaaatttg gaaggganntt ccctgggcta    46080 tgtgggttat cagccgaacg ttgtcactca tggcaaattg aatattacat ctttttgtt    46140 tgaaatttgt ttcgacacac gtatttgttt cgcagtcttt attttgctcc acttttaaaa    46200
tccctaaccc ccatagcact cttggcgttt aactttcaga gtcattagga tgctatgttt    46260
tttcattaat ttactacgtg taagtgaagc aaaccttgta aaacaattag cgtaatatga    46320
ttcctaatat ttatcgagct cctgcttact gtgttaaaca ctggggacag tggtttatcc    46380
```

```
aaagacacta atgtccctgc tttctacaga gcttacagca tagggtggga aggcagtaca   46440
caggccaata aataaacgaa cacgatgatt tcagttatac aacaaggtaa tgggggaggg   46500
agaagggaga gaaggagtgt tcgagatttc tcattgggaa gacatctgtc atttcagctt   46560
ctacttgaat gaagacaaaa atctaggccg ggcgcggttg ctcacgcctg taatcccagc   46620
actttgggag gccgaggtgg gcggatcacc tgaagtcagg agttcgagac cagcctggcc   46680
aacatgcgaa acctcgtctc tactgaaaat acaaaaatta gccaggcgtg gtggcagggt   46740
gcctgtaatc ccagctactc aggaggctga ggcaggagaa ttgcttgaac ccggagatgg   46800
aggttgcagt taagctgaga tcacaccact gcactccagc ctgggcagca gagcaagact   46860
ccatctcaaa aaaaaaaaa aatccagcca cgtagagatt tgggaaaaga gtatttccaa   46920
tagagtgaac agtaagtgaa atgagaaaca gcttggcttg tttgaagagc agaaaagaca   46980
tgatggctgt agtaaaacaa gttgttggag atgaggtgag agaggtaggc gggggccaga   47040
ttaatgtagg attttaaaga ccacactgag agatttggat tgttactgta agtgcagtgg   47100
gaagacagtt attggttgct gagcaaagga gggattgttg gttaagagtg gaagcaggga   47160
gaccagtaaa gaggccttaa caatagtccc actgaattat gttggttcaa taaaggttgg   47220
ctattataat ttttattatt ttcatgaact taatagcttg ttaatcttgg ttccacagga   47280
tttcaaatat gcgtgcatta gagaatgatt ttttcaattc tcccccaaga aaaactgttc   47340
ggtttggtgg aactgtgaca gaagtcttgc tgaagtacaa aaaggtaaga ggagataatg   47400
tgtgaggttt gcttttggtc aggtcagaat acaactattg ctgttatact aaagaccaat   47460
agaaatagca agattaatta agataccagt tgaaatcaaa tatttaataa tagcatgatg   47520
ccgtcagtgc aaaattagag taatagtgtc cttttttttcc cccaccttgg cccatttcac   47580
aggtaataat gagagagtaa taatgtcttt actgagtttt cacctcttca aatgctttat   47640
ttacaaagca tcttttaact ttagcaagtg ctagaattaa aaacaattac agcattttat   47700
ttatttattt atttgtgctg gagtcttcct ctgtcaccca ggctggagtg cagtggcgtg   47760
acctcagctc actgcatcct ccacctccca ggttcaagca attctcctgc ctcagtcttc   47820
tgaatagctg gggttacagg cacgcaccac cacacctggc taattttttaa attttttaa   47880 tagagacggg gtttcaccat gttggcctgg ctggtctcaa actcctgagc ttgtgatcca   47940
cccgccttgg cctcccaaag tgctgggatt acagatgtga gccaccatgc ctggcctaca   48000
gcattttatt ttttgaggaa cttacctaag cattactttg ggacagtaaa ccggttctct   48060
gaatagggat ttttgttttt gtggtagttt agaagcattt ctactatatc tcagcagtag   48120
agggaaaatg ttaagtaacc gtatgtttat atgaaatatc catttgtatc catatttgag   48180
tgaatacttt tttagatcct cctgaattag atcattagag ctggctgttt tttcccctca   48240
tgctttttga gaattcgcag gagtatcaac tattatattc aaatgtcaat acagaagtat   48300
agctaaatgt agtttatcat tttccttttt ccaagccctc tggctgcact aacatgagtg   48360
tttaaatttt tgtagtcatg attttataat ccgcaattga catgtgaaag ttagtgttcc   48420
ttttataatt tcatctgatg ttaaagtacg gttaaaagtc ttgctgttga tactaaacag   48480
gaaacaaaag cataacttaa ttcttttcccc ttcttgttaa gggtgaaaca aatgactttg   48540
agttgttgaa gaaccagctg ttagatccag acataaaggt aattaatttt gtgtttgatc   48600
attagcaaaa ttattgccac tttatacaga catagtttgc tctttgggtc ccattctgtt   48660
ctgcagaact tgctctctcc atggtcctcc cttactttaa tctggtggtt ctcaaccagg   48720
gacagtttta ccccctagaa gacatttggt gatggctgca gatatttttg tcacaactgg   48780
```

```
gaggaaaggg tgctactggc atctagtggg tgaatgacag agatgctgct aaacatctca    48840
cagtgcacag ggcagcctcc cataaccaag agtgatccag ccccaaatga caacagtgtt    48900
gaggctggga aaccctgctc taatgcttcc tttctattag attactacct ctttcctcca    48960
tgctgcatgc aactctttg tctctttaaa gctaaaacaa accaaaaaaa aaaacaaac     49020 cactgtttca gcatttccag gttcgagata cacctatcat gtagtaaaac cttaatacat    49080
tttgtttcac cattcttcct ttactgccca gttttgaaga aatggttta ttaccatggc     49140 agtggtagtt agattgcctg gaatgaaatt ccaattttat tatccagtgt gtgatcttga    49200
gcaaattgtt ttaacctctc tgcctctatt ttccactgtg tgaaaccaag aaaacaatag    49260
agatttaaaa aatatggagt gttttgtttt ttaagagatg tggtcttgct gtgttgctct    49320
agctattcac aggtgtgatc atagtgcact acagccttga actcctggcc tcaaatgatc    49380 cttctcttc agccttctaa aaagctggga ctataggtgc atgccactgt gcctggcttt     49440
aaacatggaa atacttaaca aggattcaat gagctaatat gcaagaagca cttagaacag    49500
tctctgactc aaagtaaggg cagtaattgt catctgttgt ttttgttcca gctgactgtg    49560
ctgtatcatt tctcactcac atttaagtcc actgttctta tcactgtagt aattaccctg    49620
acagattacc catgttttt ttttacatgc tgatttcagt ggactttttt tgagacaaag     49680
tctccttctt gtcacccagg ctggagtgca gtggtgtgat atgggctccc tgcaaccttt    49740
gcctcctggg ttcaagcaat tctcctgcct cagcctccca aatagctgag attacaggca    49800
cccgccacca tgcctggtta attttttat ttttagtaga aacggggttt caccatgttg      49860
gccaggctgg tcttgaactc ctgacctcag gtgacctgcc tgcctcggcc tcccaaagtg    49920
ctgggattac aagtgtgagc cactgagccc agcctcagtg gacttacttt tttaagcctt    49980
gtattccttg tatcagccga cactgttggc cacccacttc ttaaaacttc agtgtttctg    50040
atcctcctgt cttctgatcc tttaatctct ctctttttt tttttttt ttttttgctc       50100 tgtcgcccag gctggagtgc aatgacgcaa tcttggctca ctgcaagctc cacctcccga    50160
gttcaagtga ttctcctacc tcagcctccc gagtagctgg gactacacgc gcccgccacc    50220 accccagct aattttttgt attttagta gagatgggt ttcaccatgt tagccaggat      50280
ggtatcgatc ttctgacctc gtgatccacc cgccttggac tcccaaagtg ctaggattag    50340
aggtgtgagc caccacaccc ggccagtgat cctttaagct ctagtatctc tcgataggtt    50400
cttgatctta aatttggtgt tgattgggct tcaaaacttg actcttttct cactctgttg    50460
attcttctgt gtgatctcct catctccctt catggctttg aaatctacct gtgtcctaat    50520
atatttgtgt ctgtagccaa gattgctctt gtgggctcca gacttatttc attttcattt    50580
ttggggatgg gcagaacaga gtcttgctct gtcacctagg ctgtagtgta gtgggatgat    50640
cttggctcac tgcaacctct gcctcctggg ttcaagccat cctcccacct cagcctcctg    50700
agtagctgtg ccaccacgcc cagctaattt ttttgtattt tcagtagatt tggggtttca    50760
ccatgctggc caggctggtc tcgaactcct gacctcaagt gatccacccg cctcagcctc    50820
ccaaagtgct gggattatag acgtgagcca ctgcacccgg cctagacttg tttcttaact    50880
gtctgttaga tgcatttacc cagaatcatc atagatgctc caaacttatc atgtccactc    50940
ttggctgggc tccatctttc atggagcttt ccctggttct ctctaagcac atggttgttc    51000
cttcattgag tctatttccc cacacttccag atctctctag ttacagatct ggtttacaag   51060
gccctccatg gtctatttgg tgcttctttg ttccccagat ttattatctg ttggcttggt   51120
```

```
cactatacat gccagccata ctgaacattt ttcagttttc tgaaaacata cttttccttc    51180
tgtaagaagc agaacttcca gaaaagactc aactgtgtta ctgtttaaag acagctgaag    51240
catcactttc tctttaaagc ttttcctgac ccctgcctcc tttcccagat acaaagggac    51300
attttctttg tgttccactg tattttgtat cagcagttct cattcttggt attttgacat    51360
accaagaatt gcactagttg tgtggagtgt tgcaagtaga acttttttcg tcttgagaca    51420
gggtctcgct gtgtcaccca ggctggagtg taatgggccc gatcatggct cactgcagcc    51480
tcaacctccc aggctcaagc aatcttccca cctcaggctc ccgagcacct gggaccacaa    51540
gcatgtgcta ccatgcctgg ctaattttt tagagacgag gtctccctat gttgcccagg    51600
ctggtctcaa attcctgggc tcaagcagtt tcctcctgcc ttggcctccg aaaagtgctg    51660
ggattacagg catgagccac tgttcctgcc tgctagtaga aataataata gttcagtact    51720
aaagcatcaa agtctgcaac tgatttactt ttttttttt ctttttgaga catagttttg    51780
ctcttgttgc ccaggctgga gtgcagtggc atgatcttgg ctcactgcaa cctctgcctc    51840
cgagtttttt aagtaattct cctgcctcag cctcccgagt agctgggatt atgggcatgc    51900
accaccacgc ccagctaatt ttgtattttt agtagagacg gggtttctcc atgttggtta    51960
ggctcgtctc gaactcccaa cctcaggtga tccacccacc tcggcctccc aaagtgttgg    52020
gattacaggt gtgagccacc accccagcc tgatttactt ttaaaaatgg tacagtttaa    52080
atgttatcct tatagttttg ttgcagtctt tttagtggaa aagagatagg atagattatt    52140
ttatttacac actaacttag cttgttttct acatgccttt ggccttagtg agctaccgtt    52200
aatgttatcc ttaacagttt tggacatatg aaattaccat agtacaaatg agttgtggtt    52260
ttactttatt ttactgccag gctacttggg atttcatcag aaaatggttg atctgtggga    52320
gtttgacaca tggatatggc atagtaagca ctcagtagct gaattaaggt ggggaaaagg    52380
ggacagcttc ttctccgcat atagggaggc atgtgggatg gtggacagag gatagccttg    52440
accgagacag atgggtttgg acctgcttct ttactggcct cttggttggg cagattgctt    52500
attaatcgtt cttagcctca gcttcctgaa cagcaaaatg gaataacta aacatcttgc    52560 agagttctta ggattagaag aagatatata tgcggagtgt caggcaccat gcctggcata    52620
tggtgtattc tcactaaatg ataactccat atgaatatcc ctgtaggtat gatgaccttg    52680
tgttgctttt atttatatgt ctaagccttc cacaaattag gggcttttc ttaatggttt    52740 ttgtcctgtg cagtatatat gcatgaatat aattaatata gtaatatttt acataattga    52800
cactgtattt tataccttgc gtttcaaatt tagcagttct tctcatgtca ctaacaatta    52860
ctatgaacag taatttgatt gcctgaaaaa tatttcatgg aggaatgggg ctatcattta    52920
tacagaacaa acacatcata atatatttaa actcagccac agatttggtt tagaaaagtt    52980
atgtttattc atgaccccaa ttgatcagcc tagactgaat tttatcagca tgcttcctgg    53040
tcagcttgaa tatagaggaa atagaggtag ctattgttcc tttgtgatct tctaatattt    53100
caatctgcta gaattctgca gttttaaaa gtcccaggtg tcaacatttg aggtgatttc    53160 acttttttcag ggcaaacaaa agtgatcagg ctgaagtatt gcatttaagt ctttctcctg    53220
tgtattagag ttactagatt actttcttaa aacgattaag tttattgtga catcttttc    53280 tgttttaata cccagttttg atttccttcc aagtttgtga ccttttcccc ccaacctatt    53340
cttgataaat gattgatata agatagctgt aaatttctgt tatcttagag gatttgtgat    53400
tttgaaagta ctctttgttt aacttaagga tgaccagatc atcaactggc tgctagaatt    53460
ccgttcttct gtcatgtact tgacaaaaga ctttgagcaa cttatcagta ttatattggt    53520
```

```
aagttcacca tttattttac tgtcaagtat gtaattcaga actttggtaa tagtatatgt   53580
tatattaata acatgctgct tttatctttc ttcccccact ctagagattg ccttggttga   53640
atagaagtca aacagtagtg gaagagtatt tggcttttct tggtaatctt gtatcagcat   53700
agactgtttt cctcagaccg tgtctcagca tgattgcttc ccattttgtg cctcgtaagt   53760
cattactctt tgcttgcttg gaattttctt ttcttttctt tttaatactt ctttgttaaa   53820
ataccacctt cccctatat atgagagact gctaccatgg aagattccag atgcatattg    53880
gcaccaggtc tggtagacat atattccccg taatgacccc tatggaggtg tctagattca   53940
tttgttgctg tgagtttgat gaattataac ttgctttatt gaactcctgg tgaaatctag   54000 gaattttag ccatttaaaa actataaagt tgcattactt tttttcagat tgtgcattta    54060
attaatcatt gggctaactt tggattatgg aaaaataact tttttatag ctgtcattg     54120 tctaggtcaa taactttttt tgtatagcca ttcattgtct agatcaatga cagaacaaca   54180
tatttctttt ttccctcaaa agcccgagtg atcattaagg aaggcgatgt agatgtttca   54240
gattctgatg atgaagatga tagtaagtat aaaaaggttt aaagcctggg cacagtagct   54300
tacacccata atcccagcat tttgggaggc caagatggga ggatcacttg aggccaagag   54360
tttgagacca gcctgggcaa catagtgaga ccttgtctct gcaaaaaaac attttttttc   54420
aaatattttc ttaaaaaagg cttaaagtag aactaggcag ggtagtgtgt gtctttagtc   54480
acagctacct gggaggctta agtgggtgga ttgcttgagc ccaggagttc aagctctgcc   54540
tggtggcaag actctgtctt ctttaaaaaa aaaaagtaa agcacagaat acctggcatc    54600
tattctaata agtagactgc aacaaatgac aacttttgat gtaatctttt tgttatattt   54660
accattgata tgcagtcagt tgtcctgaat gcattattta taaattagt ccatttaatt    54720 ttcattgatg ctggtggaga aaagtcttga aattattatt tctctgataa attattccgt   54780
tttggttagc atgtgttttt agcttcaagt atgtcacttt ttgtttgttt gtttgttttt   54840
tgagacagag tctcgctctg ttgcccaggc tggagtacag tggtgtgatc ttggttcgct   54900
gcagccttca cctcctaggt tcaagtgatt ctcctgcttc agcctcctga gtagatggga   54960
ctacaggcgt ttgccaccat gcccggctaa ttttgtatt tttagtagag atgggggttc     55020
accatattgg tcaggctggt ctcgaactcc tgacctcagg tgatccaccc acctcggcct   55080
cccagagtgc tgggattaca ggcgtgagcc actgtgcccg gccagcattt attttagtt     55140 tcaagcatgt cgcccttcag ttttgttttg atgctcatac tctgaacttt tcttctttca   55200
gatcttcctg caaattttga cacatatcac agagccttgc aaataatagc aagatatgta   55260
ccatcatgag tatactttc cttattttga atgtttaatt ctcaagaaaa ttgtaatcaa     55320
ttagtaaaaa ttataaaatg ttaatagtat taaagcttga gtcttacatt gcatttttt     55380 tttttgtatc cacttgagga aacattacat tctacaaaaa gtggcatttc cattttctat   55440
ttattctctt taattgtttt tcaaagttcg tatgcagatt ctcccccaat tttgtatggt   55500
ggttggaatt ttgtttttat cttcaacaga tatgctatcc aaaattttc agtgagaaac    55560 ccctgggtgt gtttgtgtca tgccatatga ataaaaattg cacttctaag aaaagctttt   55620
caggtttgtg ggtttctttt ggaggggtgg atttctagtt ccctctgtct gttgattatt   55680
tgttaactta aaaaaatcca acttgattat tttttcttct tttaaaaata atatacatgt   55740
gtagtgggaa atgtcagcaa aagtgctgtt atgtttctgt gggagagaag ctccctcttt   55800
gatttgctgt tgatatcaga gttaacagaa gcttattttc tctaagttgt tatagacttt   55860
```

```
ctcagaagct atacattgta agttccagtt ctggccgggc gcggtggctc acacctgtaa   55920
tcccagcact ttgggaggct gaggcgggcg gatcacctga ggtcgggagt tcgagactag   55980
cctgaccaac atggagaaac cccgtctcta ctaaaaatac aaaattaggt gggcgtggtg   56040
gcgcatgcct gtaatcccag ctgtttgggg ggctgaggca ggagaatcgc ttgaacccgg   56100
gaggcagagg ttacagtgag ccgagattgt accactgcac tccagcctgg gcaacaagag   56160
cgaaactccg tctcaaaaaa caaaaaaagt tccagttctt tgaggtaagg gttcctgttt   56220
gcctcctatg tctatcgata tttgctttta gaatggtagt tttccttttt attccttttc   56280
tagaaagtaa agtcaacatg gattgattta attttttaaa aatagggcac cgtggtttct   56340
catgccaata ctggtggaaa aatttccatt tgttcgaaaa tcagagagaa cactggtaag   56400
aaatcttttc attgagaaca tcatggaaaa gttgtttgta tgatttcatt ttagatgata   56460
ttaggtcttt ttctttcttt ttctgtcttt attttttattt ttcttttttg agaccgagtc   56520
tcactctatc gcccaagctg gagtgcaatg gcgtcatctt ggctcactgc aacctctgcc   56580
tctcgggttc aagcaattct cctgcctcag cctccccatt agctgggact gcaggcacct   56640
accaccatgc ccagctaatt tttgtatttt tagtagagac aaggtttcac catattggcc   56700
acactgttat cgaacgcctg accttgtgat ctgcctgcct cggcctccca aagtgctggg   56760
attggtgaac caccgtgccc ggctgatgtt aggtcttttt cttaaaggtt actttgtctt   56820
ctagacttta aactgatgtc taagaatttg actcagattc ctttcttata aagcggctat   56880
tggggattcg cagtgccttt ttctgttatt actatgtgca agtcaaggtc tgagttcatt   56940
tccgaatat ctgtagtggc tttatgctca tacgggcaag aattactaga agataatagt   57000
tcatgtatta ctaattgtga acatgcctta ttttaacctg aaaacaaagc cttccataga   57060
agaattctgc ttaagttttt gtacaatgtt cagatcatct gtgcagtttt taataattaa   57120
tagtggttgc cttagtagaa accgaatct agtagcatac aaaagaatt cgtaccatg    57180
accaagtgcg actgatgtta ggaatgcaag attgattttt ttttcgggg gtggggac     57240
agtctctgtc tgtcacccag ctggagtgc agtggcacca tctcagctca ctgcagcctc    57300
tgcctccagg gttcaagtga ctctcccacc tcagcttccc aagtaggtgg gactatagac   57360
atggggcacc acaccccact aattttgtg ttttgtag agatggggtt ttgccatgtt    57420
ggccagactg tcttgaact cctgacctca agcgatctac ccgtctccac ctcgcaaagt   57480
gttgggatta gaggcgtgaa ccaccgtgac cggctgagat tgagttagta cctgaaaatg   57540
aattaataaa atattttgta gcaatagaac aaaggacaaa aaccacataa tcatctcagt   57600
agatgcagaa gtgtgtgaca acaccaata tcccttatg agaaaacag aaggaaattt     57660
tctcaacctg ataaagggca tctgaaaaac ccacagctaa catcatattc agtggtgaaa   57720
gaccaaaagt tttttcctaa gacaaagaac aaaacaagga tttccgctct tgctgcttgt   57780
ctagccaagg cagttaggca agaaaaagaa ttaaaagcat ccagatggaa aggaaggcgt   57840
aaactctctt ttgcatggtg atttttatatg tcattctaag aagtttacac acacacaaga   57900
aattttagag ataataaatg agttcagcat ggttacggga cagaagacta acatacacta   57960
accagttgtt caagacaatt gaatagggga gaatagtcat ttcaacaaat gctgctggca   58020
gaagtggata tgaacatgca aaagagtgaa gcatatggat atccatatac aaaaatgaac   58080
tcaataaaag ccctcactga agtgtaaaaa ctgtaaaact ctgagaagaa aacgagtaca   58140
ttttcataat gttggattag gcagtaattt ccagatttga tgcctaagca caagcaacca   58200
aagaaaaaat gcatcaattg tacttcaaaa ttaaacgttg ttatgcttca taggacatct   58260
```

```
tcaagaagat gaaagaatc  cccaaataat gggaggaaat atttctaaat tttatgtctg   58320
gtaatggact tgtatatgta aagaactctt ataattgaat aataaaaggg caaatagccc   58380
aactgaagag ggcaaaggat ctgaataggc atttctgcaa acacatgaa  aagaagctca   58440 acatcattag ccatcaggga aatgatttca cttaatgccc acaaggatgg ctataatcag   58500
aacgagaaga cagtaacaag tgttcacaag gatatggaga atgggaacg  ttggaactgt   58560 catatgttgc tgtgagaatg taaaatggtg cagccgtttt ggaaaatagc ctggcatttc   58620
ttcaaggtta aatgtagaat taacacgtga ctcagcagtt ccatttctgg gtttataccc   58680
aagagaaatg aaaatatatg tccacagaaa aacttgtaca tggatgttca tagcagcagc   58740
atccataata gcctcaagta gaagcaactc aaatgtctgt caactgatga acagatgaca   58800
aaacatggta caatggaata ttactcagca atgaaaagga atgctttata tgttacaaca   58860
tgattggacc ctaaaaacat gccaaaaggc tgtgtattat atgactccat tgataggaaa   58920
ggaatggttt acatgttaca acatgattga accttaaaaa catgccacaa actgtgtatg   58980
actccattga tatgagagga atggtttaca tgttacaaca tgattgaacc ctaaaaacat   59040
gtattatatg actccattta tatgaaatgt ctcaaagagg cagattcata gaaagactag   59100
tggttgccaa ggtcttcatt ttttaggggt gcactaatgg atgtaggatt tctttttaga   59160
gtgattaaaa tgttacaaaa ttgctggctg ggtgcagtgg cttatgccca taatcacagc   59220
acttcgggag gctgaagtgg gaagatccag gagttgaaga ccagcctggg caacatagtg   59280
agaaaatgtc tccctaaaag gaagaattaa cctcatgtgg tggtgtgcac ctgtagttct   59340
agctactagg gaggctgagg aggaaggatt gcttatcccg ggaattcaag gttgcagtga   59400
gctatgattg cacccactgt acctcatcct gagagagaga gcaagaccct gtctctaaaa   59460
gaaaaataaa tgttctgaaa ttgattatgt tgacggtcac ataactgaat atattaaaaa   59520
cttaaattgt atactttaag ttggtgattg tatgatatat gagttttatc aatacagcta   59580
cttaaaaacc tatagttatg caaattaaaa atttcattta ctggggataa ttgaaatgat   59640
tataccgaac ataatacatg tagaaacagt atagttttg  tattgctgga tagtctgttt   59700
tttttctttt caatatttga aactaaaggt catgtaattg atgttttct  tacataactg   59760 tgaaatattt attctctgtt gaaatgtttt atcttacgtt ttctccttta ggaatgttac   59820
gttcataact tactaaggat tagtgtatat tttccaacct tgaggcatga aattctggag   59880
cttattattg aaaaactact caagctggat gtaagtattg agtaatctat ttttattttc   59940 tttttttat  ttttattttt tttatttttca tttactgact tgaatttgtt ataatcacag   60000
tatgtggaaa caatagtcag tgatagaaaa gaatccactt ggccaggcat ggtggctcat   60060
gcctttattc ccagcacttt gggaggccga ggcaggcaga tcacctgagg tcaggagttc   60120
aagaccagcc tggccaacat ggcgaaaccc cgtctctata aaaaaaaaa  aaaaaaatta   60180 gccaggcatg atggtgggtg cctgtaatcc cagctactca ggaggctgag gtgggagaat   60240
tgcttgaatc cgggaggcag atcttgcagt gagctgagat cgtgccactg cactccagcc   60300
tgggcgacag agcgagactc catctcaaaa aaaaaaaag  aaagaaaag  aaagaaaacc   60360 actagcacca ttctttgctt cctttctttg aatgtgtctt gaactccatc tgtgcatgtg   60420
ctgggagttg tagacagttc cttctcatga ttggagaaca aggcgttaaa tacatagtta   60480
tccaaatgta aaagtatggt tgtggaaaat gccatgaatg aaacatacat tatgagttag   60540
agaacctgat agaatcacag tggggtcagg aagggattcc tacggaagtg attttttcctg   60600
```

```
tttggccttt cttaagggca gattataatt ataaacagtt aaaactttgt ttaaggaggc    60660
ccgcactaag gtgcagtggg aatgaaagga agtggtagat tctagtgaca ttgtgaggaa    60720
aggtgaactg gtccttgaga ctggtttgga ggaggggagg cagacagtaa gggaaaggaa    60780
tccttcaata gttgctccct gtggaatcga atcttggtgt tgccattaat ggtagttaga    60840
aatatgaaga ggaggctggg tgtggtggct cacgcatgta atcccagcac tttgggaggc    60900
cgaggcgggc ggatcacgag gtcaggagat cgagaccatc ctggctaaca tggtgaaact    60960
ctgtctcact aaaaatataa aaaattggcc gggtatggtg gtgggcacct atagtcccag    61020
ctactcggga ggctgaggca ggagaatggt gtgaacctgg gaggtggagc ttgcagtgag    61080
cccagattgt gccactctgc tccagcctgg gtgacagagc aagactctgt ctcaaaaaaa    61140
aagaaaaaaa aaatatgaag aggaggcagt tggaagagta gttccatctt ggccaggttc    61200
agttgctggt gggcagccta ccagagaata ctcacaggtc gtcgtggctg cagatgggga    61260
cctgagcata aacctttgga aagatgcagt ttaggacagg ggaggagaag ggtgatcaga    61320
agtatgggga aaaccaagag tctggatgct caggaagaat ccgctggaag gaggagtttg    61380
gtcagcagca tcagatactg ctgtcatttt ttagaaagat gaaagagca acagtccttg    61440 gatttagtgg ttagaaggta gtctttgttg ctttctggag gaccatgtca gtgaagacgc    61500
agaaactgca tttcgggaga ggatgtggat ggtggggaag cagaattggg gctgttagag    61560
accttggtgc agggttgtgg tggaaggagg ggatggagca gggctaagag gcgtggttta    61620
ggagtgggga gatgtgagca ggtttgtgga ctgagggagg aggagctttg gtggaggaaa    61680
acattgatgc tataggaaag caggaagatg gaacaaggtc ttagaagagc tggagcttgg    61740
gctcactggt gcagtgctcc cttggagttg cacctctctg gccaactgta tatgtactct    61800
ttatagtctt tctctggtat atacttaagg aacattttag aatgtttaca agaaggtca    61860 ggcatagtta ataaaaaatg gcatggtttg agtggtatgt taagatattt gaatggtgat    61920
ataccaaaat aaatattgca tcatgcacat ttggcttgca gttcatcatt tttctgctca    61980
attgattgac gatatgttta ttacacaatg tgtctgtgag tgtcttgtgc atagagattg    62040
tattagtcca ttttcacact gctgataaag acatagctga gcctgggaag aaaaagagat    62100 gttttttgttt gtttgtttga gatggtgtct cgctctgttg cccaggctgg agtgcagtgg    62160
tgcgatctcg gctcactgca acctccacct ccccgggttca agcagttctc ctgcctcagc    62220
ctcctgatta gctgggatta caggcacgtg ccaccatgcc cggctaattt tttgtatttt    62280
tagtagagat ggggttttcac tgtgttagcc aggatggtct caatctcctg acctcatgat    62340
ccatccacct cggcctccca aagtgctggg attacaggcg tgagccactg cacctggcca    62400
aaaaagaggt ttaattggac ttacagttcc acatggctgg ggagccctca gaatcatggc    62460
gggaggtgaa aggcacttct tacatggtgg cggcaagaga aaatgaggaa gatgtaaaag    62520
tggaaacccc tgataaaacc atcagatctc gtgagactta ttcactatca tgagaacagt    62580 atggggggaaa cctaccctat gattcaaatt atctcccacc agtcccccccc ccaacaacat    62640 gtgggactta caggagtaca attcaagatg agatttgggg ccaggcgtgg tggctcatgc    62700
ctgtaattcc agcactttgg gaagctgagg ccggtggatc acctgaggtc aggagttcga    62760
gaccagcctg actaacatgg agtaaccccca tctctactaa aaatacaaaa ttagctgggc    62820
acagtggcac atgcctgtaa tcccagctac tcaggaggct gaggcaggag aatctcttga    62880
acctgggggg cggagtttgc ggtgagccaa gatcttgcca ttgtattcca gcctgggcaa    62940
caagagcaaa actctgcctc aaaaaaaaaa aaaaaaaaaa gtgagatttg gtggggaca    63000
```

```
cagagccaga ccatatcaga gctagaataa atgttgaatt tgttgaggct acctgacata   63060
gagcatcatg tgatagttgt cgattttata taagtatgta gtaaaagggg cttggtttat   63120
tatatttaaa ttccttcatg acctaggtca gtttacaggc ttgcaccata attgtgtatt   63180
gtgttggggt gtgatataag gcactaatct ggacaccttg aacgtgtgta tatcagatga   63240
atttccatcc caaaataaca tagttgtatt ttttaaatcc ttttattctt ttttccccccc  63300 cctttgttat aggtgaatgc atcccggcag ggtattgaag atgctgaaga aacagcaaat   63360
caaacttgtg gtgggacaga ttccacggaa ggattgttta atatggttag cagtttatta   63420
atgaaagtgg agatgaagtt tatcataatc aaagggtgga aacagctagt gctgctcatc   63480
tttgttaagg ctttagattg aaagaattaa aatagtttag caaacttgaa aacgattcct   63540
tatatgagta atttgctgcc atgtcattta gcacttagca taattggtct atttccaagg   63600
ctttgaattt gggtttggtg aagtatgttt cacttttgtt gttgtaactt tcagtgtttg   63660 ttttttgtaag ccagatgctg tctgtgaggg cgtggctaat ggaaaagcat aactgtttaa   63720
tttctgcatt ttaccacttg tacactttat agcattactt cttacgagta gctgggacca   63780
cagattacca tgcctggcta attttttgtgt ttttagaaga ggcggggttt caccatgttg   63840
gccagactgg ttgtgaactc ctgaccgcaa gtgatctgcc cgcctcctgc cccgcaaagc   63900
gttgggatta caggtgtgaa caactgtgcc tggcccacgt tcccttctca gtacacttgg   63960
agagaaaaca gattgctgcc tgccagccca gctaggtgct ctgaaaatgt catcctgcct   64020
ttggtcacta ggtggtggtc ttcccttaag cctttctcta ttaaaatctc atatgggta    64080 attaacagta tttcctttat tctttccaag ggttgagttg taactagccc aaaccaactt   64140
attaatctag aattttaaaa actttaggct ttgacttttc ttcttcttct tcttttttt    64200 tttggtgggg gaaagaatat agaaggcttt tccttctctg caacgatttt gtggcttcct   64260
agaggtcagg agagtgttgg tcatgggaaa gaaggttgaa ttcagtctgc ccacatgggc   64320
gtgcctagct ttagaacagc gctatttagg agaagttgga agttacaccc tttggtgaga   64380
agctgtgtct gttttttttcc atgattggca taattaactc aaataccagc tgtacattag   64440
tccgtatttc tgttcatggt tgagttcagt gtgtccagag accggaaggt gctttgcact   64500
cacaggagtg cccatgtgga gctccatggg atgtgaatta ttgttggtca ctagttctgg   64560
ctgacattgg aatcacttga agagtttta taatatgtgg attccaaagc cctgtcacaa    64620
acctattgaa tttgtacctc ccaggttgaa tttttgttg ttttttgttt gtttgttttt    64680
tgagatggag tctcactctg tcacccaggc tggagtgtag tggcatgatc tcagctcact   64740
gcaacctctg cctcctgggt tcaagtgatt ctcctgcctc aacctcccaa gtagctggga   64800
ttacaggcac ctgccaccac gcctggctaa ttttttgtatt tttagtagag agagggtttc   64860
tccatgttgg ccagtctggt ctcgagctcc tgaccttggg tgatccaccc gcctcggcct   64920
cccaaagtgc tgggattaca tttacaggcg tgagccactg tgcctggccc tgggttgatt   64980
ttgatgctta gctaggtttg ggatccattg gattatttaa caccagaggt gccttttgtt   65040
tctaatgata ttctctcaac gtgttttaaa aatgaagccc atgagatagt tatgagatag   65100
tagaactttt ccctacattg gtgaagtaaa aatcttggga ttttgatagt cagattatct   65160
taggcattaa aaaatatcac accgatgccc tctctttta tagggattcg cagaggcatt    65220
tttggaacat ctttggaaaa acttgcagga tccaagtaat cctgccatca tcaggcaggc   65280
tgctggaaat tatattggaa gcttttggc aagagctaaa tttatttctc ttatgtaagt    65340
```

```
agcctaattt gccgagtact ttttaatatc atgctttaaa aagagtatag cattgtctca    65400
agtcagaaat atctcccata tgttttggc atgttttaa agtgaataaa attcctactc    65460
tgtgcaagat gtttatattt ctaagtggtg attttagaat aaagtgtctc cttttttata    65520 tataaaccc tgtatgtaag gcttttgtca tctcttttgt gtggttgcac ttaaagatcc    65580
atttgttttg tggatagagg acagtgttgt atactgtttt gattcttttt gtaggtttgt    65640 cattttttc atttgcattc caaatctatt gtatctgtta aagctgaaga aaaaccttt    65700 taaaggtaat agacctatct aggaggccag tttctttcag tggcccatga agatatcttt    65760
ggacaaggat gctgttgaaa cccttcccca agaacaaaat tattcaccca taggacttga    65820
ctggatgcat cagggaatac tgaagtccac cagactgtct ttctcttgag acgtgttggt    65880
gaacatgtcc tatttggcca atcaccctaa gaggggtgcc tttgagatgg ttaggagaac    65940 ctgcttttcca tcccttggga cgttcttagg ggctcacctg ttcctagaag gtcagagcta    66000
ctctgccttg taattggaag gttgtcttcc tacgcaccca tccttatcct tcctttcttt    66060
gcttttcctc tgtacccatg ggtattattt aaagaaacct atgaacttac ttagcatggt    66120
ttgtaatgaa aggcagttgt gtgtttttat gttattctgg ttttttttatg aagtgtaaag    66180 ttgacttgaa ttttttcttt ctctagtact gtaaaaccat gcctagatct tttggttaac    66240
tggctgcaca tataccttaa taaccaggat tcgggaacaa aggcattctg cgatgttgct    66300
ctccatggac cattttactc agcctgccaa gctgtgttct acacctttgt ttttagacac    66360
aagcagcttt tgagcggaaa cctgaaagaa ggtcagtgtt gtgggagtgc tggactggat    66420
tttccttgtg ttcttgtcac ccttcagaat ggtgattcat tactttttttg agatttttat    66480 aaaaactgga ttcagaaaac tgcatgtaca ctcaaacttc taataataat ttcaagcagc    66540
tcataggccc ctacaaaccc cttaagatag atttgagctt gagaacccta caaaccccttt    66600 aagatggatt tgaggttaag aaagaggttt ctgcctttga aggtttgaaa tgtgaagatg    66660
tctccagagg tgaggctgag ccctgggctg tgccagcgcc ctgtacaaag cttcagttgg    66720
atgcaccttc tctttgttgt ccttgtaaca gcccagtaaa tggcaggtat tctcccttta    66780
cagacagcac caaagcacgg ggaagtcatt ttcccaagat cacatggtta ctggcaggat    66840
tagaaaactg aagccaggtt cagctgaccc taaagtttga gtttatatag attacactct    66900
gcctgaagcc ttgagactta attgaccagt attgttttgc taatttctaa gagttactta    66960
taattcaaat ctatcagttg aaacttacta gattagcgta ttttagttga agagagtctc    67020
caagaacagt gtttataagt cattgtaaat tgttctgttt atgtttatga ataattcata    67080
tggttttgtg ggtcacttcc tctaaaccag ggtctgtcaa ccctgcatga ttgccatttg    67140
ggctgcatca tccttcatcg tcggggggctg tcctctgcac tgtaggatgt ttaacagcct    67200
ccacctacta gctgccaaca gcagtccctg accacccca gctgtgacaa ctaaaagtgt    67260
ctccagacac tgccaggtgt cctctgtggg ggttgcagtc tccttaggtt aacagccaca    67320
gctctaaact gacagttgta cgtgttgcat tatatatgtt tacctacatc ctacatgctt    67380
ctaaaagatg ttgtatgaac tagtaggatg aggttttatc acaaggtaag taaatacaag    67440
ctctgctttt ctttgtataa attaatgcca ggaatctgaa ttaaatatct tgttttgta    67500 agcagtgaca tcccatttag gtaattttta ttgaaatatg catcaaagaa actcctaaga    67560
aaatatactt aagtacaagt tggtcagctt gcctcttaaa ataaatgtga tgtctttatt    67620
ttactcatgt aggaaagaat tgtattcact aagtctaaga aagtggcttc tgtctaaatt    67680
tgccgtccgt tgaggtagaa ggcaaatttg gagttttctt gtttagaaaa aaaactacag    67740
```

```
atgactactg tgcacctgaa aacagcactc agcttcacta acgagacatg caagctagaa    67800
tcaaattgct gttttgtttt gttgcctgtc gtgattgtta gctgaaacca aatcacaagg    67860 tcttttctc cctctgtatt agctcagcat acactgagct tacaaacgta tgaacttcac     67920
gttgtcgtgg aatcttacag cctgctactt cctaagtttc ctttagagaa gctgccttgg    67980
tgaccaatga atgtggttag cctagtgata ctcttctggg ccatatactg tgtgactatc    68040
tgcatggacc tttattgaaa gcatttctgc aaataatttt tttaagtttt ttttaaatgt    68100
gtgataattt gtgcttttaa agatatctta cacttttcac ttatttgtac ctttaaaaat    68160
cttttttttt tttaaaccaa aggtttgcag tatcctcaga gtctgaattt tgagcggata    68220
gtgatgagcc agctaaatcc cctgaagatt tgcctgccct cagtggttaa cttttttgct    68280
gcaatcacaa agtaagttat ttatgctttc ttgatgggag ttatttaaaa tattttttatt   68340 tatgtttctc tagtattgta agagtctgtt aaatttctat gaaattagta acattataaa    68400
aggccaggcg tggtggctga cgcctgtaat ctcaacattt tgggaggctg aggtgggagg    68460
attgcttgag gccaggagtt aaaagaccag cttgagcaac atagtgagac cctatctcta    68520
taaaaaaatt ttaaaaatta gctgggtgtg gttgcctgtg cctgtagtcc caactactca    68580
ggaggctgag gtaggagaat cacttgaacc caggaggcag aggttgcagt gagctgagat    68640
cgtgccattg cactccagcc tgggtgacaa gggcaagact ccatcaaaaa aaaaaaaaaa    68700
aaaaggaatt tctgcaatac gctacaacat gaatgatttt gtaggacatt acgctaagta    68760
aaataagcca gtcacagaaa aacaaatact gtatggttct acttaaagga agcccataga    68820
gttgtcaaaa ttagagagac agaaagtaga atggtggtcc ccagcggctg cagaaagaca    68880
gagtggggaa attattgttt aatgggtaca gagttttcat tttacaggat gaagacttgt    68940
ggatatggat ggtggtgatg gttgcacaac aatatcaatt tatttatac cactgaaccg     69000 tgcacttcaa aatggttaag atggtaagtt ttatgttgtg tatttaccca taataaaaaa    69060
aattgtagag ggaaaaacag tctgcctcca cttttgatat gggactgcta acatcttcca    69120
ccctccctct cccccctctgc cccacatctg ggcaagctaa gaaagcctgc tgctctctcc    69180
tctggcacca gctggaaatt catacccaac aagcccctagc cctcccacca gacccacatt    69240
tcatccccat ccccatcgca tccccatccc catccccatc cctaaccacc ataaatgcta    69300
agggagtttc cttgcctggt tttctgaaac cattttggga cctgcttggg aatctgccct    69360
gctctctcag aaagcttcat tatatgagca ataaaccttt tcctacccctc ttggtgcatg    69420 tggtgtatca tcagtcttga catctaaaac aaattttggg tggtggggtc catgtctttg    69480
cagggtgacc acaatagtac ctggcacatt atgtgtttaa taaacagaga ttactgtcat    69540
atttatttta ttttatttt tgagatgaaa tttcactctt ttttcctagg ctgggggtgta    69600 gtggtgcgat cttggctcac tgcaacctcc acctcccggg ttcaagtgat tctcctgcct    69660
cagcctccca aggagctgag attacaggca tgcgccacca cacctggcta attttgtatt    69720
tttagtaggg atggggtttc accacgttag ccagactggt ctcgaactcc tgacctcaga    69780
tgatccaccc accttgacct cacttacagg cgtgagccac cgcgccttgt ctctgttata    69840
tttatttctc tatttaaatt gatggatata tgcaaacctg atcattatca tacttatgcc    69900
ttgacacaag agaggcaata aactaatcta agtgatgctt gtgatgccaa agatgtcaga    69960
acactttctg ggccaatggc agatacctca tgtcaccaga tgctaagggt ccacaataaa    70020
aagcgttgaa tgaaaatttt gaggataaat atctccaggt tgaggaagaa ggttgcacat    70080
```

```
atcgggtgct caataaatat ttgtcgaatg aatgaatgag tgaatggccc cagtgtgtgg    70140
ggcttgggaa gtgattggat ataggcagag aaaaggaaca agtcaaaaat aattcagaaa    70200
tcaagaacaa gcaagttgcc ttgatatact tcattcctac acttggcaaa ctttagtgat    70260
taaggaaaca atgttttaaa aaagttttg gtgatgagac attcaggaag atctatcaat     70320
aaatagcaaa cctggtcctt tttaagacac tgtgtataaa aaaattccaa aaagattaaa    70380
atcagtgcag aaaccaaaga accatttttt tctatatcat attgatcatt tcaagtggaa    70440
ctgttagcta tcttagaaaa attgtggttc tcaattggtt ttgcctctat ctctgaacca    70500
ccattcctaa aggaaaacat tcaaccagaa aatttcagca catcacaatc tctctgaaga    70560
ttaagaagtc tctgtgaagg actgaatgta taaattgaaa aattttgct gtcacattta     70620 ggtaaaagag aaatcgttct tcatatcccc ttcctttcca tctgtagctc acctatgtca    70680
actttcctct cagaagtgaa ataaaattaa agctatgaca ctgagtgtca gtcatggagg    70740
gacacgttcc ccacttagcc tttgctgaag tgtttccaga gacaactgtc taatgccagg    70800
tccccactta gtgggctgca cttttctact catttgcaca taatccagaa gtcacatttt    70860
gggttcacag tttccactgg ggtaacctca ttaggcctgg ccacctctgt gcttcttgtg    70920
aagtctctga tttgaaggat tagtatcctt tccagactgt gtgggttgac tttcacccat    70980
ctggagttgc ttggaacaaa gataactacc tcaactcctt gtcatgaaag caaaaaaaaa    71040
atagcattag agttctgaga acaggatgtc attacgggtt gtgccttgtc agctacaggt    71100
aagatatttg agtggctcct caagcctccc caactccctc tccaacctcg ctacacagtc    71160
ttcccaggtc tggtatttga cctccagact gccgcccaga aagcaactca gagctcagca    71220
acaccatgat gatgaaacac aaatatgtgg gcccccaact ttggagactc cactggttgc    71280
ttttgtgcag ctcttctat atatgacttt caaaatggca gccaaccctc tcaactgttg     71340
gttgatctga atatgtaaag ttcagccttc aaacccagca acagtcagc tataggatag     71400 agttcaggtg ctggggaatg accacggttg gctgctacgt tgggaaccct ggtgacatca    71460
tatatggacc tgggaatgta aagaaacgta ggaaatctga atttatgact tttctaatct    71520
ctctatcggg atccttttt ggaatcaaga tgatttttcct tctaaaaggt cattttatta    71580
cagtaatggg cagggtagac atacctcact agcgtactct caaaatttct tgcatgcata    71640
tgctttctcc ggcatgcata tgctttctac tacaatgtga acaagcctac gaaagctagc    71700
ctaatggagg atgagagacc acgtggagga gagctgaagt gccccagcca gcagctagcc    71760
tacacccaca gctattttgc ttgtgttcca ctcgtcctat ttgcataata ttgttcttta    71820
agttaaccca ttcttaattt attgttttaa tcttaagcaa taatattcaa gaactaatga    71880
gttttgtgta ttcattatat ttttccataa tatatattat actaataaat gcccattcaa    71940 attttgttt gagtgctcaa gtgggtatca tttaaaataa tcttatatac tatatataac      72000
agccaaggtt tgggcaacac aacagaaact gcatgagttt attttatcag aatttttaa      72060 acggtatggg agaactaaaa aagtaaaaaa gggaacccct gagttaacaa ggagataaga    72120
actacgtaaa gcagttactg tcctgaagga ataaagggaa gagcatgggg ttattagaac    72180
ctagaagttt ggaaccacca ggagctggga ccctatgagg agagggttgg ccctgacaa     72240 tgctggtgtc tctaagggag ctcctgaggc tgattctagc agtgtaggga aagaaactgg    72300
aaactggaac aatttcctct gtaatcaatg acccttgcca gggtaaagaa tcactgctga    72360
agagatgcta ctggaaaagc aagcaaacaa aaaggagggt gtcccttccc cttcttcctt    72420
ccttccagtc tccctcatga cagagcatct ggctggtgac gggaaaaggt gctccacaga    72480
```

```
gcaccacccc aacatcacac gggcatctgc tgacccacag ctgactgcag atgaggaagc   72540
tcagcctagg tcacacaaac gcctcccagc tgagtctagc ctaaattgcc aacctgccaa   72600
atcatgaact aataagtgac tattgtttta agccactacc tttaagggaa ttcagtatgc   72660
agcaatagct atctgatcca tataggccta caaggctata gaaaaactat cacatgtaat   72720
cccagcactt tgggaggcca gggcgggtgg atcaactgag gtcaggagtt cgagaccagc   72780
ctgaccaaca tggagaaacc tcgtccctac taaaaacaca aaattagcca ggcatggtgg   72840
tgcatgcctg taatcccagc tacttgggag gctgaggcag gagaatcact tgaacctggg   72900
aggcagaggt tcagtgagc caagatcgca ccattgcact ccagcctggg caaaagagc    72960 gaaactctgt caaaaaaag aaaagaaag aagagagag agagagagag aaagcagaga     73020
ggctactgca gagaaaagtc tagaaggatg ggttcatggg ttcatcgaga gacaatagct  73080
taacaaccag cacaccatag ttggcaaaac actatcattg aaaaaaaaac atgctcaaaa  73140
ggggaaatgc cagtttgggt aaatatgctt ttgtgttgga gagaaagaat ttggaacagg  73200
cttttcagac cccccttaagg cccaacaaac aaattataat ttagacaagt ctgggattct  73260
tcacagctca gcttgtggtg atggtattag cttcacaact ccaaacaagt taagctgtct   73320
gtgtgaaatc tcctcaacaa cacctcactg gcaaacctgg aggtgctgaa aacagagctt   73380
tcaattcttg tttgcaacca agggagttga gttggcagat gggcactgtg tccagccttg   73440
ggaaaggaca tcgcagactt tgcatcctaa gaactcataa ccacaacggc aaggtaagac   73500
acaagctctt gaaagtttcc atcacagtgc agcacaaatg accttggcta tgtgccctgt   73560
tattgctggt ccctgcttaa aaatctcctg tgacttccaa ccacacaaat ttcctacctg   73620
gttgcaaaaa tgcccttgat aattcacccc tccctctatc ttgccccctt tacaatgtgg   73680
cttggcagct cctcccatca agagttaaaa tctatttcct caccccttga atctaggctg   73740
gccatgggac ttgctttggc caatagatgt ggcagaaatt atggcgtgac agttctaagc   73800
atgagtctca agaggctttg catgcagcaa cttttctctta gaaccctgcc accatgtgaa   73860
caatcctgcc tgggctagcc taatggagga tgagagacca tgtggaagag agctgaggtg   73920
ccccagccaa caaccagcct accccagaag cagaggcatc tgctgaccca cagctgactc   73980
cagatgcata agggagctca gcctagatcc agaacgcctc ccagctgagt ctagcctaga   74040
ctgccagcct gccaaatcat gaagtaataa gggactattg ttttaagtca ctaccttttg   74100
ggggaatttg atatgcaaca atagctctct gatacatata ggcctacaag tctatagaaa   74160
aactatgctg cctctctctc cagccacaca atttctttct cttctcattt actattctaa   74220
ttcctctgtg ttatagtctg tgtcccaaaa ttcatgtcaa aatcctaatc tccaaggtaa   74280
tggtattaga aggtaaatct ttggtaggtg atcaggtcat gagggtggag ccctcatgaa   74340
tgggattagt aaccttataa aagagaaccc agagagctca tttgctgctt ctgccatgtg   74400
aagatacagt gaaaaagaa gcaggcccctt gccagatacg agtttgccaa tgccttgatc   74460
ttggaattcc cagcctccag aactgtgagc agtaagtttc tattgtttat aagctaccca   74520
gcctatggca ttttgttacg gcagcctgaa tggactaaga cagtctacct agaccattat   74580 ttcccttca tcatccacca gccaattcca gcacatcttt tagatctcag cttaaatact    74640
ccctccaaga cctccctcta tctctaatat gaatgaaatc catatctcaa gttcttcaca   74700
gaatcctcta ctctttcctt catggcattt gtcataattt gtaattatat atctagcaaa   74760
gttctttgtt gttaaacatc tacctcctcc actctcctag aaactccaca aggacatccc   74820
```

```
tgcacccagt gcctaggcaa tgccagacac atagcagatg ctccattaat tatctgtcga    74880
atgactgaat ggcttccaag ttagttaact gggcacccTT gataacagat tctggcctat    74940
ttgaaggatc aaagaagaaa gtggtgctac cttctcccct gccactatct tgcccacttg    75000
tggtgccagt tcaggaggtt tggaatggat gtggctaatg atagacgtag acctattgcc    75060
tttcttggat cataattctg ccaggctctg agtccatgtg gcatcgatgg ctaattgtcc    75120
tccaaaattt atcctctctt cttccattta taccctccca tggagtttta acagggcatg    75180
tggtcaccct actgggatct cacttctcag cttcccttgc aactggatgt ggccttgtga    75240
ctaaattctc atgaacagaa tgtgagtgca agtgatgtgt cagtatcttc atcactttcc    75300
taaaaaggga actgctggtc ctccacttcc tctctttcac ccttccaatg agccagaaca    75360
tgcatgtgat gctggtgagt cagcttcagt cacatgaata aaacaaaact ccaggagatg    75420
actaagcaat aagacagaag gaacccaagt ccctagacga gttcacagaa ccaagctacc    75480
tatccaaccc tgggcccacc tggattataa catgagaaaa acataagtcc taatcatatt    75540
tttgaagcac tgcattttag ggcttctttg tgacagcagc ctaccctcta gtctaatcaa    75600
tatacctcac caagtctcct gctcctaagg gagacaaaga agcaaaatga gtctcaaaac    75660
atcatccaaa tggaatagat acagacctgt aatcccaaca ctgtgggtgc ccaaggcggg    75720
tggatcactt gaggtcagga gtttgagacc aacctggcca acatggcaaa accctgtctc    75780
cactaaaaat acaaaaatta gccggacgtg gtgttgtgca cctgtaatcc cacctaccca    75840
cgaggctaag ccgggagaat tgcttgaacc caggaggggg aggttgcagt gagccgagat    75900
catgccactg cactccagcc tgggtaacag agtgagactc tgtctcaaaa aaataaataa    75960
aaataaaaat aaatagacca ttaattaata gatatagcct tggtctgtga ccaaagctca    76020
gaatgttatg atattccttt cctatgtcac ctcaacttgc ccctgtcatc agacaggaca    76080
aattccccac tggtcctttg cactcacagc tgttacattt gaaatgggag cttagccttc    76140
cctgccctgg ttcctcctta gactcatttg ggaaaacagg aaacgtaatt atttctgcca    76200
ttacctttat ctcatggagc ctgacagagt gtaaccaatg gtaggaatta aaacattcta    76260
attgccaact cacaacaact cccgaaaaaa atcattttaa ctcattatac atattaaatt    76320
atgacatgct taatgtccaa acctaataga ttcagtactc aggaaatccc ttatacaggt    76380
agacaccttt cctcctgtac tttaagaaaa tcttacatca atatgcggga cttctcaaat    76440
ttttctatca cagttttctt aataggaagg agaatttgtg ccaaaagatg tatggaaatt    76500
tagcacaaag tagccctcta caagcggagg atttcttTAA agcattgtgt tttatctcaa    76560
gattccatgg caaatgttta tcttctctgc ttgttttagt atgaaatagt tttcatttgc    76620
ttgtcatcat ttttaaggag ttgaaaatac aatcaacctc actcatcata aaataaaagc    76680
aaattaaaac tactatgaca tattttcacc tacaaaattg agaacatttt aaaatgtgat    76740
aatagttcta ttaacaaggg tgtgagaaga caattctcag gcagggcatg gtggctcaca    76800
cctgtcatcc cagagctttg ggaggctaaa gtggaggat cgcttgagct caggaattca    76860
agatccacct aggcaacata gtgagactct gtctctacaa aaagtaaaat ataaattagc    76920
tgggtgtggt ggcatgcggc tatcatccca gctactgggg aggctgaggc gggaggattg    76980
cttgaactgg ggaagaccag gttgccatga gccatgatca cgccactgta ttctagcctg    77040
ggtggcagga ccggaccctg tcccaaaaaa aaaaaaaaa aaaaaaaaat ccctcttccc    77100
tgattggtgg gactgtaagc tggtgcaacc tcttgggagg agcaggtggt tagaaaacat    77160
gtatcaaatt tttatgcaaa atttaaatag acccacaatt agaccctagg aatttattct    77220
```

```
ccagatattc tcatgcatgc gtgcaaggta tatttgcaaa gatttgtatc cagcactatc    77280
tgtaattgca aaaatccaga agcaacctca gtgtcaatcc ttagaagact gtgtacatga    77340
gatactgtac atgttggttg ggttctccga gaagcgcatg cccggataga atgcaaaaga    77400
ttcattaggg agtaacacct ctgccagaaa agcagaagag ataggattgg gcaggagggg    77460
ccattagagc acaatttaga gctaccacca tttcagaagg cagcaaagat tgcctgttag    77520
agaaatggtc aggcccttgt accctcagtc actggatggg agccactcca agaagagcat    77580
gaccatgact taacagctaa ggggaccctg aaagagctgc caggttaagg ctatcagctc    77640
ctcactcccc acagctggac agagagcctt tgtttaagga ggatctgagc agctcatctc    77700
caggtctggc acaagggtta cccataggat gaagatggaa gacatgaatc tatatgtatt    77760
agtatggaac aatctccatg atagattttt aagtgaaaga gcaatagtaa attgcaaaag    77820
agaacataac gttttgggac taggcagaag tgataaccga acaacagtgt gaatggagta    77880
aaatgtcacc gaattgtaca ctttaaagtg gctaattttg ctatgtgaat ttcacctcaa    77940
tttttttttt ttttttgag atggtgtttc actcttgttg tccaagctgg agtgcaatgg    78000
caaagtctcg gctcaccaca acctccgcct cctgggttca agcaattctc ctgcctcagc    78060
ctcttgagta gctgggatta caggtgcgtg ccaccacgcc cggctaattt tgtattttta    78120
gtagagacgg ggtttctcca tgttagtcag gctggtcttg aactcccgat ctcaggagat    78180
ctgcctgcct cggcctccca aagtgtggga ttacaggcgt gagccaccgc gcctgacccc    78240
atctcaatgt tttaaaagag agagaataca gcatgctgtc atttgtgtta attttaaaaa    78300
ggaaatgaat ttatgtgcat gtataaatgc tagacatgga atctctctga aaggagccat    78360
gaaacactca tactatgatc tccagtcagg aaagagactt aattttcact gtacgccctt    78420
ggtgctgctt aaattttat catgtgcatg taattacacc ctgtctttaa aaatcattaa    78480
agatgtttaa ttgttctgat gaaggaatac attacttgcc atcaagaaaa atgaatgaaa    78540
aattttctgc gagacaattt ttagcaagac actgttgtat tgatcattca agttcagaaa    78600
attcagcctc cgtcaagggg cacaaacatc atatatcagg ttcagtttgt cctctctctc    78660
agagtcaaag tgctttagga acatagacac aataagtttc tggaaccaaa tggcaaatat    78720
caaaacttgc tagaacagga gaaaagtgta tcttattgaa aattcaccag ctgctatacc    78780
attcagcatt gggaaaatca gcataccttc ttagacttca ttatttaaa gatggcaaaa    78840 tagccaagtc atggatgtct cccccttttca tcaaaatgta agaactagc tgcctctggg    78900 actctccacc aattttcaag cacgtctttt gaacccattt gatggtgtca ctcaataagg    78960
gcaccttttt caacttggct gcctcttttt gacccaaaat aatttcaacc cttttctgca    79020
gctccgggct tcaccaggct ttctattatt gcatatacct ttcatagtga ttctaaaccg    79080
acctcgaatg aagagacaaa tgatttttta tctattggtt tgattgcact tctccttgta    79140
ctgctccaag acaaggcttg tctttgagt tgcaaaaaat actagcgctc tatttccaaa    79200
gtcaaacaag tggcttttca atgtctctgc aagtgttttg tttcatgcag tcagtgctga    79260
cttttctcga tggagagaca tatggtttgg gcccatttta gcaactctat aataaaactg    79320
attataaaaa taagcatcta agaatatctt aggcttttaa gattgacacc actgcttgct    79380
actcaattgc tagttgtggt tggcagtgca cgcagtgtct tgtggtcaa gttcattgtg    79440 gcaagctcag aggtcatgtc agatcacaac acagggactt tgaattgggt ggacatccat    79500
tcattacgtg gcacacgtca cgagcttcaa ggttttgctt caaaaactct tctgtcttct    79560
```

```
aggtgaaagt ataagtttaa acttactgct ctttaagaaa gtaaatgaaa aatgacacta    79620
aagtcccaaa agccagaatt gtcagcaatc ctaggtgcag ttcattcatt cattcattca    79680
cgtattcatt caataaatat ttatggaggg cctatttacc tggcagcact tcatgaggcc    79740
ctggaaatac aatagtgagc aataaaaaca cactccttca ccaggtggag ctatagtcta    79800
ctagggagat atagatgtta aacaaattat cacacaggcc gggcatggtg gctcacacct    79860
gtaatcccag cactttggga ggccgaggca ggtggatcac ctgaggtcag gagtaggagt    79920
tcaagaccag gctgactaac atggtgaaac cccatcttta ctaaaaatac aaaattagct    79980
aggcatggtg gtgcatgcct gtgatccaag ctacttggga ggctgaggca ggagaattgc    80040
ttgaaccggg gaggcagagg ttgcaatgag ctgagatcgc accattgcac tccagcctgg    80100
gcaacaagag cgaaactcca actcaaaaaa aaaaaaaaat tatcacacaa acaagtacat    80160
aattctatat tgtgaagtgt cccaaagaaa aatatgccac tcttaataag tacaggaggc    80220
ttaatttgga aagttagaaa agtgatgttt aaagtgagaa ctgtaagaca agtcactttg    80280
tcagtgcaaa gtggaaagaa agtatttaa gtagcaagga gagcatgagt aaagaccacg    80340
```



```
tcagtgcaaa gtggaaagaa agtattttaa gtagcaagga gagcatgagt aaagaccacg    80340
gagaaggaaa gcgaggatgc agttagagac atgaaaggac tgcattggtg gggcaccggg    80400
atgaaggaga tgatgaagaa gatgtaacca gaaaggctgg cagggacaag gtcatgctgg    80460
gtcttgcagg ccagcatgag cacttgagat tcttaaagta attgcaaggg agcctttgag    80520
ggttttaatg agggcagtat ctttatcaga tgtgcacttg tttgggtttt ctctggattt    80580
tgttgaaaga acaatttaag cagaaggcag attaggaaat aggagaatcg agaggctgta    80640
tatgttgaga cgcagtggta gtctagggtg acaatgcagg aaatgggaag cagtggatga    80700
actggggata tgttttgaag gtagaataga tgatggctgg gaagacagtg actattcaag    80760
ggcagggggg ttgggggagg tatcaagaat gtttagaata tagctaacca catacccttt    80820
tagaaacagt cttctctgaa catttctcct gtctccaagc ctcagtttcc tcatctatga    80880
aataagaaca ctactacttc cttttttaagg ttgttaaact ggttaaatga gattatgcag    80940
ggaaagcatc actagtcagt gctcaaaaat gtgcttttta aatttcctcc ctttgcctct    81000
tattctcaac tttgtccttt gtaatattat tgttctttaa gtgggcttgg ttttgtccta    81060
tctttgccca ttcactcact gctccccatc cacccaaatc ccctctgtat tctgtttatg    81120
caagactgag tttaccccctt ctcagtccat tgacttatct ctcctcactc attgacttgt    81180
cccaggcaat ttattctgca atcttggaca aaaatctgga ttttcagcca ggtgcagtgg    81240
ctcacacctg taaacccagc actttgggag gccaaggcgg gtagatcatt tgaggtcagg    81300
agtttgagac cagcctgacc aacatgacga aaccctgtct ctactagaaa tacaaaaatt    81360
agctgggtgt ggtgacgtgt gcctgtaatt ccaggcatgc ctgtaatccc agctactcgg    81420
gaggctgagg caggagaatc gcttgaaccc aggagacgga ggttgcagtc aggcgagctc    81480
acgccactgt attccagcct gggcaacaaa gcgagacttc atctcaaaaa aaataataa    81540 taattcatta tgtaatccag ctttgaaaca ctctttggct acacttttgt atgctttaag    81600
gaggaacaaa acacagatgg tctccaactt acattggtta aatctacaat ttttcagctt    81660
tacaatggtg caaaaacaat gtgcattcag tagaaactgt acttcaagta cccatacaac    81720
cattctggtt tgccccttca gtacaatgtt caatgaatta tgtgagatat tcaacacttt    81780
attataaaac aggctttatt ttagatgatt ttgcccaacc ttaggctaat gtaagtgttc    81840
taagcatgtt taaggtaggc taggctaagc tatgatgttc agtaggttag gtgtattaaa    81900
gcaagtttta cttaagatat tttcaagtta cagtgggttt attgagatgc aacctcattg    81960
```

```
taagtcaagg aacatctgta cttcagaagt catcaaagct gcatgagcag gacacaagtc   82020
atatgaaaag ccaggtagac ataatgctat aaaaaatccc tccattgggc cgggcacggt   82080
ggctcatgcc tgtaatccca gcactttggg aggccgggga gggtggatca cgaggtcagg   82140
agattgagac catcctgact aacacagtga aaccccgtct ctactaaaaa tacaaaaaat   82200
tagccaggca tggtggcggg cacctgcagt cccagctact cgggaagctg aggcaggaga   82260
atggcaagaa cccgggaggc ggagcttgca gtgagccgag atcacgccac tgcactccag   82320
cctgggtgac agagcaagac tccatcaaaa aaaaaaaaaa atccctccat tgtcagagtg   82380
tgagcttcca gctcattatc ccagaagccc gagatagcag cagttctcag atcttgtgat   82440
aaaggtcatc tcctatcctg gggctctcag gaccataatg caagagtctc cctctaaacc   82500
tgccagcccc agggcttttc ccgccttcct catcctaagt cctgaaaagt tcactgggcc   82560
aaatggtgaa ccacgcactt attgccccat aacccttggt acaaatgtct ccaaatatat   82620
ccatcaagcc tacaggtagt actgagaata acaacagtag ctaacattga ttggacactt   82680
ctaagcccct taaatccatt atcttactta attctcacaa cactgatcaa gagttggata   82740
aaataatcca ctctcaagcc agcaaatcta aaccagccac tcttccgtat ggattcctgc   82800
tcttatggta acaagggctt gccttcccca cctttattct taaccctcct ggaaaacctc   82860
tgctcctcct tttctgagat ggaaaaattt ataagtgaaa aaccattcca tctttcgagg   82920
tgtggaggga ggaaaacaat cactcctgcc ttcaactaag agtgtgaaaa ataagcttaa   82980
ctaaacctga aatacatttt caaatgcctt tgaaaagact tataaatcaa atcacatttg   83040
tccatctctc tgctcttcaa aattatcatg catgcacctg aagtttaagc aaagaaatcc   83100
attaaacaaa caaacctaaa atcataaaac ccagatttag agatttatcc gctcagtcta   83160
atgaatgccc aattcagaat acaattttgt cttcaaagag ccctgaaggt tcttatcttt   83220
cttatctttc tatagtgtta acagaaatat tacatctttg aaaagaagaa aaacattatt   83280
cccagagcta aaacagaaaa ggctttgaac tattttaggg ataaatcaac tcacagttac   83340
caataaacca aaaagaataa aaaagactgt ttcaaaccaa gttgactact cttacatata   83400
ttcaagtgtc aacttacaaa tcagtcttta aatatacacg tacactttct aactctcctg   83460
aaatgtcacc caagccccca ttcaatcagc taaaaacaat ttaattcttt ctctagggag   83520
gaaatcaggt tatcagataa gtaaaccttA aataccattt ctaggcctga tgtggtggct   83580
catgcctgta atcccagcac tttgggaggc taaggcaggt ggatcacttg aggtcaggag   83640
tttgagaaca gcttggccac atggtgaaac cctatctcta ctaaaaatac aaaacttagc   83700
caggcatggt gacaggcacc tgtaatccca actactcaag ataatctgca taccaattgt   83760
gggtagacat aggttttttgt ccagagccct ccacagaccc atcccttacc taccattgtc   83820
tctcgggctt caaccttatt tgaaagtctt aatttgcagt tccacatact gcaaacacaa   83880
gacccagtct ttctggttct tattttacct ggagattaaa atacaggctg ggcgtggtgg   83940
ctcatgcctg taatcctagc actttgggag gccaaggtgg gtggattgct tgaggccagg   84000
agtttaagac cagcctgggc aacatggtga accccgtgtc tctactaaaa atacaaaaat   84060
catccgggtg tggtggtgtg tgccgacagt cccagctact caggtagctg aggcataaga   84120
atcgcttgaa accaggaggc agaggttgca gtgagctgaa atctcaccac tgcactccag   84180
cctgggcaac aaggcaagac tgtctccaaa aaaaaaatta gtttctgtc ttacaatatc   84240 ataagaaaat ggctggacag gttttcacca aagttggagg gtacttttgt gatgggtttg   84300
```

```
gtttaaattg gtttaaaata taagacacat agtccataga gaattcacct atggactatg   84360
ctgctaagag aatctcaaag agatgcactg ttatgctcca gagttttgtg agaggccact   84420
aaggtcagga gacacatgcc atatatatca agatgctgtc aacagagaaa accagtgagg   84480
tttcaaacag aagccccgct ccattcaacc aggcagccac tcctcattgc aggtgctgac   84540
ctgggctttg gctgcttctc acatgggcaa ctctatacac tctattcctg ggagaagggc   84600
agcaaagacc cacttattaa atgatgttta acaatcctcg gccgggcgcg gtggctcacg   84660
cctataatcc cagcactttg ggaggccgag gtgggcggat catgaggtca ggagatcgag   84720
accatcctgg ctaacaaggt gaaaccctct ctctactaaa aatacaaaaa aattagccgg   84780
gcgtggtgtc gggcacctgt agtcccagct acccaggagg ctgaggcagg agaatggtgt   84840
gaacctggga ggtggagttt gcagtgagcc gagatcatgc cactgcactc cagcctgggt   84900
gacggccgtc tcaaaaaaaa aaaaaaaata tcctccaggc aattgtgtga cagctggaat   84960
gaaaaatcag gggcaaattg tacatataag ggaacaattg ttcatatttg tgtaagctac   85020
cctccggagt ctacaagtta aaaggcacac tttaatcaat ttggcaactt gcatggcatt   85080
ttcctccact atttgtagga tgctggtatc tccttaacag ctactgtttt cctatgcaac   85140
acacaatgac ttcttgaaca catggcagct tttcatttgt tcatttaaca aatacttatt   85200
gagttactac tatgtgccaa acaccattat aaaggtactg aggatacagc ggtgaacaag   85260
atggacaaaa atccctgcct ttgtactaca ttcttgagtg ggtgtgagga acaatgaac   85320 caaagaatga acaaactgtg tattgtgcag gtgtgtcatg ggaaaaaaat gaaggaggga   85380
agaaaagcgg aaaagcagaa aatgtcagga atgcacttcc gtggcgggtg ccagacagg   85440 tggccaagaa gtgacatttg aactaaagaa ggtataagtg agcaagctat gagggaattt   85500
ggcaaaacaa tttcggaggc ggaggtcaca gccagcaggt gcaaaggcct ggggcaggag   85560
tgggtccagg gcatgggacg gatggggaga aggtcagcat ggctgaagga agtagggggt   85620
aagctcaaac aagtcgcagg tgggaaactg agtgtattgg accttgtagg caattttaag   85680
aactttagtt tccactcatt aacatggaaa accactggaa ggttttgagc aaaggaataa   85740
cataatctgc ctttttttct tcaaatgctg tgaaacaaat acttatttga ccctatcacc   85800
atttctacct ttggaaaggc tatggtgtgt tactggatgt tgaggatagc ttactcttca   85860
atgtgcagta accaaactga attcattctt tctcaagatg agagaaagat aagccaggta   85920
tggtggcttt cttagataag ccaggtatgg tggctcacgc ctgtgagctg aggcgagagg   85980
atcacttgag gccaggagtt gaagaccagc ctgggcaaca tagtgagacc cctcatctct   86040
taaaaatttt tttttagtta gccagacatt gtggcatccg cctgtaatcc cagctctttg   86100
ggaagctgaa gtgagctatg atcacgccac tgcaccccag cctgggtgac agagtgagac   86160
ccccatctct aattttgaaa aaaagactgg atagggcctg gttaatacaa ctaactcccc   86220
aaaattcaag ttttttcatat aggtctttt taaaaaatag ctttaattga cataaaattc   86280
acccatttaa agtttacaat tcaatggatt tttatatatt cacaatgtag tacaaccatc   86340
attataattt ttttttttt tttagacaga gtctagctct attgtccaga gctggagtgc   86400
agtggcgtga tctcagctca ctgcaacctc catctcctga gttcaagcga tcctcccact   86460
ttggcctccc aagtaactag gattacaggc atgtgccatc acgcctggct aagttttgta   86520
tttttagtag agatggggtt tcaccacgtt ggccacgctt gtctcaaact cctggcttca   86580
agtgatccac ctgcctcggg tccaaagtgc tgggattaca ggcatgagcc acagcacctg   86640
cccgtaatct acgttagaac ttttttatcat cccatcaccc atttaagtct ttacccatta   86700
```

```
gccatcactc cccattttct caacccttcc cgcaaaaccc ctacccagcc ttgggcaacc    86760
actaatctac tttctataca tttgcctatt ctgaacattt catatcaatg gaatcatact    86820
acatgtgaca ttttgcatct ggcttcttag aataagattt tcaaggttcg tctatgttgt    86880
agcatatatc agcacttcag tccttttgag ttttttttta acaatcttta ccattttcaa    86940
gtgtatcgtt tcatggcagt aagtatattc acactgttgt gtaaccatac ccaccatcca    87000
tctccagaac tcttgtcacc tctccaaact gaaactctgt acccattaaa caacaattcc    87060
cattccccac cccaccccag tccctggtat ggcaaccacc attgtacttt ctgtctctat    87120
aaatatgact actcatactt cattttttaa attgccaagt aatgtttcat tgtatggata    87180
tactgtacaa caatttaact atccattcag ctaatggaca tttggggttt ttttaacctt    87240
ttggctatca tgaataatgt tctgatactt cgtgtgtgtg tatagataga tagataaatt    87300
aaatagaaga tagaagagag agagagagat tggagacagg gtctcactct gtcactcagg    87360
ctggaatgca gtggcaggga cacatctccc tgcagcctca acctcccagg ctcaagtgat    87420
cctcccacct cagcctccca agcagctggg actacacgca tgtgccacca cacctgacta    87480
atgtatgtat ttacttattt atttatgtat tgtaaagaca gagtctagct atgttgccca    87540
ggctggtctc aaactcctga cctcaagtga tccttcctac ctcagcctcc caaagtacca    87600
agattacagg catgagcccc cgtgcccagc ctgatacttt tttttttaag tattattcca    87660
gttgccttgt tgaaaataga ccccaagaaa gcaaatctca aacagagaaa actgctagga    87720
agttcttgct ggaatccagg tgagaacgga tagaggctca catttaaatg aagtagtcag    87780
aaatagccac atttggatgt atttttatac aattcctgct cctgaagtct tccccactcc    87840
tttttttttt ttttttaacca ttactacaat tgctttgctg ccttttttgct gatttattgg    87900 atcacgtgtt taaaaccctg atgtgaacac ctacatttat ccttcttact gggtatgtgt    87960
taggtattta acaagtcttt agttctcctg gagtctgcct gcatgaacca accaaatata    88020
aatctgcaaa atgggaactc tacagtgtct cttcagtttt gctgtcaaga tttcacagcc    88080
tcagcttcta aaattatttc atcaagttca atggatacat attcttgaac tcttttctag    88140
cctatatttt ccaacaatgt tgctaactat atttccatac cagccttctt atctaacata    88200
ctggttaaaa tgtcaaaaag cagagggttt aaaaagcttt tctcggtgga atgtgcttct    88260
ccttcataca tgatataact tgatttgaac aatgtcacaa agatattttc tctgttagat    88320
taaaattttg tttgcatgaa ttttttcaata gctttaagca gttgaatagc aatatatgca    88380
ggaagaagct gagagactta tgtaatagat atttcatgta tctataaccc acactgctgc    88440
ccaggaaatg tgcgctgcat taatagagag gattttttcc tgctgaatac cttgaggagt    88500
tggccaacac gtttgggagt agaagtagaa agggccaggt gtgatggctc atgcctgtaa    88560
tcccagcact ctgggaggcc aagtggggag gattgcttaa gcccaggact tgaggccag     88620 cctgggcaac agagtgagac tccatctcta agaaaaaaa atcataaaaa actaaaattc     88680
tctgccaaaa tggacacaga aaaaactgac aatccagaga aagataatat gcaatgaagc     88740
tagacatggc caaattagaa aatgatattg agagagaaca agagcaagaa agaggagccc     88800
tcagcattga gagggctgag gaagcacaga aatgactgat gggttggtta gttagttact     88860
ttttgtgaag tgtgcaatgt aaatttcact ttggtctccc caccggaatc atcaactaaa     88920
gtctacactg ctatatcggc tatctattgc tgtgtaacaa attattccaa aactcagtgg     88980
cttaaaacaa cacatttatt atctcacagt ttctgtgggt taggaattcg aagatgggcc    89040
```

```
ccctgcttca gggtctccca tgggttgcta tctaggtgta agctaggtct catctcaaga  89100
ctcaactggg gcaggatcca cttccaagtg cacccacatg attattggca ggattcgttt  89160
cccatgaact gttgtcagaa gccgctttca gatccttgcc acgtgggcct ctccgaaggg  89220
cagctcacaa cacaacagct tgatttatca gagcaagcag gcaatgaggc agaacaggga  89280
cctctcttag ggacatgcag cactcccacc ctcaaacata gaaataaaga aaaatcttaa  89340
gttcctttaa gaaaaattcc aggcacttag ctagcccttt aaaaataaat aaggccgggc  89400
acggggctc atgcctgtaa tcctagcact ttgggaagcc gaggcagttg gatcacttga  89460
agtcaggagt tcaagaacag cttggccaac atgacaaaac cccatctcta ctgaaaatac  89520
aaaattagcc aggagtggtg gcgcatgcct gtagtcccag ctactcagga ggctgaagca  89580
ggagaattac ttgaacccag gaggtggagg ttgcagtgag ccgagatcat gccattgcac  89640
tccagcctgg gcaatggaga aagactctgt ctcagaaata aataaataca tcaataaaca  89700
acttaataag caagaagata atagtagctt agaataatgg gcaaaaaagt taaaatcatg  89760
ggatgtttgg cttccctata aaactaatg ttcatagatt gttttcaaa aatgaggact  89820
ccccactaaa tgggtccagc aacacacaag gtccagcaac acaactcaga taagggggac  89880
ctgaaggcta aactcttaac acttttctca gttctaaatt tcttcctaag gggagtagag  89940
gaagtcacac cccaggccag aactaacatt ccactgatct caaattttta gacaaggctt  90000
ctcctcctaa gccaattaca aatcaaaaca tcttttaaatc taccttttgac ccatgggttc  90060
ccactttgag acgtcctgcc ttttaggtc aaaccaatgt agagcctccc atatattgat  90120
ttataacttt gcatgtaacc tctgccttcc tgcaattaca aatccttacc tataagccat  90180
ccgggagctt gggacttaag cattaactaa ttatctttgc ttggtgcccc tccaataaat  90240
accccacttc ctcttgctac aatcccaata tcaatgtttg gttttgctgt gctgggcagg  90300
gggacccaag ttaggttcag tatcagcaag aaggcaagac agagtgtgtg ctagcaagac  90360
agaagtccgt gtgtttggta acctaatctc aaactgaaat gccatcaccct ttgctgtgtt  90420
ctactgatta aaagctagtc acccatatgt tcattgcagc actattcaca aaagcaaaga  90480
cattgaatca acctaggtgc ccatcaatgg agaattggaa aaagaaaatg tggtacatat  90540
ataccatgga atactacaca tccataaaaa ggaacaaaat catacccttt gcagctacat  90600
agatgcagct ggcagccatt ttcctaggtg aattaacgta ggaatggaaa accaaatact  90660
gcatgttctc atttataagc aagagctaaa cgttgggtac acatggatat aaacatatga  90720
acaataaaaa ctggggacta cagctgggca tggtggctca cacctataat cccagcactt  90780
tgggaggcca agctgggcgg atcacttgag gtcaggagtt caagaccagc ctggccaaca  90840
tggcaaaacc ctgtctctac taaaaataca aaaattagca gggcgtggtg gcaagcacct  90900
gtaatcccag ctactcagga ggctgaggca tgaggatcac ttgaatttgg aaggtggagg  90960
ttgcagtgag ccaagatcat gccactgcac tccagcctgg gcaacagagc aagactctgt  91020
ctcaaaaaaa aaaaaaaaa aaaaaaaaaa aaaaaaacg gggactgcta gatgagagag  91080
aaagggagag acaaagggc tgacaaacta tgctcactat ttggatgaca gaaccagtca  91140
taccccaaac atcagcaaca gacaacatac ccatgtaaca aacctgcaca tgtatcccct  91200
acatctaaaa taaaagttga aattataggc tgttcgcagt ggctcatgcc agtaacccca  91260
gcactttggg aggctgggc agaaggatca cttgagccta ggaaatcaag accagcctgg  91320
gcaacatagg gagacttcct ctctacaata aaattaaaaa ttagccaggc attgtgatgt  91380
gcacctgtgg tcccaactac ttggaaggct gaggtgggag gattgcttga gcccaggagt  91440
```

```
tcaaggctgc agtgagccgt gattgtgtca ctgtactcat cctgggccac agagcaagac    91500
cctgtctcaa aaaagagac agctcactgt cagctcactg caaccccac ctcctggatt      91560 caagcgattc tcctgcctca gcctcccaag tagctgggac tacaagagcg caccaccata    91620
cccagctaat ttttgcattt tttttttta gtagagacaa ggtttcacta tgttggccag     91680
gctggtcttg aactcctgac ctcgtgatcc gcccgcctca gcctcccata gtgctaggat    91740
tacaggcgtg agccaccgta cctggccgag aaattatttt ttaagtgaaa ataaaaaaat    91800
aaaagctagt cactaggtcc agcccacagt cagggcaagg ggtcacaaaa ggacgtgaat    91860
atgaggtggc agggatcatt tggggtcatc ttagaagctg tctaccacaa tgttccacta    91920
tgaattattt cagaggattc acacctgggg caaggaggta catcgatagc atgcaaccag    91980
aaggagtcct gagacagtca tttgcagaaa ccctggtgaa gttttggttt tccttggcca    92040
tgcaatcagg ggctactcac tggctgatgg actcagctga cacccagatt aatttgagaa    92100
ctgtatccac agtcattaac tacggggcag tgcccaactg tccccaagcc agaagtaaga    92160
ggtatgcatc ttcacgacct caatgacaaa cttgatcata taaaataggc agcattaatt    92220
gacctggttc aggctacgcc ggaggtggac taccacctgg aaacagagag acattgcaga    92280
agcttccctg aggttcccct tgcagccttc aggggtgaat tctttgacac tgggtgtttg    92340
aaatggagca atcaaggccc cagcaaaaaa cagatgcaca ctccaatggg gtaattgagg    92400
acagtttagg aaagagatta tttacagaag tgtggacagg attaagagaa aacaaggatg    92460
tggagcacgc tggtattatc aacagtgggg tctaaaaggg aaggagagag agagagaaa     92520 tcctggaacc cagagagagc tgtcgctgta agacagaact gcccaacagg aactgtggcc    92580
tttagggaga aactgagcta ctgcaaactc tcagcccgga aggaaagaag ccaaaggaat    92640 aaatacccctg acctcccctt ccaccctcca atctcctact gggtccccac tggccagtct    92700
ggctccctgg gcacaccaga gttgagaaga acggacagcg gatttggagg cgcaagaaga    92760
aagtatccaa aacctagaca gaaagccagg cagcttcaca tgagcttttt aaaagtgtag    92820
aagtcataaa aattctcctg gaaatgagca aacacatggg ctttcagaag atgaacacaa    92880
aatagctttt aaaatgaaag tctgctctgg aagggaaaag gtggttcctg gcaatgtgca    92940
gaggaggatt aaagtcccca ccctcaactc cagcctgctg cgtcttccaa gagagaattc    93000
cccagagcct ggactaggga agcattggcg ccactgggaa aagctgctac agcccttgtt    93060
gggcggctct ttctcacagc tactgaagct gcctttgcaa agattatgac agtgagagaa    93120
tctggtgttg ctgactccat cttgtttcta gcctcacagg ctaactgtcc tcactcattc    93180
ctgggcatag gccaagttaa tcatgagatg aattttttta ttttattat ttgcttttg     93240 agacaaggcc tcactctgtc gcccaggatg gagtgcagtg gcatgatcac ggctcaccac    93300
agcctcgaac tccctggtct cagggtggtc ctcccacctc agcctccaga gtagctagga    93360
ctgcaggcgc atgttaattt ttttgtattt tttgtggaga tggggcttcg ccatgttgcc    93420
cagtctggtc ttgaactcct gggctcaagc gatctgcctg ccttggcatc ccaaagtgct    93480
gagattgcag gtgtgagcta ctgcacctgg ataggtattt agtttatagt ttaatttgaa    93540
agcaaggatg ataatagtgt tccactaaaa ctgattccct cattgtttca gggctgaaac    93600
cacctttgta aaactaagga aaggccacaa gattagggag gggcctgaat tctgctaaaa    93660
tggaggcata gtcttaggca tagttttaga accagccatt gttctataag tcacaagatt    93720
tgtgacttcc ccaattgctc ctatagataa catcactatt atagaaccta ggattggtct    93780
```

```
tttgagatgt ttttcagact ttgcattctg gcaaataact gaccccacct ggacttgtaa    93840
ctcatgactc aactggtcct gtggcccta cccagaggtg gactcagagc accaggacca     93900
tttcccacac ctctattgca tccccaacta atcagcagca tccattgcct agtcctctgc    93960
ccaccaaact attttttgaaa aaccacaggc tgggtgcggt ggctcatacc tgtaatctca   94020
gcactttggg aggccaaggt gaggggatca cctgaggtca ggagttcgag accagcctga   94080
ccaacatgga gaaaacctgt ctctaccgaa aatacaaaat tagccgggca tggtggcaca   94140
tgcctgtaat cccagctact tgggaggctg aagcaggaga atcacttgaa cccggggggc   94200
ggaggttgtg gtgagccaag agcacaccat tgcacaccag cccaggcaac aagagcaaaa   94260
ctccacctca aaagaaaag aaaagaaaaa ccacaacctc caagtttttg gggagactga    94320
tttgagtgat aactccagtt cttccacatg gccagcctca agttaattaa actctttctt   94380
cactgcaata ccacagtctc agcaaactgg ttttgtctat gcagtgggta ggaaggttga   94440
gtaatcacac tacagttctt tctggattcc aggagtctct ctccccttcc cttttagacc   94500
tggttggtaa gggctctgtg ctgttgacag ttccagagta cctcacatcc tttgtttcat   94560
ttaacccagt cctatgcttct gtaaatactc tctttgctaa actctcctca agtaattgat  94620
tttaatgtgc atccattgcc tgccaggacc tgattagtcc atttcaagca tccaatatca   94680
aagaatgcac ccaaaacaaa gacgctgtta ggaaacacag aactgggcac tgcaaggtc    94740 tttgagcatg acacaaggat gttgcaagag cggcaggccc agaaggcaag tggggattga   94800
agaaccttaa cagcatattc acggggctca gtcctaggat tcagcatcat gacatatcac   94860
ctccaagctt ccatgctttc atttgtatag ctaagacttg acaagactag tgagggtgtc   94920
cgatgatgag gacagtcaag gatgttaaat tcctgactat acattaacaa ggaggaaaaa   94980
aactaacaaa cctgcatcag tgtgaagacc agaaaggcct gtccacagag ccagatgaca   95040
aggtacaaca ggatgctgtt gaaaaaatc agactagata agagcaggtt gctgtgtgag    95100
caaactcaga ccatacaaga gaactatagg cccctctcct ccagcccaga attcctgccc   95160
tgagtgatgc taaatcagaa ggaagaaaag caggagatga tattggctac cctccgggga   95220
caggaagcat cacctggttg gactaccaga ctgccattca cacttatata catggagtca   95280
gtcgggtatg actcagtccc ctgaggccaa atgtcagcga ggagagtggg aggagcaaat   95340
ctctctcctc cattagagtt gtctccggaa caaacccagg tctcaaggca aaggcctcac   95400
acactatttt gctattttgt cacccacgta aagttttcag aaacaggatc cctgtagctc   95460
atcaggcact caggtgcatc aaagctgaat tcagggtaaa gattgatgct gtggcccagt   95520
gaagctgaga tgcccatact ctctctgttc aggttataga gaaaatgggc actttgtgat   95580
cacttatacc cataataaaa aacaatttgt gtgcatctca tgagcaagaa aaataaacag   95640 gaaaaagaa agcaacccaa ctacttgtaa gtataaggaa atccaaccca tatttgttca   95700
tataactgaa aggtccaggg gcaaacctgc aggtatggtt tgatgcaggt gccaacatct   95760
tttgccagga cccagtgttt ctcacaccct ttcttttttc ttttttttctt tccttctttc   95820 tttcttttc ttttgtctt tccttcttttc tcttttttt ttaacagg atctcactct       95880 gtcacccaag ctggagtgca atggtgcaat ctcagctcac tatagcctca acctcccagg   95940
ctcaagcaat cctcccacct cagcctcctg agtggctagg accacaggca tgcaccacaa   96000
tgcccagcta attcttttca ttatttatag aaacagggag tctcactatg ttgccagggc   96060
tggtctcgaa ctcctgggct catgtaatcc tcccacccac ctaagcctcc caagttctg    96120 ggattacagg tgtcagccac catgcctgac ctcacaccat ttcttaactc cattcttctc   96180
```

```
actccatttc ttaatttcat tcctttataa agcttctctt cttactattt caagatggct    96240
gcccaattca tgtgcagagg aaagagaagt tctttctctt tactctgaca gttgaataaa    96300
aaatccaaag cctggctctc tttggtccat ccctgaatca gtcattatgg cctggggaat    96360
ggagtatgct aattgactta agggaatcag ggcccagcac tggagtgaag gtggggctaa    96420
tgccacctaa tccactggag agtaccaaaa gtgtgcttcc ccaaaggaaa ttcacaatac    96480
tgtgggaaag gatgaattga tgctgagtca ctatgaatga caaatgcaaa agataaacat    96540
accaggcccc actccttgca ggaagcaaaa gatcctagag ggagaggctg acatggaaca    96600
ggatgtctga ccaataaaac ttcttccaat gaggattcac agacatagtc ataccttcca    96660
ggttaagtaa ggctcaattc caggcagctg tctgtctcag ctcctcatgc acatccgtcg    96720
cttctgtcta cccagcattt gtttctccct tattcagttc tcattgctgt gtaacaaatt    96780
gacagaagtg catcaactaa agcaacacaa atgtattatc tcacagctct ataggtcaaa    96840
atccaagcac ggctcaaccg gattctctgc tcagggtctc atggggctga atcaaggtg     96900 tcagctggag ctgtagtctt atctaaagct cagggtcttc ttccaggatg attggttgtt    96960
ttcagacttc cgctccttct gattatcttg agataggagg caggacttga ctctggaggt    97020
ggggcttgga caccggacca agttcaggac taactaaaac agagctggga gggaagcagc    97080
tttccctaag acacacccac cagtgtgcca ggtcagttta ccattgacac ggcaatacct    97140
gggagttacc accccttttcc atggcaatga cctgatgacc taaagttact acccctttctc   97200 tagaaagttc tgcagaaacc acccttgaat ctgcatataa ttaaaagcag gtataaatat    97260
gactgcaaaa ctgcccagag atgccactct ctggttacag ggtagccctg ctctgcagga    97320
gccgtcatgg agctgtaaca ctgcaggagc tgtaacacca ccgcttcagt aaagctgttt    97380
tcttctacct ccagcttgcc cttgaattct ttcctgggca aggccaagaa ccctcacagg    97440
ctaagcccca gtttggagtt catctacccct gcatcaatat gactgaggtc ttttttcttg    97500
ctggctatcg accagagacc tctctcacct cctaaagaca aacctaggtc cttgccctgt    97560
ggcctctcca taggctttct cacactttga gcatctctga cttcaggaag ggcctagtcc    97620
cttttaaagg tgcacctgat taggtcaggc ccacccagat gctctccctt ttgattaact    97680
caaaatcaac taactagtag cccagtcagg gcagggctat tccatcacat cctctaattg    97740
tgcagcactg gagaggagga gattgcacag attgtgcaca ccagggagca gggatcttgg    97800
gggccatctc agaattctgc ctaccacatg ttagtaattg atctcttctg gaatcagtcc    97860
tttcctgctc agtcaatgtt atttgtggta ggatttaggg taatcagacc tagccttggc    97920
caattggtgt aaccattgtc tgggccacag tggtcagatc agaaatgggc acctgcctca    97980
agcaagccca atcagaccta acctgggggac ttttgctgaa gtaactagga aagatctctc    98040
tctctctctc tctctctctc tctctctctc tctctttctt gttattgcgg aagtgttagg    98100
ctgtaaactt agagctgatg gtggacacca tgtgctttga ttcaaatgac cccccaaaac    98160
tcatgttgaa actgaatccc aaaagtggga gcattgagag gtgggacctt aagaagcga    98220 ttgtatccct cttgagggca gagcctttac tgaccaccta atgttttatt aaagcttgtt    98280
ctgcaccacc cctatcccta ccatcaccat ctggagctct cgatcctttc ctccagattt    98340
ctttgctcca taatatttat cactatctga tacagggggtg tgtggatgtg aacatgtata    98400
tgtgtgcatg tgtgtgttta tggtccgcct ctcccagtcc ccggtagact gtaagcttca    98460
tgaaagcagg gctttgtgta ctgttgtttc tgtagcatga ggtctgccaa aaaagtaggt    98520
```

```
tccccataaa tgtttgttaa atgaatatat tctgattcta tctcccctc ctccagaatg    98580 gatctaaagc ttcccaatct ttgcctgagt gagtgtccta ctgagttcaa ttttgtttca    98640
gaaaggacgt gtgtatgttc acccatatgc tgcacaaata tgtaatggac accagccatg    98700
accagcctac tggggactgc ttggcagtag caacatggca gcgaacaaga cagatgagcc    98760
tcctgcccac agaagcttac attcgggtgg aatacaggct ggtgagttgt catgccgatt    98820
cctccaaccc aaaacccttg ccagtatggc aggtcctgga gctggactgg ccaccattga    98880
gaatccaccc aactgcccat cagcatctca agttccctgt tgcaagatgc cagggagcat    98940
gagagaggac cgtgggggag agtgagctct caatgaacct ggtgtggcag ggagaagacg    99000 aagatgggc agatccccag ggggaagaca acttaagggc agatttgttg aactaagtta    99060
cttcaaaggg tcttccatct tccagcatga gcagagaaga tgaccacaca cctgggggag    99120
agtcagatgg cttcttcaat tggaacgttc ttccctaagg atgagctaat atagcacatg    99180
acctgaaaat ccttctggga gactccaggt aaagggcct tgactgcacc agggagagaa    99240
gctaagttgt agatttgggg gaaatgagtg ttagaacagt gagtgctcaa gggaagtagt    99300
taagtgagcc atgagataca aagtctgcca tggcaaagta ggtggaacaa ccatgttatg    99360
agtataagtt ctgaccccag cttttcctgtg atttctacga cccttggtct tgaagatggg    99420
aaataaatgg gtgcatgaca gaagttaaag actattatcg ggtatcaagt accatagcac    99480
tttttggagg cagaagagct tgacaaatgg gcatagtgta catagtaaat gatggtaagg    99540
gtaaaggata aaatgtatca tcttcctgtc atcagaatgg gaccagcact gtgtaaggtg    99600
ggcatgttaa tgacatgata tataagacag cttttgctac aataacaagg aactccctag    99660
gcctggcacg gtggctcatg cctataaccc cagcactttg ggaggctaag gcgggtggat    99720
tacctgaggt caggagtttg agaccagcct ggccatcatg gcgaaaccct gtctctacca    99780
aaaaatacaa aaattagcca agcaaggtgg cactgcctgt aatcccagat actcgggagg    99840
ctgaggcact agtggtgctt gaacccagga ggcagaggtt gcagtgagcc gagatcactc    99900
cactgcactc cagcctgggt gacaaagtga gactccatct caaaaaataa caataactta    99960
aaaaaagaga aatagctctc aaatcccaat agatccctat aacaaatatt tgtttcttgc   100020
ttctgagtct tcagattggc tgtgattaca ctgggtttgg cttggctgag ctcagctagg   100080
ttctgctgag ctcagcttgg ctccaaggtt tgggttgagt tcaggtctgc tccacatgtc   100140
ccttcacatg agaagcaatt gccaagaggt caagtcaaat catgcagcac atttaaaact   100200
tctgctgggg gaaaatgtgt ctgctcacat tccaatgacc aaagcccaaa gttagaaggg   100260
caaggaatta gactctacct attgagatgt actacaaagt cacatggcaa aaagcttata   100320
attctaataa aggaactaag cagaatcact aggagcaatc acctagtccg ccacacatgg   100380
agatgtgcca cagggactca gagactggaa ggaattcccc agggccagag ttctcctggg   100440
aaactacagc ctccaccatt gcctcccaga tttcatcagc atctctgtag tctggctcat   100500
cagaggccac aacggagata aaggcaaata aagacttcag ctgctggcaa gctgcagata   100560
tctccatgga tcagccaagc ccatgtctct ttctgaaaca atcagtaatc ggggaagcga   100620
ccacagaaaa gcgtaataca aactaccctat ggtattggaa gaatcccagg aatcgttgga   100680
ggtcttgaat gaatttgaag agggtactca gttcaagact actttaagac acacactttg   100740
tagatgtccc aactagatac tgtgtggcct gggaattctg caatgtttac ttttttttcaa   100800 ttatattatg ttataatata tttataagaa atatatatca tatataagat tatatatagc   100860
ttatatatct atatataatc tagatatatt atatatctaa atataatctt tgatatatat   100920
```

```
ctcatatatt atcttataca tatgatatat tatcatatac atgagttata cgtatctcat   100980
atatattatt ttcttatata tatgaaatat atctcatata tataagatat gagagctata   101040
tatctcatat atagatagat atagatatct atctacatct atattcccag gccacacagt   101100
gtctagttgg gacatctaca aaatgtgtgt cttaaactag tcttgaacga gtaccctctt   101160
caaattcatt caagacctcc aacgattcct gggattcttc caataccata ggtagtttgt   101220
attacgcttt tctgtatatg agatatatat ctcatacaca gatagatata gatcattcca   101280
tcacccaggc tggagtgcag tggcacaatc atagttcatt gcagcctcaa aattctgggc   101340
tcaaccgatc ctcccacttc agcctcctga gtggctggga ctacaggtgt gtgccaccag   101400
gcgggggcta atttttcttt ttttggagac agagtctcac tctgttgccc agactcagat   101460
gtagtggtgc aatctcagct cactgcaacc tccacctccc aggttcaagc agttctcctg   101520
cttagcctcc caagtagctg ggactacagg cacgtgcaac cactcccagc taattttttg   101580 tatttttacta gagacgaggt ttcaccatgt tgcccaggct ggtcttgaac tcctgagctc   101640
agatacctgc ccgcctcagc ctcctaaaat actgggatta caggagtgac ccacccactg   101700
cccccagcct tttttttttt ttttttttt  ttttttttt  ttggtaggga caggatttcc   101760
ctatgttgcc catgctggac atgaactcct ggcctcaagt gatcctcctg cctcagcctc   101820
ccaaagtgct aagattatag gtatgagcca ccacgcctgg cccaatattt ctaaaggccc   101880
ctcaagaggc aaaagtgggc aaaggacttt taaggacaaa aaatgcctag tattgaatat   101940
taagttgttt actgtgttgt aactctcttc catgacttca gtaaagcaga gtaagcacac   102000
acatgcccca agacacagta acctctgttt ggtagtacag cccatcacaa gcagctgtgg   102060
ctgaacccct gggtaccagg actagagagg ataacttcat tgtaagttcc actggatgtt   102120
aggctgaagt tgcagccccc atcaagccag gcttggtgtc tggagcgggc tgaaggtag   102180 agattctgca aaaggatcta actggggtga tattcaaaaa atttagaagc cagaatggca   102240
caggtcctga ctgataagaa ccagagccaa catgctgtga tctgcataca agtgccagtg   102300
atccctgcct ccagctgagg agggctgtga aggatggagg ctagaaatcc atcaggagag   102360
ctgacattga aaggtgaatg ggagcagcac ctgccagcgt gacctgctgc tttcctgcat   102420
gcaaaggact gtgcatttca acctgagacc ctggggttcc tgcagggcat cagctagatt   102480
tgtcttcctg cctggggcga tcaccaatta tatgtgctgt gaggcaaact gtcctcccac   102540
cagaggagga ggtgaaggga tttacagaat ctctctctga tctgacttat tagagaagtt   102600
aaaggacacc tgtccaggag gcagcacagt gcagagataa agaagtcagg attcaaattt   102660
gtcctatctg ggaagcttag acaagagctc cttaacctct ctcacactca gtcccctcat   102720
ctggaaaatg ggaatcctaa cagtgcctac ctggcaggag catggccaca atgaaatgag   102780
ctaatgacac agtgaaagcc cttagacagc ctgacccaga gtcagccctc tgtaatggga   102840
gtcattattc aagatgggag gaaagaaaca ggaattagat cagaaacaaa tgaccagaaa   102900
gagagatgaa atacaaaagc tacatgaagt cggcagtgtg aagcctgact cgcaggagag   102960
tggattttgt tactgtttgc ttttttcttgt ccaggataat ccaagactgg cagaaagtga   103020
gaataccgat tgagatccaa ggacatcctc atgggagtct gtgcagacac gttttcatca   103080
agaacccctc tccaagcagc tggtccagcc cagctaaact gggggctgct gtttgtaaga   103140
aaattaatgc tctgggccaa gcacggtggc tcatgcctgt aatctcagca ctttaggagg   103200
ccaaggcagg cggatcactt gaggccagga gttcaagacc agcctggcca acgtggtgaa   103260
```

```
atcccgtctc caccaaaaat gcaaaactta gctgggcatg gtggcgcatg cctgtaatcc    103320
cagctactca ggaggctgag gcaggagaat cacttgaacc cgggaggtgg atgttgcagc    103380
gaaccaagat catgccactg cactccagcc tgggtgacag agtgaggctc catctcaaaa    103440
acaaaaacaa aaaaaattaa tgttctgtac ctgaggagca cccatttgct gctacttccc    103500
tgccaggatg aaggaaaacc aagtcagaca ttaaataaca cgtgcaggat cacaggatca    103560
cacctttcac actgcagtct tagttttcta taaaaccacg tgacctctga aaatacactc    103620
cagcctctgc aacacctact catgacgctt tgtaaaatcc accgcttttt agggacacca    103680
agattttcgg aaacatgcag ttttcttacc tccagatgag atgtctactg tggataggtg    103740
actaggagga gaacccaagg tgtgctgatg gcagaacaga agcacctagg atgccaccag    103800
ggaaacgccc tgacaagcag ctgtgatgct gtcttcgaga aggtgtttgc aaacaccact    103860 gctgccccc ttccctgagc cctgacttcc taaacctaag gctaaaagca tcctggcaat    103920
tcccggaagt aacttcattc tagcaggatc gagccagtgg gtggagtttt ctcagcccgc    103980
caggatcaca tcagtgactg acttacccaa tgtactttta tttttattt caaccaattc    104040 cccaaagccc agagcaactt aaaaccagaa gagccaccac catctccacc aaaaacaggg    104100
aatattttga gagtttaatg ataacttcac agccatccat tcagctgagt cccaaggaaa    104160
tggaagacac ctgaaaaatg tatttttaaa ttgatttaac gttgagccat gttaaatgtt    104220
ttaacttcca accaatgcaa tgcccaccaa acatcaatt agtcccagca atcaggcaag    104280
aatattggct tctgctcagg gattcattta tttcagctct gctaaatatc gtagaggaga    104340
aatccaatgt agcctgtagc ttcaagaaag tgaaattaag cccaagtaga aactagatga    104400
ggccctggct aaaatggtgc ctttctggc actgcctctc tctggtatct ctctaaagtg    104460
agggcagcaa cttgattgta agggtctcgt gctgttaaca gaaaacaccc ttccttcccc    104520
acaggttctc tgtctccaag ctggaaaaca aaagaggctg caatgggaca gagaagggct    104580
tcctgctgag gagatgagtg ggcttaagaa tttgcaagat caaaaatcaa aacaattaaa    104640
cccatggaga tagagtagaa ggagagtgaa cagaggctgg gaagggtaat gggagagttg    104700
gtggggagga ggcagatggt taacgggtac aaaaaaaaca gaaagatgag taagacctac    104760
ttttccatag cacaacagga tgactatagt caacagtaat tttttttttt tttgagataa    104820
cgtcactctg tcacccaggc tagagagcag tggcatggtc tctgcccact gcaacttctg    104880
gctcctcagt tcaagcgatt ctcctgcctc agcctcccga gtagctggaa ttacaggcgc    104940
acaccaccat gtccagctaa ttttttgtatt tttatagaga tggggtttca ccatgttggc    105000
caggctggtc ttgaactcct gacctcaggt gatccacctg cttcggcctc ccacagtgct    105060
gggattacag gcatgagcca ctgcacccga ccctatagtc aataataatt taatcgcaca    105120
ttttaaaata actaaaagag tacaattgga ttgtttgtaa cacaaaggat aaaggtttga    105180
ggtaatggat accccatttt acatgatgtg attattacac atcgcatgcc tgtatcaaaa    105240
catctcatgt acccccataaa tatatatacc tactatgtac taatgaaaat taaaatttaa    105300
aaaaattaaa aataatttgc aagatcattt ttaataatta ttttcatttt ggggtgcatt    105360
ttcaccatca aggccccagg gtttccctgc cctagatgag ggtctggatc cagggaaggg    105420
tgtcccacca tctggagcat cctgtctcta cacatgttgg ccagctgctt ggggcaacac    105480
aggacgatgc gctcaggcca ctcaccacag gagcttggcc attagaacca gcagggggaca    105540 accaagccaa agaccccacg actggagagc tcctaaaagc aaatacaaaa taagagtaca    105600
catgaagttc tggcagcaag cagaaggtag acacatgatg tccaactccc cgagtctctc    105660
```

```
tctgggcca cttgatgcag agccttgatt tgttcgtctc ttaaatggga acaatgatcc 105720
ccaaagagga ggaggggtgg gggagtgaga attaaatgag attgtgtcag tcagcatgta 105780
ctagggagct tgttagaaac accaattcca ggatcccctg gagattctga tttagcaagt 105840
ctgccaggag acccaggaat ttgtatttta agcatctctc ccaggtgatt ctgataatta 105900
agcaacttta ggaaagaaaa gattagggct ctggtccata ggaagggttc atccaatggc 105960
agccctcact taggcccttg gggtgaatga aggaggggca tccaggatct tgcccagcca 106020
gggacatgca ggaaacatct ttttaagggg ccctcatcac tttctgacac tgctgtttca 106080
agggaaaact ggtcacacct ttctgcaggg gatttgacaa catccattaa aaaaaaaaat 106140
ttaagacaga gtctcgccct gtcacccagg atggagtgca atggcgccat ctcggctcac 106200
tgtagcctct gtctcccagg ttcaagcgat tcctctgcct cagcttccct agtaactggg 106260
actaaggcat gtgccaccac acctggctaa ttttttgcatt tttagtagag acggggtttc 106320
accatattgg ccaggctcat ctcaaatttc taaccccaag tgatccacct gcctcagcct 106380
cccaaagtgc tgggattaca ggcataagct gccacatccg accaacatcc atcaaaatta 106440
taaatgcaga ccctgtgatc tagcaatctc actttgaaga gtttatccta cagacatact 106500
tgcacagatg caaattatat caggtcagga gctgcagcat tgttcataac agcaaaaaaa 106560
aaaaaaaaat agaaacaact gcaaggtcca tctacagacc tctggttgaa tacagttacg 106620
gcatagccat aaaaccaaca atggcacagc tcctgtgcac agatacagaa ctccctccaa 106680
agtatattgt taggtgaaaa atacaaggtg cagaataagg tgtataataa gcttttgtga 106740
aaagtgcaga gatcatctat atttgatttg ctgtgtatgc atagaatatc tctggacaaa 106800
tacacaagaa gctgctaaca ttggttgcct ctggggaggg aacagggtgg ctggggaca 106860 ggggctggag gaaaagattt caccacatgc cttgcagact ttatatattc ggaaccctgt 106920
gcattatcta ttgcacatat tatctattca tgcaaaacgc tataacattt acaaataact 106980
ttcaaatata tgcatatcat atttcaatgg aaagtttttt ttgttgctgt ttgtttgttt 107040
gtgatggagt tttgctctctt tgcccaggct ggagtgaact ggcatgatct cagctcactg 107100
caacctctgc ccccagtgtt caagcaactc tcctgcctta gcctcccgaa tagctgggat 107160
tacaggtgcc ccccaccaca cccggctaat ttttgtattt ttagtagaga cggggttttg 107220
ccatgttggc caggctggtc tcaaaactcc tgacctcagg tgatccgccc acctcggcct 107280
cccaaagtgc taggattaca ggcatgagcc aatgtgccca gcctcaatga aaagtgtttt 107340
aaagtaataa tataatacat caaaaggcat gatttatgtt ttcaagtgcc acctctggcc 107400
acttgtggct gtagaaatgg ggaatactcc aattccaccat ccctatgtga aggcaggaca 107460
gggagacatt caagtcagga aaggtggag tggaggtttt agtcaagcac caagtcctct 107520
gacttctctg ggcacttgcc catgccggta cctactcctg agacactgtc tacctcgcta 107580
agcccatctt cttctcacct tgtgtctcac ctgagacatc actgacttta ggaggttttc 107640
tgacccatgt gtgttcccca tctcagcacc cagcacctgc ctcatgttca ccagggtaca 107700
tgtcttccct ccccgccagg ctgcactgag agctcaatga gggcagggaa catctctgtt 107760
ccccatcttg ttagaagcta tctccccaga gcatggtcca aatgtggtgt taagaacaga 107820
agttatcaca aagaagtgag aaagtgaagg ggaaatgggg agagctgtaa gaaaggcatg 107880
ggggagaaaa aggaaagaag gccatgttcc caggatccaa tgccactccc tggggaggct 107940
tctctatctt agctcagccc tcagtcacta tcaccctccc tggtcttgtc agatttgaaa 108000
```

```
tatcttcttc atttacaaga gggccttatc tatcttggtc acctctgtat tcccagcccc 108060
tactgcggac ttggaacata gtaggtgccc agtaaacatg ggttgaatta attaatattg 108120
gacaggccag gcttggtggc tcgcgcctgt aatcccaaca ctttgggagg ctgaggtggg 108180
cagatgacct gaggtcagga gttcaagacc agcttggcca acatggtgaa gccccatctc 108240
tactaaaaat acaaaaatta accaggtgtg gtggcacaca cctgtgatcc tagctactgg 108300
gaggctgagg tgggaggatc gcttgagcct gggaggtgga ggttgcagtg agccgagatc 108360
gcggcactgc actccagcct gggcgacagg gcgagactct gagtcaaaat aataataata 108420
ataatagttc attattattg gatagtgagg agggagtttg caaggagcg gctaaaatga 108480 aattagtcct gagtttctga tgttatgcgt tctgggtagg ggcgggagaa ctggaagatg 108540
tttaatgccc cccacccaag ggcagccata gttgagaatc actaattctg aagcttggta 108600
gggaagcttg atagggactt tgggtttttc actgagggca gaatcccag tgactgtcag 108660 agacctcgct ctgaatctta agaacctccc cacccaggc ctgacaggga ggacaaggaa 108720
ggagagtggg gctgggacgc ggggcagagg gcggctctgc tcacctgcgg gagaacgcga 108780
ggatgaggtt ctagtgggac cggcgctagc gggcgcgtcc tgccaggagt gagtcttggc 108840
gccatctagc gcctgctgga ggctctgcag ctgcagtgga ctgagccgcc ggcgctgggc 108900
gtgggtcacc gccgcggcgt tctccggacc cagggaggcg atctgctccg cggacagctc 108960
ctgcaggagg caaggggca gcaccctcac acggggcccc tccccggatt tcccacatct 109020
cgggcgtccg cgcaggatgc acacaacttt gccatcccct tgtgtgtatc atgtgtggtc 109080
ctctttaaga tatttcctta aaattagatc actcttgcac taccaaagta aatgcattta 109140
aaaatagaaa atttaaaatg gaagtttcca aaaatggaaa gccggcagac ttgccataag 109200
caagcattaa ataggagccg caaaataaaa ataaaacaat attgttgaat cctagctaga 109260
tttgtccgcc aacaatatct gaacccctgg cctcttggaa aaaaagaga gagagagaga 109320 atataaaatg tactatacag ggttaaattg acacttcctt cttgaagtat ttagaagtac 109380
taatggagag ttgaaaaggg aagcatgatt tcctccctat gtggcaatgt tgtttaatgc 109440
aatgcaggac agcttcccag tgcttcaagt cttccacctc ctgaaacact gatgtggagg 109500
gggaaacaca ggccttaaag atcagaggcc tgaattcgag cccctgctct gccacatact 109560
tgctgtgtca ccttgaacaa attacacagc ctccgtgggc tttggggata aatgtgagac 109620
ggcatagaga actcatctcc tctgctgact gattctgatc ctttggtttg actgcctgag 109680
caccatgtga tgagctctgt gagggctcca tggaggaaa atgcagtcat ctattggtga 109740
tatctgctat ggacaacatg agttggaaat tctgccagcc agactatgtc ttcaaggact 109800
gtgaacaagg tgtcttctga agtcacttcc agatcaaagg acttggtgac tcgttccaat 109860
gggactggaa tacgaagggg actctatatc atcatgttta ttttctaaag gccctgaaga 109920
atctgggaaa gatgcttatg ctccctcatc ccttcctctc ctgtcagtca ccctctcctc 109980
ctcttttgtc caggtagata cttccctgga atcatatccc tctgtgtaaa gcccttccag 110040 gaacccact ccagaacaca gttcaggctc ctggaaaaaa ctctgcccac ctctccagcc 110100
tcacacatgg cattcttcac tccaggagag tgggtgccaa tatttacagt tccctagagg 110160
cagcatcttc ctgtgcacct ctttctgcct ggaacactgt ttcttcttca tcgccagctg 110220
ttctccaaga ttcagcatct ggtcggtcaa gcgccatggc tcatgcctac aatcccagca 110280
ctttaggagg ctgaggcaga atgattaacg gagctcagga gttcgagacc agcctgggca 110340
acacagtgag accccccttc tctacaaaaa gttttttaa ttagccaagt gtgtagtcct 110400
```

```
agttacttag gctgacgtga gaggattgct tgagcccagg ggatcaaggg tgcagtgagc  110460
catcattgtg ccactgcact cccttgggca acagagtgag actttgtctc aaaaaaatta  110520
aaattcagca tcacctcctc tcctctcact acacacacac acacacacac acacacacac  110580
acacacacac ggtggggtgg tcagagaggt acttttttgg cttccatata ccattaacac  110640
agagtctgta ttctaaaaat tatctctttt atcaatgttg ctgacttgcg acccacaggc  110700
cagattgaat ctctaggcct acggcactgt gttttcaaaa ataaattcag attggctgcc  110760
aacatttaat tatcaagcaa ttccatatga aaatgaagat ttctgacttc ttctcgaaaa  110820
aagtgaaaag gaaaattcag caatcttggg cccacatggc cacactgcat gaatgtgcta  110880
ggaatgagaa gcagcctcca catttagaca aggctctcca gttcacttcg gtctctaccc  110940
agcctactgc accttatgtt acctttttagg cccctgaagg cactatgtga taacccctttc  111000
acctgtgcat ccttaggtgc acctaccctg gagcctgcca caatgtaggt gatcagtagg  111060
gatttctgga atagataaat acctgtacaa ggaagcagca caacagcact ccaaacaaga  111120
ccaagagaaa gtgcttagca aaatgccagc atccaagacc aagctgcttg tcccatgcag  111180
agtgccccag aggggaagca ggtatttgct caatggcttt gaggactgct atttattgcc  111240
ctcaaacagc tattatgcct gcaatgtgct cggaactgtc caggatgctg aagtgattga  111300
aggttggctt tcttttttttt tttttgagac agagtctcgc tctgtcgccc aggctagagt  111360
gtagtggagc gatcttggct cactgcaagc tccgcccccc gggttcacac cattctcctg  111420
cctcagcctt ctgagtagct gggactacag gcacatgtga ccaccccagc taattttttt  111480
gtatttttag tagagacagg gttttaccat gttagccacg atggtctcaa tctcctgacc  111540
tggtgatcca ccctcctcgg cctcccaaag tgctgggatt acaggtgtga gccactgcac  111600
ccggcctcag ctatctttct tgaaatgaac aagtgatgtg gcactggggg agtttgtcga  111660
gcctggtttg tgtgttttat ccagaagtgc tggacaaaat gtgttcccac attacgcagc  111720
aaacaggaac accagaatga ctgcctcctc atcagagcag actattccca ccaaacactc  111780
ccctaatctt gtatacagac agaaaaaaag gacctgtcat tagatacctt gcttcccttc  111840
cttcaaatga tccaatttca ccctctcaat ttttcatag cagttttttca cctgtcctct  111900
tgtgattttc ctaatacttt tctttaaatc aactaaaaat atatatatat agaaaaaaat  111960
atatatatat agagagagag atggtttc gctcttgttg cccaggctgg agtgcaatgg  112020
tgtggtcttg gctcattgca acctctgtct cccgggttca agtgattctc ctgcctcagc  112080
ctcccaagta actgggatta caggcatcca ccaccacgcc cagctaattt tgtatttttc  112140
atagagatgg ggtttcacca cattggccag gctggtctca gactcctgac ctcaggtgat  112200
tggcctgtct cagcctccca aaatgttggg attacaggtg tgagccacca tgcctggcct  112260
aaatcaacta aaatattttt atttaattat atcttaaaag gaaatgttac agaggtccac  112320
aatccctcat ctgcaattcc aaagtccaaa aataatctga aaactgcaag ttttccccca  112380
aagtttaagt caaacttatt tatcagcaaa acttgacctg aagtaatgtg aggctattta  112440
tttatagtct ctatttattc caattagtgt ggcttgtcac agatttcttc acagaaaatat  112500
taatgtgttt gcttacaagg tgcttcccca gacactgctg ggggtatgaa gttacataca  112560
gtaaatgtac agggtgatct tttcaaaatc tgagaaattc tgaattctga actatatctg  112620
tccccagggg ttttcgtaag ggtttatgaa cctgtcatac caccataagt agaaaatcag  112680
taccacctgc tagaagaaga gaagatgacc gtaaaaataa atataattaa actacatatt  112740
```

```
gtaattttaa gaaaaatgtt ttttaaaaac acctaaactc acacagatct cctctgaccc 112800
catcagcaga gcctggtcac aagcctctaa attccaaggc ccatcacctg tttccctgtg 112860
tgatttgaaa tggggtcaag ctcccatttc tccttgaaga actgagcacc tactttgaat 112920
atctcatcag gaaggcattt tattgctgat ggctggaaat atggcatcaa atccttgtca 112980
agcatccgga gctctgcctt agttaatcca gctggggaga aaaggaatc acggggttt 113040 agttcaagcc atcagaactc cgcttgtttt attaatggtg ctgcataatg ttcagatctg 113100
agtgttctag gcaggcatca ttccttacaa aaggccctgg aaatcacact ggggaatcaa 113160
gttccttcat caactcagaa aaaaaaaatg tgggtcacat tagccctgat tggcctccta 113220
cagtgaaacg catgcccaga aggaacttca atttacacac tttcaaattt tgtataaacc 113280
tacttagggg ccaattaaat cacattctaa actagcggtt ttccaaactt tagtgtacac 113340
aagaatctcc aaaagagctt gttttaaaag cagatttgca gacccaccct ctgcaacttc 113400
aaatcatgaa atgtaggttc tactgtaacg ccactgatgt ttgctacaca tggccaagga 113460
taatgtttta ttttgtgtcc ccacatttaa gtttggaaag agagagaaag gtatgctcag 113520
ggtgagtctt acctgcaatg gtcccaagct cctgcaagac agaactggtc cactcagtgg 113580
gatccccaaa cacaacttca gccttcctct taaactcggc taagacatgt gtgctgcaga 113640
gcagggtccc aattctggcc actaccaccc tggtagtggt taagagggga gggatataat 113700
atgagcttgg actcttcagc caaaaacaaa caaacacaca cacacacaca cacacataca 113760
cacacacact gcacagtagg ctcagcaggg acagcagatc cagcttatcc cattagccca 113820
gtgggatttt agcccagaaa ggtgccaagt gtcaggaggt ggaatatctg gatggatgga 113880
tggatggatg gatggatgga tggatggatg gatggatgaa ttaacccatt tgccattttg 113940
cacattcata ttttagttac ctgaattctg agatctttat aagtgggatt tcagtgatgt 114000
ttatagcaca cagggttgca ccaagtccta ccaaatgaaa gctcttcagg tcctggatac 114060
tgtatcctga atcatccagg tacccttgca aaatggattc agcctaaaaa atagtaagaa 114120
taaaagataa accatccagg aatgatcaag gtccccaggc ctgagggat aaataagctg 114180 ttgctgtagt ctcctgactg atctcccatc ctactcctct ggaatcccca ctccaaacca 114240
tcctggcctc tgcatccaag ttcatgtcct taagatacta cttcaactga gtatgtcccc 114300
taatctatga aagtgtcttc aggcaatgaa tctcttacat ccttcaccaa tattaaaggc 114360
acttgtgtcc tgtgtgtctg ctgcttattt ccttcagtca ctcttatgac cctcagacag 114420
tttggacata caacttcttc tgcatcagga tccaaacttt tccagcatct ttttccacaa 114480
cgtttcttct ccctttttt tttttttttc gttttttgga gacggagtct tgctctgtca 114540
cccaggctgg agtgcagtgg cacagctcgc tgcaacctcc acctcccag gttcaagcaa 114600 ttctcgtgct ttagccaccc aagtagctag aattacaggt gcacatcacc acatctggct 114660
ttttgtattt tttgtagaga cggggtttca ccatgttgcc caggctggta tcaaactcct 114720
gacctcaagt gatccaccca cctcggcctc ccaaagtgct gggattatag gcatgagcca 114780
ccgcacccag cctttccaca acctccaaca aaaccttata atttcctgtc tctttgcctt 114840
tgttcaaacc agtcctttca tctgaaatgc ccttctgcac ttccaagtgc agacattctt 114900
tttttttttt ctttggttca actcaaatgt caccttcttc atgaggtttc agccagaatg 114960 atttttttctt cctctatggt cctacagaaa tatgtttacc ccttaatgat tttttcttcc 115020
tctgtggtcc tacagaaata tgttcacccc ttcaattcca atgttactc ttcaattcca 115080 agagtagcac acaaaatgct ttggtgttaa actatttaa actaagcctt gatttaaggc 115140
```

```
ggctgacaca taagtctcca taattctagc acagtggcta ttcatcattc ataacttcct  115200
ctggagaacc acctctcttg tattcctgct tcatgtggtt cagtcaaagc taactgcacc  115260
aagttccagg agtgatgaat ttcaattcat accttagcct agctgcagtc actggttctg  115320
gattggacat gtgatttaac cagagtcaac cagaactttg agtggagcat taggggaaga  115380
gctttcttta ctctggactt gaacttagaa ggatatacac aaggatctgc tggaacctac  115440
cacatgcagg catagagcct gtctctcaat gaagccaaca caaagaaaag caaagttcaa  115500
aaacatgata agagacagat tcccacccag agtgttgaag atcctggatc cagctgtatc  115560
tgaacactac ccctgaactt tccagtaatg ggagtcaata aattccttt tttttttttt  115620
tttttgagac aaggtctcac tctgtcaccc agcctggagt gcagcggcat gatctctgct  115680
cactacaacc tccctctccc aggttcaagc gattctcatg cctcagcctc ccagtagct  115740
gggattacag gcaggcatga acatgcctgg ctgattttg tatttttagt agagaagtag  115800
tttcactgtt gggccaggct ggtctcaaac tcctgacctc aagtgatctg cccgtttcag  115860
cctcccaaag ttctaggact acaggtatga gccactgcac agtgcaccca gccccttat  115920
ttgttcaagc cagtttgtgt tgggttttct gccacttgta actaaacatg tgctgattca  115980
ttttatctac ctatgtagga cctgaggagg catccaagcc aatcctatga agatcagcta  116040
caaaataaag tctgggctgg gcacggtggc tcacacctgt aatcccagca ctttgggagg  116100
ccgaagcagg aggatcactt aaagtcagga gtttgagacc agcctggctg acatggtgaa  116160
agcttgtctc taccaaaaaa tacaaaaatt agccaggcat ggtggcacgt gcctgtggtc  116220
ccagctactt gggaggctga ggtgggagga ttgcttgagc ctgggaggtg gaagttgcag  116280
tgatccaaga ttgtgccact gcactccagc ctgggtgaca gagggagact ctgtctcaca  116340
aaataaagtc tggttccttc agtgctcatg ggagcaagta aaagagatta taagacctca  116400
caaggcaaag atgaggagac atccaaggag agaccctaa gtggaagcga aaatcacagg  116460
ctatagtcaa tcttcccaac tctctttgct tttttttgtt tttttttttt gagacagcgt  116520
ctcactgtgt cacccaggct ggagtgcagt gacatgatct tggcttactg caacctccat  116580
cccccagggt tcaagtaatt cttatgcctc tgactcccaa gtagctggga ttacaggcgc  116640
ccgccaccac acccaactaa ttttttgtgt ttttagtaga cagggtttt caccattttg  116700
gccaggctgg tctcaaactc ctggcctcaa gtgatctacc cacctcagcc tcccaaagtg  116760
ctgggatcac aggcatgagc caccatgccc gaccccatc tccgtttaat gttagtcatc  116820
cccatcacac aatatagatc attaaggtgt tgagagaaag tgttgaggaa gattgtgaaa  116880
tgttgcaatg aaattccgtc ttcatgggct ggtgcttccc accctcagg tgtgtttaaa  116940
tgctacctac tcagagaaaa ctgccctctg gactctttca tctcaaacag cccttcttcc  117000
cactattccc atgagcacct tgtccatttt ccgcatcact tatcgtgatt tttcaaattt  117060
ttcactttga ttactcactt ttttgtctgt atcaccaagt aggctcccaa agaaaaggaa  117120
ccatatccag gtagtttacc aatgagtccc cagcacctag cataatgcct gccacagagt  117180
aggagttcaa taagtacttc ttgagtaagt aaatgaatga gtgaatgaat gaatgaatga  117240
aacaacatct gagtgagtga cttacaaaag tcgtgggcaa tatatattat ttgacatgct  117300
tcattttgct gccttcatgt aatagactgg cttcaggaag atttctcatg tttctgaaaa  117360
tcggactggt cagtgtcctc atcaagttgt cctccatgat tacaaagctc acagctacta  117420
tgggggcggg ggatgcagta acaccatgct tagacttata tgtctttgac ttaatgggac  117480
```

```
tgtatatcca aagtggtaat agctaacatt tattgtagct aacatttctt gagtgcatac    117540
tgtgtgctgg caccactttg accactttac acatactatc tcatctaatc ctcctaaata    117600
acactatgag gtaagtatta atagtatccc tagtttgcag atgagcaaac tgaggcaagg    117660
agaggttaag taactaggcc aagatcacac agctagaaaa tgatcgttct ggccaggcgc    117720
cgtagctcct gcccgtaatc ccagcacttt gggagacaaa ggcgggcaga tcacctgagg    117780
tcgggagttg gagaccagcc tgaccaacat ggagaaaccc cgtctctact aaaaatacaa    117840
aataagcagg gtgtgatgat gcatgcctgt aatcccagtt actcaggagg ctgaggcagg    117900
agaattgctt gaacccggga ggcagaggtt gcagtgagtg gagattacac tccagcctgg    117960
gcaacaagag caaaactcat tctaaaaaaa aaaagaaga agaagaaaga gaaagaaaa     118020 tgatggttct aggatcaaaa cccaggcagt ctgattccag ggcccatact cttagccagt    118080
gaaggtgttt ggctatggag aaaagatgga gattcaagtt agttttcaaa ttttctttat     118140
taagtcttca taatcaggtt tcactagttg actcagagca atttgggctc ctcaactatc    118200
aggcacgctc actttaaaat gaaagtgcaa aaatacaatt taaataaaat tactttgaag    118260
atatggtatt aaattgtcct tgccactgaa acccggaaaa tgcaagctca gcctgcaagg    118320
tgataagtta aaataaattt ccttgagtga cgagaccagt gtatatgtaa tgattccaag    118380
acaattaata ccaacacttt taggcaatat taactgttga aaaatgaata gctttaagat     118440
ttcaatctct ctgttcatcc ctctggcttc tataatagtt ttttcccttta tattggtttt     118500 tgagctgaac tatctgttaa tgtagttccg tcaggtctga ctattaatct agaaacctgc    118560 attaaggtt gattgggagc taagttgaa gaactgacta caaatgatac atgcaaatgt     118620
taggttttca tatcctcttc aaacatattg ataaatctca ctgccatcca tgagaattaa    118680
aatcggtgcg aagggaagga gatacctag tttctgcatg tattttttctg tttctccgag    118740 cctgcaaata gaatgatttt aatagcacag tgtgatgtgg cacttctcaa actagtcaaa    118800
accagtttta gagtcaaaga accatgggat tatagaatat cagactggaa ggaacctcag    118860
attgttgggg ctaaccctct catcttgcaa aggaggagac taacccagag aaaggggctg    118920
taatgatgat aatgttgatg atgacaatgc aatgatgtca atatcaacat aaaaacagct    118980
aatttttatt gactactatg taccagacat tgttcaaaat gttttcaagt attaactcat     119040
gtaatcttca tggccaggat ctgcatgttg cccagctcca ggggtgcacc attcacagtg    119100
tattctgttt gaatggtgcc actcagagtt atgaaacatg gccaccgtga ttacaaaaag    119160
ctcaaaagag tagggggaca ttcattggtt ttggctgctc agcgtccaca cttttttcttt     119220 ggaaaattac cctccattag cttcctattg ctactctacc aaaattcccc aaacatagtg    119280
gctttaaaac tacacgttta ttctcttata gttctggaga ctgtatgtcc taaaatggac    119340
tagaaggatg ggttccttct gggagttcta agaagaattc attttcttgc ttttttctagc    119400 ttcaagaggc cacctgcatt tccttggctc atagccccat cctccatctc caaaatcagc    119460
agcagagcac cttcagatct cttttctaggt ccctctgctt ccattatcat gtcaccttct    119520
ctatctatga ccctccttgc tccttcttaa aaggacccctt gtgattacat tgggcccacc    119580
caaataatcc aagataacct cctcatctca agatccttaa tcgcatcttc aaagtccctt    119640
ttgctccata agttaacata gtcacagctt ccaggggttc agacatggac atctttcggg    119700
gaccttaatc agcccaccac atatccttcc ccactcggct catgtggtca tgagatgctg    119760
ataagatgga ctccgctccc tgatgcaggc ctcgccaacc aacatattca accccctgacc    119820 agagtggttg ctcaggggcg ggcaactaca tgagtggagt caatgctgag gcttttccaa    119880
```

```
aaactaataa agaagaggca catttttatg ggcttgttaa ttaggttgta tataagccta 119940
gtgctgaaaa tgaccactga gagagctgcc taagaacgaa gataacatgg aagggctaac 120000
acttcccttt ccagcagtac agtggattag acaccctaaa ctcctctccc aatcaaaaca 120060
attaaaattc tgggaagaac ttcttcttta gcccatgaag gattaattaa cataggaatt 120120
ggccacccac cataaacaac tagaaaattt aacaaaatac atcagacaac tgcatccgga 120180 tatgaacaa cagaatcata atcccagaag aagaaaaaca aacaagatga gccttaaaat 120240
taccctcact tactgccaaa aagcagtttc caagacatgg atcaggaaga ggaaccaaaa 120300
caagcccagt ggcccagctg agtggaggat acagatatcc aagttcagag aggccacggc 120360
acttatcact tgggcaaagt attggagagg aggaaactgc agagggttcc agaaagctgc 120420
agagatgtct agtactgact gctattttgc acatgcaaag agtgaaactc cataggca 120480 ggaaaagagt catcagtaat cagaaaggat taggctgagc aacttccaga gctcatatgg 120540
agctggaaat agttcacatt ctcaccagcc aaagtagaga gatcttgaaa tacatggagc 120600
attaggtaac atcctcaaag gaatcatgtc acagtaatga tgataaatta acaacagaat 120660
aaaggtcact ctggttttac cctaacaaaa ctcaaaagga agcatcaaaa ggatcaagct 120720
gatttgaaag taacttaagt gtatgacaga acaaagccca atactcttca aagaaataca 120780
actaaatcaa atactcaaca atgtaaaatc cacaatgctc atcacccaat caaaattgct 120840
aggcttgcaa acaaaaaaag aaaatatgac tcataactaa gagaaaaatc agtcaacaga 120900
aacagactca aaaatgacca tcatgaggaa attaacagta aggatatgaa ggcagctctt 120960
ataaatatgg aatagttaaa agacccagaa acatccaccc acctgtcccg gggtccattc 121020
tgtttgccag cttagggaag ccacagtgtc tatggagctg aggtccagct gctccagctc 121080
actctcatta agagccagag caatgcgccc cagggagacg atatggtgtt ctctccagta 121140
agatggcatg tcccaaacct ttaggcaaaa aagaaaata gattagactg aacactgtga 121200
tggtatttac aatgatttga atgtttgtgc ccctctaaaa tgcatatgtt aaaacctaat 121260
ctccaatgtg atagtattgg aaggttgggc cttgggagat gattaggtca taagggtgga 121320
gccctcatga gtgggattag tgcccttgta aaagagaccc cagagagcta gctacaagct 121380
agtccctttc caccatgtga ggacacagtg agaaagcacc atctatgaaa aacaagtcct 121440
taccagatac tggatctgcc agtgcttcaa ttttgattt ctcaccccc agaactgtga 121500 gaaataaatt tctgtttata agttaccagt ctatgatatt tgttatagc agcctgaatg 121560 gacaaaggca gtatctaaaa tagacataag gaggctaggt gcggtggctc acacttgaa 121620 tctcagcatt tttggaggcc aaggcatgca gatcacatga ggccaggagt tcaagaccag 121680
cctggccaac ataacgaaac cctgcctcta ctaaaaatac aaaaaaaaaa aattagctgt 121740
gcatggtggc gcacatctgt aatcccagcc acttgggtgg ctgaggcaca agactcactt 121800
gcagaagttg cagttagcca agatggtgcc actgtactcc agcctgggtg acagagcgag 121860
accctgtctc aaagaaataa aaataaaaca gacatagga aacctattgt gcagcatggt 121920
gaccacagtt gataataatg tgttgaatgg ttgaaaattg tgaagagagt agatgttaaa 121980
tattctcaca acaaaaactg acaacggaca agtatgaaag gtgattgaca tgttagcttg 122040
ctttaaccat tccccaatgt atacatacat caaaacatca tattgtatat atgtatacac 122100
cataaatata tataatttgt atttgtcaac tatcccttaa taaaaaataa ataaaaatta 122160
aaaagacata gggtaaatct taatataaag ctctctttta aatcaataat aaaaacatga 122220
```

```
ctatatttgt tttaaaaaaa agatagacaa aagacatcaa caaggaattc acaaagaaa  122280 aattaaatgt atggggaaaa ctttattctc agtcataatt aaagaaatat acattaaaaa  122340
caatcagacc atgttgattc atcacatgtc aagaagtata aagacttatc accatttacg  122400
atactggaaa gatacaaggt aagggatacc ctcatttgtt gtagttgaga atataagttg  122460
gtacatactc ttgagagggc aatttggcta tctgtatcaa aagcttttaa agtatttata  122520
ttctttgacc cagaaattcc acctctggga atttagcctg agtaaatgag acaagtaccc  122580
aacagtatat gtataaaggc atacattgag gcatttttt aatgcaacct gaaagtctaa  122640
caattagcta aataaataag aactaaccat aaataaaatg aagttgcccc tgtggatacc  122700
tccaccaagg attggttcca ggacttctta aagataccaa atccatgga tattcaagtc  122760 ccttatataa aatagtgtag tatttgcata taatctatgc acatcctcat gtatacttta  122820
aatcatctct agattagtta taatacctga tgcaatataa gtgctatgta aatatgtaca  122880
aaatgttatg tcaaaaatgc tactgtattt ttatgtgtat tgtttttat tgttatattg  122940 ttatttggat catttttct aaatacattc tacctgaggt tggttgaatc tgcagatgtg  123000
gaacccactg atatgaagg ctaattgtat tacaaagcta tttaaaatac tgatataggc  123060
tagatgctgt ggcttacgcc tgtaatccca acactttggg aggccaggca gacagatcac  123120
ttgaggtcag gagttcgaga ccagcctggc caacattgtg aaaccccatc tctactaaaa  123180
atacaaaaat tagccgggca tggtggcgga tgcctgtaat ctcagctact gggaggatg   123240 aggcaggaga attgcttgaa cctgggaggc agaagttgca gtaagccaag accacactat  123300
tgtactccag cctgggcaac aagaacaaaa ctccatctca aaaataaat aaataaataa  123360 aatactgaca tagatgtaca ttttggatat gaaaaaatat gcagtctgta ctgttgggtg  123420
tagaaagcaa gttattgaat agtaggtaag tataatatca tttttgtaaa acatgagata  123480
tatgtatgaa atatataaaa taatattttt tatatacata gttttggagt ctggtaagct  123540
tcaagtgaat ataccaaaat atcaacagtg cttatctgct gaacagtgct tatcaaaata  123600
tcaacagtga gtaaaagatt atcactgatt ttcttcttta ttattttctg acttttctac  123660
aataaacttg aagtactcat ataatacata aatacagtta tatttataat tttaagcat   123720 tgaattgttt aaccctggag ggtaactaga tattccacaa ccatgtaaag agctaaaaca  123780
gggctgggtg cagtggctca tgcctgtaat cccagcactg tgggaggcca aggtgagcag  123840
atctcttgag gctagggtt tgagacaagc ctggccaaac aaacccgtc tctactaaaa   123900 tacaattatt agccaggcat ggtggcttgt gcctgtagtc ccagctactc aggtggctga  123960
gacacaagaa tcacttgaac ccgggaggca gagtttgcag tgaacaacag atcgcgctgc  124020
tgccctccag cctgtacgac agagcaagac tctgtcttaa agaaaaaga aaaaaaaag   124080 aaagaaaagc taaaacaggc cacaaaggga ccttttcctt ttatttattt atttgagaca  124140
gagtctcgct ctatcaccag gctggagtgt agtgacgcaa tctcggctca tggcagcctc  124200
cgcctcccgg gttcaagcaa ttctcctgcc tcagcctccc gagtagctgg aactacaggt  124260
gcatgccacc tgtagagatg gggtttcacc atgtgggcca ggctggtctc gatctcttga  124320
cctcgtgatc cgcctcccaa agtgctggga ttataggcat gagccactgc acccagccta  124380 tttttatttta tttttgagac aaggtatcag ctctgacgcc taggctagag tgcactggcg  124440
caatcttggc ttactgcaac ctccacctcc cgggttcaag ccattctcct gcctcagcct  124500
cctgagtagc tggaactaca ggcacatgac accacgcctg gctaatgttt gcattttgag  124560
tagagacagg gtttcaccat gttggccagc ctggtctcga actcctgacc tccgtgatc   124620
```

```
cgcccgcctc ggcctcccaa agtgttggga ttacaggcat aagccactgc acccagccaa    124680
caaagggacc tttttaaaga tggaaagcta cttccagtcc tcttttact cctttctgtt    124740 atattttcag acaaatttgc aaatgattct gagaaaacct gctgtgagca gcagctgggg   124800
ctctccaggt gaaggaataa agcctaattc ctgcaaaccg ccttggtcag aggcactggg   124860
acatccacag aacttgattc actgagcatc tgctagatgc caagacacat ctcatcccat   124920
tctctgccac agccctaaga gggaggaact ggaaatttcc tcctttctca gataaggaga   124980
tcacaatatc actgagctga tgcagtaaaa tttcaagatg atgtatggga aaactgctcg   125040
aggagggttc tatgtgcaga aatgctgaac tggttttggt gtttttcttt tttcctctgt   125100
ttaatgtttc ctccctgagg tgggcttcac ctgtattgct ttctccttca gggtcatcag   125160
ctgaggccgg ctgaaaccct ggacagctcc cagcagttcc acggtcctga tgaatgtgtc   125220
ttcctccatg caccgcaggt cctccagggc ccagcaggcg ttggcttcgg ccaacttgaa   125280
gatgtcatca agagagggg ccacgactcc atggcaacct gaagaaagga gagatgcagg    125340
gaaggagaag aggaaagaga atttcaggaa atgttagtgt attgaaatga gtaacattct   125400
ttgccagtca gatttatgca tggaagggac tacagagtaa aagcagagag caggaggcag   125460
ggaccagttt gaatcccact tctgccattt cttgctaatt actgggtaac aaagtcatgg   125520
aaatgccagc tttttgcaca tccacatgca caaactagga gcggtgcaac attacaatta   125580
aactacaaat tccttgaggg cagtaagagc tggtggtgaa cagtcctgac tttcgattca   125640
aatccaaggc tatttaacct ctctgtattt cagttttctt gtctataaaa tggaaataaa   125700
atcgcctcat aggatggttg tgaaaactaa atgtgttata tgtaaagcac ttagaacagt   125760
gccacgcata cagtaagcac tcgatacaca atttctgttg cctatcttac cccctatgcc   125820
tttgagtttg cagcccagca taaagattcc aaaattatgc agcagccttc ctataaaaat   125880
gggaagatgg gctgtgcggt ggcgcatgtc tttaatccca gcactttggg aggccaaggc   125940
agaaggatca cttgagccca ggaattcaag accagcctgg gcagcatggt aagacctcac   126000
ctctaaaaaa aaaaaaacta caaaatatta gctaggcatg gtggcacatg cctgtagtcc   126060
cagctaccca gcaggctgag gtgggaggat cacctgagcc tgggaggtca agattgcagt   126120
gagccgtgat cacacctatt ctccagcctg ggtaacggtg agaccctgtg tcaaaataaa   126180
ataaaaaata aaaccagga agatgagttg ctgtccatga aaatcatagt gggggttgtg    126240
gctttcccat cccaagagaa aagagaaatg agcctattgc atttctcttg gcaacaggaa   126300
aaacatccat ttcggtcttt gaataatgtg aaccttacct actcaaacca gctaccaacc   126360
aacatgcaag tgagatattg tctttgctgg atctgatgtg cccaacctgg gagaaaactc   126420
taggatcctt aagagcaacc ctggatttct tatcttagcc gcagaccacc actgatgctg   126480
acagatgcac caaccccacc caaggccagg gtatttcccg agccccatgg cctctctctt   126540
ctcattgcac cttcaatgga aattcactgc attccaatca cgaggcaaaa gtagaccaga   126600
tcaaagatgc cagttgtggt cctcaaacat ctttatcata agccacttgg agaggactaa   126660
agacccatcc ctccctaggc caaccccag cccaccctct agtgaaaaca acatcagtga    126720
tagcacagaa ctagagaggg cagaatggtt gactagtata tcaggaactt ggtcttatca   126780
ctgtgtctgt ccagggctta gaatagagcc tggtacatcg taggtgttca gcaaatatct   126840
gtggagtgag tgaacacaca cacacaaatt aatataaaac caagcggtaa ttctgctaat   126900
ccatcaatca ctaaagcaca gcagcaatta atacccagaa ccaactaaag aacactcaaa   126960
```

```
ctatgcactg ataccagagc ttccttcccc tgagcatgga aagccttatt ttgtgtacca    127020
catgcacaca gtaagagctc tgcaatatga tgacatggac tgctagacct tgagggcagt    127080
gggagccagt ggtggtcacc accaactttg ggtacaaatc caagaactgc catttactaa    127140
ctctgtgact ttagacaagt cccttagtct cctaagcccc agtttccttc atttaaaaaa    127200
caagagaaca cccaagcctg gaaatctgca gccctaaatg ggaataggca ttcctgtttt    127260
cacgcccaaa tgttaggttt tggcctgcca catcccacta tcctgtaccc atataaaccc    127320
caaaccccag gctccatgag catacaagca gatgagcaga tgaacagaag agaagaggag    127380
cagaagagca gcatggcaga gaaaggagca tctgaaggcc aagaagagtt tggctgggga    127440
cagttggaga ggagattggt cacaggacag ccaaactcca ggggaagatc atcttcccac    127500
tccatcccct ttctagctcc ccatccatcc caccgagagc cacctccatt acccaataaa    127560
accccacatt caccaagaaa aaaaaaaac gggagaacaa gataatgcat ggagggataa    127620
tcacccaagg tagacacaaa tccaattgtg atacttcttt gctcgatgtc acacgatgcc    127680
tccacccaga gtaaaagcca aagtcattag ggtttccttt aacagtcact acatggctgg    127740
ccttgtctct cactcccctc caaacacact ggcccttacc tcccactcat ggaagtggtc    127800
ctgttgcact ctctgcctgg aagactctaa ttgaaaatat ccacatggcc cactctccct    127860
tgggtcttca ttcaaatgtc accttctcaa taagatgttc cttcatgatt ctcttttcac    127920
atgacagtcc cctctcaaca ctcgtggtgc attcccttgc tttatttttcc ttcttggcac    127980
ttttcataca atataccata tattttactt atgtatggaa atttattgtc ttgctaccct    128040
ccatttgaaa gtaagctctt tatttacaaa attggtgctt aacgaatatt tgttgggtgg    128100
atgaaagcaa gcactgactg tcaactacta tcactggggg tgattaactt tgtctcctca    128160
tgcctggccc cagtctgcac ttagtaggtg catggtaata ataataaaat atctaacact    128220
tggacaggca tggtagctca catctataat cccagcacta tgggagacca aggcaggagg    128280
atcacttgag gctcagagtt caagatcagc ctgggcaaca cagtaagacc ctatctctac    128340
aaaaaaataa aaaattatcc agatgtggtg gttcatgcct gtagtcccaa ctacttgtga    128400
agctgaggtg ggaggatccc ttgagtccag gaggtcgagg ctgtagtgaa ccatgattgc    128460
tgcactccag cctgggtggc agagcgaggc cctgcctcta taaaatcaaa ttttaggccg    128520
ggggcagtgg ctcacgcctg taatcccagt atttcgggag gccaaggcag gtggatcacc    128580
tgaggccagc gttcaagacc agcctggcca acattgtgaa accccgtctt tactaataat    128640
acaaaactta gccaggcgtg gtggcacatg cctataatcc cagctagtca ggaggctgag    128700
gcaggagagt tgctgtaatc tgggaggtgg aggttgcagt gggccgagat catgccacta    128760
tactccagcc tgggtgacac tccagcaaga ctccatctca aaaataaaa aaaatcaaat    128820
tttaaaaata tataatactt attaaagatc tgctacatgc caggcattcc ggtaaacatg    128880
tttctgggtt taaacccatt aattctcaca ataacccagt gaggtagaga cttttcattat    128940
ccccatttga taaaggatga aaactgaggc acacagaggt taaagagctt acccaaagcc    129000
acacagccag taagtggcag actcaggagt gaaatgtagc cagcccggcc ctgtcactgc    129060
tatgttaaac cactaatcca tgttggtcct ctaagtcaat cctactgaaa tgtttgttac    129120
acatattcac gcattaaacc tactagcctg ggtatggagt atgggacatg attccaggtc    129180
actttacaaa agtgtaactc tttttttttt gagacagagt ctcgctgtca cccaggctgg    129240
agtgcagtgg tgccatctca gctcactgca accttcacct cctgggttca agcaatcctc    129300
gtgtctcagc ctcctgagta gctgagacta caggtatgca ccaccacacc cggctaattt    129360
```

```
ttgtgtttct agtagagaca gggtttcgcc atgttggcca ggctggtctc gaactcctga 129420
cctcaagtga tctgcctgcc tcaacctcac aaagtgctag gattacaggc ttgagcaacc 129480
gcacctgaac caaaagtgta attcttttgc ttatagattt tgtcattcta ttgctttgca 129540
gacatttcat ccagttccct gcataaggag gcctcttgat gtcagggacc ctgcccaaaa 129600
cattaattac tatgtcagca atggctcaga taccctgaaa acactcacca ggcatagggt 129660
catagctggg gatcttatca ctgctgttcc gaacagactg aaagacagcc cagaggaatt 129720
ctttagtggg cagggtcctg gccatcttgg aagctgcttg cagaaggatc tcaggaaact 129780
gtgtgaaaga agatgaaaga agaggaataa taattaaaac cccttaaata cagattgaaa 129840
ttagagttga aactgtcaca ctacttactg ccttcattct ttgttatagc aacttctcat 129900
ataaatctat tccctagtcc cactaatgtg gtctctataa agaatcctat aaaatgatac 129960
tcaacttcaa taaaaatcca ataaagtcta aaaacataa gtaaatcact tttcacccat 130020
cagattgtca aaataaaat gaagtgctaa tacttaatgc tgggcacatt cattttccg 130080
tgggactgtc aaactgtgca ctattagcag agcaatctgg taatatcgac aaaaaatgta 130140
ggttaggcga ggtgtggtgg ctcatacctg taatcccagc attttgggag gtcgaggcag 130200
gcaaatcact tgaggtcagg agctcaagac tggcctggcc aacatggtga aaccccatct 130260
ctactaaaaa tacaaaaatt agtcagtcgt ggtggcatga gcctgtcatc ccagctactt 130320
aggaggctga gacagaagga tcaccagagc ccaggaggct gaggttgtag tgagtcgaga 130380
gcatgccact gcactccagc ctgggtgatg ggagtacaac cctgtctcag aaaaaaacaa 130440
aaaaaatgta tgtgtaccta ccccttttt ggtttggtgc tatttctaag ttttactaa 130500
actttatatt tgacatagtt tggatgtgta ccccacccaa atcttattga aatgtaatcc 130560
ccagtgttgg aggtggggcc cagtgagagg tgattggatc atggggcag atttctcatg 130620
aatggttaaa tacaatcccc ttggtactgt cctcacaata gtgcgtgcgt tctctcgaga 130680
tcttgttgtt taaatgcatg tagcacctcc cccatcacgc tcttgctcct gtgtcggcca 130740
agtaagatgt gtctgctccc ccttcgcctt ccgccatgat tgtaagtttc ctgaggcctt 130800
cccagaagct gggcagatgc cagcatcatg cttcctgtac agtcggcaga gccatgagcc 130860
aatcaatcct ctttttcttgt ctcttttttt ttttttttt ttcagagtct tgttctgttg 130920
ctcaagctgg aatacagtgg tgtgatctcc actcactgca acctccacct cccaggctca 130980
agtaattctc gtgcctgagc ctcctgagta gctgggatta catgcatgca gcaccaagcc 131040
aggctaattt ttttttattt ttattgtaga caaggtttca ctatcttggc ctggctggtc 131100
tcaaactcct ggcctcaagt gattcgccca cctcggcctc ccaaagtgct gggattacag 131160
atgtgagcca ctgtgcctgg cagtgttgt ttgtttgttt gtttagacgg agtctcgctc 131220
tatcacccag gctggagtgc agggcacgat ctcggctcac tgcaagctct gccccctggg 131280
ttcacgccgt tctcctacct cagcctcccg agtagctggg actacatgtg cccaccacca 131340
cgcccggcta atttttgta ttttttagta gagacggggt ttcaccctct tagccaggac 131400
ggtctcaatc tcctgacctc gtgatctgcc cgcctcggcc tcccaaactg ctgggattgc 131460
aggcatgagc cactgcacct ggccctttt atttattt tttaattta acttttattt 131520
taagttcagg ggtacatggc aggtttgtta tataggtaag cttgtgtcat ggaggtttgt 131580
tgtacaaatt atttaatcac ccaggtatta agcctagtac ccattagtta tttttgctga 131640
tcttctccct cctcccacct ttcactctcc aataggcccc agtatctgct gttccattct 131700
```

```
atgtgacaac gtgttctcat catttagctc ccacttataa gtaagaacat gcggtatttg   131760
gttttctgtt tctgcattag tttgctaagg atgatggcct ccagctccat ccatgtccct   131820
gcaaagaaca cgatctcatt cttttttatg gccacatagt attccatgta aacctccttt   131880
ctttataaat tacccagtct caggtatttc tttatagcaa tgcaagaatt gcctaacaca   131940
ggtcaggtgc ggtggctcac acctgtaatc ctagcacttg ggaggccaa gcaggcagat    132000 cacctgaggt caagggttca agaccagcct ggccaacacg gtgaaacccc gtttctacaa   132060
aaaatacaaa aattcactcg gcatggtggt gtatgcctat aatccctgct actcaggagg   132120
ctgaggcagg agaatcactt gaacccagga ggtggaggtt gcagtgagcc gaaatcgtgc   132180
cactgcattc cggcctgggc aacacagcta gactccatct caaaaaagag aaagaaaaaa   132240
agaattgcct aacacaacat ttgtcatgaa aaggaggtga agaagggttg tctcaacatc   132300
ctgggtggag actagcaatg aggggactta ggggactttg ggttgccttg gagaaagtgc   132360
catttctcat ctagaacgaa tacactttgt caagacttgg gattttatta gaaggcctgc   132420
ccatgggccc agataatcca tcaggctcta caaacagcta tgcctcactg ggtcccggct   132480
cacccagaga gcaagcctct cagcctatgt agctcccctt tctagtctca tcttcagaat   132540
tagagtcaca gtctaagcca gcagttcttc aaccctggct gtacctaaga gtcacctggg   132600
acacccagag ccagccccta aagattctga ctcagtcggg ctgggctgga taccatggat    132660
tggtccctct tggaatctcc ccaggtgatt ctaatgtgca gctgaggctg aaggcaacca   132720
ctctaagaca gttaactttt agaaagcaat atgcatagcg gagtgaatgg cattttccat    132780
tttgtatttt ctaaagaaga gtgtgtatat gctcttgtgt ttttagtaga gacagggttt    132840
cgccatgttg gcgaggcttg ttatataggt atttttatac ctatataaaa cttgttatat    132900
agatattcag gatatttctg aaaggatgca gaagagattg gggacagcaa ttgcctctga   132960
agagggaggc tagggaacta gaagtctggg gtgggaggga gacttgcttc tcatcctatt    133020
acctttggtg cgattgggat tgttaaccca ggagcatgta ttacttgctt tattaaacat     133080
ttccagtatt taaaaaaga gtatacagaa taatacaaca aaacacccat gtcctcacaa    133140
cccaacttaa gaaataaaac atcacaatat aaataataag tccctccttc actctttgcc    133200
ttcctccttc cccagaagta actgtcactc tgaatttggc attcactttt acacttctct    133260
tacatataaa cttggcttac atttgcttta aattaattca gctactattt atttatttac    133320
tttgtatcct actatagata ttcttttgca atctgggttt ttttttaact ctacactgtg    133380
tttttgagat ttcacagtgt tgatgcaaga ctttttcaat ttcagaagtt gattttttta     133440
agattagata gatatatgga tgttctcact gatatgtggg agctaaacta tgaggaccca    133500
aaggcataag aatgatacaa tgggcttttgg ggacttggat ggaagagtgg gaggggccaa    133560
gggataaaag actacaaata tgttgcagtg tatactgttc aggtgatggg tgcaccaaaa    133620
tctcacaaat caccactaaa gaacttactc atgtaaccaa acaccacctg tacccccaata     133680 ccttatggaa aaataaaaat aataataaac atctaaacat aagaaaaaca aggaaggaaa    133740
aaaaatagat ggatatataa catttgtgca tcagggccgg gcatggtggc tcacgcctgt    133800
aatcccagca cttgggaggc cgaggcgggc agatcacttg aggtcaggag ttcaagacca    133860
ggctggccaa catggtgaag ccccatatct actaaaaata taaaattag ctgggcatag       133920 tgcaggggc ctgtaatccc agctactcgg gaggctgagg caggagaatc acttgaaccc     133980
aggaagcaga ggttgcagtg agccgagatt gcatcactac actccagcct gggcaacaga   134040
gggagactcc atcgcaaaat aaaataaaat aataaaataa aaataaacat gtgtgcatca   134100
```

```
actgcttata actatatatt cagacatcca gaatatgatt ttactgtgac tggacttcag   134160
aatgtgctgc gtgtgatcct aggtgaagtt gtgtgtgttc aggccctgct gagcatgtgt   134220
gaccatgtgc accttgtgcc tgcaagtgca ggtatgagag tgtgtggatg tgctttgtgg   134280
gggatctgat tgtcattcag caaacattca ctcctttcct gccctccacc tccatggaag   134340
gagactcctt cctgcccat  taaagttggt cttggtcatg taacttactt tggccattgg   134400
agtgtggcag aagtgacagc gtgccaactt ccaacctagg acttaaggag aattgtactt   134460
atcccttccc tttttggta  gtttcatacc ttcatggtaa gaaaacaag  ttctagagca   134520 gggctgcccc agcgacccac aaatcaggca gcaaggaaca tatgcgaatt gttctatgcc   134580
cttgagattg tgtggctttg ttatgcagca caaatgacta attcatgctt attttgcatg   134640
ccccttggtc tagactgtct aacttctgga gccttactcc tagaaaagcg tcatgcccaa   134700
atgtaatgat caataaagac ttgttattgg attaaatgtg cttgcacatg tgattgcata   134760
cactggacat acatgtgcat gtgcataggg caccagccag tgtgagagcc agaacagacg   134820
tgcgtgtgag atgcacacta atagcagagt ggtagctaag taatatctgt ctgcacacat   134880
ctgcctgggg ggccacacaa aagggcctga gttcatttag ctgtggactc actccctttt   134940
ccagaacctt gcacatcctg gaatggagct ggaaacatct tagcccttgg aggcagggag   135000
gaagcttcca gaaccataga cagcagtaaa cccaatgctg tataactgac cacactttct   135060
ctccccttca aactccttca gccttcttaa gatggagcac aacattacct ttgtggctat   135120
agagcttaat tcatctcctg agaaaagtac tagaaagggt cccaagtcct tcgtggtctc   135180
ggctgtccag tgctgaggga gtctaaaaag agataataac cagtaaagtg aaaaaacatg   135240
ctgtggtgga catctgttgc cttttccccc agcaccctt  tctttcagga atagattgtc   135300
ttatactcat gtcaatcaca tggtcccact tccttgacca agaaaattgg catgtgatgc   135360
aggctgacca atcagagtca tccctgggag ttttgatgga actatcagag aagctctcct   135420
ttctctggta tctctggcag tagggaggga tattggagga cattcatatt accaagtgga   135480
aaaagtaaag accacaccaa ggaacacaga gctgagggat gggaggaaca tattcctgaa   135540
gatatcattt gagacacggg attcagccat gcctgaagac caccagtgga gtttcccgtt   135600
acattccatt cctgaattca atacattccc gttctcttta gtttgaatta aattattgaa   135660
tttctgccat ttacatcaca gtgtgtcctt cttctccctc tcaatagaa  gagtaattat   135720 atatttcttc cttttacttt accataacag tcttctctta gaataagaaa aaacctttct   135780
cttgaacttg gcaggataaa ataaaggcac tgacccagaa tccactgtta ttcttgtata   135840
gatcataaat gcctacagtg aagagcatta cactatcttt ggcgacatct ctaaaggagg   135900
tctgcccaat tagcagtgac agctggtggg aatgcaaaat catacagcca ctttggaaga   135960
cattttgttg gtttcttaca aaagcaaaca tgttttgcc  atataaccca gcaaacacac   136020
tctttggtat ttacacaaag gagttgaaaa cttcgtcta  catgaaaacc tgtatatgga   136080
tgttgatagc agcttatcc  ataattgcca aaacttggaa gcaaccaaat gtccttctgt   136140
aggtgaatgg ctaaataaac tgtggttcat taagacaatg aaatatgatt cagcactaaa   136200
aagaaatgag ctatcaagcc aaaaaagac  ctggagaaaa cttaagtgca tattactaag   136260
tgaaagaagt ctatctgaaa aggctatcta ctgtatgatt ccaaatatat gatattctag   136320
aaaaggcaaa agtatcagtg gttgccagga attaggagtg agagaggaat gaacaggcaa   136380
agcccggaag gattttagg  gcagtgaaaa tactccgtat gatactataa tggtgaatac   136440
```

```
atgttattat atacttgtct gaacccatag aatgtaaagc accaagagtg aatcctaatg    136500
taaaatatgg actatggatg ataatgagaa tccaatgacg ataatgtcaa cataggttca    136560
tcagttctaa caaatgtaca actttggtgg gggatattga tcatggggag cttatgcgtg    136620
tacggggtca gagagatatg ggaaatctct atcttctcca tttttctgag aacctaaaac    136680
tagtattaaa aatagtctct agggtcaggc atggtggccc atacctataa tcccaacact    136740
gtgggaggct taggtgggtg aatcccttga gcccaggagt tcaagaccca cctaggcaac    136800
atggtgaaat tccatccctt aaaaaaaaat acaaaaatta gctgggtaca gtgatgtgca    136860
cctgtggtcc cagctacttg ggaggctcag gtgggaggat cacctgagcc cagggaggtt    136920
gaggctgcag tgagccatta ctgtgccaca gcactccagc ctgggtgaca gagcgagacc    136980
ccatttaaaa aaaaaatagt ctttaaacta ataataatac cactaccttg catctgtaaa    137040
gggccacctt ttccaaattt cccttcata tgccaagctg tgtaagaaac aactctttga    137100 gattttagg gcagctacta ttgattccac tttacagcaa atctgaagcc aaggccaggc    137160
gcggtgactc acgcctgtaa tcccagaact ttgggaggcc gaggtgggtg gattacgagg    137220
tcaggagatc aagaccatcc tggccaacat ggtgaaaccc agtctctact aaaaatgcaa    137280
aaaatagctg gcgtggtgg cacatgcctg taatcccagc tactcgggag gctgaggcag    137340
gagaatcgct tgaaccaggg agtcagaagt tgcagtgagc caaggtcgtg ccactgtact    137400
ccagcctggc cacagagcga gactccgtct aagaaaaaaa aaaaaaatct gaagccaaaa    137460
gaagaaaggt cacatttcca aaataagcat aagaatttta tctcatccta agccagagac    137520 tctgttttgca gggcaggaga gccaaggttg agtgtccctc cacagagcat accacaccac    137580
caaaagccaa acccagccgc tcctcaccca tactgtccca ggagcttgag cctcactgca    137640
gccttttgct cagggttgag gtctgggcag tctctgaggc cgtgtagagc agtcgcccaa    137700
gccctggggg agatccccct gtcgatgatg gctgccggca agtgacacag caggttcccc    137760
atgatgtcca cagtgtactc atcagcaatg gagtcgtcct gaacccaaaa agtggagcca    137820
atgggcagtt ccaacagagc ataagatcgt gagccattag aaacacatcc tgtggggtgg    137880
gcactgtggg ttatgcctat aatcccagca ctctgggagg ccgaggcaga cagatcattt    137940
gaggccagga gttcgaaatc agcctggcca acatggtgaa accccatcta tactaaaaat    138000
acaaaaatta gccaggcatt gtggcacatg cctgtagtcc cagctactcg agaggctgag    138060
gcacaagaat tgcttgaacc cgggaggcag aggtcgcagt gagcctagat gatcatgcca    138120
ttgcactcca gcctgggtga cagaggaaaa ctctgtctca aaaaaaaaa aaaaaagtt    138180 ccgatcccaa acttcttaaa gattccagga tcttaactgc ctaccctgcc atggattcct    138240
agagatggaa caggacctga tcttccccag ggatgcaggc ctcagaaatc tggaaaaccc    138300
tggcttggca caccaggagc actcagtaat tgagcgctgc tgtcactgtt attgctctga    138360
gaatattcca gacttcaacc accattatac tattggcacc acaacaatga aaacagcact    138420
tcaaagtttg tatgccactt gaaagccttc aaagctcttt tgcactttca caaatgaca    138480 aaaatagttc acatttattg tgtgtttcct atgtgcgggc accgtcctga gtatctgtgg    138540
gtctcaatct agtcatcttc aaagtaactg taagaagtaa gtactactat tatccatttt    138600
ttaaagaaaa agaaactgcc agctagtggc aaggctagga ttcacaccca gacaatctgg    138660
cctttgagcc tttacattaa ataatacatt gcccatgtca tgttttcaat actctatgag    138720
gagactaggt atggtggctc atgtctgtaa tcccaacact tgggaggcc gaggtggatg    138780 gatcacctga tgtcaggagt ttgagaccat cctggccaac atggtgaaac cctgtctcta    138840
```

```
ctaaaaatac aaaaaataac cgggtgtagt ggtacacacc tgtagtccca gctacttggg   138900
aggctgaggc aggagaatca gttgaacctg ggaggcagag gttgcagtga gctgagatcg   138960
tgctactgca ctccagcctg ggtgacagag tgagactctg tcccaaaaaa aaaaaaaaaa   139020
aaaaaactct aagggggatg tgctactccc cccaccttac agatgagaag actgaggctc   139080
agggaggaaa ggtgattcac ccaaagccac ataaccaatc actggcaccc agtctctggg   139140
tactgtgctc tttccattcc tccagagtag cctcccctcc tttgggccgt ggggcagaag   139200
tctccagaac caatggaaaa gattgttcca accagcaact ttagagtaag cttcaagacc   139260
caccagtcag acttctggcc atcacagcag gctcaagatc ctagccagat ccctcacagg   139320
gctccccaag atggccacag atacccagag ggaggggaca cccaggaaga gttttcttac   139380
caggcactgc tgcactttcc tgaggactga agtcttttg tgggaatcta aaaccaagga   139440
gtccaaccag ctcttcccca ggctgatcag aaagggcaca cactgggagg ctgggacaga   139500
agccaggtag cgggccctgg agagatgg ggagaacaag aggaggaaca catggctgct   139560
cctgttggcc cctaaaatca gggttcgcct gcccaagagc tcatcccaaa gacattcttt   139620
aaatgtttgt tcttcccagt gatgcttggg ctccctgcag caggtagcaa gcttcccacc   139680
catcatgctc ctcttctatg ggtgggaaca aacttcccat catgctcctc ttccatgaat   139740
gggcaacaaa cttcccatca tgctctcttc tatgggtggg aacaaacttc ccatcatgac   139800
cctcttctgt gggtgggaac aaacttccca tcatgctcct cttctatgcc ccagagcatt   139860
gatcagagaa tggttctcg taaatagaca tgttgattga tggactggtt gaggggagat   139920 gaaaagaaa ggaaaagta gatgaaaaaa gagacaacga ggagagagaa taactagaaa   139980
gtgagaaaga aagataagaa aaagagtgga aagagaaatt ctgtcatctc cagtccagaa   140040
ctctgccttc cactcttgat ccttcagctc ttgacaatgt attctcaaca gggtcaaagt   140100
caccctcaag aaggagaaac tggtttggat ggagataaaa aagactgtta tgacaacgat   140160
ctgtaaccca ctgaagctca ttcctactca aaatattttt cctcagtgta aatttctttt   140220
cattcaggag aaattaaaat tttctccttt ggaaggcatt aacaaaagtt gagaaagtct   140280
gcatgaaacc catccggcct actcaacccc accacttcac tgttccaaaa ccagatacaa   140340
cgtcttcccc caaacatgtt cttccgcctc tatgctatcc cacactcctt tttttctttta   140400 tcccaagcct gtcattgcta tctccttagc attatcccaa tctgttctta cttctggcca   140460
ggtgtggtgg ctcacagcta taatcccagc actttgggag gccaaggtgg gtcacctgag   140520
atcaggagtt tgagaccagc ctgagcgaca tggtgaaatc ccatctctac aaaaattca   140580 aaaaattagc tgggcatggt ggcatgcaca cctgggggttt caactactct agaggctgaa   140640
gtggaagaat cacttgaacc tgggagacag aggttgcagt gagctgagat cgcaccactg   140700
cactccaacc tgggtgacag aatgggaccc cgtctcaaaa caacaacaac aaaaaaatct   140760
attctaactt ctccattccc agtaccactg tcttatttat ttcttcattc atccagcaaa   140820
tatctacaaa gcaactacag taagccaggc actgttctag gcaccaaata taacaatgaa   140880
caagacacaa gtggtcctta attctagcag agagaagaaa cacagaaacc agtgaacaaa   140940
acaagacatt tgagctatta atagctgcca tggtggctca cgcctgtaat cccagcactt   141000
tgggaggccg aggcaagcag atcatctgag gtcaggagtt tgagaccagc ctggccatca   141060
cggtgaaacc ctgtctctac caaaaaatac aaaaattagc caggcgtggt ggcgcacacc   141120
tgtaatccca gctactgggg aggctgaggt aggagaatct cttgaaccca ggtggcggag   141180
```

```
gttgcaatga gccaagatta caccactgca ctccagcctg ggtgacagag ggagactctg   141240
tctcaaaaat aaataaatta attaattaat taattaatgt aaggaagaaa ataaaatggc   141300
tctgtaaaag agaatgacaa tggggataat caaacgagcc ccttctaagg cagttccatt   141360
tgagctgaga catgaatgag tggtagaagt gccatgccaa gatctgggtt actgaaataa   141420
tcttcagctg tctcccttct ttccattcag cctccctgca ttctatcctc tatgtgggta   141480
gtggctatga tctttctgaa atataaatct gatggctgca cacagaatat gtgtgaaaca   141540
cctcacttta caaagccccc atgatctgat gtcccttaac tctctggcct tctctcccct   141600
atctactctg cagatatacc cccatgtgtt cccagagtga ttggcttttc ttacccactg   141660
ctgaaccgga catccccatt ccactgcctg gaatgtccat cttaaactct ctatccagca   141720
ttagttcggt ctcccctgtc tctccagtct atgggtgata ttccctcctc tatgtccagt   141780
cctcattatc cctccccttt gcctctcctt tggaaggcaa taaaaaagtt gagaaaggct   141840
gcatgaaacc catctggcct agtcaaaccc accacttgac tgttcaagaa ccagattcaa   141900
catcttcccc caaacatgtt cttccacctc tgtcctaaca gaggtgtgta acagcacctg   141960
gctttcttgg aaagcaccta gttttcttg gagaaccatc tccctcactc taagtccttg   142020
tggtttctct ccagctccag gggtgcaata cagattgaag tcagtcaaag ttacccatcc   142080
tcccaacctc actgattggt tcaaggaaaa caaattcgcc caattaaggt caatgagagt   142140
caaacccaag atgtgtattg agaatgatgg gaagagaaca ttttctatt ttccctgaat   142200 atgaaactgg gaaatttaa ccttagatct tccagggttc ccacagagga caacttgcc   142260 tgatagtgaa gccaacagag aaaagctggg acaagagaca aatgacatca tttgcacccc   142320
tagatcgagc catgcctgaa gtccctctct gaactttcca gttacctgaa caaaaaattc   142380 cctttattg cataagccag tttcagtttc agttctgttg ctttcaacca aatatcaacc   142440
tgatataatt ggcttcatgt ttgtctattc cctctcccac catgagatta taaggtctta   142500
taaattaata ggaatttcta aatcttcaga tagaaaattt agctatctga gaactagcac   142560
acagcaagta ctcaatgaac tttttttttt ttttgaatga acgaagacaa taagagcaaa   142620
aaaaggtaga gggaaataaa gaaggagaga aggagagaaa caatgtccag atcatgtttg   142680
aaaagcaggg ccaccctgca ggcccaaaag ctcacacatg ccaggagaaa cgcctactgc   142740
tcccctcaac tctgattccc ctggagcctg gcacagccgc aaagccaggc cagatgggac   142800
ctgcctcact gacactcatt caggcttggg ttgctttggc ttggtttta gataacagga   142860 aaagcaagaa ggtctgtctc aaatgtctgt gtgatactca gaattgaaat cctggatctc   142920
aagggcttaa ctctctaagg catcctccac tctgcctctg gttcctgaag aaaacccagt   142980
ggggagagaa tcattttgac ttcagtgatt cccaccgatc tcactgatga gccagaaggt   143040
gggggctgat gttcacttac gggagtgcag ccaagaggaa aggtggcata gacaatctgg   143100
aaacttccca gtatttccac gccaaacaat taacctgaaa gattaagcag ttctggggat   143160
ttaatgcagt aagaagaaga acaaacacag tgctttccat gtgccaggta ctattctaag   143220
tgcttcatac gtgttcattt atgcaataga gcaccctatg atgtgagtac cactactgtg   143280
cccagtttat ggatgagaac gctgaggtaa taacaaacat gaacacggac atttaagtgt   143340
gagaatgctc atcgcaattt tgcttatatc tgcaagaaag ggagatataa ttttaatgtt   143400
cctcagcagg ggattggtta agtaaattat ggtatataca tacaatggaa tagtgcacct   143460
actttgtttt aataaggtag atttatatat atattaacac taaatgatgt ctgtgctatt   143520
ttatgcatgt gcatatatat agttatatta tatataatgt aaaaaccaca aatgggctca   143580
```

```
tattgtacac acaattctgt taaactatat atatagctta actatacata tagttatata    143640
tagcttaact atacatatag ttatatatag cttaactata tatatagttt tatacatata    143700
tatatcttag ctatatatat aaacagaaca gcatgtatag tatgagctca cttgtgtttt    143760
ttttttttgt ttttttttg agacagtctc actctgtcac ctaggctgta gtacagtggt    143820
gtaatctcag ctcactgcaa cctccgcctt ccaggttcaa gcagttctcc tgcgtcagcc    143880
tcccgagtag ctaggattac aggcaccccc caccatgcac ggctaatttt ttttttttt    143940
tgtatttta gtgggttttt ttggggtttt tttttgtat tttttaaaaa tttttttagg    144000
ttggccaggc tggtttcgaa ctcctaacct caagtaatcc acccatctcg gcctcctaaa    144060
gtgctaagat tactggcgtg agcactgtgc ccggcccact tgtggttttt atattacata    144120
tagatacttt tttaaaattt ggtttagaga tagagtctca ctctgtcacc caggctgaaa    144180
tgcagtgact ccatcataac tcactgccac cttgaactcc caggttcaag tgatcctcct    144240
gcctcagttt cccaagtagc taggactaca ggcatgtgcc accatatttg gctaattttt    144300
gtatttttt gtagagttag agtcttgctg tatgtttccc aggttggttt caaagtccta    144360
tcctcaaatg aacctcccac ttcagcctcc caaagtgcta gaattacagg catgagtcat    144420
tgtgaccggc ctatatttta tatataaaag aaaactctca aaagtaatag caaactgttc    144480
tttatagtta cctctgaaac acagttgctc acctcagtat tattgacatt ttcgaccagg    144540
tacctctgtg tagtggtgct gtcctacgca ttgtaggatg ttgagctcca cccctggcct    144600
ctacccacta gaggccagta gctctgctcc ggttgtgaca accaaaaatg tttgcagaca    144660
tggccaaaag tccctaaga gggcaaaaca gtactctgtt gagaacaact gctctgggga    144720
aaatttgggg aaattttact ttctctgtat tggttgtttg tgtgtgtgtg tgtgtgtgtg    144780
tgtgtgtgtg tgtgtgtgtg tgtaataatt atgtgttttc agaatgggcg tggtggctca    144840
tgcctgtaat cccagcactt taggaggctg aggctggtgg atcactggag gtcaggagtt    144900
caagaccagc ctggccaaca tgatgaaacc ccgtccctac taaaaataca aaaattagcc    144960
aggtgtggtg gtgcgcacct agaatcccag ttagacagga gactgaggca ggagaatcac    145020
ttgaacccag gggcggaggt tgcagtgaga ttgaaccact gcattccagc ctgggcaaca    145080
gagcaaggtc ctgtctcaat aataataata atgataataa taataataat aataataatg    145140
tgttttagta aaaatataaa cgagaaaggc aaattttcta attaactggt atttgaaggc    145200
tctgagagct ggaagcctag gaaagcacct tcactggggc aactcttcct gctcgaacat    145260
gtaggtcttc ctcaaagcag gtctagcttc catccatttg ctcagttatt ggcttgccca    145320
cctgggcagg tcttttaata tagttcagtg gtttgtacca gcaaactgat tagaaatgca    145380
aagtattagg cctcacccct tacctactat atgtaaaact ctgggagtgg ggcccccaat    145440
ttgtgttttt acagccttcc acacaatgct gatgcaagct caactttgag aatcactaac    145500
agaattaaca gtccaaggga atgagagagc ttcattaaaa ctttgcatat tcctgtaatg    145560
atcttgaagg attatacacc aagcactcta tgcttcctgg ttttctggga gataatttac    145620
tctttggaaa ttcttcattc tggtctgaaa cacaaggcca gagttgagaa ggtgcttttt    145680
aatatccatt acaggagtct gtaagccagc ggttcacacc aaaagttcaa atgctgtaag    145740
gcctgtgttt actagcttag acactgaaaa atcagtcact ggctgggtga agtggctcat    145800
gcctgtcatc ccagcacttt gagaggctga ggcaggagga tcacttgagc ccaggaattt    145860
gagaccagcc tgggcaacat atcaagaccc tatctctgca aaaataaat aaattagcca    145920
```

-continued

```
ggcatggtgg tgtgtgcctt tagttccagc tactcaagaa gttgagacgg aaggatctct 145980
tgagcccagg aggttgaggc tgcaatgaac catgattatg ccactgtact ccagcctggg 146040
tgacagggca agactgtgtc tcaaaaaaaa aaaaaaaga aatcagttac tgcttctagt 146100
ctccccaaag gttaaatagc ctccataacc ttttagaaaa tgaagtttta agtgagaaag 146160
aaaatgttct cagagtactg tttgcattca cagctactcc tggaaagtgt tggaatatta 146220
gctgaaggag taccttccat cccacgggaa cataattatg aacacacaaa atactgtccc 146280
ttatgaatat attttaaggc ttaaatttga gtatggaata accaatctgt tgattctttg 146340
gctgtagtga tgtgggtatt tggagctgtt taaaagaaa ctggaaaaaa cctggctcaa 146400
tctttggccc taagtcatca cttgcgtctg aatgattctg gcataaagat ctttagatgc 146460
cacagccaat ccaggcccag tgactggggt agggagagag aattagaagc tggaaaatgc 146520
tttaacggta cctgataggg tgaaagcagg gcgaagttgt tctgaaaatc ctggaaatgg 146580
gccagaaaga agtcagtgct catggcatca atgtgtgagc aggtcacgcc tttgaccagc 146640
tgcccagcac tagaaaacaa acaaggcac tcgggagagg aaggaagtga ggaggagagg 146700
aaagaaagag cgagagaagg cagatatgat cagatacaag ctacagatgt gactgcctaa 146760
ctctcccacc tggaaaagta ggctgctctg cagaaaggct ctgaaaggcc tgttcagcac 146820
ccaggccgag ttacattttc ctacctcaaa agctcctcag gccttctggt ggtctttaac 146880
agaagctcat acaggaacag agcctgcaag aagagaatga tcgttagcac tgatggcaca 146940
ctcagcgtgt gcccaacact gtgaggccct atcaggaagg cattccacaa tcccatttta 147000
cagatgggga aatggaggct taacaggcta tgtgagttac ctaggactag accattgcta 147060
agtggcagtg cctggatttg aaccagtgtc aaggtaattc cagagcccca ctctcacact 147120
ccagatgatt ctctacaccc catgaggcag atgagaggca aagacattgg tggcagggct 147180
ggagttttac ttcctgtgct ttaggaagct gctgaccagt tgagaactcc ctgtgtctcc 147240
tattcacatg tgcacctgcc aggttctgaa caccaggcat cccagaataa accaggatgg 147300
gctagaaagc accagcaata aagtacctgc agctagcagc atgcactgtc ttcaaaccac 147360
cccccaatga gcactctaga acaatgccta gtagacaggg gagtcatttg ttttaaggaa 147420
cataatttta cagaatccct aacttgcaga cgcaatcaag tactacattt gtctatttta 147480
tagactctga aactttgagt atcattcccc agacagaata aattatgagc tagcattaga 147540
catggtagct gagagccaaa aagcagcaca aaagcccagg caaaaggaat ggacgatgga 147600
ggaaagttct ggacactgtt tgtggcccca gagattttcc tgggctcagg gtcaaattct 147660
gggaccctcc catggtcttc cccatctcag gaaacagcaa tcccatcagc tcaatggccg 147720
agacaaaagt atcttgaagt cttcggtggc agaatgtatt ttccaaaata aaactattgg 147780
ctgggtgccc tggttcacgc ctgtaatccc aggactttgg gaggccaagg cgggcagatc 147840
acttgaggtc aagagttcga caccagcctg gccaacatgg tgaaaccctg tctctataaa 147900
aaatacaaaa attagccggg catgatggtg tgtgcctgta atcccagcta cttcaggagg 147960
tggagccatg aggattgctt gaactcagga ggaggaggtt acagtgagcc aagattgtgc 148020
cactgcaccc cagcctgggt gaccgagaga gactctgtct caaaaaataa aacagaataa 148080
aataaaacgg ttgccactgt cactaaattt agaggtggtt tgtgacacag caatagatca 148140
gcaggacatc atccagcctc atgagagacc ctgagcaaga gcgcctggaa cagacaggga 148200
tttgtgtcgt tcattcact tttgcacact cagcactgtg agcagtgcct ggcgcactgt 148260
tgggctgtgc ttgataaaca tttgctgggt gcatgtaatg aagactgact gaatacaaag 148320
```

```
gtagtcaacg atggtactaa ggcagagcat ccacttcaac agcaccatcc ccccaagcgg 148380
cctcaatgct cacagcattt aataatacac ataatagccg cgaatactta cagtacacag 148440
cccaggtggc atgtatcagt gaccctcatt ttattatcaa aattatcccc atttcgcaca 148500
tgagaaaact gaggccatat aaggaacttc tccaaagcta ataaataagt gggagccaga 148560
attcatgctc aggtcttgtc taactttttt tttaagagac agggtctcgc tctgtcgccc 148620
agactggagt ggagtagcat gaccataact cactgcattg cggaactccc atgctcatgt 148680
gatcctcctg tctcagcctc ctgagtagct gggaccacag acatgcatca ccatgcctgg 148740
ctaatttttt aacttttgt agagacagga tcttgcttgc tatgttgccc aggctggtct 148800
cgaactcctg gcgtcaagcg atcctcctgc ctcagcctgt ccaaattctt aacactatac 148860
tattctgcct cctatactaa tcccacagaa ataaatttct tttatcaaat taaccttaaa 148920
acagaccatt cattctcaca agacagatag tcagaaatac aggatcgatc tgtgtttcat 148980
ggtaatacct ggctccttcc aagttcctta tccttcagga ctgtagagtt gaatccaggt 149040
tgcctcctta aatcaaagag agacacttcc ttaaagaaag cccttgtat ctccacgatg 149100 cctggggcag tgtcttccgc ttggaccatc tgccagaagc gagaagcaac aaaacaacat 149160
tgtaaaaaat gcattgagct ttgaggaagg gccaggcact acatcacagg caataaaatc 149220
catcagaacc gctcagcaac cctaggaagt ggagagtagc atcatcccca tttcacaggt 149280
gaggaaacag agacttaaag tgtgatgagt tgaaagtcag taagtgacat tcaagcccaa 149340
gtctgtctga ttccaaaacc cgtgctcctt atttctttat tttaactgta tgggctactt 149400
gctatctgca aggtattggt gttttaggcc aaacccctta ggttttaggg ttttttcttt 149460
tttttgagat gggaatctcc ctctgtcgcc aggctggaat tcagtggcat gatattggct 149520
cgctgcagtc tccgcctcct gggttcaagc aatttccctg cctcagcctc ccgagtagct 149580
gggactacag aagtgcacta ccacacccgg ctaattttc gtattttag tagagacggg 149640 gtttcaccat gttggccagg ctggtctcaa tctcctaacc tcatgatccg cccaccttgg 149700
cctaccaaag tgctgggatt acaggcgtga gccacctcac ctggccaagt tttggtttct 149760
taacagattt tgccattgga cagaacggac ctgatagagc aagatgtcaa aagactccct 149820
gacaagtaaa aaaggggcca ggcatggtgg ctcacacctg taatcccagc actgtaggag 149880
gccggggcag gtagatcact tgagcccagg agtttgagac cagcctggc aacatggcaa 149940 gaccccatct ctagaaaaac aaaaattagt gagcagcaca ggcctgtagt cccagctact 150000
tgggaggctg aggtgggagg atcccttgag ccccagaggt ggaggctgca gtgaaccaag 150060
atcacgccac tgcatgctgg ctgggtaat agagcaagac cctatctaaa caaacaaaca 150120
aaaaaacaga atacggacat ggctgtggac catgaaaagg gctttcagat gcaccctagg 150180
actttgggtt tattttaga tttgaaaaac aaattttagg ccaggcacag tggctcacac 150240
ctataatccc agcactttgg gaggccgaag cagaaggatt atttgaggcc aggagttgga 150300
gaccagcctg ggcaacatag caatactcca tctctacaaa aaattaataa attagccaga 150360
catggtggct tgaggccagg agtttgagac tagcctgcgc aacatagcaa gaccatgtct 150420
ctacaaaaag ttaaaaaaat tagccaggca tggtgatgta tgcctgtggt cccagctact 150480
caggaggttg aggcaggagg attgcttgag cccaggagac tgtggtgagc tatgatcata 150540
ccactgtact ccagcctggg caacacagaa agactgtctc aaaaaaaaaa aaaaacttg 150600 aacctgaagt gttataagat caggaaacct gatttaagaa aagtcttcca gattagactg 150660
```

```
tctggcagaa caaaggggtc tgggaagaat gacagcatga ctgaagggct ccgtctggaa    150720
aggaaggaag gtgtgccacc aggagaaggc agagccaccc cagacaccaa cagctgagac    150780
aatcccagcc ctgggttcat ggcccaaagt cacagcccac tcaccaaccc caaaaacata    150840 cccctgtga catgtggctg agcaccagac atcttcctct caccttgctg aggatacctt    150900
gctgctgggc aggtgacaag tcggatacat actgggagac ggcacttctc aggacctgcg    150960
agatgtcctt gcgtttcatg ctgcagaagg cctgggtgct gaccccagcc agcagtgcgc    151020
ccatctggct gacattgtag aaagacagca cctggaagag gagcggctgc gcagtcaggc    151080
tctgctcccg cctttcacct ctccaacgtg cactcagccc atctatgtgc caagtatagg    151140
gatgggtgac accttagggg cacagcagtg agccagacag atgctgcctc cacaggcctt    151200
ccttccttct atcaagaaag agagttggcc aggcatggtg gctcacgcct gtaatcccag    151260
cactttgaga ggccaggcgg gtggatcacc tgaggtcaag agttcgagac cacctggcca    151320
acatggtgca accccatctc tactaaaaat acaaaaatta gccaggcatg gtagcaggtt    151380
cctgtaatcc cagctacttg ggaggctgag gcaggagaat tgcttgaacc caggaggcag    151440
aggttgcagt gagctgagat tgtaccattg cactccagac tgggcaacaa gagcaaaact    151500
ctgtcagaaa gaaagaaag aaagaaagaa agaaagaaag agagagagag ggagaggaaa    151560
gaaagaaaga agaaagaag agagagagag agaaagaaag aaagagagaa agaaaggaaa    151620
gaaagaaaga gaaagaaaga gagaaagaga gaaagagaga gagaaagaga gaaggaaaga    151680
aagaaagaaa gaaggaaagg aaggaaggaa ggaaggaagg aaggaaggaa ggaaggaaga    151740
aaggaaaaga aagaaaggaa ggaggaaaga agaaagaaaa gaaaaagaa agaaaggaaa    151800 gaaagaaaga gagagagaga aagaaagaga agaaagaaaa gaaattatac ttgggttttt    151860
tttccttcct ttagagtgaa gatgctagat agttttccat ataatcaagg acatgctttg    151920
gttctatgaa aagacagctg agtgggttcc tttagttatt ctgtgtataa tgggtgatct    151980
catgctgtct tcaaagaagg caagaccttt tgacctcttg ccttctgagt aaaagtggcc    152040
tcacccctca gtaggaagag ttgggtatta ggaaagagac aaaccacttt gtcctgggct    152100
gggagggaac aaaaccgtct ccctcaactc cctaaaatca aattcagaga ggactgtcaa    152160
ggtggaccca tggagcccca gtcaaggtcc agaaacaagg attcaaagcc ttcaacataa    152220
agtcaccacg aggctagaag agaccagatg aatgggctgg cctggtacct gagtcagaaa    152280
gtgggagtgc gtgggcattg gtcatggtgc cataatggag acagtgagca caggagttaa    152340
acaagatggc tctgaggcca ggtgccctgg gttcaatccc agctgcgtaa cttttcacgtg    152400 gccttttcca gttcccttac acactctgta cctcacatga atgaactgga aaatgaagac    152460
tacagcacta ctgacttcag aggattgttg gattaagtta ttaattcact tagaacacaa    152520
cctggcacat agtaagtgtt cagtaaatgt ttgttattcc acaccctccc tcccttggcc    152580
ccgcgatgga ggaagcaggc taggaccagc cctcggagct gcagctgccc ttcatccctc    152640
cctcgccctc tctaccgaca tcctgctcca gttcccactt ggatttactt tggggaatgt    152700
ggttggaata tatctggctc agaaccatga cataccaaac ccagctttaa aaacttgaag    152760
aaatttaaaa agactggat gccaagaaga aattccctac tccttctctt tgggaggcca    152820
aggcgagtag attgcttgag cccaggagtt tgagatctgc ctgggcaaca ttgcaaaatc    152880
ccatctctac aaaaaatac aaaaatcagc ccggcgtagt ggcatgtgcc tgtggtccca    152940
gctactcagg aggctgaggt gggaggatca cctgagcctg gggggtcaag gctgaagtga    153000
gccaagatca gatcacttca ctccagcctg ggcaacatag tgagaacctg tctcaaaaaa    153060
```

```
caaaaaaaga agaagaaacc ccccagttcc tgaggccaac tccagcactg ccttctggat    153120
gcatggattc tactctataa ctcttaaacc cctttaccgc ctgaatcaaa gcttttgtt    153180 ttcattttac cacctgaatc aaaagctttt gttttcattt ccaacctcag tgatgcgatc    153240
tcggctcact gcaagcaccg cctcccaggt tcacgccatt ctcctgcctc agcctcccga    153300
gtagctggga ctacaggcac ccgccaccat gcccagctaa ttttttttt ttttattttt    153360 agtagagaca tggtttcacc gtgttagcca ggatggtctt gatctcctga cctcgtgatc    153420
tgcctgtctc ggcctcccaa agtgctggga ttacaggcgt gagccatcgt gcctggccta    153480
gtgattttct tccttgtgag acactgtggt attttgcttt agaacaagca aaatggggcc    153540 ccttacatttt tcaacatctt cacctcttcc catatcctcc ttcaagctgc atgggaggta    153600
ctaacactag aattacggtg ctaggttagt aaacatgacc tttaaggagt agtctctcct    153660
ttattctttg ggattcctac tactttttc ttttttttt ttaagacaga gtcttgctct    153720
gtagctcagc ccagtctgga gtacagtggc atgatctcgg ctcactgcaa cctcctctgc    153780
ctcctgggtt caagtaattc ttctgcttcg gccttccaag tagctgaaat tacgggtgtg    153840
caccatcatg gccagctaat ttttctattt ttagtagaga cagggtttca ccatgttgtc    153900
cagctggtct caaaccccta gcctcaagtg atccattcat cttggcctcc caaagtgctg    153960
ggattacagg cataagccac catgcccagc ctactacctt ttgtcaaaat aaaaattgat    154020
gagttttgta tagttggtca gacacagtta aaactaaatt cacagtttag caattataat    154080
gggtgcttgt taaacatctg gtagtaaatt atgttgtttc aaagtaatta aaattaatat    154140
ccagaagcca aaaataaaca aatgtttgtt attattattt gattggaatg ggtcctaatc    154200
caatccttgt gagccagttt gcatcctggg aagtggccag gagtgtggac taaacgagaa    154260
ggacaccaaa agccaggcac ggtggctaat gcctgtaatc ccagcacttt gggaggctga    154320
ggcaggcgga ttacaaggtc tggagttcga ccagcctg gccaacatgg cgaaacctcg    154380
tctctactaa aaacacaaaa attcgctggg tgtggtggtg ggtgcctata atcccagcta    154440
ctcggaaggc tgaggcagga gaattgcttg aacccggagg cggaggttgc aatgagctga    154500
ggttgtgcca ttgcattcca gcatgggcga caagggcaag actccgtatc aaaaaaaaaa    154560
ttagatgaca ccaaaatgct tagaactcaa gtctcccaga tttggagccc tctggactgg    154620
acccaaccca gggacattaa ttgtccccaa aagaatgtcc attttccacc ccaggagcag    154680
caagaacaca gattaagact cctgtcccca ccaaagagga ctgtctgcct gacagttccc    154740
tctctgcagc ccaagattgg aataaaatag catcatccct aatcccaaag taatggcaaa    154800
aaccgcaatt acttttttgca tcaacctaat agcagcttaa cagcaggcag gaaaatcctg    154860
ggatgagtcc cacacgttga tcccactcag ggatggctaa tgcccttga gctcctactc    154920 tgtggtgtca cctggtggtc tagcttcttc atgtgtacca actcacataa tattcgcagc    154980
aatgctacag gataagtgct actgatttgt tgttgttgtt gtttaatttt ttttgaaatg    155040
gagtcttgct ctgtcgccca ggctggagtg tggtggcaca atctctgctc actgcaacct    155100
ctgcctccca ggttcaagcc atcctcctgc ctcagcctcc caagtagctg gaagtacagg    155160
catgcaccac cacgcccagc taattttgt atttttagta gagacgggat ttcaccatgt    155220
tgatcaggct ggtcccaaac tcctggcgtc aggtgatcct cccacctcag ccttccaaag    155280
tgctgggatt gcaggtgtga gccacctgcc ccggcagtaa gtgctattgt tgtccacata    155340
ttacaaatag agaaactgag tcaaagtgaa aatagcaaat tgcctagtgt cacacagcta    155400
```

-continued

```
gtaaatggca gagcaaggat ttgaacccag gcagtcctcc tcagcatcat cttcttactg   155460
attggttgcc ccctgctgtg tgtgtataac tgattgttat ggattaaata tttgtgtctc   155520
ccaagaattc atatgtcaaa gtcctaaccc ctaatgtgat ggcattggga ggtgagacct   155580
ttaagaggcc tttaagggtt agatgaggtc atgagataat gagggtcagg tggggccctg   155640
atccaatggg attagtttcc ttgtaagacg caacaccaga gagcttgctc tcatgtggtc   155700
aggtgagcac acagcaagat ggcggccacc tacaggccaa gagaagaggc ctcagaatga   155760
aacctacctt tctgacacct cgatgttgga cttcccagtc tccagaactg tgagaaataa   155820
atttatgttg tttacgtcac tcaatctaca gtatattttt atggcagcct ggcaggtcta   155880
atacacttag gtcatcttag gggaataaaa aagagtttaa aactccagct gaccttctca   155940
tgggccaagt atttggcaga caagatgatg acctggctct tggcccaacc tgagacctgg   156000
ttgagggtgg agatggctcc gtgcacagcc tcggggaga gggattccag ttggctgtag    156060
gtcaaaccta caactgcatc cgacaaagaa cccagggtct cattgagggt ctggttctcc   156120
atggcaatgt ccaggagttc tgctttgagc tggaaggaga gcaaactgga atgagtgttg   156180
acaggaagca gggcggtggc tccctctgac catatccagg gctattagga ctccacagca   156240
cctcccttga ccctgttcca tcaaagcttt tgggctcaga aacgatgaag gaaagggact   156300
cctgccatgc ccagacagtg agacaccaca cggaggacac ctcttctggc cttagctttc   156360
atgtgccaaa aattcccttt gtacttcatt taaatattaa tttgttatta aatcaacctt   156420
aatccatgtc agaaagaaat gttcctttta taactacacc acactcttat agcatctgtt   156480
gtcctctggt gaccttgaac tctatatcca tatatcagg ctgttttcct ttcattaaat    156540
agccaggggc cttttcacga taatttataa tctgtgtaaa aataactttt tttttttttct  156600 taagacagag ttttgctctt gtcacccagg ctggagtata atggtgtggt cttggctcac   156660
tgcaacactg caacctccac cttccgggtt caagcgattc tcctgcctca gtcttctgag   156720
tagctgggat tacaggcacc caccaccaca ctaatgtttg tattttagt agagacaggg    156780 tttcaccatg ttggccaggc tggtctcaaa ctcctgacct aatgtaatcc acatgcctca   156840
gcctcccaaa gtgctgggat tagaggcatg agccaccaca tccagccaaa ataactctt    156900 cacagtacaa gaaagtaaaa gtcctcctgaa catcctacca cataaaaata accatgatta  156960
gcaattgggt gtatatgctt ccaagatttc ttatacccttt ataaatatag agacactaca  157020 tagttttttac agagttgtaa tatgaacaga agcacaattt actcttctta aaattatctc  157080
ttgcacctct ttgcacattt ctatgatcat tttaataatt attttattgc aatatgcctg  157140
cctaatgata gtaaagtgtg cgttacagct gctttcggta aggaatgtga taaagtcacc   157200
tactatacaa tgagctctgt aacaaaaaac aagaatggtt catatttaa cacccgaatt    157260 tacgtaataa cgtagtcatt tcaggcaggt gcacaaaacg ggtttctggc aatattgaaa   157320
tagccactgg ggggcagcag agtgaagtag aagaaacaac tgtcaaagcg cctgggttct   157380
ctaagttcgg caactgcctt acctagaaat cagtttccac atctgtaaaa cgaagggggtg 157440 gactacagtg gcagctccca aagtgtggag cacacccagc ggcatctgca acacctggga   157500
acttgttaga aacgcagatt gccaggctgc tcccggacct cctgaatcag agactggtg    157560 gggctccgaa atccagggat ccccagactc cgggtcacag atggggacca ccgggaccct   157620
ggcctgttag gaaccagcca cagcaggagg tgagcagcag gccagtgagc attaccgcct   157680
gagctctgcc tcctgccaga tcagaagcgg cattagattc tcctaagagc aaaccctatt   157740
gtgcactgtg catgcaaggg acctagtctg tgcgctcttt atgagaatct aatgcctgat   157800
```

```
gatctgtcac tgtctctcat cacccccaga tgggaccgtc tagttgcagg aaaacaagct  157860
cagagctccc actgatttca cattatggtg agttctatag ttatttcatt atatattaca  157920
atgtaataat agaaataaag tgcacagacc gggcgtggtg gctcacgcct gtagtcccag  157980
tactttaaga ggccatggca ggcggatcac gaggttaaga gaatgagatc atcctggcca  158040
catggtgaaa ccccgtctct actacaaata caataaatag ctgggcgtgg tggcgtgcac  158100
ctgtagtccc agctactcag gaggctgagg cagagaattg cttgaacctg ggaggcgag   158160
gttgcagtga gccaagatcg tgctaccgca ctccagcctg gcaacagagc gacactccat  158220
caagaaagga gaggagaggg aaggggaaa gggatggggg gggagggggg agggagggag    158280
ggaaggagga agaaagaaa gagagagagt gagaaagaga agaaagaaag gaaggaagga   158340
gggaagaaag aaagagagag acagaaagag aaagaaagaa agaaagaaag aaagaaagaa  158400
agaaagaaag aaagaaagaa agaaagaaag aaaggaagg agaaggaagg tagggaggga   158460
gggagggagg gaggaaggga gggaaggaag gaagagcaca ataaatgtca tgcacttgaa  158520
tcatcctgaa acaatccccc ggccccagtc cacggaaaaa aattgtcttc cacaaaaccg  158580
gtccctgatg ccaaaaaatt gtcttccaca aaactggagc gctgccacaa gctgtatttg  158640
aacaggccct ccctgtgatt tagatgcacc ctccagtttg agaacaactg agctagatga  158700
tcccaaaggg ctccctcgta tctaattgca tgccaccttc tccttggtca gggctgccac  158760
atgttgagac ccctgggcct taaaatacat ttatcttctt attttttgctt gagcttgctt  158820
aggacggatt cttttccttg gaaacaaaaa tatgcattca caggctaggc tcggtggctg  158880
acgcctgtaa tcccagtact ttgggaggcc aaggcaggtg gatcacttga ggtcaggagt  158940
tcaagaccag cctagtcaac atggtaaaac cccatctcta ctaaaaacac aaaaaattag  159000
ccgggcatgg tggcatgcac ctgtagtccc agctactcca gaggctgagg caaggcgaag  159060
gttgcaatga gctgaaattg tgccacttga acccggaagg tggaggttgc agtgagctga  159120
gattatgcca ctgcattcca gcctgggtga cagaatgaaa ctcaaaaaaa aaaaaaaat   159180
gaatcttata aaaaaaaaaa aaagatgcg ctgaccaaaa tagatgacca cactctcaaa  159240
tgtcaaatgt gtttggggac tttatggtga tgtgtgggaa actgctgtga aattattgat   159300
ggctttatca aaatttcatt taatattatt ttcatgtcat cgtttcgatt ttaagcaaat   159360
tgaaaagggc cacaaaaagt ggaatggaag ggggtagaat tgagacttga ctggaaggaa  159420
gaagagagag atggagagga aggaaaatga gagagagcgt gtttgctcat ctggtcttgg  159480
gaactcataa ccaccctgca atccagtgtt ctcaatcctg gctgcattga aatcacctga  159540
gaagcattaa aatcaggcca tacctcaggc cacaccccag aacaataaca tcagattctc  159600
tgagggtggc acctggcagg gatgttacta atctagaggc aggtttgaga accactgctt  159660
tatctcctgc cgctccaggt gtgctcacca gagcagcggt tccagaatca cctggaagct  159720
tgttggaagt gcagcgtcag ctgggcgcaa tggctcacac ctgtaatcca acactttgg   159780
gaggccaagg gaagaaggag gaagaagagg aagatgggag tcctgggcct caaccaagag  159840
ctcctgaatc agaatctgca tttaagatcc ccaggtgatc tgtatgcata tttaagttcg  159900
aagtagctgt ccctttcttt tcttttctgt tcttttttt agataggtc ttgctctgtc     159960
atccaactag agtgcaaagt cactatcata gctcactgca ggctggcact cctgggctca  160020
agcgatcctc ctacctcagc ctcccaagta gctggcacta taggcacatg cttttttttt  160080
ttttcttttg agacagagtc tcactctgtc acccaggctg gagtgcagtg gcacgatctc  160140
```

```
agctcgccac aacctctgcc tcccaggctc aagcaattct cctgcctcag cctcctgagt 160200
agctgggatt acaggcgcat gccaccacgc ctgtttttgt attttttagta gagacagggg 160260
tttaccatgt tggccatgct ggtctcaaac tgacctcagg tgatctgcct gccttggcct 160320
cccaaagtgc tgggattaca ggtgtgaacc accgtgccca gccatttttt tgtattttt 160380
gcagagacaa gggtctcatg atgttgacca ggctggtatc aaactcctgg cctcaaatga 160440
tcctcccatc ttggcctccc aaagtgctgg gattacaggc atgagccacc gcgcctggct 160500
gagacagctt tctgattaaa ttttgatctc cccagggtct gttcctttgc tattttctgt 160560
ctgggcttcg atgttacact tacctcagta tttgagatgc catctgctgt gactggactt 160620
aaatcccgac taatgctgtg tgttttctcc caaaggctaa gctaggctgt tctccccatt 160680
tctctggcta gtgacactga ggcagaggcc tcagggcctt gcaccccagc tgtaccttct 160740
ggacgccagc ctggaagccc ctcaggtggc tgcacttgat catctggtaa agcaggactt 160800
gagccacagt ggcatccagc aattccaggt cattgtagaa acaaaccagc agccccagcc 160860
tgtgtgagaa gaggagggat ggtggtggag gtgtaaccgc agaaccagcc cattctggtt 160920
caattttgtg taataaaatg gtgagttgtt tttcagttgc cacggactcc caggttgaag 160980
gtcacataac ctgaacatcc tcagatgaac caaatgtgca accacaggcg gaacctaact 161040
gctcagacga gaccaaggaa tgggggctga attatgaagt ggacaccaca tggcatggtc 161100
cacgatccaa tcagaatgag tcctggcatc acctcatggc atgatccaat cagatcacac 161160
ctcccagcat caccttgtag caagacccaa tcagatcaag tctcattacc ctccgcctat 161220
aaaacctgcc ccagtcccca gctcagagac acagatttga gcactgtctt ctgtctcctt 161280
ggcagttgat tcacagtaac cgttctctc tacaaaaacc tagtgcttca gtgtttggtt 161340
ttccattgcg catgggcaaa cagacccagt ttggttccat aacagagcgc tgagagctgg 161400
tggacacgac acccctccc cagtccaaac caatgggtc ttgattatat taatagcagc 161460
taccacttat caggtcttgc actgagccgt ttacctgcat tatctcatta cagcaaccct 161520
acaaggcagg tgctctcatt agccccattt cacagatggg gaaactgaga tttgatttgt 161580
ccaaggcaag tcggtggagc tgggacttaa atgtagatcc atccacctat gccatctctc 161640
cacctgggat gaataaaggg aataaggaaa gaaggtgcc ggtagccaca gaaaactccc 161700
cattttccac attacaatca ctaaattcta gagctgatct caccctgagg gattctctga 161760
ggcagagatc tgtttctagg atgccttctg gtacccaccc agatgatgca aagatttcag 161820
aaggaaaaca aaaagactg gaggaaaaca atggaagggc agaagtgaga ttggaaccct 161880
ggtataactg agagcaatgt ttctaatcat taagagcatt gattcaggcc tactgcagtt 161940
tgaagcccag ctctgtgaga tgtttgctct ccaccaagtt acttaacttc tctgtgaggc 162000
cgctatacac agttctgcag tgcacactct gtactcccat actgtacaga dacagggtgc 162060
ctctcccctct ctgagcctct aataaatggg aggttttctt tgttcatcgt agcacatcat 162120
aataaacatg agtgaaagaa agaggatgat tgtgaaagtg aaatgagaag tggtatacca 162180
actgatttgc atacatcctg gtggaaacca agcactcatt cattaatgaa tgctcttaga 162240
gttagaatga agactaccta gttgaccaca gtcagcctgg ctccaccctc tcagagcgat 162300
attgacatat tcagacatgc ccacaggaga gctgccaggt ccagggaaaa gatttgaaag 162360
tgtgtctcat gaggaaaaga gatctgctta acttcgagta aagaagactc aggggaagtg 162420
agggctgaac gttaataacc acgttgagaa taactattca caacagccaa gacatggaat 162480
catcctaagt gtccaacacg tcagtggatg aatggatttt ttttttaatt tggtggatac 162540
```

```
acaatggaat gctcttcagc tttgaaaaag aaggaaattc tatcatatgg gaccccatgg  162600
atgaacttgg aggatcttat gctaagtgca ataagctagg cacagaaaga caaatactgt  162660
atgacctcat ttatattatg aatctgaaaa acaaataaac aaacgtcata ctcatggaag  162720
cagagcctta gaatggttgg taccaggggc tggaggtggg aagggagttg gagagacttg  162780
gacaaaggac acaatgtttc agttaaatag gaaataggt tctggagatc tattgtacat  162840
gctgactaca gttaataaca atgtatcata tactcaaaaa ttgctaagag tagattttaa  162900
gtgttctcac cgcaaaaaaa gtatgtgagg taatgataac ttaattagct tgatttagcc  162960
attccacaat gaatatatat ctcaaaacat gttgcacacc atagatataa tttttattta  163020
tcaatttaaa aaaataaatt ataaaagaaa ataggcttg gcgtggtagt tcatgcctct  163080
aatcccagca ctttgggagg ccgaggcggg cggatcacaa ggtcaagaga tcaagaccat  163140
cctggccaac atggtgaaac cccgtctcta ctaaaaatac agaaattagc tgggcgtggt  163200
ggcgtgtgcc tgtagtccca gctacttggg aggctgaggc aggagaatca cttgaaccca  163260
ggaggcagag gttgcagtaa gccgagattg tgctactgca ctccagcctg cgacagagt  163320 gagactccgt ctcaataaat aaataaataa aagaaaaaa tattattcat tgagcactta  163380
ctatgtgtca agtgtgcaaa tccctacaaa gaccttaatg cagtaggcat atttttatct  163440
cccattttac agatggggaa gcggaagtat agagaggtga tgtaaaaata gcaaagatca  163500
caccattagt aagcagcagg gaaggattaa gccacgaagt ctggctcgag gtcccatgtt  163560
cttaatcatg aggctatttt tgtgtgtgtg aaaccataga aaaatgagac acatgctaat  163620
aagtgaaaat tactaaaggt aggtgaaaca gatgtaattg tttcctatga gtacattccc  163680
taagagtggc tcatttgaaa aaccttaagg taatatggga tgggagcagt gtggcaataa  163740
taagaccttg agagacggac acaagaggat tgaatgatgg cccagcacag tggctcacgc  163800
ctgtaatctc agcactttgg aagtccaaga tgggtggatc acttgaggtc aggagtttga  163860
gaccagcctg gccaacatgg cgaaacccag tctccactaa aaatacaaaa attagctggg  163920
tgtggtggca cacgcctgta atcccagcta cttgggaggc tgaggcagga ggatctcttg  163980
aatctggagg tggaggttgt agtgagctgg tattgcacca ctgccctcca gcctggacaa  164040
caaagtgaga ctctgtctca aaaaaaaaa aaaaaaacag gattgaatgg gccaggcgtg  164100
gtggctcatg cctgtaatcc cagcagtttg ggaggccaag gcaggcagac cacctgaggt  164160
cagcagttca agaggtcagg agtttgagac cagcctgacc aacatggcaa accccatct  164220 ctactgaaaa tacaaaaaat ttagctgggc atggtggcac acatctgtag tcccagctac  164280
tctggaggct gaggcatgag gattgcttga acccaggagg tggaggttgc agtgagccaa  164340
ggtcacatca ctgcactcca gcctgggtga caggacaaga ctctgtctca aaaaataaa  164400 taaataaaag gaaaggagg gagtattgag ctgtactcac cacctccttc ccattgccca  164460
ctcccttcct gacaccccctg gaatgtagag ttcctgtccc tcctccctg ctgggaatgg  164520 ttttagggag gatcacatta cagtcactaa attctagagc tgatctcatc caggggctcc  164580
ccagctaaga gtctgataac aagtggttct catatatggg gacccatgag ttatttccaa  164640
cacttgactc aacttaaacg gaaatcacac attcactttg gaacaggacc cagtcctgag  164700
tatttaaaat gtttcatttc tgtgctgaga gacagaatta gcacttgata aggttgcata  164760
aaatgcctgg cacacaggag atgctcagaa agcatttatc cttttcaccca gcttcataac  164820 ctcttcataa aaaagttgc agacacctct cctcacatgc acagagaaat atgggactat  164880
```

```
tcaaagagat ggaccagcca cctcccttcc ctccctgggt gttttgctgc tcagagaatt    164940
ctgatgctta gatcacatct tgggaaaggg ctccaaggcc cagagctcat gcgcttgcct    165000
gtggatggtg gaggtattcc tcatgttaaa gttggaggag ctgatcctct ccagaaacgc    165060
ctgggccagc tcaggtgtga tgtcatagac catgtccagc tgcttggtgg cgttgtcata    165120
gctgataaac agcccaatct agttggtgga caaggacgag aatatcagtg aggagggtgg    165180
aagtggccca gtgtggcccc accctggtgg tctgcactgt gccccatcat ggacacttgg    165240
atacacctcc tggttctcat tgtcattgat gtcttttttt cttttctttt ttttttttt     165300 tttgagatgg agtctcactc tgtcgcccag gctggagtgc agtgacatga tctcagttca    165360
ctgcaacctc cacctcctga gttcaagcaa ttctcctgcc tcagcctccg gagtagctgg    165420
gactacaggt gcccaccacc acgcttggct aatatttgta ttttagtag atatggggat     165480 tcaccatgtt gtccaggtg gtctcgaact cccagcatca agtgatccac ccgcctcggc     165540
ctcccaaagt gctgggatta caggcgtaag ccaccatgcc tggcctcatt gtcattgatt    165600
tcttagtggt ctgtaactgc tactttagtt tcctcctcaa cctaactatt ctttaggaaa    165660
gaattatttt ttaatatctg agaaactggg ctttttaaaa gctaatcttt gcacatttat    165720
ttctagattt gttatatgga ggtcagagaa tgtggtccac aaactttctg ctttgaagaa    165780
tcagaatttt tttaatagat gaatgagttt ataaatggcc cttgggtgat ggaaagagt     165840 atgtgttctc tttgtaagac acaaagtttg gtgcatatat attcaactta ttaaatatac    165900
tattcagatt cccaacattc ttgttccttt ttggcccaca tgtccaaggg tgccacgtgc    165960
aagtcttcta ctactacagg actcatatct atctattctt ccttgtattt ctagcagatt    166020
ataaattata tatataattt tgggggggaca ctgactcact ctttttattt tattttgtt    166080 tttattttta tttttatttt tattttttg agatggagtc tcgctctgtc acccaggctg     166140
gagtgcagtg gcacaatctc agctcactgc aacttcagcc tcccgggttc aagtgatact    166200
cctgcctcag cctcctgagt agctgggatt acaggcatgt gcaaacatgc ccagctaatt    166260
attgtatttt tagtagagac ggggtttcgc catgttggcc aggctggtct tgaacacctg    166320
acctcacatg atcccaccgc ctcagcctcc caaagtgctg ggagtagagg cgtgagccac    166380
tgcgcccggc caagacacag tctcactctt ttacccaggc ttgggtgcag tggtgtgatc    166440
atggcttatt gcagcctcga cctcctgggc tcaagtgatc ctcccacctc agcctcccaa    166500
gtagctgaga cctcaggcac acaccactac acctggctaa ttttttaaatt ttttttgtaga   166560 gatgaggttt cactatgttg cccaggctgg tcttgcactt ctgggctcaa gtgatcctcc    166620
cgccttggcc tcccaaagtg ctgggattac tggcatgggc cacggcagcc ggcacattct    166680
atattttgag acagtattat gctgtgctca aaggggctca taaagttgtc tctcctttgt    166740
ggatcgtact ctttgtccat ataaaattcc ttttaggct gggtgcggtg tctcacacct     166800
gtaataccag cactttggga ggctgaggca aggcagatca cctgaggtca agagttcaag    166860
accagcctgg ccaacatggt gaaacctcgt ctctgctaaa aatataaaaa ttagccaggc    166920
atggtggcat gtgcctgtaa tcccagctac tcaagaggct gaggcaggag aatcaattga    166980
atctgggaga aggaggttgc agtgagctga gatcacgcca ctgcacttta gcctggacga    167040
cagaacgaga ctccatttca taaataaaca aataaaataa aataaaattc ccttttagca    167100
gtgttattct tgacttctcc cttctctaca tttttagcga ataaaaagtt gcaaatgagt    167160
gcttgacctt agaatttttcc tctagggggc tcagcttttct aagaatttaa gctgttacct    167220
actcaaagca actctacatt gagagagtaa atggcagtgg ggtgcggggt taattctagg    167280
```

```
actgcgggtt ataaaaatcg aagacactt gaaatactcc cagcccccta ggtaaaagag    167340
agaaagctcg ttctgcctct ggtttcataa taaccacaca ttgctgggtc aatgggtcct    167400
tgaacaggcc agtcatttga tgcaaacact tctctcactg gccagaagag tcagggcaca    167460
tatgacttaa aaaagaagaa gaagaagaag aaaaattgga agcaaggccc acagtctctt    167520
catgaatccc tttgtgttgg cagcattctt ggagaccgc attcaagaat catgatgccc    167580
aagggatttt agtgtcattg ggtcaacatc aaaaggagag ggacaggttg actagtgagt    167640
taagtaatcc tagaatgtgt gtatttctcc actgtaaact ctagaattaa aatctaacca    167700
ttgctcatgc tcaagtagct attaacagaa gtagctataa atagaagtag ctattaatcc    167760 attttgctt tgctttgagt tcatgatccc aaggatggga aactttatat cttttgtcct    167820
tggccttctc cagtacaaaa ataccttaa atgattttg gttcatagcc aacaatccct    167880
ttaaatcatg tttgctcaca tcagagatgt gatcttagtt gtccacaatt cttttctt    167940 tcttagccct tccacactaa acaatccca tgactgccca cttgaaactt tcttccaata    168000
gttttcttca gaggcccaag gtctattggg ctgaggaggg tacacaattt ccaaggcacc    168060
ttgactggct ggatgaacat tagagtttga gaatacacct tacccaagt gtattagtaa    168120 tggtgacata taaatgtact tttccaactt acttctatag gactaatttt cgtaatttct    168180
tcaaacgata ggtgaaccat gtatctgccc aaaacccata agtgttccgc actgaccccat    168240 gaagcagagt catctacaaa aaataaagaa atgaataat gagtacatac ataataaaa    168300 gcctttacac tggtatgtga tagtcaacag catctttgct gtcaagacct acttcttgca    168360
ttcattaatt cgttattttg tttttcgggg ttttttgaga cagaatctca ctctgttgcc    168420
taggttggag tgcagtggtg tgatctcagc tcatctcaac ctccgcctgc cggttcaagc    168480
gattctcctg cctcagtctc ccaagtagct gggattacag gcacccacca ccatgcccag    168540 ctaattttg tattttagt agagacagag tttcaccatg ttggtcaggc tggtctcaaa    168600
ctcctgacct caggtgatct gcccgcctct tgcctcccca agtgctggga ttacaggcat    168660
gagccaccat gcccagccac attaatttgt tattaactca ttcaacaatc atatacgtag    168720
ggcctacctg tgagatcaca cgtaggatgt gaacacagat tcgcaccacc tcagaccttg    168780
ttactcaata gtgtggtctt tggaattgca acatctgtgt cacctggcca cttgttagaa    168840
atacagatta ttcttctgg ccaggcacct gtaatctcag cattttggga ggctgaggca    168900
ggaggattgc ttgaggccag gagtttgaga ccagcctgag caatatatca gaccctcat    168960 cgctacaaaa aaaaaaaaa aaaaaaaaa agccagctgt agtcccagct actcaggaaa    169020
ctgagaaggg aggattgctt gaaccagga atttgaggct acagtgagct atgtgctcac    169080
tctactgcac tccagcctgg gcaacagagt gagaccctgt ctctttaaaa aagtaataat    169140
aattaaaaat aaataaataa ataagaaatg caggttattt ttaatactta aacccacaa    169200 aatgtagttt tatttttca ttcgattggt tactaaataa tctggaaaca tgaggccaga    169260
tgtggtggct cacacctgta atcacgaaat cccgtctcta ctaaaaatac aaagaaaaat    169320
tagccaggtg taatcccagc tacttgggag gctgaggcag gagaatctct tgagcccggg    169380
aggtggaggt ggcagtgagc cgggatcaca tcactgcatt ccagcctagg tgacagagcg    169440
agactctgtc taataataat aataatgata ataatctggc aacatgaaat atgtttgact    169500
gtcttgcatc actaccacta gtaaggatca tcctcactga ttatcaccat gttactatac    169560
ttgaaccaaa gcaaactact tgtacctccc caaaacattc tccaaatctt ggctggcctt    169620
```

```
ggccctgctc accacctaca atgcttttcc ttaccccttc tgcatccaaa tcctactttta    169680 agatcaagct caaattttcc tctcccttaa agccttctct tatctccttc acgagaagta    169740 cttttctccct ccactgaatt cccagaggac tctctctgac accccgttct ggcttttgaa   169800
attccccatc actgagatgt cagtggaatt ttaaaaacca tcaagtcagc caggtgcggt    169860
ggctcaagcc tgtaatccca gactttggg aggccgaggc aggtggatca caaggtcagg     169920
agatcgagag catactggtc aacatggcga aaccccatct ctaataaaac tacaaaaatt    169980
agccaggcgt ggtagcgcac gcctgtagtc ccagctactc aggaagctga ggcaggagaa    170040
tcacttgaac ccgggaggca gaagttgcag tgagctgaga tcataccact gcactccagc    170100
ctgagtgaca gagccagact ccatctcaga aaaaaaaaaa aaaaaaaaaa aaaatatata    170160
tatatatata tatatctcaa gtctaggatc agacttcaag tttcactgag ctggaagtgg    170220
ctgccaatgc tccccagctc tttagcaaaa gacatttaca cacgatattg tattggaggc    170280
atttggggaa aatgaaggaa gtggggagca tttacagggt gcagtgactc taacatcaag    170340
agctatttgc agaagccgtg ggcaatgaca gatgccaaaa caagatggag aaatcaactt    170400
ttatatagac tgattcacaa gaaaatatgg agtgcctctc ccaaaccagg aatcaaagat    170460
gttggggtga cacaggcaga ctcctacgat cctctagatg gggaccctgg acatttgcct    170520
tgcctatata gagggctgga aacttttgag gctagaacca cacattcaca aagaaccaag    170580
cttagttgtt tattttttaa cttattacta agcataaact gtatttctgt agatcaatca    170640
tccccaagct tgggattttt ttttttcttc ctctgttgtc caggctggag tgcagttgga    170700
tgatcatagc tcactgaagc ctcaaactcc tgcctcagcc tccctagtag ctaggactac    170760
aggcacacat caccacatca ggctaatctt ttaattttt tgtatggggg gggggtctc     170820 actacattgc ccaggctggc cttgaactcc tggcctcaag caatcctcct tcctcagcct    170880
tccaaaatgc taggattaga ggtgtaagcg accacacctg gccagcaagg ttgggatatt   170940
tttaacagcc aaagtatttc cagttccctc aagggccttc atgaaaaac aatttaagtc    171000 caaacagaat taatttttaac tcactgtagt ttaataatga agcgcaccgt ataagaattt    171060
tagaaggaaa gtctgtgcct aattaaactc tggcaataaa gacagagaag tctgaaggta    171120
gagaggcttt ctcatggtta cccagtgtga gactctgatt cctggagacc acaattatgc    171180
accaggcaga gggaattcta ctatgcattt gagactttga ttatgatgtt gtttaatgtt    171240
cattatgcac aaatctcaga gctgaattcc aggaaaagat tgattggcat tccccatcct    171300
ccagccccat ctgctttcct tatgttttcc ccacaccgag ctcattcccg tctcagggcc    171360
tttgtatttc ctgggatttc tctctgggat gccctttctc cagagcctta cgtgactggt    171420
tccatctcct cattttggtc ttgattcaaa tgtcacccac ttgagaggtc ttccctgatt    171480
ccttagtcca agagttggca aactacaatc catggggcaa actctgccca tcacctgttt    171540
ttatacagcc catgagccaa aagtggtttt tacatttatt attttggact tttttttaga    171600
gacaaggtct cgctctgtca cccaggctgg agtccagtgg ctccatcacg gctcactgca    171660
gtctcaaact cctaggttca agggatcctc ccccctcag cctccagggt agctgggact    171720
acaggcatgt accaggacac cggctatttt taaaaaatt ttttaagaaa tggggtcttg    171780
ctatgttgcc caggctggtc ttgaactttt ggcttcaagt aatcctcctg cctgggcctc    171840
ccaaagtgct gggattacaa gcatgagcca ctgcaccctg cctgcttttt acctttttta    171900
atagctgaaa ggaaaatcaa aagaagaatc ctatttggtg acacatgaaa attatgcaaa    171960
tttcagcatc cattagtaaa gctttactgg gacacaggca tgctcattca tctattgtct    172020
```

```
acagctgtct tcaagctgca gcgtcagagc tgaatagttg aggcagagat ggtaggctta  172080
caaagcctaa aatatttacc tggtccttta cagaaaacat ttgccaagcg ctcttctagt  172140
ctaaagtacc tgtaatatcc tttctgcctg ggtgcagtgg tttatgcctg taatcccagc  172200
actttgggag gccaagccag gtggatctgt tgaggtcagg agtttgagac cagcctggcc  172260
aacatggagg aatcacatct ctactaaaaa tacaaaaatc agctggacat ggtggcaggc  172320
acctatactc tcagctattc aggagctgag agaatcactt gaactctgga ggcagaggtt  172380
gcagtgagcc gagattgtgc cactgcactc cagcctgggt gacagagtaa gactccgtct  172440
caacaaacta ttttattttc ttcatagccg ctaccagtat ctaaatttct aagttctctc  172500
tctctcttta tttacttaca tgtttaaaaa aattgtctcc accaacactc ccacaataaa  172560
acaatagggc cgtaagagca gagactttgt tttgtttcct tctctatctt cagctattga  172620
tacataatgg gcttttaaaa agtttattct gtttacatta ctgacattaa aggtttaaca  172680
aattgaagct atctgagaaa ttgtttgtat tgctaatcta tatagccatt cttttctatc  172740
gctgttttgt ttgtttgttt gtttgtttgc ttgttttgcg acaaggtctc actacatcac  172800
tcaggctgga atgcagtggc acaatcccag ctcactgcaa gttctgcctc ccgggctcaa  172860
gtgattctcc cacctcagcc tcctgagtag ctgggaccac aggcgcacgc caccacacct  172920
ggcttttgtt tttttgtttg tttgttttgg taaagacaga gttttgccat gttggccagg  172980
ctggtctcaa actcctaacc tcaagtgatc tgcccgtctc agcctcccaa agtgctggga  173040
ttacaggtgt aagccaccgc acttggcccc aattttcttt tcttttcttt ctttcttttt  173100
tttttttttt ttttgagaca gagtctcact ctgtcaccca ggatgcagtg caattgcatg  173160
atctcagttc actgtaacct ccacctcctg ggttcaagtg attctcctgc ctctgcctcc  173220
caaatagctg ggattacaga catgaaccac cacgccaggc taatttttg tatttttagt  173280 agagaagggg gttcaccatg ttggccaggc tggtctcgaa ctcctgacct cagttgatct  173340
gcctgactca gcctcccaaa gtgctggatt gtaggcatga gccaccatgc ccggcccacc  173400 tggcccccатт tттаagтгтa gagttgagcg ggagtaagta cattcacatc cacactattg  173460
tgcaaccgtc actaccagcc atatccagaa tattttgaac cttgcaaaat cgaaactgta  173520
ccaccattct aatttctgtc tctatgaatt tgactgctct aggacacaag gaggctttaa  173580
gcaacatcca tcaaataaat aaatcctgac ctacctgctt tggtagccag gacgctcaga  173640
gttaaatttc tgtgttttat tgcctagatt tcctaataaa attctcttct gtctctctct  173700 cttttttttt тттгcgagac gggtctcgc tctgtcaccc aggccggagt gcagtggtgc  173760
aatctcagct cactgcaatc tctgcctccc cggttgaagc gattctcctg cctcaacctc  173820
ctgagtagct gggattacag gtgcccgcca ccacgctcgg ttaatctttg tatttttagt  173880
agagatgtgg tttcaccatg tcggtcaggc tggtctcaaa ctcctgacct ccggcaatcc  173940
tcctgccttg gcctcccaaa gtgctgggat tacaggcgtg agccaccacg cccagcctct  174000
tctctcattt taatatagat ttttttatac agattttgaa cttgtacccc tactcaaggt  174060

tcacattgaa tctaagttac catcattatt tatattccac tgaaaaacta ggacacaaca  174120

tagattatga aatacaaaca catcattatt tcagacttcc acatgtgcga attgcattga  174180
cgaaatggag tatgtgtttt actccataag ccacatcaaa ctgtttttcg aagcagtggg  174240
aggtggtaaa aatcagaaga gaacaacatc aaatccatgt tttcagagat gaaacacctc  174300

ttctgaagat attcttcccc caaaaagtga ccccacctcc aagtacaggc tcaccagtgg  174360
```

```
cattggagga tgtctgcagt attccagtca tccaggaata gagagctctc tgggaatgag 174420
ccgaggtttt gtcgtagaga tctttgaaca ctgcagatct aaatgacaca aacacaggca 174480
tcagctaata acaagcaggt gggggctgca ttaaaaaggg agtcacaaca gcaaatgtga 174540
cccaaagctg tcttgtgtta aaacccttcc ctctcctgga tgtggagaaa tagaaacgct 174600
tttacactgt tggttggaat gtaaattgat tcaaccattg tggaagacag cgtggtgatt 174660
cctcaagaat ctaggactag aattaccatt tgacccagca atcccatttc tgggtatgta 174720
cccaaaggat tataaatcat gctactataa agacacatgc acacgtatgt ttattgtggc 174780
actattcaca atagcaaaga cttggaacca acccaaatgt cctccaatga tggactggat 174840
taagaaaatg tgacacatat acaccatgga atactatgca gccctaaaaa aggatgagtt 174900
cgtgtccttt gcagggacat ggatgaagct ggaaaccacc attctcagca aactatcaca 174960
aggacagaaa accaaacacc gcatgttctc actcataggt gggaattgaa caatgagatc 175020
acttgggcac agcaagggga acatcacaca ccggggcctg ttgggggtg gggggagggg 175080 gtggggatag cattaggaga tatacctaat gtaaatgatg agttgatggg tgcagcaaac 175140
caacatggca catgtatacc tatgtatcaa acctgcacgt tgtgcacatg taccctagaa 175200
cttaaagtat atttaaaaaa aaaaaacctt ccctttcttg aatgtaaatt ggttcaacca 175260
ttgtggaaga cagtgtagcg attcctcaga gatctagaac tagaaatacc atttgaccca 175320
gcaatcccat tatcgggtat atcccaaaa atatataaat cattctgtca caaagataaa 175380
tgcacacatg atcattgcag cactaatcac aatagtaaag acatgtagtc aacccaaatg 175440
cccatcaata atagactgga taaagaaaat gtggtacata tataccatgg aatactatgc 175500
agccataaaa atgaacaaga ttatgtcttt gcagggaca tgaatggacc tggaagccat 175560
tatcctcagc aaactaacgc aggaacagaa aatgaaacac cccatgttct cacttgtaag 175620
tggaagctga acgatgagat cacatggaca cagggagggg aacaacacac actgggtcct 175680
attgtggggg tggggtgggg gagggagagc attaggaaaa atatctaatg catgctgggc 175740
ttgataccta ggtggtgggt tgataggtac agcaaaccac catggtacac gtttacctat 175800
gtaacaaacc tgcacatcct gcacgtgtac cccagaactt aaaaataaaa aatacccca 175860 aacacactcc ttaggtatat gtaactattt ttcccatttt cctcttcccc ttcacagcta 175920
aacaccttcc aaagaatatt ccatacatat tgtctccact tcctcacctc ttggtccttt 175980
tttggggaag tggggcagc tctgttgaga tataattccc acaccttaca attcacccat 176040
ttaaagtaca caattgggcc gggtgcagtg gctcacacct gtaatcccag cactttggga 176100
agccaaggca ggcggatcac ctgaggtcag gagtttgaga ccagcctgac caatatgatg 176160
aaactctgtc tctactaaaa atacaaaaag tagccaggcg tggtggcatg cacctgtaat 176220
cccagctact tgggaggctg agacaggaga atcacttgaa cctgggaggt ggaggttgca 176280
gtgagccgag atgggccat tgcactccag cctgggcaac aagagtgaaa ctctgtctca 176340
aaaaaaaaaa aattacataa ataaagtgca caattcagtg gttttcagca tataagacaa 176400
agagccaaag atgtttctga tggcatcatt tgagtctctg gatccagctg cgtctgaagt 176460
cagccctaca cctaaaacta ttcaattaca tgttccaata attccctttt tgcttcaagc 176520
cagtttgaat gggttttttct gccacttggg cttactgctt actcaggtga gcagtaacca 176580
ataaactctc tctcccaatg atgttctctt ccacaatctg catgaacgga ggagggaaga 176640
gatgctgaat ttaaaggaa tagtataata gcctgcagag caaaagggtt tcatttatat 176700
acatcttagt gaaaaaaact ggcaacctag agaaacgatg aggtcagcat actgtctgtt 176760
```

```
ttccttactg tcatttggct acaaaagata aaaggaatct cccacattgt tatcatcata   176820
ttggtctttt ccttcttcta aatcattttt agatttagaa agagtgcttt atggccataa   176880
agcactacga ttagtaaaag gagggagttg gcggtggttg caatgcctat ggcccttcaa   176940
gtcctagaca caatcctcga atttggttta catcaaagcg caatttcatg cagggctagg   177000
tgtaaccaat ctaagctggc atggcatctc aaaggagaa gtcctccttt ttcagtgctc    177060
tgtcactcct tctgttgtcc ctcaagaaca aagtctcagt ttagtgccag tgaatcttta   177120
aaacacactc agattgtttt taaatcaatg gaacaagacc caggctcaga gcctttgtgc   177180
tgtggactga atgtttgcgt ttccccaaat ttcatgtgtt gaaatcctaa ttcccaacat   177240
gaaggtatta agaggtggag ttttgaggag gtgattaggt catgaggctg atacctcat    177300
gaatgggatt agtgccctta taaaagagat cccagagggc ttgcccaccc cttccaccac   177360
aaggggacac agcgagaagg tgccacctat aaaccagaaa gcgagccctc accagacacc   177420
aagtctgtca gcaccttgat cttggacttc ccagcctcca gaaccatgag aaataaatgc   177480
ttcttgttta ctagccacac agtctatggt attttgtta cagcagccca atctgactaa    177540
cacacttaag caagcaacat atctagctag gatttagtaa cacttttttt cccactgtat   177600
ttatttatgt gggttttttt gttttgttt tttgtttgtt tgttttgtt tttgagatgg     177660
agtctcactc tgtcgcccag gttggagtgc agtggcatga tcccagctca ctgcaacctc   177720
cacctcccag gttcaagcaa ttctcctgcc tcaagcctcc caagtagctg agattacagg   177780
cgccaccac catgcccaac taattttgt attttagta gagacgtggt ttcattatgt      177840
tggccaggct ggtctcgaac tgctgacatc atgatccacc cacctctgct tcccaaagtg   177900
ctgggatcac aggtgtgagc taccacaccc agcctaactc tacagatgtt aagcttttgc   177960
tccaaaacgt gcatatcaac ctgtccccac ttgtcttctc cctgctgcca ggtgagatct   178020
ctttgcattc tcacggcagc ccctgaagga tactgtgatg agttaagaag gtgggagtgg   178080
ctgggtgcag tggctcatgc ccgtaatcca agcactttgg gaggccaagg caggtggatc   178140
acttgatgtc aggagttcga aaccagcctg gccaacatgg tgaaactcca tctgtacaaa   178200
aatacaaaaa ttagtcgggt gtggtaggcg cccctgtagt cccagctact tggaattgag   178260
gcaggagaat cacttgaacc tgggaggcag aggttgcagt gagccgagac tgcaccactg   178320
cactccaacc tgggcgacag agtgaaactc catctcaaaa aaaaaaaaa aaagttcgg     178380
aggaaccact cacaggttct taaaggcatc ctcgcgcagg tcccgaggga gccgctctgt   178440
gatgtctggc tggagaaagc tccctgagga cccctcagc accttgccca ggatctccac    178500
acactccagg gagttcagca tctggaaaca cctctccagt gtgatgagaa acaggctgcg   178560
gttcacgcca gggctctgca aggctcgttc tcgaatctct cctaagtcga tgatgatgtc   178620
tttcaggtcc taaagcaatg acagaagcca gggtcagttt gagagctgcc tctcaatttg   178680
gaagccctgg gagggaccac acattgcaac agtggggaaa gtcaggatca ctgtttaaca   178740
ccatgctgct atgttgaaac ttctagaact ttccattccc tgcagaacaa agtcaaggcc   178800
tttacctgct ccactcactg tggagcctcc ccactctcca gatacacctg accagcatac   178860
atcaggccct tggtctacct ggaattctgc atctttcctt tttctggtga aatctagctc   178920
atcctttaag tctgggctcc attgccatca ccttcgtgaa gtctctgatc cctccaactt   178980
cctacttcag atcagatttc cctcccttat gtggccccag ggcatcttga accaaactct   179040
ataatgcatt aaagggactc atgcgtcttt cctccaagcc cgtggttctc atctctgggt   179100
```

```
gcacatcaga atcacctggg gagcttttt aaagttttat tttattttg agacagggtc    179160
tcgctctgtc acccagtccg cagtgcagtg gtgtgattat agctcactgc agcctcaacc    179220
tcctgggatt gagcgatcct cccacctcag cctcccaagt agctgggact acaggcacac    179280
accaccatgc tcagctgttt tttgtagaga tggagttttg ccatgttgtc caggctggtc    179340
tcaaactact gggctcaagc aatctgccca caacctccca aagtgctagg gttacaggta    179400
tgagccacca tgcccagccc atctggggag attttgaaaa ggactgattg gcctggaaca    179460
gtggctcaca tctataaccc cagcatgttg ggaggctgag gcaggttgat cgcttgagcc    179520
taggagtttg agaccagcct aggcaacaca gggagacccc gtccctaaaa aataaatttt    179580
ttaaaattag ctgggtgtgc taatgcgcac ctgtagtcct agctgcttga gaggctgagg    179640
tgggaggatc acttgggctc aggatatcaa ggctgcagtg agctataatt ataccactgc    179700
actccagcct ggatgacaga gcaagcccct gtctctaaga aaaaaaaaa aagcctccat    179760
tttactgagc attgactcta ctgtgccaag cttggagcaa acgcatcatc tgattaattc    179820
tcatgacaat cctaccggtt aagccccatg gtactaggg tcaggcattc ccaggttcca    179880
gtcccagggc ctccattatc tgtgtgtcct gagcaaatga cttacctttt ttaagtccca    179940
gtttttaagg tctcagaggc cttgctttgt gatattcttg gatcactaaa ctcattttgt    180000
ggaaattaac tgttcctgtt ttttgtctcc cctccagacc gtgagctcct tgagtgcagg    180060
aggatctctg tgtccactgg tgcatagtaa ttttactag tggatgttta ttgacccaaa    180120
caaccaggag attctcagat ccttaattag gacccgtcat ttcttagtac tgacaaaaat    180180
atgaattagg ccaggcatgg tggctcacac ctgtaatccc agcactttgg gatgccgagg    180240
caggcaaatc acttgaggcc aggagtttga ccagcctg gcaaaatctc gtctctacta    180300
aaaatacaaa aattagccag gcatggtggt gcacacttgt aatcccagct acttgggagg    180360
ctgaggcaca gaatcactt aaacccagga ggcagaagtt acagtgagct gagattgtgc    180420
cactgcactc cagcctgagt gacagagtga gactctaaaa caaaaataaa ataaaaatt    180480
gtaaggctct tcattttaac tttggagaaa gtaagtgaga aaacttaggt cctaaagccc    180540
ccaggggtt ggaggaggca gaaggagaga ggaagagaca atgaagtgcc aaggcctaag    180600
tcaggctcca tttattcaat tcaacaaaca ccacgtggtg ctggacttcc tctatccccg    180660
ggatgccaag ggctcctcac caagccgtcc ttcttgtctt ctaagaggca tttcatggca    180720
gtgcggaact gctgggcgtc tgtcttcctc aggtcctcca gcagcttctg gggctggtgc    180780
agacgctgct ccaggtggtt ttccacggct gcctgtattt ggggtgttgg gagagtcggt    180840
gagaacagaa agagcaggag cacatggtca gcaccatggc cagcggccca gcccggcccc    180900
ctcattccct gcagagacca caactagtgg ccagcagtct ggtttggcca cctccaaatt    180960
tcctcattag ccgccaacat ttaaaaatga ggggccgggc gcggtggctc atgcctgtaa    181020
tcccagcact ttgggaggcc gaggcgggtg gatcacgagg tgaagagatc aagaccatcc    181080
tggccaacat ggtgaaaccc cgtctctact aaaaatacaa aaattagctg ggtgtggtgg    181140
cgcacgcctg tagtcccagc tacttgggag gctgaggcag gagaatcgct taaacccggg    181200
aggcggaggt tgcagtgagc cgagatcacg ccactgcact ccagcctggt gacagagcga    181260
gactccacct aaataataat aataataata ataataataa taataagggg attcctcaca    181320
agatcaagat ttccaacttc tcttgaaaaa gtaaaggttt ggcaacaccg ggcgcacatc    181380
ccctttagg caataattgg caagccaagg gacagctgct tgttgaagta actctcaggc    181440
ccagccagcc cgattccccc attccatggc ctgcctggtc cctgtaggtg attgagtttc    181500
```

```
ccatcagcag cagctggcct ttgtccagga agtttagaac cccagatggc actgtgccca    181560
aacccaagct accagcgcag gagcaaaata caggcgaaat gaacatactc tgtggcgccc    181620
cctacagggc aaggagcaga agccatcagc ctctcctgaa agagatttcc tctgctgtct    181680
ggggaattgt tctctaaatc tccgttaaac agacatgccc agtgtgatgt catgggcaaa    181740
aggtgaactc tagacccaga caagccacat gcaaatcccc accttgacac ttactagctg    181800
tgtggcttgg acgagttact taactagggt tgctgggtaa aatacaggat gctcagttaa    181860
atttgaattt cgggaaaaac tacacatttt tttttttta gtataagtat gtctcaaatg    181920
ttgcatagga catacttaac ttaaaaaatc actcattgtt tgccaggcaa ggtggcccac    181980
acctgtaatc ccagcacttt gggaggccaa gacaggcgga tcatgaggtc aggagtttga    182040
gaccagcctg gccaacatag tgaaacccca tctctactaa aaatacacaa attagccagg    182100
catgatggca tgcacctgta gtcccagcta ctcaggaggc tgaggcagga gaattgcttg    182160
aacctgggag gaggaggttg tggtgagctg aggtggcacc actgcactcc agcctgggca    182220
acagagcaag actctgtctc aaaaaaaaaa aaatcactca ttatttatct gaaattcaaa    182280
cgaaattgga catctgtttt ttgtttttgt ttttgtttta gagacggggt cttgctctgt    182340
tgcccaggct gaaatgcagt ggtatgatca tagctcaccg taacctcaaa ctcctgggct    182400
caagcaatcc tcctgcctca gccttccaag tagctgggac tacaggccac accaccacac    182460
tcagctaatt ttttgtttgt ttgtttgttt gtttttgtag agacaaggtc tcgctatgtt    182520
ggcaaggctt gtctccaact cctggtatca agcaatcctc ccaccatgc ctctcaaagt     182580 gctgggatta caggcatgag ccaccacgca gagtcacatc tgtattttta tttgctaaat    182640
cagcaacatt tcttctgggc ctcagttttc ttatctgcaa aatggaggca ataaaaggac    182700
ttaccacata gagttattac gaggattcag tgtgtaaagt gttttcaata gttgctagca    182760
cacagtaagt gctcaatagt gccagctatt attctctatc ttgaccaagg tgaataatgg    182820
cttaattaaa gcctcacccc taaaatgaaa ggtccttgtg ggtagtatca tgactgcctt    182880
gttccctact gagtcctcag tgtctagagc tatgcctggc agaaagcaga tgttaactca    182940
gtagatatta aatgaataaa taaatatggt atatacacag gaagaaacgt atcagattaa    183000
agtggataca tctcatgagt atccattact gctagagaga aaagtggcaa gcattgcttc    183060
tctttcagtt tccctgactg atgaagaaga aagaaaagc agatgccatg tggggccaac    183120
agccacctcc agctagtggc tgtcctggga cctggcagac aacaagctct ctgagtatat    183180
ttgtgatatc aatgttggtt gatgtttcca ttttcattca aacataagta aaaatggaaa    183240
caatgaagac atatgtcaga actttattca ttaattaatg acataaatgg tctttttgcta   183300 aactgaataa ctttctcaat actgaaagaa tttttctcca attttctgtg ttatccacag    183360
tgtgatgata aagacacaac atgccacact aggctaacag tcaggcaggt gctgtgcagt    183420
tcaccgcagt caccaccaca ggcacgagcc ctattgcccc ttaaggcaaa tatcctttgc    183480
cacctatcaa cacgcttgtg ctattgtttt cattacagta gtacatttct tggacccatg    183540
gtagaaagac tgatcactat atccaaatat ccactctctc actgctcttt atcaattgaa    183600
cccttcaact tttagttggg tacatggctc ctttgcagta agatgtgact atggtgtgtg    183660
agccaatcta atgtgtgcag agggaattgt gtaacttgcg tcatatcctc agaagagaag    183720
atgctaccct tgtcttcttc ttcccaccca tccctggat tggagaaagg aagaggtgtt     183780
tccaccacat gggcaataac tccccaggag atgacaaagc aaaaagataa aaggaacctg    183840
```

```
ggtccttgga taacctcatg gaatagagct gccttttctc tgtggctttc ccacttagct    183900
ctggactatt gtacgagaaa gaaataaact aaattgtttg agctgctgtc atctgggggt    183960 cttttttgtta tagcagctca gcctatatcc taatatacca tgtctccatc aaaggtggga   184020
aaatgaaaga aagacaaaat agcttatatc atgttcaag aaaaactgga cagaacccctt   184080 ttccttgcag aagcaaagac tatctctaca tccagcccac ttctccaact tacctggccc    184140
ctgagtttgc aatccctgag cactgagatg ggaacatata gatgggtctc aggtacacac    184200
ctgcaggctg gggatggtga aggcaacatt ccgggaattc agataggcca ggactctgtg    184260
ggacaggtca tccgtccaca cgtgggagct tcagttgaag acagacagga aaagatcaca    184320
atgacagatt ctcctacaag cactactgta ctagctaagt gcccagggga caggtaggga    184380
tggaccaggg gtgttaggac tttgtacttg gaagtgggag gtttctcttt tcttttcttt    184440
ccttttttct tttctctttt tttgaaacag gtcttgctc tgttgcgcga tcacggctca    184500
ctgcagcctc aatctcccca gcccaagtga tcttccaacc tcagccaccc aagcagctgg    184560
gatcacaggt gcatgccaca acaccccagct aattttttgt agagatgggg tctcactatg    184620
ttgcccaggc tggtctcaaa ctcctgggct caagcaatcc tcccacctct gcctcccaaa    184680
gtgctgggat tacaggagtg agctgctgca cccagcctga agtaaaaaat ttcttaacca    184740
ggcacagtga taggatagtt tccaattcta ggaatctgcc tggatcccat tctctcaaag    184800
ccaattccca aatttctaag ctgtatgcaa tattctaatt cccgtaacaa tctgcttaga    184860
ttgactacaa tccaaactga ttgtgttaga aagatgtaca tttaaaagca gacgctaggt    184920
acaccatgag aggctggaat agcatagtta ggagtgtggg ctccaaactg gatttgaatc    184980
ctagttccat cacttagttg tgtggcttga gacaatttga taaattttct tgtgcctcag    185040 tttccctta tatgaaatat ggttaacaac tgtgagatta aaatttgttc acacatgaaa    185100
attgcgtaag actgtgccca acacacagta aatgcccatg aatagccttt tctcattttt    185160 ttttttttt ttggagacag agtctcactc tgttacccag gctggagtgc agtggtgcaa    185220
tctcagctca ctgcaaccctc cgcctcccag gttcaagcga ttctcctgcc tcagccttcc    185280
aagtagctgg aattacaggc gtgcaccacc acatccagct cattttttcta tttttagtag    185340 atactgagtt ttgccatgtt ggccgggctg gctggaact cctggcctta agcgatcctc    185400
ctaccttggc ctcccaaagt gctgggatta caggataagc caccatgccc agcctatgaa    185460
aagccttttg taatcttacg tttgcttctt tgtttgtttg tttgtttgtt ttgcgatgga    185520
gtctcactct gttgcccagg ctggagtgca gtggctcaat cttggcttat cacaacctca    185580
gcctcccgcg ttcaagtgat cctcctgcct cagcctcctg agtagctggg actacaggta    185640
tgcaccacca tgcctagcta attcttttgt acttttagta gggacagggt ttcactatgt    185700
tggccaggct ggtcccgaac tcctgacttc atgatccgcc caccttggcc tctcaaagtc    185760
ctggaattat aggcatgagc caccgcgccc ggcctgtaat cttataaaga gatggatgga    185820
tggatggatg gatggatgga tggataaatt aataaacaaa taaatactt agactgaaag    185880 aatatatcca aaagtacccca ttggtgttat cttagggaaa ggagtggtta tgggagtctt    185940
tcactttaac ataactgggt atccctgata tgaggcccca agaccctat ttcttatcga    186000 tcatagtact catcatatta gaattgttta ttaatattgg cgtttccaca ctacctagtt    186060
ccctgcccca tgtccctggt atctgtctgt atgcagctta taatgcaaca gtaaagggaa    186120
tgggtcctgg agccaggcca ctggttcaca tcccagttgt gtgtccttga tttacccttc    186180
ctggacctca gtttcaccat tgtgtgcaat gggataacaa tgggaactac attgtgtggc    186240
```

```
acttgtgagg attagattgt ttctatacca agcgcttagt agaataccca ctacatagaa  186300
agcactcaat aaatttcagc tcttaggccg gttgcggtgg ctcacacctg taatcccagc  186360
actttgggag gctgaggccg gcagatcacc tgaggtcagg agtttgagac cagcctggcc  186420
aacatggtga aaacccatct ctactaaaaa tacaaaaatt agccgggcat ggtgacaggt  186480
acctgttacc ccagctactc aggaggctga ggcaggaaaa ttgcttgaac cccggaggca  186540
gaggttgcag tagtgagcca agatagcacc actgcactcc atcctgggca acaagagcga  186600
aactccattc aaaaaagaa aaaaattgg cccttatgct agagtgagga ggaatgatgc  186660
ccgtggagca agggtgtttg ttgacttta acacattgtg cattgattga cattttttgt  186720
aatgagcaca tattactttt tacaattaag agacttccat taagaatttt tattaaaaat  186780
ctataccatc ccttcccctc tcctctaggg catttttacct ttgaaactgt atgagatcca  186840
gcagtgctac aatgggagta aaatgaaaag acatctttaa aaggaatcat tccagagaga  186900
tcacagctac attctgtttg aaattcttag aagaagcaag tggagatcaa gggggcacat  186960
taccattcag atagcttcca tctattattt cttcctaaaa ggcaaagaga taacatcaag  187020
tataacaacc aaaagttggc aattccagta gaggggactc tgattaacag aaaatagaat  187080
actcaccgcc atgttttgca acaatggatg caaatctgta agaaagccat tgaatgtata  187140
actagaattg aattgtgtga ccttcaaaac tacaaatatg ggttagagga aaagccccag  187200
aaagccactc atgaaggaaa tttttagtga atttttaatta taactgtcca ctctgagaaa  187260
accgtggctt gaaaaatcct cttagaataa tcctgaaaaa tcatacatgc acacacacac  187320
agcccaaaaa caacttacag catcatgtac ctaatgtatc tatcccacct cattccctaa  187380
actgtgtgga aaccacaaag ggtgattctt ccctcaggac ttaccctgcc tggaatttgg  187440
cactgtataa ctcgacactc catggctcag aaaaaggaat aggaaaaggg agtatgtcgt  187500
aggttcctga gacattctcc tgtagttaat ttaagcatag aagtgattca tgttttttt  187560
atatatatat atatacacac acacacatat atatacatgt atataaacat atatatatat  187620
atggacattc agaagacaaa aggaaaaacc aagtacaccc agaatccctt gaagtctttt  187680
ttaaaaataa tttttaaaact cacctacttt cctccatcta aaccccatt cttgtctaag  187740
acactatcat ctctctcctt ggtgactaca atggcctgtt tatcttacca ctaccccaa  187800
ctcctctcaa tccagcaaaa aggtatagtc aaaagtagac tctgggccaa gcatggtggc  187860
tcacacctgt aatcccagca ctttgcatgg ccaaggtggg tggatctctt gaggtcagga  187920
gttcgagacc agcctggcca acatagtgaa accctgtctc tactaaaaat aaaaaattaa  187980
ctgggtatgg tggtgcatgt ctgtagtccc agctacttgg gaggctaaga caggagaagt  188040
gcctgaatct gtgaggtaga ggttgcagtg agccaagatt gtgccactgc actccagcct  188100
gggcaacaga gcgagactct ggaaaaaaaa aagtatagac tctattttat ctgcaagaaa  188160
tttatatcca gaatacaaaa actactctta taattcaata agaagataga caagccaagg  188220
ggaaaaaatg ttaaaaagat atgaagttgg ccaggcgcag tggctcacgc ctgtaatccc  188280
agcactttgg gaggctgagg tgggcggatc atgaggtcag gagatccaga ccatcctggc  188340
taacacggtg aaacccgtc tctaataaaa atacaaaaaa attagacggg cgtggtggcg  188400
ggcgcctgta gtcccagcta ctcaggaggc tgaggaagaa gaatggcgtg aaccctggat  188460
gcggagcttg cagtgagccg agatcacgcc actgcactcc agcctgggcg acagagcaag  188520
actccgtctc aaaaaaaaa aaaaaaaaa gatatgaagc taaacttcat aaaaacagat  188580
```

```
gtaaaaatgg ccaataagca cacaaatgat tatcacatta gctaacaaga actagcaaat   188640
taaactcaca acgagaccac tacaaagtca ctagaatggg caaaaatttc aaagactgac   188700
tatcaaatgt tggtgatgat atggaacaac aggaactctg atacagctgc ttggaaaaac   188760
tgtttgacag tgtcttacag agttaaatat acaatacccct atgatcaaga aatgccaccc   188820
ctaggtattt aagcaagaga atgaaaaca tgtctacaca aagatttata tagcttcatt   188880
catagtagcc agatattgga aacaatcaca tatccaataa caggtgaaag gttaaacatg   188940
gatctccatt cagtgggata ccattcagta ataacaataa aaagaaattc atcataattt   189000
tattctagct atgatggagt aattggcaat ggataaaccg tcctgcctta aacaattaaa   189060
aagctggctg aaatatgtgc atccaaaggt ttttcagaca ttgggcagca ggtagcacaa   189120
gactgagatc cctgagcaag gaaggcaaac aagctgagct ctataattgc tcctgctcac   189180
tgcctggagt ctccatccaa cagcacaagg agggagaatc caaacagagc ctacaggtct   189240
cactgagcag aagagacgga gtggaacttc agggaaatca aggcagctag aatccataag   189300
aagaatactt ggagaggagg aagttgcaca gagagaaagt tctggagatc tgaagaaggg   189360
tcttttgaga ctttggctga atatttatct acctttgcat gtaagaaacc tcctgaggct   189420
ggagaatgaa ccaccagtag gcagaacaat ccttggacct cacaggggaa tgagaatagc   189480
tcctgcaagc tgcaatggaa aaacctccaa acacattggg catcagggtc aatcatcaaa   189540
gaacaattgc ctccatgata ggccaaatta gccctaggct aaagtttatt ccagatctgc   189600
cctaacaaat ctcaaaagca agttctggaa ggatctaatt gattccaagt aactgaattg   189660
cattccagaa caaaacccaa caatatttaa agcagtatca taaaacccag aaacttcaga   189720 aaccagaag atggagaaag aaaaaaaaga aaaaaaaaat ccagcaatgt aaaatccgaa   189780
gtgtccagat ctaatcaaaa attatcaggc aggccaagca cagtggctca tgcctataat   189840
cccagccctt tgggaggcca aggaaggtga attgtctgag ctcaggagtt tgtgaccagc   189900
ctgggcaaca tggtgaaact ctgtctttac caaaaatgca aaactttgcc agggatgtgg   189960
caggtgccca actactcagg aggctgaggt gggagggtca ctgaagcctg gaaagttgag   190020
gctgcaatga gccatgatta tgccactgca ctccagccag ggtgacagag cgagaacctg   190080
tctcaaagaa atttttaat aaataaataa aaattaccag gcatactagg aagcaggaaa   190140
atatggctga ttatcaggag aaaaatccaa tcaatagaac agatccagaa atgcacagaa   190200
agatccaatt aatggacaag gatgtttatt ataaatacac tctggaagtt caagaaagta   190260
gggaaaactg cgagcatgtt aaagggagag acatggtagg tgcgaaaaaa acccccaagag   190320 gaacttctag agataaaaat acaatatctg aaatggaaaaa tacacggggat agagttaaca   190380 gcatattaga cactgcagaa gaaaaattag tgaacttgaa gtcatagcaa aataaaatat   190440
ccaaagtaaa atgcaggggg aaaaagactg aaaaaattaa gagggctctg gagcaatatg   190500
aaactatttg aaatatgtgt aactggagtc ccaggaaagg aggggtggc acaaaaatat   190560 ctgaataaat cattagcagg gcacagtggc tcacgcctgt aatcccacat tttgaaggt    190620 tgaggtgggc aaatcacttg aggccaagag ttcaaaacca gcctggccaa catggtgaag   190680
ccccatctct ataaaaaaaa aaaaaaaaaa aaaaaaaaaa atagccaggt gtggtggctg   190740
taatcccagc tactcaggag gctgggcaca aaaatcactt gaacctggga ggcggaagtt   190800
gtagtgagcc aagattgcac cactgcactc cagcctaggt gacagaatga gactgaaaaa   190860
aaaaagagag agagagaaag aaaagaaaag aaggaaagaa agagagaaag aaaaagaaag   190920
aaagaaagaa agaaagaaag aaagaaagaa agacagaaag aaaacatgac ctcatgacca   190980
```

```
aatttgtgta aagtttgata gaactacaga tccacagatc caagaagctc aaccaacccc 191040
aagcagagga atcatgaata aagccacgcc aaggcatata ataatcaaat tgctaaaaaa 191100
aaaaaaaaaa aaaaaaaaaa gattttaaa aaaatccag caaaaaggag ttgcatctag 191160
actatattga aaaactctta aaactaaaaa ataaataagc aatccaatca gaaaacgagc 191220
agaagatatg tgcagatata tcatcaaagt atatatacag atagcaaata aacacatggg 191280
aagatactca gcactgttag ccattaggaa aatgaccact gaaaccacag tataattata 191340
ggcctatcag atggctaaaa taaaaaaaaa aaaaccataa tgaagccagg cgcagtgaat 191400
catgcctgta atcccagcac tttggaaggc cgaggtgggt gaatcacctg agatcaggag 191460
tttgagacca gcctggccaa catggtgaaa ccccatctct actaaaaata caaatattag 191520
ccgggcatgg tggctcatgc ctgtagtccc agctactcag gaggctgagg caggagaatt 191580
gcttgaaccg aggaggcgga ggttgcagtg actgggaggc agaggttgca gtgagccaag 191640
attgcaccac tgcactccag cctgggcaac agagtgagac ttcaactcaa aaataaataa 191700
ataaatgtaa ccataatgcc attaactaga aagaatgagg agaaactgga tcactcacac 191760
attgctgatg agaatataag gtggtacagc tattctggaa aatagttttg ttgtttctta 191820
taaaattaaa tgtgtactta acgtacagcc caacaattac actcttgggc atttatccca 191880
gaaaaatgaa aatttatgtt cataaaaaa cctgtacaca ggctgggcat ggtggctcac 191940
gcctataatc ccagcacttt gggaggctga ggcgggtgga tcacgaggtc aggagatcaa 192000
gaccatcctg gctaacatgg tgaaacccca tctctactaa aaatacaaaa aattagctag 192060
gcgtggtggt gggcgcctgt agtcccagct acttgggagg ctgaggcagg agaatggcat 192120
gaacccagga gacagagctt gcagtgatgc agtgagccaa gatcacgcca ctgcattcca 192180
gcctgggtga cagtgtgaga ctccaactca aaaaacaaac aaacaaacaa acaaaacctg 192240
tacacaaatg ttcatagcat ctttattcat agtagctgaa aaattgaacc aatctaaatg 192300
tcattccgta ggtgaatggt taaactcact gtgtgtggta tgtccacgcc attgaatact 192360
actcagcaat gaaaaggaat gaactattga tacaggcaac aactttgatg cacctaaagg 192420
gaattatgca gagggaagaa agccaatcac tgaaagttat atactaatga ttccaattat 192480
aaagcattct tgaaataaaa ttatagaaat gcagactaga ttggtatttg ccatggggag 192540
agggagataa ggctgtcaag ggatgcatga aagaggcttg tgatcaccag gagagttctg 192600
ggtcctgatt agggtagctg atacattagt ctacacatgt cacaaaattg aagaaaacga 192660
tataaaatat acacacaaag gagtgcatgt aaaactagtg aaatctgaat aagccctgaa 192720
tttgtaccat gatttcctga attttatatg gtactattgt tacataacat gtaaccaatg 192780
ggggaaactg ggtgaagagt acacaggata tttcttttgc aacttcctat gaatctgtag 192840
ttatttcaaa ttcttttta ttttcttgag agacagagtc tttctctgtc acccagcctg 192900
cagtgcagtg gcatgatcat ggctcactgc agccttgaac tcctgtgttc aagtgatcct 192960
ctggtctcag cctcctgaga agctgagact acaggcatgc actaccatgc ccagctaatt 193020
cttttagttc ttgtagaaat gggttcttgc tatgtttccc aggctgatct caaactcctg 193080
gcctcaagca atcctcccat ctcggcctcc caaagtgcta ggaatacagg catgggccac 193140
catccctggc cacacaattg tttttaatt tagttatagt agtctgtacc actgtaggat 193200
gacaatagtt aacaataata tatagtttca aatagctaga aggaagatac tgaacagaaa 193260
gaaatgagaa atgtttgaga tggtagacat gctaattacc ctgactgatc accatacatt 193320
```

```
atacacatca aaacatcttt atgtacccca taaatatgta caattattat atgtcaattt    193380
ttttttttt ttttgagatg gagtctcact ctgtcaccca ggctggagtg tagtggcgca    193440
atctcggctc actgcaacct ccgcctccca ggtgcaagcg attctcctgc ctcagcctcc    193500
tgagtagctg ggataacagg catgcgccac cacacccagc taattttgt attttagta     193560
gagatggggt ttcgccatgt tggtcaggct ggtctggaac tcctgacctc tggtgatcag    193620
cccacttcag cctcccaaag tgctgggatt gctggcgtga gccaccgtgc ccggcgtata    193680
tgtcaatttt ttaaataaat aaaataataa atttttaagc acccaaaggg aaaaaccca    193740
tattatatgc ataggaaaag gaatacacta ctgatatagg caacaacaca gatgaacctc    193800
agaaacatta tgcttatgct gagcaaaaga agccagtcaa aaaagaccac ataacatatg    193860
attccatttc tgtgaaactc taagttatct agaatatcta gattctaggt tatctaggtt    193920
acctagaata atcttcagtg acaggaaaca aattaggatt ggtctggggc attattaggg    193980
tacaatggga aaagtttatt gcaacagggc acagggaac ttcttggagt gatggaaaaa    194040
ttttttttgt agatataggg tctcactata gtgcccaagc tggtctcaaa ctcctggttt    194100
caagcaatcc tcccttcgag cttcccaaag tactgggatt acaggtggat gccattgcac    194160
ccagccccca ttttttgtat cttgattgtg gtggttgtca cacagataca tacatttatc    194220
agatctcact gaactgtaca cttagtgtgc attgtattgc ctgtaaattt atacctcaca    194280
aaagtcagta tcaaacagaa atggaaaagc atggactgtg gagccagtca cctgttctga    194340
atcacgtctc cgccacttac tagctgtgca atgttggaca tatttctttc ttttttttt    194400
tcttttttct ttttctttt ttttttttt gatatggagt cttactctct tgcccaggct    194460
ggagtgcagt ggtgcaatgt aggctcactg caacctctgc ttcccaggtt caagcgattc    194520
ttctgcctca gcctcctgag tagctaggat tacaggtacc caccaccaca ccaggctaag    194580
ttttgtatttt ttagtagaga caggctccca ccatgttggc caggctgatc tcgaactcct    194640
gacctcaagt gatccaccca ctttggcctc ccaaagtgct gagattacag gtgtgagcca    194700
ctgagcccgg ccttggacga gtttcttaat ctctctgcac tccaattttc tcgtctgtaa    194760
aatgagatta atgatggtac cagcatcact gtgtcgtatg agggtaaaat gagttgttaa    194820
tagtgaatca cttcaaacag ggcttgacac aaagtcagct ctgtatacaa gtttattaaa    194880
taagcaaaga aaccagattg ctgttttcaa acagatgctg ttttgaaaaa caccatctca    194940
ataaactcat gtcaccctcc gcctctcccc attaccctca agataaagcc caaagctttt    195000
ccagtggctg tatcaccctc ctctttgccc ctcattcccc aaggttcctg cccgggccat    195060
ctgtctgtcc ctccaaggtg ctatcctccc cagattaaga ccctctcaca ggctgttcct    195120
cggcccagag gattcttccc cttcctcttt gcccggctaa gatcaattca ttgtaaattt    195180
caagtcttca atgaagcctt ccctgaattc tctgaccagg ccaaagcaat tagccagaag    195240
aaaaggccaa tacttctctt ttatagcacc aagcacagct ataatacata tttatgtttg    195300
tgtaattatt tcatgctttc attcttcaaa tatttgttga gtagtgctgt gagccaggca    195360
ttattctatg ctctgagaat acagcagttt acaaaactaa ctccctgctg gtgtgttgga    195420
atgaaccagg cagaaaatag ataatcaaat aactatatta tgtcagggag tgatgagtgc    195480
catggagaaa aatacaacag ggtaggaaaa aggagccaaa gaaggagcag gtactattat    195540
agacagtttg gtcagggaag acctgaggag gtgacattta agcagagacc tcaggaagtg    195600
aaggaatgaa ccacgggaat atctggagaa agaaagttcc agaaagaaaa gaaaatgaca    195660
gtgcaaaggc tttgatatta ggagcataat ttgcatgttc ttcagtaaat tgcacgaaga    195720
```

```
ggatataaca gtaggacatg gggttggaga ggtatcaggg ccagagtgag tagggtcttt   195780
caggccattg tgagcgctct gacttttact tggaggagg tgggagccac tgaagggata    195840
ttagccagga tggatgctct gacttgtttt tgttttgtt ttgttttgtt tgagatggtg    195900
tctcactctg tcgcccaggc tagagtgcag tggcacaatc tcagctcact gcaacctctg   195960
cctccccggc tcaagtgatt ctcctgcctc agcctctcaa gtagctggga ttataggtgc   196020
ccaccaccac acccagctaa tttttatatt tttggtagag acgagatttc accctgttgg   196080
ccaggctggt ctcgaactcc taagctcaag tgatccaccc acctcagcct cccaaagctc   196140
tgggatgaca ggtgtgagcc actgtgcctg gccctgactt ttattttaac tggatcaagc   196200
acattgattg ctgtgttgag aatacctgg agtggaacaa tggctgtagc aggcagacca    196260
atctaggaaa gagatgacaa taacttggtc attgatagca gtgaaggtgg tgagaagtgg   196320
ttggattttg gaggtatttg gaaggcggaa ccaaagatc gaatgtaggg aataaaagaa    196380
atagacaggt caaagacaac gccaaggatt tggcctgagc atgtagagag ggagatggga   196440
aaaccatagg agttccaagt ttagggaagg atccctggag ctcagttttg gacatactaa   196500
gcttgagaag ccttttagag tgcagatagc atagcaagta ggcagtttga tgtttgagcc   196560
tgcaggttag gggagaggtg ctgtcagaag cagctatcta aacagagata gtcagtggtt   196620
ttttgtgttt gcttttttgt ttgttcttct gttttgggg tttttttggg gtgggggaca    196680
gagtctcact ctgtcacgca cgctggagtg cagtggcacg atctcagctc actgcaacct   196740
ctgcctccca ggttcaagtg attcttgtgt ctcaacctcc cgagtagctg ggattacagg   196800
cttgtgccac cgcaccggct aattttttgta tttttagtag acgggggtt tcaccatgtt    196860 ggccaggctg gtctcaaact catgacctca agggatccac ctgacacagg ctcccaaagt    196920
gctgggatta caggcatgta atcccactgc acccggcccc agatagtcag catgtattta    196980
aaccctgaat gatatcacca agaaagtaaa tttacggaga aattaggtga gttttaagga    197040
ctgagaccca tggcaccccc attgccaaga cgttgagtag actaggtgca gccagagaaa   197100
tcaagactgt ggaaaactcc ccaaaacaaa caacctagtt tctttagcca atatattaca    197160
gagagagaga gaaagagaac ctattaactc aaaaacaaaa gattgatcac ttgtagaatc   197220
tagactttat ttggatcctg attcaaacac gtcatgtctg ggcacggtgg ctcacacctg    197280
taatcccagc actttgggag gccgaggcgg gcagatcact tgaggtcagg agtttgagac   197340
cagcctggcc aacatggtga aaacccatct ctactaaaga tacaaaaact tagctgggca   197400
tggtggcgca tgctaataat cccagctact cgggaggctg aggcaggaga atctcttgaa   197460
cccgggaggc agaggttgca gtgacccgag atcatcccat tgcactccaa cctggatgac    197520
aagagtgaaa ctctgtctcc aaaaaaaaaa aaaaaagaa agaaacaaag caaacaaaca    197580 aaaatacca taaataaaa taaaaaatta ggccaggcac agtggctcac acctaatccc     197640
agtgttttgg gaggccaagg cggaggattg tttgaggcca ggagtttgag accagcctgg   197700
gcaacacagc atgactccat ctctataaaa acatttaaaa tttagcctgg cgtggtgatg   197760
cacacctgta gtcctagcca ctcaggaggc tgagatggga ggatctcttg agctccagaa    197820
ttcaaggctg cagtgagcta tgatcatgcc acagcactcc agcctgagtg acagaacaag   197880
atcctgtctc aaaaaaaccc aaaaaattgt gagacaattg aggaaatttg aaccccctgat  197940 tagatatttg aagattttaa agaattattg ttaatagttt taagtttgat aatgaaactg    198000
tggttatatt tttaaaggag tccttattgt ttcaaggagg ggttagtaaa gtaccaccca    198060
```

```
cggaccaaat ggaaatggcc acctgatttt gcgtggctca tgagcttaaa atgattttt   198120 aggttgttta aatagttttt taaaaccaaa agaataatat ttattgacat atgaaaattt   198180
cctgtgtgaa atttaaattt aagtgtctat aaataaagtt ttattggcac atgtccatgc   198240
ccattcattg gcctattgtc catggcagct tcctgctacc atagcagagt tgagtacttg   198300
ggacagggac cacacggcct ccaaagctca aaatatgtat tccatgttcc cttactgaaa   198360
aagcttgcca gcccttcttt tattttatgt atttatttaa ttgttttttt tttttaaga    198420 cagagtctct ctctgttacc cacgctgggg ttaccatgcc tcagcctccc aagtagctgg   198480
gactacaggc gcccgccact acgcccggct aattttttgt attttagta gagacagggg    198540 ttcgccgtgt tggccaggat ggtctcgatc tcctgatctt gtgatctgcc cgcctcggcc   198600
tcccaaagtg ctgggattac aggcgtgagc caccgcgccc agccgccatc ccagcattct   198660
ttaatacaga tttcctcgt attgtctaac ttgttatgca aatggattat ttttccccca    198720
aggggacctc cacaaccagc tttgaaaaca attatgctta ctttactgcc caggacaaaa   198780
acagtaaaac ttttgaagtt cccagacacc aaaagccctg cattctaaca ggttttgagc   198840
aaacctgatc ccaaagcact ttgtaggtgt gttggcccac catcaccatc ctgtaactgg   198900
aatgctcaac tccaattaga agtcttcctg gtttgggtca tttggggctt tggggaacct   198960 ttgaccctt ttctccctt cccttttgggc agctgccctg ggacattggc cccattcaca    199020
attctccagt ttcccagaca atgtggcttc ttgtgctctt tgctcgggcc cctctattaa   199080
ccctacagag aggtttcagg ttactgaaac agacgccttg ctttctgctg tgcataatgt   199140
ccttttccca gcgagaaact gcagcccatc aggatctggt tttcattaaa ggcactttgg   199200
gtcacttttt tagcagattg gtcaaaagga ctgaaaggac tgggcagggc gatgatgatt   199260
tggaggtcaa tagcttttctc tatgggccat acccttccc cactgaaaga ttcccccact   199320
gcagactgga ggaaatcagt caggcaagga tccctgtggt gaaaactact cgaaaacagc   199380
aacaataacc acaaacctga aatgaagaca atttcctgag aaactatgaa tgtttggatg   199440
tgcaaggtga tcaactttcc cagttgcccg ggaccaaaag gtttcccagg actcaaaact   199500
ttccattttg aaaccagaaa gtcacaggca aaccggagg agttggtcaa cccatggatc    199560
agagtcactt catcttctgt gaaatttgca aagatgctag gaggttcccc tcctgctggg   199620 acacccccagc ccagacacaa accattaatt cacaattaca tggagtttca ctgtctgcaa   199680
ggctgctcca tttaagctct gggtcatgaa cacataactc taggcatact gacactagct   199740
gggagatttt ccaccaaaaa aaaaaaaaa aaatgccatt tcatgactat taatccaaaa    199800
taggtaaatg tgtctggctt atagaatacc agcctgatta caaatgcttg gtgttggaat   199860
ggcccagctc acagtggttg tagaagtcca gtaggcccag gctttgtggc tcactcctgt   199920
aaccccagca ctttgggagg ccaaggtggg aggatcactt gagtccagaa gttcaaaacc   199980
agcctgggca ataggggag actccatttc tacaaataat ttaaaaatta gctgggtgca   200040
tgcttgtagc cctagctact caggaggttg aggcaggaga attgcctgag cctggaggt    200100 cgaggccaca gtgagccgcg atcacatgtc actacattcc agcctgggtg acagagcaaa   200160
accctggctg aaaaaaaaa aaattcaagc agtcaagggg atgggagctt ggtggactag   200220
agatgcccag acttgagttc ctgtcccagc cctgccacta atagtgagat tttaggcaca   200280
gctattcccc ttcttctctc ctaagtctcc ggagaacaaa tggctttgga ttcaatgagg   200340
aaaagaagga aagaaaggaa gaaactggtc tcactgagca tcctctatga gccgggcatc   200400
acaccaaacc ctcctccctg ccatttactc tttccaccag ccttgaaggg ttaccgtact   200460
```

```
cagtttcaca gatgagttca gtgcacatga acgatcacac agcaagcgaa tggcagggag   200520
ggggttatga tgcagggctg tggggctccc tagtaacctt aatcccagca gtcatttaat   200580
gagacagaac taagtacacg cctctctaac atacattgtc tcgcttaatt cttgtagaat   200640
ctttgaggca agcattacca ttatctctac ttcacagatg agcaaatggg ttctgagagg   200700
tcaagtgacc tgcccaaggt cacacagcta tgcatgcaca gccaggtggc aaacccagag   200760
ctaaatgatt ccaacgctca ctggctttgc tctccagtgt cagctcagca gccctgaacc   200820
taaaactcca ggtggcaggt gccaccccag ggataagacc ccagctttaa cctgaaccaa   200880
accttaacca gctgtgtgct attgggcaaa ttccttaacc tctataggct tgcatttcct   200940
cctctgcata gtaggcatgg cactcatacc tccctggcaa aaaactatca actttatttg   201000
tttatttatt tatttattta tttatttatt tatttattca ttcatgagac agagtctccc   201060
tgtgtcgccc agaatggagg gcagtggcct gatctcggct cactgcaacc tccacctgcc   201120
ggattgatgc gattctcctg cctcagcctc cggagtagct gagattacag gcgcccgcca   201180
ccacacctgg ctaatatttg tatttttagt agagatggaa tttcaccact ttggccaggc   201240
tggtctcgaa ctcctggcct caagtgattc ccctgcctca gcctcccaaa gtgctgggat   201300
tacaggtgtg agccccggcc tttacctgca ttttccatt tcttccacac aactgttatg   201360
aggtaggcat tactttatac ataaaataca taaagaacta gcccagcac tggcacatat   201420
aagaatgcaa tgaatcgtag ctattattac taatgctatt gttttactg ctgctatatt    201480
attataacaa ataatcattg tgatagttat tgcaacagtt gtcatcgctg ttattatatt   201540
actaagtagt tttggatccc ttttctcgaa gtttcatcgt cccccccctc caagtgccct   201600
ccaatcccag gagcccttaa agccgctgca cccacacttt gcccaccctc tttctctcgg   201660
tctgtccccc acgccatcca tcacctgcac cccttcccta gggaggccca gcggtgggcg   201720
cccacccgct ccccccagcg ctttgcccgt gagtcctccg cccaggcccc cgcgcgcgcc   201780
tcacctgcgg agcccggctt ggccgcactg agtcccacgg gcgggcgggt ggcgcagggc   201840
ggggccgcgg ggctcatgcg gggagcgggc aggcaggaga gcggcggggc ggcgccagcc   201900
ggcagctctg cgacctcctc cctgcagcgg cccaggtggg aactcagcca gggcagcggc   201960
ggggggtcaca gtccccgcct gggacttcct atctgtcgaa gctt                  202004
```

<210> SEQ ID NO 19
<211> LENGTH: 3796
<212> TYPE: DNA
<213> ORGANISM: Homo sapiens

<400> SEQUENCE: 19

```
gctgaaggtt gcgctggcac gcgcaacttc cggacagag gctgtggctg gaaggagctg      60
ggcatccggc ctgaggcgca gcggtcgcgt tagttcggcc caatggcggc accgctgctt    120
cacacgcgtt tgccgggaga tgcggccgct tcgtcctctg cagttaagaa gctgggcgcg    180
tcgaggactg ggatttcaaa tatgcgtgca ttagagaatg acttttcaa ttctccccca     240
agaaaaactg ttcggtttgg tggaactgtg acagaagtct tgctgaagta caaaaagggt    300
gaaacaaatg actttgagtt gttgaagaac cagctgttag atccagacat aaaggatgac    360
cagatcatca actggctgct agaattccgt tcttctatca tgtacttgac aaaagacttt    420
gagcaactta tcagtattat attaagattg ccttggttga atagaagtca aacagtagtg    480
gaagagtatt tggctttct tggtaatctt gtatcagcac agactgtttt cctcagaccg    540
```

| | |
|---|---|
| tgtctcagca tgattgcttc ccattttgtg cctccccgag tgatcattaa ggaaggcgat | 600 |
| gtagatgttt cagattctga tgatgaagat gataatcttc ctgcaaattt tgacacatgt | 660 |
| cacagagcct tgcaaataat agcaagatat gtaccatcga caccgtggtt tctcatgcca | 720 |
| atactggtgg aaaaatttcc atttgttcga aaatcagaga gaacactgga atgttacgtt | 780 |
| cataacttac taaggattag tgtatatttt ccaaccttga ggcatgaaat tctggagctt | 840 |
| attattgaaa aactactcaa gttggatgtg aatgcatccc ggcagggtat tgaagatgct | 900 |
| gaagaaacag caactcaaac ttgtggtggg acagattcca cggaaggatt gtttaatatg | 960 |
| gatgaagatg aagaaactga acatgaaaca aaggctggtc ctgaacggct cgaccagatg | 1020 |
| gtgcatcctg tagccgagcg cctggacatc ctgatgtctt tggttttgtc ctacatgaag | 1080 |
| gatgtctgct atgtagatgg taaggttgat aacggcaaaa caaaggatct atatcgcgac | 1140 |
| ctgataaaca tctttgacaa actcctgttg cccacccatg cctcctgcca tgtacagttt | 1200 |
| ttcatgtttt acctctgtag tttcaaattg ggattcgcag aggcattttt ggaacatctc | 1260 |
| tggaaaaaat tgcaggaccc aagtaatcct gccatcatca ggcaggctgc tggaaattat | 1320 |
| attggaagct ttttggcaag agctaaattt attcctctta ttactgtaaa atcatgccta | 1380 |
| gatcttttgg ttaactggct gcacatatac cttaataacc aggattcggg aacaaaggca | 1440 |
| ttctgcgatg ttgctctcca tggaccattt tactcagcct gccaagctgt gttctacacc | 1500 |
| tttgttttta gacacaagca gcttttgagc ggaaacctga agaaggttt gcagtatctt | 1560 |
| cagagtctga attttgagcg gatagtgatg agccagctaa atcccctgaa gatttgcctg | 1620 |
| ccctcagtgg ttaacttttt tgctgcaatc acaaataagt accagctcgt cttctgctac | 1680 |
| accatcattg agaggaacaa tcgccagatg ctgccagtca ttaggagtac cgctggagga | 1740 |
| gactcagtgc agatctgcac aaacccgctg gacaccttct tccccttga tccctgtgtg | 1800 |
| ctgaagaggt caaagaaatt cattgatcct atttatcagg tgtgggaaga catgagtgct | 1860 |
| gaagagctac aggagttcaa gaaacccatg aaaaaggaca tagtggaaga tgaagatgat | 1920 |
| gactttctga aaggcgaagt gccccagaat gatacccgtga ttgggatcac accaagctcc | 1980 |
| tttgacacgc atttccgaag tccttcaagt agtgtgggct ccccacccgt gttgtacatg | 2040 |
| caacccagtc ccctctgacg gcagaaattt gtgactgaga tgtgacattt gggattcccc | 2100 |
| atcacttgtc atgccctcag cacccagctt gtgccattgg gcattgatgg cattgaacta | 2160 |
| gagcgagtgc ctgcctcggc tgtggcactt ccaggttcga ctgaatcaag catctgaaga | 2220 |
| ctgggttttt tgttgttgt tgttccccctt acagacaaaa tgaagactat catgtgcaat | 2280 |
| cttttacagt ggggttgatg atacatttgg aaggatttgc ttgttaata tgtacatttt | 2340 |
| ttgtgttaac agcttttttga cacaattact gggtaatttc taatataggc agcagactgt | 2400 |
| tttacgggtt gctgttttaa catgggtttt tgtcagatcc atggtcttag gacttgactg | 2460 |
| atgagctttc agtgaagaat cctctaagat aaaacttcta tttaaagact ttaactagaa | 2520 |
| agtgtttatt ttggctacat tgttcacctt ctgctgtatt ggtatttgtc tgtttgggatt | 2580 |
| tcaagggagt gtagagaaga cagaaggaaa gctgagagct ggcccgacat ggtctgggac | 2640 |
| acagagttgg agctggcact gaagatctcc agggacttca gagaccaata aaagcccata | 2700 |
| gggaagagag agaggatata gggaaacaga atcagatgtg taatatactt ggcacagcga | 2760 |
| aaaaatggat ttaaaagaca aaaatggagg tccaggtaga tgtaattcac acagactgaa | 2820 |
| agtgagttcg ggcttgtgta aaacacatga gattggattt gaccccttgg ctctcaagtg | 2880 |
| tccccttaga tctagaactg ctccttggtg gccattagat cgagtcagtt ttgatctgca | 2940 |

-continued

| | |
|---|---|
| tcacttagtt attgggaatt tctttgttgg aaacaggaaa attttttttag attatttggt | 3000 |
| gtacggtttt gctcacaaca ataggtggaa gttgctagtg cagtcttggt ctgatggctg | 3060 |
| tgtgcatcgc acattcggct tggtgaaatc cttctctaaa gcctcttttt gtattttat | 3120 |
| aactaaacag aggaagtctt cagaagacct cgctttaaaa caaatttgtg caaacactgc | 3180 |
| tagagtcatt tgaagctca agcatttca ctttgtttct tacatgtgta ctttttgtt | 3240 |
| tacttgtgaa aatggccatc tttaagcata tttattttct gccactttat ttaaaggcaa | 3300 |
| gcaatatttt cttgatcata aatattttgt aatgaaatac ttcctctttt ccagggcttt | 3360 |
| gtatgcactt gtataattac attgatgca atgtagagtt tgaatttcag tctgtaaata | 3420 |
| cttttttgga aaatagaaat tttattgct ttaaagtttt ggatatgggt ggttttcttt | 3480 |
| tccgggtttg gtgaaagta atttgagaac tttaaggttg tcttttaac tgctggcaaa | 3540 |
| atgttgattt tttaatatta gataaaacga gtaaacgaaa ttccccagaa attagtagta | 3600 |
| agtgggtct ttgtgggttg ggaagtagtt ttaatgtaga aagacattta catataagtc | 3660 |
| tgtttaattt caaaggagtt tgtgaaaaaa aatccatggt gaaaatgaaa caatgacatg | 3720 |
| gttaatctgg aacttacgtt cttataccaa taaaaggtac ctcaatacat gttctttcaa | 3780 |
| aaaaaaaaaa aaaaaa | 3796 |

<210> SEQ ID NO 20
<211> LENGTH: 719
<212> TYPE: DNA
<213> ORGANISM: Homo sapiens
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t

<400> SEQUENCE: 20

| | |
|---|---|
| acataaagaa aattttcatt tattttttccc tcagatatac ttcaaaataa catgtagaca | 60 |
| cagaatcaca aatatataca aaacaaagta tcgcctggtt atttcaagaa gagttttccc | 120 |
| tcaattttct tagctgctgt gcataaaatt caaagctttc aggggggttca atgaaaggga | 180 |
| caggctctcc agcatacttc agcaaagatg cgtaacgctt tagaaacaga tcatccaatt | 240 |
| ttgtattctt tgcagtcaaa tgttcataca gtgctttagc agatgtgaca tctttctctg | 300 |
| agacatagct tttcatgagg gaattgtatg cttcttcctt ttcatttaat tcaggaatca | 360 |
| attctaacac agatttcaca gttgatgcct ttccttgttt cctagaattc ctaaggagga | 420 |
| acaacaacaa aatcgggggtt tgttcagcaa ttgcaccaca tctctgtagg agagctctgg | 480 |
| catcatccac cttgcctgca tccacaagtt gaaggaaaan atcagtgaca ggtttataaa | 540 |
| ttgcaaactg attggccaat ctctccgcca tgatggctta tctttcaaac tgctggtcca | 600 |
| actgctcctc tattactttc tggataagat gccaaggccg agtantcggg tcaatgactt | 660 |
| tatcctctga agtaagctat tntcatggtt tctattgcgg catctatgta atcattctt | 719 |

<210> SEQ ID NO 21
<211> LENGTH: 6637
<212> TYPE: DNA

<213> ORGANISM: Homo sapiens

<400> SEQUENCE: 21

```
acatgctcct cctgtccttc tggcggagcg tgcttcccgc tgcggggacg ttcgagcaat      60
ggcagccctg ctgagatccg cgcgttggtt gctgcgtgcc ggggcggccc cgcgcctccc     120
gctctccctg cgcctcctcc ctggcggccc gggccggctg catgccgcct cctatctgcc     180
cgccgctcgc gccgggcccg tggccggagg actactgagc ccagccaggc tgtatgccat     240
tgctgccaaa gaaaagata ttcaagagga gtccactttt tcttctagga agatttccaa      300
tcagtttgat tgggctctaa tgagactaga tctttctgtt cgaagaactg ccgcattcc      360
aaagaagctt ctacaaaaag tttttaatga tacctgccgc tcaggtggcc taggtggtag     420
tcatgccttg cttctactac gtagttgtgg ttctctcttg cctgaactaa gcttgaaga     480
gagaacagaa tttgctcata ggatatggga cacacttcag aaattaggtg ctgtgtatga     540
tgtgagtcac tataatgctt tacttaaagt ctatcttcaa aatgaatata aattctcacc     600
aactgatttc ctggcaaaaa tggaggaagc aaacattcaa ccaaatcgag tgacatacca     660
gagattgatt gcttcttatt gtaatgtagg agatattgaa ggtgccagca agattcttgg     720
atttatgaaa actaaggatc tcccagttac agaggcagta ttcagtgccc ttgtgacagg     780
gcatgccaga gctggtgata tggagaatgc agaaaacatt ctcacagtga tgagagatgc     840
cggaattgag cctggtccag acacatacct cgcattattg aatgcatatg ctgagaaggg     900
cgacattgac catgttaagc agactctgga aaggtggag aagtccgagc ttcaccttat      960
ggaccgtgat ttactgcaaa ttatttttag cttcagtaaa gctgggtatc ctcagtatgt    1020
ctcagaaatt ttggaaaaag ttacatgtga aagaagatat attccagatg caatgaacct    1080
cattttactt ttagtcactg aaaaattgga agatgtagcg ttgcaaattt tactagcatg    1140
ccccgtatca aaggaagatg gcccaagtgt ctttggcagt ttcttttttac aacactgtgt    1200
gactatgaat acgcctgtgg agaagctaac agactactgt aagaagttaa aggaagtcca    1260
gatgcactcc tttcctctgc agttcaccct ccattgtgct ttactcgcca ataaaactga    1320
tttggcaaaa gccttaatga aggctgtgaa ggaggaaggt tttcctatca gacctcacta    1380
tttctggcca ttgctagttg gacgtcggaa ggaaaaaaat gttcaaggta taattgaaat    1440
cctcaaagga atgcaagaat tgggagtaca tcctgatcag gaaacatata cagattatgt    1500
gattccatgc tttgatagtg taaactcagc acgagccatt ttgcaggaaa atggatgtct    1560
gtctgatagt gatatgtttt ctcaagctgg attgagaagt gaagcagcaa atgggaactt    1620
agactttgta ttatcatttt tgaaatcaaa tacattgccc atctcgctgc agtctataag    1680
aagtagccta ctgctaggct tcaggaggtc tatgaatata atctttgga gcagataac      1740
agaattgttg tacaaggatg gacgttattg ccaggagcct cgaggaccga cggaagctgt    1800
tggctatttt ctttataact tgattgacag catgagtgac tcagaggtac aggccaagga    1860
ggagcatttg agacaatact ccatcagct ggagaagatg aatgtaaaaa ttcctgaaaa     1920
tatctacaga ggcattcgta atctcctgga aagctaccat gttcctgaat tgattaagga    1980
tgctcacttg ttggttgaga gtaagaattt agactttcaa aaaactgtgc aacttacatc    2040
atctgaattg gagtccacac ttgaaacact aaaagctgaa atcaaccta agagatgt       2100
cctaaagcaa ctcatattag tgctttgttc agaagagaat atgcaaaaag cccttgaatt    2160
gaaagcaaaa tatgaatccg acatggttac tggtggctat gcagctttaa taaatttatg    2220
ctgtcgacat gataaagtag aagatgcctt gaacttgaaa gaagaatttg accgcttaga    2280
```

```
ttcatctgct gtccttgaca ccggcaagta tgtaggcctt gtaagagtat tggcaaagca   2340
tggcaagctc caagatgcta ttaacattct gaaggagatg aaagagaagg atgttcttat   2400
caaagataca acagccttgt ccttttccca catgctaaat ggcgcagctt aagaggtga    2460 aattgaaaca gtaaacagt tgcatgaagc catcgtgact ctagggttag cagaaccatc    2520
caccaacata agtttcccat tggtcactgt acacttggaa aagggcgacc tatctactgc   2580
tcttgaggtc gccattgact gctatgaaaa gtataaagta ttaccaagga ttcatgatgt   2640
cttgtgtaaa ctggtagaga aaggcgagac tgatctaatt cagaaagcaa tggactttgt   2700
gagccaagaa caaggtgaaa tggtgatgct ctatgatctc ttctttgcct tcctacaaac   2760
aggaaattac aaagaggcca agaagatcat tgagactcca gggattagag ctcgatctgc   2820
aaggcttcag tggttttgtg acagatgtgt tgcaaataat caggttgaaa ctctggaaaa   2880
attagtggag ctgacacaga agctatttga atgtgataga gaccagatgt actacaatct   2940
gctaaaactg tataaaataa acggtgactg gcaaagagct gatgcagtct ggaataaaat   3000
ccaagaagaa aatgttattc ctcgtgaaaa gacattaaga ttattagcag aaatccttag   3060
agagggtaac caggaagttc cgtttgacgt acctgagttg tggtatgaag atgaaaaaca   3120
ttccctgaat tcttcgtcag cctcaaccac agaacctgat ttccagaaag atatattgat   3180
tgcctgccga ttgaaccaaa aaaaggggc atatgatatt ttcctgaatg caaaagagca   3240
aaacattgtg tttaatgctg aaacctacag caatctcatt aaattactga tgtcagaaga   3300
ttattttaca caagcaatgg aagtgaaagc attcgcggag acccacatca agggcttcac   3360
actgaacgat gctgccaaca gccgcctcat cataacgcaa gttaggcggg attatttgaa   3420
agaggctgtg acaacactga aaacagtatt ggatcagcag cagacccctt ctaggttagc   3480
agtgacccgt gtcatccagg cattggccat gaagggtgat gttgaaaaca tagaagtagt   3540
tcagaagatg ttaaatggac tcgaagactc cattggactt tcaaaaatgg ttttcatcaa   3600
taacattgct ttggctcaaa taagaataa taacatagat gccgcaatag aaaacattga   3660
aaatatgctt acttcagaga ataaagtcat tgaaccccaa tacttcggct tggcatactt   3720
attcagaaaa gtaatagagg agcagttgga accagcagtt gaaaagataa gcatcatggc   3780
ggagagattg gccaatcagt ttgcaattta taaacctgtc actgattttt tccttcaact   3840
tgtggatgca ggcaaggtgg atgatgccag agctctccta cagagatgtg gtgcaattgc   3900
tgaacaaacc ccgatttgt tgttgttcct ccttaggaat tctaggaaac aaggaaaggc    3960
atcaactgtg aaatctgtgt tagaattgat tcctgaatta aatgaaaagg aagaagcata   4020
caattccctc atgaaaagct atgtctcaga gaaagatgtc acatctgcta aagcactgta   4080
tgaacatttg actgcaaaga atacaaaatt ggatgatctg tttctaaagc gttacgcatc   4140
tttgctgaag tatgctggag agcctgtccc tttcattgaa cccctgaaa gctttgaatt    4200 ttatgcacag cagctaagaa aattgaggga aaactcttct tgaaataacc aggcgatact   4260
ttgttttgta tatatttgtg attctgtgtc tacatgttat tttgaagtat atctgaggga   4320
aaaataaatg aaaattttct ttatgtactt atgtatgtgt gatgcatgtt caaagtctta   4380
ttgaccataa ctctgtgcac ttggttattg acattttttg gagtttttt ctctgggaaa    4440 aatcgatagt gttttcttca atgctgctgc tgtgtgaagc catacttttt caggattctt   4500
cccctaattg gctctttggt ttccctgctc tgtttcattt atttcattaa aatgttattc   4560
ctttatttaa gattcactta ttagtctgct gtttctctga aaaattttag agctaggtat   4620
```

```
agtgaccgtg aactttctaa cgcataatat tctgtgatac agccattccg tacatgtgtg      4680
aagtcctgca taactttcga actttgttaa atgttggcac taggagtcat cagatctagg      4740
cttcatcatt ttccagtgag aagcagagac ccaaagggcc tgttacttgt gcttggtcag      4800
gggactgtct gtcatgcctg gaggctcttc ggcacacttc cccatctttc ccttctgcca      4860
ctgtggcttc aagcacctct gttcatagag cgtctctgaa attgagtctc ggtcatgact      4920
tatcccgaag tagagcaatg tgtttcctct cattgtagtt tcaggacttt gtcagtacaa      4980
gctctgccct aggcttgtta ctttatactc atatcctgaa aagatgtgat ttcatctatg      5040
aaggggtaaa atattggttt gtatttaatt gtttgaaata aaagtgatcc ctatattgaa      5100
tctcatgcct gttaatatct acactgtaag tagtgacttc aaaaaaattc taagataggt      5160
agtcaggaga gtttgccatt ataaaaggtg tcttaataat atggaatatt gacctaactg      5220
gagatgaggt aattaattac cgaaatgttg aaaatgtttt gagaactctc cccatttttgg     5280
ggtattcctt gttcatttga atttggtgac tccctactgt tccagtttca gtgccaactt      5340
gggtcacact gttcacatca ggggagacct tgccttgggg acgtaggcgg gcctcttgca      5400
acttgtgctg ttgaccttct gtcttgtgga actctctctc ctgcatctgc tacctgcccg      5460
cagatggtgt gagggagggt tgatggcggg aagccaggaa gtagatgtca tcatggtatt      5520
ggccaggctt ttacttcaac tcttttttgtg gcgttagatt taaggaagca gggggcatgg     5580
ccaacgttga gtcttggccc agtggacata gtgcggcttt cccttgagca ctgcccagat      5640
gcaggacctg cacatgttac aggtttgcca aaagcatctt tttttttttt tttttttttg      5700
agatagtctt gctctgttgc ttaagccaga gtgcagtggc gcaatctcag ctcactgcaa      5760
cctccgcctc ctgggttcaa gtgattcttg tgcctcagcc tcccacgtag ctgagattac      5820
aggcttgcac caccatgttc agctaatttt tgtatggtaa agacggagtt tcaccatgtt      5880
ggccaggttg gtctcgaact cctggcccca agtgatcctc ccctgcgct cgcttcagcc       5940
tcccaaagtg ctgggattac aggtgtgagc caccacgcct ggccaagagc ctcactcctg      6000
tctttagtga ttgcactgaa gcaggcctca ttttttttgca gtcatgctaa ccacaagtta      6060
gtcaacattc actaattgac attcattaga ataggtctcc aaggtgaggc ataacgttgg      6120
ggtgtaatct ggatttcgca gtcatctttt tggggaaact gaaagtacca tctcatttgc      6180
atgaagtgac tccacactgg ccctgtatat ggactctggt aaaatgtgag tgtggtacag      6240
aggaaatagg taagacccccc ttatctagcc ctctcggcag cagcggggg gtgttacaaa       6300
ggactagctg ttcaaatatc ttttgtattg tattgattcc cctattgaat ataaatattt       6360
aaagtataat aactatactg taggtgggct tatgagtgtt ctaaatatct aatagctaaa      6420
ttgaaataag tagaaatata aacaatttag cagctttctg taatacattt acactcaaat      6480
tataagcagc taattctaaa aaagatgtca ctgtaaacta ttgagaacta tagtattttta     6540
tatataatta tatgttcatg tatttgaacc caaaataatt ttaactgaaa tgctttgaat      6600
aaagtatact gtaaatatca aaaaaaaaa aaaaaaa                                6637
```

<210> SEQ ID NO 22
<211> LENGTH: 5427
<212> TYPE: DNA
<213> ORGANISM: Homo sapiens

<400> SEQUENCE: 22

```
agatgcgacg aggttagcgg ggcccgacca ctccttggct tcccaggggt gagcctcgcg        60
agttaggagt tgggtagaga gtcagcccgg ggccggcat ccgctttttc gttgaagcaa        120
```

```
cgactttggc cggatgactc cccagggtcg gcatcagcgt gggactggga acaggtgaag    180
ggaaacagaa gagagcctga gaagaccgct ctcctccgat cctaattgac tgagccaatg    240
agagccaaag aggtcacatg ctcaactggg cggggagcgg gtttccacct gcggcatctt    300
tcgcgagcgg ggagatgagt ggggcggaat atgggagaaa gggagggccc gccacgctct    360
ggctggacac ggccttaatc ggcccgttca ctcgacgttt ttggttctac gttgaccccg    420 agaaccgaa accgcagggc ctagggcggg tggaacgaga ggaactaca tttcccagca     480 ggctgcggaa acgggactgc ggccactact tccggcgtgt accgagagac tggcgtccgg    540
cgtgtaccga gagactggcg tccggtgtgc aggtggccac atggatcctg cagccggtg    600 gcggaacctg cccagcgggc ctagcctaaa gcacttgact gacccctctt atggaatccc    660
gcgggaacag caaaaggcag cgttgcagga gctgacgcgg gcgcacgtgg agtccttcaa    720
ctacgctgtg cacgagggtc tcggcctcgc ggtgcaggct atacctccct ttgaatttgc    780
tttcaaagat gagcgtatct cttttactat tctggatgct gttatcagtc cacctacagt    840
tccaaagggg accatctgca aagaggccaa tgtttatcca gcagaatgcc ggggccgaag    900
gagtacctac cgtgggaagt tgacagctga tatcaactgg gcagtgaatg gaatctcaaa    960
aggaatcatt aagcagtttc ttggctatgt tcccatcatg gtgaaatcca gctttgcaa    1020 cttacgtaac cttcccccac aagccctcat tgagcaccat gaggaggcag aggaaatggg    1080
gggctatttt ataatcaatg gcattgaaaa agtcatccga atgttgatta tgcctcggag    1140
aaattttccc attgcaatga taagaccaaa atggaaaacc agagggcctg gttatactca    1200
gtatggagtt tcaatgcact gtgtgaggga agaacattcc gctgtcaata tgaacctcca    1260
ctacttggaa aatggcactg ttatgttgaa ctttatttac cgaaaagaac tgttcttttct   1320 tcctttggga tttgcactta aggcacttgt cagcttttct gattatcaga tctttcagga    1380
gctcatcaaa ggaaaagagg atgattcttt ccttaggaac tctgtttctc agatgttaag    1440
gattgtaatg gaagagggtt gttcgacaca aaaacaggtc cttaactacc taggtgaatg    1500
cttcagagta aaactcaatg ttcctgactg gtacccaaat gagcaagctg cggagttcct    1560
gtttaaccag tgcatctgta tccacttgaa atccaatact gaaaagtttt atatgctttg    1620
tctcatgacg cgaaagctct ttgctttagc caaaggagag tgcatggagg acaatcctga    1680
tagtttggtg aaccaggaag tcctcacacc gggtcagctc ttccttatgt tcctgaagga    1740
aaaactggaa ggttggttag tgtctattaa aatagctttt gataagaagg ctcagaagac    1800
cagtgtttcc atgaacactg acaatttgat gaggattttt acaatgggca tagaccttac    1860
aaaaccattt gaatacccttt ttgctactgg gaatctgcgt tctaaaacag gtcttggcct    1920
cctacaagat tctggacttt gtgttgtggc tgacaagctg aacttcatac gctacctctc    1980
ccatttccgc tgcgtgcaca gagggctga ttttgccaag atgaggacca ccacagtacg     2040
caggctgctg ccagagtcct ggggcttcct ttgtcccgtg catacccag acggggagcc     2100 ctgtggcctg atgaaccacc taactgccgt atgtgaggtt gtcacacagt ttgtgtatac    2160
ggcatctatt ccagctttac tgtgcaactt gggggtcact cccattgatg gagctcccca    2220
ccgatcatac agtgagtgct accctgtcct gctggacggt gtcatggttg ctgggtgga    2280 taaggatctt gctccaggca tcgcagattc tcttcgtcat tttaaggtgt tgagagagaa    2340
aagaattcct ccctgatgg aagtggtcct tatacccatg acaggaaaac caagtctgta    2400
cccaggattg ttcctttttta ccactccttg tagactggta cggcctgtgc agaacttagc    2460
```

```
attgggcaaa gaagagctaa ttggaactat ggaacagatc ttcatgaatg tcgctatctt    2520
tgaggatgaa gtttttgctg gagttaccac acaccaggaa ctctttccac acagcctgct    2580
gagtgtgatt gccaacttca tcccttctc tgatcacaac cagagtccac ggaacatgta     2640
ccaatgccag atgggtaagc aaactatggg ctttccactt ctcacttatc aagaccgatc    2700
ggataacaaa ctgtatcgtc ttcagactcc tcagagtccc ttggtgagac cctccatgta    2760
tgattattat gacatggata actatccaat tgggaccaat gccatcgttg ctgtgatttc    2820
ttacactggc tatgatatgg aagatgccat gattgtgaat aaggcctctt gggaacgagg    2880 cttttgcccat ggaagtgtct acaagtctga gttcatagac ctctctgaaa aaattaaaca   2940
aggagatagt agcctggtgt ttggcatcaa acctggtgac ccacgcgttc tgcagaagtt    3000
agatgacgat ggattgccgt ttataggagc aaaactgcag tacggagatc cgtattacag    3060
ctacctcaac ctcaacaccg gggaaagttt tgtgatgtac tataagagta aagaaaattg    3120
tgttgtggat aacatcaaag tgtgcagtaa tgacactggg agtggaaaat tcaagtgtgt    3180
ttgcatcact atgagagtgc ctcggaaccc aactatcgga gataaatttg ccagtcgcca    3240
tgggcagaag ggcattttaa gcagattgtg gccggctgag gacatgcctt ttactgagag    3300
tgggatggtc ccagacattc tgttcaatcc ccatggtttt ccatcccgca tgaccattgg    3360
gatgttaatt gagagtatgg ccgggaagtc tgcagctttg catggtctct gccatgatgc    3420
tacacccttc atcttctcag aggagaactc ggccttagaa tacttggtg agatgttaaa     3480 ggctgctggc tacaatttct atggcaccga gaggttatat agtggcatca gtgggctaga    3540 actgaagca gacatcttca taggagtggt ttattatcag cgcttacgcc atatggtctc    3600
agacaaattt caagtaagga caactggagc ccgagacaga gtcaccaacc agcctattgg    3660
gggaagaaat gtccagggtg gaatccgttt tggggagatg gaacgggatg cgcttttagc    3720
tcatggtaca tcttttctcc ttcatgaccg cctcttcaac tgctcagatc ggtcggtagc    3780
ccatgtgtgt gtgaagtgtg gcagtttact ctctccactg ttggagaagc cacccccttc    3840
ttggtctgcc atgcgcaaca gaaaatacaa ctgtactctg tgtagtcgca gtgacactat    3900
cgatactgtt tctgtgcctt atgttttttcg gtattttgta gctgaactgg cagctatgaa    3960
catcaaagtg aaactggatg ttgtttaact tgatgttgac cttttggatt aagaggacta    4020
tcagattaaa gcaaaatgta attttaattc aatgaagata tcattaccag ttactcttg     4080 agattttca acggtgttag aactctcaac caagacctga aaaccaagta tgcaaggttt     4140
ctgaatctct ctggtagatt aactattgac aatgattttc tgttatcttt gttcaaaaag    4200
ttcatgtctt ctcaaaatat gaaatattga taaatggaag agcatacggt gacaagtctc    4260 cttttccaacc ccaggttccc tacaccctgc tctcagcagg cagtgagtgt cacacacctg   4320
ttaatccatc ttgagcagga cagtactata caaatagaat gcaagctgta atgtaatttt    4380
atattttctt atagccacgt tgaagtaaaa acaaacaggt acagtgtttt ttaccagctt    4440
tatagaagta cagttgttac atatttaatg aatacaattt gatgggtctg actatatgca    4500
cacacctttg ataccatcac cacaatcagg gtaataaaca tacctgtcat ctccacaagt    4560
ttcctcctgc ccctttgttt tttgcttttt ggttgctgtt gagttttgt tttgtcttct     4620 gtggtaagaa cacttaactc aagacctacc ctcttaacaa atctttaagt gcacgatata    4680
gtattgttaa ttccaggcac catgttgtac aacagatctt tagaccttac ttgtcttgca    4740
taactgaagc tttatacctg ttgaacaact ctccatttcc ctggcccta gcaaccaccc     4800 ttctaccctg tttctatgag tttgactatt acagatatct catatagtgg gatcatgcaa    4860
```

| | |
|---|---|
| tatttgtcct gtgactggct tatttcactt agcatagtga aataagattc atccattttg | 4920 |
| gaagccaggc atggtgctgt gcatctatag tccctgctat ttgagaggct gaggtgggag | 4980 |
| gatcatttga gtgcaggagt tcaaggacag cctgggtaat ataggaagac cctgtcttga | 5040 |
| agaccctgac ctcaagtgat ccacccacct cggcctccga aagtgctagg attacaggtg | 5100 |
| tgagccactg tgcctggcct ccggtgagta ttttatattt agtctacact tccatacttg | 5160 |
| gcttttttct gcttttatat tgatctgctt tcatagcagt gtgtagagtg ccacttatgt | 5220 |
| tttctttctt gtgtacagta ttttattgta tggatttacc atcccctgtg tatttaagtt | 5280 |
| gttccattct ttggccatta taactttttt ctgcaaatat tctggtgact tatctttggc | 5340 |
| cattataaac tgttgataat agatcatctt gtatatactt ctgcaattat aagatgtttt | 5400 |
| ttgatgatga aaaaaaaaaa aaaaaaa | 5427 |

<210> SEQ ID NO 23
<211> LENGTH: 1138
<212> TYPE: DNA
<213> ORGANISM: Homo sapiens

<400> SEQUENCE: 23

| | |
|---|---|
| agggctacta ggacgcacgc gcgagataga acctctagtc tcgtggagag attgaagatg | 60 |
| gcggcttctc aggcggtgga ggaaatgcgg agccgcgtgg ttctggggga gtttggggtt | 120 |
| cgcaatgtcc atactactga cttcccggt aactattccg gttatgatga tgcctgggac | 180 |
| caggaccgct tcgagaagaa tttccgtgtg gatgtagtac acatggatga aaactcactg | 240 |
| gagtttgaca tggtgggaat tgacgcagcc attgccaatg cttttcgacg aattctgcta | 300 |
| gctgaggtgc caactatggc tgtggagaag gtcctggtgt acaataatac atccattgtt | 360 |
| caggatgaga ttcttgctca ccgtctgggg ctcattccca ttcatgctga tccccgtctt | 420 |
| tttgagtatc ggaaccaagg agatgaagaa ggcacagaga tagatactct acagtttcgt | 480 |
| ctccaggtca gatgcactcg gaaccccat gctgctaaag attcctctga ccccaacgaa | 540 |
| ctgtacgtga accacaaagt gtataccagg catatgacat ggatcccct ggggaaccag | 600 |
| gctgatctct ttccagaggg cactatccga ccagtgcatg atgatatcct catcgctcag | 660 |
| ctgcggcctg ccaagaaaat tgacctgctc atgcactgtg tcaagggcat tggcaaagat | 720 |
| catgccaagt tttcaccagt ggcaacagcc agttacaggc tcctgccaga catcaccctg | 780 |
| cttgagcccg tggaagggga ggcagctgag gagttgagca ggtgcttctc acctggtgtt | 840 |
| attgaggtgc aggaagtcca aggtaaaaag gtggccagag ttgccaaccc ccggctggat | 900 |
| accttcagca gagaaatctt ccggaatgag aagctaaaga aggttgtgag gcttgcccgg | 960 |
| gttcgagatc attatatctg taagaaagat ttgctggctg cggtggctca cacctgtaat | 1020 |
| cccagcactt tgggaggcca aggcgagtgg atcacggggt caagagagcg agaccatcct | 1080 |
| ggctaacatg gtgaaacccc gtctctataa aaaaaaaaa aaaaaaaaaa aaaaaaa | 1138 |

<210> SEQ ID NO 24
<211> LENGTH: 817
<212> TYPE: DNA
<213> ORGANISM: Homo sapiens

<400> SEQUENCE: 24

| | |
|---|---|
| gtcggggcgg gggctggggg tggagcctca tgccccgccc cgcggctggg ccctgccgcg | 60 |
| ccgctgcggc tcctcctccc tccttccgtc ctccgcgcct tccgtcggtc ggtccttgct | 120 |

| | |
|---|---:|
| tcctgcttcg cctccgcgcc tcgcgctatg ggacagagcc cccgatccgc cagcaccacc | 180 |
| tgaggatcca gaaaccgccc cagcgatgga agaggatcag gagctggaga gaaaaatatc | 240 |
| tggattgaag acctcaatgg ctgaaggcga gaggaagaca gccctggaaa tggtccaggc | 300 |
| agctggaaca gatagacact gtgtgacatt tgtattgcac gaggaagacc atccctagg | 360 |
| aaattctcta cgttacatga tcatgaagaa cccggaagtg gaattttgtg gttacactac | 420 |
| gacccatcct tcagagagca aaattaattt acgcattcag actcgaggta cccttccagc | 480 |
| tgttgagcca tttcagagag gcctgaatga gctcatgaat gtctgccaac atgtgcttga | 540 |
| caagtttgag gccagcataa aggactataa ggatcaaaaa gcaagcagaa atgaatccac | 600 |
| attctagtcc tttatgcagt atacaaggag aactgtcctg taggatattc tcttcctgat | 660 |
| ggtgcagaac ccagaattag aagtttgtgg ttacagcata ctctgtcctt cagaaaggcg | 720 |
| tgattctagc tgttgacccc ttgcagctgt tggaatctct gcaagaacct ctgtattctt | 780 |
| ctaataaatt ccctctttta tttaaactag aaaaaaa | 817 |

<210> SEQ ID NO 25
<211> LENGTH: 2732
<212> TYPE: DNA
<213> ORGANISM: Homo sapiens

<400> SEQUENCE: 25

| | |
|---|---:|
| ctttcgcctc agtctcgagc tctcgctggc cttcgggtgt acgtgctccg ggatcttcag | 60 |
| cacccgcggc cgccatcgcc gtcgcttggc ttcttctgga ctcatctgcg ccacttgtcc | 120 |
| gcttcacact ccgccgccat catggtgaag ctcgcgaagg caggtaaaaa tcaaggtgac | 180 |
| cccaagaaaa tggctcctcc tccaaaggag gtagaagaag atagtgaaga tgaggaaatg | 240 |
| tcagaagatg aagaagatga tagcagtgga gaagaggtcg tcatacctca gaagaaaggc | 300 |
| aagaaggctg ctgcaaccctc agcaaagaag gtggtcgttt ccccaacaaa aaaggttgca | 360 |
| gttgccacac cagccaagaa agcagctgtc actccaggca aaaaggcagc agcaacacct | 420 |
| gccaagaaga cagttacacc agccaaagca gttaccacac ctggcaagaa gggagccaca | 480 |
| ccaggcaaag cattggtagc aactcctggt aagaagggtg ctgccatccc agccaagggg | 540 |
| gcaaagaatg gcaagaatgc caagaaggaa gacagtgatg aagaggagga tgatgacagt | 600 |
| gaggaggatg aggaggatga cgaggacgag gatgaggatg aagatgaaat tgaaccagca | 660 |
| gcgatgaaag cagcagctgc tgcccctgcc tcagaggatg aggacgatga ggatgacgaa | 720 |
| gatgatgagg atgacgatga cgatgaggaa gatgactctg aagaagaagc tatggagact | 780 |
| acaccagcca aaggaaagaa agctgcaaaa gttgttcctg tgaaagccaa gaacgtggct | 840 |
| gaggatgaag atgaagaaga ggatgatgag gacgaggatg acgacgacga cgaagatgat | 900 |
| gaagatgatg atgatgaaga tgatgaggag gaggaagaag aggaggagga gagcctgtc | 960 |
| aaagaagcac ctggaaaacg aaagaaggaa atggccaaac agaaagcagc tcctgaagcc | 1020 |
| aagaaacaga aagtggaagg cacagaaccg actacggctt tcaatctctt tgttggaaac | 1080 |
| ctaaacttta caaatctgc tcctgaatta aaaactggta tcagcgatgt ttttgctaaa | 1140 |
| aatgatcttg ctgttgtgga tgtcagaatt ggtatgacta ggaaatttgg ttatgtggat | 1200 |
| tttgaatctg ctgaagacct ggagaaagcg ttggaactca ctggtttgaa agtctttggc | 1260 |
| aatgaaatta actagagaa accaaaagga aagacagta agaaagagcg agatgcgaga | 1320 |
| acactttgg ctaaaaatct cccttacaaa gtcactcagg atgaattgaa agaagtgttt | 1380 |
| gaagatgctg cggagatcag attagtcagc aaggatggga aaagtaaagg gattgcttat | 1440 |

```
attgaattta agacagaagc tgatgcagag aaaacctttg aagaaaagca gggaacagag    1500
atcgatgggc gatctatttc cctgtactat actggagaga aaggtcaaaa tcaagactat    1560
agaggtggaa agaatagcac ttggagtggt gaatcaaaaa ctctggtttt aagcaacctc    1620
tcctacagtg caacagaaga aactcttcag gaagtatttg agaaagcaac ttttatcaaa    1680
gtacccagga accaaaatgg caaatctaaa gggtatgcat ttatagagtt tgcttcattc    1740
gaagacgcta aagaagcttt aaattcctgt aataaaaggg aaattgaggg cagagcaatc    1800
aggctggagt tgcaaggacc caggggatca cctaatgcca gaagccagcc atccaaaact    1860
ctgtttgtca aaggcctgtc tgaggatacc actgaagaga cattaaagga gtcatttgac    1920
ggctccgttc gggcaaggat agttactgac cgggaaactg ggtcctccaa agggtttggt    1980
tttgtagact tcaacagtga ggaggatgcc aaagctgcca aggaggccat ggaagacggt    2040
gaaattgatg gaaataaagt taccttggac tgggccaaac ctaagggtga aggtggcttc    2100
gggggtcgtg gtggaggcag aggcggcttt ggaggacgag gtggtggtag aggaggccga    2160
ggaggatttg gtggcagagg ccggggaggc tttggagggc gaggaggctt ccgaggaggc    2220
agaggaggag gaggtgacca caagccacaa ggaaagaaga cgaagtttga atagcttctg    2280
tccctctgct ttccctttc catttgaaag aaaggactct ggggttttta ctgttacctg    2340
atcaatgaca gagccttctg aggacattcc aagacagtat acagtcctgt ggtctccttg    2400
gaaatccgtc tagttaacat ttcaagggca ataccgtgtt ggttttgact ggatattcat    2460
ataaactttt taaagagttg agtgatagag ctaacccctta tctgtaagtt ttgaatttat    2520
attgtttcat cccatgtaca aaaccatttt ttcctacaaa tagtttgggt tttgttgttg    2580
tttctttttt ttgttttgtt tttgttttt ttttttttgc gttcgtgggg ttgtaaaaga    2640
aaagaaagca gaatgttta tcatggtttt tgcttcagcg gctttaggac aaattaaaag    2700
tcaactctgg tgccagaaaa aaaaaaaaaa aa                                 2732
```

<210> SEQ ID NO 26
<211> LENGTH: 583
<212> TYPE: DNA
<213> ORGANISM: Homo sapiens
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:

```
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 26
ttttgttgta aaaaaaacca agttttttttt ctttcctaat agctagttcc aatgatgtta      60
attacccgcc ctgagctgaa ataacagtag acaaagatag aagctagcct ctggttttac     120
aaagcctttg tacaagtcct ctctgtcttt tctgtccatn gccagggaaa tgtattgctg     180
gtgctagagg gagaggaaac gtggacggcc aagaacaggg cggcacagtc ctctgggctg     240
gaggctcgtg ttccttccca taagcagggc ctgtggggtg tatggggcag aacataggcc     300
tccacaccaa actgacagca gagaaaagcc aggcaacctg ttcaatcgcc ccagcagttg     360
acctgggttc tatgtgtggg agtgaactgc tgcggccctg ggagcnactg tccccagcct     420
tggggctgat gtggtctana aggacacctc ggccacacag tggaaggggc cagggancct     480
ggccaggcaa anaagttngg ttgggtggag gactatgcta cgctgtactt gactcnggga     540
agaagtcttg attggggncc tttnttggat ntggccccng ggg                       583

<210> SEQ ID NO 27
<211> LENGTH: 1884
<212> TYPE: DNA
<213> ORGANISM: Homo sapiens

<400> SEQUENCE: 27
ggcggggcca cgccttttcc ggcccgcagc gcggcctggg ctcccgcgtg tttaaaagtg      60
cgcttgtggc tgctgctgtc ttaactcctg tgcttggcgg acagacaggc gagatggcgg     120
cggaggtgtt gccgagtgcg aggtggcagt attgtgtggc gcccgacggg agccagagag     180
ctgtactggt ccagttctcc aacgggaagc tacagagtcc aggcaacatg cgctttacct     240
tgtatgagaa caaagattcc accaacccca ggaagaggaa tcaacggatc ctggcagctg     300
aaacagatag gctctcctat gtgggaaaca ttttgggac tggagccctc aaatgcaaca     360 cttttgtgcag gcactttgtg ggaattttga acaagacctc tggccaaatg gaagtatatg     420
atgctgaatt gttcaacatg cagccactat tttcagatgt atcagttgag agtgaactgg     480
cgctagagag tcagaccaaa acttacagag aaaagatgga ttcttgtatt gaagcctttg     540
gtaccaccaa acagaagcga gctctgaaca ccaggagaat gaacagagtt ggcaatgaat     600 cctttgaatcg tgcagtggct aaagctgcag agactatcat tgatacgaag ggtgtgactg     660
ctctggtcag cgatgctatc cacaatgact tgcaagatga ctccctctac cttcctccct     720
gctatgatga tgcagccaag cctgaagacg tgtataaatt tgaagatctt cttttcccctg     780 cggagtatga agctcttcag agcccatctg aagctttcag gaacgtcacg tcagaagaaa     840
tactgaagat gattgaggag aacagccatt gcacctttgt catagaagcg ttgaagtctt     900
tgccatcaga tgtggagagc cgagaccgcc aggcccgatg catatggttt ctggataccc     960
tcatcaaatt tcgagctcat agggtagtta agcggaaaag tgctctggga cctggagttc    1020
```

```
cccacatcat caacaccaaa ctgctgaagc actttacttg cttgacctac aacaatggca    1080
gattacggaa cttaatttcg gattctatga aggcgaagat tactgcatat gtgatcatac    1140
ttgccttgca catacatgac ttccaaattg acctgacagt gttacagagg gacttgaagc    1200
tcagtgagaa aaggatgatg gagatagcca aagccatgag gctgaagatc tccaaaagaa    1260
gggtgtctgt ggccgccggc agtgaagaag atcacaaact gggcaccctg tccctcccgc    1320
tgcctccagc ccagacctca gaccgcctgg caaagcggag gaagattacc tagacgcatg    1380
ctttccagac agggcgtttt ggctgcatca cagccactgg ctggtcctat tcatttccat    1440
ttttatgtat gttttgaaaa gaaaaggtcc ggggatggtg gctcacacct gaaatcccag    1500
cactttggga ggccgaggca ggaagatcat tgagctcagg agtttgaaac cagtctggac    1560
aacatagggg accccatct ctaccggagg aaaaaaaaaa gagtcaggcc tggtggtgtg    1620
cgcctgtaat cccagctact cgggaggctg aggcaggacg attacttgag cttgggaaat    1680
caaggttgca gtgagctatg attgtgtggc cacactccat cctgggtcac agagtgagac    1740
cttgtctcaa aaaagtaaca taaggaaaaa agaagccttg ctttagcaca ggtatgaagc    1800
cagaagccag catctcaact gtgcttgtct tatgcagaaa tataaagcga tggccaggtt    1860
ggacttcaaa aaaaaaaaaa aaaa                                          1884

<210> SEQ ID NO 28
<211> LENGTH: 3216
<212> TYPE: DNA
<213> ORGANISM: Homo sapiens

<400> SEQUENCE: 28
gcggacggtg agtggggatg gactggagtt gaagagctcg agatgaaggg cttgagggcg      60
tgtgttattt gttttcttca agcatttggt cgagattaag aattaaaaat gtcatccaaa     120
caagaaataa tgagtgacca gcggtttaga cgggttgcaa aggacccgag attttgggaa     180
atgccagaaa aggatcgaaa agtcaaaatt gacaagagat ttcgagccat gtttcatgac     240
aagaagttca agttgaacta tgccgtggat aaaagagggc gccccattag ccatagcact     300
acagaggatt tgaagcgttt ttacgacctt tcagattctg attccaatct ctctggtgaa     360
gatagcaaag cattgagtca aagaaaata agaagaaaa aaacccagac taaaaaagaa     420
atcgattcaa aaaatctagt tgagaaaaag aaagaaacca agaaggctaa tcacaagggt     480
tctgaaaata aaactgattt agataattct ataggaatta aaaaaatgaa aacctcatgt     540
aaatttaaga tagattcaaa cataagtccg aagaaggata gcaaagaatt tacacaaaaa     600 ataagaaag agaaaaaaaa cattgttcaa catactacag actcttctct cgaagaaaaa     660
caaaggacat tagactcagg cacctctgaa attgtgaaat ctcccagaat cgagtgttct     720
aagacaagaa gagaaatgca atcagtggtt caactcataa tgacaagaga cagtgatggt     780
tatgaaaact caacagatgg tgaaatgtgt gacaaagatg ctctggagga agattcagaa     840
agcgttagtg aaataggaag tgatgaggaa tctgaaaatg aaattacaag tgttggtaga     900
gcttcaggtg atgacgatgg aagtgaagat gatgaagagg aggatgaaga tgaagaggag     960
gatgaagatg aggatagtga ggatgatgat aaaagtgaca gtggccctga tcttgcaagg    1020
ggtaaaggaa atatagaaac tagttctgaa gatgaagatg atacggcaga tttgtttcca    1080
gaagaatctg gttttgagca tgcttggaga gaattagata aagatgctcc tcgtgctgat    1140
gagattacac gtcgattagc agtttgtaac atggactggg atagattaaa ggcaaaagat    1200
```

```
ttgctggctc tgttcaattc atttaaaccc aaaggaggtg taatattttc cgtcaagata   1260
tatccttcag aatttggaaa ggagaggatg aaggaagagc aagttcaagg accagtagag   1320
ctattaagta ttcctgaaga tgccccagaa aaagactgga cgtctagaga aaaattgaga   1380
gattatcaat tcaaacgact gaagtactat tatgcagtag tagactgtga ttctccggaa   1440
acagctagta aaatttatga ggattgtgat ggcctggaat ttgaaagtag ttgttctttc   1500
atagatctaa ggtttatacc agatgatatt acttttgatg atgagcctaa ggatgtagcc   1560
tcagaagtga atttaacagc atataaacca aaatatttca cttctgctgc aatgggaaca   1620
tcaacggtgg aaatcacttg ggatgagact gatcatgaaa gaattacaat gctcaacagg   1680
aagtttaaaa aggaagagct tttggacatg gattttcaag cctacttagc ttcctctagt   1740
gaagatgaag aggagataga agaggagcta caaggtgatg atggagtcaa tgtagaagaa   1800
gatgggaaaa caaagaaaag tcagaaggat gatgaagaac aaattgctaa atacaggcag   1860
ctcttgcagg ttattcaaga aaagaaaag aaggcaaag aaaatgatat ggaaatggaa   1920
attaaatggg ttccaggtct taaagaaagt gcagaagaga tggtcaaaaa caaattggaa   1980
ggaaaggata aactgacccc ttgggaacaa ttttagaga agaagaaga gaaaaaaga    2040 ctgaaaagga aacagaaggc tcttgctgaa gaggccagtg aagaggaact tccctctgat   2100
gttgatttga atgacccata ctttgctgaa gaagttaaac aaataggtat aaataaaaaa   2160
tcggtaaaat ctgcaaaaga tggcacatct ccagaagaag aaattgaaat agaaagacaa   2220
aaggctgaaa tggctttgct tatgatggat gaggacgagg acagtaagaa acacttcaat   2280
tacaacaaga ttgtggagca ccagaatctg agcaaaaaga gaaaaagca gctcatgaaa   2340 aagaaggaat taatagagga tgactttgag gtaaatgtta acgatgcacg gtttcaggca   2400
atgtacactt cccacttgtt caatttggac ccctcagatc ccaatttcaa gaaaacaaaa   2460
gctatggaaa aaatccttga ggagaaggcc cggcaaagag aacggaaaga caagaacttt   2520
actcaggcaa taagaaaaa agagagtgag attgaaaagg aatcacaaag gaagtccatt   2580
gatcctgctt tgtcaatgtt gattaaatct ataaaaacca aaacagagca gtttcaagca   2640
agaaaaaagc aaaaagtcaa ataactggat gttacttatt tttgaactga atacatcttt   2700
tcctaaaatg tacaaaaata ataggaggga atatttattg ggaacaaagc tatctttcaa   2760
gaacatgaat aaaatctttt tctggacata gtaaaatttt tctccataaa taattgtact   2820
taattgtgga tgactgacaa atttttattg tatattccta cagatcagtc ataattaaat   2880
tacctgcatt atagggttta taaaatttt atattttaca atgttcagtt ctaactagtg   2940
gaaagttact ctagcttttt aaaaggctgt ttacaattct gtgtaaaaat agagcagtat   3000
ctactcaagt ttgtgtaaat gttagggata atttgaaaaa tatatatatt taatacatta   3060
atttctctgg aagcaggagg catgtttaaa taactattaa aataatttat ttttctagcc   3120
ataaaggatg gaagtcaaga acttttgtt gtttagtcat gttaagtata gtttatgaaa   3180
ttaacttgta aataaaagtg taaaatattt tcatta                            3216

<210> SEQ ID NO 29
<211> LENGTH: 1931
<212> TYPE: DNA
<213> ORGANISM: Homo sapiens

<400> SEQUENCE: 29
acttccgggg tcgaggcgag gccaacgata cgcctgctgc agcaggagga gttacgagcc     60
gggccgcgcg ctgcctaaat acctaaacca ggtttagcgc ctgctcatat aaagctctcc    120
```

```
taactcgtct tccggtggga atttcttcac gtgggccgga gtcggagact gagtttagct    180
ttactgagga gctctaaatt taggcgggta tgagtgattt cagtgaagaa ttaaaagggc    240
ctgtgacaga tgatgaagaa gtggaaacat ctgtgctcag tggtgcagga atgcattttc    300
cttggcttca aacatacgta gaaactgtgg ccattggagg gaaaaggagg aaggattttg    360
ctcagacaac aagtgcttgt ttaagtttta tccaagaagc tctgctgaag caccaatggc    420
agcaagctgc agaatacatg tacagttatt ttcagacctt ggaagattca gatagctaca    480
aaaggcaggc tgcacctgag attatttgga agctcggaag tgaaattcta ttttatcatc    540
ccaaaagcaa catggagagt ttcaatactt ttgctaaccg gatgaaaaat attggcgtca    600
tgaattattt aaagatctcc ttacaacatg cattatacct tctgcatcat ggaatgctta    660
aagatgctaa gagaaatctg agtgaggcag agacatggag acatggtgaa aatacgtctt    720
cccgggaaat attaatcaac cttattcagg cctataaagg gcttttacag tattatacct    780
ggtctgaaaa gaagatggaa ttgtcaaagc ttgataagga tgattatgct tacaatgcag    840
tagcccagga tgtgttcaac cacagctgga agacatctgc aaatatttct gcattgatta    900
aaattcctgg agtttgggac ccttttgtga gagttatgt agaaatgctg gaattctatg    960
gggatcgaga tggagcccaa gaggtactca ccaattatgc atatgatgaa aagtttccat    1020
caaatccaaa tgcccatatc tacttataca actttctaaa gagacagaag gcaccaagat    1080
caaaattgat aagtgtgctt aagattttgt atcagattgt accatctcat aaattgatgt    1140
tggaattcca tacattactt agaaaatcag aaaaagaaga acaccgtaaa ctggggttgg    1200
aggtattatt tggagtctta gattttgccg gatgcactaa gaatataact gcttggaaat    1260
acttggcaaa atatctgaaa aatatcttaa tgggaaacca ccttgcgtgg gttcaagaag    1320
agtggaactc caggaaaaac tggtggccag gctttcattt cagctacttt tgggcaaaaa    1380
gtgattggaa ggaagataca gctttggcct gtgagaaagc ttttgtggct ggtttactgt    1440
taggaaaagg ttgtagatat ttccggtata tttttaaagca agatcaccaa atcttaggga    1500
agaaaattaa gcggatgaag agatctgtga aaaaatacag tatttgtaaat ccaagactct    1560 gatactgaat tttagttatt tcacagttgt agctacacag taagtagctt ggtagatagt    1620
tattgaatgt atttatgtag tgtattaaga agcttatatt actacaaaaa acttattttt    1680
atatattttt atattttgt attatttata gctagagaaa caatattact gcctttgctc    1740
tttgtaacta tgtctgttt ctttttgta atgttaaatg ttacatttgt taaggaataa    1800
ttcttcaaat gacaaactaa ttacagaata tagctctaca gcagttattg tttgcaaata    1860
ctttgcctct tgctattgtg taataaactg taacttgtag tgctgtgaaa tgtaaaaaaa    1920 aaaaaaaaa a                                                         1931

<210> SEQ ID NO 30
<211> LENGTH: 409
<212> TYPE: DNA
<213> ORGANISM: Homo sapiens
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (234)..(234)
```

```
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 30
aacattcttg agaaagttaa acaatagca aattgtataa ttgtatccag aaatgtatac      60
tcatcgtatt ttaaagctaa atttattttt taaactagat cccttcatta ttctttatgc     120
cccagagtaa atcccagatg gatcaaagat ctaaacataa tctttcatat gtaaaaatat     180
aaaagtattn gtagaaaacn natatgaatg ctttgatgat cttggaatgg caangtcaat     240
ttttgcagca tatggtggac aaaggagata atttctttaa tgtatcaata gctcttgcaa     300
agcaaacagg anaaaagcaa actgagtang ggatatgana attagtnttc tgagccaccg     360
tgcccagcct aatttttgta actntgtata ntggagactt acacagtgg                409

<210> SEQ ID NO 31
<211> LENGTH: 229
<212> TYPE: DNA
<213> ORGANISM: Homo sapiens

<400> SEQUENCE: 31
tttttttttt tttttttaca aaagaaacta ctactgtatt tgttgccct gtcccttcaa      60 cttggctcca aattgcttgg ctcatcatca cagtggcctc cagaaggtgg cgagctctgc    120
ttctcaagtt tcaactgtgg aaggcacatc tggtcccaga ggaaggatga ggggctctct    180
ggggcttgag gcagcccac cttgtgtcct cagaagcccc ctcgtgccg                 229

<210> SEQ ID NO 32
<211> LENGTH: 1323
<212> TYPE: DNA
<213> ORGANISM: Homo sapiens

<400> SEQUENCE: 32
gatttcggcc tgactattac ttgggccacg gaaatagcca acccttttct tccgcacggt      60
tggaggaggt cggctggtta tcgggagttg gagggctgag gtcgggaggg tggtgtgtac     120
agagctctag gacaccaggc cagtcgcggg ttttgggccg aggcctgggt tacaagcagc     180
aagtgcgcgg ttggggccac tgcgaggccg ttttagaaaa ctgtttaaaa caaagagcaa     240
ttgatggata aatcaggaat agattctctt gaccatgtga catctgatgc tgtggaactt     300
gcaaatcgaa gtgataactc ttctgatagc agcttattta aaactcagtg tatcccttac     360
tcacctaaag gggagaaaag aaaccccatt cgaaaatttg ttcgtacacc tgaaagtgtt     420
```

-continued

| | |
|---|---|
| cacgcaagtg attcatcaag tgactcatct tttgaaccaa taccattgac tataaaagct | 480 |
| atttttgaaa gattcaagaa caggaaaaag agatataaaa aaaagaaaaa gaggaggtac | 540 |
| cagccaacag gaagaccacg gggaagacca gaaggaagga gaaatcctat atactcacta | 600 |
| atagataaga agaaacaatt tagaagcaga ggatctggct tcccattttt agaatcagag | 660 |
| aatgaaaaaa acgcaccttg gagaaaaatt ttaacgtttg agcaagctgt tgcaagagga | 720 |
| tttttttaact atattgaaaa actgaagtat gaacaccacc tgaaagaatc attgaagcaa | 780 |
| atgaatgttg gtgaagattt agaaaatgaa gattttgaca gtcgtagata caaattttg | 840 |
| gatgatgatg gatccatttc tcctattgag gagtcaacag cagaggatga ggatgcaaca | 900 |
| catcttgaag ataacgaatg tgatatcaaa ttggcagggg atagtttcat agtaagttct | 960 |
| gaattccctg taagactgag tgtatactta aagaagagg atattactga agaagctgct | 1020 |
| ttgtctaaaa agagagctac aaaagccaaa aatactggac agagaggcct gaaaatgtga | 1080 |
| caggatcatg aatgtcaaag gtgaagcata tagaaaaaac gacttcatag aaatgaataa | 1140 |
| agataaatgt ggatatatgt accagtctgg tggtgaagaa attctgaaac ccagaacttt | 1200 |
| ataacaagaa aaaaattttt taaccctgtg aagaagtttg tgaaagaaac ttgtgaagta | 1260 |
| gtaataatta gaaaaaaaac cattaaaaca ccagagaaaa tacatagaaa aaaaaaaaaa | 1320 |
| aaa | 1323 |

<210> SEQ ID NO 33
<211> LENGTH: 2489
<212> TYPE: DNA
<213> ORGANISM: Homo sapiens

<400> SEQUENCE: 33

| | |
|---|---|
| ctccgccgcg ggagggagct gcggctgtgc cggccgagcg ggggagggcg ccgccactca | 60 |
| gagccaggga gggagccgct ggagcggaag cccggaggcc gcgctgcgcc ggggtgaggt | 120 |
| ggctttgacc ccgggttgcc cggccagcac gaccgaggag gtggctggac agctggagga | 180 |
| tgaacggaga agccgactgc cccacagacc tggaaatggc cgccccccaaa ggccaagacc | 240 |
| gttggtccca ggaagacatg ctgactttgc tggaatgcat gaagaacaac cttccatcca | 300 |
| atgacagctc caagttcaaa accaccgaat cacacatgga ctgggaaaaa gtagcattta | 360 |
| aagactttc tggagacatg tgcaagctca aatgggtgga gatttctaat gaggtgagga | 420 |
| agttccgtac attgacagaa ttgatcctcg atgctcagga acatgttaaa atccttaca | 480 |
| aaggcaaaaa actcaagaaa cacccagact tcccaaagaa gccccctgacc ccttatttcc | 540 |
| gcttcttcat ggagaagcgg gccaagtatg cgaaactcca ccctgagatg agcaacctgg | 600 |
| acctaaccaa gattctgtcc aagaaataca aggagcttcc ggagaagaag aagatgaaat | 660 |
| atattcagga cttccagaga gagaaacagg agttcgagcg aaacctggcc cgattcaggg | 720 |
| aggatcaccc cgacctaatc cagaatgcca agaaatcgga catcccagag aagcccaaaa | 780 |
| ccccccagca gctgtggtac acccacgaga agaaggtgta tctcaaagtg cggccagatg | 840 |
| agatcatgag agactatatc cagaagcacc cagagctgaa catcagtgag gagggtatca | 900 |
| ccaagtccac cctcaccaag gccgaacgcc agctcaagga caagtttgac gggcgaccca | 960 |
| ccaagccacc tccgaacagc tactcgctgt actgcgcaga gctcatggcc aacatgaagg | 1020 |
| acgtgcccag cacagagcgc atggtgctgt cagccagca gtggaagctg ctgtcccaga | 1080 |
| aggagaagga cgcctatcac aagaagtgtg atcagaaaaa gaaagattac gaggtggagc | 1140 |

```
tgctccgttt cctcgagagc ctgcctgagg aggagcagca gcgggtcttg ggggaagaga    1200
agatgctgaa catcaacaag aagcaggcca ccagccccgc ctccaagaag ccagcccagg    1260 aaggggcaa gggcggctcc gagaagccca agcggcccgt gtcggccatg ttcatcttct    1320
cggaggagaa acggcggcag ctgcaggagg agcggcctga gctctccgag agcgagctga    1380
cccgcctgct ggcccgaatg tggaacgacc tgtctgagaa gaagaaggcc aagtacaagg    1440
cccgagaggc ggcgctcaag gctcagtcgg agaggaagcc cggcggggag cgcgaggaac    1500
ggggcaagct gcccgagtcc cccaaaagag ctgaggagat ctggcaacag agcgttatcg    1560
gcgactacct ggcccgcttc aagaatgacc gggtgaaggc cttgaaagcc atggaaatga    1620
cctggaataa catggaaaag aaggagaaac tgatgtggat taagaaggca gccgaagacc    1680
aaaagcgata tgagagagag ctgagtgaga tgcgggcacc tccagctgct acaaattctt    1740
ccaagaagat gaaattccag ggagaaccca agaagcctcc catgaacggt taccagaagt    1800
tctcccagga gctgctgtcc aatggggagc tgaaccacct gccgctgaag gagcgcatgg    1860
tggagatcgg cagtcgctgg cagcgcatct cccagagcca aaggagcac tacaaaaagc    1920 tggccgagga gcagcaaaag cagtacaagg tgcacctgga cctctgggtt aagagcctgt    1980
ctccccagga ccgtgcagca tataaagagt acatctccaa taaacgtaag agcatgacca    2040
agctgcgagg cccaaacccc aaatccagcc ggactactct gcagtccaag tcggagtccg    2100
aggaggatga tgaagaggat gaggatgacg aggacgagga tgaagaagag gaagatgatg    2160
agaatgggga ctcctctgaa gatggcggcg actcctctga gtccagcagc gaggacgaga    2220
gcgaggatgg ggatgagaat gaagaggatg acgaggacga agacgacgac gaggatgacg    2280
atgaggatga agataatgag tccgagggca gcagctccag ctcctcctcc tcagggggact    2340 cctcagactc tgactccaac tgaggctcag ccccacccca gggcagccag ggagagccca    2400
ggagctcccc tccccaactg accacctttg tttctccccc atgttctgtc ccttgccccc    2460
ctggcctccc ccactttctt tctttctttt                                    2489
```

<210> SEQ ID NO 34
<211> LENGTH: 3154
<212> TYPE: DNA
<213> ORGANISM: Homo sapiens
<400> SEQUENCE: 34

```
acttccgctt cctcaacagc agcacttccg ggttgggaga aaggtggcgg cgctttcgga     60
gggaataaaa tggaaggaga atcaagcaga tttgaaatcc acactccagt ttctgacaag    120
aaaaagaaaa agtgttctat acataaggaa agacctcaga acattccca cgaaattttc     180 agagactcct ccctggtgaa tgaacagtct caaataacta ggaggaaaaa gaggaaaaaa    240
gatttccagc atctcatttc ttctccttg aaaaaatcca gaatctgtga tgagactgca    300
aatgccactt ccacactcaa aaagagaaaa aagagaagat atagtgcttt ggaggtggac    360
gaggaagcag gtgttacagt tgtccttgtg gataaagaaa atattaacaa cacaccaaag    420 catttagaa aggatgttga tgttgtttgt gttgatatga gcatagaaca gaagttacca    480
agaaagccta aacagacaa atttcaggta cttgctaagt cacatgcaca taatcagaa     540 gccctgcaca gtaaagttag ggagaaaaag aataaaagc atcagaggaa agctgcatcc    600
tgggagagcc agcgggcaag ggacaccctg cctcagtcag aatcccacca ggaggagtcc    660
tggctttctg tgggtccagg gggtgaaatt acagaactac cagcatctgc tcataaaaac    720
aagtctaaga aaaaaaagaa aaagtccagt aaccgggaat atgagacact ggccatgcct    780
```

```
gaaggatcgc aagcaggcag agaggccggg actgatatgc aggaatccca gcctactgtg     840
ggcttggatg atgaaactcc acaactacta ggacctactc acaaaaaaaa gtctaagaaa     900
aaaaagaaga aaaagtccaa tcaccaggaa tttgaggcat tggccatgcc tgaaggatca     960
caagtgggca gtgaggttgg ggctgatatg caggaatccc ggcctgctgt gggcctgcat    1020
ggtgaaactg caggaatacc agcacctgct tataaaaaca agtctaagaa aaaaaagaaa    1080
aagtccaatc accaggaatt tgaggcagtg gccatgcctg agagcctcga gagtgcatac    1140
cctgaaggat cacaggtggg cagtgaggtt gggactgtgg aaggcagtac agctcttaaa    1200
gggttcaagg aatccaacag tacaaagaag aagtctaaga aaaggaagct tacgtctgtc    1260
aaaagggcac gagtgtctgg tgatgatttt tcagtgccca gtaagaactc tgagagcaca    1320
ctctttgatt cagtagaagg tgatggcgcc atgatggaag aaggtgtgaa atctaggccc    1380
cgacaaaaga aaacccaggc ctgtttggca agcaagcacg tgcaagaggc gccaaggtta    1440
gaacctgcaa atgaagaaca caatgtggaa acagctgaag attccgaaat aagatactta    1500
tctgcagatt caggagatgc cgatgattca gatgcggatt tgggttctgc cgtgaaacag    1560
cttcaggagt tcattcctaa catcaaggac agggccacca gcacaatcaa gcggatgtac    1620
cgggacgact tggaacggtt taaggaattt aaagcacaag gtgtcgctat taaatttggc    1680
aagttttctg taaaggaaaa taagcagtta gagaaaaatg tggaagactt tctagccctg    1740
acaggcattg agagtgcaga aagctgctg tacacggaca gatatcctga ggaaaaatct    1800
gtgatcacca acttaaaaag gagatactcg tttagattac acattggtag gaacattgcc    1860
cggccctgga aacttatata ctatcgagca aagaagatgt tcgatgtcaa caattacaaa    1920
ggcaggtata gcgaaggaga tactgagaag ttaaagatgt accattctct ccttgggaat    1980
gactggaaga cgattggtga gatggtggcc cgaagtagcc tctccgtggc cctcaagttc    2040
tcacagatca gcagtcaaag aaatcgtggt gcttggagta agtctgaaac ccggaaacta    2100
atcaaggctg tcgaagaagt gattctgaag aagatgtctc cccaggagtt aaaagaggtg    2160
gattccaaac tccaagaaaa tcctgaaagt tgcctatcaa ttgttcggga aaaactctac    2220
aagggcatat cttgggtaga agtagaagct aaagtgcaaa ccagaaattg gatgcagtgt    2280
aaaagtaagt ggacagaaat tctaaccaag aggatgacta atggtcggcg tatctactat    2340
ggcatgaatg ccctgcgggc caaggtcagc cttattgaaa ggttgtatga aataaatgtg    2400
gaagatacta atgaaataga ctgggaagat cttgctagtg ccataggtga tgttcctcca    2460
tcttacgttc aaactaaatt ttctaggctg aaagctgtct atgttccatt ttggcagaaa    2520
aagacttttc cagagatcat cgactacctt tatgagacga ctctaccttt gctgaaggaa    2580
aagttagaaa aaatgatgga gaaaaaggc actaaaatcc agactcctgc agcacccaag    2640
caagttttcc catttcgaga catcttttat tatgaagacg atagtgaagg agaggacata    2700
gaaaagaaa gcgaaggcca ggcgccatgc atggctcacg cctgtaattc cagtactttg    2760
ggaggccaag gccggtggat catctgaggt caggagttcg agaccggcct gaccaacatg    2820
gtgaagacct gtcactatta aaaatgcaaa aattagccgg gtgtggtagt gcacacctgt    2880
aatttcaact acttgggagg ctgaggcagg agaattgctt gaacccagga ggtggaggtt    2940
gcagtgagcc aagatcgcac caccgcatga gagagagaga ttactatttc ttgtcccttt    3000
ttctcagttt gattatattt atatacatat gtcagtaaat ctgttttcag tattgatgtt    3060
taataaagaa tgtacaatgg ccagagttct actctttcct ctggagcatt aaaatatatt    3120
```

| | |
|---|---:|
| gccattccta ttaaaacgta tttgaatgtg aaaa | 3154 |

<210> SEQ ID NO 35
<211> LENGTH: 2362
<212> TYPE: DNA
<213> ORGANISM: Homo sapiens

<400> SEQUENCE: 35

| | |
|---|---:|
| acctgattcc gttcctcagc tcgcattcct ccgcccgtcc cgctcccgcc gccagcggag | 60 |
| gccctagtct cccgctccaa ctattccaac catcccggga agggtggggc gctcggctct | 120 |
| tgggtccccc tccgccgccc cgcctcgtcg atctcccctt ctaccccggt ccctcccttt | 180 |
| ctggggtggg gccagccaat cagcgatcag actccggagt ttggcccggg agctggggag | 240 |
| ctcaccgatc ccccgcccag cagttctggc cgctgtcccg gtgcgcacgg acgtggctcg | 300 |
| agtttcctct gctctccgct ctcgcccgct agctctcctc ccttccgctc ctgcttctct | 360 |
| ccgggtctcc cgctccagct ccagcccac ccggccggtc ccgcacggct ccgggtagcc | 420 |
| atggaggacc ccacgctcta tattgtcgag cggccgcttc ccgggtaccc cgacgccgag | 480 |
| gccccggagc cttcctccgc tggggctcag gcagcggagg agccgtcggg ggccggctca | 540 |
| gaagagctga tcaagtcgga ccaggtgaac ggcgtgctgg tgctgagcct cctggacaaa | 600 |
| atcatcgggg ccgtagacca gatccagctg actcaagcac agctggagga gcggcaggcg | 660 |
| gagatggagg gcgcagtgca gagcatccag ggcgagctga gcaagctggg caaggcgcac | 720 |
| gccaccacga gcaatacggt gagcaagctg ctggagaagg tgcgcaaggt cagcgtcaac | 780 |
| gtgaagaccg tgcgcggcag cctggagcgc caggcggggc agatcaagaa gctggaggtc | 840 |
| aacgaggccg agctgctgcg gcgccgcaac tttaaagtca tgatctacca ggatgaagtg | 900 |
| aagctgccgc ccaaactgag catcagcaaa tcgctgaaag agtcggaggc gctgccagag | 960 |
| aaggagggcg aggagctggg cgagggcgag cggcccgagg aggacgcagc ggcgctggag | 1020 |
| ctttcgtcgg acgaagcggt ggaggttgag gaggttattg aggagtcccg cgcaaagcgt | 1080 |
| atcaagcgca gcggcctgcg gcgcgtggac gacttcaaga aggccttctc caaggagaag | 1140 |
| atggagaaga ccaaggtgcg tacccgcgag aacctggaga agacgcgcct caagaccaag | 1200 |
| gaaaacctgg agaagacgcg gcacaccctg gagaagcgca tgaacaagct gggcacgcgc | 1260 |
| ctggtgcccg ccgagcggcg cgagaaactg aagacgtcgc gggacaagtt gcgcaaatcc | 1320 |
| ttcacgcccg accacgtggt gtacgcgcgc tccaagaccg cggtctacaa ggtgccaccc | 1380 |
| ttcaccttcc acgtcaagaa gatccgcgag ggccaggtgg aagtgctcaa ggccaccgag | 1440 |
| atggtggagg tgggcgccga cgacgacgag ggcggcgcgg agcgcgggga ggccggcgac | 1500 |
| ctgcggcgcg ggagcagccc cgacgtgcac gcgctgctgg agatcaccga ggagtcggac | 1560 |
| gccgtgctgg tggacaagag cgacagcgac tgagccgccc ccgctgccac ccaccccatt | 1620 |
| cctcgctcct tccgaacttc ctcttttcgca ttctctctcg gctcgagctg gctgagattt | 1680 |
| ttctaaattg aaaacacgcc cccctcccca cacctcagg aactccactc ccagtcttag | 1740 |
| agctgttagg acccgatggg gaggcagccc ccgcagtgga cagccccgc ttggacacag | 1800 |
| tccgagtgga atgggaaggg aatggtcaat cctgtcctg gttgtccaag tcgggatctc | 1860 |
| agaggaaatt gcagtgattc cacggttagg ccccctggg ggggctgcct tccctcagc | 1920 |
| ctctccccac accacccacc cagctgctgt cattccgctc actgagctct tcttcattct | 1980 |
| caccctgatc cctgggggac tcaaagccaa aactgcccaa agaggaaaga ttgaatccta | 2040 |
| aagggggatcc ttgcccccat gggaggcccc ctactagaag gacgtgaaag cagcttttgg | 2100 |

```
gggaaactga ggcagtgggg aagacagagc agaatgagcc ctcaccctgg ctgggggtcc    2160
agcacaggct gtatctgcag agggtcccag aggaacgctg gagccaagag aagccctggg    2220
aaggaggggt ggggaacgac atgcatgtga gggatggcac actgatgtgt ttatgcacct    2280
gtacacagga gcgcatggcc atggctttgg aaaggagaat ggaaaaatag aagaaggtcg    2340
gccgggcttg gtggcttatg cc                                             2362

<210> SEQ ID NO 36
<211> LENGTH: 2328
<212> TYPE: DNA
<213> ORGANISM: Homo sapiens

<400> SEQUENCE: 36
gtggccgtgg ctaccgatgg gatagtcgcc gcggtcgcca tcttcccagc aacaacgtca      60
cttcccttcc ggaccacaag gggcgctgac tccgaactta ggacaggaag aaacaggcac     120
atttccggtc tctatgcttt ctcatccggc cggcttgctt tccctgcgg tcgtccagac      180 tattgggcgc tagcgagacg aactattggt acggggctag agaggaaggc tttgggattg     240
ccggggagca gcgagcgacc gacttccgtt tccagttacc aaggcacgag atccggtgt      300 tccaacccag ggggaaaaat gcggcctttg actgaagagg agaccgtgt catgtttgag      360 aagatagcga aatacattgg ggagaatctt caactgctgg tggaccggcc cgatggcacc     420
tactgtttcc gtctgcacaa cgaccgggtg tactatgtga gtgagaagat tatgaagctg     480
gccgccaata tttccgggga caagctggtg tcgctgggga cctgctttgg aaaattcact    540
aaaacccaca gtttcggtt gcacgtcaca gctctggatt accttgcacc ttatgccaag     600
tataaagttt ggataaagcc tggtgcagag cagtccttcc tgtatgggaa ccatgtgttg    660
aaatctggtc tgggtcgaat cactgaaaat acttctcagt accagggcgt ggtggtgtac    720
tccatggcag acatcccttt ggttttggg gtggcagcca atctacaca agactgcaga     780 aaagtagacc ccatggcgat gtggtatttt catcaagcag acattgggga atatgtgcgg    840
catgaagaga cgttgactta aaacgaagcc attccaagga cagacggctg tatgaaagg      900 ccgagctttg tttcctgtgt ttgtgtggac tccaccatca tgttgaattt tgtcaacact     960
ctggcctctt cagggacttc ttatttactg tactctctat cactgacaaa tgcaggctgg   1020
attcttatta tatacagaga tggctcaaaa atggggtttc agatctttgt gacgaaatag    1080
aatactgttt catatttgaa tcagagggct tcttgttctg agaaataggt tcaaaatcat    1140
tggaaccagg aacaagaata gcttattgtt atctgtgata cactgttttt ctaaacacaa    1200 ggatttctt ttttattaat atgcaacata gacattgcca taacagaata ataaaccaca    1260
tgtgggtttt taaaaatgaa atttggctaa taggagcaat tcagctattt ttctatacag    1320
taattggtgt gtggtataga agaaaaacgg gttcaaaccc cacttctgcc acctaccagc    1380
tatatggcct tgaatgagtc attcagcttt aataaggttc attttcttct gttaaaaag    1440 acacaaaact tgaaaatcag ctttggccat ctacctgaga attagaaagt ctgattttg    1500 gaattagaaa tcatgattgt aggctgggca cagtggctcg cgcctgtaat cccagcactt    1560
tgggaggcca aggcggacgg atcacttgag gttaggagtt tgagaccagc ctggccaaca   1620
tggtgaaacc ccatctctac taaaaaaaaa aaaaaaatta ggtgtggtga cacatggctg    1680
tggtcctagt tacttgggag gctgaggcag gagaatggct tgaactgggg aagcagagct    1740
tgcagtgagc caagatggtg ccattgcact ccagcctggg cgtgacagag tgagactcca    1800
```

```
tctgattgta aagcatctag tacagtgtac agtgccttgg aaatgatagg tatgaataa    1860 atggtaatta ttttatatt atatatatta tgtattcctg ttattaagtg tagagttta     1920 tgagtataat ttgattttat taccttcttt tttacaagct gttttctcag tattttcctt  1980
ggatgggatg acgctaggct ggaaagtttt tttcatcact atgattttat aaaacaattt  2040
tttctatgaa cctttactta cttgactgga ttggactaaa agcactgatc agaggccacg  2100
acataaaaat tcagtccctt tgtccttccc cgtgcctccc aaagttactt taagatcctt  2160
agaatatttc tttaaatatt ttatagacaa aaaatttaaa gactatctgt attgcaaaat  2220 taaactatt  cttaatgaa  tatattgctt  attttaagtt  ccaaaggtga agtctttaag  2280
aataaaacat taccaactcc tgcttttata tgtaagcaaa aaaaaaaa               2328

<210> SEQ ID NO 37
<211> LENGTH: 13357
<212> TYPE: DNA
<213> ORGANISM: Homo sapiens

<400> SEQUENCE: 37
gctgacacgc tgtcctctgg cgacctgtcg ctggagaggt tgggcctccg gatgcgcgcg    60
gggctctggc ctaccggtga cccggctagc cggccgcgct cctgcttgag ccgcctgccg   120
gggcccgcgg gcctgctgtt ctctcgcgcg tccgagcgtc ccgactcccg gtgccggccc   180
gggtccgggt ctctgaccca cccggggcg gcggggaagg cggcgagggc caccgtgccc    240
ccgtgcgctc tccgctgcgg gcgcccgggg cggccgcgac aaccccaccc cgctggctcc   300
gtgccgtgcg tgtcaggcgt tctcgtctcc gcggggttgt ccgccgcccc ttccccggag   360 tgggggggttg gccggagccg atcggctcgc tggccggccg gccggcctcc gctcccgggg  420
ggctcttcgt gatcgatgtg gtgacgtcgt gctctcccgg gccgggtccg agccgcgacg   480
ggcgaggggc ggacgttcgt ggcgaacggg accgtccttc tcgctccgcc ccgcggggt    540 cccctcgtct ctcctctccc cgcccgccgg cggtgcgtgt gggaaggcgt gggggtgcgga 600 ccccggcccg acctcgccgt cccgcccgcc gccttctgcg tcgcggggcg ggccggcggg  660
gtcctctgac gcggcagaca gccctcgctg tcgcctccag tggttgtcga cttgcgggcg  720 gccccctcc gcggcggtgg gggtgccgtc ccgccggccc gtcgtgctgc cctctcgggg   780
ggtttgcgcg agcgtcggct ccgcctgggc ccttgcggtg ctcctggagc gctccgggtt  840
gtccctcagg tgcccgaggc cgaacggtgg tgtgtcgttc ccgccccggg cgccccctcc  900
tccggtcgcc gccgcggtgt ccgcgcgtgg gtcctgaggg agctcgtcgg tgtgggttc   960 gaggcggttt gagtgagacg agacgagacg cgcccctccc acgcggggaa gggcgcccgc   1020
ctgctctcgg tgagcgcacg tcccgtgctc ccctctggcg ggtgcgcgcg ggccgtgtga  1080
gcgatcgcgg tgggttcggg ccggtgtgac gcgtgcgccg gccggccgcc gaggggctgc  1140
cgttctgcct ccgaccggtc gtgtgtgggt tgacttcgga ggcgtctgc ctcggaagga   1200 aggaggtggg tggacggggg ggcctggtgg ggttgcgcgc acgcgcgcac cggccgggcc   1260
cccgccctga acgcgaacgc tcgaggtggc cgcgcgcagg tgtttcctcg taccgcaggg   1320 cccctccct tccccaggcg tcctcggcg cctctgcggg cccgaggagg agcggctggc    1380
gggtgggggg agtgtgaccc accctcggtg agaaaagcct tctctagcga tctgagaggc  1440
gtgccttggg ggtaccggat cccccgggcc gccgcctctg tctctgcctc cgttatggta  1500
gcgctgccgt agcgacccgc tcgcagagga ccctcctccg cttccccctc gacgggttg   1560 ggggggagaa gcgagggttc cgccggccac cgcggtggtg gccgagtgcg gctcgtcgcc  1620
```

-continued

```
tactgtggcc cgcgcctccc ccttccgagt cggggggagga tcccgccggg ccgggcccgg    1680
cgttcccagc gggttgggac gcggcggccg cgggcggtg gtgtgcgcg cccggcgctc      1740
tgtccggcgc gtgaccccct ccgccgcgag tcggctctcc gcccgctccc gtgccgagtc    1800
gtgaccggtg ccgacgaccg cgtttgcgtg gcacggggtc gggcccgcct ggccctggga    1860
aagcgtccca cggtgggggc gcgccggtct cccggagcgg gaccgggtcg gaggatggac    1920
gagaatcacg agcgacggtg gtgcgggcgt gtcgggttcg tggctgcggt cgctccgggg    1980
cccccggtgg cggggccccg gggctcgcga ggcggttctc ggtgggggcc gagggccgtc    2040
cggcgtccca ggcggggcgc gcgcgggaccg ccctcgtgtc tgtggcggtg ggatcccgcg   2100
gccgtgtttt cctggtggcc cggccgtgcc tgaggtttct ccccgagccg ccgcctctgc    2160
gggctccccgg gtgcccttgc cctcgcggtc cccggccctc gcccgtctgt gccctcttcc   2220
ccgcccgccg cccgccgatc ctcttcttcc ccccgagcgg ctcaccggct tcacgtccgt    2280
tggtggcccc gcctgggacc gaacccggca ccgcctcgtg gggcgccgcc gcggccact    2340
gatcggcccg gcgtccgcgt ccccggcgc gcgccttggg gaccgggtcg gtggcgcccc    2400
gcgtgggcc cggtgggctt cccggagggt tccggggtc ggcctgccgg cgtgcgggg     2460
gaggagacgg ttccggggga ccggccgcga ctgcggcggc ggtggtgggg gcagccgcgg    2520
ggatcgccga gggccggtcg gccgccccgg gtgccgcgcg gtgccgccgg cggcggtgag    2580
gccccgcgcg tgtgtcccgg ccgcggtcgg ccgcgctcga ggggtccccg tggcgtcccc    2640
ttccccgccg gccgccttc tcgcgccttc cccgtcgccc cggcctcgcc cgtggtctct    2700
cgtcttctcc cggcccgctc ttccgaaccg ggtcggcgcg tcccccgggt gcgcctcgct    2760
tcccgggcct gccgcggccc ttccccgagg cgtccgtccc gggcgtcggc gtcggggaga   2820
gcccgtcctc cccgcgtggc gtcgccccgt tcggcgcgcg cgtgcgcccg agcgcggccc    2880
ggtggtccct gccggacagg cgttcgtgcg acgtgtggcg tgggtcgacc tccgccttgc    2940
cggtcgctcg ccctttcccc gggtcggggg gtggggcccg gccgggggcc tcggcccggg    3000
tcgcggtccc ccgtcccggg cggggggcggg cgcgccggcc ggcctcggtc ggccctccct    3060
tggccgtcgt gtggcgtgtg ccaccccttgc gcccgcgccc gcggcgggg ctcggagccg    3120
ggcttcggcc gggccccggg ccctcgaccg gaccggtgcg cgggcgctgc ggccgcacgg    3180
cgcgactgtc cccgggccgg gcaccgcggt ccgcctctcg ctcgccgccc ggacgtcggg    3240
gccgccccgc ggggcgggcg gagcgccgtc cccgcctcgc cgccgccgc gggcgccggc     3300
cgcgcgcgcg cgcgcgtggc cgccggtccc tcccggccgc cgggcgcggg tcgggccgtc   3360
cgcctcctcg cgggcgggcg cgacgaagaa gcgtcgcggg tctgtggcgc ggggccccgg    3420
tggtcgtgtc gcgtggggg cggtggttg gggcgtccgg ttcgccgcgc cccgccccgg     3480
ccccaccggt cccggccgcc gccccgcgc ccgctcgctc cctcccgtcc gcccgtccgc    3540
ggcccgtccg tccgtccgtc gtcctcctcg cttgcgggc gccgggcccg tcctcgcgag    3600
gcccccggc cggccgtccg gccgcgtcgg ggcctcgccg cgctctacct tacctacctg    3660
gttgatcctg ccagtagcat atgcttgtct caaagattaa gccatgcatg tctgagtacg    3720
cacggccggt acagtgaaac tgcgaatggc tcattaaatc agttatggtt cctttggtcg    3780
ctcgctcctc tcctacttgg ataactgtgg taattctaga gctaatacat gccgacgggc    3840
gctgacccc ttcgcggggg ggatgcgtgc atttatcaga tcaaaccaa cccggtcagc     3900
ccctctccgg ccccggccgg ggggcgggcg ccggcggctt tggtgactct agataaccct    3960
```

```
gggccgatcg cacgccccccc gtggcggcga cgacccattc gaacgtctgc cctatcaact    4020
ttcgatggta gtcgccgtgc ctaccatggt gaccacgggt gacggggaat cagggttcga    4080
ttccggagag ggagcctgag aaacggctac cacatccaag gaaggcagca ggcgcgcaaa    4140
ttacccactc ccgacccggg gaggtagtga cgaaaaataa caatacagga ctctttcgag    4200
gccctgtaat tggaatgagt ccactttaaa tcctttaacg aggatccatt ggagggcaag    4260
tctggtgcca gcagccgcgg taattccagc tccaatagcg tatattaaag ttgctgcagt    4320
taaaaagctc gtagttggat cttgggagcg ggcgggcggt ccgccgcgag gcgagccacc    4380
gcccgtcccc gccccttgcc tctcggcgcc ccctcgatgc tcttagctga gtgtcccgcg    4440
gggcccgaag cgtttacttt gaaaaaatta gagtgttcaa agcaggcccg agccgcctgg    4500
ataccgcagc taggaataat ggaataggac cgcggttcta ttttgttggt tttcggaact    4560
gaggccatga ttaagaggga cggccggggg cattcgtatt gcgccgctag aggtgaaatt    4620
cttggaccgg cgcaagacgg accagagcga aagcatttgc caagaatgtt ttcattaatc    4680
aagaacgaaa gtcggaggtt cgaagacgat cagataccgt cgtagttccg accataaacg    4740
atgccgaccg gcgatgcggc ggcgttattc ccatgacccg ccgggcagct tccgggaaac    4800
caaagtcttt gggttccggg gggagtatgg ttgcaaagct gaaacttaaa ggaattgacg    4860
gaagggcacc accaggagtg gagcctgcgg cttaatttga ctcaacacgg gaaacctcac    4920
ccggcccgga cacggacagg attgacagat tgatagctct ttctcgattc cgtgggtggt    4980
ggtgcatggc cgttcttagt tggtggagcg atttgtctgg ttaattccga taacgaacga    5040
gactctggca tgctaactag ttacgcgacc cccgagcggt cggcgtcccc caacttctta    5100
gagggacaag tggcgttcag ccacccgaga ttgagcaata acaggtctgt gatgcccta    5160
gatgtccggg gctgcacgcg cgctacactg actggctcag cgtgtgccta ccctacgccg    5220
gcaggcgcgg gtaacccgtt gaaccccatt cgtgatgggg atcggggatt gcaattattc    5280
cccatgaacg aggaattccc agtaagtgcg ggtcataagc ttgcgttgat taagtccctg    5340
ccctttgtac acaccgcccg tcgctactac cgattggatg gtttagtgag gccctcggat    5400
cggccccgcc ggggtcggcc cacggccctg gcggagcgct gagaagacgg tcgaacttga    5460
ctatctagag gaagtaaaag tcgtaacaag gtttccgtag gtgaacctgc ggaaggatca    5520
ttaacggagc ccggagggcg aggcccgcgc cggcgccgcc gccgccgcgc gcttccctcc    5580
gcacacccac cccccaccg cgacgcggcg cgtgcgcggg cggggcccgc gtgcccgttc    5640
gttcgctcgc tcgttcgttc gccgcccggc ccgccggcc gcgagagccg gagaactcgg    5700
gagggagacg ggggagagag agagagagag agaaagagaa agaagggcgt gtcgttggtg    5760
tgcgcgtgtc gtggggccgg cgggcggcgg ggagcggtcc ccggccgcgg ccccgacgac    5820
gtgggtgtcg gcgggcgcgg gggcggttct cggcggcgtc gcggcgggtc tgggggggtc    5880
tcggtgccct cctccccgcc ggggcccgtc gtccggcccc gccgcgcgg ctccccgtct    5940
tcggggccgg ccggattccc gtcgcctccg ccgcgccgct ccgcgccgcc gggcacggcc    6000
ccgctcgctc tccccggcct tccgctagg gcgtctcgag ggtcggggc cggacgccgg    6060
tccccctcccc cgcctcctcg tccgcccccc cgccgtccag gtacctagcg cgttccggcg    6120
cggaggttta agaccccctt ggggggatcg cccgtccgcc cgtgggtcgg gggcggtggt    6180
gggcccgcgc gggagtcccg tcgggagggg cccggcccct cccgcgcctc caccgcggac    6240
tccgctcccc ggccggggcc gcgccgccgc cgccgccgcg gcggccgtcg ggtgggggct    6300
ttacccggcg gccgtcgcgc gcctgccgcg cgtgtggcgt gcgcccgcg ccgtgggggc    6360
```

```
gggaaccccc gggcgcctgt ggggtggtgt ccgcgctcgc ccccgcgtgg cggcgcgcg    6420
cctccccgtg gtgtgaaacc ttccgacccc tctccggagt ccggtcccgt ttgctgtctc   6480
gtctggccgg cctgaggcaa cccctctcc tcttgggcgg ggggggggg gacgtgccgc     6540
gccaggaagg gcctcctccc ggtgcgtcgt cgggagcgcc ctcgccaaat cgacctcgta   6600
cgactcttag cggtggatca ctcggctcgt gcgtcgatga agaacgcagc tagctgcgag   6660
aattaatgtg aattgcagga cacattgatc atcgacactt cgaacgcact tgcggccccg   6720
ggttcctccc ggggctacgc ctgtctgagc gtcgcttgcc gatcaatcgc ccccggggt    6780
gcctccgggc tcctcggggt gcgcggctgg ggttccctc gcagggcccg ccgggggccc    6840
tccgtccccc taagcgcaga cccggcggcg tccgccctcc tcttgccgcc gcgcccgccc   6900
cttccccctc ccccgcggg ccctgcgtgg tcacgcgtcg ggtggcgggg gggagagggg    6960
ggcgcgcccg gctgagagag acggggaggg cggcgccgcc gccgcccgcg aagacggaga   7020
gggaaagaga gagccggctc gggccgagtt cccgtggccg ccgcctgcgg tccgggttcc   7080
tccctcgggg ggctccctcg cgccgcgcgc ggctcggggt tcggggttcg tcggccccgg   7140
ccgggtggaa ggtcccgtgc ccgtcgtcgt cgtcgtcgtc gcgcgtcgtc ggcggtgggg   7200
gcgtgttgcg tgcggtgtgg tggtgggga ggaggaaggc gggtccggaa ggggaagggt    7260
gccggcgggg agagagggtc gggggagcgc gtcccggtcg ccgcggttcg ccgcccgccc   7320
ccggtggcgg cccggcgtcc ggccgaccgc cgctcccgcg cccctcctcc tccccgccgc   7380
ccctcctccg aggccccgcc cgtcctcctc gccctccccg cgcgtacgcg cgcccgcccg   7440
cccggctcgc ctcgcggcgc gtcggccggg gcgggagcc cgccccgcgg cccgcccggc    7500
cgcgcccgtg gccgcggcgc cggggttcgc gtgtccccgg cggcgacccg cgggacgccg   7560
cggtgtcgtc cgccgtcgcg cgcccgcctc cggctcgcgg ccgcgccgcg ccgcgccggg   7620
gccccgtccc gagcttccgc gtcggggcgg ggcggctccg ccgccgcgtc ctcggacccg   7680
tcccccgac ctccgcgggg gagacgggtc ggggcgtgcg gcgcccgtcc cgcccccggc    7740
ccgtgccccct ccctccggtc gtcccgctcc ggcggggcgg cgcggggtg ccgccggccg    7800
cgcgctctct ctcccgtcgc ctctccccct cgccgggccc gtctcccgac ggagcgtcgg   7860
gcgggcggtc gggccggcgc gattccgtcc gtccgtccgc cgagcggccc gtccccctcc   7920
gagacgcgac ctcagatcag acgtggcgac ccgctgaatt taagcatatt agtcagcgga   7980
ggagaagaaa ctaaccagga ttccctcagt aacggcgagt gaacagggaa gagcccagcg   8040
ccgaatcccc gccccgcggc ggggcgcggg acatgtggcg tacggaagac ccgctccccg   8100
gcgccgctcg tgggggccc aagtccttct gatcgaggcc cagcccgtgg acggtgtgag    8160
gccggtagcg gccccggcg cgccgggccc gggtcttccc ggagtcgggt tgcttgggaa    8220
tgcagcccaa agcgggtggt aaactccatc taaggctaaa taccggcacg agaccgatag   8280
tcaacaagta ccgtaaggga agttgaaaa gaactttgaa gagagagttc aagagggcgt    8340
gaaaccgtta agaggtaaac gggtggggtc cgcgcagtcc gcccggagga ttcaacccgg   8400
cggcgggtcc ggccgtgtcg gcggcccggc ggatctttcc cgcccccgt tcctcccgac    8460
ccctccaccc gccctccctt ccccgccgc cctcctcct cctccccgga ggggcgggc      8520
tccggcgggt gcggggtgg gcggcgggg ccggggtgg ggtcggcggg ggaccgtccc      8580
ccgaccggcg accggccgcc gccgggcgca tttccaccgc ggcggtgcgc cgcgaccggc   8640
tccgggacgg ctgggaaggc ccggcgggga aggtggctcg gggggcccg tccgtccgtc    8700
```

-continued

```
cgtccgtcct cctcctcccc cgtctccgcc ccccggcccc gcgtcctccc tcgggagggc    8760
gcgcgggtcg gggcggcggc ggcggcggcg gtggcggcgg cggcggcggc ggcgggaccg    8820
aaaccccccc cgagtgttac agccccccg gcagcagcac tcgccgaatc ccggggccga    8880
gggagcgaga cccgtcgccg cgctctcccc cctcccggcg cccacccccg cggggaatcc    8940
cccgcgaggg gggtctcccc cgcggggcg cgccggcgtc tcctcgtggg ggggccgggc    9000
cacccctccc acggcgcgac cgctctccca ccctcctcc ccgcgccccc gccccggcga    9060
cgggggggt gccgcgcgcg ggtcggggg cggggcggac tgtccccagt gcgccccggg    9120
cgggtcgcgc cgtcgggccc gggggaggtt ctctcggggc cacgcgcgcg tcccccgaag    9180
aggggacgg cggagcgagc gcacgggtc ggcggcgacg tcggctaccc acccgacccg    9240
tcttgaaaca cggaccaagg agtctaacac gtgcgcgagt cggggctcg cacgaaagcc    9300
gccgtggcgc aatgaaggtg aaggccggcg cgctcgccgg ccgaggtggg atcccgaggc    9360
ctctccagtc cgccgagggc gcaccaccgg cccgtctcgc ccgccgcgcc ggggaggtgg    9420
agcacgagcg cacgtgttag gacccgaaag atggtgaact atgcctgggc agggcgaagc    9480
cagaggaaac tctggtggag gtccgtagcg gtcctgacgt gcaaatcggt cgtccgacct    9540
gggtataggg gcgaaagact aatcgaacca tctagtagct ggttccctcc gaagtttccc    9600
tcaggatagc tggcgctctc gcagacccga cgcacccccg ccacgcagtt ttatccggta    9660
aagcgaatga ttagaggtct tggggccgaa acgatctcaa cctattctca aactttaaat    9720
gggtaagaag cccggctcgc tggcgtggag ccgggcgtgg aatgcgagtg cctagtgggc    9780
cactttggt aagcagaact ggcgctgcgg gatgaaccga acgccgggtt aaggcgcccg    9840
atgccgacgc tcatcagacc ccagaaaagg tgttggttga tatagacagc aggacggtgg    9900
ccatggaagt cggaatccgc taaggagtgt gtaacaactc acctgccgaa tcaactagcc    9960
ctgaaaatgg atggcgctgg agcgtcgggc ccatacccgg ccgtcgccgg cagtcgagag   10020
tggacgggag cggcggggc ggcgcgcgcg gcgcgcgtg tggtgtgcgt cggagggcgg   10080
cggcggcgc ggcggcgggg gtgtggggtc cttcccccgc ccccccccc acgcctcctc   10140
ccctcctccc gcccacgccc cgctccccgc ccccggagcc ccgcggacgc tacgccgcga   10200
cgagtaggag ggccgctgcg gtgagccttg aagcctaggg cgcgggcccg ggtggagccg   10260
ccgcaggtgc agatcttggt ggtagtagca aatattcaaa cgagaacttt gaaggccgaa   10320
gtggagaagg gttccatgtg aacagcagtt gaacatgggt cagtcggtcc tgagagatgg   10380
gcgagcgcc ttccgaaggg acgggcgatg gcctccgttg ccctcggccg atcgaaaggg   10440
agtcgggttc agatccccga atccggagtg gcggagatgg gcgccgcgag gcgtccagtg   10500
cggtaacgcg accgatcccg gagaagccgg cgggagcccc ggggagagtt ctcttttctt   10560
tgtgaagggc agggcgccct ggaatgggtt cgccccgaga gaggggcccg tgccttggaa   10620
agcgtcgcg ttccgcggc gtccggtgag ctctcgctgg cccttgaaaa tccggggag   10680
agggtgtaaa tctcgcgccg ggccgtaccc atatccgcag caggtctcca aggtgaacag   10740
cctctggcat gttggaacaa tgtaggtaag ggaagtcggc aagccggatc cgtaacttcg   10800
ggataaggat tggctctaag ggctgggtcg gtcgggctgg ggcgcgaagc ggggctgggc   10860
gcgcgccgcg gctggacgag gcgccgccgc ccccccacg cccggggcac ccccctcgcg   10920
gccctccccc gccccacccc gcgcgccgcg ctcgctccct ccccgccccg cgccctctct   10980
ctctctctct ccccgctcc ccgtcctccc ccctccccgg gggagcgccg cgtgggggcg   11040
gcggcggggg gagaagggtc ggggcggcag gggcggcgg cggccgccg cggggccccg   11100
```

```
gcggcggggg cacggtcccc cgcgaggggg gcccgggcac ccgggggggcc ggcggcggcg    11160
gcgactctgg acgcgagccg ggcccttccc gtggatcgcc ccagctgcgg cgggcgtcgc    11220
ggccgccccc ggggagcccg gcgggcgccg gcgcgccccc cccccacccc cacgtctcgt    11280
cgcgcgcgcg tccgctgggg gcggggagcg gtcgggcggc ggcggtcggc gggcggcggg    11340
gcggggcggt tcgtccccccc gccctacccc cccggccccg tccgccccccc gttccccccct   11400
cctcctcggc gcgcggcggc ggcggcggca ggcggcggag gggccgcggg ccggtccccc    11460
ccgccgggtc cgcccccggg gccgcggttc cgcgcggcgc ctcgcctcgg ccggcgccta    11520
gcagccgact tagaactggt gcggaccagg ggaatccgac tgtttaatta aacaaagca    11580
tcgcgaaggc ccgcggcggg tgttgacgcg atgtgatttc tgcccagtgc tctgaatgtc    11640
aaagtgaaga aattcaatga agcgcgggta acggcggga gtaactatga ctctcttaag    11700
gtagccaaat gcctcgtcat ctaattagtg acgcgcatga atggatgaac gagattccca    11760
ctgtccctac ctactatcca gcgaaaccac agccaaggga acgggcttgg cggaatcagc    11820
ggggaaagaa gaccctgttg agcttgactc tagtctggca cggtgaagag acatgagagg    11880
tgtagaataa gtgggaggcc cccggcgccc ccccggtgtc cccgcgaggg gcccggggcg    11940
gggtccgccg gccctgcggg ccgccggtga ataccacta ctctgatcgt tttttcactg    12000
acccggtgag gcgggggggc gagccccgag gggctctcgc ttctggcgcc aagcgcccgg    12060
ccgcgcgccg gccgggcgcg accgctccg gggacagtgc caggtgggga gtttgactgg    12120
ggcggtacac ctgtcaaacg gtaacgcagg tgtcctaagg cgagctcagg gaggacagaa    12180
acctcccgtg gagcagaagg gcaaaagctc gcttgatctt gattttcagt acgaatacag    12240
accgtgaaag cggggcctca cgatccttct gaccttttgg gttttaagca ggaggtgtca    12300
gaaaagttac cacagggata actggcttgt ggcggccaag cgttcatagc gacgtcgctt    12360
tttgatcctt cgatgtcggc tcttcctatc attgtgaagc agaattcacc aagcgttgga    12420
ttgttcaccc actaataggg aacgtgagct gggtttagac cgtcgtgaga caggttagtt    12480
ttaccctact gatgatgtgt tgttgccatg gtaatcctgc tcagtacgag aggaaccgca    12540
ggttcagaca tttggtgtat gtgcttggct gaggagccaa tggggcgaag ctaccatctg    12600
tgggattatg actgaacgcc tctaagtcag aatcccgccc aggcggaacg atacggcagc    12660
gccgcggagc ctcggttggc ctcggatagc cggtcccccg cctgtccccg ccggcgggcc    12720
gcccccccccc tccacgcgcc ccgcgcgcgc gggagggcgc gtgccccgcc gcgcgccggg    12780
accggggtcc ggtgcggagt gcccttcgtc ctgggaaacg gggcgcggcc ggagaggcgg    12840
ccgcccccctc gcccgtcacg caccgcacgt tcgtggggaa cctggcgcta aaccattcgt    12900
agacgacctg cttctgggtc ggggtttcgt acgtagcaga gcagctccct cgctgcgatc    12960
tattgaaagt cagccctcga cacaagggtt tgtccgcgcg cgcgcgcgcg cgcgcgtgcg    13020
gggggcccgg cggggcgtgc gcgtccgcg ccgtccgtcc ttccgttcgt cttcctcccct   13080
cccggcctct cccgccgacc gcgggcgtgg tggtgggggt gtgggggga gggcgcgcga    13140
ccccggtcgg cgcgcccgc ttcttcggtt cccgcctcct ccccgttcac cgccggggcg    13200
gctcgtccgc tccgggccgg gacggggtcc ggggagcgtg gtttgggagc gcggaggcg    13260
gccgcgccga gccgggcccg tggcccgccg gtccccgtcc cggggggttgg ccgcgcgggc    13320
cccggtgggg cggccacccg gggtcccggc cctcgcg                             13357

<210> SEQ ID NO 38
```

```
<211> LENGTH: 651
<212> TYPE: PRT
<213> ORGANISM: Homo sapiens

<400> SEQUENCE: 38
```

| | | | | | | | | | | | | | | | |
|---|---|---|---|---|---|---|---|---|---|---|---|---|---|---|---|
| Met | Ala | Ala | Pro | Leu | Leu | His | Thr | Arg | Leu | Pro | Gly | Asp | Ala | Ala | Ala |
| 1 | | | | 5 | | | | | 10 | | | | | 15 | |
| Ser | Ser | Ser | Ala | Val | Lys | Lys | Leu | Gly | Ala | Ser | Arg | Thr | Gly | Ile | Ser |
| | | | 20 | | | | | 25 | | | | | 30 | | |
| Asn | Met | Arg | Ala | Leu | Glu | Asn | Asp | Phe | Phe | Asn | Ser | Pro | Pro | Arg | Lys |
| | | 35 | | | | | 40 | | | | | 45 | | | |
| Thr | Val | Arg | Phe | Gly | Gly | Thr | Val | Thr | Glu | Val | Leu | Leu | Lys | Tyr | Lys |
| 50 | | | | | 55 | | | | | 60 | | | | | |
| Lys | Gly | Glu | Thr | Asn | Asp | Phe | Glu | Leu | Leu | Lys | Asn | Gln | Leu | Leu | Asp |
| 65 | | | | | 70 | | | | | 75 | | | | | 80 |
| Pro | Asp | Ile | Lys | Asp | Asp | Gln | Ile | Ile | Asn | Trp | Leu | Leu | Glu | Phe | Arg |
| | | | | 85 | | | | | 90 | | | | | 95 | |
| Ser | Ser | Ile | Met | Tyr | Leu | Thr | Lys | Asp | Phe | Glu | Gln | Leu | Ile | Ser | Ile |
| | | | 100 | | | | | 105 | | | | | 110 | | |
| Ile | Leu | Arg | Leu | Pro | Trp | Leu | Asn | Arg | Ser | Gln | Thr | Val | Val | Glu | Glu |
| | | 115 | | | | | 120 | | | | | 125 | | | |
| Tyr | Leu | Ala | Phe | Leu | Gly | Asn | Leu | Val | Ser | Ala | Gln | Thr | Val | Phe | Leu |
| 130 | | | | | 135 | | | | | 140 | | | | | |
| Arg | Pro | Cys | Leu | Ser | Met | Ile | Ala | Ser | His | Phe | Val | Pro | Pro | Arg | Val |
| 145 | | | | | 150 | | | | | 155 | | | | | 160 |
| Ile | Ile | Lys | Glu | Gly | Asp | Val | Asp | Val | Ser | Asp | Ser | Asp | Asp | Glu | Asp |
| | | | | 165 | | | | | 170 | | | | | 175 | |
| Asp | Asn | Leu | Pro | Ala | Asn | Phe | Asp | Thr | Cys | His | Arg | Ala | Leu | Gln | Ile |
| | | | 180 | | | | | 185 | | | | | 190 | | |
| Ile | Ala | Arg | Tyr | Val | Pro | Ser | Thr | Pro | Trp | Phe | Leu | Met | Pro | Ile | Leu |
| | | 195 | | | | | 200 | | | | | 205 | | | |
| Val | Glu | Lys | Phe | Pro | Phe | Val | Arg | Lys | Ser | Arg | Thr | Leu | Glu | Cys |
| 210 | | | | | 215 | | | | | 220 | | | | | |
| Tyr | Val | His | Asn | Leu | Leu | Arg | Ile | Ser | Val | Tyr | Phe | Pro | Thr | Leu | Arg |
| 225 | | | | | 230 | | | | | 235 | | | | | 240 |
| His | Glu | Ile | Leu | Glu | Leu | Ile | Ile | Glu | Lys | Leu | Leu | Lys | Leu | Asp | Val |
| | | | | 245 | | | | | 250 | | | | | 255 | |
| Asn | Ala | Ser | Arg | Gln | Gly | Ile | Glu | Asp | Ala | Glu | Gly | Thr | Ala | Thr | Gln |
| | | | 260 | | | | | 265 | | | | | 270 | | |
| Thr | Cys | Gly | Gly | Thr | Asp | Ser | Thr | Glu | Gly | Leu | Phe | Asn | Met | Asp | Glu |
| | | 275 | | | | | 280 | | | | | 285 | | | |
| Asp | Glu | Glu | Thr | Glu | His | Glu | Thr | Lys | Ala | Gly | Pro | Glu | Arg | Leu | Asp |
| 290 | | | | | 295 | | | | | 300 | | | | | |
| Gln | Met | Val | His | Pro | Val | Ala | Glu | Arg | Leu | Asp | Ile | Leu | Met | Ser | Leu |
| 305 | | | | | 310 | | | | | 315 | | | | | 320 |
| Val | Leu | Ser | Tyr | Met | Lys | Asp | Val | Cys | Tyr | Val | Asp | Gly | Lys | Val | Asp |
| | | | | 325 | | | | | 330 | | | | | 335 | |
| Asn | Gly | Lys | Thr | Lys | Asp | Leu | Tyr | Arg | Asp | Leu | Ile | Asn | Ile | Phe | Asp |
| | | | 340 | | | | | 345 | | | | | 350 | | |
| Lys | Leu | Leu | Pro | Thr | His | Ala | Ser | Cys | His | Val | Gln | Phe | Phe | Met |
| | | 355 | | | | | 360 | | | | | 365 | | | |
| Phe | Tyr | Leu | Cys | Ser | Phe | Lys | Leu | Gly | Phe | Ala | Glu | Ala | Phe | Leu | Glu |
| 370 | | | | | 375 | | | | | 380 | | | | | |
| His | Leu | Trp | Lys | Lys | Leu | Gln | Asp | Pro | Ser | Asn | Pro | Ala | Ile | Ile | Arg |

-continued

```
                385                 390                 395                 400
        Gln Ala Ala Gly Asn Tyr Ile Gly Ser Phe Leu Ala Arg Ala Lys Phe
                        405                 410                 415
        Ile Pro Leu Ile Thr Val Lys Ser Cys Leu Asp Leu Val Asn Trp
                    420                 425                 430
        Leu His Ile Tyr Leu Asn Asn Gln Asp Ser Gly Thr Lys Ala Phe Cys
                        435                 440                 445
        Asp Val Ala Leu His Gly Pro Phe Tyr Ser Ala Cys Gln Ala Val Phe
                    450                 455                 460
        Tyr Thr Phe Val Phe Arg His Lys Gln Leu Leu Ser Gly Asn Leu Lys
        465                 470                 475                 480
        Glu Gly Leu Gln Tyr Leu Gln Ser Leu Asn Phe Glu Arg Ile Val Met
                            485                 490                 495
        Ser Gln Leu Asn Pro Leu Lys Ile Cys Leu Pro Ser Val Val Asn Phe
                        500                 505                 510
        Phe Ala Ala Ile Thr Asn Lys Tyr Gln Leu Val Phe Cys Tyr Thr Ile
                    515                 520                 525
        Ile Glu Arg Asn Asn Arg Gln Met Leu Pro Val Ile Arg Ser Thr Ala
                530                 535                 540
        Gly Gly Asp Ser Val Gln Ile Cys Thr Asn Pro Leu Asp Thr Phe Phe
        545                 550                 555                 560
        Pro Phe Asp Pro Cys Val Leu Lys Arg Ser Lys Lys Phe Ile Asp Pro
                            565                 570                 575
        Ile Tyr Gln Val Trp Glu Asp Met Ser Ala Glu Glu Leu Gln Glu Phe
                        580                 585                 590
        Lys Lys Pro Met Lys Lys Asp Ile Val Glu Asp Glu Asp Asp Asp Phe
                    595                 600                 605
        Leu Lys Gly Glu Val Pro Gln Asn Asp Thr Val Ile Gly Ile Thr Pro
                    610                 615                 620
        Ser Ser Phe Asp Thr His Phe Arg Ser Pro Ser Ser Ser Val Gly Ser
        625                 630                 635                 640
        Pro Pro Val Leu Tyr Met Gln Pro Ser Pro Leu
                            645                 650

<210> SEQ ID NO 39
<211> LENGTH: 1394
<212> TYPE: PRT
<213> ORGANISM: Homo sapiens

<400> SEQUENCE: 39

Met Ala Ala Leu Leu Arg Ser Arg Trp Leu Leu Arg Ala Gly Ala
        1               5                   10                  15
        Ala Pro Arg Leu Pro Leu Ser Leu Arg Leu Pro Gly Gly Pro Gly
                    20                  25                  30
        Arg Leu His Ala Ala Ser Tyr Leu Pro Ala Ala Arg Ala Gly Pro Val
                        35                  40                  45
        Ala Gly Gly Leu Leu Ser Pro Ala Arg Leu Tyr Ala Ile Ala Ala Lys
                    50                  55                  60
        Glu Lys Asp Ile Gln Glu Glu Ser Thr Phe Ser Ser Arg Lys Ile Ser
        65                  70                  75                  80
        Asn Gln Phe Asp Trp Ala Leu Met Arg Leu Asp Leu Ser Val Arg Arg
                            85                  90                  95
        Thr Gly Arg Ile Pro Lys Lys Leu Leu Gln Lys Val Phe Asn Asp Thr
                        100                 105                 110
```

```
Cys Arg Ser Gly Gly Leu Gly Ser His Ala Leu Leu Leu Arg
            115                 120                 125
Ser Cys Gly Ser Leu Leu Pro Glu Leu Lys Leu Glu Glu Arg Thr Glu
130                 135                 140
Phe Ala His Arg Ile Trp Asp Thr Leu Gln Lys Leu Gly Ala Val Tyr
145                 150                 155                 160
Asp Val Ser His Tyr Asn Ala Leu Leu Lys Val Tyr Leu Gln Asn Glu
                165                 170                 175
Tyr Lys Phe Ser Pro Thr Asp Phe Leu Ala Lys Met Glu Glu Ala Asn
                180                 185                 190
Ile Gln Pro Asn Arg Val Thr Tyr Gln Arg Leu Ile Ala Ser Tyr Cys
            195                 200                 205
Asn Val Gly Asp Ile Glu Gly Ala Ser Lys Ile Leu Gly Phe Met Lys
210                 215                 220
Thr Lys Asp Leu Pro Val Thr Glu Ala Val Phe Ser Ala Leu Val Thr
225                 230                 235                 240
Gly His Ala Arg Ala Gly Asp Met Glu Asn Ala Glu Asn Ile Leu Thr
                245                 250                 255
Val Met Arg Asp Ala Gly Ile Glu Pro Gly Pro Asp Thr Tyr Leu Ala
            260                 265                 270
Leu Leu Asn Ala Tyr Ala Glu Lys Gly Asp Ile Asp His Val Lys Gln
            275                 280                 285
Thr Leu Glu Lys Val Glu Lys Ser Glu Leu His Leu Met Asp Arg Asp
            290                 295                 300
Leu Leu Gln Ile Ile Phe Ser Phe Ser Lys Ala Gly Tyr Pro Gln Tyr
305                 310                 315                 320
Val Ser Glu Ile Leu Glu Lys Val Thr Cys Glu Arg Arg Tyr Ile Pro
                325                 330                 335
Asp Ala Met Asn Leu Ile Leu Leu Val Thr Glu Lys Leu Glu Asp
                340                 345                 350
Val Ala Leu Gln Ile Leu Leu Ala Cys Pro Val Ser Lys Glu Asp Gly
            355                 360                 365
Pro Ser Val Phe Gly Ser Phe Phe Leu Gln His Cys Val Thr Met Asn
370                 375                 380
Thr Pro Val Glu Lys Leu Thr Asp Tyr Cys Lys Lys Leu Lys Glu Val
385                 390                 395                 400
Gln Met His Ser Phe Pro Leu Gln Phe Thr Leu His Cys Ala Leu Leu
                405                 410                 415
Ala Asn Lys Thr Asp Leu Ala Lys Ala Leu Met Lys Ala Val Lys Glu
            420                 425                 430
Glu Gly Phe Pro Ile Arg Pro His Tyr Phe Trp Pro Leu Leu Val Gly
            435                 440                 445
Arg Arg Lys Glu Lys Asn Val Gln Gly Ile Ile Glu Ile Leu Lys Gly
450                 455                 460
Met Gln Glu Leu Gly Val His Pro Asp Gln Glu Thr Tyr Thr Asp Tyr
465                 470                 475                 480
Val Ile Pro Cys Phe Asp Ser Val Asn Ser Arg Ala Ile Leu Gln
                485                 490                 495
Glu Asn Gly Cys Leu Ser Asp Ser Asp Met Phe Ser Gln Ala Gly Leu
                500                 505                 510
Arg Ser Glu Ala Ala Asn Gly Asn Leu Asp Phe Val Leu Ser Phe Leu
            515                 520                 525
Lys Ser Asn Thr Leu Pro Ile Ser Leu Gln Ser Ile Arg Ser Ser Leu
```

```
                530              535              540
Leu Leu Gly Phe Arg Arg Ser Met Asn Ile Asn Leu Trp Ser Glu Ile
545                  550                  555                  560

Thr Glu Leu Leu Tyr Lys Asp Gly Arg Tyr Cys Gln Glu Pro Arg Gly
                 565                  570                  575

Pro Thr Glu Ala Val Gly Tyr Phe Leu Tyr Asn Leu Ile Asp Ser Met
             580                  585                  590

Ser Asp Ser Glu Val Gln Ala Lys Glu His Leu Arg Gln Tyr Phe
         595                  600                  605

His Gln Leu Glu Lys Met Asn Val Lys Ile Pro Glu Asn Ile Tyr Arg
     610                  615                  620

Gly Ile Arg Asn Leu Leu Glu Ser Tyr His Val Pro Glu Leu Ile Lys
625                  630                  635                  640

Asp Ala His Leu Leu Val Glu Ser Lys Asn Leu Asp Phe Gln Lys Thr
                 645                  650                  655

Val Gln Leu Thr Ser Ser Glu Leu Glu Ser Thr Leu Glu Thr Leu Lys
             660                  665                  670

Ala Glu Asn Gln Pro Ile Arg Asp Val Leu Lys Gln Leu Ile Leu Val
         675                  680                  685

Leu Cys Ser Glu Glu Asn Met Gln Lys Ala Leu Glu Leu Lys Ala Lys
     690                  695                  700

Tyr Glu Ser Asp Met Val Thr Gly Gly Tyr Ala Ala Leu Ile Asn Leu
705                  710                  715                  720

Cys Cys Arg His Asp Lys Val Glu Asp Ala Leu Asn Leu Lys Glu Glu
                 725                  730                  735

Phe Asp Arg Leu Asp Ser Ser Ala Val Leu Asp Thr Gly Lys Tyr Val
             740                  745                  750

Gly Leu Val Arg Val Leu Ala Lys His Gly Lys Leu Gln Asp Ala Ile
         755                  760                  765

Asn Ile Leu Lys Glu Met Lys Glu Lys Asp Val Leu Ile Lys Asp Thr
     770                  775                  780

Thr Ala Leu Ser Phe Phe His Met Leu Asn Gly Ala Ala Leu Arg Gly
785                  790                  795                  800

Glu Ile Glu Thr Val Lys Gln Leu His Glu Ala Ile Val Thr Leu Gly
                 805                  810                  815

Leu Ala Glu Pro Ser Thr Asn Ile Ser Phe Pro Leu Val Thr Val His
             820                  825                  830

Leu Glu Lys Gly Asp Leu Ser Thr Ala Leu Glu Val Ala Ile Asp Cys
         835                  840                  845

Tyr Glu Lys Tyr Lys Val Leu Pro Arg Ile His Asp Val Leu Cys Lys
     850                  855                  860

Leu Val Glu Lys Gly Glu Thr Asp Leu Ile Gln Lys Ala Met Asp Phe
865                  870                  875                  880

Val Ser Gln Glu Gln Gly Glu Met Val Met Leu Tyr Asp Leu Phe Phe
                 885                  890                  895

Ala Phe Leu Gln Thr Gly Asn Tyr Lys Glu Ala Lys Lys Ile Ile Glu
             900                  905                  910

Thr Pro Gly Ile Arg Ala Arg Ser Ala Arg Leu Gln Trp Phe Cys Asp
         915                  920                  925

Arg Cys Val Ala Asn Asn Gln Val Glu Thr Leu Glu Lys Leu Val Glu
     930                  935                  940

Leu Thr Gln Lys Leu Phe Glu Cys Asp Arg Asp Gln Met Tyr Tyr Asn
945                  950                  955                  960
```

```
Leu Leu Lys Leu Tyr Lys Ile Asn Gly Asp Trp Gln Arg Ala Asp Ala
                965                 970                 975
Val Trp Asn Lys Ile Gln Glu Glu Asn Val Ile Pro Arg Glu Lys Thr
            980                 985                 990
Leu Arg Leu Leu Ala Glu Ile Leu Arg Glu Gly Asn Gln Glu Val Pro
        995                 1000                1005
Phe Asp Val Pro Glu Leu Trp Tyr Glu Asp Glu Lys His Ser Leu
    1010                1015                1020
Asn Ser Ser Ser Ala Ser Thr Thr Glu Pro Asp Phe Gln Lys Asp
    1025                1030                1035
Ile Leu Ile Ala Cys Arg Leu Asn Gln Lys Lys Gly Ala Tyr Asp
    1040                1045                1050
Ile Phe Leu Asn Ala Lys Glu Gln Asn Ile Val Phe Asn Ala Glu
    1055                1060                1065
Thr Tyr Ser Asn Leu Ile Lys Leu Leu Met Ser Glu Asp Tyr Phe
    1070                1075                1080
Thr Gln Ala Met Glu Val Lys Ala Phe Ala Glu Thr His Ile Lys
    1085                1090                1095
Gly Phe Thr Leu Asn Asp Ala Ala Asn Ser Arg Leu Ile Ile Thr
    1100                1105                1110
Gln Val Arg Arg Asp Tyr Leu Lys Glu Ala Val Thr Thr Leu Lys
    1115                1120                1125
Thr Val Leu Asp Gln Gln Gln Thr Pro Ser Arg Leu Ala Val Thr
    1130                1135                1140
Arg Val Ile Gln Ala Leu Ala Met Lys Gly Asp Val Glu Asn Ile
    1145                1150                1155
Glu Val Val Gln Lys Met Leu Asn Gly Leu Glu Asp Ser Ile Gly
    1160                1165                1170
Leu Ser Lys Met Val Phe Ile Asn Asn Ile Ala Leu Ala Gln Ile
    1175                1180                1185
Lys Asn Asn Asn Ile Asp Ala Ala Ile Glu Asn Ile Glu Asn Met
    1190                1195                1200
Leu Thr Ser Glu Asn Lys Val Ile Glu Pro Gln Tyr Phe Gly Leu
    1205                1210                1215
Ala Tyr Leu Phe Arg Lys Val Ile Glu Glu Gln Leu Glu Pro Ala
    1220                1225                1230
Val Glu Lys Ile Ser Ile Met Ala Glu Arg Leu Ala Asn Gln Phe
    1235                1240                1245
Ala Ile Tyr Lys Pro Val Thr Asp Phe Phe Leu Gln Leu Val Asp
    1250                1255                1260
Ala Gly Lys Val Asp Asp Ala Arg Ala Leu Leu Gln Arg Cys Gly
    1265                1270                1275
Ala Ile Ala Glu Gln Thr Pro Ile Leu Leu Leu Phe Leu Leu Arg
    1280                1285                1290
Asn Ser Arg Lys Gln Gly Lys Ala Ser Thr Val Lys Ser Val Leu
    1295                1300                1305
Glu Leu Ile Pro Glu Leu Asn Glu Lys Glu Glu Ala Tyr Asn Ser
    1310                1315                1320
Leu Met Lys Ser Tyr Val Ser Glu Lys Asp Val Thr Ser Ala Lys
    1325                1330                1335
Ala Leu Tyr Glu His Leu Thr Ala Lys Asn Thr Lys Leu Asp Asp
    1340                1345                1350
```

```
Leu Phe Leu Lys Arg Tyr Ala Ser Leu Leu Lys Tyr Ala Gly Glu
    1355                1360                1365

Pro Val Pro Phe Ile Glu Pro Pro Glu Ser Phe Glu Phe Tyr Ala
    1370                1375                1380

Gln Gln Leu Arg Lys Leu Arg Glu Asn Ser Ser
    1385                1390

<210> SEQ ID NO 40
<211> LENGTH: 1079
<212> TYPE: PRT
<213> ORGANISM: Homo sapiens

<400> SEQUENCE: 40

Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
            20                  25                  30

Ala Ala Leu Gln Glu Leu Thr Arg Ala His Val Glu Ser Phe Asn Tyr
        35                  40                  45

Ala Val His Glu Gly Leu Gly Leu Ala Val Gln Ala Asp Ile Asn Trp
    50                  55                  60

Ala Val Asn Gly Ile Ser Lys Gly Ile Ile Lys Gln Phe Leu Gly Tyr
65                  70                  75                  80

Val Pro Ile Met Val Lys Ser Lys Leu Cys Asn Leu Arg Asn Leu Pro
                85                  90                  95

Pro Gln Ala Leu Ile Glu His His Glu Glu Ala Glu Glu Met Gly Gly
            100                 105                 110

Tyr Phe Ile Ile Asn Gly Ile Glu Lys Val Ile Arg Met Leu Ile Met
        115                 120                 125

Pro Arg Arg Asn Phe Pro Ile Ala Met Ile Arg Pro Lys Trp Lys Thr
    130                 135                 140

Arg Gly Pro Gly Tyr Thr Gln Tyr Gly Val Ser Met His Cys Val Arg
145                 150                 155                 160

Glu Glu His Ser Ala Val Asn Met Asn Leu His Tyr Leu Glu Asn Gly
                165                 170                 175

Thr Val Met Leu Asn Phe Ile Tyr Arg Lys Glu Leu Phe Phe Leu Pro
            180                 185                 190

Leu Gly Phe Ala Leu Lys Ala Leu Val Ser Phe Ser Asp Tyr Gln Ile
        195                 200                 205

Phe Gln Glu Leu Ile Lys Gly Lys Glu Asp Asp Ser Phe Leu Arg Asn
    210                 215                 220

Ser Val Ser Gln Met Leu Arg Ile Val Met Glu Glu Gly Cys Ser Thr
225                 230                 235                 240

Gln Lys Gln Val Leu Asn Tyr Leu Gly Glu Cys Phe Arg Val Lys Leu
                245                 250                 255

Asn Val Pro Asp Trp Tyr Pro Asn Glu Gln Ala Ala Glu Phe Leu Phe
            260                 265                 270

Asn Gln Cys Ile Cys Ile His Leu Lys Ser Asn Thr Glu Lys Phe Tyr
        275                 280                 285

Met Leu Cys Leu Met Thr Arg Lys Leu Phe Ala Leu Ala Lys Gly Glu
    290                 295                 300

Cys Met Glu Asp Asn Pro Asp Ser Leu Val Asn Gln Glu Val Leu Thr
305                 310                 315                 320

Pro Gly Gln Leu Phe Leu Met Phe Leu Lys Glu Lys Leu Glu Gly Trp
                325                 330                 335
```

```
Leu Val Ser Ile Lys Ile Ala Phe Asp Lys Ala Gln Lys Thr Ser
                340                 345                 350

Val Ser Met Asn Thr Asp Asn Leu Met Arg Ile Phe Thr Met Gly Ile
            355                 360                 365

Asp Leu Thr Lys Pro Phe Glu Tyr Leu Phe Ala Thr Gly Asn Leu Arg
        370                 375                 380

Ser Lys Thr Gly Leu Gly Leu Leu Gln Asp Ser Gly Leu Cys Val Val
385                 390                 395                 400

Ala Asp Lys Leu Asn Phe Ile Arg Tyr Leu Ser His Phe Arg Cys Val
                405                 410                 415

His Arg Gly Ala Asp Phe Ala Lys Met Arg Thr Thr Thr Val Arg Arg
            420                 425                 430

Leu Leu Pro Glu Ser Trp Gly Phe Leu Cys Pro Val His Thr Pro Asp
        435                 440                 445

Gly Glu Pro Cys Gly Leu Met Asn His Leu Thr Ala Val Cys Glu Val
    450                 455                 460

Val Thr Gln Phe Val Tyr Thr Ala Ser Ile Pro Ala Leu Leu Cys Asn
465                 470                 475                 480

Leu Gly Val Thr Pro Ile Asp Gly Ala Pro His Arg Ser Tyr Ser Glu
                485                 490                 495

Cys Tyr Pro Val Leu Leu Asp Gly Val Met Val Gly Trp Val Asp Lys
            500                 505                 510

Asp Leu Ala Pro Gly Ile Ala Asp Ser Leu Arg His Phe Lys Val Leu
        515                 520                 525

Arg Glu Lys Arg Ile Pro Pro Trp Met Glu Val Val Leu Ile Pro Met
    530                 535                 540

Thr Gly Lys Pro Ser Leu Tyr Pro Gly Leu Phe Leu Phe Thr Thr Pro
545                 550                 555                 560

Cys Arg Leu Val Arg Pro Val Gln Asn Leu Ala Leu Gly Lys Glu Glu
                565                 570                 575

Leu Ile Gly Thr Met Glu Gln Ile Phe Met Asn Val Ala Ile Phe Glu
            580                 585                 590

Asp Glu Val Phe Ala Gly Val Thr Thr His Gln Glu Leu Phe Pro His
        595                 600                 605

Ser Leu Leu Ser Val Ile Ala Asn Phe Ile Pro Phe Ser Asp His Asn
    610                 615                 620

Gln Ser Pro Arg Asn Met Tyr Gln Cys Gln Met Gly Lys Gln Thr Met
625                 630                 635                 640

Gly Phe Pro Leu Leu Thr Tyr Gln Asp Arg Ser Asp Asn Lys Leu Tyr
                645                 650                 655

Arg Leu Gln Thr Pro Gln Ser Pro Leu Val Arg Pro Ser Met Tyr Asp
            660                 665                 670

Tyr Tyr Asp Met Asp Asn Tyr Pro Ile Gly Thr Asn Ala Ile Val Ala
        675                 680                 685

Val Ile Ser Tyr Thr Gly Tyr Asp Met Glu Asp Ala Met Ile Val Asn
    690                 695                 700

Lys Ala Ser Trp Glu Arg Gly Phe Ala His Gly Ser Val Tyr Lys Ser
705                 710                 715                 720

Glu Phe Ile Asp Leu Ser Glu Lys Ile Lys Gln Gly Asp Ser Ser Leu
                725                 730                 735

Val Phe Gly Ile Lys Pro Gly Asp Pro Arg Val Leu Gln Lys Leu Asp
            740                 745                 750
```

```
Asp Asp Gly Leu Pro Phe Ile Gly Ala Lys Leu Gln Tyr Gly Asp Pro
            755                 760                 765

Tyr Tyr Ser Tyr Leu Asn Leu Asn Thr Gly Glu Ser Phe Val Met Tyr
770                 775                 780

Tyr Lys Ser Lys Glu Asn Cys Val Val Asp Asn Ile Lys Val Cys Ser
785                 790                 795                 800

Asn Asp Thr Gly Ser Gly Lys Phe Lys Cys Val Cys Ile Thr Met Arg
                805                 810                 815

Val Pro Arg Asn Pro Thr Ile Gly Asp Lys Phe Ala Ser Arg His Gly
            820                 825                 830

Gln Lys Gly Ile Leu Ser Arg Leu Trp Pro Ala Glu Asp Met Pro Phe
            835                 840                 845

Thr Glu Ser Gly Met Val Pro Asp Ile Leu Phe Asn Pro His Gly Phe
            850                 855                 860

Pro Ser Arg Met Thr Ile Gly Met Leu Ile Glu Ser Met Ala Gly Lys
865                 870                 875                 880

Ser Ala Ala Leu His Gly Leu Cys His Asp Ala Thr Pro Phe Ile Phe
                885                 890                 895

Ser Glu Glu Asn Ser Ala Leu Glu Tyr Phe Gly Glu Met Leu Lys Ala
                900                 905                 910

Ala Gly Tyr Asn Phe Tyr Gly Thr Glu Arg Leu Tyr Ser Gly Ile Ser
            915                 920                 925

Gly Leu Glu Leu Glu Ala Asp Ile Phe Ile Gly Val Val Tyr Tyr Gln
            930                 935                 940

Arg Leu Arg His Met Val Ser Asp Lys Phe Gln Val Arg Thr Thr Gly
945                 950                 955                 960

Ala Arg Asp Arg Val Thr Asn Gln Pro Ile Gly Gly Arg Asn Val Gln
                965                 970                 975

Gly Gly Ile Arg Phe Gly Glu Met Glu Arg Asp Ala Leu Leu Ala His
            980                 985                 990

Gly Thr Ser Phe Leu Leu His Asp  Arg Leu Phe Asn Cys  Ser Asp Arg
            995                 1000                1005

Ser Val  Ala His Val Cys Val  Lys Cys Gly Ser Leu  Leu Ser Pro
    1010                1015                1020

Leu Leu  Glu Lys Pro Pro  Ser Trp Ser Ala Met  Arg Asn Arg
    1025                1030                1035

Lys Tyr  Asn Cys Thr Leu Cys  Ser Arg Ser Asp Thr  Ile Asp Thr
    1040                1045                1050

Val Ser  Val Pro Tyr Val Phe  Arg Tyr Phe Val Ala  Glu Leu Ala
    1055                1060                1065

Ala Met  Asn Ile Lys Val Lys  Leu Asp Val Val
    1070                1075

<210> SEQ ID NO 41
<211> LENGTH: 1135
<212> TYPE: PRT
<213> ORGANISM: Homo sapiens

<400> SEQUENCE: 41

Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
                20                  25                  30

Ala Ala Leu Gln Glu Leu Thr Arg Ala His Val Glu Ser Phe Asn Tyr
            35                  40                  45
```

```
Ala Val His Glu Gly Leu Gly Leu Ala Val Gln Ala Ile Pro Pro Phe
     50              55              60
Glu Phe Ala Phe Lys Asp Glu Arg Ile Ser Phe Thr Ile Leu Asp Ala
65              70              75              80
Val Ile Ser Pro Pro Thr Val Pro Lys Gly Thr Ile Cys Lys Glu Ala
                 85              90              95
Asn Val Tyr Pro Ala Glu Cys Arg Gly Arg Arg Ser Thr Tyr Arg Gly
             100             105             110
Lys Leu Thr Ala Asp Ile Asn Trp Ala Val Asn Gly Ile Ser Lys Gly
         115             120             125
Ile Ile Lys Gln Phe Leu Gly Tyr Val Pro Ile Met Val Lys Ser Lys
         130             135             140
Leu Cys Asn Leu Arg Asn Leu Pro Pro Gln Ala Leu Ile Glu His His
145             150             155             160
Glu Glu Ala Glu Glu Met Gly Gly Tyr Phe Ile Ile Asn Gly Ile Glu
                 165             170             175
Lys Val Ile Arg Met Leu Ile Met Pro Arg Arg Asn Phe Pro Ile Ala
             180             185             190
Met Ile Arg Pro Lys Trp Lys Thr Arg Gly Pro Gly Tyr Thr Gln Tyr
         195             200             205
Gly Val Ser Met His Cys Val Arg Glu Glu His Ser Ala Val Asn Met
     210             215             220
Asn Leu His Tyr Leu Glu Asn Gly Thr Val Met Leu Asn Phe Ile Tyr
225             230             235             240
Arg Lys Glu Leu Phe Phe Leu Pro Leu Gly Phe Ala Leu Lys Ala Leu
                 245             250             255
Val Ser Phe Ser Asp Tyr Gln Ile Phe Gln Glu Leu Ile Lys Gly Lys
             260             265             270
Glu Asp Asp Ser Phe Leu Arg Asn Ser Val Ser Gln Met Leu Arg Ile
         275             280             285
Val Met Glu Glu Gly Cys Ser Thr Gln Lys Gln Val Leu Asn Tyr Leu
         290             295             300
Gly Glu Cys Phe Arg Val Lys Leu Asn Val Pro Asp Trp Tyr Pro Asn
305             310             315             320
Glu Gln Ala Ala Glu Phe Leu Phe Asn Gln Cys Ile Cys Ile His Leu
                 325             330             335
Lys Ser Asn Thr Glu Lys Phe Tyr Met Leu Cys Leu Met Thr Arg Lys
             340             345             350
Leu Phe Ala Leu Ala Lys Gly Glu Cys Met Glu Asp Asn Pro Asp Ser
         355             360             365
Leu Val Asn Gln Glu Val Leu Thr Pro Gly Gln Leu Phe Leu Met Phe
         370             375             380
Leu Lys Glu Lys Leu Glu Gly Trp Leu Val Ser Ile Lys Ile Ala Phe
385             390             395             400
Asp Lys Lys Ala Gln Lys Thr Ser Val Ser Met Asn Thr Asp Asn Leu
                 405             410             415
Met Arg Ile Phe Thr Met Gly Ile Asp Leu Thr Lys Pro Phe Glu Tyr
             420             425             430
Leu Phe Ala Thr Gly Asn Leu Arg Ser Lys Thr Gly Leu Gly Leu Leu
         435             440             445
Gln Asp Ser Gly Leu Cys Val Val Ala Asp Lys Leu Asn Phe Ile Arg
         450             455             460
```

```
Tyr Leu Ser His Phe Arg Cys Val His Arg Gly Ala Asp Phe Ala Lys
465                 470                 475                 480

Met Arg Thr Thr Thr Val Arg Arg Leu Leu Pro Glu Ser Trp Gly Phe
            485                 490                 495

Leu Cys Pro Val His Thr Pro Asp Gly Glu Pro Cys Gly Leu Met Asn
        500                 505                 510

His Leu Thr Ala Val Cys Glu Val Val Thr Gln Phe Val Tyr Thr Ala
    515                 520                 525

Ser Ile Pro Ala Leu Leu Cys Asn Leu Gly Val Thr Pro Ile Asp Gly
530                 535                 540

Ala Pro His Arg Ser Tyr Ser Glu Cys Tyr Pro Val Leu Leu Asp Gly
545                 550                 555                 560

Val Met Val Gly Trp Val Asp Lys Asp Leu Ala Pro Gly Ile Ala Asp
            565                 570                 575

Ser Leu Arg His Phe Lys Val Leu Arg Glu Lys Arg Ile Pro Pro Trp
            580                 585                 590

Met Glu Val Val Leu Ile Pro Met Thr Gly Lys Pro Ser Leu Tyr Pro
        595                 600                 605

Gly Leu Phe Leu Phe Thr Thr Pro Cys Arg Leu Val Arg Pro Val Gln
    610                 615                 620

Asn Leu Ala Leu Gly Lys Glu Glu Leu Ile Gly Thr Met Glu Gln Ile
625                 630                 635                 640

Phe Met Asn Val Ala Ile Phe Glu Asp Glu Val Phe Ala Gly Val Thr
            645                 650                 655

Thr His Gln Glu Leu Phe Pro His Ser Leu Leu Ser Val Ile Ala Asn
            660                 665                 670

Phe Ile Pro Phe Ser Asp His Asn Gln Ser Pro Arg Asn Met Tyr Gln
        675                 680                 685

Cys Gln Met Gly Lys Gln Thr Met Gly Phe Pro Leu Leu Thr Tyr Gln
    690                 695                 700

Asp Arg Ser Asp Asn Lys Leu Tyr Arg Leu Gln Thr Pro Gln Ser Pro
705                 710                 715                 720

Leu Val Arg Pro Ser Met Tyr Asp Tyr Tyr Asp Met Asp Asn Tyr Pro
            725                 730                 735

Ile Gly Thr Asn Ala Ile Val Ala Val Ile Ser Tyr Thr Gly Tyr Asp
            740                 745                 750

Met Glu Asp Ala Met Ile Val Asn Lys Ala Ser Trp Glu Arg Gly Phe
        755                 760                 765

Ala His Gly Ser Val Tyr Lys Ser Glu Phe Ile Asp Leu Ser Glu Lys
    770                 775                 780

Ile Lys Gln Gly Asp Ser Ser Leu Val Phe Gly Ile Lys Pro Gly Asp
785                 790                 795                 800

Pro Arg Val Leu Gln Lys Leu Asp Asp Gly Leu Pro Phe Ile Gly
            805                 810                 815

Ala Lys Leu Gln Tyr Gly Asp Pro Tyr Tyr Ser Tyr Leu Asn Leu Asn
            820                 825                 830

Thr Gly Glu Ser Phe Val Met Tyr Tyr Lys Ser Lys Glu Asn Cys Val
        835                 840                 845

Val Asp Asn Ile Lys Val Cys Ser Asn Asp Thr Gly Ser Gly Lys Phe
    850                 855                 860

Lys Cys Val Cys Ile Thr Met Arg Val Pro Arg Asn Pro Thr Ile Gly
865                 870                 875                 880

Asp Lys Phe Ala Ser Arg His Gly Gln Lys Gly Ile Leu Ser Arg Leu
```

```
                    885                 890                 895
Trp Pro Ala Glu Asp Met Pro Phe Thr Glu Ser Gly Met Val Pro Asp
            900                 905                 910
Ile Leu Phe Asn Pro His Gly Phe Pro Ser Arg Met Thr Ile Gly Met
            915                 920                 925
Leu Ile Glu Ser Met Ala Gly Lys Ser Ala Ala Leu His Gly Leu Cys
            930                 935                 940
His Asp Ala Thr Pro Phe Ile Phe Ser Glu Glu Asn Ser Ala Leu Glu
945                 950                 955                 960
Tyr Phe Gly Glu Met Leu Lys Ala Ala Gly Tyr Asn Phe Tyr Gly Thr
            965                 970                 975
Glu Arg Leu Tyr Ser Gly Ile Ser Gly Leu Glu Leu Glu Ala Asp Ile
            980                 985                 990
Phe Ile Gly Val Val Tyr Tyr Gln Arg Leu Arg His Met Val Ser Asp
            995                 1000                1005
Lys Phe Gln Val Arg Thr Thr Gly Ala Arg Asp Arg Val Thr Asn
        1010                1015                1020
Gln Pro Ile Gly Gly Arg Asn Val Gln Gly Gly Ile Arg Phe Gly
        1025                1030                1035
Glu Met Glu Arg Asp Ala Leu Leu Ala His Gly Thr Ser Phe Leu
        1040                1045                1050
Leu His Asp Arg Leu Phe Asn Cys Ser Asp Arg Ser Val Ala His
        1055                1060                1065
Val Cys Val Lys Cys Gly Ser Leu Leu Ser Pro Leu Leu Glu Lys
        1070                1075                1080
Pro Pro Pro Ser Trp Ser Ala Met Arg Asn Arg Lys Tyr Asn Cys
        1085                1090                1095
Thr Leu Cys Ser Arg Ser Asp Thr Ile Asp Thr Val Ser Val Pro
        1100                1105                1110
Tyr Val Phe Arg Tyr Phe Val Ala Glu Leu Ala Ala Met Asn Ile
        1115                1120                1125
Lys Val Lys Leu Asp Val Val
        1130                1135

<210> SEQ ID NO 42
<211> LENGTH: 346
<212> TYPE: PRT
<213> ORGANISM: Homo sapiens

<400> SEQUENCE: 42

Met Ala Ala Ser Gln Ala Val Glu Glu Met Arg Ser Arg Val Val Leu
1               5                   10                  15
Gly Glu Phe Gly Val Arg Asn Val His Thr Thr Asp Phe Pro Gly Asn
            20                  25                  30
Tyr Ser Gly Tyr Asp Asp Ala Trp Asp Gln Asp Arg Phe Glu Lys Asn
        35                  40                  45
Phe Arg Val Asp Val Val His Met Asp Glu Asn Ser Leu Glu Phe Asp
    50                  55                  60
Met Val Gly Ile Asp Ala Ala Ile Ala Asn Ala Phe Arg Arg Ile Leu
65                  70                  75                  80
Leu Ala Glu Val Pro Thr Met Ala Val Glu Lys Val Leu Val Tyr Asn
                85                  90                  95
Asn Thr Ser Ile Val Gln Asp Glu Ile Leu Ala His Arg Leu Gly Leu
            100                 105                 110
```

```
Ile Pro Ile His Ala Asp Pro Arg Leu Phe Glu Tyr Arg Asn Gln Gly
            115                 120                 125

Asp Glu Glu Gly Thr Glu Ile Asp Thr Leu Gln Phe Arg Leu Gln Val
130                 135                 140

Arg Cys Thr Arg Asn Pro His Ala Ala Lys Asp Ser Ser Asp Pro Asn
145                 150                 155                 160

Glu Leu Tyr Val Asn His Lys Val Tyr Thr Arg His Met Thr Trp Ile
                165                 170                 175

Pro Leu Gly Asn Gln Ala Asp Leu Phe Pro Gly Thr Ile Arg Pro
                180                 185                 190

Val His Asp Asp Ile Leu Ile Ala Gln Leu Arg Pro Gly Gln Glu Ile
                195                 200                 205

Asp Leu Leu Met His Cys Val Lys Gly Ile Gly Lys Asp His Ala Lys
210                 215                 220

Phe Ser Pro Val Ala Thr Ala Ser Tyr Arg Leu Pro Asp Ile Thr
225                 230                 235                 240

Leu Leu Glu Pro Val Glu Gly Glu Ala Ala Glu Leu Ser Arg Cys
                245                 250                 255

Phe Ser Pro Gly Val Ile Glu Val Gln Glu Val Gln Gly Lys Lys Val
                260                 265                 270

Ala Arg Val Ala Asn Pro Arg Leu Asp Thr Phe Ser Arg Glu Ile Phe
                275                 280                 285

Arg Asn Glu Lys Leu Lys Lys Val Val Arg Leu Ala Arg Val Arg Asp
                290                 295                 300

His Tyr Ile Phe Ser Val Glu Ser Thr Gly Val Leu Pro Pro Asp Val
305                 310                 315                 320

Leu Val Ser Glu Ala Ile Lys Val Leu Met Gly Lys Cys Arg Arg Phe
                325                 330                 335

Leu Asp Glu Leu Asp Ala Val Gln Met Asp
                340                 345

<210> SEQ ID NO 43
<211> LENGTH: 133
<212> TYPE: PRT
<213> ORGANISM: Homo sapiens

<400> SEQUENCE: 43

Met Glu Glu Asp Gln Glu Leu Glu Arg Lys Ile Ser Gly Leu Lys Thr
1               5                   10                  15

Ser Met Ala Glu Gly Glu Arg Lys Thr Ala Leu Glu Met Val Gln Ala
                20                  25                  30

Ala Gly Thr Asp Arg His Cys Val Thr Phe Val Leu His Glu Glu Asp
            35                  40                  45

His Thr Leu Gly Asn Ser Leu Arg Tyr Met Ile Met Lys Asn Pro Glu
50                  55                  60

Val Glu Phe Cys Gly Tyr Thr Thr Thr His Pro Ser Glu Ser Lys Ile
65                  70                  75                  80

Asn Leu Arg Ile Gln Thr Arg Gly Thr Leu Pro Ala Val Glu Pro Phe
                85                  90                  95

Gln Arg Gly Leu Asn Glu Leu Met Asn Val Cys Gln His Val Leu Asp
            100                 105                 110

Lys Phe Glu Ala Ser Ile Lys Asp Tyr Lys Asp Gln Lys Ala Ser Arg
        115                 120                 125

Asn Glu Ser Thr Phe
        130
```

<210> SEQ ID NO 44
<211> LENGTH: 122
<212> TYPE: PRT
<213> ORGANISM: Homo sapiens

<400> SEQUENCE: 44

Met Glu Glu Asp Gln Glu Leu Glu Arg Lys Ala Ile Glu Glu Leu Leu
1               5                   10                  15

Lys Glu Ala Lys Arg Gly Lys Thr Arg Ala Glu Thr Met Gly Pro Met
                20                  25                  30

Gly Trp Met Lys Cys Pro Leu Ala Ser Thr Asn Lys Arg Phe Leu Ile
            35                  40                  45

Asn Thr Ile Lys Asn Thr Leu Pro Ser His Lys Glu Gln Asp His Glu
        50                  55                  60

Gln Lys Glu Gly Asp Lys Glu Pro Ala Lys Ser Gln Ala Gln Lys Glu
65                  70                  75                  80

Glu Asn Pro Lys Lys His Arg Ser His Pro Tyr Lys His Ser Phe Arg
                85                  90                  95

Ala Arg Gly Ser Ala Ser Tyr Ser Pro Pro Arg Lys Arg Ser Ser Gln
            100                 105                 110

Asp Lys Tyr Glu Lys Arg Ser Asn Arg Arg
        115                 120

<210> SEQ ID NO 45
<211> LENGTH: 710
<212> TYPE: PRT
<213> ORGANISM: Homo sapiens

<400> SEQUENCE: 45

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
                20                  25                  30

Met Ser Glu Asp Glu Glu Asp Asp Ser Ser Gly Glu Glu Val Val Ile
            35                  40                  45

Pro Gln Lys Lys Gly Lys Lys Ala Ala Ala Thr Ser Ala Lys Lys Val
        50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
        130                 135                 140

Ser Asp Glu Glu Glu Asp Asp Ser Glu Glu Asp Glu Glu Asp Asp
145                 150                 155                 160

Glu Asp Glu Asp Glu Asp Glu Asp Ile Pro Ala Ala Met Lys
                165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Asp Ser Glu Glu
        195                 200                 205

```
Glu Ala Met Glu Thr Thr Pro Ala Lys Gly Lys Lys Ala Ala Lys Val
    210                 215                 220
Val Pro Val Lys Ala Lys Asn Val Ala Glu Asp Glu Asp Glu Glu Glu
225                 230                 235                 240
Asp Asp Glu Asp Glu Asp Asp Asp Glu Asp Asp Glu Asp Asp
            245                 250                 255
Asp Asp Glu Asp Asp Glu Glu Glu Glu Glu Glu Glu Glu Glu Glu Pro
        260                 265                 270
Val Lys Glu Ala Pro Gly Lys Arg Lys Lys Glu Met Ala Lys Gln Lys
    275                 280                 285
Ala Ala Pro Glu Ala Lys Lys Gln Lys Val Glu Gly Thr Glu Pro Thr
290                 295                 300
Thr Ala Phe Asn Leu Phe Val Gly Asn Leu Asn Phe Asn Lys Ser Ala
305                 310                 315                 320
Pro Glu Leu Lys Thr Gly Ile Ser Asp Val Phe Ala Lys Asn Asp Leu
                325                 330                 335
Ala Val Val Asp Val Arg Ile Gly Met Thr Arg Lys Phe Gly Tyr Val
            340                 345                 350
Asp Phe Glu Ser Ala Glu Asp Leu Glu Lys Ala Leu Glu Leu Thr Gly
        355                 360                 365
Leu Lys Val Phe Gly Asn Glu Ile Lys Leu Glu Lys Pro Lys Gly Lys
370                 375                 380
Asp Ser Lys Lys Glu Arg Asp Ala Arg Thr Leu Leu Ala Lys Asn Leu
385                 390                 395                 400
Pro Tyr Lys Val Thr Gln Asp Glu Leu Lys Glu Val Phe Glu Asp Ala
                405                 410                 415
Ala Glu Ile Arg Leu Val Ser Lys Asp Gly Lys Ser Lys Gly Ile Ala
            420                 425                 430
Tyr Ile Glu Phe Lys Thr Glu Ala Asp Ala Glu Lys Thr Phe Glu Glu
        435                 440                 445
Lys Gln Gly Thr Glu Ile Asp Gly Arg Ser Ile Ser Leu Tyr Tyr Thr
450                 455                 460
Gly Glu Lys Gly Gln Asn Gln Asp Tyr Arg Gly Gly Lys Asn Ser Thr
465                 470                 475                 480
Trp Ser Gly Glu Ser Lys Thr Leu Val Leu Ser Asn Leu Ser Tyr Ser
                485                 490                 495
Ala Thr Glu Glu Thr Leu Gln Glu Val Phe Glu Lys Ala Thr Phe Ile
            500                 505                 510
Lys Val Pro Gln Asn Gln Asn Gly Lys Ser Lys Gly Tyr Ala Phe Ile
        515                 520                 525
Glu Phe Ala Ser Phe Glu Asp Ala Lys Glu Ala Leu Asn Ser Cys Asn
530                 535                 540
Lys Arg Glu Ile Glu Gly Arg Ala Ile Arg Leu Glu Leu Gln Gly Pro
545                 550                 555                 560
Arg Gly Ser Pro Asn Ala Arg Ser Gln Pro Ser Lys Thr Leu Phe Val
                565                 570                 575
Lys Gly Leu Ser Glu Asp Thr Thr Glu Glu Thr Leu Lys Glu Ser Phe
            580                 585                 590
Asp Gly Ser Val Arg Ala Arg Ile Val Thr Asp Arg Glu Thr Gly Ser
        595                 600                 605
Ser Lys Gly Phe Gly Phe Val Asp Phe Asn Ser Glu Glu Asp Ala Lys
610                 615                 620
```

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
            645                 650                 655

Gly Gly Gly Arg Gly Gly Phe Gly Gly Arg Gly Gly Arg Gly Gly
        660                 665                 670

Arg Gly Gly Phe Gly Gly Arg Gly Arg Gly Gly Phe Gly Gly Arg Gly
        675                 680                 685

Gly Phe Arg Gly Gly Arg Gly Gly Gly Asp His Lys Pro Gln Gly
    690                 695                 700

Lys Lys Thr Lys Phe Glu
705                 710

<210> SEQ ID NO 46
<211> LENGTH: 6637
<212> TYPE: PRT
<213> ORGANISM: Homo sapiens

<400> SEQUENCE: 46

Ala Thr Thr Gly Gly Cys Thr Gly Ala Ala Gly Cys Gly Gly Ala Ala
1               5                   10                  15

Gly Ala Ala Gly Ala Cys Gly Ala Ala Gly Cys Ala Ala Thr Cys
            20                  25                  30

Ala Thr Ala Ala Ala Thr Gly Gly Ala Gly Gly Thr Thr Gly
        35                  40                  45

Cys Ala Ala Gly Cys Thr Cys Ala Thr Gly Gly Thr Thr Gly Ala
50                  55                  60

Ala Ala Gly Ala Cys Thr Thr Cys Thr Gly Thr Cys Ala Cys Gly Gly Ala
65                  70                  75                  80

Ala Gly Cys Thr Ala Ala Ala Gly Cys Thr Cys Thr Ala Thr Ala
            85                  90                  95

Cys Ala Cys Cys Cys Gly Ala Thr Thr Thr Gly Cys Cys Thr Cys Gly
        100                 105                 110

Gly Ala Gly Gly Ala Ala Thr Thr Thr Cys Cys Thr Ala Ala Ala
            115                 120                 125

Thr Gly Ala Thr Thr Ala Thr Thr Thr Gly Ala Thr Gly Thr Cys
        130                 135                 140

Thr Thr Ala Thr Ala Thr Ala Cys Thr Thr Gly Ala Thr Thr
145                 150                 155                 160

Gly Thr Thr Thr Cys Ala Ala Ala Cys Ala Ala Ala Gly
        165                 170                 175

Ala Gly Cys Gly Ala Gly Cys Ala Gly Ala Gly Thr Cys Gly
        180                 185                 190

Thr Ala Cys Ala Ala Cys Thr Ala Thr Thr Gly Thr Cys Cys
        195                 200                 205

Cys Cys Cys Cys Cys Ala Thr Gly Thr Ala Gly Ala Ala Gly Thr
        210                 215                 220

Gly Ala Thr Cys Thr Cys Ala Thr Cys Ala Cys Gly Thr Ala Ala
225                 230                 235                 240

Ala Thr Gly Thr Cys Gly Thr Cys Cys Thr Gly Cys Gly Ala Cys
            245                 250                 255

Cys Gly Cys Thr Thr Cys Cys Gly Gly Cys Gly Cys Ala Ala Gly
        260                 265                 270

Cys Gly Cys Ala Cys Gly Thr Thr Gly Ala Ala Thr Cys Gly Cys Gly
        275                 280                 285

-continued

```
Thr Gly Gly Thr Gly Ala Cys Thr Cys Cys Gly Gly Cys Thr Thr
    290                 295                 300

Gly Ala Gly Gly Thr Thr Gly Ala Ala Thr Thr Ala Ala Gly Ala Ala
305                 310                 315                 320

Thr Ala Gly Thr Cys Ala Gly Gly Thr Gly Thr Gly Ala Gly Thr
            325                 330                 335

Gly Gly Ala Ala Cys Gly Thr Cys Thr Cys Thr Thr Gly Gly Gly
                340                 345                 350

Thr Gly Thr Cys Gly Gly Ala Ala Thr Thr Cys Ala Ala Ala Cys
    355                 360                 365

Gly Gly Ala Cys Cys Thr Gly Gly Ala Gly Gly Ala Thr Gly Thr Thr
370                 375                 380

Gly Ala Thr Cys Thr Cys Cys Ala Ala Gly Ala Ala Cys Ala Thr Gly
385                 390                 395                 400

Cys Cys Cys Thr Gly Gly Cys Gly Gly Cys Gly Gly Cys Thr Gly Cys
                405                 410                 415

Ala Gly Gly Gly Cys Ala Thr Thr Thr Cys Cys Thr Thr Cys Gly Gly
                420                 425                 430

Gly Ala Thr Gly Thr Ala Thr Thr Cys Gly Gly Cys Thr Gly Ala Ala
        435                 440                 445

Gly Ala Gly Cys Thr Cys Ala Ala Gly Ala Ala Ala Thr Thr Ala Ala
450                 455                 460

Gly Thr Gly Thr Thr Ala Ala Ala Thr Cys Cys Ala Thr Thr Ala Cys
465                 470                 475                 480

Gly Ala Ala Cys Cys Cys Thr Cys Gly Ala Thr Ala Cys Cys Thr Gly
                485                 490                 495

Gly Ala Cys Ala Gly Cys Cys Thr Gly Gly Gly Ala Ala Cys Cys
        500                 505                 510

Cys Ala Thr Cys Gly Gly Cys Ala Ala Ala Cys Gly Gly Cys Cys Thr
        515                 520                 525

Gly Thr Ala Cys Gly Ala Thr Thr Thr Ala Gly Cys Thr Thr Thr Gly
        530                 535                 540

Gly Gly Cys Cys Cys Thr Gly Cys Ala Gly Ala Thr Thr Cys Cys Ala
545                 550                 555                 560

Ala Ala Gly Ala Gly Gly Thr Gly Thr Gly Cys Thr Cys Cys Ala Cys
                565                 570                 575

Cys Thr Gly Cys Gly Thr Gly Cys Ala Gly Gly Ala Cys Thr Thr Cys
        580                 585                 590

Ala Gly Cys Ala Ala Cys Thr Gly Thr Thr Cys Thr Gly Gly Gly Cys
        595                 600                 605

Ala Cys Cys Thr Gly Gly Cys Cys Ala Cys Ala Thr Thr Gly Ala Ala
    610                 615                 620

Gly Cys Thr Cys Cys Cys Ala Cys Thr Cys Ala Cys Ala Gly Thr Gly
625                 630                 635                 640

Thr Ala Thr Ala Ala Cys Cys Cys Thr Cys Cys Thr Cys Thr
                645                 650                 655

Thr Cys Gly Ala Thr Ala Ala Gly Cys Thr Gly Thr Ala Cys Cys Thr
        660                 665                 670

Gly Cys Thr Gly Cys Thr Thr Cys Gly Gly Gly Gly Cys Thr Cys Thr
        675                 680                 685

Thr Gly Thr Thr Ala Ala Ala Cys Thr Gly Cys Cys Ala Cys Ala
    690                 695                 700
```

-continued

```
Thr Gly Cys Thr Gly Ala Cys Thr Gly Thr Cys Cys Cys Cys Gly
705                 710                 715                 720

Gly Gly Cys Cys Gly Thr Gly Ala Thr Thr Cys Ala Cys Cys Thr Cys
                725                 730                 735

Thr Thr Ala Cys Thr Cys Thr Gly Cys Cys Ala Gly Cys Thr Gly Ala
            740                 745                 750

Gly Gly Gly Thr Thr Cys Thr Gly Ala Ala Gly Thr Cys Gly Gly
        755                 760                 765

Gly Gly Cys Cys Cys Thr Ala Cys Ala Ala Gly Cys Ala Gly Thr Cys
    770                 775                 780

Thr Ala Cys Gly Ala Gly Cys Thr Thr Gly Ala Gly Ala Gly Ala Ala
785                 790                 795                 800

Thr Thr Cys Thr Gly Ala Ala Cys Ala Gly Gly Thr Thr Thr Cys Thr
                805                 810                 815

Gly Gly Ala Ala Gly Ala Ala Ala Thr Cys Cys Cys Gly Ala Thr
        820                 825                 830

Cys Cys Cys Thr Cys Thr Gly Cys Cys Thr Cys Thr Gly Ala Ala Ala
                835                 840                 845

Thr Thr Cys Gly Gly Gly Ala Gly Gly Ala Ala Thr Thr Ala Gly Ala
850                 855                 860

Ala Cys Ala Ala Thr Ala Cys Ala Cys Ala Ala Cys Thr Gly Ala Ala
865                 870                 875                 880

Ala Thr Thr Gly Thr Gly Cys Ala Gly Ala Ala Cys Ala Ala Cys Cys
                885                 890                 895

Thr Cys Cys Thr Gly Gly Gly Thr Cys Cys Cys Ala Gly Gly Gly
            900                 905                 910

Cys Gly Cys Ala Cys Ala Thr Gly Thr Ala Ala Gly Ala Ala Cys
        915                 920                 925

Gly Thr Gly Thr Gly Thr Gly Ala Gly Ala Ala Gly Cys Ala Ala Gly Ala
    930                 935                 940

Gly Cys Ala Ala Gly Cys Thr Cys Ala Thr Thr Gly Cys Thr Cys Thr
945                 950                 955                 960

Cys Thr Thr Cys Thr Gly Gly Ala Ala Gly Gly Cys Ala Cys Ala Thr
                965                 970                 975

Ala Thr Gly Ala Ala Thr Gly Cys Thr Ala Ala Gly Cys Gly Cys Thr
            980                 985                 990

Gly Thr Cys Cys Cys Cys Ala Cys  Thr Gly Cys Ala Ala  Gly Ala Cys
        995                 1000                1005

Cys Gly Gly Gly Cys Gly Ala  Thr Cys Cys Gly Thr  Thr Gly Thr
    1010                1015                1020

Cys Cys Gly Ala Ala Ala Gly  Gly Ala Ala Cys Ala  Cys Ala Ala
    1025                1030                1035

Cys Ala Gly Cys Ala Ala Gly  Thr Thr Gly Ala Cys  Thr Ala Thr
    1040                1045                1050

Cys Ala Cys Gly Thr Thr Thr  Cys Cys Ala Gly Cys  Cys Ala Thr
    1055                1060                1065

Gly Gly  Thr Gly Cys Ala Cys  Ala Gly Gly Ala Cys  Ala Gly Cys
    1070                1075                1080

Thr Gly  Gly Cys Thr Ala Gly  Ala Ala Gly Gly Ala  Cys Thr Cys
    1085                1090                1095

Thr Gly  Ala Gly Cys Cys Cys  Thr Gly Gly Gly  Ala Ala Thr
    1100                1105                1110

Thr Gly  Ala Gly Gly Ala Ala  Gly Cys Thr Cys Ala  Gly Ala Thr
```

1115                1120                1125

Ala Gly Gly Ala Ala Ala Cys Gly Ala Gly Ala Thr Ala
    1130                1135                1140

Cys Thr Thr Ala Ala Cys Ala Cys Cys Cys Ala Cys Cys Ala Gly
    1145                1150                1155

Thr Gly Cys Cys Cys Gly Cys Gly Ala Ala Cys Ala Cys Cys Thr
    1160                1165                1170

Thr Thr Cys Thr Gly Cys Cys Thr Gly Thr Gly Gly Ala Ala
    1175                1180                1185

Gly Ala Ala Thr Gly Ala Ala Gly Gly Ala Thr Thr Cys Thr Thr
    1190                1195                1200

Thr Cys Thr Gly Ala Ala Cys Thr Ala Cys Cys Thr Thr Thr Thr
    1205                1210                1215

Thr Thr Cys Gly Gly Gly Ala Ala Thr Gly Gly Ala Thr Gly Ala
    1220                1225                1230

Thr Gly Ala Thr Gly Gly Thr Ala Thr Gly Gly Ala Ala Thr Cys
    1235                1240                1245

Cys Ala Gly Ala Thr Thr Cys Ala Ala Thr Cys Cys Cys Ala Gly
    1250                1255                1260

Thr Gly Thr Gly Thr Thr Cys Thr Thr Thr Cys Thr Ala Gly Ala
    1265                1270                1275

Thr Thr Thr Cys Thr Thr Gly Gly Thr Gly Gly Thr Gly Cys Cys
    1280                1285                1290

Gly Cys Cys Cys Thr Cys Ala Ala Gly Gly Thr Ala Thr Cys Gly
    1295                1300                1305

Cys Cys Cys Ala Gly Thr Cys Ala Gly Thr Cys Gly Cys Cys Thr
    1310                1315                1320

Ala Gly Gly Ala Gly Ala Cys Cys Ala Gly Ala Thr Gly Thr Thr
    1325                1330                1335

Thr Ala Cys Thr Ala Ala Thr Gly Gly Cys Cys Ala Gly Ala Cys
    1340                1345                1350

Gly Gly Thr Gly Ala Ala Cys Thr Thr Gly Cys Ala Gly Gly Cys
    1355                1360                1365

Thr Gly Thr Cys Ala Thr Gly Ala Ala Gly Gly Ala Thr Gly Thr
    1370                1375                1380

Ala Gly Thr Thr Cys Thr Gly Ala Thr Thr Cys Gly Ala Ala Ala
    1385                1390                1395

Ala Cys Thr Thr Cys Thr Gly Cys Ala Thr Thr Gly Ala Thr
    1400                1405                1410

Gly Gly Cys Cys Cys Ala Ala Gly Ala Ala Cys Ala Gly Ala Ala
    1415                1420                1425

Gly Thr Thr Gly Cys Cys Ala Gly Ala Gly Gly Ala Ala Gly Thr
    1430                1435                1440

Gly Gly Cys Cys Ala Cys Ala Cys Cys Cys Ala Cys Thr Ala Cys
    1445                1450                1455

Ala Gly Ala Thr Gly Ala Gly Gly Ala Ala Ala Ala Gly Ala
    1460                1465                1470

Cys Thr Cys Thr Thr Thr Gly Ala Thr Thr Gly Cys Thr Ala Thr
    1475                1480                1485

Thr Gly Ala Cys Cys Gly Ala Thr Cys Cys Thr Thr Thr Thr
    1490                1495                1500

Gly Ala Gly Thr Ala Cys Ala Cys Thr Cys Cys Ala Gly Gly
    1505                1510                1515

```
Cys Cys  Ala Gly Thr Cys Cys  Cys Thr Cys Ala Thr  Ala Gly Ala
    1520                 1525                 1530

Cys Ala  Ala Ala Cys Thr Thr  Thr Ala Cys Ala Ala  Cys Ala Thr
    1535                 1540                 1545

Thr Thr  Gly Gly Ala Thr Thr  Cys Gly Cys Cys Thr  Thr Cys Ala
    1550                 1555                 1560

Gly Ala  Gly Cys Cys Ala Cys  Gly Thr Cys Ala Ala  Thr Ala Thr
    1565                 1570                 1575

Thr Gly  Thr Gly Thr Thr Thr  Gly Ala Thr Ala Gly  Cys Gly Ala
    1580                 1585                 1590

Gly Ala  Thr Gly Gly Ala Cys  Ala Ala Ala Cys Thr  Ala Ala Thr
    1595                 1600                 1605

Gly Ala  Thr Gly Gly Ala Cys  Ala Ala Gly Thr Ala  Cys Cys Cys
    1610                 1615                 1620

Ala Gly  Gly Cys Ala Thr Thr  Ala Gly Gly Cys Ala  Gly Ala Thr
    1625                 1630                 1635

Cys Cys  Thr Gly Gly Ala Gly  Ala Ala Gly Ala Ala  Ala Gly Ala
    1640                 1645                 1650

Ala Gly  Gly Cys Cys Thr Gly  Thr Thr Cys Cys Gly  Ala Ala Ala
    1655                 1660                 1665

Ala Cys  Ala Cys Ala Thr Gly  Ala Thr Gly Gly Gly  Ala Ala Ala
    1670                 1675                 1680

Gly Cys  Gly Ala Gly Thr Gly  Gly Ala Cys Thr Ala  Cys Gly Cys
    1685                 1690                 1695

Thr Gly  Cys Gly Cys Gly Cys  Thr Cys Ala Gly Thr  Cys Ala Thr
    1700                 1705                 1710

Cys Thr  Gly Cys Cys Cys Ala  Gly Ala Cys Ala Thr  Gly Thr Ala
    1715                 1720                 1725

Cys Ala  Thr Cys Ala Ala Cys  Ala Cys Cys Ala Ala  Cys Gly Ala
    1730                 1735                 1740

Ala Ala  Thr Thr Gly Gly Ala  Ala Thr Thr Cys Cys  Cys Ala Thr
    1745                 1750                 1755

Gly Gly  Thr Gly Thr Thr Thr  Gly Cys Cys Ala Cys  Ala Ala Ala
    1760                 1765                 1770

Ala Cys  Thr Gly Ala Cys Cys  Thr Ala Cys Cys Cys  Ala Cys Ala
    1775                 1780                 1785

Gly Cys  Cys Ala Gly Thr Thr  Ala Cys Cys Cys Cys  Ala Thr Gly
    1790                 1795                 1800

Gly Ala  Ala Thr Gly Thr Thr  Cys Ala Gly Gly Ala  Ala Cys Thr
    1805                 1810                 1815

Thr Ala  Gly Gly Cys Ala Ala  Gly Cys Gly Gly Thr  Cys Ala Thr
    1820                 1825                 1830

Cys Ala  Ala Cys Gly Gly Cys  Cys Cys Thr Ala Ala  Thr Gly Thr
    1835                 1840                 1845

Gly Cys  Ala Cys Cys Cys Ala  Gly Gly Ala Gly Cys  Cys Thr Cys
    1850                 1855                 1860

Cys Ala  Thr Gly Gly Thr Cys  Ala Thr Cys Ala Ala  Thr Gly Ala
    1865                 1870                 1875

Gly Gly  Ala Cys Gly Gly Cys  Ala Gly Cys Cys Gly  Cys Ala Cys
    1880                 1885                 1890

Ala Gly  Cys Cys Cys Thr Gly  Ala Gly Cys Gly Cys  Thr Gly Thr
    1895                 1900                 1905
```

```
Gly Gly  Ala Cys Ala Thr Gly  Ala Cys Cys Cys Ala  Gly Cys Gly
    1910                 1915                 1920

Ala Gly  Ala Gly Gly Cys Cys  Gly Thr Gly Gly Cys  Cys Ala Ala
    1925                 1930                 1935

Gly Cys  Ala Gly Cys Thr Thr  Cys Thr Gly Ala Cys  Cys Cys Cys
    1940                 1945                 1950

Ala Gly  Cys Cys Ala Cys Gly  Gly Gly Gly Gly Cys  Ala Cys Cys
    1955                 1960                 1965

Thr Ala  Ala Gly Cys Cys Cys  Cys Ala Gly Gly Gly  Gly Ala Cys
    1970                 1975                 1980

Ala Ala  Ala Ala Ala Thr Thr  Gly Thr Gly Thr Gly  Cys Cys Gly
    1985                 1990                 1995

Gly Cys  Ala Thr Gly Thr Gly  Ala Ala Gly Ala Ala  Thr Gly Gly
    2000                 2005                 2010

Gly Gly  Ala Cys Ala Thr Thr  Cys Thr Gly Cys Thr  Ala Cys Thr
    2015                 2020                 2025

Gly Ala  Ala Cys Cys Gly Ala  Cys Ala Gly Cys Cys  Cys Ala Cys
    2030                 2035                 2040

Ala Cys  Thr Gly Cys Ala Cys  Ala Gly Ala Cys Cys  Cys Thr Cys
    2045                 2050                 2055

Cys Ala  Thr Cys Cys Ala Gly  Gly Cys Cys Cys Ala  Cys Cys Gly
    2060                 2065                 2070

Thr Gly  Cys Cys Cys Gly Cys  Ala Thr Cys Cys Thr  Gly Cys Cys
    2075                 2080                 2085

Thr Gly  Ala Ala Gly Ala Gly  Ala Ala Ala Gly Thr  Gly Cys Thr
    2090                 2095                 2100

Gly Cys  Gly Gly Cys Thr Cys  Cys Ala Cys Thr Ala  Thr Gly Cys
    2105                 2110                 2115

Cys Ala  Ala Cys Thr Gly Cys  Ala Ala Gly Gly Cys  Cys Thr Ala
    2120                 2125                 2130

Thr Ala  Ala Thr Gly Cys Cys  Gly Ala Cys Thr Thr  Thr Gly Ala
    2135                 2140                 2145

Thr Gly  Gly Ala Gly Ala Cys  Gly Ala Gly Ala Thr  Gly Ala Ala
    2150                 2155                 2160

Thr Gly  Cys Cys Cys Ala Thr  Thr Thr Cys Cys Cys  Cys Cys Ala
    2165                 2170                 2175

Gly Ala  Gly Thr Gly Ala Gly  Cys Thr Gly Gly Gly  Cys Cys Gly
    2180                 2185                 2190

Gly Gly  Cys Cys Gly Ala Gly  Gly Cys Cys Thr Ala  Cys Gly Thr
    2195                 2200                 2205

Cys Cys  Thr Gly Gly Cys Cys  Thr Gly Cys Ala Cys  Thr Gly Ala
    2210                 2215                 2220

Thr Cys  Ala Gly Cys Ala Gly  Thr Ala Cys Cys Thr  Thr Gly Thr
    2225                 2230                 2235

Thr Cys  Cys Cys Ala Ala Gly  Gly Ala Thr Gly Gly  Cys Cys Ala
    2240                 2245                 2250

Ala Cys  Cys Ala Thr Thr Gly  Gly Cys Gly Gly Gly  Ala Cys Thr
    2255                 2260                 2265

Gly Ala  Thr Cys Cys Ala Gly  Gly Ala Thr Cys Ala  Cys Ala Thr
    2270                 2275                 2280

Gly Gly  Thr Thr Thr Cys Ala  Gly Gly Gly Gly Cys  Ala Ala Gly
    2285                 2290                 2295

Cys Ala  Thr Gly Ala Cys Thr  Ala Cys Thr Cys Gly  Gly Gly Gly
```

```
            2300                2305                2310
Thr  Thr  Gly  Cys  Thr  Thr  Thr  Thr  Cys  Ala  Cys  Cys  Cys  Gly
     2315                2320                2325

Gly  Gly  Ala  Gly  Cys  Ala  Cys  Thr  Ala  Thr  Ala  Thr  Gly  Gly  Ala
     2330                2335                2340

Gly  Cys  Thr  Gly  Gly  Thr  Gly  Thr  Ala  Cys  Cys  Gly  Ala  Gly  Gly
     2345                2350                2355

Ala  Cys  Thr  Cys  Ala  Cys  Gly  Gly  Ala  Cys  Ala  Ala  Ala  Gly  Thr
     2360                2365                2370

Gly  Gly  Gly  Gly  Cys  Gly  Cys  Gly  Thr  Gly  Ala  Ala  Gly  Cys  Thr
     2375                2380                2385

Cys  Cys  Thr  Thr  Thr  Cys  Thr  Cys  Cys  Thr  Thr  Cys  Cys  Ala  Thr
     2390                2395                2400

Cys  Cys  Thr  Gly  Ala  Ala  Gly  Cys  Cys  Cys  Thr  Thr  Thr  Cys  Cys
     2405                2410                2415

Gly  Cys  Thr  Gly  Thr  Gly  Gly  Ala  Cys  Ala  Gly  Gly  Ala  Ala  Ala
     2420                2425                2430

Ala  Cys  Ala  Gly  Gly  Thr  Thr  Gly  Thr  Gly  Thr  Cys  Ala  Ala  Cys
     2435                2440                2445

Gly  Cys  Thr  Gly  Cys  Thr  Cys  Ala  Thr  Ala  Ala  Ala  Thr  Ala  Thr
     2450                2455                2460

Ala  Ala  Thr  Cys  Cys  Cys  Ala  Gly  Ala  Gly  Gly  Ala  Cys  Cys  Ala
     2465                2470                2475

Cys  Ala  Thr  Cys  Cys  Cys  Ala  Cys  Thr  Gly  Ala  Ala  Cys  Thr  Thr
     2480                2485                2490

Ala  Thr  Cys  Thr  Gly  Gly  Ala  Ala  Ala  Gly  Gly  Cys  Gly  Ala  Ala
     2495                2500                2505

Ala  Ala  Thr  Cys  Ala  Cys  Thr  Gly  Gly  Gly  Ala  Ala  Ala  Gly  Cys
     2510                2515                2520

Cys  Thr  Gly  Gly  Gly  Thr  Gly  Ala  Ala  Gly  Gly  Ala  Ala  Ala  Cys
     2525                2530                2535

Thr  Cys  Cys  Thr  Cys  Gly  Ala  Thr  Cys  Cys  Gly  Thr  Thr  Cys  Cys
     2540                2545                2550

Thr  Gly  Gly  Cys  Thr  Thr  Thr  Ala  Ala  Cys  Cys  Cys  Thr  Gly  Ala
     2555                2560                2565

Cys  Thr  Cys  Gly  Ala  Thr  Gly  Thr  Gly  Cys  Gly  Ala  Gly  Thr  Cys
     2570                2575                2580

Cys  Cys  Ala  Gly  Gly  Thr  Gly  Ala  Thr  Cys  Ala  Thr  Cys  Ala  Gly
     2585                2590                2595

Gly  Gly  Ala  Ala  Gly  Gly  Gly  Gly  Ala  Gly  Cys  Thr  Gly  Cys  Thr
     2600                2605                2610

Cys  Thr  Gly  Cys  Gly  Gly  Ala  Gly  Thr  Gly  Cys  Thr  Gly  Gly  Ala
     2615                2620                2625

Cys  Ala  Ala  Gly  Gly  Cys  Gly  Cys  Ala  Cys  Thr  Ala  Thr  Gly  Gly
     2630                2635                2640

Gly  Ala  Gly  Cys  Thr  Cys  Cys  Gly  Cys  Cys  Thr  Ala  Cys  Gly  Gly
     2645                2650                2655

Cys  Cys  Thr  Gly  Gly  Thr  Cys  Cys  Ala  Cys  Thr  Gly  Cys  Thr  Gly
     2660                2665                2670

Cys  Thr  Ala  Thr  Gly  Ala  Gly  Ala  Thr  Cys  Thr  Ala  Thr  Gly  Gly
     2675                2680                2685

Ala  Gly  Gly  Cys  Gly  Ala  Gly  Ala  Cys  Cys  Ala  Gly  Cys  Gly  Gly
     2690                2695                2700
```

```
Cys Ala Ala Gly Gly Thr Thr Cys Thr Ala Cys Cys Thr Gly
    2705                2710                2715

Cys Cys Thr Gly Gly Cys Cys Cys Gly Cys Cys Thr Cys Thr Thr
    2720                2725                2730

Cys Ala Cys Cys Gly Cys Cys Thr Ala Cys Cys Thr Gly Cys Ala
    2735                2740                2745

Gly Cys Thr Cys Thr Ala Cys Ala Gly Ala Gly Cys Thr Thr
    2750                2755                2760

Cys Ala Cys Cys Thr Thr Gly Gly Cys Gly Thr Gly Gly Ala
    2765                2770                2775

Ala Gly Ala Cys Ala Thr Thr Thr Thr Gly Gly Thr Gly Ala Ala
    2780                2785                2790

Gly Cys Cys Ala Ala Ala Gly Gly Cys Ala Gly Ala Thr Gly Thr
    2795                2800                2805

Cys Ala Ala Gly Ala Gly Gly Cys Ala Ala Cys Gly Thr Ala Thr
    2810                2815                2820

Cys Ala Thr Thr Gly Ala Ala Gly Ala Ala Thr Cys Cys Ala Cys
    2825                2830                2835

Cys Cys Ala Cys Thr Gly Cys Gly Gly Gly Cys Cys Cys Cys Ala
    2840                2845                2850

Gly Gly Cys Thr Gly Thr Cys Ala Gly Gly Cys Thr Gly Cys
    2855                2860                2865

Ala Thr Thr Ala Ala Ala Cys Cys Thr Gly Cys Cys Ala Gly Ala
    2870                2875                2880

Ala Gly Cys Cys Gly Cys Ala Thr Cys Ala Thr Ala Thr Gly Ala
    2885                2890                2895

Thr Gly Ala Gly Gly Thr Cys Cys Gly Ala Gly Gly Ala Ala Ala
    2900                2905                2910

Ala Thr Gly Gly Cys Ala Gly Gly Ala Thr Gly Cys Cys Cys Ala
    2915                2920                2925

Thr Cys Thr Gly Gly Gly Cys Ala Ala Gly Gly Ala Cys Cys Ala
    2930                2935                2940

Gly Ala Gly Gly Gly Ala Thr Thr Thr Thr Ala Ala Cys Ala Thr
    2945                2950                2955

Gly Ala Thr Thr Gly Ala Thr Cys Thr Gly Ala Ala Gly Thr Thr
    2960                2965                2970

Cys Ala Ala Gly Gly Ala Gly Gly Ala Ala Gly Thr Gly Ala Ala
    2975                2980                2985

Cys Cys Ala Thr Thr Ala Cys Ala Gly Cys Ala Ala Thr Gly Ala
    2990                2995                3000

Gly Ala Thr Thr Ala Ala Cys Ala Ala Gly Gly Cys Ala Thr Gly
    3005                3010                3015

Cys Ala Thr Gly Cys Cys Thr Thr Thr Gly Gly Cys Cys Thr
    3020                3025                3030

Ala Cys Ala Cys Ala Gly Ala Cys Ala Gly Thr Thr Cys Cys Cys
    3035                3040                3045

Ala Gly Ala Gly Ala Ala Cys Ala Gly Cys Cys Thr Gly Cys Ala
    3050                3055                3060

Gly Ala Thr Gly Ala Thr Gly Gly Thr Gly Cys Ala Gly Thr Cys
    3065                3070                3075

Gly Gly Gly Ala Gly Cys Cys Ala Ala Ala Gly Gly Thr Thr Cys
    3080                3085                3090
```

```
Ala Ala Cys Thr Gly Thr Gly Ala Ala Cys Ala Cys Gly Ala Thr
        3095                3100                3105

Gly Cys Ala Gly Ala Thr Cys Thr Cys Gly Thr Gly Cys Cys Thr
        3110                3115                3120

Gly Cys Thr Gly Gly Gly Cys Cys Ala Gly Ala Thr Thr Gly Ala
        3125                3130                3135

Ala Cys Thr Gly Gly Ala Ala Gly Gly Thr Cys Gly Gly Ala Gly
        3140                3145                3150

Ala Cys Cys Cys Cys Cys Gly Cys Thr Gly Ala Thr Gly Gly Cys
        3155                3160                3165

Gly Thr Cys Thr Gly Gly Cys Ala Ala Gly Thr Cys Ala Cys Thr
        3170                3175                3180

Gly Cys Cys Cys Thr Gly Cys Thr Thr Thr Gly Ala Gly Cys Cys
        3185                3190                3195

Thr Thr Ala Thr Gly Ala Gly Thr Thr Cys Ala Cys Cys Cys Cys
        3200                3205                3210

Cys Ala Gly Gly Gly Cys Thr Gly Gly Thr Gly Gly Cys Thr Thr
        3215                3220                3225

Thr Gly Thr Cys Ala Cys Thr Gly Gly Cys Ala Gly Gly Thr Thr
        3230                3235                3240

Cys Cys Thr Cys Ala Cys Cys Gly Gly Cys Ala Thr Cys Ala Ala
        3245                3250                3255

Ala Cys Cys Thr Cys Thr Gly Ala Gly Thr Thr Cys Thr Thr
        3260                3265                3270

Cys Thr Thr Cys Cys Ala Cys Thr Gly Cys Ala Thr Gly Gly Cys
        3275                3280                3285

Ala Gly Gly Ala Cys Gly Ala Gly Ala Gly Gly Cys Cys Cys Thr
        3290                3295                3300

Gly Gly Thr Gly Gly Ala Cys Ala Cys Thr Gly Cys Thr Gly Thr
        3305                3310                3315

Gly Ala Ala Ala Ala Cys Cys Ala Gly Cys Cys Gly Cys Thr Cys
        3320                3325                3330

Ala Gly Gly Cys Thr Ala Thr Cys Thr Cys Cys Ala Ala Ala Gly
        3335                3340                3345

Gly Thr Gly Cys Ala Thr Cys Ala Thr Cys Ala Ala Gly Cys Ala
        3350                3355                3360

Cys Cys Thr Ala Gly Ala Gly Gly Gly Gly Cys Thr Gly Gly Thr
        3365                3370                3375

Cys Gly Thr Gly Cys Ala Gly Thr Ala Thr Gly Ala Thr Cys Thr
        3380                3385                3390

Cys Ala Cys Gly Gly Thr Cys Gly Thr Gly Ala Cys Ala Gly
        3395                3400                3405

Thr Gly Ala Cys Gly Gly Cys Ala Gly Thr Gly Thr Gly Gly Thr
        3410                3415                3420

Gly Cys Ala Gly Thr Thr Cys Cys Thr Gly Thr Ala Thr Gly Gly
        3425                3430                3435

Gly Gly Ala Gly Gly Ala Thr Gly Gly Cys Cys Thr Gly Gly Ala
        3440                3445                3450

Cys Ala Thr Cys Cys Cys Ala Ala Gly Ala Cys Ala Cys Ala
        3455                3460                3465

Gly Thr Thr Cys Cys Thr Gly Cys Ala Gly Cys Cys Cys Ala Ala
        3470                3475                3480

Gly Cys Ala Gly Thr Thr Cys Cys Cys Cys Thr Thr Cys Cys Thr
```

```
    3485                3490                3495

Gly Gly  Cys Cys Ala Gly Cys  Ala Ala Cys Thr Ala  Cys Gly Ala
    3500                3505                3510

Gly Gly  Thr Gly Ala Thr Ala  Ala Thr Gly Ala Ala  Ala Thr Cys
    3515                3520                3525

Ala Cys  Ala Gly Cys Ala Thr  Cys Thr Cys Cys Ala  Thr Gly Ala
    3530                3535                3540

Ala Gly  Thr Thr Thr Thr Ala  Thr Cys Cys Ala Gly  Ala Gly Cys
    3545                3550                3555

Ala Gly  Ala Thr Cys Cys Cys  Ala Ala Ala Ala Ala  Ala Gly Cys
    3560                3565                3570

Thr Cys  Thr Cys Cys Ala Cys  Cys Ala Cys Thr Thr  Cys Ala Gly
    3575                3580                3585

Ala Gly  Cys Thr Ala Thr Cys  Ala Ala Ala Ala Ala  Ala Thr Gly
    3590                3595                3600

Gly Cys  Ala Ala Ala Gly Cys  Ala Ala Gly Cys Ala  Cys Cys Cys
    3605                3610                3615

Cys Ala  Ala Cys Ala Cys Cys  Cys Thr Gly Cys Thr  Gly Ala Gly
    3620                3625                3630

Ala Ala  Gly Ala Gly Gly Cys  Gly Cys Cys Thr Thr  Cys Thr Thr
    3635                3640                3645

Gly Ala  Gly Thr Thr Ala Thr  Thr Cys Cys Cys Ala  Gly Ala Ala
    3650                3655                3660

Ala Ala  Thr Thr Cys Ala Gly  Gly Ala Ala Gly Cys  Thr Gly Thr
    3665                3670                3675

Gly Ala  Ala Ala Gly Cys Cys  Cys Thr Gly Ala Ala  Ala Cys Thr
    3680                3685                3690

Thr Gly  Ala Gly Ala Gly Thr  Gly Ala Ala Ala Ala  Cys Cys Gly
    3695                3700                3705

Cys Ala  Ala Thr Gly Gly Cys  Cys Gly Cys Ala Gly  Cys Cys Cys
    3710                3715                3720

Thr Gly  Gly Gly Ala Cys Thr  Cys Ala Gly Gly Ala  Gly Ala Thr
    3725                3730                3735

Gly Cys  Thr Gly Ala Gly Gly  Ala Thr Gly Thr Gly  Gly Thr Ala
    3740                3745                3750

Thr Gly  Ala Gly Thr Thr Gly  Gly Ala Thr Gly Ala  Gly Gly Ala
    3755                3760                3765

Ala Ala  Gly Cys Cys Gly Ala  Ala Gly Gly Ala Ala  Ala Thr Ala
    3770                3775                3780

Cys Cys  Ala Gly Ala Ala Gly  Ala Ala Gly Gly Cys  Gly Gly Cys
    3785                3790                3795

Cys Gly  Cys Thr Thr Gly Thr  Cys Cys Thr Gly Ala  Cys Cys Cys
    3800                3805                3810

Cys Ala  Gly Thr Cys Thr Gly  Thr Cys Thr Gly Thr  Cys Thr Gly
    3815                3820                3825

Gly Cys  Gly Thr Cys Cys Thr  Gly Ala Cys Ala Thr  Cys Thr Ala
    3830                3835                3840

Cys Thr  Thr Thr Gly Cys Ala  Thr Cys Ala Gly Thr  Gly Thr Cys
    3845                3850                3855

Ala Gly  Ala Ala Ala Cys Ala  Thr Thr Thr Gly Ala  Ala Ala Cys
    3860                3865                3870

Ala Ala  Ala Gly Gly Thr Thr  Gly Ala Thr Gly Ala  Cys Thr Ala
    3875                3880                3885
```

-continued

Cys Ala Gly Thr Cys Ala Ala Gly Ala Thr Gly Gly Gly Cys
3890                3895                3900

Ala Gly Cys Thr Cys Ala Ala Ala Cys Ala Gly Ala Gly Ala Ala
3905                3910                3915

Gly Ala Gly Thr Thr Ala Thr Gly Ala Gly Ala Ala Ala Thr Cys
3920                3925                3930

Ala Gly Ala Gly Cys Thr Thr Thr Cys Thr Cys Thr Cys Gly Ala
3935                3940                3945

Cys Ala Gly Gly Thr Thr Gly Ala Gly Gly Ala Cys Cys Thr Thr
3950                3955                3960

Gly Cys Thr Gly Cys Ala Gly Cys Thr Gly Ala Ala Gly Thr Gly
3965                3970                3975

Gly Cys Ala Gly Cys Gly Cys Thr Cys Ala Cys Thr Gly Thr Gly
3980                3985                3990

Thr Gly Ala Gly Cys Cys Gly Gly Cys Gly Ala Gly Gly Cys
3995                4000                4005

Thr Gly Thr Gly Gly Gly Cys Cys Thr Gly Cys Thr Gly Gly Cys
4010                4015                4020

Thr Gly Cys Cys Cys Ala Gly Ala Gly Cys Ala Thr Cys Gly Gly
4025                4030                4035

Ala Gly Ala Gly Cys Cys Thr Cys Cys Ala Cys Cys Cys Ala
4040                4045                4050

Gly Ala Thr Gly Ala Cys Cys Thr Cys Ala Ala Cys Ala Cys
4055                4060                4065

Cys Thr Thr Cys Thr Ala Cys Thr Thr Thr Gly Cys Ala Gly Gly
4070                4075                4080

Cys Ala Gly Ala Gly Gly Cys Gly Ala Gly Ala Thr Gly Ala Ala
4085                4090                4095

Cys Gly Thr Cys Ala Cys Cys Thr Gly Gly Gly Cys Ala Thr
4100                4105                4110

Thr Cys Cys Ala Ala Gly Gly Thr Thr Gly Cys Gly Gly Gly Ala
4115                4120                4125

Gly Ala Thr Thr Cys Thr Cys Ala Thr Gly Thr Gly Gly Cys
4130                4135                4140

Cys Ala Gly Cys Gly Cys Cys Ala Ala Cys Ala Thr Cys Ala Ala
4145                4150                4155

Gly Ala Cys Ala Cys Cys Ala Thr Gly Ala Thr Gly Ala Gly
4160                4165                4170

Cys Gly Thr Gly Cys Cys Cys Gly Thr Gly Cys Thr Cys Ala Ala
4175                4180                4185

Cys Ala Cys Cys Ala Ala Gly Ala Ala Ala Gly Cys Cys Cys Thr
4190                4195                4200

Gly Ala Ala Gly Ala Gly Ala Gly Thr Gly Ala Ala Ala Ala Gly
4205                4210                4215

Cys Cys Thr Gly Ala Ala Gly Ala Ala Gly Cys Ala Ala Cys Thr
4220                4225                4230

Cys Ala Cys Cys Ala Gly Gly Gly Thr Gly Thr Gly Cys Thr Thr
4235                4240                4245

Gly Gly Gly Gly Gly Ala Gly Gly Thr Gly Thr Thr Gly Cys Ala
4250                4255                4260

Gly Ala Ala Ala Ala Thr Thr Gly Ala Cys Gly Thr Cys Cys Ala
4265                4270                4275

```
Gly Gly Ala Gly Thr Cys Cys Thr Thr Cys Thr Gly Thr Ala Thr
        4280            4285            4290

Gly Gly Ala Ala Gly Ala Ala Ala Ala Ala Cys Ala Gly Ala Ala
        4295            4300            4305

Cys Ala Ala Ala Thr Thr Cys Cys Ala Gly Gly Thr Gly Thr Ala
        4310            4315            4320

Cys Cys Ala Gly Cys Thr Gly Cys Gly Gly Thr Thr Thr Cys Ala
        4325            4330            4335

Gly Thr Thr Cys Cys Thr Gly Cys Cys Ala Cys Ala Thr Gly Cys
        4340            4345            4350

Ala Thr Ala Thr Thr Ala Cys Cys Ala Gly Cys Ala Gly Gly Ala
        4355            4360            4365

Gly Ala Ala Gly Thr Gly Cys Cys Thr Gly Ala Gly Ala Cys Cys
        4370            4375            4380

Cys Gly Ala Gly Gly Ala Cys Ala Thr Cys Cys Thr Gly Cys Gly
        4385            4390            4395

Cys Thr Thr Cys Ala Thr Gly Gly Ala Ala Ala Cys Ala Ala Gly
        4400            4405            4410

Ala Thr Thr Cys Thr Thr Thr Ala Ala Ala Cys Thr Thr Cys Thr
        4415            4420            4425

Gly Ala Thr Gly Gly Ala Ala Thr Cys Cys Ala Thr Cys Ala Ala
        4430            4435            4440

Ala Ala Ala Gly Ala Ala Gly Ala Ala Thr Ala Ala Thr Ala Ala
        4445            4450            4455

Ala Gly Cys Ala Thr Cys Ala Gly Cys Thr Thr Thr Cys Ala Gly
        4460            4465            4470

Gly Ala Ala Cys Gly Thr Ala Ala Ala Cys Ala Cys Thr Cys Gly
        4475            4480            4485

Ala Ala Gly Ala Gly Cys Thr Ala Cys Ala Cys Ala Gly Cys Gly
        4490            4495            4500

Gly Gly Ala Thr Cys Thr Gly Gly Ala Cys Ala Ala Cys Gly Cys
        4505            4510            4515

Thr Gly Gly Gly Gly Ala Gly Thr Thr Gly Gly Gly Gly Ala Gly
        4520            4525            4530

Gly Ala Gly Thr Cys Gly Gly Gly Gly Ala Gly Ala Gly Cys Ala
        4535            4540            4545

Gly Gly Ala Gly Gly Gly Thr Gly Ala Thr Gly Ala Gly Gly Ala
        4550            4555            4560

Ala Gly Ala Gly Gly Ala Gly Gly Gly Gly Cys Ala Cys Ala Thr
        4565            4570            4575

Thr Gly Thr Gly Gly Ala Thr Gly Cys Thr Gly Ala Ala Gly Cys
        4580            4585            4590

Thr Gly Ala Gly Gly Ala Gly Gly Gly Gly Ala Cys Gly Cys
        4595            4600            4605

Cys Gly Ala Thr Gly Cys Cys Thr Cys Thr Gly Ala Thr Gly Cys
        4610            4615            4620

Cys Ala Ala Ala Cys Gly Cys Ala Ala Gly Gly Ala Gly Ala Ala
        4625            4630            4635

Gly Cys Ala Gly Gly Ala Gly Gly Ala Gly Gly Ala Gly Gly Thr
        4640            4645            4650

Thr Gly Ala Thr Thr Ala Thr Gly Ala Gly Ala Gly Thr Gly Ala
        4655            4660            4665

Gly Gly Ala Ala Gly Ala Gly Gly Ala Gly Gly Ala Gly Ala Gly
```

```
                  4670              4675              4680

Gly Gly Ala Gly Gly Gly Cys Gly Ala Gly Gly Ala Gly Ala Ala
            4685              4690              4695

Cys Gly Ala Cys Gly Ala Thr Gly Ala Ala Gly Ala Cys Ala Thr
            4700              4705              4710

Gly Cys Ala Gly Gly Ala Gly Gly Ala Ala Cys Gly Ala Ala Ala
            4715              4720              4725

Thr Cys Cys Cys Cys Ala Cys Ala Gly Gly Ala Ala Gly Gly
            4730              4735              4740

Thr Gly Cys Thr Cys Gly Ala Ala Ala Gly Ala Cys Cys Cys Ala
            4745              4750              4755

Ala Gly Ala Gly Cys Ala Ala Gly Ala Thr Gly Ala Ala Gly Ala
            4760              4765              4770

Gly Gly Thr Gly Gly Gly Cys Thr Thr Ala Gly Gly Cys Ala Cys
            4775              4780              4785

Thr Gly Ala Gly Gly Ala Gly Gly Ala Cys Cys Cys Gly Thr Cys
            4790              4795              4800

Cys Cys Thr Thr Cys Cys Gly Cys Cys Thr Cys Cys Thr
            4805              4810              4815

Gly Ala Cys Gly Cys Ala Gly Cys Cys Cys Gly Gly Ala Ala
            4820              4825              4830

Ala Cys Cys Cys Ala Cys Cys Ala Cys Ala Gly Cys Cys Ala
            4835              4840              4845

Gly Gly Ala Gly Cys Cys Cys Ala Gly Gly Gly Cys Cys
            4850              4855              4860

Cys Gly Ala Gly Gly Cys Cys Ala Thr Gly Gly Ala Gly Cys Gly
            4865              4870              4875

Cys Cys Gly Gly Gly Thr Cys Cys Ala Gly Gly Cys Thr Gly Thr
            4880              4885              4890

Gly Cys Gly Thr Gly Ala Gly Ala Thr Cys Cys Ala Cys Cys Cys
            4895              4900              4905

Gly Thr Thr Cys Ala Thr Ala Gly Ala Thr Gly Ala Cys Thr Ala
            4910              4915              4920

Cys Cys Ala Gly Thr Ala Cys Gly Ala Cys Ala Cys Cys Gly Ala
            4925              4930              4935

Gly Gly Ala Gly Ala Gly Cys Cys Thr Gly Thr Gly Gly Thr Gly
            4940              4945              4950

Cys Cys Ala Gly Gly Thr Gly Ala Cys Ala Gly Thr Gly Ala Ala
            4955              4960              4965

Gly Cys Thr Cys Cys Cys Thr Cys Thr Gly Ala Thr Gly Ala Ala
            4970              4975              4980

Gly Ala Thr Cys Ala Ala Cys Thr Thr Thr Gly Ala Cys Ala Thr
            4985              4990              4995

Gly Ala Gly Cys Thr Cys Cys Thr Gly Gly Thr Ala Gly Thr
            5000              5005              5010

Ala Thr Cys Thr Thr Thr Gly Gly Cys Cys Cys Ala Thr Gly Gly
            5015              5020              5025

Thr Gly Cys Cys Gly Thr Cys Ala Thr Cys Thr Ala Thr Gly Cys
            5030              5035              5040

Gly Ala Cys Cys Ala Ala Gly Gly Gly Cys Ala Thr Cys Ala Cys
            5045              5050              5055

Thr Cys Gly Gly Thr Gly Cys Cys Thr Cys Thr Gly Ala Ala
            5060              5065              5070
```

```
Thr Gly  Ala Ala Ala Cys Ala  Ala Cys Cys Ala Ala  Cys Ala Ala
    5075                 5080                 5085

Thr Ala  Ala Gly Ala Ala Cys  Gly Ala Gly Ala Ala  Gly Gly Ala
    5090                 5095                 5100

Gly Cys  Thr Thr Gly Thr Gly  Cys Thr Ala Ala Ala  Cys Ala Cys
    5105                 5110                 5115

Ala Gly  Ala Ala Gly Gly Ala  Ala Thr Cys Ala Ala  Cys Cys Thr
    5120                 5125                 5130

Cys Cys  Cys Ala Gly Ala Gly  Cys Thr Ala Thr Thr  Cys Ala Ala
    5135                 5140                 5145

Gly Thr  Ala Thr Gly Cys Ala  Gly Ala Gly Gly Thr  Cys Cys Thr
    5150                 5155                 5160

Gly Gly  Ala Thr Cys Thr Gly  Cys Gly Cys Cys Gly  Cys Cys Thr
    5165                 5170                 5175

Cys Thr  Ala Cys Thr Cys Cys  Ala Ala Cys Gly Ala  Cys Ala Thr
    5180                 5185                 5190

Cys Cys  Ala Cys Gly Cys Cys  Ala Thr Ala Gly Cys  Cys Ala Ala
    5195                 5200                 5205

Cys Ala  Cys Gly Thr Ala Thr  Gly Gly Cys Ala Thr  Thr Gly Ala
    5210                 5215                 5220

Gly Gly  Cys Cys Gly Cys Gly  Cys Thr Gly Cys Gly  Gly Gly Thr
    5225                 5230                 5235

Gly Ala  Thr Cys Gly Ala Gly  Ala Ala Gly Gly Ala  Gly Ala Thr
    5240                 5245                 5250

Cys Ala  Ala Gly Gly Ala Thr  Gly Thr Gly Thr Thr  Thr Gly Cys
    5255                 5260                 5265

Cys Gly  Thr Gly Thr Ala Thr  Gly Gly Cys Ala Thr  Cys Gly Cys
    5270                 5275                 5280

Gly Gly  Thr Cys Gly Ala Cys  Cys Cys Thr Cys Gly  Cys Cys Ala
    5285                 5290                 5295

Thr Cys  Thr Cys Thr Cys Cys  Cys Thr Gly Gly Thr  Thr Gly Cys
    5300                 5305                 5310

Thr Gly  Ala Thr Thr Ala Thr  Ala Thr Gly Thr Gly  Cys Thr Thr
    5315                 5320                 5325

Cys Gly  Ala Gly Gly Gly Thr  Gly Thr Thr Thr Ala  Cys Ala Ala
    5330                 5335                 5340

Gly Cys  Cys Ala Cys Thr Gly  Ala Ala Thr Cys Gly  Cys Thr Thr
    5345                 5350                 5355

Thr Gly  Gly Gly Ala Thr Cys  Cys Gly Gly Thr Cys  Ala Ala Ala
    5360                 5365                 5370

Cys Thr  Cys Thr Thr Cys Cys  Cys Cys Gly Cys Thr  Ala Cys Ala
    5375                 5380                 5385

Gly Cys  Ala Gly Ala Thr Gly  Ala Cys Ala Thr Thr  Thr Gly Ala
    5390                 5395                 5400

Ala Ala  Cys Cys Ala Gly Cys  Thr Thr Cys Cys Ala  Gly Thr Thr
    5405                 5410                 5415

Thr Cys  Thr Gly Ala Ala Gly  Cys Ala Ala Gly Cys  Cys Ala Cys
    5420                 5425                 5430

Cys Ala  Thr Gly Cys Thr Gly  Gly Gly Ala Thr Cys  Cys Cys Ala
    5435                 5440                 5445

Cys Gly  Ala Thr Gly Ala Gly  Cys Thr Gly Ala Gly  Gly Thr Cys
    5450                 5455                 5460
```

| | | | | | | | | | | | |
|---|---|---|---|---|---|---|---|---|---|---|---|
| Thr | Cys | Cys | Thr | Thr | Cys | Thr | Gly | Cys | Thr | Gly | Cys Cys Thr |
| | 5465 | | | | 5470 | | | | 5475 | | |
| Thr | Gly | Thr | Gly | Gly | Thr | Cys | Gly | Gly | Gly | Ala | Ala Gly Gly Thr |
| | 5480 | | | | 5485 | | | | 5490 | | |
| Cys | Gly | Thr | Cys | Ala | Gly | Gly | Gly | Cys | Gly | Gly | Gly Ala Cys |
| | 5495 | | | | 5500 | | | | 5505 | | |
| Ala | Gly | Gly | Cys | Cys | Thr | Gly | Thr | Thr | Cys | Gly | Ala Gly Cys Thr |
| | 5510 | | | | 5515 | | | | 5520 | | |
| Cys | Ala | Ala | Gly | Cys | Ala | Gly | Cys | Cys | Thr | Cys | Thr Gly Ala Gly |
| | 5525 | | | | 5530 | | | | 5535 | | |
| Ala | Thr | Ala | Gly | Cys | Ala | Gly | Cys | Thr | Ala | Cys | Cys Cys Gly |
| | 5540 | | | | 5545 | | | | 5550 | | |
| Gly | Cys | Ala | Cys | Cys | Ala | Thr | Cys | Thr | Gly | Cys | Cys Ala Gly |
| | 5555 | | | | 5560 | | | | 5565 | | |
| Cys | Thr | Cys | Cys | Ala | Ala | Gly | Gly | Ala | Cys | Cys | Thr Thr Gly |
| | 5570 | | | | 5575 | | | | 5580 | | |
| Gly | Thr | Gly | Ala | Gly | Gly | Gly | Cys | Gly | Thr | Gly | Cys Cys Cys |
| | 5585 | | | | 5590 | | | | 5595 | | |
| Ala | Gly | Cys | Cys | Thr | Gly | Cys | Cys | Thr | Thr | Cys | Thr Gly Cys Ala |
| | 5600 | | | | 5605 | | | | 5610 | | |
| Thr | Gly | Ala | Gly | Ala | Gly | Gly | Ala | Cys | Cys | Ala | Gly Gly Ala Gly |
| | 5615 | | | | 5620 | | | | 5625 | | |
| Ala | Cys | Thr | Gly | Gly | Ala | Ala | Thr | Cys | Cys | Ala | Gly Gly Gly Cys |
| | 5630 | | | | 5635 | | | | 5640 | | |
| Ala | Gly | Thr | Thr | Cys | Cys | Ala | Ala | Gly | Thr | Gly | Ala Cys Ala Gly |
| | 5645 | | | | 5650 | | | | 5655 | | |
| Thr | Ala | Cys | Ala | Gly | Ala | Gly | Cys | Ala | Cys | Ala | Gly Cys Ala Gly |
| | 5660 | | | | 5665 | | | | 5670 | | |
| Cys | Gly | Ala | Cys | Cys | Thr | Thr | Gly | Gly | Gly | Cys | Cys Thr Gly Ala |
| | 5675 | | | | 5680 | | | | 5685 | | |
| Ala | Ala | Gly | Cys | Ala | Gly | Thr | Gly | Gly | Gly | Cys | Cys Thr Cys Thr |
| | 5690 | | | | 5695 | | | | 5700 | | |
| Gly | Ala | Gly | Cys | Thr | Gly | Gly | Gly | Cys | Cys | Ala | Gly Cys Thr Thr |
| | 5705 | | | | 5710 | | | | 5715 | | |
| Cys | Ala | Cys | Cys | Thr | Gly | Gly | Ala | Ala | Ala | Gly | Thr Gly Ala Cys |
| | 5720 | | | | 5725 | | | | 5730 | | |
| Ala | Gly | Ala | Gly | Thr | Thr | Gly | Cys | Thr | Cys | Ala | Thr Cys Cys Thr |
| | 5735 | | | | 5740 | | | | 5745 | | |
| Thr | Gly | Cys | Cys | Cys | Cys | Thr | Cys | Cys | Cys | Thr | Gly Thr Cys Thr |
| | 5750 | | | | 5755 | | | | 5760 | | |
| Cys | Thr | Gly | Gly | Ala | Thr | Thr | Thr | Thr | Ala | Thr | Cys Ala Ala |
| | 5765 | | | | 5770 | | | | 5775 | | |
| Gly | Gly | Thr | Thr | Thr | Ala | Cys | Cys | Ala | Ala | Gly | Thr Cys Thr Thr |
| | 5780 | | | | 5785 | | | | 5790 | | |
| Cys | Thr | Gly | Ala | Gly | Thr | Cys | Cys | Cys | Cys | Thr | Gly Ala Gly |
| | 5795 | | | | 5800 | | | | 5805 | | |
| Ala | Thr | Gly | Gly | Cys | Thr | Gly | Gly | Gly | Cys | Cys | Thr Cys Ala |
| | 5810 | | | | 5815 | | | | 5820 | | |
| Cys | Cys | Thr | Gly | Thr | Gly | Cys | Thr | Gly | Cys | Ala | Gly Gly Ala Gly |
| | 5825 | | | | 5830 | | | | 5835 | | |
| Gly | Cys | Cys | Thr | Cys | Thr | Gly | Thr | Gly | Gly | Cys | Ala Thr Ala Ala |
| | 5840 | | | | 5845 | | | | 5850 | | |
| Cys | Cys | Cys | Cys | Thr | Ala | Ala | Gly | Gly | Ala | Gly | Ala Ala Gly Thr |

```
    5855                5860                5865

Cys Cys  Thr Gly Ala Thr Thr  Cys Ala Cys Gly Ala  Thr Thr Cys
    5870                5875                5880

Ala Cys  Thr Gly Ala Gly Ala  Ala Gly Ala Cys Cys  Ala Ala Gly
    5885                5890                5895

Gly Gly  Gly Ala Ala Gly Cys  Cys Ala Thr Gly Cys  Thr Thr Thr
    5900                5905                5910

Gly Cys  Thr Gly Cys Thr Gly  Gly Gly Gly Ala Cys  Cys Cys Cys
    5915                5920                5925

Ala Gly  Gly Cys Ala Cys Cys  Thr Cys Cys Ala Gly  Ala Gly Thr
    5930                5935                5940

Ala Gly  Gly Gly Ala Ala Gly  Cys Gly Gly Gly Gly  Thr Thr Cys
    5945                5950                5955

Thr Thr  Thr Thr Gly Cys Thr  Gly Thr Gly Ala Gly  Thr Gly Gly
    5960                5965                5970

Cys Cys  Ala Gly Gly Gly Ala  Cys Ala Ala Cys Ala  Gly Ala Cys
    5975                5980                5985

Ala Ala  Gly Ala Thr Thr Cys  Cys Thr Gly Gly Gly  Gly Gly Cys
    5990                5995                6000

Thr Cys  Cys Cys Gly Ala Thr  Gly Ala Gly Cys Ala  Gly Gly Ala
    6005                6010                6015

Ala Cys  Gly Thr Gly Gly Ala  Gly Cys Cys Thr Gly  Cys Thr Gly
    6020                6025                6030

Cys Cys  Cys Ala Ala Gly Gly  Cys Cys Thr Gly Cys  Thr Cys Cys
    6035                6040                6045

Thr Thr  Cys Cys Gly Gly Cys  Thr Gly Cys Thr Cys  Cys Ala Gly
    6050                6055                6060

Cys Cys  Cys Cys Thr Gly Gly  Gly Gly Gly Cys Ala  Gly Ala Gly
    6065                6070                6075

Thr Cys  Cys Ala Cys Ala Ala  Ala Gly Ala Gly Thr  Cys Cys Cys
    6080                6085                6090

Cys Ala  Thr Cys Ala Ala Gly  Ala Cys Thr Thr Cys  Thr Thr Cys
    6095                6100                6105

Cys Cys  Thr Gly Ala Gly Thr  Cys Ala Ala Gly Thr  Ala Cys Ala
    6110                6115                6120

Gly Cys  Gly Thr Ala Gly Cys  Ala Thr Ala Gly Thr  Cys Cys Thr
    6125                6130                6135

Cys Cys  Ala Cys Cys Cys Ala  Cys Cys Cys Ala Ala  Cys Cys Thr
    6140                6145                6150

Cys Thr  Cys Thr Gly Cys Cys  Thr Gly Gly Cys Cys  Ala Gly Gly
    6155                6160                6165

Gly Thr  Cys Cys Thr Gly Gly  Cys Cys Cys Thr Gly  Cys Cys Ala
    6170                6175                6180

Cys Thr  Gly Thr Gly Thr Gly  Gly Cys Gly Ala Gly  Gly Thr Gly
    6185                6190                6195

Thr Cys  Cys Thr Thr Cys Thr  Ala Gly Ala Cys Cys  Ala Cys Ala
    6200                6205                6210

Thr Cys  Ala Gly Cys Cys Cys  Cys Ala Ala Gly Gly  Cys Thr Gly
    6215                6220                6225

Gly Gly  Ala Gly Cys Ala Gly  Thr Cys Gly Cys Thr  Cys Cys Ala
    6230                6235                6240

Gly Gly  Gly Cys Cys Gly Cys  Ala Gly Cys Ala Gly  Thr Thr Cys
    6245                6250                6255
```

```
Ala Cys Thr Cys Cys Cys Ala Cys Ala Cys Ala Thr Ala Gly Ala
    6260                6265                6270

Ala Cys Cys Cys Ala Gly Gly Thr Cys Ala Cys Thr Gly Cys Thr
    6275                6280                6285

Gly Gly Gly Gly Cys Gly Ala Thr Thr Gly Ala Ala Cys Ala Gly
    6290                6295                6300

Gly Thr Thr Gly Cys Cys Thr Gly Gly Cys Thr Thr Thr Thr Cys
    6305                6310                6315

Thr Cys Thr Gly Cys Thr Gly Thr Cys Ala Gly Thr Thr Thr Gly
    6320                6325                6330

Gly Thr Gly Thr Gly Gly Ala Gly Gly Cys Cys Thr Ala Thr Gly
    6335                6340                6345

Thr Thr Cys Thr Gly Cys Cys Cys Cys Ala Thr Ala Cys Ala Cys
    6350                6355                6360

Cys Cys Cys Ala Cys Ala Gly Gly Cys Cys Cys Thr Gly Cys Thr
    6365                6370                6375

Thr Ala Thr Gly Gly Gly Ala Ala Gly Gly Ala Ala Cys Ala Cys
    6380                6385                6390

Ala Gly Gly Cys Cys Thr Cys Cys Ala Gly Cys Cys Cys Ala Gly
    6395                6400                6405

Ala Gly Gly Ala Cys Thr Gly Thr Gly Cys Cys Gly Cys Cys Cys
    6410                6415                6420

Thr Gly Thr Thr Cys Thr Thr Gly Gly Cys Cys Gly Thr Cys Cys
    6425                6430                6435

Ala Cys Gly Thr Thr Thr Cys Cys Thr Cys Thr Cys Cys Cys Thr
    6440                6445                6450

Cys Thr Ala Gly Cys Ala Cys Cys Ala Gly Cys Ala Ala Thr Ala
    6455                6460                6465

Cys Ala Thr Thr Thr Cys Cys Cys Thr Gly Gly Cys Ala Thr Gly
    6470                6475                6480

Gly Ala Cys Ala Gly Ala Ala Ala Ala Gly Ala Cys Ala Gly Ala
    6485                6490                6495

Gly Ala Gly Gly Ala Cys Thr Thr Ala Thr Ala Cys Ala Ala Ala
    6500                6505                6510

Gly Gly Cys Thr Thr Thr Gly Thr Ala Ala Ala Ala Cys Cys Ala
    6515                6520                6525

Gly Ala Gly Gly Cys Thr Ala Gly Cys Thr Thr Cys Thr Ala Thr
    6530                6535                6540

Cys Thr Thr Thr Gly Thr Cys Thr Ala Cys Thr Gly Thr Thr Ala
    6545                6550                6555

Thr Thr Thr Cys Ala Gly Cys Thr Cys Ala Gly Gly Gly Cys Gly
    6560                6565                6570

Gly Gly Thr Ala Ala Thr Thr Ala Ala Cys Ala Thr Cys Ala Thr
    6575                6580                6585

Thr Gly Gly Ala Ala Cys Thr Ala Gly Cys Thr Ala Thr Thr Ala
    6590                6595                6600

Gly Gly Ala Ala Ala Gly Ala Ala Ala Ala Ala Ala Ala Ala Cys
    6605                6610                6615

Thr Thr Gly Gly Thr Thr Thr Thr Thr Thr Thr Ala Cys Ala
    6620                6625                6630

Ala Cys Ala Ala
    6635
```

<210> SEQ ID NO 47
<211> LENGTH: 419
<212> TYPE: PRT
<213> ORGANISM: Homo sapiens

<400> SEQUENCE: 47

```
Met Ala Ala Glu Val Leu Pro Ser Ala Arg Trp Gln Tyr Cys Gly Ala
1               5                   10                  15

Pro Asp Gly Ser Gln Arg Ala Val Leu Val Gln Phe Ser Asn Gly Lys
            20                  25                  30

Leu Gln Ser Pro Gly Asn Met Arg Phe Thr Leu Tyr Glu Asn Lys Asp
        35                  40                  45

Ser Thr Asn Pro Arg Lys Arg Asn Gln Arg Ile Leu Ala Ala Glu Thr
 50                  55                  60

Asp Arg Leu Ser Tyr Val Gly Asn Asn Phe Gly Thr Gly Ala Leu Lys
 65                  70                  75                  80

Cys Asn Thr Leu Cys Arg His Phe Val Gly Ile Leu Asn Lys Thr Ser
                85                  90                  95

Gly Gln Met Glu Val Tyr Asp Ala Glu Leu Phe Asn Met Gln Pro Leu
            100                 105                 110

Phe Ser Asp Val Ser Val Glu Ser Glu Leu Ala Leu Glu Ser Gln Thr
        115                 120                 125

Lys Thr Tyr Arg Glu Lys Met Asp Ser Cys Ile Glu Ala Phe Gly Thr
130                 135                 140

Thr Lys Gln Lys Arg Ala Leu Asn Thr Arg Arg Met Asn Arg Val Gly
145                 150                 155                 160

Asn Glu Ser Leu Asn Arg Ala Val Ala Lys Ala Ala Glu Thr Ile Ile
                165                 170                 175

Asp Thr Lys Gly Val Thr Ala Leu Val Ser Asp Ala Ile His Asn Asp
            180                 185                 190

Leu Gln Asp Asp Ser Leu Tyr Leu Pro Pro Cys Tyr Asp Asp Ala Ala
        195                 200                 205

Lys Pro Glu Asp Val Tyr Lys Phe Glu Asp Leu Leu Ser Pro Ala Glu
210                 215                 220

Tyr Glu Ala Leu Gln Ser Pro Ser Glu Ala Phe Arg Asn Val Thr Ser
225                 230                 235                 240

Glu Glu Ile Leu Lys Met Ile Glu Glu Asn Ser His Cys Thr Phe Val
                245                 250                 255

Ile Glu Ala Leu Lys Ser Leu Pro Ser Asp Val Glu Ser Arg Asp Arg
            260                 265                 270

Gln Ala Arg Cys Ile Trp Phe Leu Asp Thr Leu Ile Lys Phe Arg Ala
        275                 280                 285

His Arg Val Val Lys Arg Lys Ser Ala Leu Gly Pro Gly Val Pro His
290                 295                 300

Ile Ile Asn Thr Lys Leu Leu Lys His Phe Thr Cys Leu Thr Tyr Asn
305                 310                 315                 320

Asn Gly Arg Leu Arg Asn Leu Ile Ser Asp Ser Met Lys Ala Lys Ile
                325                 330                 335

Thr Ala Tyr Val Ile Ile Leu Ala Leu His Ile His Asp Phe Gln Ile
            340                 345                 350

Asp Leu Thr Val Leu Gln Arg Asp Leu Lys Leu Ser Glu Lys Arg Met
        355                 360                 365

Met Glu Ile Ala Lys Ala Met Arg Leu Lys Ile Ser Lys Arg Arg Val
370                 375                 380
```

Ser Val Ala Ala Gly Ser Glu Glu Asp His Lys Leu Gly Thr Leu Ser
385                 390                 395                 400

Leu Pro Leu Pro Pro Ala Gln Thr Ser Asp Arg Leu Ala Lys Arg Arg
            405                 410                 415

Lys Ile Thr

<210> SEQ ID NO 48
<211> LENGTH: 851
<212> TYPE: PRT
<213> ORGANISM: Homo sapiens

<400> SEQUENCE: 48

Met Ser Ser Lys Gln Glu Ile Met Ser Asp Gln Arg Phe Arg Arg Val
1               5                   10                  15

Ala Lys Asp Pro Arg Phe Trp Glu Met Pro Lys Asp Arg Lys Val
            20                  25                  30

Lys Ile Asp Lys Arg Phe Arg Ala Met Phe His Asp Lys Lys Phe Lys
        35                  40                  45

Leu Asn Tyr Ala Val Asp Lys Arg Gly Arg Pro Ile Ser His Ser Thr
    50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Lys Glu Ile Asp Ser Lys Asn Leu Val Glu
            100                 105                 110

Lys Lys Lys Glu Thr Lys Lys Ala Asn His Lys Gly Ser Glu Asn Lys
        115                 120                 125

Thr Asp Leu Asp Asn Ser Ile Gly Ile Lys Lys Met Lys Thr Ser Cys
130                 135                 140

Lys Phe Lys Ile Asp Ser Asn Ile Ser Pro Lys Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
        195                 200                 205

Glu Met Gln Ser Val Val Gln Leu Ile Met Thr Arg Asp Ser Asp Gly
210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255

Asn Glu Ile Thr Ser Val Gly Arg Ala Ser Gly Asp Asp Gly Ser
            260                 265                 270

Glu Asp Asp Glu Glu Glu Asp Glu Glu Glu Asp Glu Asp Glu
        275                 280                 285

Asp Ser Glu Asp Asp Lys Ser Asp Ser Gly Pro Asp Leu Ala Arg
290                 295                 300

Gly Lys Gly Asn Ile Glu Thr Ser Ser Glu Asp Glu Asp Thr Ala
305                 310                 315                 320

Asp Leu Phe Pro Glu Glu Ser Gly Phe Glu His Ala Trp Arg Glu Leu
                325                 330                 335

```
Asp Lys Asp Ala Pro Arg Ala Asp Glu Ile Thr Arg Arg Leu Ala Val
            340                 345                 350

Cys Asn Met Asp Trp Asp Arg Leu Lys Ala Lys Asp Leu Leu Ala Leu
            355                 360                 365

Phe Asn Ser Phe Lys Pro Lys Gly Gly Val Ile Phe Ser Val Lys Ile
            370                 375                 380

Tyr Pro Ser Glu Phe Gly Lys Glu Arg Met Lys Glu Glu Val Gln
385                 390                 395                 400

Gly Pro Val Glu Leu Leu Ser Ile Pro Glu Asp Ala Pro Glu Lys Asp
                405                 410                 415

Trp Thr Ser Arg Glu Lys Leu Arg Asp Tyr Gln Phe Lys Arg Leu Lys
                420                 425                 430

Tyr Tyr Tyr Ala Val Val Asp Cys Asp Ser Pro Glu Thr Ala Ser Lys
                435                 440                 445

Ile Tyr Glu Asp Cys Asp Gly Leu Glu Phe Glu Ser Ser Cys Ser Phe
                450                 455                 460

Ile Asp Leu Arg Phe Ile Pro Asp Asp Ile Thr Phe Asp Asp Glu Pro
465                 470                 475                 480

Lys Asp Val Ala Ser Glu Val Asn Leu Thr Ala Tyr Lys Pro Lys Tyr
                485                 490                 495

Phe Thr Ser Ala Ala Met Gly Thr Ser Thr Val Glu Ile Thr Trp Asp
                500                 505                 510

Glu Thr Asp His Glu Arg Ile Thr Met Leu Asn Arg Lys Phe Lys Lys
                515                 520                 525

Glu Glu Leu Leu Asp Met Asp Phe Gln Ala Tyr Leu Ala Ser Ser Ser
                530                 535                 540

Glu Asp Glu Glu Glu Ile Glu Glu Leu Gln Gly Asp Asp Gly Val
545                 550                 555                 560

Asn Val Glu Glu Asp Gly Lys Thr Lys Ser Gln Lys Asp Glu
                565                 570                 575

Glu Gln Ile Ala Lys Tyr Arg Gln Leu Leu Gln Val Ile Gln Glu Lys
                580                 585                 590

Glu Lys Lys Gly Lys Glu Asn Asp Met Glu Met Glu Ile Lys Trp Val
                595                 600                 605

Pro Gly Leu Lys Glu Ser Ala Glu Glu Met Val Lys Asn Lys Leu Glu
                610                 615                 620

Gly Lys Asp Lys Leu Thr Pro Trp Glu Gln Phe Leu Glu Lys Lys Lys
625                 630                 635                 640

Glu Lys Lys Arg Leu Lys Arg Lys Gln Lys Ala Leu Ala Glu Glu Ala
                645                 650                 655

Ser Glu Glu Glu Leu Pro Ser Asp Val Asp Leu Asn Asp Pro Tyr Phe
                660                 665                 670

Ala Glu Glu Val Lys Gln Ile Gly Ile Asn Lys Lys Ser Val Lys Ser
                675                 680                 685

Ala Lys Asp Gly Thr Ser Pro Glu Glu Ile Glu Ile Glu Arg Gln
                690                 695                 700

Lys Ala Glu Met Ala Leu Leu Met Met Asp Glu Asp Glu Asp Ser Lys
705                 710                 715                 720

Lys His Phe Asn Tyr Asn Lys Ile Val Glu His Gln Asn Leu Ser Lys
                725                 730                 735

Lys Lys Lys Lys Gln Leu Met Lys Lys Glu Leu Ile Glu Asp Asp
                740                 745                 750
```

```
Phe Glu Val Asn Val Asn Asp Ala Arg Phe Gln Ala Met Tyr Thr Ser
            755                 760                 765

His Leu Phe Asn Leu Asp Pro Ser Asp Pro Asn Phe Lys Lys Thr Lys
            770                 775                 780

Ala Met Glu Lys Ile Leu Glu Lys Ala Arg Gln Arg Glu Arg Lys
785                 790                 795                 800

Glu Gln Glu Leu Thr Gln Ala Ile Lys Lys Glu Ser Glu Ile Glu
            805                 810                 815

Lys Glu Ser Gln Arg Lys Ser Ile Asp Pro Ala Leu Ser Met Leu Ile
            820                 825                 830

Lys Ser Ile Lys Thr Lys Thr Glu Gln Phe Gln Ala Arg Lys Lys Gln
            835                 840                 845

Lys Val Lys
    850

<210> SEQ ID NO 49
<211> LENGTH: 851
<212> TYPE: PRT
<213> ORGANISM: Homo sapiens

<400> SEQUENCE: 49

Met Ser Ser Lys Gln Glu Ile Met Ser Asp Gln Arg Phe Arg Arg Val
1               5                   10                  15

Ala Lys Asp Pro Arg Phe Trp Glu Met Pro Gly Lys Asp Arg Lys Val
            20                  25                  30

Lys Ile Asp Lys Arg Phe Arg Ala Met Phe His Asp Lys Lys Phe Lys
            35                  40                  45

Leu Asn Tyr Ala Val Asp Lys Arg Gly Arg Pro Ile Ser His Ser Thr
    50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Lys Glu Ile Asp Ser Lys Asn Leu Val Glu
            100                 105                 110

Lys Lys Lys Glu Thr Lys Lys Ala Asn His Lys Gly Ser Glu Asn Lys
            115                 120                 125

Thr Asp Leu Asp Asn Ser Ile Gly Ile Lys Lys Met Lys Thr Ser Cys
    130                 135                 140

Lys Phe Lys Ile Asp Ser Asn Ile Ser Pro Lys Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
            195                 200                 205

Glu Met Gln Ser Val Val Gln Leu Ile Met Thr Arg Asp Ser Asp Gly
    210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255

Asn Glu Ile Thr Ser Val Gly Arg Ala Ser Gly Asp Asp Gly Ser
            260                 265                 270
```

-continued

```
Glu Asp Asp Glu Glu Asp Glu Asp Glu Glu Asp Glu Asp Glu
        275                 280                 285
Asp Ser Glu Asp Asp Lys Ser Asp Ser Gly Pro Asp Leu Ala Arg
    290                 295                 300
Gly Lys Gly Asn Ile Glu Thr Ser Ser Glu Asp Glu Asp Thr Ala
305                 310                 315                 320
Asp Leu Phe Pro Glu Glu Ser Gly Phe Glu His Ala Trp Arg Glu Leu
                325                 330                 335
Asp Lys Asp Ala Pro Arg Ala Asp Glu Ile Thr Arg Arg Leu Ala Val
            340                 345                 350
Cys Asn Met Asp Trp Asp Arg Leu Lys Ala Lys Asp Leu Leu Ala Leu
            355                 360                 365
Phe Asn Ser Phe Lys Pro Lys Gly Gly Val Ile Phe Ser Val Lys Ile
    370                 375                 380
Tyr Pro Ser Glu Phe Gly Lys Glu Arg Met Lys Glu Glu Gln Val Gln
385                 390                 395                 400
Gly Pro Val Glu Leu Leu Ser Ile Pro Glu Asp Ala Pro Glu Lys Asp
                405                 410                 415
Trp Thr Ser Arg Glu Lys Leu Arg Asp Tyr Gln Phe Lys Arg Leu Lys
            420                 425                 430
Tyr Tyr Tyr Ala Val Val Asp Cys Asp Ser Pro Glu Thr Ala Ser Lys
            435                 440                 445
Ile Tyr Glu Asp Cys Asp Gly Leu Glu Phe Glu Ser Ser Cys Ser Phe
    450                 455                 460
Ile Asp Leu Arg Phe Ile Pro Asp Ile Thr Phe Asp Glu Pro
465                 470                 475                 480
Lys Asp Val Ala Ser Glu Val Asn Leu Thr Ala Tyr Lys Pro Lys Tyr
                485                 490                 495
Phe Thr Ser Ala Ala Met Gly Thr Ser Thr Val Glu Ile Thr Trp Asp
            500                 505                 510
Glu Thr Asp His Glu Arg Ile Thr Met Leu Asn Arg Lys Phe Lys Lys
            515                 520                 525
Glu Glu Leu Leu Asp Met Asp Phe Gln Ala Tyr Leu Ala Ser Ser Ser
    530                 535                 540
Glu Asp Glu Glu Glu Ile Glu Glu Glu Leu Gln Gly Asp Asp Gly Val
545                 550                 555                 560
Asn Val Glu Glu Asp Gly Lys Thr Lys Lys Ser Gln Lys Asp Asp Glu
                565                 570                 575
Glu Gln Ile Ala Lys Tyr Arg Gln Leu Leu Gln Val Ile Gln Glu Lys
            580                 585                 590
Glu Lys Lys Gly Lys Glu Asn Asp Met Glu Met Glu Ile Lys Trp Val
            595                 600                 605
Pro Gly Leu Lys Glu Ser Ala Glu Glu Met Val Lys Asn Lys Leu Glu
    610                 615                 620
Gly Lys Asp Lys Leu Thr Pro Trp Glu Gln Phe Leu Glu Lys Lys Lys
625                 630                 635                 640
Glu Lys Lys Arg Leu Lys Arg Lys Gln Lys Ala Leu Ala Glu Glu Ala
                645                 650                 655
Ser Glu Glu Glu Leu Pro Ser Asp Val Asp Leu Asn Asp Pro Tyr Phe
            660                 665                 670
Ala Glu Glu Val Lys Gln Ile Gly Ile Asn Lys Lys Ser Val Lys Ser
            675                 680                 685
```

```
Ala Lys Asp Gly Thr Ser Pro Glu Glu Ile Glu Ile Glu Arg Gln
    690                 695                 700
Lys Ala Glu Met Ala Leu Leu Met Met Asp Glu Asp Glu Asp Ser Lys
705                 710                 715                 720
Lys His Phe Asn Tyr Asn Lys Ile Val Glu His Gln Asn Leu Ser Lys
                    725                 730                 735
Lys Lys Lys Lys Gln Leu Met Lys Lys Glu Leu Ile Glu Asp Asp
                740                 745                 750
Phe Glu Val Asn Val Asn Asp Ala Arg Phe Gln Ala Met Tyr Thr Ser
                755                 760                 765
His Leu Phe Asn Leu Asp Pro Ser Asp Pro Asn Phe Lys Lys Thr Lys
770                 775                 780
Ala Met Glu Lys Ile Leu Glu Glu Lys Ala Arg Gln Arg Glu Arg Lys
785                 790                 795                 800
Glu Gln Glu Leu Thr Gln Ala Ile Lys Lys Lys Glu Ser Glu Ile Glu
                805                 810                 815
Lys Glu Ser Gln Arg Lys Ser Ile Asp Pro Ala Leu Ser Met Leu Ile
                820                 825                 830
Lys Ser Ile Lys Thr Lys Thr Glu Gln Phe Gln Ala Arg Lys Lys Gln
                835                 840                 845
Lys Val Lys
    850

<210> SEQ ID NO 50
<211> LENGTH: 450
<212> TYPE: PRT
<213> ORGANISM: Homo sapiens

<400> SEQUENCE: 50

Met Ser Asp Phe Ser Glu Glu Leu Lys Gly Pro Val Thr Asp Asp Glu
1               5                   10                  15
Glu Val Glu Thr Ser Val Leu Ser Gly Ala Gly Met His Phe Pro Trp
                20                  25                  30
Leu Gln Thr Tyr Val Glu Thr Val Ala Ile Gly Gly Lys Arg Arg Lys
                35                  40                  45
Asp Phe Ala Gln Thr Thr Ser Ala Cys Leu Ser Phe Ile Gln Glu Ala
    50                  55                  60
Leu Leu Lys His Gln Trp Gln Gln Ala Glu Tyr Met Tyr Ser Tyr
65                  70                  75                  80
Phe Gln Thr Leu Glu Asp Ser Asp Ser Tyr Lys Arg Gln Ala Ala Pro
                85                  90                  95
Glu Ile Ile Trp Lys Leu Gly Ser Glu Ile Leu Phe Tyr His Pro Lys
                100                 105                 110
Ser Asn Met Glu Ser Phe Asn Thr Phe Ala Asn Arg Met Lys Asn Ile
                115                 120                 125
Gly Val Met Asn Tyr Leu Lys Ile Ser Leu Gln His Ala Leu Tyr Leu
            130                 135                 140
Leu His His Gly Met Leu Lys Asp Ala Lys Arg Asn Leu Ser Glu Ala
145                 150                 155                 160
Glu Thr Trp Arg His Gly Glu Asn Thr Ser Arg Glu Ile Leu Ile
                165                 170                 175
Asn Leu Ile Gln Ala Tyr Lys Gly Leu Leu Gln Tyr Tyr Thr Trp Ser
                180                 185                 190
Glu Lys Lys Met Glu Leu Ser Lys Leu Asp Lys Asp Asp Tyr Ala Tyr
                195                 200                 205
```

Asn Ala Val Ala Gln Asp Val Phe Asn His Ser Trp Lys Thr Ser Ala
            210                 215                 220

Asn Ile Ser Ala Leu Ile Lys Ile Pro Gly Val Trp Asp Pro Phe Val
225                 230                 235                 240

Lys Ser Tyr Val Glu Met Leu Glu Phe Tyr Gly Asp Arg Asp Gly Ala
                245                 250                 255

Gln Glu Val Leu Thr Asn Tyr Ala Tyr Asp Glu Lys Phe Pro Ser Asn
            260                 265                 270

Pro Asn Ala His Ile Tyr Leu Tyr Asn Phe Leu Lys Arg Gln Lys Ala
            275                 280                 285

Pro Arg Ser Lys Leu Ile Ser Val Leu Lys Ile Leu Tyr Gln Ile Val
            290                 295                 300

Pro Ser His Lys Leu Met Leu Glu Phe His Thr Leu Arg Lys Ser
305                 310                 315                 320

Glu Lys Glu Glu His Arg Lys Leu Gly Leu Glu Val Leu Phe Gly Val
                325                 330                 335

Leu Asp Phe Ala Gly Cys Thr Lys Asn Ile Thr Ala Trp Lys Tyr Leu
            340                 345                 350

Ala Lys Tyr Leu Lys Asn Ile Leu Met Gly Asn His Leu Ala Trp Val
            355                 360                 365

Gln Glu Glu Trp Asn Ser Arg Lys Asn Trp Trp Pro Gly Phe His Phe
370                 375                 380

Ser Tyr Phe Trp Ala Lys Ser Asp Trp Lys Glu Asp Thr Ala Leu Ala
385                 390                 395                 400

Cys Glu Lys Ala Phe Val Ala Gly Leu Leu Leu Gly Lys Gly Cys Arg
                405                 410                 415

Tyr Phe Arg Tyr Ile Leu Lys Gln Asp His Gln Ile Leu Gly Lys Lys
            420                 425                 430

Ile Lys Arg Met Lys Arg Ser Val Lys Lys Tyr Ser Ile Val Asn Pro
            435                 440                 445

Arg Leu
    450

<210> SEQ ID NO 51
<211> LENGTH: 450
<212> TYPE: PRT
<213> ORGANISM: Homo sapiens

<400> SEQUENCE: 51

Met Ser Asp Phe Ser Glu Glu Leu Lys Gly Pro Val Thr Asp Asp Glu
1               5                   10                  15

Glu Val Glu Thr Ser Val Leu Ser Gly Ala Gly Met His Phe Pro Trp
            20                  25                  30

Leu Gln Thr Tyr Val Glu Thr Val Ala Ile Gly Gly Lys Arg Arg Lys
            35                  40                  45

Asp Phe Ala Gln Thr Thr Ser Ala Cys Leu Ser Phe Ile Gln Glu Ala
        50                  55                  60

Leu Leu Lys His Gln Trp Gln Gln Ala Ala Glu Tyr Met Tyr Ser Tyr
65                  70                  75                  80

Phe Gln Thr Leu Glu Asp Ser Asp Ser Tyr Lys Arg Gln Ala Ala Pro
                85                  90                  95

Glu Ile Ile Trp Lys Leu Gly Ser Glu Ile Leu Phe Tyr His Pro Lys
            100                 105                 110

Ser Asn Met Glu Ser Phe Asn Thr Phe Ala Asn Arg Met Lys Asn Ile

```
                115                 120                 125
Gly Val Met Asn Tyr Leu Lys Ile Ser Leu Gln His Ala Leu Tyr Leu
        130                 135                 140

Leu His His Gly Met Leu Lys Asp Ala Lys Arg Asn Leu Ser Glu Ala
145                 150                 155                 160

Glu Thr Trp Arg His Gly Glu Asn Thr Ser Arg Glu Ile Leu Ile
                165                 170                 175

Asn Leu Ile Gln Ala Tyr Lys Gly Leu Leu Gln Tyr Tyr Thr Trp Ser
                180                 185                 190

Glu Lys Lys Met Glu Leu Ser Lys Leu Asp Lys Asp Tyr Ala Tyr
            195                 200                 205

Asn Ala Val Ala Gln Asp Val Phe Asn His Ser Trp Lys Thr Ser Ala
        210                 215                 220

Asn Ile Ser Ala Leu Ile Lys Ile Pro Gly Val Trp Asp Pro Phe Val
225                 230                 235                 240

Lys Ser Tyr Val Glu Met Leu Glu Phe Tyr Gly Asp Arg Asp Gly Ala
                245                 250                 255

Gln Glu Val Leu Thr Asn Tyr Ala Tyr Asp Glu Lys Phe Pro Ser Asn
            260                 265                 270

Pro Asn Ala His Ile Tyr Leu Tyr Asn Phe Leu Lys Arg Gln Lys Ala
        275                 280                 285

Pro Arg Ser Lys Leu Ile Ser Val Leu Lys Ile Leu Tyr Gln Ile Val
        290                 295                 300

Pro Ser His Lys Leu Met Leu Glu Phe His Thr Leu Leu Arg Lys Ser
305                 310                 315                 320

Glu Lys Glu Glu His Arg Lys Leu Gly Leu Glu Val Leu Phe Gly Val
                325                 330                 335

Leu Asp Phe Ala Gly Cys Thr Lys Asn Ile Thr Ala Trp Lys Tyr Leu
                340                 345                 350

Ala Lys Tyr Leu Lys Asn Ile Leu Met Gly Asn His Leu Ala Trp Val
            355                 360                 365

Gln Glu Glu Trp Asn Ser Arg Lys Asn Trp Trp Pro Gly Phe His Phe
        370                 375                 380

Ser Tyr Phe Trp Ala Lys Ser Asp Trp Lys Glu Asp Thr Ala Leu Ala
385                 390                 395                 400

Cys Glu Lys Ala Phe Val Ala Gly Leu Leu Gly Lys Gly Cys Arg
                405                 410                 415

Tyr Phe Arg Tyr Ile Leu Lys Gln Asp His Gln Ile Leu Gly Lys Lys
            420                 425                 430

Ile Lys Arg Met Lys Arg Ser Val Lys Lys Tyr Ser Ile Val Asn Pro
        435                 440                 445

Arg Leu
    450

<210> SEQ ID NO 52
<211> LENGTH: 336
<212> TYPE: PRT
<213> ORGANISM: Homo sapiens

<400> SEQUENCE: 52

Met Glu Ser Phe Asn Thr Phe Ala Asn Arg Met Lys Asn Ile Gly Val
1               5                   10                  15

Met Asn Tyr Leu Lys Ile Ser Leu Gln His Ala Leu Tyr Leu Leu His
            20                  25                  30
```

His Gly Met Leu Lys Asp Ala Lys Arg Asn Leu Ser Glu Ala Glu Thr
            35                  40                  45

Trp Arg His Gly Glu Asn Thr Ser Ser Arg Glu Ile Leu Ile Asn Leu
 50                  55                  60

Ile Gln Ala Tyr Lys Gly Leu Leu Gln Tyr Tyr Thr Trp Ser Glu Lys
 65                  70                  75                  80

Lys Met Glu Leu Ser Lys Leu Asp Lys Asp Asp Tyr Ala Tyr Asn Ala
                 85                  90                  95

Val Ala Gln Asp Val Phe Asn His Ser Trp Lys Thr Ser Ala Asn Ile
                100                 105                 110

Ser Ala Leu Ile Lys Ile Pro Gly Val Trp Asp Pro Phe Val Lys Ser
                115                 120                 125

Tyr Val Glu Met Leu Glu Phe Tyr Gly Asp Arg Asp Gly Ala Gln Glu
130                 135                 140

Val Leu Thr Asn Tyr Ala Tyr Asp Glu Lys Phe Pro Ser Asn Pro Asn
145                 150                 155                 160

Ala His Ile Tyr Leu Tyr Asn Phe Leu Lys Arg Gln Lys Ala Pro Arg
                165                 170                 175

Ser Lys Leu Ile Ser Val Leu Lys Ile Leu Tyr Gln Ile Val Pro Ser
                180                 185                 190

His Lys Leu Met Leu Glu Phe His Thr Leu Leu Arg Lys Ser Glu Lys
                195                 200                 205

Glu Glu His Arg Lys Leu Gly Leu Glu Val Leu Phe Gly Val Leu Asp
                210                 215                 220

Phe Ala Gly Cys Thr Lys Asn Ile Thr Ala Trp Lys Tyr Leu Ala Lys
225                 230                 235                 240

Tyr Leu Lys Asn Ile Leu Met Gly Asn His Leu Ala Trp Val Gln Glu
                245                 250                 255

Glu Trp Asn Ser Arg Lys Asn Trp Trp Pro Gly Phe His Phe Ser Tyr
                260                 265                 270

Phe Trp Ala Lys Ser Asp Trp Lys Glu Asp Thr Ala Leu Ala Cys Glu
                275                 280                 285

Lys Ala Phe Val Ala Gly Leu Leu Gly Lys Gly Cys Arg Tyr Phe
                290                 295                 300

Arg Tyr Ile Leu Lys Gln Asp His Gln Ile Leu Gly Lys Lys Ile Lys
305                 310                 315                 320

Arg Met Lys Arg Ser Val Lys Lys Tyr Ser Ile Val Asn Pro Arg Leu
                325                 330                 335

<210> SEQ ID NO 53
<211> LENGTH: 588
<212> TYPE: PRT
<213> ORGANISM: Homo sapiens

<400> SEQUENCE: 53

Met Asp Leu Glu Glu Ala Glu Glu Phe Lys Glu Arg Cys Thr Gln Cys
 1               5                  10                  15

Ala Ala Val Ser Trp Gly Leu Thr Asp Glu Gly Lys Tyr Tyr Cys Thr
                 20                  25                  30

Ser Cys His Asn Val Thr Glu Arg Tyr Gln Glu Val Thr Asn Thr Asp
                 35                  40                  45

Leu Ile Pro Asn Thr Gln Ile Lys Ala Leu Asn Arg Gly Leu Lys Lys
 50                  55                  60

Lys Asn Asn Thr Glu Lys Gly Trp Asp Trp Tyr Val Cys Glu Gly Phe
 65                  70                  75                  80

-continued

```
Gln Tyr Ile Leu Tyr Gln Gln Ala Glu Ala Leu Lys Asn Leu Gly Val
                 85                  90                  95
Gly Pro Glu Leu Lys Asn Asp Val Leu His Asn Phe Trp Lys Arg Tyr
            100                 105                 110
Leu Gln Lys Ser Lys Gln Ala Tyr Cys Lys Asn Pro Val Tyr Thr Thr
        115                 120                 125
Gly Arg Lys Pro Thr Val Leu Glu Asp Asn Leu Ser His Ser Asp Trp
    130                 135                 140
Ala Ser Glu Pro Glu Leu Leu Ser Asp Val Ser Cys Pro Pro Phe Leu
145                 150                 155                 160
Glu Ser Gly Ala Glu Ser Gln Ser Asp Ile His Thr Arg Lys Pro Phe
                165                 170                 175
Pro Val Ser Lys Ala Ser Gln Ser Glu Thr Ser Val Cys Ser Gly Ser
            180                 185                 190
Leu Asp Gly Val Glu Tyr Ser Gln Arg Lys Glu Lys Gly Ile Val Lys
        195                 200                 205
Met Thr Met Pro Gln Thr Leu Ala Phe Cys Tyr Leu Ser Leu Leu Trp
    210                 215                 220
Gln Arg Glu Ala Ile Thr Leu Ser Asp Leu Leu Arg Phe Val Glu Glu
225                 230                 235                 240
Asp His Ile Pro Tyr Ile Asn Ala Phe Gln His Phe Pro Glu Gln Met
                245                 250                 255
Lys Leu Tyr Gly Arg Asp Arg Gly Ile Phe Gly Ile Glu Ser Trp Pro
            260                 265                 270
Asp Tyr Glu Asp Ile Tyr Lys Lys Thr Ile Glu Val Gly Thr Phe Leu
        275                 280                 285
Asp Leu Pro Arg Phe Pro Asp Ile Thr Glu Asp Cys Tyr Leu His Pro
    290                 295                 300
Asn Ile Leu Cys Met Lys Tyr Leu Met Glu Val Asn Leu Pro Asp Glu
305                 310                 315                 320
Met His Ser Leu Thr Cys His Val Val Lys Met Thr Gly Met Gly Glu
                325                 330                 335
Val Asp Phe Leu Thr Phe Asp Pro Ile Ala Lys Met Ala Lys Thr Val
            340                 345                 350
Lys Tyr Asp Val Gln Ala Val Ala Ile Ile Val Val Leu Lys Leu
        355                 360                 365
Leu Phe Leu Leu Asp Asp Ser Phe Glu Trp Ser Leu Ser Asn Leu Ala
    370                 375                 380
Glu Lys His Asn Glu Lys Asn Lys Lys Asp Lys Pro Trp Phe Asp Phe
385                 390                 395                 400
Arg Lys Trp Tyr Gln Ile Met Lys Lys Ala Phe Asp Glu Lys Lys Gln
                405                 410                 415
Lys Trp Glu Glu Ala Arg Ala Lys Tyr Leu Trp Lys Ser Glu Lys Pro
            420                 425                 430
Leu Tyr Tyr Ser Phe Val Asp Lys Pro Val Ala Tyr Lys Lys Arg Glu
        435                 440                 445
Met Val Val Asn Leu Gln Lys Gln Phe Ser Thr Leu Val Glu Ser Thr
    450                 455                 460
Ala Thr Ala Gly Lys Lys Ser Pro Ser Ser Phe Gln Phe Asn Trp Thr
465                 470                 475                 480
Glu Glu Asp Thr Asp Arg Thr Cys Phe His Gly His Ser Leu Gln Gly
                485                 490                 495
```

Val Leu Lys Glu Lys Gly Gln Ser Leu Leu Thr Lys Asn Ser Leu Tyr
                500                 505                 510

Trp Leu Ser Thr Gln Lys Phe Cys Arg Cys Tyr Cys Thr His Val Thr
            515                 520                 525

Thr Tyr Glu Glu Ser Asn Tyr Ser Leu Ser Tyr Gln Phe Ile Leu Asn
        530                 535                 540

Leu Phe Ser Phe Leu Leu Arg Ile Lys Thr Ser Leu Leu His Glu Glu
545                 550                 555                 560

Val Ser Leu Val Glu Lys Lys Leu Phe Glu Lys Lys Tyr Ser Val Lys
                565                 570                 575

Arg Lys Lys Ser Arg Ser Lys Lys Val Arg Arg His
                580                 585

<210> SEQ ID NO 54
<211> LENGTH: 843
<212> TYPE: PRT
<213> ORGANISM: Homo sapiens

<400> SEQUENCE: 54

Met Asp Phe Pro Ser Ser Leu Arg Pro Ala Leu Phe Leu Thr Gly Pro
1               5                   10                  15

Leu Gly Leu Ser Asp Val Pro Asp Leu Ser Phe Met Cys Ser Trp Arg
                20                  25                  30

Asp Ala Leu Thr Leu Pro Glu Ala Gln Pro Gln Asn Ser Glu Asn Gly
            35                  40                  45

Ala Leu His Val Thr Lys Asp Leu Leu Trp Glu Pro Ala Thr Pro Gly
        50                  55                  60

Pro Leu Pro Met Leu Pro Pro Leu Ile Asp Pro Trp Asp Pro Gly Leu
65                  70                  75                  80

Thr Ala Arg Asp Leu Leu Phe Arg Gly Gly Tyr Arg Tyr Arg Lys Arg
                85                  90                  95

Pro Arg Val Val Leu Asp Val Thr Glu Gln Ile Ser Arg Phe Leu Leu
                100                 105                 110

Asp His Gly Asp Val Ala Phe Ala Pro Leu Gly Lys Leu Met Leu Glu
            115                 120                 125

Asn Phe Lys Leu Glu Gly Ala Gly Ser Arg Thr Lys Lys Lys Thr Val
        130                 135                 140

Val Ser Val Lys Lys Leu Leu Gln Asp Leu Gly Gly His Gln Pro Trp
145                 150                 155                 160

Gly Cys Pro Trp Ala Tyr Leu Ser Asn Arg Gln Arg Arg Phe Ser Ile
                165                 170                 175

Leu Gly Gly Pro Ile Leu Gly Thr Ser Val Ala Ser His Leu Ala Glu
                180                 185                 190

Leu Leu His Glu Glu Leu Val Leu Arg Trp Gln Leu Leu Leu Leu Asp
            195                 200                 205

Glu Ala Cys Thr Gly Gly Ala Leu Ala Trp Val Pro Gly Arg Thr Pro
        210                 215                 220

Gln Phe Gly Gln Leu Val Tyr Pro Ala Gly Gly Ala Gln Asp Arg Leu
225                 230                 235                 240

His Phe Gln Glu Val Leu Thr Pro Gly Asp Asn Pro Gln Phe Leu
                245                 250                 255

Gly Lys Pro Gly Arg Ile Gln Leu Gln Gly Pro Val Arg Gln Val Val
                260                 265                 270

Thr Cys Thr Val Gln Gly Glu Thr Leu Leu Ala Val Arg Ser Asp Tyr
            275                 280                 285

```
His Cys Ala Val Trp Lys Phe Gly Lys Gln Trp Gln Pro Thr Leu Leu
    290                 295                 300
Gln Ala Met Gln Val Glu Lys Gly Ala Thr Gly Ile Ser Leu Ser Pro
305                 310                 315                 320
His Leu Pro Gly Glu Leu Ala Ile Cys Ser Arg Ser Gly Ala Val Cys
                325                 330                 335
Leu Trp Ser Pro Glu Asp Gly Leu Arg Gln Ile Tyr Arg Asp Pro Glu
                340                 345                 350
Thr Leu Val Phe Arg Asp Ser Ser Trp Arg Trp Ala Asp Phe Thr
                355                 360                 365
Ala His Pro Arg Val Leu Thr Val Gly Asp Arg Thr Gly Val Lys Met
    370                 375                 380
Leu Asp Thr Gln Gly Pro Pro Gly Cys Gly Leu Leu Leu Phe Arg Leu
385                 390                 395                 400
Gly Ala Glu Ala Ser Cys Gln Lys Gly Glu Arg Val Leu Leu Thr Gln
                405                 410                 415
Tyr Leu Gly His Ser Ser Pro Lys Cys Leu Pro Pro Thr Leu His Leu
                420                 425                 430
Val Cys Thr Gln Phe Ser Leu Tyr Leu Val Asp Glu Arg Leu Pro Leu
    435                 440                 445
Val Pro Met Leu Lys Trp Asn His Gly Leu Pro Ser Pro Leu Leu Leu
450                 455                 460
Ala Arg Leu Leu Pro Pro Arg Pro Ser Cys Val Gln Pro Leu Leu
465                 470                 475                 480
Leu Gly Gly Gln Gly Gly Gln Leu Gln Leu His Leu Ala Gly Glu
                485                 490                 495
Gly Ala Ser Val Pro Arg Leu Ala Gly Pro Pro Gln Ser Leu Pro Ser
                500                 505                 510
Arg Ile Asp Ser Leu Pro Ala Phe Pro Leu Leu Glu Pro Lys Ile Gln
                515                 520                 525
Trp Arg Leu Gln Glu Arg Leu Lys Ala Pro Thr Ile Gly Leu Ala Ala
    530                 535                 540
Val Val Pro Pro Leu Pro Ser Ala Pro Thr Pro Gly Leu Val Leu Phe
545                 550                 555                 560
Gln Leu Ser Ala Ala Gly Asp Val Phe Tyr Gln Gln Leu Arg Pro Gln
                565                 570                 575
Val Asp Ser Ser Leu Arg Arg Asp Ala Gly Pro Pro Gly Asp Thr Gln
                580                 585                 590
Pro Asp Cys His Ala Pro Thr Ala Ser Trp Thr Ser Gln Asp Thr Ala
        595                 600                 605
Gly Cys Ser Gln Trp Leu Lys Ala Leu Leu Lys Val Pro Leu Ala Pro
    610                 615                 620
Pro Val Trp Thr Ala Pro Thr Phe Thr His Arg Gln Met Leu Gly Ser
625                 630                 635                 640
Thr Glu Leu Arg Arg Glu Glu Glu Gly Gln Arg Leu Gly Val Leu
                645                 650                 655
Arg Lys Ala Met Ala Arg Gly Gln Leu Leu Leu Gln Arg Asp Leu Gly
                660                 665                 670
Ser Leu Pro Ala Ala Glu Pro Pro Ala Pro Glu Ser Gly Leu Glu
        675                 680                 685
Asp Lys Leu Ser Glu Arg Leu Gly Glu Ala Trp Ala Gly Arg Gly Ala
    690                 695                 700
```

```
Ala Trp Trp Glu Arg Gln Gln Gly Arg Thr Ser Glu Pro Gly Arg Gln
705                 710                 715                 720

Thr Arg Arg Pro Lys Arg Arg Thr Gln Leu Ser Ser Ser Phe Ser Leu
            725                 730                 735

Ser Gly His Val Asp Pro Ser Glu Asp Thr Ser Ser Pro His Ser Pro
            740                 745                 750

Glu Trp Pro Pro Ala Asp Ala Leu Pro Leu Pro Thr Thr Pro Pro Pro
        755                 760                 765

Ser Gln Glu Leu Thr Pro Asp Ala Cys Ala Gln Gly Val Pro Ser Glu
    770                 775                 780

Gln Arg Gln Met Leu Arg Asp Tyr Met Ala Lys Leu Pro Pro Gln Arg
785                 790                 795                 800

Asp Thr Pro Gly Cys Ala Thr Thr Pro His Ser Gln Ala Ser Ser
            805                 810                 815

Val Arg Ala Thr Arg Ser Gln Gln His Thr Pro Val Leu Ser Ser Ser
            820                 825                 830

Gln Pro Leu Arg Lys Lys Pro Arg Met Gly Phe
            835                 840

<210> SEQ ID NO 55
<211> LENGTH: 537
<212> TYPE: PRT
<213> ORGANISM: Homo sapiens

<400> SEQUENCE: 55

Met Gln Val Glu Lys Gly Ala Thr Gly Ile Ser Leu Ser Pro His Leu
1               5                   10                  15

Pro Gly Glu Leu Ala Ile Cys Ser Arg Ser Gly Ala Val Cys Leu Trp
            20                  25                  30

Ser Pro Glu Asp Gly Leu Arg Gln Ile Tyr Arg Asp Pro Glu Thr Leu
        35                  40                  45

Val Phe Arg Asp Ser Ser Ser Trp Arg Trp Ala Asp Phe Thr Ala His
    50                  55                  60

Pro Arg Val Leu Thr Val Gly Asp Arg Thr Gly Val Lys Met Leu Asp
65                  70                  75                  80

Thr Gln Gly Pro Pro Gly Cys Gly Leu Leu Leu Phe Arg Leu Gly Ala
                85                  90                  95

Glu Ala Ser Cys Gln Lys Gly Glu Arg Val Leu Leu Thr Gln Tyr Leu
            100                 105                 110

Gly His Ser Ser Pro Lys Cys Leu Pro Pro Thr Leu His Leu Val Cys
        115                 120                 125

Thr Gln Phe Ser Leu Tyr Leu Val Asp Glu Arg Leu Pro Leu Val Pro
    130                 135                 140

Met Leu Lys Trp Asn His Gly Leu Pro Ser Pro Leu Leu Ala Arg
145                 150                 155                 160

Leu Leu Pro Pro Arg Pro Ser Cys Val Gln Pro Leu Leu Leu Gly
                165                 170                 175

Gly Gln Gly Gly Gln Leu Gln Leu Leu His Leu Ala Gly Glu Gly Ala
            180                 185                 190

Ser Val Pro Arg Leu Ala Gly Pro Pro Gln Ser Leu Pro Ser Arg Ile
        195                 200                 205

Asp Ser Leu Pro Ala Phe Pro Leu Leu Glu Pro Lys Ile Gln Trp Arg
    210                 215                 220

Leu Gln Glu Arg Leu Lys Ala Pro Thr Ile Gly Leu Ala Ala Val Val
225                 230                 235                 240
```

-continued

```
Pro Pro Leu Pro Ser Ala Pro Thr Pro Gly Leu Val Leu Phe Gln Leu
            245                 250                 255

Ser Ala Ala Gly Asp Val Phe Tyr Gln Leu Arg Pro Gln Val Asp
            260                 265                 270

Ser Ser Leu Arg Arg Asp Ala Gly Pro Gly Asp Thr Gln Pro Asp
            275                 280                 285

Cys His Ala Pro Thr Ala Ser Trp Thr Ser Gln Asp Thr Ala Gly Cys
            290                 295                 300

Ser Gln Trp Leu Lys Ala Leu Leu Lys Val Pro Leu Ala Pro Pro Val
305                 310                 315                 320

Trp Thr Ala Pro Thr Phe Thr His Arg Gln Met Leu Gly Ser Thr Glu
            325                 330                 335

Leu Arg Arg Glu Glu Glu Gly Gln Arg Leu Gly Val Leu Arg Lys
            340                 345                 350

Ala Met Ala Arg Gly Gln Leu Leu Gln Arg Asp Leu Gly Ser Leu
            355                 360                 365

Pro Ala Ala Glu Pro Pro Ala Pro Glu Ser Gly Leu Glu Asp Lys
            370                 375                 380

Leu Ser Glu Arg Leu Gly Glu Ala Trp Ala Gly Arg Gly Ala Ala Trp
385                 390                 395                 400

Trp Glu Arg Gln Gln Gly Arg Thr Ser Glu Pro Gly Arg Gln Thr Arg
            405                 410                 415

Arg Pro Lys Arg Arg Thr Gln Leu Ser Ser Ser Phe Ser Leu Ser Gly
            420                 425                 430

His Val Asp Pro Ser Glu Asp Thr Ser Ser Pro His Ser Pro Glu Trp
            435                 440                 445

Pro Pro Ala Asp Ala Leu Pro Leu Pro Pro Thr Thr Pro Pro Ser Gln
            450                 455                 460

Glu Leu Thr Pro Asp Ala Cys Ala Gln Gly Val Pro Ser Glu Gln Arg
465                 470                 475                 480

Gln Met Leu Arg Asp Tyr Met Ala Lys Leu Pro Pro Gln Arg Asp Thr
            485                 490                 495

Pro Gly Cys Ala Thr Thr Pro Pro His Ser Gln Ala Ser Ser Val Arg
            500                 505                 510

Ala Thr Arg Ser Gln Gln His Thr Pro Val Leu Ser Ser Ser Gln Pro
            515                 520                 525

Leu Arg Lys Lys Pro Arg Met Gly Phe
            530                 535
```

<210> SEQ ID NO 56
<211> LENGTH: 537
<212> TYPE: PRT
<213> ORGANISM: Homo sapiens

<400> SEQUENCE: 56

```
Met Gln Val Glu Lys Gly Ala Thr Gly Ile Ser Leu Ser Pro His Leu
1               5                   10                  15

Pro Gly Glu Leu Ala Ile Cys Ser Arg Ser Gly Ala Val Cys Leu Trp
            20                  25                  30

Ser Pro Glu Asp Gly Leu Arg Gln Ile Tyr Arg Asp Pro Glu Thr Leu
            35                  40                  45

Val Phe Arg Asp Ser Ser Ser Trp Arg Trp Ala Asp Phe Thr Ala His
        50                  55                  60

Pro Arg Val Leu Thr Val Gly Asp Arg Thr Gly Val Lys Met Leu Asp
```

```
                65                  70                  75                  80
Thr Gln Gly Pro Pro Gly Cys Gly Leu Leu Leu Phe Arg Leu Gly Ala
                        85                  90                  95

Glu Ala Ser Cys Gln Lys Gly Glu Arg Val Leu Leu Thr Gln Tyr Leu
               100                 105                 110

Gly His Ser Ser Pro Lys Cys Leu Pro Pro Thr Leu His Leu Val Cys
               115                 120                 125

Thr Gln Phe Ser Leu Tyr Leu Val Asp Glu Arg Leu Pro Leu Val Pro
               130                 135                 140

Met Leu Lys Trp Asn His Gly Leu Pro Ser Pro Leu Leu Leu Ala Arg
145                 150                 155                 160

Leu Leu Pro Pro Arg Pro Ser Cys Val Gln Pro Leu Leu Leu Leu Gly
                   165                 170                 175

Gly Gln Gly Gly Gln Leu Gln Leu Leu His Leu Ala Gly Glu Gly Ala
               180                 185                 190

Ser Val Pro Arg Leu Ala Gly Pro Gln Ser Leu Pro Ser Arg Ile
               195                 200                 205

Asp Ser Leu Pro Ala Phe Pro Leu Leu Glu Pro Lys Ile Gln Trp Arg
210                 215                 220

Leu Gln Glu Arg Leu Lys Ala Pro Thr Ile Gly Leu Ala Ala Val Val
225                 230                 235                 240

Pro Pro Leu Pro Ser Ala Pro Thr Pro Gly Leu Val Leu Phe Gln Leu
                   245                 250                 255

Ser Ala Ala Gly Asp Val Phe Tyr Gln Gln Leu Arg Pro Gln Val Asp
               260                 265                 270

Ser Ser Leu Arg Arg Asp Ala Gly Pro Pro Gly Asp Thr Gln Pro Asp
       275                 280                 285

Cys His Ala Pro Thr Ala Ser Trp Thr Ser Gln Asp Thr Ala Gly Cys
       290                 295                 300

Ser Gln Trp Leu Lys Ala Leu Leu Lys Val Pro Leu Ala Pro Pro Val
305                 310                 315                 320

Trp Thr Ala Pro Thr Phe Thr His Arg Gln Met Leu Gly Ser Thr Glu
                   325                 330                 335

Leu Arg Arg Glu Glu Glu Gly Gln Arg Leu Gly Val Leu Arg Lys
               340                 345                 350

Ala Met Ala Arg Gly Gln Leu Leu Leu Gln Arg Asp Leu Gly Ser Leu
               355                 360                 365

Pro Ala Ala Glu Pro Pro Ala Pro Glu Ser Gly Leu Glu Asp Lys
       370                 375                 380

Leu Ser Glu Arg Leu Gly Glu Ala Trp Ala Gly Arg Gly Ala Ala Trp
385                 390                 395                 400

Trp Glu Arg Gln Gln Gly Arg Thr Ser Glu Pro Gly Arg Gln Thr Arg
                   405                 410                 415

Arg Pro Lys Arg Arg Thr Gln Leu Ser Ser Ser Phe Ser Leu Ser Gly
                   420                 425                 430

His Val Asp Pro Ser Glu Asp Thr Ser Ser Pro His Ser Pro Glu Trp
               435                 440                 445

Pro Pro Ala Asp Ala Leu Pro Leu Pro Thr Thr Pro Pro Ser Gln
       450                 455                 460

Glu Leu Thr Pro Asp Ala Cys Ala Gln Gly Val Pro Ser Glu Gln Arg
465                 470                 475                 480

Gln Met Leu Arg Asp Tyr Met Ala Lys Leu Pro Pro Gln Arg Asp Thr
                   485                 490                 495
```

```
Pro Gly Cys Ala Thr Thr Pro Pro His Ser Gln Ala Ser Ser Val Arg
            500                 505                 510

Ala Thr Arg Ser Gln Gln His Thr Pro Val Leu Ser Ser Gln Pro
            515                 520                 525

Leu Arg Lys Lys Pro Arg Met Gly Phe
            530                 535

<210> SEQ ID NO 57
<211> LENGTH: 460
<212> TYPE: PRT
<213> ORGANISM: Homo sapiens

<400> SEQUENCE: 57

Met Leu Asp Thr Gln Gly Pro Pro Gly Cys Gly Leu Leu Phe Arg
1               5                   10                  15

Leu Gly Ala Glu Ala Ser Cys Gln Lys Gly Glu Arg Val Leu Leu Thr
            20                  25                  30

Gln Tyr Leu Gly His Ser Ser Pro Lys Cys Leu Pro Pro Thr Leu His
            35                  40                  45

Leu Val Cys Thr Gln Phe Ser Leu Tyr Leu Val Asp Glu Arg Leu Pro
        50                  55                  60

Leu Val Pro Met Leu Lys Trp Asn His Gly Leu Pro Ser Pro Leu Leu
65                  70                  75                  80

Leu Ala Arg Leu Leu Pro Pro Arg Pro Ser Cys Val Gln Pro Leu
                85                  90                  95

Leu Leu Gly Gly Gln Gly Gly Gln Leu Gln Leu Leu His Leu Ala Gly
            100                 105                 110

Glu Gly Ala Ser Val Pro Arg Leu Ala Gly Pro Pro Gln Ser Leu Pro
            115                 120                 125

Ser Arg Ile Asp Ser Leu Pro Ala Phe Pro Leu Leu Glu Pro Lys Ile
        130                 135                 140

Gln Trp Arg Leu Gln Glu Arg Leu Lys Ala Pro Thr Ile Gly Leu Ala
145                 150                 155                 160

Ala Val Val Pro Pro Leu Pro Ser Ala Pro Thr Pro Gly Leu Val Leu
                165                 170                 175

Phe Gln Leu Ser Ala Ala Gly Asp Val Phe Tyr Gln Gln Leu Arg Pro
            180                 185                 190

Gln Val Asp Ser Ser Leu Arg Arg Asp Ala Gly Pro Pro Gly Asp Thr
            195                 200                 205

Gln Pro Asp Cys His Ala Pro Thr Ala Ser Trp Thr Ser Gln Asp Thr
        210                 215                 220

Ala Gly Cys Ser Gln Trp Leu Lys Ala Leu Leu Lys Val Pro Leu Ala
225                 230                 235                 240

Pro Pro Val Trp Thr Ala Pro Thr Phe Thr His Arg Gln Met Leu Gly
                245                 250                 255

Ser Thr Glu Leu Arg Arg Glu Glu Glu Gly Gln Arg Leu Gly Val
            260                 265                 270

Leu Arg Lys Ala Met Ala Arg Gly Gln Leu Leu Leu Gln Arg Asp Leu
            275                 280                 285

Gly Ser Leu Pro Ala Ala Glu Pro Pro Ala Pro Glu Ser Gly Leu
        290                 295                 300

Glu Asp Lys Leu Ser Glu Arg Leu Gly Glu Ala Trp Ala Gly Arg Gly
305                 310                 315                 320

Ala Ala Trp Trp Glu Arg Gln Gln Gly Arg Thr Ser Glu Pro Gly Arg
```

```
            325                 330                 335
Gln Thr Arg Arg Pro Lys Arg Arg Thr Gln Leu Ser Ser Ser Phe Ser
            340                 345                 350

Leu Ser Gly His Val Asp Pro Ser Glu Asp Thr Ser Ser Pro His Ser
            355                 360                 365

Pro Glu Trp Pro Pro Ala Asp Ala Leu Pro Leu Pro Pro Thr Thr Pro
            370                 375                 380

Pro Ser Gln Glu Leu Thr Pro Asp Ala Cys Ala Gln Gly Val Pro Ser
385                 390                 395                 400

Glu Gln Arg Gln Met Leu Arg Asp Tyr Met Ala Lys Leu Pro Pro Gln
                405                 410                 415

Arg Asp Thr Pro Gly Cys Ala Thr Thr Pro Pro His Ser Gln Ala Ser
                420                 425                 430

Ser Val Arg Ala Thr Arg Ser Gln Gln His Thr Pro Val Leu Ser Ser
            435                 440                 445

Ser Gln Pro Leu Arg Lys Lys Pro Arg Met Gly Phe
            450                 455                 460

<210> SEQ ID NO 58
<211> LENGTH: 392
<212> TYPE: PRT
<213> ORGANISM: Homo sapiens

<400> SEQUENCE: 58

Met Leu Lys Trp Asn His Gly Leu Pro Ser Pro Leu Leu Leu Ala Arg
1               5                   10                  15

Leu Leu Pro Pro Pro Arg Pro Ser Cys Val Gln Pro Leu Leu Leu Gly
            20                  25                  30

Gly Gln Gly Gly Gln Leu Gln Leu Leu His Leu Ala Glu Gly Ala Ser
            35                  40                  45

Val Pro Arg Leu Ala Gly Pro Pro Gln Ser Leu Pro Ser Arg Ile Asp
        50                  55                  60

Ser Leu Pro Ala Phe Pro Leu Leu Glu Pro Lys Ile Gln Trp Arg Leu
65                  70                  75                  80

Gln Glu Arg Leu Lys Ala Pro Thr Ile Gly Leu Ala Ala Val Val Pro
                85                  90                  95

Pro Leu Pro Ser Ala Pro Thr Pro Gly Leu Val Leu Phe Gln Leu Ser
            100                 105                 110

Ala Ala Gly Asp Val Phe Tyr Gln Gln Leu Arg Pro Gln Val Asp Ser
            115                 120                 125

Ser Leu Arg Arg Asp Ala Gly Pro Pro Gly Asp Thr Gln Pro Asp Cys
        130                 135                 140

His Ala Pro Thr Ala Ser Trp Thr Ser Gln Asp Thr Ala Gly Cys Ser
145                 150                 155                 160

Gln Trp Leu Lys Ala Leu Leu Lys Val Pro Leu Ala Pro Pro Val Trp
                165                 170                 175

Thr Ala Pro Thr Phe Thr His Arg Gln Met Leu Gly Ser Thr Glu Leu
            180                 185                 190

Arg Arg Glu Glu Glu Glu Gly Gln Arg Leu Gly Val Leu Arg Lys Ala
            195                 200                 205

Met Ala Arg Gly Gln Leu Leu Leu Gln Arg Asp Leu Gly Ser Leu Pro
        210                 215                 220

Ala Ala Glu Pro Pro Pro Ala Pro Glu Ser Gly Leu Glu Asp Lys Leu
225                 230                 235                 240
```

```
Ser Glu Arg Leu Gly Glu Ala Trp Ala Gly Arg Ala Ala Trp Trp
                245                 250                 255

Glu Arg Gln Gln Gly Arg Thr Ser Glu Pro Gly Arg Gln Thr Arg Arg
            260                 265                 270

Pro Lys Arg Arg Thr Gln Leu Ser Ser Ser Phe Ser Leu Ser Gly His
            275                 280                 285

Val Asp Pro Ser Glu Asp Thr Ser Ser Pro His Ser Pro Glu Trp Pro
    290                 295                 300

Pro Ala Asp Ala Leu Pro Leu Pro Pro Thr Thr Pro Pro Ser Gln Glu
305                 310                 315                 320

Leu Thr Pro Asp Ala Cys Ala Gln Gly Val Pro Ser Glu Gln Arg Gln
                325                 330                 335

Met Leu Arg Asp Tyr Met Ala Lys Leu Pro Pro Gln Arg Asp Thr Pro
            340                 345                 350

Gly Cys Ala Thr Thr Pro Pro His Ser Gln Ala Ser Ser Val Arg Ala
            355                 360                 365

Thr Arg Ser Gln Gln His Thr Pro Val Leu Ser Ser Ser Gln Pro Leu
            370                 375                 380

Arg Lys Lys Pro Arg Met Gly Phe
385                 390

<210> SEQ ID NO 59
<211> LENGTH: 278
<212> TYPE: PRT
<213> ORGANISM: Homo sapiens

<400> SEQUENCE: 59

Met Asp Lys Ser Gly Ile Asp Ser Leu Asp His Val Thr Ser Asp Ala
1               5                   10                  15

Val Glu Leu Ala Asn Arg Ser Asp Asn Ser Ser Asp Ser Ser Leu Phe
            20                  25                  30

Lys Thr Gln Cys Ile Pro Tyr Ser Pro Lys Gly Glu Lys Arg Asn Pro
        35                  40                  45

Ile Arg Lys Phe Val Arg Thr Pro Glu Ser Val His Ala Ser Asp Ser
50                  55                  60

Ser Ser Asp Ser Ser Phe Glu Pro Ile Pro Leu Thr Ile Lys Ala Ile
65                  70                  75                  80

Phe Glu Arg Phe Lys Asn Arg Lys Lys Arg Tyr Lys Lys Lys Lys
                85                  90                  95

Arg Arg Tyr Gln Pro Thr Gly Arg Pro Arg Gly Arg Pro Glu Gly Arg
            100                 105                 110

Arg Asn Pro Ile Tyr Ser Leu Ile Asp Lys Lys Gln Phe Arg Ser
            115                 120                 125

Arg Gly Ser Gly Phe Pro Phe Leu Glu Ser Glu Glu Lys Asn Ala
            130                 135                 140

Pro Trp Arg Lys Ile Leu Thr Phe Glu Gln Ala Val Ala Arg Gly Phe
145                 150                 155                 160

Phe Asn Tyr Ile Glu Lys Leu Lys Tyr Glu His His Leu Lys Glu Ser
                165                 170                 175

Leu Lys Gln Met Asn Val Gly Glu Asp Leu Glu Asn Glu Asp Phe Asp
            180                 185                 190

Ser Arg Arg Tyr Lys Phe Leu Asp Asp Gly Ser Ile Ser Pro Ile
        195                 200                 205

Glu Glu Ser Thr Ala Glu Asp Glu Asp Ala Thr His Leu Glu Asp Asn
210                 215                 220
```

```
Glu Cys Asp Ile Lys Leu Ala Gly Asp Ser Phe Ile Val Ser Ser Glu
225                 230                 235                 240

Phe Pro Val Arg Leu Ser Val Tyr Leu Glu Glu Asp Ile Thr Glu
            245                 250                 255

Glu Ala Ala Leu Ser Lys Lys Arg Ala Thr Lys Ala Lys Asn Thr Gly
            260                 265                 270

Gln Arg Gly Leu Lys Met
        275

<210> SEQ ID NO 60
<211> LENGTH: 727
<212> TYPE: PRT
<213> ORGANISM: Homo sapiens

<400> SEQUENCE: 60

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Glu Ile Met Arg
    210                 215                 220

Asp Tyr Ile Gln Lys His Pro Glu Leu Asn Ile Ser Glu Glu Gly Ile
225                 230                 235                 240

Thr Lys Ser Thr Leu Thr Lys Ala Glu Arg Gln Leu Lys Asp Lys Phe
                245                 250                 255

Asp Gly Arg Pro Thr Lys Pro Pro Asn Ser Tyr Ser Leu Tyr Cys
            260                 265                 270

Ala Glu Leu Met Ala Asn Met Lys Asp Val Pro Ser Thr Glu Arg Met
        275                 280                 285

Val Leu Cys Ser Gln Gln Trp Lys Leu Leu Ser Gln Lys Glu Lys Asp
    290                 295                 300

Ala Tyr His Lys Lys Cys Asp Gln Lys Lys Lys Asp Tyr Glu Val Glu
```

```
        305                 310                 315                 320
Leu Leu Arg Phe Leu Glu Ser Leu Pro Glu Glu Gln Gln Arg Val
                325                 330                 335
Leu Gly Glu Glu Lys Met Leu Asn Ile Asn Lys Lys Gln Ala Thr Ser
                340                 345                 350
Pro Ala Ser Lys Lys Pro Ala Gln Glu Gly Gly Lys Gly Gly Ser Glu
                355                 360                 365
Lys Pro Lys Arg Pro Val Ser Ala Met Phe Ile Phe Ser Glu Glu Lys
                370                 375                 380
Arg Arg Gln Leu Gln Glu Glu Arg Pro Glu Leu Ser Glu Ser Glu Leu
385                 390                 395                 400
Thr Arg Leu Leu Ala Arg Met Trp Asn Asp Leu Ser Glu Lys Lys Lys
                405                 410                 415
Ala Lys Tyr Lys Ala Arg Glu Ala Ala Leu Lys Ala Gln Ser Glu Arg
                420                 425                 430
Lys Pro Gly Gly Glu Arg Glu Glu Arg Gly Lys Leu Pro Glu Ser Pro
                435                 440                 445
Lys Arg Ala Glu Glu Ile Trp Gln Gln Ser Val Ile Gly Asp Tyr Leu
                450                 455                 460
Ala Arg Phe Lys Asn Asp Arg Val Lys Ala Leu Lys Ala Met Glu Met
465                 470                 475                 480
Thr Trp Asn Asn Met Glu Lys Lys Glu Lys Leu Met Trp Ile Lys Lys
                485                 490                 495
Ala Ala Glu Asp Gln Lys Arg Tyr Glu Arg Glu Leu Ser Glu Met Arg
                500                 505                 510
Ala Pro Pro Ala Ala Thr Asn Ser Ser Lys Lys Met Lys Phe Gln Gly
                515                 520                 525
Glu Pro Lys Lys Pro Pro Met Asn Gly Tyr Gln Lys Phe Ser Gln Glu
                530                 535                 540
Leu Leu Ser Asn Gly Glu Leu Asn His Leu Pro Leu Lys Glu Arg Met
545                 550                 555                 560
Val Glu Ile Gly Ser Arg Trp Gln Arg Ile Ser Gln Ser Gln Lys Glu
                565                 570                 575
His Tyr Lys Lys Leu Ala Glu Glu Gln Lys Gln Tyr Lys Val His
                580                 585                 590
Leu Asp Leu Trp Val Lys Ser Leu Ser Pro Gln Asp Arg Ala Ala Tyr
                595                 600                 605
Lys Glu Tyr Ile Ser Asn Lys Arg Lys Ser Met Thr Lys Leu Arg Gly
                610                 615                 620
Pro Asn Pro Lys Ser Ser Arg Thr Thr Leu Gln Ser Lys Ser Glu Ser
625                 630                 635                 640
Glu Glu Asp Asp Glu Asp Glu Asp Glu Asp Glu Asp Glu Glu
                645                 650                 655
Glu Glu Asp Asp Glu Asn Gly Asp Ser Ser Glu Asp Gly Asp Ser
                660                 665                 670
Ser Glu Ser Ser Ser Glu Asp Glu Ser Glu Asp Gly Asp Glu Asn Glu
                675                 680                 685
Glu Asp Asp Glu Asp Glu Asp Asp Glu Asp Asp Glu Asp Glu
                690                 695                 700
Asp Asn Glu Ser Glu Gly Ser Ser Ser Ser Ser Ser Gly Asp
705                 710                 715                 720
Ser Ser Asp Ser Asp Ser Asn
                725
```

```
<210> SEQ ID NO 61
<211> LENGTH: 727
<212> TYPE: PRT
<213> ORGANISM: Homo sapiens

<400> SEQUENCE: 61
```

| | | | | | | | | | | | | | | | |
|---|---|---|---|---|---|---|---|---|---|---|---|---|---|---|---|
| Met | Asn | Gly | Glu | Ala | Asp | Cys | Pro | Thr | Asp | Leu | Glu | Met | Ala | Ala | Pro |
| 1 | | | | 5 | | | | | 10 | | | | | 15 | |
| Lys | Gly | Gln | Asp | Arg | Trp | Ser | Gln | Glu | Asp | Met | Leu | Thr | Leu | Leu | Glu |
| | | | 20 | | | | | 25 | | | | | 30 | | |
| Cys | Met | Lys | Asn | Asn | Leu | Pro | Ser | Asn | Asp | Ser | Ser | Lys | Phe | Lys | Thr |
| | | 35 | | | | | 40 | | | | | 45 | | | |
| Thr | Glu | Ser | His | Met | Asp | Trp | Glu | Lys | Val | Ala | Phe | Lys | Asp | Phe | Ser |
| | 50 | | | | | 55 | | | | | 60 | | | | |
| Gly | Asp | Met | Cys | Lys | Leu | Lys | Trp | Val | Glu | Ile | Ser | Asn | Glu | Val | Arg |
| 65 | | | | | 70 | | | | | 75 | | | | | 80 |
| Lys | Phe | Arg | Thr | Leu | Thr | Glu | Leu | Ile | Leu | Asp | Ala | Gln | Glu | His | Val |
| | | | | 85 | | | | | 90 | | | | | 95 | |
| Lys | Asn | Pro | Tyr | Lys | Gly | Lys | Lys | Leu | Lys | Lys | His | Pro | Asp | Phe | Pro |
| | | | 100 | | | | | 105 | | | | | 110 | | |
| Lys | Lys | Pro | Leu | Thr | Pro | Tyr | Phe | Arg | Phe | Phe | Met | Glu | Lys | Arg | Ala |
| | | | 115 | | | | | 120 | | | | | 125 | | |
| Lys | Tyr | Ala | Lys | Leu | His | Pro | Glu | Met | Ser | Asn | Leu | Asp | Leu | Thr | Lys |
| | 130 | | | | | 135 | | | | | 140 | | | | |
| Ile | Leu | Ser | Lys | Lys | Tyr | Lys | Glu | Leu | Pro | Glu | Lys | Lys | Met | Lys |
| 145 | | | | | 150 | | | | | 155 | | | | | 160 |
| Tyr | Ile | Gln | Asp | Phe | Gln | Arg | Glu | Lys | Gln | Phe | Glu | Arg | Asn | Leu |
| | | | | 165 | | | | | 170 | | | | | 175 | |
| Ala | Arg | Phe | Arg | Glu | Asp | His | Pro | Asp | Leu | Ile | Gln | Asn | Ala | Lys | Lys |
| | | | 180 | | | | | 185 | | | | | 190 | | |
| Ser | Asp | Ile | Pro | Glu | Lys | Pro | Lys | Thr | Pro | Gln | Gln | Leu | Trp | Tyr | Thr |
| | | | 195 | | | | | 200 | | | | | 205 | | |
| His | Glu | Lys | Lys | Val | Tyr | Leu | Lys | Val | Arg | Pro | Asp | Glu | Ile | Met | Arg |
| | 210 | | | | | 215 | | | | | 220 | | | | |
| Asp | Tyr | Ile | Gln | Lys | His | Pro | Glu | Leu | Asn | Ile | Ser | Glu | Glu | Gly | Ile |
| 225 | | | | | 230 | | | | | 235 | | | | | 240 |
| Thr | Lys | Ser | Thr | Leu | Thr | Lys | Ala | Glu | Arg | Gln | Leu | Lys | Asp | Lys | Phe |
| | | | | 245 | | | | | 250 | | | | | 255 | |
| Asp | Gly | Arg | Pro | Thr | Lys | Pro | Pro | Asn | Ser | Tyr | Ser | Leu | Tyr | Cys |
| | | | 260 | | | | | 265 | | | | | 270 | | |
| Ala | Glu | Leu | Met | Ala | Asn | Met | Lys | Asp | Val | Pro | Ser | Thr | Glu | Arg | Met |
| | | 275 | | | | | 280 | | | | | 285 | | | |
| Val | Leu | Cys | Ser | Gln | Gln | Trp | Lys | Leu | Leu | Ser | Gln | Lys | Glu | Lys | Asp |
| | 290 | | | | | 295 | | | | | 300 | | | | |
| Ala | Tyr | His | Lys | Lys | Cys | Asp | Gln | Lys | Lys | Asp | Tyr | Glu | Val | Glu |
| 305 | | | | | 310 | | | | | 315 | | | | | 320 |
| Leu | Leu | Arg | Phe | Leu | Glu | Ser | Leu | Pro | Glu | Glu | Glu | Gln | Arg | Val |
| | | | | 325 | | | | | 330 | | | | | 335 | |
| Leu | Gly | Glu | Glu | Lys | Met | Leu | Asn | Ile | Asn | Lys | Lys | Gln | Ala | Thr | Ser |
| | | | 340 | | | | | 345 | | | | | 350 | | |
| Pro | Ala | Ser | Lys | Lys | Pro | Ala | Gln | Glu | Gly | Gly | Lys | Gly | Gly | Ser | Glu |
| | | 355 | | | | | 360 | | | | | 365 | | | |
| Lys | Pro | Lys | Arg | Pro | Val | Ser | Ala | Met | Phe | Ile | Phe | Ser | Glu | Glu | Lys |
| | 370 | | | | | 375 | | | | | 380 | | | | |

Arg Arg Gln Leu Gln Glu Glu Arg Pro Glu Leu Ser Glu Ser Glu Leu
385                 390                 395                 400

Thr Arg Leu Leu Ala Arg Met Trp Asn Asp Leu Ser Glu Lys Lys Lys
            405                 410                 415

Ala Lys Tyr Lys Ala Arg Glu Ala Ala Leu Lys Ala Gln Ser Glu Arg
        420                 425                 430

Lys Pro Gly Gly Glu Arg Glu Arg Gly Lys Leu Pro Glu Ser Pro
        435                 440                 445

Lys Arg Ala Glu Glu Ile Trp Gln Gln Ser Val Ile Gly Asp Tyr Leu
450                 455                 460

Ala Arg Phe Lys Asn Asp Arg Val Lys Ala Leu Lys Ala Met Glu Met
465                 470                 475                 480

Thr Trp Asn Asn Met Glu Lys Lys Glu Lys Leu Met Trp Ile Lys Lys
            485                 490                 495

Ala Ala Glu Asp Gln Lys Arg Tyr Glu Arg Glu Leu Ser Glu Met Arg
        500                 505                 510

Ala Pro Pro Ala Ala Thr Asn Ser Ser Lys Lys Met Lys Phe Gln Gly
        515                 520                 525

Glu Pro Lys Lys Pro Pro Met Asn Gly Tyr Gln Lys Phe Ser Gln Glu
        530                 535                 540

Leu Leu Ser Asn Gly Glu Leu Asn His Leu Pro Leu Lys Glu Arg Met
545                 550                 555                 560

Val Glu Ile Gly Ser Arg Trp Gln Arg Ile Ser Gln Ser Gln Lys Glu
            565                 570                 575

His Tyr Lys Lys Leu Ala Glu Glu Gln Gln Lys Gln Tyr Lys Val His
        580                 585                 590

Leu Asp Leu Trp Val Lys Ser Leu Ser Pro Gln Asp Arg Ala Ala Tyr
        595                 600                 605

Lys Glu Tyr Ile Ser Asn Lys Arg Lys Ser Met Thr Lys Leu Arg Gly
        610                 615                 620

Pro Asn Pro Lys Ser Ser Arg Thr Thr Leu Gln Ser Lys Ser Glu Ser
625                 630                 635                 640

Glu Glu Asp Asp Glu Glu Asp Glu Asp Glu Asp Glu Asp Glu Glu Glu
            645                 650                 655

Glu Glu Asp Asp Glu Asn Gly Asp Ser Ser Glu Asp Gly Gly Asp Ser
        660                 665                 670

Ser Glu Ser Ser Ser Glu Asp Ser Glu Asp Gly Asp Glu Asn Glu
        675                 680                 685

Glu Asp Asp Glu Asp Glu Asp Asp Glu Asp Asp Glu Asp Glu Asp Glu
690                 695                 700

Asp Asn Glu Ser Glu Gly Ser Ser Ser Ser Ser Ser Ser Gly Asp
705                 710                 715                 720

Ser Ser Asp Ser Asp Ser Asn
            725

<210> SEQ ID NO 62
<211> LENGTH: 764
<212> TYPE: PRT
<213> ORGANISM: Homo sapiens

<400> SEQUENCE: 62

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

-continued

Cys Met Lys Asn Asn Leu Pro Ser Asn Asp Ser Lys Phe Lys Thr
         35                  40                  45

Thr Glu Ser His Met Asp Trp Glu Lys Val Ala Phe Lys Asp Phe Ser
     50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                 85                  90                  95

Lys Asn Pro Tyr Lys Gly Lys Lys Leu Lys Lys His Pro Asp Phe Pro
             100                 105                 110

Lys Lys Pro Leu Thr Pro Tyr Phe Arg Phe Phe Met Glu Lys Arg Ala
         115                 120                 125

Lys Tyr Ala Lys Leu His Pro Glu Met Ser Asn Leu Asp Leu Thr Lys
         130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                 165                 170                 175

Ala Arg Phe Arg Glu Asp His Pro Asp Leu Ile Gln Asn Ala Lys Lys
             180                 185                 190

Ser Asp Ile Pro Glu Lys Pro Lys Thr Pro Gln Gln Leu Trp Tyr Thr
         195                 200                 205

His Glu Lys Lys Val Tyr Leu Lys Val Arg Pro Asp Ala Thr Thr Lys
     210                 215                 220

Glu Val Lys Asp Ser Leu Gly Lys Gln Trp Ser Gln Leu Ser Asp Lys
225                 230                 235                 240

Lys Arg Leu Lys Trp Ile His Lys Ala Leu Glu Gln Arg Lys Glu Tyr
                 245                 250                 255

Glu Glu Ile Met Arg Asp Tyr Ile Gln Lys His Pro Glu Leu Asn Ile
             260                 265                 270

Ser Glu Glu Gly Ile Thr Lys Ser Thr Leu Thr Lys Ala Glu Arg Gln
         275                 280                 285

Leu Lys Asp Lys Phe Asp Gly Arg Pro Thr Lys Pro Pro Pro Asn Ser
     290                 295                 300

Tyr Ser Leu Tyr Cys Ala Glu Leu Met Ala Asn Met Lys Asp Val Pro
305                 310                 315                 320

Ser Thr Glu Arg Met Val Leu Cys Ser Gln Gln Trp Lys Leu Leu Ser
                 325                 330                 335

Gln Lys Glu Lys Asp Ala Tyr His Lys Lys Cys Asp Gln Lys Lys Lys
             340                 345                 350

Asp Tyr Glu Val Glu Leu Leu Arg Phe Leu Glu Ser Leu Pro Glu Glu
         355                 360                 365

Glu Gln Gln Arg Val Leu Gly Glu Glu Lys Met Leu Asn Ile Asn Lys
     370                 375                 380

Lys Gln Ala Thr Ser Pro Ala Ser Lys Lys Pro Ala Gln Glu Gly Gly
385                 390                 395                 400

Lys Gly Gly Ser Glu Lys Pro Lys Arg Pro Val Ser Ala Met Phe Ile
                 405                 410                 415

Phe Ser Glu Glu Lys Arg Arg Gln Leu Gln Glu Glu Arg Pro Glu Leu
             420                 425                 430

Ser Glu Ser Glu Leu Thr Arg Leu Leu Ala Arg Met Trp Asn Asp Leu
         435                 440                 445

```
Ser Glu Lys Lys Lys Ala Lys Tyr Lys Ala Arg Glu Ala Ala Leu Lys
    450                 455                 460
Ala Gln Ser Glu Arg Lys Pro Gly Gly Glu Arg Glu Glu Arg Gly Lys
465                 470                 475                 480
Leu Pro Glu Ser Pro Lys Arg Ala Glu Glu Ile Trp Gln Gln Ser Val
                485                 490                 495
Ile Gly Asp Tyr Leu Ala Arg Phe Lys Asn Asp Arg Val Lys Ala Leu
            500                 505                 510
Lys Ala Met Glu Met Thr Trp Asn Asn Met Glu Lys Lys Glu Lys Leu
        515                 520                 525
Met Trp Ile Lys Lys Ala Glu Asp Gln Lys Arg Tyr Glu Arg Glu
    530                 535                 540
Leu Ser Glu Met Arg Ala Pro Pro Ala Ala Thr Asn Ser Ser Lys Lys
545                 550                 555                 560
Met Lys Phe Gln Gly Glu Pro Lys Lys Pro Pro Met Asn Gly Tyr Gln
                565                 570                 575
Lys Phe Ser Gln Glu Leu Leu Ser Asn Gly Glu Leu Asn His Leu Pro
            580                 585                 590
Leu Lys Glu Arg Met Val Glu Ile Gly Ser Arg Trp Gln Arg Ile Ser
        595                 600                 605
Gln Ser Gln Lys Glu His Tyr Lys Lys Leu Ala Glu Glu Gln Gln Lys
    610                 615                 620
Gln Tyr Lys Val His Leu Asp Leu Trp Val Lys Ser Leu Ser Pro Gln
625                 630                 635                 640
Asp Arg Ala Ala Tyr Lys Glu Tyr Ile Ser Asn Lys Arg Lys Ser Met
                645                 650                 655
Thr Lys Leu Arg Gly Pro Asn Pro Lys Ser Ser Arg Thr Thr Leu Gln
            660                 665                 670
Ser Lys Ser Glu Ser Glu Glu Asp Glu Glu Asp Glu Asp Asp Glu
        675                 680                 685
Asp Glu Asp Glu Glu Glu Asp Asp Glu Asn Gly Asp Ser Ser Glu
690                 695                 700
Asp Gly Gly Asp Ser Ser Glu Ser Ser Ser Glu Asp Glu Ser Glu Asp
705                 710                 715                 720
Gly Asp Glu Asn Glu Glu Asp Glu Asp Glu Asp Asp Glu Asp
            725                 730                 735
Asp Asp Glu Asp Glu Asp Asn Glu Ser Glu Gly Ser Ser Ser Ser
        740                 745                 750
Ser Ser Ser Gly Asp Ser Ser Asp Ser Asp Ser Asn
    755                 760

<210> SEQ ID NO 63
<211> LENGTH: 390
<212> TYPE: PRT
<213> ORGANISM: Homo sapiens

<400> SEQUENCE: 63

Met Tyr Arg Asp Asp Leu Glu Arg Phe Lys Glu Phe Lys Ala Gln Gly
1               5                   10                  15
Val Ala Ile Lys Phe Gly Lys Phe Ser Val Lys Glu Asn Lys Gln Leu
            20                  25                  30
Glu Lys Asn Val Glu Asp Phe Leu Ala Leu Thr Gly Ile Glu Ser Ala
        35                  40                  45
Asp Lys Leu Leu Tyr Thr Asp Arg Tyr Pro Glu Glu Lys Ser Val Ile
    50                  55                  60
```

```
Thr Asn Leu Lys Arg Arg Tyr Ser Phe Arg Leu His Ile Gly Arg Asn
 65                  70                  75                  80

Ile Ala Arg Pro Trp Lys Leu Ile Tyr Tyr Arg Ala Lys Lys Met Phe
                 85                  90                  95

Asp Val Asn Asn Tyr Lys Gly Arg Tyr Ser Glu Gly Asp Thr Glu Lys
            100                 105                 110

Leu Lys Met Tyr His Ser Leu Leu Gly Asn Asp Trp Lys Thr Ile Gly
        115                 120                 125

Glu Met Val Ala Arg Ser Ser Leu Ser Val Ala Leu Lys Phe Ser Gln
    130                 135                 140

Ile Ser Ser Gln Arg Asn Arg Gly Ala Trp Ser Lys Ser Glu Thr Arg
145                 150                 155                 160

Lys Leu Ile Lys Ala Val Glu Glu Val Ile Leu Lys Lys Met Ser Pro
                165                 170                 175

Gln Glu Leu Lys Glu Val Asp Ser Lys Leu Gln Glu Asn Pro Glu Ser
            180                 185                 190

Cys Leu Ser Ile Val Arg Glu Lys Leu Tyr Lys Gly Ile Ser Trp Val
        195                 200                 205

Glu Val Glu Ala Lys Val Gln Thr Arg Asn Trp Met Gln Cys Lys Ser
    210                 215                 220

Lys Trp Thr Glu Ile Leu Thr Lys Arg Met Thr Asn Gly Arg Arg Ile
225                 230                 235                 240

Tyr Tyr Gly Met Asn Ala Leu Arg Ala Lys Val Ser Leu Ile Glu Arg
                245                 250                 255

Leu Tyr Glu Ile Asn Val Glu Asp Thr Asn Glu Ile Asp Trp Glu Asp
            260                 265                 270

Leu Ala Ser Ala Ile Gly Asp Val Pro Pro Ser Tyr Val Gln Thr Lys
        275                 280                 285

Phe Ser Arg Leu Lys Ala Val Tyr Val Pro Phe Trp Gln Lys Lys Thr
    290                 295                 300

Phe Pro Glu Ile Ile Asp Tyr Leu Tyr Glu Thr Thr Leu Pro Leu Leu
305                 310                 315                 320

Lys Glu Lys Leu Glu Lys Met Met Glu Lys Lys Gly Thr Lys Ile Gln
                325                 330                 335

Thr Pro Ala Ala Pro Lys Gln Val Phe Pro Phe Arg Asp Ile Phe Tyr
            340                 345                 350

Tyr Glu Asp Asp Ser Glu Gly Glu Asp Ile Glu Lys Glu Ser Glu Gly
        355                 360                 365

Gln Ala Pro Cys Met Ala His Ala Cys Asn Ser Ser Thr Leu Gly Gly
    370                 375                 380

Gln Gly Arg Trp Ile Ile
385                 390

<210> SEQ ID NO 64
<211> LENGTH: 905
<212> TYPE: PRT
<213> ORGANISM: Homo sapiens

<400> SEQUENCE: 64

Met Glu Gly Glu Ser Ser Arg Phe Glu Ile His Thr Pro Val Ser Asp
 1               5                  10                  15

Lys Lys Lys Lys Lys Cys Ser Ile His Lys Glu Arg Pro Gln Lys His
                20                  25                  30

Ser His Glu Ile Phe Arg Asp Ser Leu Val Asn Glu Gln Ser Gln
            35                  40                  45
```

```
Ile Thr Arg Arg Lys Lys Arg Lys Asp Phe Gln His Leu Ile Ser
    50                  55                  60

Ser Pro Leu Lys Lys Ser Arg Ile Cys Asp Glu Thr Ala Asn Ala Thr
65                  70                  75                  80

Ser Thr Leu Lys Lys Arg Lys Lys Arg Arg Tyr Ser Ala Leu Glu Val
                85                  90                  95

Asp Glu Glu Ala Gly Val Thr Val Val Leu Val Asp Lys Glu Asn Ile
            100                 105                 110

Asn Asn Thr Pro Lys His Phe Arg Lys Asp Val Asp Val Val Cys Val
            115                 120                 125

Asp Met Ser Ile Glu Gln Lys Leu Pro Arg Lys Pro Lys Thr Asp Lys
130                 135                 140

Phe Gln Val Leu Ala Lys Ser His Ala His Lys Ser Glu Ala Leu His
145                 150                 155                 160

Ser Lys Val Arg Glu Lys Lys Asn Lys His Gln Arg Lys Ala Ala
                165                 170                 175

Ser Trp Glu Ser Gln Arg Ala Arg Asp Thr Leu Pro Gln Ser Glu Ser
            180                 185                 190

His Gln Glu Glu Ser Trp Leu Ser Val Gly Pro Gly Gly Glu Ile Thr
            195                 200                 205

Glu Leu Pro Ala Ser Ala His Lys Asn Lys Ser Lys Lys Lys Lys
    210                 215                 220

Lys Ser Ser Asn Arg Glu Tyr Glu Thr Leu Ala Met Pro Glu Gly Ser
225                 230                 235                 240

Gln Ala Gly Arg Glu Ala Gly Thr Asp Met Gln Glu Ser Gln Pro Thr
                245                 250                 255

Val Gly Leu Asp Asp Glu Thr Pro Gln Leu Leu Gly Pro Thr His Lys
            260                 265                 270

Lys Lys Ser Lys Lys Lys Lys Lys Lys Ser Asn His Gln Glu Phe
        275                 280                 285

Glu Ala Leu Ala Met Pro Glu Gly Ser Gln Val Gly Ser Glu Val Gly
    290                 295                 300

Ala Asp Met Gln Glu Ser Arg Pro Ala Val Gly Leu His Gly Glu Thr
305                 310                 315                 320

Ala Gly Ile Pro Ala Pro Ala Tyr Lys Asn Lys Ser Lys Lys Lys Lys
                325                 330                 335

Lys Lys Ser Asn His Gln Glu Phe Glu Ala Val Ala Met Pro Glu Ser
            340                 345                 350

Leu Glu Ser Ala Tyr Pro Glu Gly Ser Gln Val Gly Ser Glu Val Gly
            355                 360                 365

Thr Val Glu Gly Ser Thr Ala Leu Lys Gly Phe Lys Glu Ser Asn Ser
    370                 375                 380

Thr Lys Lys Lys Ser Lys Lys Arg Lys Leu Thr Ser Val Lys Arg Ala
385                 390                 395                 400

Arg Val Ser Gly Asp Asp Phe Ser Val Pro Ser Lys Asn Ser Glu Ser
                405                 410                 415

Thr Leu Phe Asp Ser Val Glu Gly Asp Gly Ala Met Met Glu Glu Gly
            420                 425                 430

Val Lys Ser Arg Pro Arg Gln Lys Lys Thr Gln Ala Cys Leu Ala Ser
            435                 440                 445

Lys His Val Gln Glu Ala Pro Arg Leu Glu Pro Ala Asn Glu Glu His
450                 455                 460
```

-continued

```
Asn Val Glu Thr Ala Glu Asp Ser Glu Ile Arg Tyr Leu Ser Ala Asp
465                 470                 475                 480

Ser Gly Asp Ala Asp Ser Asp Ala Asp Leu Gly Ser Ala Val Lys
                485                 490                 495

Gln Leu Gln Glu Phe Ile Pro Asn Ile Lys Asp Arg Ala Thr Ser Thr
            500                 505                 510

Ile Lys Arg Met Tyr Arg Asp Asp Leu Glu Arg Phe Lys Glu Phe Lys
        515                 520                 525

Ala Gln Gly Val Ala Ile Lys Phe Gly Lys Phe Ser Val Lys Glu Asn
    530                 535                 540

Lys Gln Leu Glu Lys Asn Val Glu Asp Phe Leu Ala Leu Thr Gly Ile
545                 550                 555                 560

Glu Ser Ala Asp Lys Leu Leu Tyr Thr Asp Arg Tyr Pro Glu Glu Lys
                565                 570                 575

Ser Val Ile Thr Asn Leu Lys Arg Arg Tyr Ser Phe Arg Leu His Ile
            580                 585                 590

Gly Arg Asn Ile Ala Arg Pro Trp Lys Leu Ile Tyr Tyr Arg Ala Lys
        595                 600                 605

Lys Met Phe Asp Val Asn Asn Tyr Lys Gly Arg Tyr Ser Glu Gly Asp
    610                 615                 620

Thr Glu Lys Leu Lys Met Tyr His Ser Leu Leu Gly Asn Asp Trp Lys
625                 630                 635                 640

Thr Ile Gly Glu Met Val Ala Arg Ser Ser Leu Ser Val Ala Leu Lys
                645                 650                 655

Phe Ser Gln Ile Ser Ser Gln Arg Asn Arg Gly Ala Trp Ser Lys Ser
            660                 665                 670

Glu Thr Arg Lys Leu Ile Lys Ala Val Glu Val Ile Leu Lys Lys
        675                 680                 685

Met Ser Pro Gln Glu Leu Lys Glu Val Asp Ser Lys Leu Gln Glu Asn
    690                 695                 700

Pro Glu Ser Cys Leu Ser Ile Val Arg Glu Lys Leu Tyr Lys Gly Ile
705                 710                 715                 720

Ser Trp Val Glu Val Glu Ala Lys Val Gln Thr Arg Asn Trp Met Gln
                725                 730                 735

Cys Lys Ser Lys Trp Thr Glu Ile Leu Thr Lys Arg Met Thr Asn Gly
            740                 745                 750

Arg Arg Ile Tyr Tyr Gly Met Asn Ala Leu Arg Ala Lys Val Ser Leu
        755                 760                 765

Ile Glu Arg Leu Tyr Glu Ile Asn Val Glu Asp Thr Asn Glu Ile Asp
770                 775                 780

Trp Glu Asp Leu Ala Ser Ala Ile Gly Asp Val Pro Pro Ser Tyr Val
785                 790                 795                 800

Gln Thr Lys Phe Ser Arg Leu Lys Ala Val Tyr Val Pro Phe Trp Gln
            805                 810                 815

Lys Lys Thr Phe Pro Glu Ile Ile Asp Tyr Leu Tyr Glu Thr Thr Leu
        820                 825                 830

Pro Leu Leu Lys Glu Lys Leu Glu Lys Met Met Glu Lys Lys Gly Thr
    835                 840                 845

Lys Ile Gln Thr Pro Ala Ala Pro Lys Gln Val Phe Pro Arg Asp
850                 855                 860

Ile Phe Tyr Tyr Glu Asp Asp Ser Glu Gly Glu Asp Ile Glu Lys Glu
865                 870                 875                 880
```

```
Ser Glu Gly Gln Ala Pro Cys Met Ala His Ala Cys Asn Ser Ser Thr
                885                 890                 895

Leu Gly Gly Gln Gly Arg Trp Ile Ile
        900                 905

<210> SEQ ID NO 65
<211> LENGTH: 390
<212> TYPE: PRT
<213> ORGANISM: Homo sapiens

<400> SEQUENCE: 65

Met Glu Asp Pro Thr Leu Tyr Ile Val Glu Arg Pro Leu Pro Gly Tyr
1               5                   10                  15

Pro Asp Ala Glu Ala Pro Glu Pro Ser Ser Ala Gly Ala Gln Ala Ala
            20                  25                  30

Glu Glu Pro Ser Gly Ala Gly Ser Glu Leu Ile Lys Ser Asp Gln
        35                  40                  45

Val Asn Gly Val Leu Val Leu Ser Leu Leu Asp Lys Ile Ile Gly Ala
    50                  55                  60

Val Asp Gln Ile Gln Leu Thr Gln Ala Gln Leu Glu Glu Arg Gln Ala
65                  70                  75                  80

Glu Met Glu Gly Ala Val Gln Ser Ile Gln Gly Glu Leu Ser Lys Leu
                85                  90                  95

Gly Lys Ala His Ala Thr Thr Ser Asn Thr Val Ser Lys Leu Leu Glu
            100                 105                 110

Lys Val Arg Lys Val Ser Val Asn Val Lys Thr Val Arg Gly Ser Leu
        115                 120                 125

Glu Arg Gln Ala Gly Gln Ile Lys Lys Leu Glu Val Asn Glu Ala Glu
    130                 135                 140

Leu Leu Arg Arg Arg Asn Phe Lys Val Met Ile Tyr Gln Asp Glu Val
145                 150                 155                 160

Lys Leu Pro Ala Lys Leu Ser Ile Ser Lys Ser Leu Lys Glu Ser Glu
                165                 170                 175

Ala Leu Pro Glu Lys Glu Gly Glu Leu Gly Glu Gly Glu Arg Pro
            180                 185                 190

Glu Glu Asp Ala Ala Ala Leu Glu Leu Ser Ser Asp Glu Ala Val Glu
        195                 200                 205

Val Glu Glu Val Ile Glu Glu Ser Arg Ala Glu Arg Ile Lys Arg Ser
    210                 215                 220

Gly Leu Arg Arg Val Asp Asp Phe Lys Lys Ala Phe Ser Lys Glu Lys
225                 230                 235                 240

Met Glu Lys Thr Lys Val Arg Thr Arg Glu Asn Leu Glu Lys Thr Arg
                245                 250                 255

Leu Lys Thr Lys Glu Asn Leu Glu Lys Thr Arg His Thr Leu Glu Lys
            260                 265                 270

Arg Met Asn Lys Leu Gly Thr Arg Leu Val Pro Ala Glu Arg Arg Glu
        275                 280                 285

Lys Leu Lys Thr Ser Arg Asp Lys Leu Arg Lys Ser Phe Thr Pro Asp
    290                 295                 300

His Val Val Tyr Ala Arg Ser Lys Thr Ala Val Tyr Lys Val Pro Pro
305                 310                 315                 320

Phe Thr Phe His Val Lys Lys Ile Arg Glu Gly Gln Val Glu Val Leu
                325                 330                 335

Lys Ala Thr Glu Met Val Glu Val Gly Ala Asp Asp Glu Gly Gly
            340                 345                 350
```

```
Ala Glu Arg Gly Glu Ala Gly Asp Leu Arg Arg Gly Ser Pro Asp
            355                 360                 365

Val His Ala Leu Leu Glu Ile Thr Glu Ser Asp Ala Val Leu Val
            370                 375                 380

Asp Lys Ser Asp Ser Asp
385                 390

<210> SEQ ID NO 66
<211> LENGTH: 133
<212> TYPE: PRT
<213> ORGANISM: Homo sapiens

<400> SEQUENCE: 66

Met Arg Pro Leu Thr Glu Glu Thr Arg Val Met Phe Glu Lys Ile
1               5                   10                  15

Ala Lys Tyr Ile Gly Glu Asn Leu Gln Leu Leu Val Asp Arg Pro Asp
            20                  25                  30

Gly Thr Tyr Cys Phe Arg Leu His Asn Asp Arg Val Tyr Tyr Val Ser
            35                  40                  45

Glu Lys Ile Met Lys Leu Ala Ala Asn Ile Ser Gly Asp Lys Leu Val
        50                  55                  60

Ser Leu Gly Thr Cys Phe Gly Lys Phe Thr Lys Thr His Lys Phe Arg
65                  70                  75                  80

Leu His Val Thr Ala Leu Asp Tyr Leu Ala Pro Tyr Ala Lys Gly Phe
                85                  90                  95

Gly Val Ala Ala Lys Ser Thr Gln Asp Cys Arg Lys Val Asp Pro Met
            100                 105                 110

Ala Ile Val Val Phe His Gln Ala Asp Ile Gly Glu Tyr Val Arg His
            115                 120                 125

Glu Glu Thr Leu Thr
        130

<210> SEQ ID NO 67
<211> LENGTH: 180
<212> TYPE: PRT
<213> ORGANISM: Homo sapiens

<400> SEQUENCE: 67

Met Arg Pro Leu Thr Glu Glu Thr Arg Val Met Phe Glu Lys Ile
1               5                   10                  15

Ala Lys Tyr Ile Gly Glu Asn Leu Gln Leu Leu Val Asp Arg Pro Asp
            20                  25                  30

Gly Thr Tyr Cys Phe Arg Leu His Asn Asp Arg Val Tyr Tyr Val Ser
            35                  40                  45

Glu Lys Ile Met Lys Leu Ala Ala Asn Ile Ser Gly Asp Lys Leu Val
        50                  55                  60

Ser Leu Gly Thr Cys Phe Gly Lys Phe Thr Lys Thr His Lys Phe Arg
65                  70                  75                  80

Leu His Val Thr Ala Leu Asp Tyr Leu Ala Pro Tyr Ala Lys Tyr Lys
                85                  90                  95

Val Trp Ile Lys Pro Gly Ala Glu Gln Ser Phe Leu Tyr Gly Asn His
            100                 105                 110

Val Leu Lys Ser Gly Leu Gly Arg Ile Thr Glu Asn Thr Ser Gln Tyr
            115                 120                 125

Gln Gly Val Val Val Tyr Ser Met Ala Asp Ile Pro Leu Gly Phe Gly
            130                 135                 140
```

```
Val Ala Ala Lys Ser Thr Gln Asp Cys Arg Lys Val Asp Pro Met Ala
145                 150                 155                 160

Ile Val Val Phe His Gln Ala Asp Ile Gly Glu Tyr Val Arg His Glu
                165                 170                 175

Glu Thr Leu Thr
            180

<210> SEQ ID NO 68
<211> LENGTH: 13357
<212> TYPE: DNA
<213> ORGANISM: Homo sapiens

<400> SEQUENCE: 68
```

| | | | | | |
|---|---|---|---|---|---|
| gctgacacgc | tgtcctctgg | cgacctgtcg | ctggagaggt | tgggcctccg | gatgcgcgcg | 60 |
| gggctctggc | ctaccggtga | cccggctagc | cggccgcgct | cctgcttgag | ccgcctgccg | 120 |
| gggcccgcgg | gcctgctgtt | ctctcgcgcg | tccgagcgtc | ccgactcccg | gtgccggccc | 180 |
| gggtccgggt | ctctgaccca | ccccggggcg | gcggggaagg | cggcgagggc | caccgtgccc | 240 |
| ccgtgcgctc | tccgctgcgg | gcgcccgggg | cggccgcgac | aaccccaccc | cgctggctcc | 300 |
| gtgccgtgcg | tgtcaggcgt | tctcgtctcc | gcggggttgt | ccgccgcccc | ttccccggag | 360 |
| tgggggggttg | gccggagccg | atcggctcgc | tggccggccg | gccggcctcc | gctcccgggg | 420 |
| ggctcttcgt | gatcgatgtg | gtgacgtcgt | gctctcccgg | gccgggtccg | agccgcgacg | 480 |
| ggcgaggggc | ggacgttcgt | ggcgaacggg | accgtccttc | tcgctccgcc | ccgcggggt | 540 |
| cccctcgtct | ctcctctccc | cgcccgccgg | cggtgcgtgt | gggaaggcgt | ggggtgcgga | 600 |
| ccccggcccg | acctcgccgt | cccgcccgcc | gccttctgcg | tcgcggggcg | ggccggcggg | 660 |
| gtcctctgac | gcggcagaca | gccctcgctg | tcgcctccag | tggttgtcga | cttgcgggcg | 720 |
| gccccctcc | gcggcggtgg | gggtgccgtc | ccgccggccc | gtcgtgctgc | cctctcgggg | 780 |
| ggtttgcgcg | agcgtcggct | ccgcctgggc | ccttgcggtg | ctcctggagc | gctccgggtt | 840 |
| gtccctcagg | tgcccgaggc | cgaacggtgg | tgtgtcgttc | ccgccccggg | cgcccctcc | 900 |
| tccggtcgcc | gccgcggtgt | ccgcgcgtgg | gtcctgaggg | agctcgtcgg | tgtggggttc | 960 |
| gaggcggttt | gagtgagacg | agacgagacg | cgccctccc | acgcggggaa | gggcgccgc | 1020 |
| ctgctctcgg | tgagcgcacg | tccgtgctc | ccctctggcg | ggtgcgcgcg | ggccgtgtga | 1080 |
| gcgatcgcgg | tgggttcggg | ccggtgtgac | gcgtgcgccg | gccggccgcc | gaggggctgc | 1140 |
| cgttctgcct | ccgaccggtc | gtgtgtgggt | tgacttcgga | ggcgctctgc | ctcggaagga | 1200 |
| aggaggtggg | tggacgggg | ggcctggtgg | ggttgcgcgc | acgcgcgcac | cggccgggcc | 1260 |
| cccgccctga | cgcgaacgc | tcgaggtggc | cgcgcgcagg | tgtttcctcg | taccgcaggg | 1320 |
| ccccctccct | tccccaggcg | tccctcggcg | cctctgcggg | cccgaggagg | agcggctggc | 1380 |
| gggtgggggg | agtgtgaccc | accctcggtg | agaaaagcct | tctctagcga | tctgagaggc | 1440 |
| gtgccttggg | ggtaccggat | ccccccggggcc | gccgcctctg | tctctgcctc | cgttatggta | 1500 |
| gcgctgccgt | agcgacccgc | tgcagaggag | ccctcctccg | cttccccctc | gacggggttg | 1560 |
| gggggggagaa | gcgagggttc | cgccggccac | cgcggtggtg | gccgagtgcg | gctcgtcgcc | 1620 |
| tactgtggcc | cgcgcctccc | ccttccgagt | cgggggagga | tccgccgggg | ccgggcccgg | 1680 |
| cgttcccagc | gggttgggac | gcggcggccg | gcgggcggtg | ggtgtgcgcg | ccggcgctc | 1740 |
| tgtccggcgc | gtgaccccct | ccgccgcgag | tcggctctcc | gcccgctccc | gtgccgagtc | 1800 |
| gtgaccggtg | ccgacgaccg | cgtttgcgtg | gcacggggtc | gggcccgcct | ggccctggga | 1860 |

```
aagcgtccca cggtgggggc gcgccggtct cccggagcgg gaccgggtcg gaggatggac    1920
gagaatcacg agcgacggtg gtgcgggcgt gtcgggttcg tggctgcggt cgctccgggg    1980
cccccggtgg cggggccccg ggctcgcga ggcggttctc ggtgggggcc gagggccgtc     2040
cggcgtccca ggcggggcgc cgcgggaccc ccctcgtgtc tgtggcggtg ggatcccgcg    2100
gccgtgtttt cctggtggcc cggccgtgcc tgaggtttct ccccgagccg ccgcctctgc    2160
gggctcccgg gtgcccttgc cctcgcggtc cccggccctc gcccgtctgt gccctcttcc    2220
ccgcccgccg cccgccgatc ctcttcttcc ccccgagcgg ctcaccggct tcacgtccgt    2280
tggtggcccc gcctgggacc gaacccggca ccgcctcgtg gggcgccgcc gccggccact    2340
gatcggcccg gcgtccgcgt cccccggcgc gcgccttggg gaccgggtcg gtggcgcccc    2400
gcgtggggcc cggtgggctt cccggagggt tccgggggtc ggcctgcggc gcgtgcgggg    2460
gaggagacgg ttccggggga ccggccgcga ctgcggcggc ggtggtgggg gcagccgcgg    2520
ggatcgccga gggccggtcg gccgccccgg gtgccgcgcg gtgccgccgg cggcggtgag    2580
gccccgcgcg tgtgtcccgg ccgcggtcgg ccgcgctcga ggggtccccg tggcgtcccc    2640
ttccccgccg gccgcctttc tcgcgccttc cccgtcgccc cggcctcgcc cgtggtctct    2700
cgtcttctcc cggcccgctc ttccgaaccg ggtcggcgcg tcccccgggt gcgcctcgct    2760
tcccgggcct gccgcggccc ttccccgagg cgtccgtccc gggcgtcggc gtcggggaga    2820
gcccgtcctc cccgcgtggc gtcgcccgt tcggcgcgcg cgtgcgcccg agcgcggccc     2880
ggtggtccct gccggacagg cgttcgtgcg acgtgtggcg tgggtcgacc tccgccttgc    2940
cggtcgctcg ccctttcccc gggtcggggg gtggggcccg ggccggggcc tcggcccgg    3000 tcgcggtccc ccgtcccggg cggggcggg cgcgccggcc ggcctcggtc ggccctccct    3060
tggccgtcgt gtggcgtgtg ccaccccctgc gcccgcgccc gccggcgggg ctcggagccg   3120
ggcttcggcc gggccccggg ccctcgaccg gaccggtgcg cgggcgctgc ggccgcacgg    3180
cgcgactgtc cccgggccgg gcaccgcggt ccgcctctcg ctcgccgccc ggacgtcggg    3240
gccgccccgc ggggcgggcg gagcgccgtc cccgcctcgc cgccgcccgc gggcgccggc    3300
cgcgcgcgcg cgcgcgtggc cgccggtccc tccggccgc cggggcgggg tcgggccgtc     3360
cgcctcctcg cgggcgggcg cgacgaagaa gcgtcgcggg tctgtggcgc ggggcccccgg   3420 tggtcgtgtc gcgtgggggg cgggtggttg gggcgtccgg ttcgccgcgc ccgcccccgg    3480
ccccaccggt cccggccgcc gccccgcgc ccgctcgctc cctcccgtcc gcccgtccgc     3540 ggccgtccg tccgtccgtc gtcctcctcg cttgcggggc gccgggcccg tcctcgcgag     3600
gccccccggc cggccgtccg gccgcgtcgg ggcctcgccg cgctctacct tacctacctg    3660
gttgatcctg ccagtagcat atgcttgtct caaagattaa gccatgcatg tctgagtacg    3720
cacggccggt acagtgaaac tgcgaatggc tcattaaatc agttatggtt cctttggtcg    3780
ctcgctcctc tcctacttgg ataactgtgg taattctaga gctaatacat gccgacgggc    3840 gctgacccc ttcgcggggg ggatgcgtgc atttatcaga tcaaaccaa cccggtcagc      3900 ccctctccgg ccccggccgg ggggcgggcg ccggcggctt tggtgactct agataacctc    3960
gggccgatcg cacgccccc gtggcggcga cgaccattc gaacgtctgc cctatcaact      4020
ttcgatggta gtcgccgtgc ctaccatggt gaccacgggt gacgggaat cagggttcga     4080 ttccggagag ggagcctgag aaacggctac cacatccaag gaaggcagca ggcgcgcaaa    4140
ttacccactc ccgacccggg gaggtagtga cgaaaaataa caatacagga ctctttcgag    4200
gccctgtaat tggaatgagt ccactttaaa tcctttaacg aggatccatt ggagggcaag    4260
```

```
tctggtgcca gcagccgcgg taattccagc tccaatagcg tatattaaag ttgctgcagt    4320
taaaaagctc gtagttggat cttgggagcg ggcgggcggt ccgccgcgag gcgagccacc    4380
gcccgtcccc gccccttgcc tctcggcgcc ccctcgatgc tcttagctga gtgtcccgcg    4440
gggcccgaag cgtttacttt gaaaaaatta gagtgttcaa agcaggcccg agccgcctgg    4500
ataccgcagc taggaataat ggaataggac cgcggttcta ttttgttggt tttcggaact    4560
gaggccatga ttaagaggga cggccggggg cattcgtatt gcgccgctag aggtgaaatt    4620
cttggaccgg cgcaagacgg accagagcga aagcatttgc caagaatgtt ttcattaatc    4680
aagaacgaaa gtcggaggtt cgaagacgat cagataccgt cgtagttccg accataaacg    4740
atgccgaccg gcgatgcggc ggcgttattc ccatgacccg ccgggcagct tccgggaaac    4800
caaagtcttt ggttccggg ggagtatgg ttgcaaagct gaaacttaaa ggaattgacg    4860
gaagggcacc accaggagtg gagcctgcgg cttaatttga ctcaacacgg gaaacctcac    4920
ccggcccgga cacggacagg attgacagat tgatagctct ttctcgattc cgtgggtggt    4980
ggtgcatggc cgttcttagt tggtggagcg atttgtctgg ttaattccga taacgaacga    5040
gactctggca tgctaactag ttacgcgacc cccgagcggt cggcgtcccc caacttctta    5100
gagggacaag tggcgttcag ccacccgaga ttgagcaata acaggtctgt gatgccctta    5160
gatgtccggg gctgcacgcg cgctacactg actggctcag cgtgtgccta ccctacgccg    5220
gcaggcgcgg gtaacccgtt gaaccccatt cgtgatgggg atcggggatt gcaattattc    5280
cccatgaacg aggaattccc agtaagtgcg ggtcataagc ttgcgttgat taagtccctg    5340
ccctttgtac acaccgcccg tcgctactac cgattggatg gtttagtgag gccctcggat    5400
cggccccgcc ggggtcggcc cacggccctg gcggagcgct gagaagacgg tcgaacttga    5460
ctatctagag gaagtaaaag tcgtaacaag gtttccgtag gtgaacctgc ggaaggatca    5520
ttaacggagc ccggagggcg aggcccgcgg cggcgccgcc gccgccgcgc gcttccctcc    5580
gcacacccac cccccaccg cgacgcgcg cgtgcgcggg cggggcccgc gtgcccgttc    5640
gttcgctcgc tcgttcgttc gccgcccggc ccgccggcc gcgagagccg gagaactcgg    5700
gagggagacg ggggagagag agagagagag agaaagagaa agaagggcgt gtcgttggtg    5760
tgcgcgtgtc gtggggccgg cgggcggcgg ggagcggtcc ccggccgcgg ccccgacgac    5820
gtgggtgtcg gcgggcgcgg gggcggttct cggcggcgtc gcggcgggtc tgggggggtc    5880
tcggtgccct cctccccgcc ggggcccgtc gtccggcccc gccgcgccgg ctccccgtct    5940
tcggggccgg ccggattccc gtcgcctccg ccgcgccgct ccgcgccgcc gggcacggcc    6000
ccgctcgctc tccccggcct tcccgctagg gcgtctcgag ggtcgggggc cggacgccgg    6060
tcccctcccc cgcctcctcg tccgcccccc gccgtccag gtacctagcg cgttccggcg    6120
cggaggttta aagacccctt gggggggatcg cccgtccgcc cgtgggtcgg gggcggtggt    6180
gggcccgcgg gggagtcccg tcgggagggg ccggccccct cccgcgcctc caccgcggac    6240
tccgctcccc ggccggggcc gcgccgccgc cgccgccgcg gcggccgtcg ggtggggct    6300
ttacccggcg gccgtcgcgc gcctgccgcg cgtgtggcgt gcgccccgcg ccgtgggggc    6360
gggaacccc gggcgcctgt ggggtggtgt ccgcgctcgc ccccgcgtgg gcggcgcgcg    6420
cctccccgtg gtgtgaaacc ttccgacccc tctccggagt ccggtcccgt ttgctgtctc    6480
gtctggccgg cctgaggcaa ccccctctcc tcttgggcgg gggggggggg gacgtgccgc    6540
gccaggaagg gcctcctccc ggtgcgtcgt cgggagcgcc ctcgccaaat cgacctcgta    6600
cgactcttag cggtggatca ctcggctcgt gcgtcgatga agaacgcagc tagctgcgag    6660
```

```
aattaatgtg aattgcagga cacattgatc atcgacactt cgaacgcact tgcggccccg    6720
ggttcctccc ggggctacgc ctgtctgagc gtcgcttgcc gatcaatcgc ccccgggggt    6780
gcctccgggc tcctcggggt gcgcggctgg gggttccctc gcagggcccg ccgggggccc    6840
tccgtccccc taagcgcaga cccggcgcg  tccgccctcc tcttgccgcc gcgcccgccc    6900
cttccccctc ccccgcggg  ccctgcgtgg tcacgcgtcg ggtggcgggg gggagagggg    6960
ggcgcgcccg gctgagagag acggggaggg cggcgccgcc gccgcccgcg aagacggaga    7020
gggaaagaga gagccggctc gggccgagtt cccgtggccg ccgcctgcgg tccgggttcc    7080
tccctcgggg ggctccctcg cgccgcgcgc ggctcgggt  tcggggttcg tcggccccgg    7140
ccgggtggaa ggtcccgtgc ccgtcgtcgt cgtcgtcgtc gcgcgtcgtc ggcggtgggg    7200
gcgtgttgcg tgcggtgtgg tggtggggga ggaggaaggc gggtccggaa ggggaagggt    7260
gccggcgggg agagagggtc gggggagcgc gtccggtcg  ccgcggttcg ccgcccgccc    7320
ccggtggcgg cccggcgtcc ggccgaccgc cgctcccgcg ccctcctcc  tccccgccgc    7380
ccctcctccg aggccccgcc cgtcctcctc gccctccccg cgcgtacgcg cgcccgcccg    7440
cccggctcgc ctcgcggcgc gtcggccggg gccgggagcc cgccccgcgg ccgcccggc     7500
cgcgcccgtg gccgcggcgc cggggttcgc gtgtccccgg cggcgacccg cgggacgccg    7560
cggtgtcgtc cgccgtcgcg cgccccgcctc cggctcgcgg ccgcgccgcg ccgcgccggg    7620
gccccgtccc gagcttccgc gtcggggcgg ggcggctccg ccgccgcgtc ctcggacccg    7680
tcccccccgac ctccgcgggg gagacgggtc ggggcgtgcg gcgcccgtcc cgccccccggc    7740
ccgtgcccct ccctccggtc gtcccgctcc ggcggggcgg cgcgggggtg ccgccggccg    7800
cgcgctctct ctcccgtcgc ctctccccct cgccgggccc gtctcccgac ggagcgtcgg    7860
gcgggcggtc gggccggcgc gattccgtcc gtccgtccgc cgagcggccc gtcccccctcc    7920
agacgcgac ctcagatcag acgtggcgac ccgctgaatt taagcatatt agtcagcgga    7980
ggagaagaaa ctaaccagga ttccctcagt aacggcgagt gaacagggaa gagcccagcg    8040
ccgaatcccc gccccgcggc ggggcgcggg acatgtggcg tacggaagac ccgctccccg    8100
gcgccgctcg tggggggccc aagtccttct gatcgaggcc cagcccgtgg acggtgtgag    8160
gccggtagcg gccccccggcg cgccgggccc gggtcttccc ggagtcgggt tgcttgggaa    8220
tgcagcccaa agcgggtggt aaactccatc taaggctaaa taccggcacg agaccgatag    8280
tcaacaagta ccgtaaggga agttgaaaa  gaactttgaa gagagagttc aagagggcgt    8340
gaaaccgtta agaggtaaac gggtggggtc cgcgcagtcc gcccggagga ttcaacccgg    8400
cggcgggtcc ggccgtgtcg gcggcccggc ggatctttcc cgcccccgt  tcctcccgac    8460
ccctccaccc gccctcccctt ccccgccgc  ccctcctcct cctccccgga ggggcgggc    8520
tccggcgggt gcggggtgg  gcgggcgggg ccggggtgg  ggtcggcggg ggaccgtccc    8580
ccgaccggcg accggccgcc gccgggcgca tttccaccgc ggcggtgcgc gcgaccggc     8640
tccgggacgg ctgggaaggc ccggcgggga aggtggctcg gggggcccg  tccgtccgtc    8700
cgtccgtcct cctcctcccc cgtctccgcc cccggcccc  gcgtcctccc tcgggagggc    8760
gcgcgggtcg gggcggcggc ggccggcgcg gtggcggcgc cggcggcggc ggcgggaccg    8820
aaacccccccc cgagtgttac agcccccccg gcagcagcac tcgccgaatc ccggggccga    8880
gggagcgaga cccgtcgccg cgctctcccc cctcccggcg cccacccccg cggggaatcc    8940
cccgcgaggg gggtctcccc cgcggggcg  cgccggcgtc tcctcgtggg ggggccggc     9000
caccccctccc acggcgcgac cgctctccca ccctcctcc  ccgcgccccc gcccggcga    9060
```

```
cggggggggt gccgcgcgcg ggtcggggg cggggcggac tgtccccagt gcgcccgg     9120
cgggtcgcgc cgtcgggccc gggggaggtt ctctcgggc cacgcgcgcg tcccccgaag   9180
aggggacgg cggagcgagc gcacgggtc ggcggcgacg tcggctaccc acccgacccg   9240
tcttgaaaca cggaccaagg agtctaacac gtgcgcgagt cggggctcg cacgaaagcc   9300
gccgtggcgc aatgaaggtg aaggccggcg cgctcgccgg ccgaggtggg atcccgaggc   9360
ctctccagtc cgccgaggc gcaccaccgg cccgtctcgc ccgccgcgcc ggggaggtgg   9420
agcacgagcg cacgtgttag gacccgaaag atggtgaact atgcctgggc agggcgaagc   9480
cagaggaaac tctggtggag gtccgtagcg gtcctgacgt gcaaatcggt cgtccgacct   9540
gggtataggg gcgaaagact aatcgaacca tctagtagct ggttccctcc gaagtttccc   9600
tcaggatagc tggcgctctc gcagacccga cgcaccccg ccacgcagtt ttatccggta   9660
aagcgaatga ttagaggtct tggggccgaa acgatctcaa cctattctca aactttaaat   9720
gggtaagaag cccggctcgc tggcgtggag ccgggcgtgg aatgcgagtg cctagtgggc   9780
cacttttggt aagcagaact ggcgctgcgg gatgaaccga acgccgggtt aaggcgcccg   9840
atgccgacgc tcatcagacc ccagaaaagg tgttggttga tatagacagc aggacggtgg   9900
ccatggaagt cggaatccgc taaggagtgt gtaacaactc acctgccgaa tcaactagcc   9960
ctgaaaatgg atggcgctgg agcgtcgggc ccatacccgg ccgtcgccgg cagtcgagag   10020
tggacgggag cggcggggc ggcgcgcgcg cgcgcgcgtg tggtgtgcgt cggagggcgg   10080
cggcggcggc ggcggcgggg gtgtggggtc cttcccccgc ccccccccc acgcctcctc   10140
ccctcctccc gcccacgccc cgctcccgc cccggagcc ccgcggacgc tacgccgcga   10200
cgagtaggag ggccgctgcg gtgagccttg aagcctaggg cgcgggcccg ggtggagccg   10260
ccgcaggtgc agatcttggt ggtagtagca aatattcaaa cgagaacttt gaaggccgaa   10320
gtggagaagg gttccatgtg aacagcagtt gaacatgggt cagtcggtcc tgagagatgg   10380
gcgagcgccg ttccgaaggg acgggcgatg gcctccgttg ccctcggccg atcgaaaggg   10440
agtcgggttc agatccccga atccggagtg gcggagatgg gcgccgcgag cgtccagtg    10500
cggtaacgcg accgatcccg gagaagccgg cgggagcccc ggggagagtt ctcttttctt   10560
tgtgaagggc agggcgccct ggaatgggtt cgccccgaga gagggccccg tgccttggaa   10620
agcgtcgcgc ttccggcggc gtccggtgag ctctcgctgg cccttgaaaa tccggggag    10680
agggtgtaaa tctcgcgccg ggccgtaccc atatccgcag caggtctcca aggtgaacag   10740
cctctggcat gttggaacaa tgtaggtaag ggaagtcggc aagccggatc cgtaacttcg   10800
ggataaggat tggctctaag ggctgggtcg gtcgggctgg ggcgcgaagc ggggctgggc   10860
gcgcgccgcg gctggacgag gcgccgccgc cccccccacg cccggggcac ccccctcgcg   10920
gccctccccc gccccacccc gcgcgcgccg ctcgctccct cccgcccg cgccctctct   10980
ctctctctct ccccgctcc ccgtcctccc ccctccccgg gggagcgccg cgtggggcg    11040
gcggcggggg gagaagggtc ggggcggcag gggccggcgg cggccgccg cggggcccg    11100
gcggcggggg cacggtcccc cgcgagggg gcccgggcac ccggggggcc ggcggcggcg   11160
gcgactctgg acgcgagccg ggcccttccc gtggatcgcc ccagctgcgg cgggcgtcgc   11220
ggccgccccc ggggagcccg gcgggcgccg gcgcgccccc cccccaccc cacgtctcgt   11280
cgcgcgcgcg tccgctgggg gcggggagcg gtcgggcggc ggcggtcggc gggcggcggg   11340
gcggggcggt tcgtcccccc gccctacccc ccggccccg tccgcccccc gttcccccct   11400
cctcctcggc gcgcggcggc ggcggcggca ggcggcggag gggccgcggg ccggtccccc   11460
```

```
ccgccgggtc cgcccccggg gccgcggttc cgcgcggcgc ctcgcctcgg ccggcgccta    11520
gcagccgact tagaactggt gcggaccagg ggaatccgac tgtttaatta aaacaaagca    11580
tcgcgaaggc ccgcggcggg tgttgacgcg atgtgatttc tgcccagtgc tctgaatgtc    11640
aaagtgaaga aattcaatga agcgcgggta aacggcggga gtaactatga ctctcttaag    11700
gtagccaaat gcctcgtcat ctaattagtg acgcgcatga atggatgaac gagattccca    11760
ctgtccctac ctactatcca gcgaaaccac agccaaggga acgggcttgg cggaatcagc    11820
ggggaaagaa gaccctgttg agcttgactc tagtctggca cggtgaagag acatgagagg    11880
tgtagaataa gtgggaggcc cccggcgccc cccggtgtc cccgcgaggg gcccggggcg     11940
gggtccgccg gccctgcggg ccgccggtga ataccacta ctctgatcgt tttttcactg     12000
acccggtgag gcggggggc gagccccgag gggctctcgc ttctggcgcc aagcgcccgg     12060
ccgcgcgccg gccgggcgcg acccgctccg gggacagtgc caggtgggga gtttgactgg    12120
ggcggtacac ctgtcaaacg gtaacgcagg tgtcctaagg cgagctcagg gaggacagaa    12180
acctcccgtg gagcagaagg gcaaaagctc gcttgatctt gattttcagt acgaatacag    12240
accgtgaaag cggggcctca cgatccttct gaccttttgg gttttaagca ggaggtgtca    12300
gaaaagttac cacagggata actggcttgt ggcggccaag cgttcatagc gacgtcgctt    12360
tttgatcctt cgatgtcggc tcttcctatc attgtgaagc agaattcacc aagcgttgga    12420
ttgttcaccc actaataggg aacgtgagct gggtttagac cgtcgtgaga caggttagtt    12480
ttaccctact gatgatgtgt tgttgccatg gtaatcctgc tcagtacgag aggaaccgca    12540
ggttcagaca tttggtgtat gtgcttggct gaggagccaa tggggcgaag ctaccatctg    12600
tgggattatg actgaacgcc tctaagtcag aatcccgccc aggcggaacg atacggcagc    12660
gccgcggagc ctcggttggc ctcggatagc cggtcccccg cctgtccccg ccggcgggcc    12720 gcccccccc tccacgcgcc ccgcgcgcgc gggagggcgc gtgccccgcc gcgcgccggg     12780
accggggtcc ggtgcggagt gcccttcgtc ctgggaaacg gggcgcggcc ggagaggcgg    12840
ccgccccctc gcccgtcacg caccgcacgt tcgtggggaa cctggcgcta aaccattcgt    12900
agacgacctg cttctgggtc ggggtttcgt acgtagcaga gcagctccct cgctgcgatc    12960
tattgaaagt cagccctcga cacaagggtt tgtccgcgcg cgcgcgcgcg cgcgcgtgcg    13020
gggggcccgg cggggcgtgc gcgtccggcg ccgtccgtcc ttccgttcgt cttcctccct    13080 cccgcctct cccgccgacc gcgggcgtgg tggtgggggt gtgggggga gggcgcgcga     13140 ccccggtcgg cgcgccccgc ttcttcggtt cccgcctcct ccccgttcac cgccggggcg    13200
gctcgtccgc tccgggccgg gacggggtcc ggggagcgtg gtttgggagc gcggaggcg    13260 gccgcgccga gccgggcccg tggcccgccg gtccccgtcc cggggttggg ccgcgcgggc    13320
cccggtgggg cggccacccg ggtcccggcc cctcgcg                            13357
```

<210> SEQ ID NO 69
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 69
tttcttgtaa gcgtcgaggt g                                                 21

```
<210> SEQ ID NO 70
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 70
agcaggcacc taggagacaa                                              20

<210> SEQ ID NO 71
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 71
tcaggcgttc tcgtctcc                                                18

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
caccacatcg atcacgaaga                                              20

<210> SEQ ID NO 73
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 73
ctatgcgcac ccgttctc                                                18

<210> SEQ ID NO 74
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 74
gtagcgaagc gagcagga                                                18
```